(12) United States Patent
Kubota et al.

(10) Patent No.: US 7,932,271 B2
(45) Date of Patent: Apr. 26, 2011

(54) HETEROCYCLIC METHYL SULFONE DERIVATIVE

(75) Inventors: Hideki Kubota, Tokyo (JP); Takanori Yasukouchi, Tokyo (JP); Satoru Miyauchi, Tokyo (JP); Kayoko Motoki, Tokyo (JP); Masanori Saito, Tokyo (JP); Hitoshi Iimori, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 1445 days.

(21) Appl. No.: 10/561,838

(22) PCT Filed: Jun. 29, 2004

(86) PCT No.: PCT/JP2004/009132
§ 371 (c)(1),
(2), (4) Date: Dec. 22, 2005

(87) PCT Pub. No.: WO2005/000798
PCT Pub. Date: Jan. 6, 2005

(65) Prior Publication Data
US 2006/0241302 A1 Oct. 26, 2006

(30) Foreign Application Priority Data

Jun. 30, 2003 (JP) .................................. 2003-187796
Mar. 30, 2004 (JP) .................................. 2004-099151

(51) Int. Cl.
*A61K 31/44* (2006.01)
*C07D 401/00* (2006.01)
*C07D 213/72* (2006.01)
*C07D 213/00* (2006.01)

(52) U.S. Cl. ..................... 514/336; 514/352; 546/268.1; 546/304; 546/339

(58) Field of Classification Search .................. 514/352, 514/336; 546/268.1, 304, 339
See application file for complete search history.

(56) References Cited

U.S. PATENT DOCUMENTS

| | | | |
|---|---|---|---|
| 3,849,423 A | 11/1974 | Krumkalns et al. | |
| 4,055,652 A | 10/1977 | Walker | |
| 4,116,665 A | 9/1978 | Krumkalns | |
| 4,157,399 A | 6/1979 | Sauter | |
| 4,675,316 A | 6/1987 | Chan | |
| 2005/0234109 A1 | 10/2005 | Yasukouchi et al. | |
| 2006/0241302 A1 | 10/2006 | Kubota et al. | |

FOREIGN PATENT DOCUMENTS

| | | |
|---|---|---|
| DE | 42 15 437 | 11/1993 |
| EP | 0 000 112 | 12/1978 |
| EP | 0 000 752 | 2/1979 |
| EP | 0 046 658 | 3/1982 |
| EP | 0 117 485 | 9/1984 |
| EP | 0 153 657 | 9/1985 |
| FR | 2 509 725 | 1/1983 |
| GB | 1 554 299 | 10/1979 |
| JP | 55-33473 | 3/1980 |
| JP | 62-39563 | 2/1987 |
| JP | 6-25168 | 2/1994 |
| JP | 6-56780 | 3/1994 |
| JP | 9-95444 | 4/1997 |
| WO | 93 25536 | 12/1993 |
| WO | 96/41799 | 12/1996 |
| WO | WO 98/38156 | 9/1998 |
| WO | WO 00/50391 | 8/2000 |
| WO | WO 01/70677 A1 | 9/2001 |
| WO | WO 01/94318 A2 | 12/2001 |
| WO | 02/81433 | 10/2002 |
| WO | 02 081435 | 10/2002 |
| WO | WO 03/013527 A1 | 2/2003 |
| WO | WO 03/014075 A2 | 2/2003 |
| WO | 03 018543 | 3/2003 |
| WO | 03/55850 | 7/2003 |
| WO | 03 059335 | 7/2003 |
| WO | WO 03/053912 A1 | 7/2003 |
| WO | WO 03/066592 A1 | 8/2003 |

(Continued)

OTHER PUBLICATIONS

Anders et al., "Ferngesteuerte Nucleophile Eigenschaften Der Anionen Einiger 4-Alkylpyridine: AM1-UND MNDO-Berechnungen Sowie Experimentelle Untersuchungen", Chemische Berichte, vol. 122, No. 1, pp. 105-111, 1989 (with English abstract).

Wojciechowski, "Synthesis of Nitrobenzophenones From Nitro-Alpha-Sulfonyldiphenylmethane Derivatives", Synthetic Communications, vol. 27, No. 1, pp. 135-144, 1997.

Yau et al., "Synthesis of Complex 6'-Alkynyl-6'-Dethia Nucleoside Analogues of S-Adenosylhomocysteine as Potential Inhibitors of Methyltransferases", Journal of Organic Chemistry, vol. 55, No. 10, pp. 3147-3158, 1990.

(Continued)

*Primary Examiner* — Taylor Victor Oh
(74) *Attorney, Agent, or Firm* — Oblon, Spivak, McClelland, Maier & Neustadt, L.L.P.

(57) ABSTRACT

Provided is a compound capable of inhibiting production or secretion of β amyloid protein.

A compound represented by the following formula (1):

[Chemical formula 1]

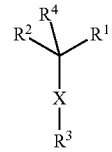

(1)

(wherein, $R^1$ represents a heterocyclic group which may have a substituent, $R^2$ represents a cyclic hydrocarbon group which may have a substituent or a heterocyclic group which may have a substituent, $R^3$ represents a cyclic hydrocarbon group which may have a substituent or a heterocyclic group which may have a substituent, $R^4$ represents a hydrogen atom or a $C_{1-6}$ alkyl group, and X represents —S—, —SO— or —$SO_2$—); an N-oxide or S-oxide thereof; a salt thereof; or a solvate thereof; and a medicament containing any of them.

11 Claims, No Drawings

FOREIGN PATENT DOCUMENTS

| | | |
|---|---|---|
| WO | WO 03/093251 A1 | 11/2003 |
| WO | WO 03/093252 A1 | 11/2003 |
| WO | WO 03/093253 A1 | 11/2003 |
| WO | WO 03/093264 A1 | 11/2003 |
| WO | WO 03/103660 A1 | 12/2003 |
| WO | 2004/017977 | 3/2004 |
| WO | 2004 031137 | 4/2004 |
| WO | 2004/031138 | 4/2004 |
| WO | 2004 031139 | 4/2004 |
| WO | WO 2004/039370 A1 | 5/2004 |
| WO | WO 2004/039800 A1 | 5/2004 |

OTHER PUBLICATIONS

Lapkin et al., "Reactions of Halogen Metal Alcoholates-New Method of Synthesizing Sulfides of Thiophenic Series", Khimiya Geterotsiklicheskih Soedinenii, No. 1, pp. 53-57, 1968 (with partial English translation).

Xio-Dan Cai, et al., "Release of Excess Amyloid β Protein from a Mutant Amyloid β Protein Precursor", Science, vol. 259, Jan. 22, 1993, pp. 514-516.

J. E. Cranham, et al., "The Toxicity of Organic Sulphides to the Eggs and Larvae of the Glasshouse Red Spider Mite., VII.—Benzyl Phenyl Sulphides (α-substituted)", J. Sci. Food Agric , vol. 9, Mar. 1958, pp. 147-150.

Jean-Paul Fournier, et al, "(Hydroxy-2alkyl)-et (hydroxy-3 alkyl)-phénylsulfones à activité hypolipidémiante", Eur. J. Med. Chem- Chim. Ther., vol. 17, No. 1, 1982, pp. 53-58 (with English Abstract).

Stephen A. Gravina, et al., "Communication Amyloid β Protein (Aβ) in Alzheimer's Disease Brain", The Journal of Biological Chemistry, vol. 270, No. 13, Mar. 31, 1995, pp. 7013-7016.

I. Hussain, et al., "ASP1 (BACE2) Cleaves the Amyloid Precursor Protein at the β-Secretase Site", Molecular and Cellular Neuroscience, vol. 16, 2000, pp. 609-619.

Hiroyuki Ishibashi, et al., "Lewis Acid-Promoted Alkylations of Arenes and 1-Trimethylsilylalkynes with β-Chloro-β-thiopropanoic Esters", Chem. Pharm. Bull., vol. 39, No. 5, 1991, pp. 1148-1151.

V. S. Karavan, et al., "Correlation of isoselectivity in halogen-seeking reaction of α-chlorodesyl aryl sulfone with sodium thiophenolate", vol. 25, No. 5, 1989, pp. 905-910 (with partial English translation).

M. Mühlstädt, et al., "Untersuchungen zur Stereochemie der Cyclofunktionalisierung β,γ-ungesättigter Carbamidsäureester", vol. 328, No. 3, 1986, pp. 309-313 (with English Abstract).

A. G. Panteleimonof, et al., "Addition of nucleophilic agents to 1-aryl-2-trifiouoromethylsulfonyl ethylene", Organic Chemical Journal, vol. 25, No. 5, 1989, pp. 1976-1980 (with English translation).

Jacek Skarzewski, et al., "Simple preparation of enantiomeric Michael adducts of thiophenol to chalcones: easily available new chiral building blocks", Tetrahedron Asymmetry, vol. 12, No. 13, 2001, pp. 1923-1928.

Robert Vassar, et al., "β-Secretase Cleavage of Alzheimer's Amyloid Precursor Protein by the Transmembrane Aspartic Protease BACE", Science, vol. 286, Oct. 22, 1999, pp. 735-741.

Keith A. M. Walker, "A Convenient Preparation of Thioethers From Alcohols", Tetrahedron Letters, No. 51, 1977, pp. 4475-4478.

Michael S. Wolfe, "Secretase Targets for Alzheimer's Disease: Identification and Therapeutic Potential", Journal of Medicinal Chemistry, vol. 44, No. 13, Jun. 21, 2001, pp. 4039-2060.

Michael S. Wolfe, et al., "Two transmembrane aspartates in presenilin-1 required for presenilin endoproteolysis and γ-secretase activity", Letters to Nature, vol. 398, Apr. 8, 1999, pp. 513-517.

A. H. Wragg, et al., "The Rearrangement of Sulphinic Esters", J. Chem. Soc, Jun. 1958, pp. 3603-3605.

Ibro Tabakovic, et al.. "The Alkylation of Coumarin At C-3 of 4-Hydroxycoumarin", Organic Preparations and Procedures International, vol. 29, No. 2, Apr. 1997, pp. 223-226.

U.S. Appl. No. 11/829,533, filed Jul. 27, 2007, Yasukouchi, et al.

Mohammed A. Ali, et al., "Spatial Requirements of the Antagonist Binding Site of the $NK_2$ Receptor", Bioorganic & Medicinal Chemistry Letters, XP004230940, vol. 11,(6), 2001, pp. 819-822.

Richard D. Chambers, et al., "A New Approach to Di (perfluoroaryl) methanes utilising sulphone-stabilised carbanions", Journal of Fluorine Chemistry, vol. 27,(2), XP002521704, 1985, pp. 237-240.

Khalid Nawaz, et al., Condensation of 4-hydroxycoumarin with aldehyde under Knoevenagel conditions, Journal of the Chemical Society of Pakistan, vol. 13,(4), XP002521707, 1991, 2 Pages.

Bum Tae Kim, et al., "Exocyclization of Novel β, β-Difluoro-α-Phenylvinyl Sulfide with Bidendate Heteroatom (N, O, S) Nucleophiles", Heterocycles, vol. 41., No. 4, XP002521705, 1995, pp. 641-646.

Ibro Tabakovic, et al., "Anodic oxidation of substituted [4-hydroxy-3-coumarinyl]-phenylthiomethanes in acetonitrile. Evidence for a cationic intermediate in carbon-sulfur bond fragmentation", Electrochimica Acta, vol. 43., No. 12-13, 1998, pp. 1773-1778.

Yijun Deng, et al., "Synthetic Applications of Azolium Ylides to a Traceless Solid-Phase Synthesis of 2-Substituted Azoles", Organic Letters, Vo. 4,(23), XP002521708, 2002, 2 Pages.

Adam Bieniek, et al., "Application of Organolithium and Related Reagents in Synthesis. Part XXVIII [1]. Synthesis strategies based on aromatic Metallation: A Conversion of Benzoic Acids into Arylthiomethyl Aromatic Carboxylic Acids", Monatshefte Fuer Chemie, vol. 134, XP002521706, 2003, pp. 533-538.

Giorgio Chelucci, et al., "Chiral Sulfoxides and Sulfides Tethered to Pyridines as Ligands for Enantioselective Catalysis: Palladium Catalyzed Allylic Substitution and Addition of Diethylzinc to Benzaldehyde". Tetrahedron, vol. 53, No. 10, 1997, pp. 3843-3848.

HETEROCYCLIC METHYL SULFONE DERIVATIVE

TECHNICAL FIELD

The present invention relates to novel compounds having an inhibitory activity against production or secretion of β-amyloid protein; and a medicament to treat various diseases caused by abnormal production or secretion of β-amyloid protein such as Alzheimer disease, Down syndrome and the other diseases associated with amyloid deposition.

BACKGROUND ART

Alzheimer disease is a neurodegenerative disease having pathological features such as degeneration or loss of nerve cells, formation of senile plaques and neurofibrillary tangles. Alzheimer disease causes symptoms of dementia such as gradual loss of memory, recognition, thinking, judgment or the like, and it eventually leads to death. No effective method for treating or preventing this disease has hitherto been known.

The main protein constituting a senile plaque deposited in the brain is β-amyloid protein (amyloid β protein, Aβ) which is composed of from 39 to 43 amino acids. β-Amyloid protein exhibits cytotoxicity, which is presumed to induce Alzheimer disease (Non-patent Document 1). β-Amyloid protein secreted from cells is a polypeptide composed mainly of 40 or 42 amino acids and particularly, that composed of 42 amino acids is known to deposit in the brain quickly because of strong aggregation property and in addition, have strong cytotoxicity (Non-patent Document 2). Amyloid protein is produced ubiquitously in vivo, but its function remains unknown.

β-Amyloid protein is produced by processing of an amyloid precursor protein (APP) which is a membrane protein. Mutation of an APP gene is observed from patients suffering from familial Alzheimer disease. An increase in the production or secretion amount of β-amyloid protein is known to occur in the cells having this mutated APP gene introduced therein. This suggests that a medicament inhibiting the production or secretion of β-amyloid protein is effective for the prevention or treatment of Alzheimer disease.

In the processing step of an amyloid precursor protein to produce β-amyloid protein, BACE (β-site APP Cleaving Enzyme) (Non-patent Document 3) or Asp1 (Non-patent Document 4), each an aspartic protease, is reported as a β secretase for cleaving the N terminal of β-amyloid protein. It is suggested strongly that γ-secretase which cleaves the C-terminal region is partially composed of presenilin (Non-patent Document 5). Although inhibitors of β-secretase and γ-secretase have been reported (Non-patent document 6), most of them are peptide like compounds.

In Patent document 1, SMITH, et al., disclose compounds having a sulfonamide skeleton and capable of controlling production of β-amyloid protein. In Patent Document 2, BELANGER, et al., disclose compounds having a bicycloalkylsulfonamide skeleton and inhibiting γ-secretase. Also in Patent Documents 3, 4 and 5, diarylsulfone compounds inhibiting γ-secretase are disclosed. In Patent Document 6, thionaphthalene derivatives inhibiting aggregation of amyloid protein are disclosed.

Non-patent Document 1: Science, 259, 514(1993)
Non-patent Document 2: Journal of Biological Chemistry, 270, 7013(1995)
Non-patent Document 3: Science, 286, 735(1999)
Non-patent Document 4: Molecular and Cellular Neuroscience, 16, 609(2000)
Non-patent Document 5: Journal of Medicinal Chemistry, 44, 2039(2001)
Patent Document 1: WO00/50391
Patent Document 2: WO01/70677
Patent Document 3: WO02/081433
Patent Document 4: WO02/081435
Patent Document 5: WO03/18543
Patent Document 6: JP-A-1997-95444

DISCLOSURE OF THE INVENTION

Problems that the Invention is to Solve

An object of the present invention is to provide compounds having a structure different from that of the above-described known compounds, having an excellent inhibitory activity against production or secretion of β-amyloid protein and having desirable properties as pharmaceuticals.

Means for Solving the Problems

The present inventors have carried out various investigations. As a result, it has been found that heterocyclic methylthio compounds, heterocyclic methyl sulfine compounds and heterocyclic methyl sulfone compounds represented by the below-described formula (1) have an excellent inhibitory activity against production or secretion of β-amyloid protein and are therefore useful as a medicament for treating various diseases resulting from the abnormal production or secretion of β-amyloid protein, leading to the completion of the present invention.

In the present invention, there is thus provided a compound represented by the following formula (1):

[Chemical formula 1]

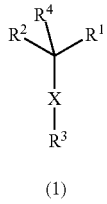

(1)

(wherein, $R^1$ and $R^3$ each independently represents an aromatic hydrocarbon group which may have a substituent or an aromatic heterocyclic group which may have a substituent, $R^2$ represents a saturated or unsaturated monocyclic heterocyclic group or unsaturated polycyclic heterocyclic group which may have a substituent, $R^4$ represents a hydrogen atom or a $C_{1-6}$ alkyl group, and X represents —S—, —SO— or —SO$_2$—); an N-oxide or S-oxide thereof; a salt thereof; or a solvate thereof.

In the present invention, there is also provided a medicament containing, as an effective ingredient, the compound represented by the formula (1); an N-oxide or S-oxide thereof; a salt thereof; or a solvate thereof.

In the present invention, there is also provided a pharmaceutical composition containing the compound represented by the formula (1), an N-oxide or S-oxide thereof, a salt thereof, or a solvate thereof; and a pharmaceutically acceptable carrier.

In the present invention, there is also provided use of the compound represented by the formula (1), an N-oxide or S-oxide thereof, a salt thereof, or a solvate thereof for the preparation of a medicament.

In the present invention, there is also provided a method of treating a disease resulting from abnormal production or secretion of β-amyloid protein, which comprises administering an effective amount of the compound represented by the formula (1), an N-oxide or S-oxide thereof, a salt thereof, or a solvate thereof.

Advantageous Effect of the Invention

The present invention makes it possible to provide compounds having an excellent inhibitory activity against production or section of β-amyloid protein and having desirable properties as a medicament.

BEST MODE FOR CARRYING OUT THE INVENTION

The compound represented by the formula (1) is described bellow.

Examples of the aromatic hydrocarbon group represented by $R^1$ or $R^3$ include phenyl and naphthyl groups, of which phenyl group is preferred.

Examples of the aromatic heterocyclic group represented by $R^1$ or $R^3$ include 5- or 6-membered aromatic heterocyclic groups having 1 to 4 atoms selected from nitrogen, oxygen and sulfur atoms. Specific examples include pyrrolyl, furyl, thienyl, pyrazolyl, imidazolyl, triazolyl, oxazolyl, thiazolyl, isoxazolyl, isothiazolyl, pyridyl, pyrimidinyl, tetrazolyl, thiadiazolyl, pyrazinyl, and pyridazinyl groups.

Of these groups, thienyl, pyrazolyl, imidazolyl, triazolyl, oxazolyl, thiazolyl, thiadiazolyl, pyridyl, pyrimidinyl, and pyridazinyl groups are preferred; thienyl, pyridyl, pyrimidinyl and pyridazinyl groups are more preferred; and thienyl, pyridyl and pyrimidinyl groups are especially preferred.

Examples of the saturated monocyclic heterocyclic group represented by $R^2$ include 3- to 7-membered heterocyclic groups having 1 to 4 atoms selected from nitrogen, oxygen and sulfur atoms. Specific examples include pyrrolidinyl, tetrahydrofuranyl, oxetanyl, tetrahydrothienyl, piperidinyl, piperazinyl, homopiperazinyl, morpholinyl, thiomorpholinyl, aziridinyl, imidazolidinyl, pyrazolidinyl, tetrahydropyranyl, tetrahydrothiopyranyl, dioxolanyl, oxathiolanyl and hexahydropyrimidinyl groups.

Of these, pyrrolidinyl, tetrahydrofuranyl, tetrahydrothienyl, piperidinyl, piperazinyl, homopiperazinyl, morpholinyl, thiomorpholinyl, imidazolidinyl, pyrazolidinyl, tetrahydropyranyl and tetrahydrothiopyranyl groups are preferred; and piperidinyl, tetrahydropyranyl, tetrahydrothiopyranyl and hexahydropyrimidinyl groups are more preferred.

Examples of the unsaturated monocyclic heterocyclic group represented by $R^2$ include 4- to 7-membered groups having 1 to 4 atoms selected from nitrogen, oxygen and sulfur atoms. Specific examples include pyrrolyl, furyl, thienyl, pyrazolyl, imidazolyl, triazolyl, oxazolyl, thiazolyl, isoxazolyl, isothiazolyl, triazinyl, tetrazolyl, thiadiazolyl, oxadiazolyl, pyridyl, pyrimidinyl, pyrazinyl, pyridazinyl, pyrrolyl, imidazolinyl, pyrazolinyl, oxazolinyl, thiazolinyl, isoxazolinyl, isothiazolinyl, pyranyl, dihydropyridyl, tetrahydropyridyl, dihydropyrimidinyl, tetrahydropyridazinyl and tetrahydropyrimidinyl groups.

Of these, pyrrolyl, furyl, thienyl, pyrazolyl, imidazolyl, triazolyl, oxazolyl, thiazolyl, isoxazolyl, isothiazolyl, pyridyl, pyrimidinyl, pyrazinyl, triazinyl, tetrazolyl, pyrrolinyl, imidazolinyl, pyrazolinyl, thiadiazolyl, pyrazinyl, pyridazinyl, tetrahydropyridyl, dihydropyrimidinyl and tetrahydropyridazinyl groups are preferred; and imidazolyl, pyridyl, pyrimidinyl and thiazolyl groups are more preferred.

Examples of the unsaturated polycyclic heterocyclic group represented by $R^2$ include 8- to 10-membered groups having 1 to 4 atoms selected from nitrogen, oxygen and sulfur atoms. Specific examples include benzofuranyl, benzothiazolyl, indolyl, quinolyl, isoquinolyl, benzopyranyl, benzoxazolyl, benzothiazolyl, benzimidazolyl, benzodioxanyl, benzothiophenyl, benzisothiazolyl, benzisoxazolyl, chromenyl, chromanyl, isochromenyl, isochromanyl, indolinyl, indazolyl, indolizinyl, isoindolyl, isoindolinyl, quinolizinyl, quinoxalinyl, quinazolinyl, cinnolinyl, phthalazinyl, naphthyridinyl, purinyl, tetrahydrothiazolopyridyl, imidazopyridyl, triazolopyridyl, pyrrolopyridyl, carbazolyl, xanthenyl, acridinyl, phenazinyl, phenoxazinyl, phenothiazinyl and quinuclidinyl groups.

Of these group, benzofuranyl, benzothiazolyl, indolyl, quinolyl, isoquinolyl, benzopyranyl, benzoxazolyl, benzothiazolyl, benzimidazolyl, benzodioxanyl, benzothiophenyl, benzisothiazolyl, benzisoxazolyl, chromenyl, chromanyl, isochromenyl, isochromanyl, indolinyl, indazolyl, indolizinyl, quinolizinyl, quinoxalinyl, quinazolinyl, cinnolinyl, phthalazinyl, naphthyridinyl, imidazopyridyl and triazolopyridyl groups are preferred; and benzimidazolyl, chromenyl, imidazopyridyl and triazolopyridyl groups are more preferred.

The aromatic hydrocarbon group or aromatic heterocyclic group represented by $R^1$ or $R^3$ may be substituted by 1 to 3 substituents, which are the same or different, selected from halogen atoms, $C_{1-6}$ alkyl groups, trihalogenomethyl groups, $C_{1-6}$ alkoxy groups, $C_{2-6}$ alkenyl groups, formyl group, $C_{2-6}$ alkanoyl groups, carboxyl group, carboxyamino $C_{1-6}$ alkyl groups, $C_{1-6}$ alkoxycarbonylamino $C_{1-6}$ alkyl groups, oxo group, nitro group, cyano group, amidino group, $C_{2-6}$ alkenyloxy groups, hydroxy group, thioxo group, amino group, $C_{1-6}$ alkylamino groups, di($C_{1-6}$ alkyl)amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, mercapto group, $C_{1-6}$ alkylthio groups, $C_{1-6}$ alkylsulfinyl groups, $C_{1-6}$ alkylsulfonyl groups, and $C_{6-10}$ aromatic hydrocarbon-$C_{1-6}$ alkyl groups.

As the substituent for the aromatic hydrocarbon group or aromatic heterocyclic group represented by $R^1$ or $R^3$, halogen atoms, $C_{1-6}$ alkyl groups, trihalogenomethyl groups, $C_{1-6}$ alkoxy groups, cyano group, amidino group, hydroxy group, $C_{1-6}$ alkylamino groups, di($C_{1-6}$ alkyl)amino groups, carbamoyl group, $C_{1-6}$ alkylcarbamoyl groups and di($C_{1-6}$ alkyl)carbamoyl groups are preferred; halogen atoms, $C_{1-6}$ alkyl groups, trihalogenomethyl groups, $C_{1-6}$ alkoxy groups and cyano group are more preferred; and halogen atoms and cyano group are especially preferred. Among the halogen atoms, chlorine and fluorine atoms are still more preferred.

Examples of the substituent for the saturated or unsaturated monocyclic heterocyclic group or unsaturated polycyclic heterocyclic group represented by $R^2$ include a group -$Q^{101}$-$Q^{102}$-$Q^{103}$-$Q^{104}$-$Q^{105}$-$Q^{106}$-$Q^{107}$ (wherein, $Q^{101}$ represents a single bond, a $C_{1-6}$ alkylene group, a $C_{2-6}$ alkenylene group or a heterocyclic group; $Q^{102}$ represents a single bond, —O—, —NH—, —CH=N—, —C(alkyl)=N—, —N(alkyl)- or —S—; $Q^{103}$ represents a single bond, —CO—, —CS—, —SO—, —SO$_2$— or —CONH—; $Q^{104}$ represents a single bond, a $C_{1-6}$ alkylene group, a $C_{2-6}$ alkenylene group, a $C_{3-8}$ cycloalkylene group, a $C_{4-7}$ cycloalkenylene group, an aromatic hydrocarbon group or a heterocyclic group; $Q^{105}$ represents a single bond, —NH— or —N(alkyl)-; $Q^{106}$ represents a single bond, —O—, —CO—, —CS—, —SO$_2$—, —SO— or —S—; and $Q^{107}$ represents a hydrogen atom, a halogen atom, a hydroxy group, an oxo group, a $C_{1-6}$ alkyl group, a $C_{2-6}$ alkenyl group, a $C_{3-7}$ cycloalkyl group, a $C_{1-6}$ alkoxy group, a $C_{2-6}$ alkenyloxy group, an azide group, a cyano group, an amino group, a $C_{1-6}$ alkylamino group, a di($C_{1-6}$ alkyl)amino group, a $C_{2-6}$ alkanoylamino group, a di($C_{2-6}$ alkanoyl)amino group, a carboxyamino group, a $C_{1-6}$ alkoxycarbonylamino group, a di($C_{1-6}$ alkoxycarbonyl) amino group, a heterocyclic group, an aromatic hydrocarbon group, a $C_{4-7}$ cycloalkenyl group, a heterocycle-oxy group or an aromatic hydrocarbon-oxy group, in which the $C_{1-6}$ alkylene or alkyl group, $C_{2-6}$ alkenylene or alkenyl group, $C_{3-7}$ cycloalkylene or $C_{3-7}$ cycloalkyl group, $C_{4-7}$ cycloalkenylene or $C_{4-7}$ cycloalkenyl group, heterocyclic group, heterocycle-oxy group, aromatic hydrocarbon group or aromatic hydrocarbon-oxy group may be substituted with 1 to 3 substituents selected from halogen atoms, $C_{1-6}$ alkyl groups, $C_{1-6}$ alkoxy groups, $C_{2-6}$ alkenyl groups, carboxyamino $C_{1-6}$ alkyl groups, $C_{1-6}$ alkoxycarbonylamino $C_{1-6}$ alkyl groups, formyl group, $C_{2-6}$ alkanoyl groups, oxo group, nitro group, cyano group, azide group, amidino group, $C_{2-6}$ alkenyloxy groups, hydroxy group, carboxyl group, $C_{7-16}$ aralkyl groups, thioxo group, $C_{2-6}$ alkanoyl groups, $C_{2-6}$ thioalkanoyl groups, thioformyl group, amino group, $C_{1-6}$ alkylamino groups, di($C_{1-6}$ alkyl) amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, $C_{1-6}$ alkoxycarbamoylamino groups, $C_{1-6}$ alkoxycarbamoyl($C_{1-6}$ alkyl)amino groups, $C_{2-6}$ alkanoylamino groups, $C_{2-6}$ alkanoyl($C_{1-6}$ alkyl) amino groups, thio $C_{2-6}$ alkanoylamino groups, thio $C_{2-6}$ alkanoyl($C_{1-6}$ alkyl)amino groups, formylamino group, formyl($C_{1-6}$ alkyl)amino groups, thioformylamino group, thioformyl($C_{1-6}$ alkyl)amino groups, $C_{2-6}$ alkanoyloxy groups, formyloxy group, $C_{1-6}$ alkoxycarbonyloxy groups, carbamoyloxy group, $C_{1-6}$ alkylcarbamoyloxy groups, di($C_{1-6}$ alkyl)carbamoyloxy groups, aminocarbonylamino group, $C_{1-6}$ alkylaminocarbonylamino groups, di($C_{1-6}$ alkyl) aminocarbonylamino groups, aminocarbonyl($C_{1-6}$ alkyl) amino groups, $C_{1-6}$ alkylaminocarbonyl($C_{1-6}$ alkyl)amino groups, di($C_{1-6}$ alkyl)aminocarbonyl($C_{1-6}$ alkyl)amino groups, mercapto group, $C_{1-6}$ alkylthio groups, $C_{1-6}$ alkylsulfinyl groups, $C_{1-6}$ alkylsulfonyl groups, aminosulfonyl group, $C_{1-6}$ alkylaminosulfonyl groups, di($C_{1-6}$ alkyl)aminosulfonyl groups, aminosulfonylamino group, $C_{1-6}$ alkylaminosulfonylamino groups, di($C_{1-6}$ alkyl)aminosulfonylamino groups, aminosulfonyl($C_{1-6}$ alkyl)amino groups, $C_{1-6}$ alkylaminosulfonyl($C_{1-6}$ alkyl)amino groups and di($C_{1-6}$ alkyl) aminosulfonyl($C_{1-6}$ alkyl)amino groups.

The substituents for the heterocyclic group represented by $R^2$ are described more specifically as follows.

The heterocyclic group represented by $R^2$ may be substituted with 1 to 3 substituents selected from halogen atoms, cyano group, $C_{1-6}$ alkyl groups, hydroxy group, $C_{1-6}$ alkoxy groups, $C_{2-6}$ alkenyloxy groups, carboxy $C_{1-6}$ alkyl groups, $C_{1-6}$ alkoxycarbonyl $C_{1-6}$ alkyl groups, heterocycle-carbonyl $C_{1-6}$ alkyl groups, hydroxy $C_{1-6}$ alkyl groups, $C_{6-10}$ aromatic hydrocarbon-sulfonyl $C_{1-6}$ alkyl groups, N,N-dialkylaminosulfonyl $C_{1-6}$ alkyl groups, heterocycle-$C_{1-6}$ alkyl groups, $C_{6-10}$ aromatic hydrocarbon-$C_{1-6}$ alkyl groups, $C_{6-10}$ aromatic hydrocarbon-thio $C_{1-6}$ alkyl groups, azido-$C_{1-6}$ alkyl groups, amino $C_{1-6}$ alkyl groups, $C_{1-6}$ alkylamino $C_{1-6}$ alkyl groups, di($C_{1-6}$ alkyl)amino $C_{1-6}$ alkyl groups, hydroxy $C_{1-6}$ alkylamino $C_{1-6}$ alkyl groups, $C_{1-6}$ alkoxy $C_{1-6}$ alkylamino$C_{1-6}$ alkyl groups, di($C_{1-16}$ alkoxy$C_{1-6}$ alkyl)amino $C_{1-6}$ alkyl groups, N-hydroxy $C_{1-6}$ alkyl-N—$C_{1-6}$ alkoxy $C_{1-6}$ alkylamino $C_{1-6}$ alkyl groups, $C_{2-6}$ alkanoylamino $C_{1-6}$ alkyl groups, di($C_{2-6}$ alkanoyl)amino $C_{1-6}$ alkyl groups, carboxyamino $C_{1-6}$ alkyl groups, di($C_{1-6}$ alkylcarbonylamino $C_{1-6}$ alkyl)amino $C_{1-6}$ alkyl groups, $C_{1-6}$ alkoxycarbonylamino $C_{1-6}$ alkyl groups, di($C_{1-6}$ alkoxycarbonyl)amino $C_{1-6}$ alkyl groups, carbamoylamino $C_{1-6}$ alkyl groups, N—$C_{1-6}$ alkylcarbamoylamino $C_{1-6}$ alkyl groups, (N,N-di($C_{1-6}$ alkyl) carbamoyl)amino $C_{1-6}$ alkyl groups, aminosulfonylamino $C_{1-6}$ alkyl groups, N—$C_{1-6}$ alkylsulfonylamino $C_{1-6}$ alkyl groups, (di($C_{1-6}$ alkyl)aminosulfonyl)amino $C_{1-6}$ alkyl groups, $C_{6-10}$ aromatic hydrocarbon-sulfonylamino-$C_{2-6}$ alkanoylamino $C_{1-6}$ alkyl groups, amino $C_{1-6}$ alkylcarbonylamino $C_{1-6}$ alkyl groups, N—$C_{1-6}$ alkylamino $C_{1-6}$ alkylcarbonylamino $C_{1-6}$ alkyl groups, N,N-di($C_{1-6}$ alkyl)amino $C_{1-6}$ alkylcarbonylamino $C_{1-6}$ alkyl groups, heterocycle-$C_{1-6}$ alkylcarbonylamino $C_{1-6}$ alkyl groups, heterocycle-$C_{2-6}$ alkenylcarbonylamino $C_{1-6}$ alkyl groups, $C_{6-10}$ aromatic hydrocarbon-$C_{2-6}$ alkenylcarbonylamino $C_{1-6}$ alkyl groups, $C_{6-10}$ aromatic hydrocarboncarbonylamino $C_{1-6}$ alkyl groups, $C_{6-10}$ aromatic hydrocarbon-thiocarbonylamino $C_{1-6}$ alkyl groups, heterocycle-carbonylamino $C_{1-6}$ alkyl groups, $C_{1-6}$ alkoxyoxalylamino $C_{1-6}$ alkyl groups, N—($C_{6-10}$ aromatic hydrocarbon-sulfonyl)-N—$C_{1-6}$ alkylamino $C_{1-6}$ alkyl groups, $C_{1-6}$ alkylsulfonylamino $C_{1-6}$ alkylamino groups, carbamoyloxy $C_{1-6}$ alkyl groups, N—$C_{1-6}$ alkylcarbamoyloxy $C_{1-6}$ alkyl groups, N,N-di($C_{1-6}$ alkyl)carbamoyloxy $C_{1-6}$ alkyl groups, $C_{6-10}$ aromatic hydrocarbon-$C_{1-6}$ alkylcarbamoyloxy $C_{1-6}$ alkyl groups, $C_{1-6}$ alkoxycarbonyloxy-$C_{1-6}$ alkyl groups, $C_{6-10}$ aromatic hydrocarbon oxycarbonyloxy $C_{1-6}$ alkyl groups, heterocyclic carbonylhydrazonomethyl groups, $C_{6-10}$ aromatic hydrocarbon carbonylhydrazonomethyl groups, $C_{2-6}$ alkenyl groups, carboxy-$C_{2-6}$ alkenyl groups, $C_{1-6}$ alkoxycarbonyl-$C_{2-6}$ alkenyl groups, carbamoyl $C_{2-6}$ alkenyl groups, heterocycle-$C_{2-6}$ alkenyl groups, formyl group, carboxyl group, heterocycle-carbonyl groups, $C_{6-10}$ aromatic hydrocarbon-carbonyl groups, $C_{1-6}$ alkoxycarbonyl groups, carbamoyl group, N—$C_{1-6}$ alkylcarbamoyl groups, N,N-di ($C_{1-6}$ alkyl) carbamoyl groups, ($C_{3-7}$ cycloalkyl-$C_{1-6}$ alkyl) carbamoyl groups, $C_{1-6}$ alkylthio $C_{1-6}$ alkylcarbamoyl groups, $C_{1-6}$ alkylsulfinyl $C_{1-6}$ alkylcarbamoyl groups, $C_{1-6}$ alkylsulfonyl $C_{1-6}$ alkylcarbamoyl groups, hydroxyaminocarbonyl group, $C_{1-6}$ alkoxycarbamoyl groups, hydroxy $C_{1-6}$ alkylcarbamoyl groups, $C_{1-6}$ alkoxy $C_{1-6}$ alkylcarbamoyl groups, amino $C_{1-6}$ alkylcarbamoyl groups, amino $C_{1-6}$ alkylthiocarbamoyl groups, hydroxy $C_{1-6}$ alkylcarbamoyl groups, $C_{1-6}$ alkoxycarbonyl $C_{1-6}$ alkylcarbamoyl groups, ($C_{1-6}$ alkoxycarbonylamino)$C_{1-6}$ alkylcarbamoyl groups, ($C_{1-6}$ alkoxycarbonylamino)$C_{1-6}$ alkylthiocarbamoyl groups, heterocycle-carbamoyl groups, heterocycle-$C_{1-6}$ alkylcarbamoyl groups, $C_{6-10}$ aromatic hydrocarbon-carbamoyl groups, hydrazinocarbonyl groups, N—$C_{1-6}$ alkylhydrazinocarbonyl groups, N'—$C_{1-6}$ alkylhydrazinocarbonyl groups, N',N'-di ($C_{1-6}$ alkyl)hydrazinocarbonyl groups, N,N'-di($C_{1-6}$ alkyl) hydrazinocarbonyl groups, N,N',N'-tri($C_{1-6}$ alkyl)hydrazinocarbonyl groups, N'-(heterocycle-carbonyl)-hydrazinocarbonyl groups, amino group, $C_{1-6}$ alkoxy $C_{1-6}$ alkylamino groups, amino $C_{1-6}$ alkylamino groups, ($C_{1-6}$ alkylamino $C_{1-6}$ alkyl)amino groups, N—$C_{1-6}$ alkylamino $C_{1-6}$ alkyl-N—$C_{1-6}$ alkylamino groups, ($C_{1-6}$ alkoxycarbonylamino $C_{1-6}$ alkyl)amino groups, (di($C_{1-6}$ alkyl)amino $C_{1-6}$ alkyl)amino groups, heterocycle-amino $C_{1-6}$ alkylamino groups, carboxyl $C_{1-6}$ alkylamino groups, N-carboxyl $C_{1-6}$ alkyl-N—$C_{1-6}$ alkylamino groups, heterocycle-$C_{1-6}$ alkylamino groups, N-(heterocycle-$C_{1-6}$ alkyl)-N—$C_{1-6}$ alkylamino groups, hydroxy$C_{1-6}$ alkylamino groups, N-hydroxy $C_{1-6}$ alkyl-N—$C_{1-6}$ alkylamino groups, ($C_{1-6}$ alkylthio $C_{1-6}$ alkyl)amino groups, ($C_{1-6}$ alkylcarbamoyloxy $C_{1-6}$ alkyl) amino groups, N—$C_{1-6}$ alkylaminocarbonyloxy $C_{1-6}$ alkyl-N—$C_{1-6}$ alkylamino groups, $C_{1-6}$ alkylsulfinyl $C_{1-6}$ alkylamino groups, $C_{1-6}$ alkylsulfonyl $C_{1-6}$ alkylamino groups, groups represented by the formula: —N($R^{12}$)$SO_2R^{11}$ (wherein, $R^{11}$ represents a $C_{1-6}$ alkyl group, heterocyclic group, $C_{1-6}$ alkyl-heterocyclic group, heterocycle-$C_{1-6}$ alkyl group, hydroxy $C_{1-6}$ alkyl group, amino $C_{1-6}$ alkyl group, $C_{1-6}$ alkylamino $C_{1-6}$ alkyl group, di($C_{1-6}$ alkyl)amino $C_{1-6}$ alkyl group, carboxy $C_{1-6}$ alkyl group, carbamoyl $C_{1-6}$ alkyl group, trifluoromethyl group, difluoromethyl group, fluoromethyl group, amino group, $C_{1-6}$ alkylamino group or di($C_{1-6}$ alkyl) amino group, and $R^{12}$ represents a hydrogen atom, $C_{1-6}$ alkyl group, hydroxy group or amino group), hydroxy $C_{1-6}$ alkoxy $C_{1-6}$ alkylamino groups, $C_{6-10}$ aromatic hydrocarbon-$C_{1-6}$ alkylamino groups, heterocycle-carbonylamino groups, $C_{1-6}$ alkoxycarbonylamino groups, heterocycle-$C_{1-6}$ alkylcarbonylamino groups, $C_{6-10}$ aromatic hydrocarboncarbonylamino groups, heterocycle-amino groups, hydroxyimino group, $C_{1-6}$ alkoxyimino groups, oxo group, hydroxyimino $C_{1-6}$ alkyl groups, $C_{1-6}$ alkoxycarbonyl $C_{1-6}$ alkylamino groups, ($C_{2-6}$ alkanoylamino $C_{1-6}$ alkyl)amino groups, $C_{6-10}$ aromatic hydrocarbon groups, and heterocyclic groups (in which, the $C_{6-10}$ aromatic hydrocarbon group or heterocycle or heterocyclic group may be substituted with 1 to 3 substituents selected from halogen atoms, $C_{1-6}$ alkyl groups, $C_{1-6}$ alkoxy groups, $C_{2-6}$ alkenyl groups, formyl group, $C_{2-6}$ alkanoyl groups, carboxyl group, carboxyamino $C_{1-6}$ alkyl groups, $C_{1-6}$ alkoxycarbonylamino $C_{1-6}$ alkyl groups, oxo group, nitro group, cyano group, amidino group, $C_{2-6}$ alkenyloxy groups, hydroxy group, thioxo group, amino group, $C_{1-6}$ alkylamino groups, di($C_{1-6}$ alkyl)amino groups, amino $C_{1-6}$ alkyl groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, $C_{2-6}$ alkanoylamino groups, $C_{2-6}$ alkanoyl($C_{1-6}$ alkyl)amino groups, thio $C_{2-6}$ alkanoylamino groups, thio $C_{2-6}$ alkanoyl($C_{1-6}$ alkyl)amino groups, formylamino group, formyl($C_{1-6}$ alkyl)amino groups, thioformylamino group, thioformyl($C_{1-6}$ alkyl) amino groups, $C_{2-6}$ alkanoyloxy groups, formyloxy group, mercapto group, $C_{1-6}$ alkylthio groups, $C_{1-6}$ alkylsulfinyl groups, $C_{1-6}$ alkylsulfonyl groups, aminosulfonyl groups, $C_{1-6}$ alkylaminosulfonyl groups, di($C_{1-6}$ alkyl)aminosulfonyl groups, $C_{1-6}$ alkylsulfonylamino groups, $C_{1-6}$ alkylsulfonyl ($C_{1-6}$ alkyl)amino groups, and hydroxy $C_{1-6}$ alkyl groups).

The heterocyclic group represented by $R^2$ is preferably substituted with 1 to 3, more preferably 2 substituents selected from halogen atoms, cyano group, $C_{1-6}$ alkyl groups, hydroxy group, $C_{1-6}$ alkoxy groups, $C_{2-6}$ alkenyloxy groups, carboxy $C_{1-6}$ alkyl groups, $C_{1-6}$ alkoxycarbonyl $C_{1-6}$ alkyl groups, hydroxy $C_{1-6}$ alkyl groups, $C_{6-10}$ aromatic hydrocarbon-sulfonyl $C_{1-6}$ alkyl groups, heterocycle-$C_{1-6}$ alkyl groups, $C_{6-10}$ aromatic hydrocarbon-$C_{1-6}$ alkyl groups, $C_{6-10}$ aromatic hydrocarbon-thio $C_{1-6}$ alkyl groups, azido-$C_{1-6}$ alkyl groups, amino $C_{1-6}$ alkyl groups, di($C_{1-6}$ alkyl)amino $C_{1-6}$ alkyl groups, di($C_{1-6}$ alkoxy $C_{1-6}$ alkyl)amino $C_{1-6}$ alkyl groups, $C_{2-6}$ alkanoylamino $C_{1-6}$ alkyl groups, di($C_{2-6}$ alkanoyl)amino $C_{1-6}$ alkyl groups, $C_{1-6}$ alkoxycarbonylamino $C_{1-6}$ alkyl groups, di($C_{1-6}$ alkoxycarbonyl)amino $C_{1-6}$ alkyl groups, (N,N-di($C_{1-6}$ alkyl)carbamoyl)amino $C_{1-6}$ alkyl groups, N—$C_{1-6}$ alkylsulfonylamino $C_{1-6}$ alkyl groups, (di ($C_{1-6}$ alkyl)aminosulfonyl)amino $C_{1-6}$ alkyl groups, $C_{6-10}$ aromatic hydrocarbon-sulfonylamino-$C_{2-6}$ alkanoylamino $C_{1-6}$ alkyl groups, N,N-di($C_{1-6}$ alkyl)amino$C_{1-6}$ alkylcarbonylamino $C_{1-6}$ alkyl groups, heterocycle-$C_{1-6}$ alkylcarbonylamino $C_{1-6}$ alkyl groups, heterocycle-$C_{2-6}$ alkenylcarbonylamino $C_{1-6}$ alkyl groups, $C_{6-10}$ aromatic hydrocarbon-carbonylamino $C_{1-6}$ alkyl groups, $C_{6-10}$ aromatic hydrocarbon-thiocarbonylamino $C_{1-6}$ alkyl groups, heterocycle-carbonylamino $C_{1-6}$ alkyl groups, $C_{1-6}$ alkoxyoxalylamino $C_{1-6}$ alkyl groups, N—($C_{6-10}$ aromatic hydrocarbonsulfonyl)-N—$C_{1-6}$ alkylamino $C_{1-6}$ alkyl groups, $C_{1-6}$ alkylsulfonylamino $C_{1-6}$ alkylamino groups, N,N-di($C_{1-6}$ alkyl)carbamoyloxy $C_{1-6}$ alkyl groups, $C_{6-10}$ aromatic hydrocarbon-$C_{1-6}$ alkylcarbamoyloxy $C_{1-6}$ alkyl groups, $C_{1-6}$ alkoxycarbonyloxy-$C_{1-6}$ alkyl groups, $C_{6-10}$ aromatic hydrocarbon-oxycarbonyloxy $C_{1-6}$ alkyl groups, carboxy-$C_{2-6}$ alkenyl groups, $C_{1-6}$ alkoxycarbonyl-$C_{2-6}$ alkenyl groups, carbamoyl $C_{2-6}$ alkenyl groups, heterocycle-$C_{2-6}$ alkenyl groups, formyl group, carboxyl group, heterocycle-carbonyl groups, $C_{1-6}$ alkoxycarbonyl groups, carbamoyl group, N,N-di($C_{1-6}$ alkyl)carbamoyl groups, ($C_{3-7}$ cycloalkyl-$C_{1-6}$ alkyl)carbamoyl groups, $C_{1-6}$ alkylthio $C_{1-6}$ alkylcarbamoyl groups, $C_{1-6}$ alkylsulfinyl $C_{1-6}$ alkylcarbamoyl groups, $C_{1-6}$ alkylsulfonyl $C_{1-6}$ alkylcarbamoyl groups, $C_{1-6}$ alkoxycarbamoyl groups, amino $C_{1-6}$ alkylcarbamoyl groups, amino $C_{1-6}$ alkylthiocarbamoyl groups, hydroxy $C_{1-6}$ alkylcarbamoyl groups, $C_{1-6}$ alkoxycarbonyl $C_{1-6}$ alkylcarbamoyl groups, ($C_{1-6}$ alkoxycarbonylamino)$C_{1-6}$ alkylcarbamoyl groups, ($C_{1-6}$ alkoxycarbonylamino)$C_{1-6}$ alkylthiocarbamoyl groups, heterocyclecarbamoyl groups, heterocycle-$C_{1-6}$ alkylcarbamoyl groups, N',N'-di($C_{1-6}$ alkyl)hydrazinocarbonyl groups, N'-(heterocycle-carbonyl)-hydrazinocarbonyl groups, amino group, $C_{1-6}$ alkoxy $C_{1-6}$ alkylamino groups, amino $C_{1-6}$ alkylamino groups, $C_{1-6}$ alkylamino $C_{1-6}$ alkylamino groups, ($C_{1-6}$ alkylamino $C_{1-6}$ alkyl)($C_{1-6}$ alkyl)amino groups, $C_{1-6}$ alkoxycarbonylamino $C_{1-6}$ alkylamino groups, di($C_{1-6}$ alkyl) amino $C_{1-6}$ alkylamino groups, heterocycle-amino $C_{1-6}$ alkylamino groups, carboxyl $C_{1-6}$ alkylamino groups, (carboxyl $C_{1-6}$ alkyl)($C_{1-6}$ alkyl)amino groups, heterocycle-$C_{1-6}$ alkylamino groups (heterocycle-$C_{1-6}$ alkyl)($C_{1-6}$ alkyl)amino groups, hydroxy $C_{1-6}$ alkylamino groups, (hydroxy $C_{1-6}$ alkyl)($C_{1-6}$ alkyl)amino groups, $C_{1-6}$ alkylthio $C_{1-6}$ alkylamino groups, $C_{1-6}$ alkylaminocarbonyloxy $C_{1-6}$ alkylamino groups, ($C_{1-6}$ alkylaminocarbonyloxy $C_{1-6}$ alkyl)($C_{1-6}$ alkyl) amino groups, $C_{1-6}$ alkylsulfinyl $C_{1-6}$ alkylamino groups, $C_{1-6}$ alkylsulfonyl $C_{1-6}$ alkylamino groups, groups represented by the formula: —N($R^{12}$)$SO_2R^{11}$ (wherein, $R^{11}$ represents a $C_{1-6}$ alkyl group, heterocyclic group, $C_{1-6}$ alkyl-heterocyclic group, heterocycle-$C_{1-6}$ alkyl group, hydroxy $C_{1-6}$ alkyl group, amino $C_{1-6}$ alkyl group, $C_{1-6}$ alkylamino $C_{1-6}$ alkyl group, di($C_{1-6}$ alkyl)amino $C_{1-6}$ alkyl group, carboxy $C_{1-6}$ alkyl group, carbamoyl $C_{1-6}$ alkyl group, trifluoromethyl group, difluoromethyl group, fluoromethyl group, amino group, $C_{1-6}$ alkylamino group or di($C_{1-6}$ alkyl)amino group, and $R^{12}$ represents a hydrogen atom, $C_{1-6}$ alkyl group, hydroxy group or amino group), hydroxy $C_{1-6}$ alkoxy $C_{1-6}$ alkylamino groups, $C_{6-10}$ aromatic hydrocarbon-$C_{1-6}$ alkylamino groups, heterocycle-carbonylamino groups, $C_{1-6}$ alkoxycarbonylamino groups, heterocycle-alkylcarbonylamino groups, $C_{6-10}$ aromatic hydrocarbon-carbonylamino groups, oxo group, hydroxyimino $C_{1-6}$ alkyl groups, $C_{1-6}$ alkoxycarbonyl $C_{1-6}$ alkylamino groups, ($C_{2-6}$ alkanoylamino $C_{1-6}$ alkyl)amino groups, $C_{6-10}$ aromatic hydrocarbon groups, and heterocyclic groups (in which, the $C_{6-10}$ aromatic hydrocarbon group or heterocyclic group may be substituted with 1 to 3 substituents selected from halogen atoms, $C_{1-6}$ alkyl groups, $C_{1-6}$ alkoxy groups, $C_{2-6}$ alkanoyl groups, oxo group, nitro group, cyano group, hydroxy group, amino $C_{1-6}$ alkyl groups, $C_{1-6}$ alkoxycarbonyl groups, formylamino group, and hydroxy $C_{1-6}$ alkyl groups).

As $R^2$, more preferred is a group represented by the following formula:

[Chemical formula 2]

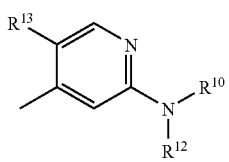

(wherein, $R^{10}$ represents a hydrogen atom, $C_{1-6}$ alkyl group, hydroxy $C_{1-6}$ alkyl group, $C_{1-6}$ alkylsulfinyl $C_{1-6}$ alkyl group, $C_{1-6}$ alkylsulfonyl $C_{1-6}$ alkyl group, carboxy $C_{1-6}$ alkyl group, heterocycle-$C_{1-6}$ alkyl group, or a group represented by the formula: —$SO_2$—$R^{11}$ (in which, $R^{11}$ represents a $C_{1-6}$ alkyl, heterocyclic, $C_{1-6}$ alkyl-heterocyclic, heterocycle-$C_{1-6}$ alkyl, hydroxy $C_{1-6}$ alkyl, amino $C_{1-6}$ alkyl, $C_{1-6}$ alkylamino $C_{1-6}$ alkyl, di($C_{1-6}$ alkyl)amino $C_{1-6}$ alkyl, carboxy $C_{1-6}$ alkyl, carbamoyl $C_{1-6}$ alkyl, trifluoromethyl, difluoromethyl, fluoromethyl, amino, $C_{1-6}$ alkylamino, or di($C_{1-6}$ alkyl)amino group), $R^{12}$ represents a hydrogen atom, $C_{1-6}$ alkyl group, hydroxy group, or amino group, or $R^{11}$ and $R^{12}$ may, taken together with a sulfur atom to which $R^{11}$ is attached and a nitrogen atom to which $R^{12}$ is attached, form a 5- or 6-membered aliphatic heterocycle, and $R^{13}$ represents a $C_{1-6}$ alkyl group, halogen atom or cyano group).

As $R^2$, a group represented by the following formula:

[Chemical formula 3]

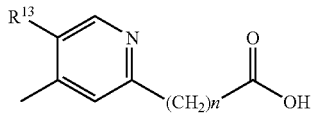

(wherein, $R^{13}$ represents a $C_{1-6}$ alkyl group, halogen atom or cyano group and n stands for an integer of from 0 to 6) is also preferred.

As $R^4$, a hydrogen atom is especially preferred. As X, —$SO_2$— and —SO— are preferred from the standpoint of its pharmacological effect, of which —$SO_2$— is especially preferred from the standpoint of its pharmacological effect.

Substituents for the aromatic hydrocarbon group or aromatic heterocyclic group represented by $R^1$ or $R^3$, and substituents for the saturated or unsaturated monocyclic heterocyclic group or unsaturated polycyclic heterocyclic group represented by $R^2$ will next be described specifically.

The term "heterocycle" means a cycle having from 1 to 4 hetero atoms (N, O, S, etc.) as a component of its cyclic structure and it may be any one of a saturated, unsaturated or aromatic cycle, or may be either one of a monocycle or polycycle. The polycyclic heterocycle embraces a heterocyclic spiro compound and a heterocyclic compound having a crosslinked cyclic structure. The term "heterocycle" in the description of "heterocycle-$C_{1-6}$ alkyl group" and the like means a heterocyclic group introduced from the above-described heterocycle. The term "heterocyclic group" means a monovalent group introduced from "heterocycle".

Examples of the saturated monocyclic heterocyclic group include 3- to 7-membered ones having 1 to 4 atoms selected from nitrogen, oxygen and sulfur atoms. Specific examples include pyrrolidinyl, tetrahydrofuranyl, oxetanyl, tetrahydrothienyl, piperidinyl, piperazinyl, homopiperazinyl, morpholinyl, thiomorpholinyl, oxiranyl, thiolanyl, dioxanyl, aziridinyl, imidazolidinyl, pyrazolidinyl, tetrahydropyranyl, tetrahydrothiopyranyl, oxazolidinyl, thiazolidinyl, isoxazolidinyl, isothiazolidinyl, dioxolanyl, oxathiolanyl, and hexahydropyrimidinyl groups.

Examples of the unsaturated or aromatic monocyclic heterocyclic group include 4- to 7-membered ones having 1 to 4 atoms selected from nitrogen, oxygen and sulfur atoms. Specific examples include pyrrolyl, furyl, thienyl, pyrazolyl, imidazolyl, triazolyl, oxazolyl, thiazolyl, isoxazolyl, isothiazolyl, triazinyl, tetrazolyl, thiadiazolyl, oxadiazolyl, pyridyl, pyrimidinyl, pyrazinyl pyridazinyl, pyrrolidinyl, imidazolidinyl, pyrazolidinyl, oxazolidinyl, thiazolidinyl, isoxazolidinyl, isothiazolidinyl, pyranyl, dihydropyridyl, tetrahydropyridyl, dihydropyridazinyl, dihydropyrimidinyl, tetrahydropyridazinyl and tetrahydropyrimidinyl.

Examples of the polycyclic heterocyclic group include 8- to 14-membered ones having 1 to 4 atoms selected from nitrogen, oxygen and sulfur atoms. Specific examples include benzofuranyl, benzothiazolyl, indolyl, quinolyl, isoquinolyl, benzopyranyl, benzoxazolyl, benzothiazolyl, benzimidazolyl, benzodioxanyl, benzothiophenyl, benzisothiazolyl, benzisoxazolyl, chromenyl, chromanyl, isochromenyl, isochromanyl, indolinyl, indazolyl, indolizinyl, isoindolyl, isoindolinyl, quinolizinyl, quinoxalinyl, quinazolinyl, cinnolinyl, phthalazinyl, naphthyridinyl, purinyl, tetrahydrothiazolopyridyl, imidazopyridyl, pyrrolopyridyl, carbazolyl, xanthenyl, acridinyl, phenazinyl, phenoxazinyl, phenothiazinyl and quinuclidinyl groups.

The term "halogen atoms" means chlorine, fluorine, bromine and iodine atoms, of which chlorine and fluorine atoms are preferred.

The term "$C_{1-6}$ alkyl group" means a linear or branched $C_{1-6}$ alkyl group. Specific examples of the alkyl group include methyl, ethyl, n-propyl, isopropyl, n-butyl, isobutyl, s-butyl, t-butyl, n-pentyl, 2-methylpentyl and n-hexyl.

The term "$C_{1-6}$ alkylene group" means a linear or branched $C_{1-6}$ alkylene group. Specific examples of the alkylene group include methylene, ethylene, propylene, trimethylene, tetramethylene, pentamethylene and hexamethylene.

The term "$C_{2-6}$ alkenyl group" means a linear or branched $C_{2-6}$ alkenyl group. Specific examples of the alkenyl group include vinyl, allyl, propenyl, butenyl and pentenyl.

The term "$C_{2-6}$ alkenylene group" means a linear or branched $C_{2-6}$ alkenylene group. Specific examples of the alkenylene group include vinylene, propenylene, butenine, and pentenylene.

Examples of the "$C_{3-7}$ cycloalkyl group" include $C_{3-7}$ cycloalkyl groups such as cyclopropyl, cyclobutyl, cyclopentyl, cyclohexyl and cycloheptyl.

Examples of the $C_{4-7}$ cycloalkenyl group include $C_{4-7}$ cycloalkenyl groups such as cyclopentenyl and cyclohexenyl.

Examples of the combination of a cycloalkyl group and an alkyl group include cycloalkyl-alkyl groups, of which $C_{3-7}$ cycloalkyl-$C_{1-6}$ alkyl groups are especially preferred.

The term "$C_{1-7}$ alkoxy group" means an alkoxy group having the above-described alkyl or cycloalkyl group. Examples include methoxy, ethoxy, propoxy, isopropoxy, butoxy, isobutoxy, pentoxy, cyclopentyloxy, cyclohexyloxy, and cycloheptyloxy.

The term "$C_{2-6}$ alkanoyl group" means a linear or branched $C_{2-6}$ alkanoyl group and examples include acetyl, propionyl, butyryl, valeryl, and hexanoyl.

As $R^1$, 2,5-difluorophenyl or 2-fluoro-5-cyanophenyl group is especially preferred. As $R^3$, 4-chlorophenyl, 4-fluorophenyl, 2,4-difluorophenyl, 3,4-difluorophenyl, 3-fluoro-4-chlorophenyl, 4-trifluoromethylphenyl, 5-chloro-2-thienyl, 5-chloro-2-pyridyl, 6-chloro-3-pyridyl and 6-trifluoromethyl-3-pyridyl groups are especially preferred.

The compounds of the present invention represented by the formula (1) may have a stereoisomer or an enantiomer derived from an asymmetric hydrocarbon. Any one of the stereoisomer and enantiomer, and mixture thereof are all embraced in the present invention. The S-oxide of the compound of the invention exists when the heterocyclic group contains a sulfur atom. Either one of a monoxide or dioxide is embraced in the S-oxide.

No particular limitation is imposed on the salt of the compound of the present invention represented by the formula (1) insofar as it is a pharmaceutically acceptable salt. Specific examples of the salt include mineral acid salts such as hydrochloride, hydrobromide, hydroiodide, phosphate, nitrate and sulfate, organic sulfonates such as methanesulfonate, 2-hydroxyethanesulfonate and p-toluenesulfonate, and organic carboxylates such as benzoate, acetate, propanoate, oxalate, malonate, succinate, glutarate, adipate, tartrate, maleate, malate and mandelate.

When the compound represented by the formula (1) has an acid group, the compound may be a salt of an alkali metal ion or alkaline earth metal ion. No particular limitation is imposed on the solvate insofar as it is pharmaceutically acceptable. Specific examples of it include hydrates and ethanol solvates.

Preparation processes of the compounds of the present invention represented by the formula (1) will next be described.

The compounds of the present invention represented by the formula (1) or salts thereof, or solvates thereof can be prepared using generally known chemical preparation processes in combination. Typical synthesis processes will next be described.

Typical preparation processes of a sulfide compound (1a), a sulfinyl compound (1b) and a sulfonyl compound (1c) according to the present invention represented by the formula (1) will hereinafter be described.

1) Preparation Process of Sulfide Compound (1a)

The sulfide compound (1a) in the present invention can be prepared by the below-described process.

[Chemical formula 4]

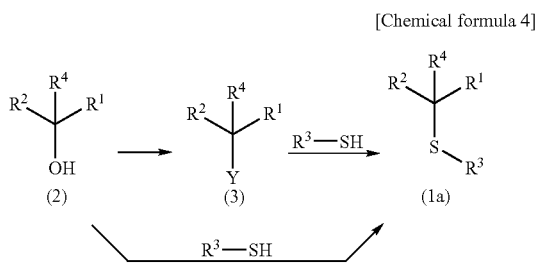

(wherein, Y represents an eliminating group and $R^1$ to $R^4$ have the same meanings as described above.)

The sulfide compound (1a) of the present invention can be prepared by transferring an alcohol derivative (2) to a compound (3), and then reacting the resulting compound (3) with a thiol compound ($R^3$—SH) in the presence of a base. In this case, the thiol compound may be used as an alkali metal or alkaline earth metal salt (for example, lithium salt, sodium salt or potassium salt).

The reaction temperature of the compound (3) and thiol compound ($R^3$—SH) is usually from −20 to 200° C., preferably from room temperature to 100° C. The reaction temperature higher than the above-described range is sometimes preferred, depending on the compound (3) or thiol compound ($R^3$—SH). The reaction in a sealed tube is sometimes preferred. The reaction time usually ranges from 0.5 hour to a day.

Examples of the base include hydrides of an alkali metal or alkaline earth metal (such as lithium hydride, sodium hydride, potassium hydride and calcium hydride); amides of an alkali metal or alkaline earth metal (such as lithium amide, sodium amide, lithium diisopropylamide, lithium dicyclohexylamide, lithium hexamethyldisilazide, sodium hexamethyldisilazide and potassium hexamethyldisilazide); lower alkoxides of an alkali metal or alkaline earth metal (such as sodium methoxide, sodium ethoxide and potassium t-butoxide); hydroxides of an alkali metal, alkaline earth metal or silver (such as silver hydroxide, sodium hydroxide, potassium hydroxide, lithium hydroxide and barium hydroxide); carbonates of an alkali metal, alkaline earth metal or silver (sodium carbonate, potassium carbonate, cesium carbonate and silver carbonate); bicarbonates of an alkali metal (such as sodium bicarbonate and potassium bicarbonate); alkyl lithiums (such as n-butyl lithium) or alkyl Grignard reagents (such as methyl magnesium bromide); inorganic bases such as silver oxide, or amines (such as triethylamine, diisopropylethylamine and N-methylmorpholine); and organic bases, for example, basic heterocyclic compounds (such as dimethylaminopyridine, pyridine, imidazole, 2,6-lutidine, collidine, 1,8-diazabicyclo[5.4.0]undec-7-en, 1,5-diazabicyclo[4.3.0]non-5-en, and 1,4-diazabicyclo[2.2.2]octane).

Examples of the solvent include alcohol solvents, ether solvents, halogen solvents, aromatic solvents, nitrile solvents, amide solvents, ketone solvents, sulfoxide solvents and water. Two of these solvents may be used as a mixture. Of these, methylene chloride, tetrahydrofuran and dimethylformamide are preferred.

The alcohol derivative (2) used in the above-described preparation step can be prepared in a known manner. Various processes are known and one example will next be described. The alcohol derivative (2) is available by adding an organometal reagent (typically, an organolithium reagent represented by $R^2$—Li, or a Grignard reagent represented by $R^2$—MgCl, $R^2$—MgBr or the like) in an amount of from equivalent to excess to an aldehyde or ketone represented by $R^1(C=O)$—$R^4$ in a solvent such as tetrahydrofuran or diethyl ether to react them. The above-described organometal reagent can be readily prepared, for example, when $R^2$ represents an aromatic hydrocarbon group or an aromatic heterocyclic group, by adding an alkyl lithium reagent or alkyl Grignard reagent to an aryl halide or a heteroaryl halide to cause metal exchange, as reported in the thesis of H. Gilman, et. al., J. Org. Chem., 16, 1788-1791(1951), or in the thesis of F. Trecourt, et al., Tetrahedron, 56, 1349-1460(2000).

The compound (3) having an eliminating group Y can be prepared by converting the hydroxyl group of the alcohol derivative (2) to an eliminating group in a known manner. Examples of the eliminating group represented by Y include halogen atoms (such as chlorine, bromine and iodine), $C_{1-6}$ alkylsulfonyloxy groups which may be halogenated (such as methanesulfonyloxy, ethanesulfonyloxy and trifluoromethanesulfonyloxy), and $C_{6-10}$ aromatic hydrocarbon sulfonyloxy groups which may have a substituent. Substituents for the aromatic hydrocarbon sulfonyloxy group include 1 to 3 halogen atoms, $C_{1-6}$ alkyl groups which may be halogenated and $C_{1-6}$ alkoxy groups. Preferred examples of the eliminating group include benzenesulfonyloxy, p-toluenesulfonyloxy, 1-naphthalenesulfonyloxy and 2-naphthalensulfonyloxy.

As an alternate synthesizing process of the sulfide compound (1a), the Mitsunobu reaction between the alcohol derivative (2) and a thiol compound ($R^3$—H) can be mentioned. Described specifically, the compound (1a) can be prepared by reacting between the alcohol derivative (2) and 1 to 3 equivalents of the thiol compound ($R^3$—SH) in a solvent in the presence of both 1 to 3 equivalents of a triarylphosphine (such as triphenylphosphine) or trialkylphosphine (such as tributylphosphine) and 1 to 2 equivalents of an azodicarboxylic acid compound (such as diethyl azodicarboxylate, diisopropyl azodicarboxylate, azodicarboxylic acid dipiperidineamide or azodicarboxylic acid bisdimethylamide).

The reaction temperature is usually from −20° C. to 150° C., preferably from 0 to 80° C. The reaction time usually ranges from 0.5 hour to 5 days. Examples of the solvent include ether solvents, halogen solvents and aromatic solvents. Two or more of these solvents may be used as a mixture. Of these, tetrahydrofuran is preferred.

2) Preparation Process of Sulfinyl Compound (1b)

The sulfinyl compound (1b) in the present invention can be prepared, as described below, by oxidizing the sulfide compound (1a) with an oxidizing agent in a solvent.

[Chemical formula 5]

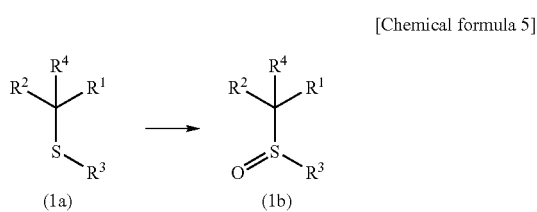

(wherein, $R^1$ to $R^4$ each has the same meaning as described above).

The reaction temperature usually ranges from −20° C. to 200° C., preferably from 0 to 100° C. The reaction time usually ranges from 0.1 hour to 7 days, preferably from 0.5 hour to 2 days. Examples of the solvent include alcohol solvents, ether solvents, halogen solvents, aromatic solvents, nitrile solvents, amide solvents, ketone solvents, sulfoxide solvents and water. Two or more of these solvents may be used as a mixture. Of these, methylene chloride, chloroform, methanol and ethanol are preferred.

Examples of the oxidizing agent include hydrogen peroxide, organic peracid compounds (such as peracetic acid and meta-chloroperbenzoic acid), metaperiodates (such as sodium metaperiodate), acyl nitrate, dinitrogen tetroxide, halogens, N-halogen compounds (such as N-chlorosuccinimide and N-bromosuccinimide), hydroperoxides (such as t-butylhydroperoxide), iodobenzene diacetate, iodobenzene dichloride, t-butyl hypochlorite, sulfuryl chloride, singlet oxygen, ozone, selenium oxide, and seleninic acid.

Specific reaction conditions are as follows. The sulfinyl compound (1b) can be prepared by treating the sulfide compound (1a) with from 1 to 2 equivalents of metachloroperbenzoic acid, sodium periodate or hydrogen peroxide in a solvent such as methylene chloride, tetrahydrofuran-water, methanol or the like at 0 to 100° C. for about 1 hour to 2 days.

An optically active sulfoxide (1b) can be prepared by using titanium tetraisopropoxide/optically pure diethyl tartrate/t-butylhydroperoxide, titanium tetraisopropoxide/optically pure diethyl tartrate/peracetic acid or the like as the oxidizing agent.

3-1) Preparation Process of Sulfonyl Compound (1c)

The sulfonyl compound (1c) in the present invention can be prepared, as described below, by oxidizing the sulfide compound (1a) or sulfinyl compound (1b) with an oxidizing agent in a solvent.

[Chemical formula 6]

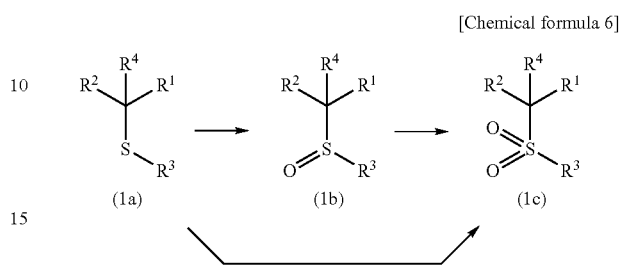

(wherein, $R^1$ to $R^4$ each has the same meaning as described above).

The reaction temperature is usually from −20° C. to 150° C., preferably from 0° C. to 100° C. and the reaction time usually ranges from 0.1 hour to 7 days, preferably from 1 hour to 5 days.

Examples of the solvent include alcohol solvents, ether solvents, halogen solvents, aromatic solvents, carboxylic acid solvents, nitrile solvents, amide solvents, ketone solvents, sulfoxide solvents and water. Two or more of them may be used as a mixture. Of these, methylene chloride, chloroform, methanol, ethanol, acetic acid, water and the like are preferred.

Examples of the oxidizing agent include hydrogen peroxide, hydrogen peroxide-transition metal catalyst (such as ammonium molybdate or iron (III) chloride), organic peracid compounds (such as peracetic acid and metachloroperbenzoic acid), metaperiodates (such as sodium metaperiodate), potassium peroxysulfate, permanganates (such as potassium permanganate), sodium perborate, halogens, N-halogen compounds (such as N-chlorosuccinimide and N-bromosuccinimide), hydroperoxides (such as t-butylhydroperoxide), iodobenzene diacetate, iodobenzene dichloride, hypochlorites (such as sodium hypochlorite or t-butyl hypochlorite), singlet oxygen, ozone, selenium oxide, and seleninic acid. The preferred example of the reaction conditions include reaction of the sulfide compound (1a) with from 2 to 5 equivalents of an oxidizing agent (such as meta-chloroperbenzoic acid, sodium periodate, hydrogen peroxide or hydrogen peroxide-ammonium molybdate) in methylene chloride, tetrahydrofuran-water or methanol at from 0 to 100° C. for from about 1 hour to 5 days.

3-2) Preparation Process of Sulfonyl Compound (1c)

The sulfonyl compound (1c) can also be prepared by the below-described process.

[Chemical formula 7]

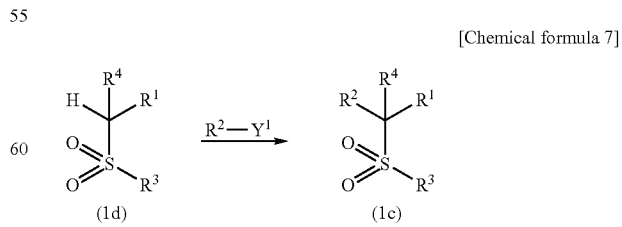

[wherein, $Y^1$ represents an eliminating group or a hydroxyl group and $R^1$ to $R^4$ each has the same meaning as described above].

The sulfonyl compounds (1c) having a variety of groups as $R^2$ can each be prepared by reacting the sulfonyl compound (1d), which can be prepared in a known method or in accordance with the known method, with an electrophilic reagent ($R^2$—$Y^1$) in the presence of a base.

Described specifically, the compound (1d) is reacted with an equivalent to excess amount of $R^2$—$Y^1$ in the presence of an equivalent to excess amount of a base. The reaction temperature usually ranges from −78° C. to 200° C. and the reaction time usually ranges from 0.5 hour to 1 day.

As the solvent, ether solvents, halogen solvents, aromatic solvents, nitrile solvents, amide solvents and the like can be used either singly or in combination. Of these, tetrahydrofuran, dimethoxyethane, diethyl ether, dimethylformamide, toluene and the like are preferred.

Examples of the eliminating group represented by $Y^1$ include halogen atoms (such as chlorine, bromine and iodine), $C_{1-6}$ alkylsulfonyloxy groups which may be halogenated (such as methanesulfonyloxy, ethanesulfonyloxy and trifluoromethanesulfonyloxy) and $C_{6-10}$ aromatic hydrocarbon sulfonyloxy groups which may have a substituent. Examples of the substituent for the aromatic hydrocarbon sulfonyloxy group include 1 to 3 halogen atoms, $C_{1-6}$ alkyl groups which may be halogenated and $C_{1-6}$ alkoxy groups. Specific of the $C_{6-10}$ aromatic hydrocarbon sulfonyloxy groups which may have a substituent include benzenesulfonyloxy, p-toluenesulfonyloxy, 1-naphthalenesulfonyloxy and 2-naphthalensulfonyloxy.

Examples of the base include alkyl lithiums (such as n-butyl lithium, s-butyl lithium and t-butyl lithium), hydrides of an alkali metal or alkaline earth metal (such as lithium hydride, sodium hydride, potassium hydride and calcium hydride), amides of an alkali metal or alkaline earth metal (such as lithium amide, sodium amide, lithium diisopropylamide, lithium dicyclohexylamide, lithium hexamethyldisilazide, sodium hexamethyldisilazide and potassium hexamethyldisilazide), lower alkoxides of an alkali metal or alkaline earth metal (such as sodium methoxide, sodium ethoxide and potassium t-butoxide), hydroxides of an alkali metal, alkaline earth metal or silver (such as silver hydroxide, sodium hydroxide, potassium hydroxide, lithium hydroxide and barium hydroxide), carbonates of an alkali metal, alkaline earth metal or silver (sodium carbonate, potassium carbonate, cesium carbonate and silver carbonate), bicarbonates of an alkali metal (such as sodium bicarbonate and potassium bicarbonate), and silver oxide.

3-3) Preparation Process of Sulfonyl Compound (1c)

The sulfonyl compound (1c) in the present invention can be also be prepared, as described below, by reacting the compound (3) with an alkali metal, alkaline earth metal or tetrabutylammonium salt of a sulfinic acid represented by $R^3$—$SO_2^-M^+$ (5).

[Chemical formula 8]

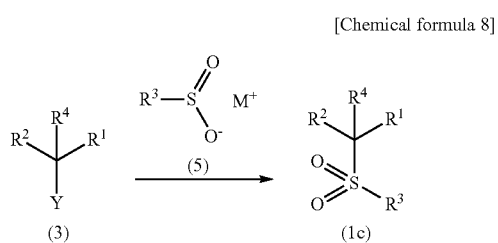

(wherein, Y represents an eliminating group, $M^+$ represents a metal ion, and $R^1$ to $R^4$ each has the same meaning as described above).

Described specifically, the compound (3) is reacted with an equivalent to excess amount of sulfinic acid or salt thereof (5) in a solvent. The reaction temperature usually ranges from −20° C. to 200° C., preferably from room temperature to 100° C. A reaction temperature higher than the above-described range is sometimes preferred, depending on the kind of the compound (3) or sulfinate (5). The reaction in a sealed tube is sometimes preferred. The reaction time usually ranges from 0.5 hour to 3 days, preferably from 0.5 hour to 1 day.

Examples of the solvent include alcohol solvents, ether solvents, halogen solvents, aromatic solvents, nitrile solvents, amide solvents, ketone solvents, sulfoxide solvents and water. These solvents may be used as a mixture. Of these, butanol, dimethoxyethane, N-methylpyrrolidone, dimethylformamide and the like are preferred.

In the above-described preparation processes of the compound (1) according to the present invention, a substituent such as nitrogen atom, hydroxyl group or carboxyl group sometimes needs protection and in this case, a generally known protecting group which can be removed as needed can be employed. The protecting group can be eliminated by the general organic chemical method if necessary.

One or more substituents in $R^1$ to $R^4$ of the sulfide compound (1a), sulfinyl compound (1b) and sulfonyl compound (1c) prepared in any one of the above-described processes can be subjected to further structure conversion. For example, when the compound has, in any one of $R^1$ to $R^4$, a substituent substituted with a 1,3-dioxolan-2-yl group, it can be converted into a compound substituted with a formyl group by the hydrolysis in a known manner. When the compound has, in any one of $R^1$ to $R^4$, a substituent substituted with a bromo group, it can be converted into a compound substituted with a formyl group in a known manner. The formyl group can be converted into, in a known manner, a carboxylic acid, substituted or unsubstituted aminomethyl group, hydroxymethyl group, 2-(alkoxycarbonyl)ethenyl group or the like. Moreover, the hydroxyl group portion of the hydroxymethyl group can be converted into ester, carbonate, carbamate, halogen, nitrile, sulfonate or the like group in a known manner. Furthermore, these groups can be converted into an alkoxy, amine, amide, carboxylic acid, sulfide or the like group. The 2-(alkoxycarbonyl)ethenyl group can be converted into a 2-carboxyethyl group or the like in a known manner. Not only the above-described groups but also various functional groups besides a hydroxyl group can be subjected to such conversion. Conversion can be carried out based on the known technique. Described specifically, when $R^2$ represents a 2-chloro-4-pyridyl group, by reacting the compound with an amine such as alkylamine, dialkylamine, benzylamine, pyrrolidine, piperidine or morpholine, a pyridine derivative having the chloro group at the 2-position substituted with the above-described amine can be prepared. In this case, use of 3,4-dimethoxybenzylamine yields a 3,4-dimethoxybenzylaminopyridine, and treatment of the resulting compound with trifluoroacetic acid or cerium diammonium nitrate yields a 2-aminopyridine derivative. Moreover, treatment of the 2-aminopyridine derivative with methanesulfonyl chloride in the presence of pyridine converts it into a 2-methanesulfonylaminopyridine derivative. In these conversion steps, reagents, solvents and reaction conditions known to those skilled in the art may be used.

The compounds (1) of the present invention prepared by the above-described process can be introduced into their salts or solvates by the ordinary process.

The compounds (1) of the present invention strongly inhibit production or secretion of β-amyloid protein so that they are useful as a medicament for preventing or treating diseases resulting from abnormal production or secretion of β-amyloid protein such as Alzheimer disease and Down syndrome or the other diseases associated with amyloid deposition.

When the compound of the present invention is used as a medicament for human, the adult daily dose ranges from 1 mg to 1 g, preferably from 10 mg to 300 mg. When it is administered to animals, the dose varies, depending on the purpose of administration (treatment or prevention), kind or size of the animal to be treated, the kind or degree of bacteria with which the animal has been infected, but daily dose usually ranges from 0.1 mg to 200 mg, preferably from 0.5 mg to 100 mg per kg of the weight of the animal. The daily dose is administered once a day or from two to four portions a day. The daily dose may exceed the above-described amount, if necessary.

The pharmaceutical composition containing the compound of the present invention can be formulated into a desired form selected in accordance with the administration route by using various ordinarily employed preparation processes. Examples of the form of the pharmaceutical composition having the compound of the present invention as a main ingredient include oral administrable preparations such as tablets, powders, granules, capsules, liquids, syrups, elixirs, oily or aqueous suspensions.

Injections may contain therein a stabilizer, antiseptic, solubilizing agent or the like. It is also possible to reconstitute a solid preparation, which has been obtained by filling a vessel with a solution which may contain such an agent and then lyophilizing it, upon use. An amount to be administered once may be filled in one vessel or an amount to be administered plural times may be filled in one vessel.

Examples of the preparation for external use include liquids, suspensions, emulsions, ointments, gels, creams, lotions, sprays and plasters.

The solid preparation contains, together with the compound of the present invention, pharmaceutically acceptable additives. It can be prepared by mixing the compound of the present invention with additives selected from fillers, extenders, binders, disintegrants, solubilizing promoters, humectants and lubricants as needed.

Examples of the liquid preparations include solutions, suspensions and emulsions. They may contain a suspending agent or emulsifier as an additive.

EXAMPLES

The present invention will hereinafter be described more specifically by examples. It should however be borne in mind that the scope of the present invention is not limited to the below-described examples. All the compounds obtained by the below-described examples belong to either one of E type or Z type unless specifically indicated.

Referential Example 1

2-[(4-Chlorophenyl)sulfonylmethyl]-1,4-difluorobenzene

[Chemical formula 9]

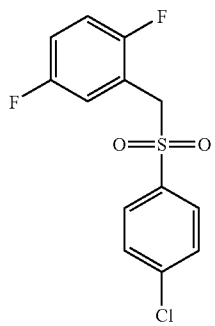

Process 1:

1) At 0° C., 4-chlorobenzenethiol (5.45 g, 38.2 mmol), triphenylphosphine (11.1 g, 41.6 mmol) and diisopropyl azodicarboxylate (8.16 ml, 41.6 mmol) were sequentially added to a tetrahydrofuran (150 ml) solution of 2,5-difluorobenzyl alcohol (5.00 g, 34.7 mmol). The reaction mixture was stirred at room temperature for 4 days, followed by concentration. The residue thus obtained was purified by silica gel column chromatography (1% ethyl acetate-hexane) to give 2-[(4-chlorophenyl)thiomethyl]-1,4-difluorobenzene (2.68 g, 29%) as a colorless oil.

$^1$H-NMR (400 MHz, CDCl$_3$) δ: 4.04 (2H, s), 6.85-7.00 (3H, m), 7.23 (4H, s).

2) After addition of 3-chloroperbenzoic acid (225 mg, 1.30 mmol) to a methylene chloride (5 ml) solution of 2-[(4-chlorophenyl)thiomethyl]-1,4-difluorobenzene (271 mg, 1.00 mmol) at 0° C., the resulting mixture was stirred at room temperature for 15 hours. The reaction mixture was diluted with methylene chloride, washed with a saturated aqueous solution of potassium bicarbonate and brine, dried (over MgSO$_4$), and concentrated. The residue thus obtained was dissolved in methylene chloride (5 ml). After cooling to 0° C., 3-chloroperbenzoic acid (450 mg, 2.60 mmol) was added and the resulting mixture was stirred at room temperature for 15 hours. The reaction mixture was diluted with methylene chloride. The diluted solution was washed with a saturated aqueous solution of potassium bicarbonate and brine, dried (over MgSO$_4$), and concentrated. The residue thus obtained was purified by silica gel column chromatography (9%-ethyl acetate-hexane) to give the title compound (210 mg, 69%) as a colorless solid substance.

$^1$H-NMR (400 MHz, CDCl$_3$) δ: 4.36 (2H, s), 6.91 (1H, td, J=9.0, 4.4 Hz), 6.99-7.06 (1H, m), 7.11 (1H, ddd, J=8.3, 5.6, 3.2 Hz), 7.45 (2H, d, J=8.8 Hz), 7.62 (2H, d, J=8.8 Hz).

MS (m/z): 303 (M$^+$+H)

Process 2:

1) After addition of potassium carbonate (4.00 g, 29.0 mmol) and 2-bromomethyl-1,4-difluorobenzene (5.00 g, 24.2 mmol) to an N,N-dimethylformamide (120 ml) solution of 4-chlorobenzenethiol (3.86 g, 26.6 mmol), the resulting mixture was stirred at room temperature for 3 hours. To the reaction mixture were added saturated ammonium chloride (50 ml) and water (20 ml), followed by extraction with diethyl ether. The extracts were combined, washed with water and brine, dried (over MgSO$_4$), and concentrated. The residue thus obtained was purified by silica gel column chromatography (1% ethyl acetate-hexane) to give 2-[(4-chlorophenyl)thiomethyl]-1,4-difluorobenzene (6.41 g, 98%) as a colorless oil.

2) At 0° C., H$_2$O (16.4 ml), 30% H$_2$O$_2$ (16.4 ml, 145 mmol) and hexaammonium heptamolybdate tetrahydrate (425 mg, 0.344 mmol) were added to a methanol (100 ml) solution of 2-[(4-chlorophenyl)thiomethyl]-1,4-difluorobenzene (6.54 g, 24.1 mmol). The resulting mixture was stirred for 1 hour, followed by stirring at room temperature for 15 hours. The solid thus precipitated was collected by filtration and the filtrate was concentrated to about half of its amount. The resulting aqueous solution was extracted with methylene chloride. The solid obtained previously was dissolved in the extract. The resulting solution was washed sequentially with water and brine, dried (over MgSO$_4$) and concentration. The residue thus obtained was recrystallized from hexane to give the title compound (6.34 g, 87%) as colorless needle crystals.

Process 3: To a butanol (200 ml) suspension of sodium 4-chlorobenzenesulfinate (19.0 g, 95.5 mmol) was added 2-bromomethyl-1,4-difluorobenzene (12.3 ml, 95.5 mmol). The resulting mixture was heated under reflux for 5 hours. The solid thus precipitated was collected by filtration, and dissolved in methylene chloride. The resulting solution was washed with brine, dried (over MgSO$_4$). After concentration, the solid thus obtained was recrystallized from hexane to give the title compound (12.3 g, 43%) as colorless needle crystals.

Referential Example 2

4-(4-Chlorophenylsulfonylmethyl)pyridine

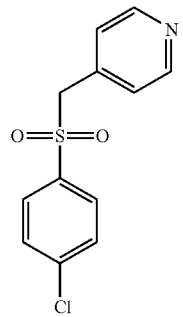

[Chemical formula 10]

A 1-propanol (50 ml) solution of 4-chloromethylpyridine hydrochloride (1.26 g, 7.65 mmol), sodium 4-chlorobenzenesulfinate (1.52 g, 7.65 mmol) and potassium acetate (1.50 g, 15.3 mmol) was stirred under heating at 70° C. for 8 hours. The reaction mixture was cooled to room temperature and then concentrated under reduced pressure. The residue thus obtained was caused to pass through a short column (silica gel, ethyl acetate) and the eluate was concentrated under reduced pressure. The residue thus obtained was subjected to silica gel column chromatography, and the fraction obtained from the hexane:ethyl acetate (=2:3) eluate was concentrated under reduced pressure to give the title compound (1.26 g, 62%) as a white solid.

$^1$H-NMR (400 MHz, CDCl$_3$) δ: 4.29 (2H, s), 7.06 (2H, d, J=6.1 Hz), 7.47 (2H, d, J=8.8 Hz), 7.59 (2H, d, J=8.5 Hz), 8.57 (2H, d, J=6.1 Hz).

MS (m/z): 268 (M$^+$+H)

Referential Example 3

2-[(2,5-Difluorophenyl)-hydroxymethyl]pyridine

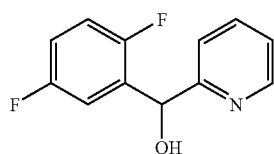

[Chemical formula 11]

A hexane solution (1.53M, 3.92 ml, 0.6 mmol) of n-butyl lithium was added dropwise to a tetrahydrofuran (10 ml) solution of 2-bromopyridine (572 μl, 6 mmol) under an argon atmosphere at −78° C., followed by stirring for 30 minutes. To the resulting brown solution was added dropwise 2,5-difluorobenzaldehyde (655 μl, 6 mmol) and the temperature of the reaction mixture was gradually raised to room temperature. To the reaction mixture was added water. The resulting mixture was then extracted with ethyl acetate. After the solvent was dried, the residue obtained by concentration under reduced pressure was purified by purification by silica gel chromatography to give the title compound (120 mg, 9%) as a white solid.

$^1$H-NMR (400 MHz, CDCl$_3$) δ: 5.45 (1H, br), 6.08 (1H, s), 6.87-7.15 (3H, m), 7.2-7.3 (2H, m), 7.65 (1H, m), 8.56 (1H, m).

mp: 65 to 66° C.

Referential Example 4

2-[Chloro-(2,5-difluorophenyl)methyl]-3-methylpyridine hydrochloride

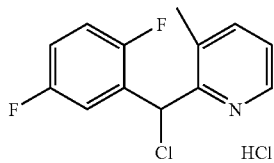

[Chemical formula 12]

Under an argon atmosphere, a tetrahydrofuran solution (1.5 ml, 3 mmol) of isopropylmagnesium chloride was added dropwise to a tetrahydrofuran (2.0 ml) solution of 2-bromo-3-methylpyridine (510 mg, 3 mmol) under ice cooling. The resulting mixture was stirred at room temperature for 60 minutes. To the resulting brown solution, 2,5-difluorobenzaldehyde (328 μl, 3 mmol) was added dropwise under ice cooling. The temperature of the reaction mixture was then raised to room temperature gradually. After addition of a saturated aqueous solution of ammonium chloride, the resulting mixture was extracted with ethyl acetate. After the solvent was dried, the residue obtained by concentration under reduced pressure was purified by silica gel chromatography (hexane:ethyl acetate=8:1) to give a mixture containing the title compound. Thionyl chloride (2.0 ml) and one drop of dimethylformamide were added to the mixture. The resulting mixture was stirred at room temperature for 14 hours. Excess thionyl chloride was distilled off under reduced pressure to yield a white precipitate. The resulting precipitate was triturated with hexane and diethyl ether to give the title compound (101 mg, 12%).

$^1$H-NMR (400 MHz, CDCl$_3$) δ: 2.37 (3H, s), 6.95-7.10 (2H, m), 7.28 (1H, s), 7.7-7.8 (2H, m), 8.11 (1H, d, J=6.3 Hz), 8.72 (1H, d, J=4.9 Hz).

mp: 118 to 119° C.

MSm/z: 254 (M$^+$+H).

Referential Example 5

2-[(2,5-Difluorophenyl)-hydroxymethyl]-5-methylpyridine

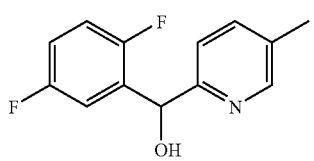

[Chemical formula 13]

Under an argon atmosphere, a tetrahydrofuran solution (1.5 ml, 3 mmol) of isopropylmagnesium chloride was added dropwise to tetrahydrofuran (2 ml) solution of 2-bromo-5-methylpyridine (510 mg, 3 mmol) under ice cooling. The resulting mixture was stirred at room temperature for 60 minutes. To the resulting brown solution was added dropwise 2,5-difluorobenzaldehyde (328 μl, 3 mmol) under ice cooling and then, the temperature of the reaction mixture was raised to room temperature gradually. A saturated aqueous solution of ammonium chloride was added to the reaction mixture and then, the mixture was extracted with ethyl acetate. After drying the solvent, the residue obtained by concentration under reduced pressure was purified by silica gel chromatography (hexane:ethyl acetate=5:1) to give the title compound (130 mg, 18%) as an oil.

$^1$H-NMR (400 MHz, CDCl$_3$) δ: 2.31 (3H, s), 5.38 (1H, br), 6.04 (1H, s), 6.83-7.18 (4H, m), 7.44 (1H, dd, J=2.0, 8.0 Hz), 8.37 (1H, m).

MSm/z: 236 (M$^+$+H).

Referential Example 6

2-[(2,5-Difluorophenyl)-hydroxymethyl]-4-methylpyridine

[Chemical formula 14]

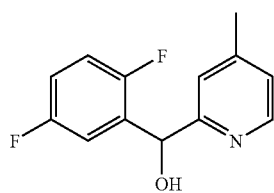

Under an argon atmosphere, a tetrahydrofuran solution (1.5 ml, 3 mmol) of isopropylmagnesium chloride was added dropwise to a tetrahydrofuran (2 ml) solution of 2-bromo-4-methylpyridine (334 μl, 3 mmol) under ice cooling. The resulting mixture was stirred at room temperature for 60 minutes. To the resulting brown solution was added dropwise 2,5-difluorobenzaldehyde (328 μl, 3 mmol) under ice cooling. The temperature of the resulting mixture was gradually raised to room temperature. After addition of a saturated aqueous solution of ammonium chloride, the resulting mixture was extracted with ethyl acetate. The solvent was then dried. The residue obtained by concentration under reduced pressure was purified by silica gel chromatography (hexane:ethyl acetate=5:1) to give the title compound (456 mg, 65%) as needle crystals.

$^1$H-NMR (400 MHz, CDCl$_3$) δ: 2.30 (3H, s), 5.48 (1H, br-s), 6.02 (1H, s), 6.83-7.13 (5H, m), 8.38 (1H, m).

mp: 105 to 106° C.

MSm/z: 236 (M$^+$+H).

Referential Example 7

2-Bromo-3-methoxypyridine

[Chemical formula 15]

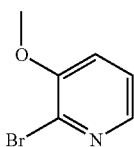

Under a nitrogen atmosphere, sodium hydride 60% in oil (605 mg, 15.1 mmol) was added in portions to methanol (10 ml) under ice cooling. Twenty minutes later, a dimethylformamide (20 ml) solution of 2-bromo-3-hydroxypyridine (2.5 g, 14.4 mmol) was added. From the resulting mixture, methanol was distilled off under reduced pressure. To the residue was added methyl iodide (0.94 ml, 15.1 mmol), followed by stirring at room temperature for 3 hours. After the reaction mixture was concentrated to dryness, water (50 ml) and ether (50 ml) were added to the concentrate. The organic layer was separated and washed with a saturated aqueous solution of sodium bicarbonate and brine. The extract was dried over anhydrous magnesium sulfate, and concentrated under reduced pressure to remove the solvent. The residue was purified by silica gel chromatography (hexane:ethyl acetate=8:1) to give the title compound (1.51 g, 56%) as colorless needle crystals.

$^1$H-NMR (400 MHz, CDCl$_3$) δ: 3.90 (3H, s), 7.12 (1H, m), 7.21 (1H, dd, J=4.8, 8.0 Hz), 7.97 (1H, m).

mp: 34° C.

Referential Example 8

3-Allyloxy-2-bromopyridine

[Chemical formula 16]

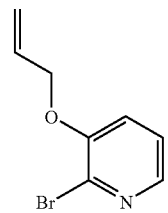

Synthesis was performed in a similar manner to that employed for the synthesis of 2-bromo-3-methoxypyridine to give the title compound (2.35 g, 76%) as an oil.

$^1$H-NMR (400 MHz, CDCl$_3$) δ: 4.62 (2H, m), 5.33 (1H, dd, J=1.2, 10.4 Hz), 5.47 (1H, dd, J=1.2, 17.6 Hz), 6.06 (1H, m), 7.11 (1H, dd, J=1.2 Hz, 8.0 Hz), 7.18 (1H, dd, J=4.8, 8.0 Hz), 7.98 (1H, m).

MSm/z: 215 (M$^+$+H).

Referential Example 9

2-[(2,5-Difluorophenyl)-hydroxymethyl]-3-methoxypyridine

[Chemical formula 17]

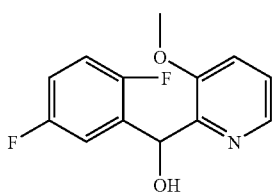

Under an argon atmosphere, a tetrahydrofuran solution (1.5 ml, 3 mmol) of isopropylmagnesium chloride was added dropwise to a tetrahydrofuran (2 ml) solution of 2-bromo-3-methoxypyridine (564 mg, 3 mmol) under ice cooling. The reaction mixture was then stirred at room temperature for 60 minutes. To the resulting brown solution, 2,5-difluorobenzaldehyde (328 μl, 3 mmol) was added dropwise under ice cooling. The temperature of the reaction mixture was gradually raised to room temperature. After addition of a saturated aqueous solution of ammonium chloride, the resulting mixture was extracted with ethyl acetate. After the solvent was dried, needle crystals obtained by concentration under reduced pressure were triturated with hexane to give the title compound (660 mg, 88%).

$^1$H-NMR (400 MHz, CDCl$_3$) δ: 3.71 (3H, s), 5.56 (1H, br, J=6.0 Hz), 6.16 (1H, d, J=6.0 Hz), 6.75-7.00 (3H, m), 7.14 (1H, m), 7.26 (1H, m), 8.18 (1H, m).

mp: 94 to 95° C.

MSm/z: 252 (M$^+$+H).

Referential Example 10

3-Allyloxy-2-[(2,5-difluorophenyl)-hydroxymethyl]pyridine

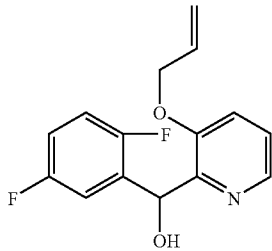

[Chemical formula 18]

Under an argon atmosphere, a tetrahydrofuran solution (1.5 ml, 3 mmol) of isopropylmagnesium chloride was added dropwise to a tetrahydrofuran (2 ml) solution of the 3-allyloxy-2-bromopyridine (642 mg, 3 mmol) obtained in Referential Example 8 under ice cooling. The resulting mixture was stirred at room temperature for 60 minutes. To the resulting brown solution was added dropwise 2,5-difluorobenzaldehyde (328 μl, 3 mmol) under ice cooling. The temperature of the reaction mixture was gradually raised to room temperature. A saturated aqueous solution of ammonium chloride was added to the reaction mixture, followed by extraction with ethyl acetate. The solvent was then dried and the residue obtained by concentration under reduced pressure was purified by silica gel chromatography (hexane:ethyl acetate=4:1) to give the title compound (375 mg, 45%) as an oil.

$^1$H-NMR (400 MHz, CDCl$_3$) δ: 4.38 (1H, m), 4.44 (1H, m), 5.16 (1H, m), 5.18 (1H, m), 5.61 (1H, br, J=6.4 Hz), 5.78 (1H, m), 6.17 (1H, d, J=6.0 Hz), 6.73-6.96 (3H, m), 7.10 (1H, m), 7.22 (1H, m), 8.19 (1H, m).

MSm/z: 278 (M$^+$+H).

Referential Example 11

3-[(2,5-Difluorophenyl)-hydroxymethyl]pyridine

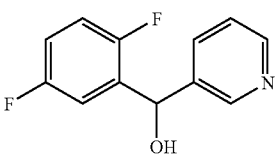

[Chemical formula 19]

Under an argon atmosphere, a tetrahydrofuran solution (1.5 ml, 3 mmol) of isopropylmagnesium chloride was added dropwise to a tetrahydrofuran (2 ml) solution of 3-bromopyridine (286 μl, 3 mmol) under ice cooling. The resulting mixture was stirred at room temperature for 60 minutes. To the resulting brown solution thus obtained was added dropwise 2,5-difluorobenzaldehyde (328 μl, 3 mmol) under ice cooling. The temperature of the reaction mixture was gradually raised to room temperature. A saturated aqueous solution of ammonium chloride was added to the reaction mixture, followed by extraction with ethyl acetate. The solvent was then dried. The residue remaining after concentration under reduced pressure was purified by silica gel chromatography (hexane:ethyl acetate=1:1) to give the title compound (296 mg, 45%) as needle crystals.

$^1$H-NMR (400 MHz, CDCl$_3$) δ: 3.76 (1H, br), 6.10 (1H, s), 6.88-6.98 (2H, m), 7.20-7.30 (2H, m), 7.70 (1H, m), 8.42 (1H, d, J=4.8 Hz), 8.53 (1H, m).

mp: 79 to 80° C.

Referential Example 12

5-[(2,5-Difluorophenyl)-hydroxymethyl]pyrimidine

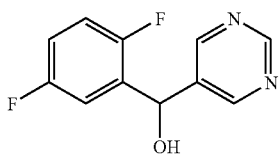

[Chemical formula 20]

In a similar manner to Referential Example 11, the title compound (117 mg, 18%) as an oil by using 5-bromopyrimidine.

$^1$H-NMR (400 MHz, CDCl$_3$) δ: 6.12 (1H, s), 6.90-7.02 (2H, m), 7.26 (1H, m), 8.70 (2H, s), 9.04 (1H, s).

MSm/z: 205 (M$^+$-OH).

Referential Example 13

2-[(t-Butoxycarbonyloxy)-(2,5-difluorophenyl)methyl]-1-methyl-1H-benzimidazole

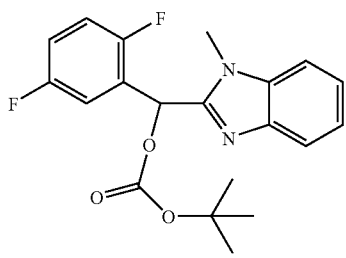

[Chemical formula 21]

An acetonitrile (3 ml) solution of 2,5-difluorobenzaldehyde (164 μl, 1.5 mmol), 1-methylbenzimidazole (132 mg, 1 mmol) and di-t-butyl dicarbonate (252 μl, 1.1 mmol) was stirred at room temperature for 20 hours. The precipitate thus formed was collected by filtration and then triturated with hexane to give the title compound (310 mg, 83%) as a white solid.

$^1$H-NMR (400 MHz, CDCl$_3$) δ: 1.45 (9H, s), 3.86 (3H, s), 6.9-7.0 (2H, m), 7.12 (1H, s), 7.22-7.35 (3H, m), 7.45 (1H, m), 7.77 (1H, d, J=8.0 Hz).

Referential Example 14

2-[(t-Butoxycarbonyloxy)-(2,5-difluorophenyl)methyl]-1-methyl-5-chloro-1H-imidazole

[Chemical formula 22]

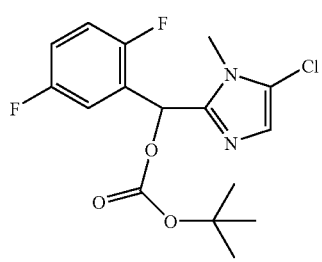

An acetonitrile (6 ml) solution of 2,5-difluorobenzaldehyde (327 µl, 3 mmol), 5-chloro-1-methylimidazole (187 µg, 2 mmol) and di-t-butyl dicarbonate (504 µl, 2.2 mmol) was stirred at room temperature for 20 hours. The precipitate thus formed was collected by filtration, followed by trituration with hexane to give the title compound (472 mg, 66%) as a white solid.

$^1$H-NMR (400 MHz, CDCl$_3$) δ: 1.48 (9H, s), 3.67 (3H, s), 6.88-7.1 (4H, m), 7.39 (1H, m).

mp: 125 to 126° C.

MSm/z: 359 (M$^+$+H).

Referential Example 15

2-[(2,5-Difluorophenyl)-hydroxymethyl]thiazole

[Chemical formula 23]

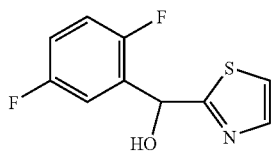

To a tetrahydrofuran (10 ml) solution of 2-bromothiazole (180 µg, 2 mmol) was added dropwise a hexane solution (1.57M, 1.40 ml, 2.2 mmol) of n-butyl lithium at −78° C., followed by stirring for 10 minutes. Then, 2,5-difluorobenzaldehyde (238 µl, 2.2 mmol) was added and the temperature of the resulting mixture was raised gradually to 0° C. under stirring. An aqueous solution of ammonium chloride was added to terminate the reaction and ether was added to the reaction mixture. The ether layer was washed with water and brine, and then dried over anhydrous magnesium sulfate. After filtration, the solution was concentrated under reduced pressure. The residue was purified by silica gel chromatography (hexane:ethyl acetate=1:1) to give the title compound (358 mg, 79%) as an oil.

$^1$H-NMR (400 MHz, CDCl$_3$) δ: 3.77 (1H, d, J=4.0 Hz), 6.33 (1H, d, J=4.0 Hz), 6.95-7.10 (2H, m), 7.24 (1H, m), 7.34 (1H, d, J=3.6 Hz), 7.75 (1H, d, J=3.6 Hz),

MSm/z: 228 (M$^+$+H).

Referential Example 16

2-[(t-Butoxycarbonyloxy)-(2,5-difluorophenyl)methyl]-1-(4-methoxyphenyl)-1H-imidazole

[Chemical formula 24]

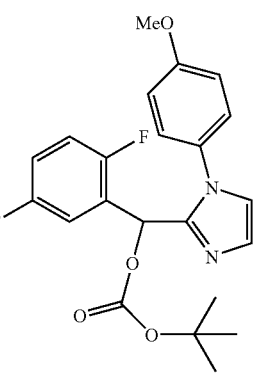

An acetonitrile (6 ml) solution of 2,5-difluorobenzaldehyde (327 µl, 3 mmol), 1-(4-methoxyphenyl)imidazole (348 mg, 2 mmol) and di-t-butyl dicarbonate (504 µl, 2.2 mmol) was stirred at room temperature for 20 hours. The reaction mixture was concentrated and then the residue was purified by silica gel chromatography (hexane:ethyl acetate=5:1 to 1:1) to give the title compound (774 mg, 93%) as an oil.

$^1$H-NMR (400 MHz, CDCl$_3$) δ: 1.40 (9H, s), 3.86 (3H, s), 6.76 (1H, s), 6.90-7.00 (4H, m), 7.02 (1H, s), 7.11 (1H, s), 7.26 (2H, m), 7.33 (1H, m).

MSm/z: 417 (M$^+$+H).

Referential Example 17

5-Chloro-2-pyridinethiol

[Chemical formula 25]

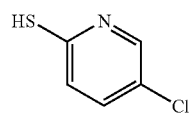

Thiourea (152 mg, 2.00 mmol) was added to an ethanol (4 ml) solution of 2,5-dichloropyridine (296 mg, 2.00 mmol). The mixture was then heated under reflux for 18 hours. After the reaction mixture was cooled to room temperature, a water (1 ml) solution of potassium hydroxide (198 mg, 3.00 mmol) was added and the mixture was heated under reflux for 3 hours. The reaction mixture was cooled to room temperature. Water was then added and the mixture was washed with dichloromethane. The water layer was acidified with acetic acid, followed by extraction with dichloromethane. The organic layer was dried over anhydrous sodium sulfate and then filtered. After filtration, the filtrate was concentrated under reduced pressure. The solid thus obtained was washed with diethyl ether and collected by filtration to give the title compound (83 mg, 0.57 mmol, 29%) as a yellow powder.

$^1$H-NMR (400 MHz, CDCl$_3$) δ: 7.35 (1H, dd, J=9.3, 2.4 Hz), 7.46 (1H, d, J=9.3 Hz), 7.64 (1H, d, J=2.4 Hz).

MSm/z: 146 (M$^+$+H).

Referential Example 18

2,5-Difluorophenyl-4-pyridylmethanol

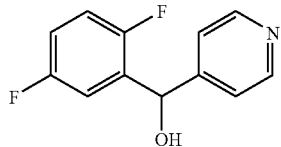

[Chemical formula 26]

A tetrahydrofuran (30 ml) solution of 1-bromo-2,5-difluorobenzene (1.08 ml, 9.60 mmol) was stirred at −78° C., followed by the addition of a hexane solution (7.32 ml, 11.5 mmol) of n-butyl lithium. To the reaction mixture was added a tetrahydrofuran (10 ml) solution of 4-pyridinecarboxyaldehyde (0.764 ml, 8.00 mmol) at −78° C. The resulting mixture was stirred at the same temperature for 30 minutes. After the temperature of the reaction mixture was raised to room temperature, diethyl ether was added thereto. The resulting mixture was washed with a saturated aqueous solution of sodium bicarbonate. The organic layer was dried over anhydrous sodium sulfate and then filtered. The filtrate was concentrated under reduced pressure. The residue thus obtained was subjected to flash silica gel chromatography. The fraction obtained from the hexane:ethyl acetate=7:3 eluate was concentrated under reduced pressure. The solid thus obtained was washed with diisopropyl ether and then collected by filtration to give the title compound (1.15 g, 5.20 mmol, 65%) as a white powder.
$^1$H-NMR (400 MHz, CDCl$_3$) δ: 4.25 (1H, brs), 6.09 (1H, s), 6.89-7.05 (2H, m), 7.14-7.23 (1H, m), 7.34 (2H, d, J=5.4 Hz), 8.44 (2H, d, J=5.4 Hz)

Referential Example 19

Tetrahydrothiopyran-4-ol

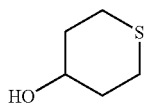

[Chemical formula 27]

Tetrahydrothiopyran-4-one (5.00 g, 43.0 mmol) was dissolved in methanol (100 ml). After sodium borohydride (1.6 g, 42.3 mmol) was added to the resulting solution under ice cooling, the resulting mixture was stirred at room temperature for 14 hours. Water (50 ml) was added to the residue obtained by concentrating the reaction mixture under reduced pressure. The liquid property of the resulting mixture was then made weakly acidic with 1N hydrochloric acid, followed by extraction with diethyl ether. The extract was washed sequentially with 1N hydrochloric acid, a saturated aqueous solution of sodium bicarbonate, and brine. The organic layer was dried over anhydrous magnesium sulfate. After filtration, the filtrate was concentrated under reduced pressure to give the title compound (4.40 g, 37.2 mmol, 87%) as a pale yellowish brown solid.
$^1$H-NMR (400 MHz, CDCl$_3$) δ: 1.47 (1H, brs), 1.64-1.80 (2H, m), 2.10-2.24 (2H, m), 2.55-2.70 (2H, m), 2.73-2.88 (2H, m), 3.60-3.75 (1H, m).
MS m/z: 119 (M$^+$+H).

Referential Example 20

5-Dibromomethyl-2-(2,5-difluorobenzoyl)pyridine (Compound A) and 5-bromomethyl-2-(2,5-difluorobenzoyl)pyridine (Compound B)

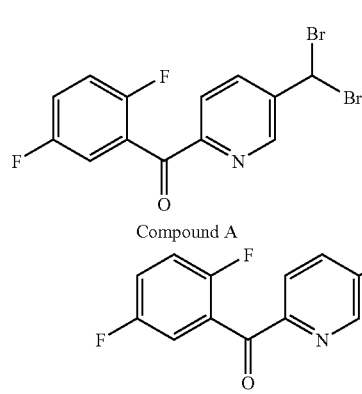

[Chemical formula 28]

Compound A

Compound B

Under heating and refluxing, N-bromosuccinimide (17.0 g, 95.7 mmol) and a catalytic amount of 2,2'-azobis(2-methylpropionitrile) were added to a carbon tetrachloride (100 ml) solution of the 2-[(2,5-difluorophenyl)-hydroxymethyl]-5-methylpyridine (7.50 g, 31.9 mmol) obtained in Referential Example 5. The resulting mixture was stirred at reflux for 24 hours. The reaction mixture was cooled to room temperature and the precipitate thus formed was filtered off. The precipitate was added to an aqueous solution of sodium thiosulfate, followed by extraction with chloroform. The extract was washed with a saturated aqueous solution of sodium bicarbonate and brine, and then dried over sodium sulfate. The residue obtained by concentrating the solution under reduced pressure was purified by silica gel chromatography (hexane:ethyl acetate=10:1) to give the title compound A (3.91 g, 31%) and the title compound B (3.34 g, 34%), each as an oil.
Compound A
$^1$H-NMR (400 MHz, CDCl$_3$) δ: 6.70 (1H, s), 7.12 (1H, m), 7.24 (1H, m), 7.39 (1H, m), 8.12 (1H, d, J=8.4 Hz), 8.19 (1H, dd, J=2.0, 8.4 Hz), 8.77 (1H, d, J=2.0 Hz).
MS m/z: 392 (M$^+$+H).
Compound B
$^1$H-NMR (400 MHz, CDCl$_3$) δ: 4.52 (2H, s), 7.12 (1H, m), 7.21 (1H, m), 7.39 (1H, m), 7.94 (1H, dd, J=2.0, 8.0 Hz), 8.08 (1H, d, J=8.0 Hz), 8.67 (1H, d, J=2.0 Hz).
MS m/z: 313 (M$^+$+H).

Referential Example 21

[6-(2,5-Difluorophenylcarbonyl)pyridin-3-yl]methyl acetate

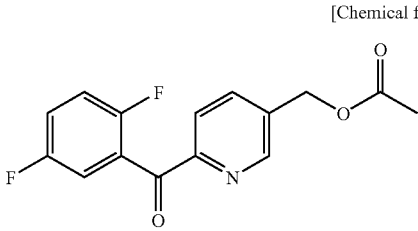

[Chemical formula 29]

Under heating and refluxing, N-bromosuccinimide (6.0 g, 33.6 mmol) and a catalytic amount of 2,2'-azobis(2-methylpropionitrile) were added to a carbon tetrachloride (60 ml) solution of the 2-[(2,5-difluorophenyl)-hydroxymethyl]-5-methylpyridine (2.64 g, 11.2 mmol) obtained in Referential Example 5. The resulting mixture was then stirred. After refluxing for 7 hours, the reaction mixture was cooled to room temperature and added to an aqueous solution of sodium thiosulfate. The resulting mixture was extracted with ether. The extract was washed with saturated water and brine, and then dried over sodium sulfate. The residue obtained by concentrating the solution under reduced pressure was dissolved in toluene. The resulting solution was concentrated again.

The residue thus obtained was dissolved in N,N-dimethylformamide (20 ml). To the resulting solution was added sodium acetate (4.59 g, 56 mmol) and the mixture was stirred at 70° C. for 17 hours. After cooling, the reaction mixture was dissolved in ethyl acetate (100 ml). The solution was washed with water and brine, dried over anhydrous magnesium sulfate and then concentrated under reduced pressure. The residue thus obtained was purified by silica gel chromatography (hexane:ethyl acetate=5:1) to yield the title compound (600 mg, 18%) as an oil.

$^1$H-NMR (400 MHz, CDCl$_3$) δ: 2.12 (3H, s), 5.19 (2H, s), 7.10 (1H, m), 7.19 (1H, m), 7.37 (1H, s), 7.88 (1H, dd, J=2.4, 8.0 Hz), 8.07 (1H, d, J=8.0 Hz), 8.62 (1H, d, J=2.4 Hz).
MSm/z: 292 (M$^+$+H).

Referential Example 22

2-[(2,5-Difluorophenyl)-hydroxymethyl]-5-(1,3-dioxolan-2-yl)pyridine

[Chemical formula 30]

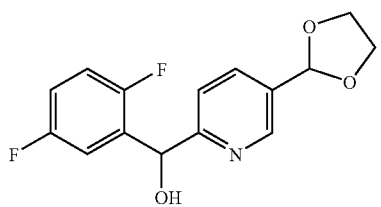

To a pyridine solution (60 ml) of the 5-dibromomethyl-2-(2,5-difluorobenzoyl)pyridine (Compound A) (3.91 g, 10 mmol) obtained in Referential Example 20 was added ethylene glycol (6.2 g, 100 mmol). While heating at 90° C., the resulting mixture was stirred for 17 hours. The reaction mixture was concentrated under reduced pressure. The residue thus obtained was dissolved in ether (200 ml). The resulting solution was washed with water, a saturated aqueous solution of sodium bicarbonate and brine, dried over anhydrous magnesium sulfate, and concentrated under reduced pressure. The residue thus obtained was dissolved in ethanol (60 ml). To the resulting solution was added sodium borohydride (190 mg, 5 mmol) under ice cooling. The resulting mixture was stirred at room temperature for 1 hour. After the addition of water, the mixture was extracted with ethyl acetate. The extract was washed with brine, dried over anhydrous magnesium sulfate, and then concentrated under reduced pressure. The residue thus obtained was purified by silica gel chromatography (hexane:ethyl acetate=5:1 to 1:1) to give the title compound (1.52 g, 52%) as an oil.

$^1$H-NMR (400 MHz, CDCl$_3$) δ: 4.0-4.2 (4H, m), 5.84 (1H, s), 6.10 (1H, s), 6.91 (1H, m), 6.99 (1H, m), 7.09 (1H, m), 7.26 (1H, d, J=8.0 Hz), 7.76 (1H, dd, J=2.0, 8.0 Hz), 8.64 (1H, d, J=2.0 Hz).
MSm/z: 294 (M$^+$+H).

Referential Example 23

3-Chloro-4-[(2,5-difluorophenyl)-hydroxymethyl]pyridine

[Chemical formula 31]

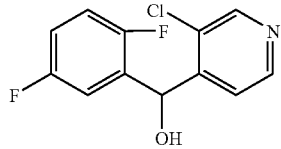

To a tetrahydrofuran solution (14 ml) of diisopropylamine (1.4 ml, 10 mmol) was added n-butyl lithium (6.3 ml, a 1.59M hexane solution) at −78° C. After the resulting mixture was stirred for 10 minutes, 3-chloropyridine (1.13 g, 10 mmol) was added thereto. Thirty minutes later, 2,5-difluorobenzaldehyde (1.09 ml, 10 mmol) was added and the temperature of the resulting mixture was raised gradually to 0° C. Stirring was conducted for further 10 minutes. After addition of an aqueous solution of ammonium chloride, the resulting mixture was diluted with ethyl acetate (80 ml). The organic layer was separated, washed with brine and then dried. After filtration, the precipitate obtained by concentrating the resulting solution under reduced pressure was triturated with ethanol to give the title compound (1.33 g, 52%).

$^1$H-NMR (400 MHz, CDCl$_3$) δ: 4.87 (1H, br), 6.26 (1H, s), 6.90-7.02 (3H, m), 7.58 (1H, d, J=4.8 Hz), 8.47 (1H, s), 8.48 (1H, d, J=4.8 Hz).
mp: 169 to 170° C.
MSm/z: 255 (M$^+$).

Referential Example 24

2,5-Dichloro-4-[(2,5-difluorophenyl)-hydroxymethyl]pyridine

[Chemical formula 32]

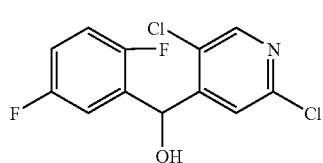

To a tetrahydrofuran solution (14 ml) of diisopropylamine (1.4 ml, 10 mmol) was added n-butyl lithium (6.3 ml, a 1.59M hexane solution) at −78° C. After stirring for 10 minutes, 2,5-dichloropyridine (1.48 g, 10 mmol) was added to the reaction mixture. Thirty minutes later, 2,5-difluorobenzaldehyde (1.09 ml, 10 mmol) was added and the temperature of the resulting mixture was raised gradually to 0° C. Stirring was conducted for further 10 minutes. After addition of an aqueous solution of ammonium chloride, the resulting mixture was diluted with ethyl acetate (80 ml). The organic layer was separated, washed with brine and then dried. After filtration, the precipitate obtained by concentrating the filtrate under reduced pressure was triturated with ethanol to give the title compound (1.93 g, 67%).

$^1$H-NMR (400 MHz, CDCl$_3$) δ: 2.64 (1H, d, J=4.0 Hz), 6.28 (1H, d, J=4.0 Hz), 6.89 (1H, m), 7.02 (2H, m), 7.64 (1H, s), 8.30 (1H, s).

mp: 160 to 161° C.

MSm/z: 289 (M$^+$).

Referential Example 25

(3,6-Dichloropyridin-2-yl)(pyridin-4-yl)methanol

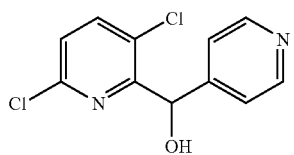

[Chemical formula 33]

Under stirring at −78° C., t-butyl lithium (a 1.51M pentane solution: 4.6 ml) was added dropwise to an ether (20 ml) solution of 2,5-dichloropyridine (1.02 g, 6.89 mmol). After stirring at −78° C. for 2 hours, pyridine-4-carbaldehyde (0.65 ml, 6.89 mmol) was added to the reaction mixture. The resulting mixture was stirred at −78° C. for 1 hour. Water was then added to the reaction mixture. The temperature of the resulting mixture was raised to room temperature. The mixture was extracted with methylene chloride. The extract was then dried over anhydrous sodium sulfate. After filtration, the filtrate was concentrated under reduced pressure. The residue thus obtained was subjected to silica gel column chromatography. The fraction obtained from the methanol:methylene chloride (=1:50) eluate was concentrated under reduced pressure. The solid thus obtained was washed with ether and then collected by filtration to give the title compound (819 mg, 3.21 mmol, 47%) as a white powder.

$^1$H-NMR (400 MHz, CDCl$_3$) δ: 4.64 (1H, brd, J=6.3 Hz), 6.00 (1H, brd, J=6.3 Hz), 7.27 (1H, d, J=8.6 Hz), 7.31 (2H, d, J=5.8 Hz), 7.67 (1H, d, J=8.6 Hz), 8.57 (2H, d, J=5.8 Hz).

MS (m/z): 254 (M$^+$).

Referential Example 26

O-ethyl S-(6-chloro-3-pyridyl)dithiocarbonate

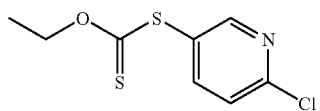

[Chemical formula 34]

5-Amino-2-chloropyridine (643 mg, 3.00 mmol) was dissolved in 1N hydrochloric acid (10 ml). A water (1 ml) solution of sodium nitrite (207 mg, 3.00 mmol) was added dropwise at −5° C. The reaction mixture was stirred at 60° C. for 30 minutes and then, at the same temperature, a water (1 ml) solution of potassium O-ethyl dithiocarbonate (481 mg, 3.00 mmol) was added dropwise. After the reaction mixture was stirred at 80° C. for 1 hour, the reaction mixture was cooled to room temperature. Ethyl acetate was added and the resulting mixture was washed with a saturated aqueous solution of sodium bicarbonate. The organic layer was dried over anhydrous sodium sulfate and then filtered. The filtrate was concentrated under reduced pressure. The residue thus obtained was subjected to flash silica gel column chromatography. The fraction obtained from the hexane:ethyl acetate=49:1 eluate was concentrated under reduced pressure to give the title compound (148 mg, 0.63 mmol, 21%) as a yellow oil.

$^1$H-NMR (400 MHz, CDCl$_3$) δ: 1.37 (3H, t, J=7.1 Hz), 4.63 (2H, t, J=7.1 Hz), 7.41 (1H, d, J=8.3 Hz), 7.76 (1H, dd, J=8.3, 2.4 Hz), 8.45 (1H, d, J=2.4 Hz).

MSm/z: 234 (M$^+$+H).

Referential Example 27

(2,6-Dichloro-5-fluoropyridin-3-yl)methanol

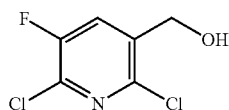

[Chemical formula 35]

Under ice cooling, ethyl chloroformate (1.32 ml, 13.8 mmol) was added to a toluene (60 ml) solution of 2,6-dichloro-5-fluoronicotinic acid (2.76 g, 13.1 mmol) and triethylamine (1.92 ml, 13.8 mmol). After stirring at room temperature for 1 hour, the reaction mixture was concentrated under reduced pressure.

The residue was dissolved in tetrahydrofuran (30 ml). The resulting solution was added dropwise, at −78° C., to a tetrahydrofuran (20 ml) suspension of lithium aluminum hydride (524 mg, 13.8 mmol). The temperature of the reaction mixture was raised to 0° C. A 1N aqueous sodium hydroxide solution (3.25 ml) was added dropwise thereto. The precipitate was filtered off through Celite and the filtrate was concentrated under reduced pressure. The residue thus obtained was subjected to flash silica gel chromatography. The fraction obtained from the hexane:ethyl acetate=9:1 eluate was concentrated under reduced pressure to give the title compound (1.93 g, 9.85 mmol, 75%) as an orange solid.

$^1$H-NMR (400 MHz, CDCl$_3$) δ: 2.18 (1H, brs), 4.77 (2H, s), 7.77 (1H, d, J=7.8 Hz).

mp: 65 to 67° C.

Referential Example 28

3-(t-Butyldiphenylsilyloxymethyl)-5-fluoropyridine

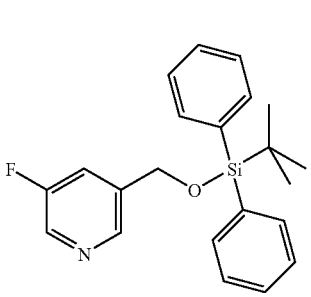

[Chemical formula 36]

To an ethanol (650 ml) solution of the (2,6-dichloro-5-fluoropyridin-3-yl)methanol (18.9 g, 96.2 mmol) obtained in Referential Example 27 and triethylamine (32.2 ml, 231 mmol) was added a 10% palladium-carbon catalyst (3.20 g). The resulting mixture was stirred for 7 hours under a hydrogen atmosphere. The catalyst was filtered off through Celite, and then, the filtrate was concentrated under reduced pressure. To the residue thus obtained was added a saturated aqueous solution of sodium bicarbonate, followed by extraction with chloroform. The organic layer was dried over anhydrous sodium sulfate and then filtered. The filtrate was concentrated under reduced pressure.

The residue thus obtained was dissolved in dichloromethane (600 ml). To the resulting solution were sequentially added triethylamine (14.8 ml, 106 mmol), t-butylchlorodiphenylsilane (25.0 ml, 96.3 mmol) and 4-dimethylaminopyridine (1.18 g, 9.63 mmol). The resulting mixture was stirred at room temperature for 14 hours. The reaction mixture was washed with a saturated aqueous solution of sodium bicarbonate. The organic layer was dried over anhydrous sodium sulfate and then filtered. The filtrate was concentrated under reduced pressure. The residue thus obtained was subjected to flash silica gel chromatography, and The fraction obtained from the hexane:ethyl acetate=19:1 eluate was concentrated under reduced pressure to give the title compound (30.0 g, 81.9 mmol, 85%) as a colorless oil.

$^1$H-NMR (400 MHz, CDCl$_3$) δ: 1.10 (9H, s), 4.78 (2H, s), 7.36-7.49 (7H, m), 7.63-7.70 (4H, m), 8.32 (1H, s), 8.36 (1H, d, J=2.4 Hz).

MSm/z: 366 (M$^+$+H).

Referential Example 29

[5-(t-Butyldiphenylsilyloxymethyl)-3-fluoropyridin-2-yl](2,5-difluorophenyl)methanol

[Chemical formula 37]

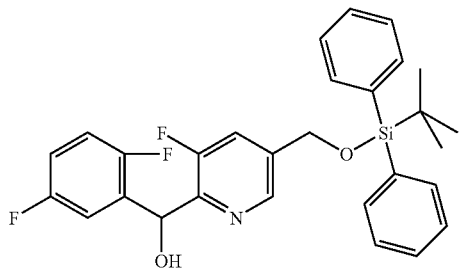

At −78° C., a hexane solution (30.0 ml, 46.8 mmol) of n-butyl lithium and N,N,N'N'-tetramethylethylenediamine (7.06 ml, 46.8 mmol) were added sequentially to diethyl ether (250 ml). After stirring at −20° C. for 30 minutes, the reaction mixture was cooled to −78° C., and a diethyl ether (50 ml) solution of 3-(t-butyldiphenylsilyloxymethyl)-5-fluoropyridine (15.5 g, 42.5 mmol) was added thereto. The resulting mixture was stirred at the same temperature for 30 minutes. To the reaction mixture was added 2,5-difluorobenzaldehyde (6.04 g, 42.5 mmol). The resulting mixture was stirred for 2 hours. Water and then, a saturated aqueous solution of sodium bicarbonate were added to the reaction mixture. The resulting mixture was extracted with diethyl ether. The organic layer was dried over anhydrous sodium sulfate and then, filtered. The filtrate was concentrated under reduced pressure. The residue thus obtained was subjected to flash silica gel chromatography. The fraction obtained from the hexane:ethyl acetate=9:1 eluate was concentrated under reduced pressure to give the title compound (17.0 g, 33.5 mmol, 79%) as a colorless oil.

$^1$H-NMR (400 MHz, CDCl$_3$) δ: 1.10 (9H, s), 4.78 (2H, s), 5.12 (1H, d, J=6.6 Hz), 6.22 (1H, d, J=6.6 Hz), 6.87-7.04 (3H, m), 7.33-7.48 (7H, m), 7.61-7.70 (4H, m), 8.32 (1H, s).

MSm/z: 508 (M$^+$+H).

Referential Example 30

(2,5-Difluorophenyl)(3-fluoro-5-hydroxymethylpyridin-2-yl)methanol

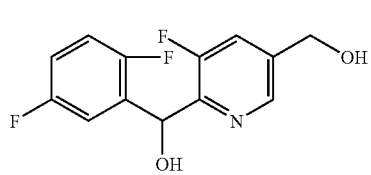

[Chemical formula 38]

To a tetrahydrofuran (7 ml) solution of [5-(t-butyldiphenylsilyloxymethyl)-3-fluoropyridin-2-yl](2,5-difluorophenyl)methanol (853 mg, 1.68 mmol) was added a tetrahydrofuran solution (1.04 ml, 1.04 mmol) of tetrabutylammonium fluoride. The mixture was stirred at room temperature for 5 hours. After the reaction mixture was concentrated under reduced pressure, the residue thus obtained was dissolved in ethyl acetate. The resulting solution was washed with a saturated aqueous solution of sodium bicarbonate. The organic layer was dried over anhydrous sodium sulfate and then, filtered. The filtrate was concentrated under reduced pressure. The residue thus obtained was subjected to flash silica gel chromatography. The fraction obtained from the hexane:ethyl acetate=1:1 eluate was concentrated under reduced pressure to give the title compound (413 mg, 1.53 mmol, 91%) as a white solid.

$^1$H-NMR (400 MHz, CDCl$_3$) δ: 1.91 (1H, t, J=5.4 Hz), 4.79 (2H, d, J=5.4 Hz), 5.16 (1H, d, J=6.6 Hz), 6.23 (1H, d, J=6.6 Hz), 6.75-7.04 (3H, m), 7.46 (1H, d, J=9.8 Hz), 8.41 (1H, s).

mp: 94 to 96° C.

MSm/z: 270 (M$^+$+H).

Referential Example 31

6-(2,5-Difluorophenyl)hydroxymethyl-5-fluoronicotinamide

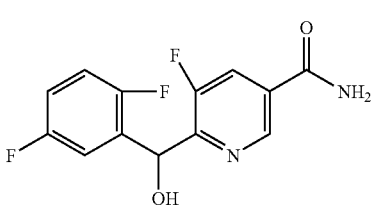

[Chemical formula 39]

To an acetone (9 ml) solution of the (2,5-difluorophenyl)(3-fluoro-5-hydroxymethylpyridin-2-yl)methanol (406 mg, 1.51 mmol) obtained in Referential Example 30 was added a water (9 ml) solution of potassium permanganate (795 mg, 7.03 mmol) and the resulting mixture was heated under reflux for 4 hours. The precipitate was filtered off through Celite.

The filtrate was acidified with 1N hydrochloric acid, followed by extraction with dichloromethane. The organic layer was dried over anhydrous sodium sulfate and filtered. The filtrate was concentrated under reduced pressure. The residue thus obtained was washed with a mixed solvent of hexane and dichloromethane, and then collected by filtration to give a white solid (367 mg).

To an N,N-dimethylformamide (8 ml) solution of the resulting solid (240 mg) were added 1H-benzotriazol-1-yloxytripyrrolidinophosphonium hexafluorophosphate (666 mg, 1.28 mmol), benzotriazol-1-ol (173 mg, 1.28 mmol), N-ethyldiisopropylamine (0.595 ml, 3.41 mmol) and ammonium chloride (91 mg, 1.71 mmol) and the resulting mixture was stirred at room temperature for 9 hours. To the reaction mixture was added ethyl acetate. The resulting mixture was washed sequentially with a saturated aqueous solution of ammonium chloride, a saturated aqueous solution of sodium bicarbonate, and brine. The organic layer was dried over anhydrous sodium sulfate and filtered. The filtrate was concentrated under reduced pressure. The residue thus obtained was subjected to flash silica gel chromatography, and the fraction obtained from the hexane:ethyl acetate=1:4 eluate was concentrated under reduced pressure.

The residue thus obtained was dissolved in ethanol (8 ml). At 0° C., sodium borohydride (30 mg, 0.79 mmol) was added to the resulting solution. After stirring at room temperature for 1 hour, water was added to the reaction mixture. The resulting mixture was extracted with dichloromethane. The organic layer was dried over anhydrous sodium sulfate and filtered. The filtrate was concentrated under reduced pressure. The residue thus obtained was subjected to flash silica gel chromatography. The fraction obtained from the ethyl acetate eluate was concentrated under reduced pressure to give the title compound (118 mg, 0.42 mmol, 42%) as a white solid.

$^1$H-NMR (400 MHz, CDCl$_3$) δ: 4.97 (1H, d, J=6.6 Hz), 6.27 (1H, d, J=6.6 Hz), 6.91-7.06 (3H, m), 7.87 (1H, dd, J=9.4, 1.6 Hz), 8.81 (1H, s).

mp: 162 to 164° C.

MSm/z: 283 (M$^+$+H).

Referential Example 32

2-[(2,5-Difluorophenyl)hydroxymethyl]-6-(1,3-dioxolan-2-yl)pyridine

[Chemical formula 40]

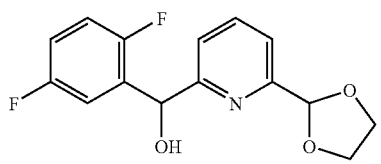

Under an argon atmosphere, a tetrahydrofuran solution (2.0M, 12.4 ml, 24.8 mmol) of isopropylmagnesium chloride was added dropwise to a tetrahydrofuran (20 ml) solution of 2-bromo-6-(1,3-dioxolan-2-yl)pyridine (2.7 ml, 24.8 mmol) under ice cooling. The reaction mixture was stirred at room temperature for 3 hours. To the resulting brown solution was added dropwise 2,5-difluorobenzaldehyde (2.7 ml, 24.8 mmol) under ice cooling. The temperature of the reaction mixture was raised gradually to room temperature and then, stirring was conducted for 16 hours. After a saturated aqueous solution of ammonium chloride was added, the resulting mixture was extracted with ethyl acetate. The extract was washed sequentially with water and brine. The organic layer thus obtained was dried over magnesium sulfate and concentrated under reduced pressure. The residue was subjected to silica gel column chromatography. The fraction obtained from the hexane:ethyl acetate=4:1 eluate was concentrated under reduced pressure to give the title compound (2.90 g, 9.89 mmol, 40%) as a colorless oil.

$^1$H-NMR (400 MHz, CDCl$_3$) δ: 4.09-4.21 (4H, m), 5.43 (1H, d, J=4.4 Hz), 5.90 (1H, s), 6.11 (1H, d, J=4.4 Hz), 6.87-6.95 (1H, m), 6.99-7.05 (1H, m), 7.10-7.15 (1H, m), 7.23 (1H, d, J=7.8 Hz), 7.48 (1H, d, J=7.8 Hz), 7.72 (1H, t, J=7.8 Hz).

MSm/z: 294 (M$^+$+H).

Referential Example 33

1-[3-(t-Butyldimethylsilyloxy)propyl]piperidin-2-one

[Chemical formula 41]

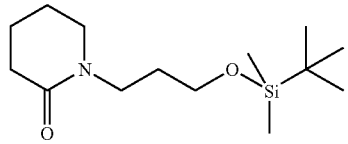

At 0° C., sodium hydride (60% in oil, 2.22 g, 55.6 mmol) was added in portions to a tetrahydrofuran solution (200 ml) of piperidin-2-one (5.00 g, 50.5 mmol). The reaction mixture was then stirred at room temperature for 3 hours. After addition of (3-bromopropoxy)-t-butyldimethylsilane (14.1 ml, 60.6 mmol) and N,N-dimethylformamide (20 ml) to the reaction mixture, the resulting mixture was stirred at room temperature for 4 days. Water was added to the reaction mixture, followed by extraction with ethyl acetate. The extract was washed with water and brine, dried over magnesium sulfate and concentrated. The residue thus obtained was subjected to silica gel column chromatography. The fraction obtained from the hexane:ethyl acetate=2:1 eluate was concentrated to give the title compound (6.44 g, 23.8 mmol, 47%) as a colorless oil.

$^1$H-NMR (400 MHz, CDCl$_3$) δ: 0.05 (6H, s), 0.89 (9H, s), 1.74-1.85 (6H, m), 2.36 (2H, t, J=6.0 Hz), 3.27-3.32 (2H, m), 3.39-3.43 (2H, m), 3.65 (2H, t, J=6.3 Hz).

MSm/z: 272 (M$^+$+H).

Referential Example 34

3-Bromo-1-[3-(t-butyldimethylsilyloxy)propyl]piperidin-2-one

[Chemical formula 42]

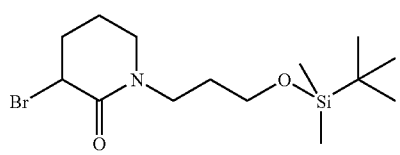

Under an argon atmosphere, t-butyl lithium (a 1.50M pentane solution, 1.40 ml, 2.10 mmol) was added dropwise to a tetrahydrofuran solution (5 ml) of 1-[3-(t-butyldimethylsily-loxy)propyl]piperidin-2-one (542 mg, 2.00 mmol) at −78° C. The reaction mixture was stirred at −78° C. for 15 minutes. After a tetrahydrofuran solution (5 ml) of tetrabutylammonium tribromide (1.16 g, 2.40 mmol) was added to the reaction mixture, the temperature of the resulting mixture was gradually raised to −40° C. under stirring. Water was added to the reaction mixture at −40° C. and then, the temperature of the mixture was raised to room temperature. The reaction mixture was extracted with ethyl acetate. The extract was washed with water and brine, dried over magnesium sulfate and concentrated. The residue thus obtained was subjected to flash silica gel column chromatography. The fraction obtained from the hexane:ethyl acetate=2:3 eluate was concentrated to give the title compound (72.8 mg, 0.208 mmol, 10%) as a colorless oil.

$^1$H-NMR (400 MHz, CDCl$_3$) δ: 0.05 (6H, s), 0.89 (9H, s), 1.74-1.88 (3H, m), 2.18-2.32 (3H, m), 3.28-3.48 (4H, m), 3.65 (2H, t, J=6.1 Hz), 4.53-4.57 (1H, m).

MS m/z: 350 (M$^+$+H).

Example 1

2-[[(4-Chlorophenyl)sulfonyl](cyclohexyl)methyl]-1,4-difluorobenzene

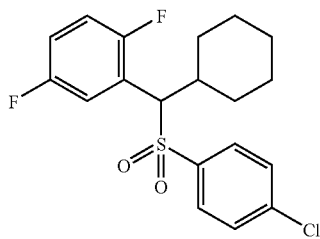

[Chemical formula 43]

The 2-[(4-chlorophenyl)sulfonylmethyl]-1,4-difluorobenzene (240 mg, 0.793 mmol) obtained in Referential Example 1 was dissolved in toluene (20 ml). After addition of cyclohexanol (0.11 ml, 1.0 mmol) and cyanomethylenetri-n-butylphosphorane (250 mg, 1.0 mmol), the resulting mixture was heated under reflux for 14 hours under an argon atmosphere. The reaction mixture was allowed to cool and then, cyclohexanol (0.22 ml, 2.1 mmol) and cyanomethylenetri-n-butylphosphorane (500 mg, 2.08 mmol) were added thereto. Under an argon atmosphere, the resulting mixture was heated under reflux for 14 hours. The reaction mixture was allowed to cool and concentrated under reduced pressure. The residue thus obtained was purified by silica gel chromatography (hexane:ethyl acetate=30:1) to give a white solid. The white solid was washed with hexane to give the title compound (188 mg, 62%) as a white powder.

Melting point: 107 to 109° C.

$^1$H-NMR (400 MHz, CDCl$_3$) δ: 0.92-1.08 (1H, m), 1.08-1.22 (1H, m), 1.22-1.50 (3H, m), 1.60-1.75 (3H, m), 1.75-1.88 (1H, m), 2.37 (1H, brd, J=12.5 Hz), 2.48-2.62 (1H, m), 4.44 (1H, d, J=7.6 Hz), 6.68-6.80 (1H, m), 6.86-6.95 (1H, m), 7.30 (2H, dm, J=8.6 Hz), 7.38-7.52 (1H, m), 7.49 (2H, dm, J=8.6 Hz).

Elemental Analysis for C$_{19}$H$_{19}$ClF$_2$O$_2$S: Calculated: C, 59.29; H, 4.98; Cl, 9.21; F, 9.87; S, 8.33. Found: C, 59.11; H, 4.93; Cl, 9.18; F, 9.82; S, 8.49.

Example 2

4-[(4-Chlorophenylsulfonyl)(cyclopentyl)methyl]pyridine

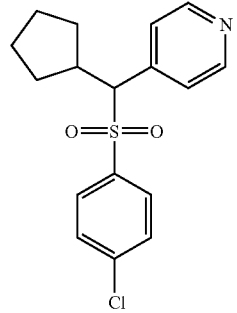

[Chemical formula 44]

A toluene (5 ml) solution of the 4-(4-chlorophenylsulfonylmethyl)pyridine (70 mg, 0.261 mmol) obtained in Referential Example 2, cyclopentanol (49 μl, 0.538 mmol) and cyanomethylenetri-n-butylphosphorane (129 mg, 0.538 mol) was heated under reflux for 3 days under an argon atmosphere. After cooling to room temperature, cyclopentanol (49 μl, 0.538 mmol) and cyanomethylenetri-n-butylphosphorane (129 mg, 0.538 mol) were added to the reaction mixture. Under an argon atmosphere, the reaction mixture was heated under reflux for 22 hours. The reaction mixture was cooled to room temperature and then, concentrated under reduced pressure. The residue thus obtained was subjected to flash silica gel column chromatography, and the fraction obtained from the hexane:ethyl acetate (=2:1) eluate was concentrated under reduced pressure to give the title compound (77 mg, 88%) as a white solid. The solid thus obtained was washed with hexane-ether and filtered to give the title compound as a white powder.

Melting point: 133 to 135° C.

$^1$H-NMR (400 MHz, CDCl$_3$) δ: 0.92-1.08 (1H, m), 1.44-1.83 (6H, m), 2.33-2.45 (1H, m), 2.78-2.90 (1H, m), 3.88 (1H, d, J=10.3 Hz), 7.03 (2H, d, J=5.1 Hz), 7.32 (2H, d, J=8.6 Hz), 7.43 (2H, d, J=8.6 Hz), 8.46 (2H, d, J=5.6 Hz)

Elemental Analysis for C$_{17}$H$_{18}$ClNO$_2$S: Calculated: C, 60.80; H, 5.40; Cl, 10.56; N, 4.17; S, 9.55. Found: C, 60.76; H, 5.44; Cl, 10.68; N, 4.20; S, 9.61.

Example 3

4-[(4-Chlorophenylsulfonyl)(tetrahydropyran-4-yl)methyl]pyridine

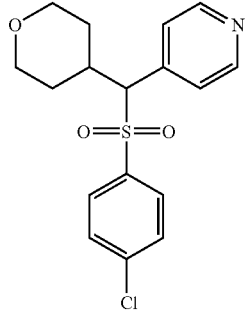

[Chemical formula 45]

A toluene (5 ml) solution of the 4-(4-chlorophenylsulfonylmethyl)pyridine (70 mg, 0.261 mmol) obtained in Referential Example 2, tetrahydropyran-4-ol (51 µl, 0.538 mmol) and cyanomethylenetri-n-butylphosphorane (129 mg, 0.538 mol) was heated under reflux for 3 days under an argon atmosphere. After the reaction mixture was cooled to room temperature, tetrahydropyran-4-ol (51 µl, 0.538 mmol) and cyanomethylenetri-n-butylphosphorane (129 mg, 0.538 mol) were added thereto. The mixture was heated under reflux for 22 hours under an argon atmosphere. After cooling to room temperature, the reaction mixture was concentrated under reduced pressure. The residue thus obtained was subjected to flash silica gel column chromatography. The fraction obtained from the hexane:ethyl acetate (=1:2) eluate was concentrated under reduced pressure to give the title compound (65 mg, 71%) a white solid. The solid thus obtained was washed with hexane-ether, and filtered to give the title compound as a white powder.

Melting point: 208 to 209° C.

$^1$H-NMR (400 MHz, CDCl$_3$) δ: 1.22-1.42 (2H, m), 1.60-1.75 (1H, m), 2.30-2.40 (1H, m), 2.78-3.01 (1H, m), 3.41 (1H, td, J=11.7, 2.4 Hz), 3.51 (1H, td, J=11.9, 2.0 Hz), 3.80-3.93 (1H, m), 3.87 (1H, d, J=8.6 Hz), 3.98-4.06 (1H, m), 7.00-7.12 (2H, m), 7.30 (2H, d, J=8.8 Hz), 7.43 (2H, d, J=8.6 Hz), 8.47 (2H, d, J=5.4 Hz).

MS (m/z): 352 (M$^+$+H).

Example 4

4-[(1-Benzylpiperidin-4-yl)(4-chlorophenylsulfonyl)methyl]pyridine

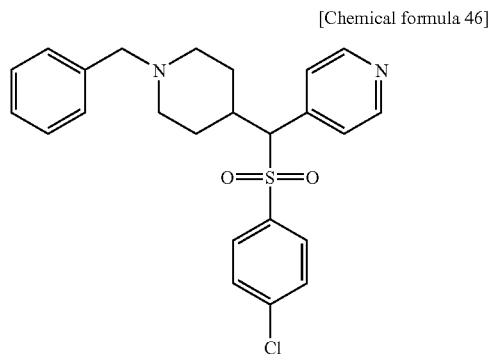

[Chemical formula 46]

A toluene (5 ml) solution of the 4-(4-chlorophenylsulfonylmethyl)pyridine (70 mg, 0.261 mmol) obtained in Referential Example 2,1-benzylpiperidin-4-ol (103 mg, 0.538 mmol) and cyanomethylenetri-n-butylphosphorane (129 mg, 0.538 mol) was heated under reflux for 3 days under an argon atmosphere. After cooling to room temperature, 1-benzylpiperidin-4-ol (103 mg, 0.538 mmol) and cyanomethylenetri-n-butylphosphorane (129 mg, 0.538 mol) were added to the reaction mixture. Under an argon atmosphere, the resulting mixture was heated under reflux for 22 hours. After cooling to room temperature, the reaction mixture was concentrated under reduced pressure. The residue thus obtained was subjected to flash silica gel column chromatography. The fraction obtained from the methanol:methylene chloride (=1:10) eluate was concentrated under reduced pressure. The residue thus obtained was purified by high performance liquid chromatography (by using a mixed solvent system of water/acetonitrile/formic acid) to give the title compound (40 mg, 35%) as an amorphous substance.

$^1$H-NMR (400 MHz, CDCl$_3$) δ: 1.21-1.37 (2H, m), 1.49-1.70 (1H, m), 1.92-2.01 (1H, m), 2.03-2.14 (1H, m), 2.25-2.35 (1H, m), 2.52-2.65 (1H, m), 2.79-2.85 (1H, m), 2.90-3.00 (1H, m), 3.47 (2H, s), 3.86 (1H, d, J=8.1 Hz), 7.02-7.12 (2H, m), 7.20-7.38 (7H, m), 7.43 (2H, d, J=8.5 Hz), 8.45 (2H, d, J=5.4 Hz).

HRMS (FAB): as C$_{24}$H$_{26}$O$_2$N$_2$ClS (M$^+$+H)

Calculated: 441.1404. Found: 441.1387.

Example 5

4-[(4-Chlorophenylsulfonyl)(1-methylpiperidin-4-yl)methyl]pyridine

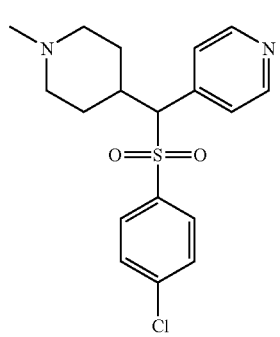

[Chemical formula 47]

A toluene (5 ml) solution of the 4-(4-chlorophenylsulfonylmethyl)pyridine (70 mg, 0.261 mmol) obtained in Referential Example 2, 1-methylpiperidin-4-ol (62 µl, 0.538 mmol) and cyanomethylenetri-n-butylphosphorane (62 µl, 0.538 mol) was heated under reflux for 3 days under an argon atmosphere. After cooling to room temperature, 1-methylpiperidin-4-ol (62 µl, 0.538 mmol) and cyanomethylenetri-n-butylphosphorane (129 mg, 0.538 mol) were added to the reaction mixture. Under an argon atmosphere, the resulting mixture was heated under reflux for 22 hours. After cooling to room temperature, the reaction mixture was concentrated under reduced pressure. The residue thus obtained was subjected to silica gel column chromatography. The fraction obtained from the methanol:methylene chloride (=1:50) eluate was concentrated under reduced pressure. The residue thus obtained was purified by high performance liquid chromatography (using a mixed solvent system of water/acetonitrile/formic acid) to give the title compound (31 mg, 33%) as a white solid. The solid thus obtained was washed with hexane-ether and filtered to give the title compound as a white powder.

Melting point: 176 to 177° C.

$^1$H-NMR (400 MHz, CDCl$_3$) δ: 1.22-1.38 (2H, m), 1.50-1.68 (1H, m), 1.88-1.99 (1H, m), 2.00-2.10 (1H, m), 2.25 (3H, s), 2.30-2.40 (1H, m), 2.50-2.63 (1H, m), 2.74-2.83 (1H, m), 2.89-2.95 (1H, m), 3.86 (1H, d, J=8.3 Hz), 7.08 (2H, d, J=4.6 Hz), 7.30 (2H, d, J=8.6 Hz), 7.44 (2H, d, J=8.6 Hz), 8.46 (2H, d, J=5.6 Hz).

Elemental Analysis for C$_{18}$H$_{21}$ClN$_2$O$_2$S: Calculated: C, 59.25; H, 5.80; Cl, 9.72; N, 7.68; S, 8.79. Found: C, 59.00; H, 5.76; Cl, 9.75; N, 7.61; S, 8.77.

Example 6

2-[[(4-Chlorophenyl)thio]-(2,5-difluorophenyl)methyl]pyridine

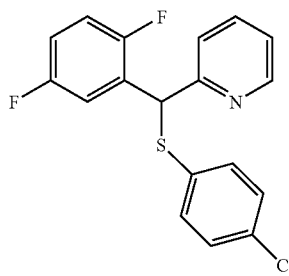

[Chemical formula 48]

The 2-[(2,5-difluorophenyl)-hydroxymethyl]pyridine (88 mg, 0.40 mmol) obtained in Referential Example 3 was dissolved in thionyl chloride (2.0 ml). To the resulting solution was added a catalytic amount of dimethylformamide, followed by stirring for 15 hours. The reaction mixture was concentrated under reduced pressure. To the residue was added dioxane, and the resulting mixture was concentrated further. The residue was dissolved in dimethylformamide (5 ml). To the resulting solution were added 4-chlorobenzenethiol (79 mg, 0.55 mmol) and potassium carbonate (226 mg, 1.64 mmol) under a nitrogen atmosphere, and the mixture was stirred at 50° C. for 1 hour. After the reaction mixture was cooled to room temperature, diethyl ether (50 ml) was added thereto. The resulting mixture was washed with water and brine. The organic layer was dried over magnesium sulfate, and concentrated under reduced pressure. The residue was subjected to silica gel chromatography (hexane:ethyl acetate=10:1) to give the title compound (128 mg, 92%) as an oil.

$^1$H-NMR (400 MHz, CDCl$_3$) δ: 5.89 (1H, s), 6.80-7.27 (7H, m), 7.38 (1H, d, J=7.6 Hz), 7.48 (1H, m), 7.65 (1H, m), 8.63 (1H, m).

MSm/z: 348 (M$^+$+H).

Example 7

2-[[(4-Chlorophenyl)thio]-(2,5-difluorophenyl)methyl]-3-methylpyridine

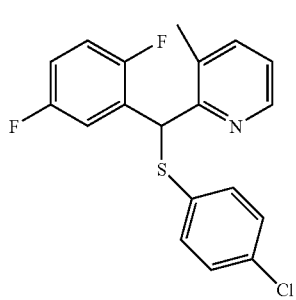

[Chemical formula 49]

To a dimethylformamide (5 ml) solution of the 2-[chloro-(2,5-difluorophenyl)methyl]-3-methylpyridine hydrochloride (94 mg, 0.32 mmol) obtained in Referential Example 4 were added 4-chlorobenzenethiol (70 mg, 0.49 mmol) and potassium carbonate (265 mg, 1.92 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate and concentrated under reduced pressure. The residue thus obtained was subjected to silica gel chromatography (hexane:ethyl acetate=10:1) to give the title compound (103 mg, 89%) as an oil.

$^1$H-NMR (400 MHz, CDCl$_3$) δ: 2.21 (3H, s), 5.87 (1H, s), 6.77 (1H, m), 7.00-7.19 (5H, m), 7.36 (1H, m), 7.45 (1H, m), 8.45 (1H, dd, J=1.2, 4.8 Hz).

MSm/z: 362 (M$^+$+H).

Example 8

2-[[(4-Chlorophenyl)thio]-(2,5-difluorophenyl)methyl]-4-methylpyridine

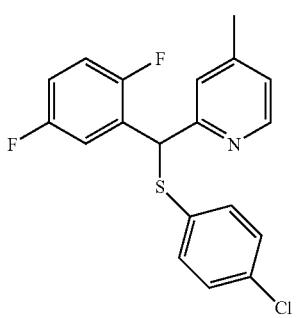

[Chemical formula 50]

After the 2-[(2,5-difluorophenyl)-hydroxymethyl]-4-methylpyridine (235 mg, 0.53 mmol) obtained in Referential Example 6 was dissolved in thionyl chloride (2.0 ml), a catalytic amount of dimethylformamide was added to the resulting solution. The resulting mixture was stirred for 16 hours. The reaction mixture was concentrated under reduced pressure. To the residue was added dioxane, followed by further concentration. The residue thus obtained was dissolved in dimethylformamide (10 ml). To the resulting solution were added 4-chlorobenzenethiol (217 mg, 1.5 mmol) and potassium carbonate (828 mg, 6.0 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate and concentrated under reduced pressure. The residue thus obtained was subjected to silica gel chromatography (hexane:ethyl acetate=10:1) to give the title compound (290 mg, 80%) as an oil.

$^1$H-NMR (400 MHz, CDCl$_3$) δ: 2.31 (3H, s), 5.82 (1H, s), 6.80-7.0 (3H, m), 7.15 (2H, d, J=8.8 Hz), 7.16 (1H, m), 7.21 (2H, d, J=8.8 Hz), 7.45 (1H, m), 8.45 (1H, d, J=5.6 Hz).

MSm/z: 362 (M$^+$+H).

Example 9

2-[[(4-Chlorophenyl)thio]-(2,5-difluorophenyl)methyl]-3-methoxypyridine

[Chemical formula 51]

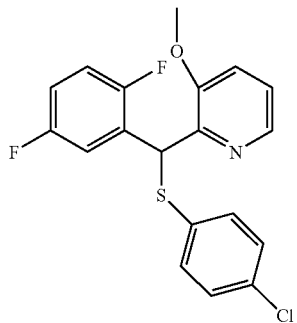

After the 2-[(2,5-difluorophenyl)-hydroxymethyl]-3-methoxypyridine (251 mg, 1.0 mmol) obtained in Referential Example 9 was dissolved in thionyl chloride (2.0 ml), a catalytic amount of dimethylformamide was added to the resulting solution. The resulting mixture was stirred for 16 hours. The reaction mixture was concentrated under reduced pressure. To the residue was added dioxane, followed by further concentration. The residue thus obtained was dissolved in dimethylformamide (10 ml). To the resulting solution were added 4-chlorobenzenethiol (289 mg, 2.0 mmol) and potassium carbonate (1.10 g, 8.0 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate and concentrated under reduced pressure. The residue was subjected to silica gel chromatography (hexane:ethyl acetate=10:1) to give the title compound (256 mg, 58%) as an oil.

$^1$H-NMR (400 MHz, CDCl$_3$) δ: 3.77 (3H, s), 6.25 (1H, s), 6.82 (2H, m), 7.15 (2H, d, J=8.4 Hz), 7.10-7.20 (2H, m), 7.25 (2H, d, J=8.8 Hz), 7.52 (1H, m), 8.24 (1H, m).

MSm/z: 378 (M$^+$+H).

Example 10

3-Allyloxy-2-[[(4-chlorophenyl)thio]-(2,5-difluorophenyl)methyl]pyridine

[Chemical formula 52]

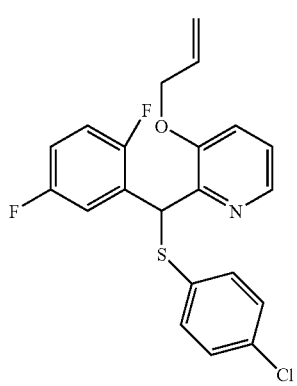

The 3-allyloxy-2-[(2,5-difluorophenyl)-hydroxymethyl]pyridine (370 mg, 1.33 mmol) obtained in Referential Example 10 was dissolved in thionyl chloride (2.0 ml). To the resulting solution was added a catalytic amount of dimethylformamide. The resulting mixture was stirred for 16 hours. The reaction mixture was concentrated under reduced pressure. Dioxane was added to the residue, followed by further concentration. The residue thus obtained was dissolved in dimethylformamide (10 ml). To the resulting solution were added 4-chlorobenzenethiol (217 mg, 1.5 mmol) and potassium carbonate (828 mg, 6.0 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate and concentrated under reduced pressure. The residue was subjected to silica gel chromatography (hexane:ethyl acetate=10:1) to give the title compound (256 mg, 68%) as an oil.

$^1$H-NMR (400 MHz, CDCl$_3$) δ: 4.46 (2H, m), 5.24 (1H, d, J=10.6 Hz), 5.28 (1H, d, J=17.2 Hz), 5.90 (1H, m), 6.29 (1H, d, J=1.2 Hz), 6.82 (2H, m), 7.15 (2H, d, J=8.4 Hz), 7.06-7.20 (2H, m), 7.24 (2H, d, J=8.4 Hz), 7.50 (1H, m), 8.24 (1H, m).

MSm/z: 404 (M$^+$+H).

Example 11

3-[[(4-Chlorophenyl)thio]-(2,5-difluorophenyl)methyl]pyridine

[Chemical formula 53]

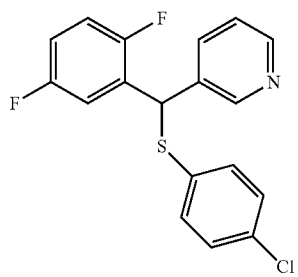

The 3-[(2,5-difluorophenyl)-hydroxymethyl]pyridine (87 mg, 0.39 mmol) obtained in Referential Example 11 was dissolved in thionyl chloride (1.0 ml). A catalytic amount of dimethylformamide was added to the resulting solution and the resulting mixture was stirred for 14 hours. The reaction mixture was concentrated under reduced pressure. To the residue was added dioxane and the resulting mixture was concentrated further. The residue thus obtained was dissolved in dimethylformamide (5 ml), followed by the addition of 4-chlorobenzenethiol (84 mg, 0.58 mmol) and potassium carbonate (323 mg, 2.34 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate and concentrated under reduced pressure. The residue thus obtained was subjected to silica gel chromatography (hexane:ethyl acetate=1:1) to give the title compound (131 mg, 96%) as an oil.

$^1$H-NMR (400 MHz, CDCl$_3$) δ: 5.73 (1H, s), 6.84-6.96 (2H, m), 7.18 (2H, m), 7.19 (2H, m), 7.15-7.22 (2H, m), 7.71 (1H, m), 8.49 (1H, dd, J=1.6, 4.8 Hz), 8.58 (1H, d, J=2.0 Hz).

MSm/z: 348 (M$^+$+H).

Example 12

5-[[(4-Chlorophenyl)thio]-(2,5-difluorophenyl)methyl]pyrimidine

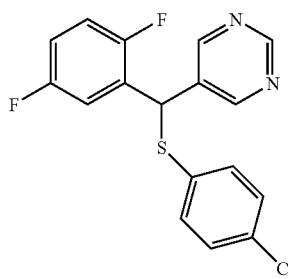

[Chemical formula 54]

The 5-[(2,5-difluorophenyl)-hydroxymethyl]pyrimidine (111 mg, 0.5 mmol) obtained in Referential Example 12 was dissolved in thionyl chloride (1.0 ml). A catalytic amount of dimethylformamide was added and the resulting mixture was stirred for 16 hours. The reaction mixture was concentrated under reduced pressure. To the residue was added dioxane, and the resulting mixture was concentrated further. The residue was dissolved in dimethylformamide (5 ml), followed by the addition of 4-chlorobenzenethiol (108 mg, 0.75 mmol) and potassium carbonate (414 mg, 3.0 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate and concentrated under reduced pressure. The residue was subjected to silica gel chromatography (hexane:ethyl acetate=4:1) to give a mixture (202 mg) of the title compound and an unidentified compound as an oil.

$^1$H-NMR (400 MHz, CDCl$_3$) δ: 5.66 (1H, s), 6.96 (2H, m), 7.17-7.34 (5H, d), 8.70 (2H, s), 9.09 (1H, s).

MSm/z: 349 (M$^+$+H).

Example 13

2-[[(4-Chlorophenyl)sulfonyl]-(2,5-difluorophenyl)methyl]pyridine

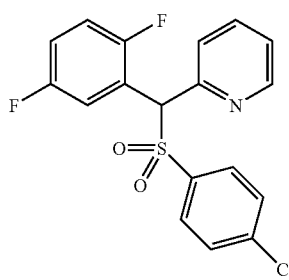

[Chemical formula 55]

To a methanol (12 ml) solution of the 2-[[(4-chlorophenyl)thio]-(2,5-difluorophenyl)methyl]pyridine (120 mg, 0.345 mmol) obtained in Example 6 was added hexaammonium heptamolybdate tetrahydrate (80 mg). To the resulting mixture was added 30% aqueous hydrogen peroxide (6 ml), followed by stirring for 24 hours. The precipitate thus formed was collected by filtration and recrystallized from ethanol to give the title compound (96 mg, 73%) as colorless needle crystals.

$^1$H-NMR (400 MHz, CDCl$_3$) δ: 5.93 (1H, s), 6.87-7.00 (2H, m), 7.28 (1H, m), 7.37 (2H, d, J=8.8 Hz), 7.53 (2H, d, J=8.8 Hz), 7.60 (1H, d, J=8.0 Hz), 7.71 (1H, m), 8.00 (1H, m), 8.59 (1H, m).

mp: 171 to 172° C.

MSm/z: 380 (M$^+$+H).

Elemental Analysis for C$_{18}$H$_{12}$ClF$_2$NO$_2$S: Calculated: C, 56.92; H, 3.18; N, 3.69; S, 8.44; Cl, 9.33; F, 10.00. Found: C, 56.76; H, 3.19; N, 3.77; S, 8.55; Cl, 9.27; F, 10.02.

Example 14

2-[[(4-Chlorophenyl)sulfonyl]-(2,5-difluorophenyl)methyl]-3-methylpyridine

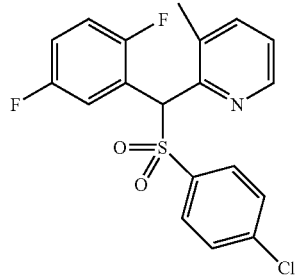

[Chemical formula 56]

In a similar manner to Example 13, the title compound (35 mg, 35%) as colorless needle crystals by synthesizing using the 2-[[(4-chlorophenyl)thio]-(2,5-difluorophenyl)methyl]-3-methylpyridine obtained in Example 7 and purifying by silica gel chromatography (hexane:ethyl acetate=5:1).

$^1$H-NMR (400 MHz, CDCl$_3$) δ: 2.36 (3H, s), 6.18 (1H, s), 6.89-7.02 (2H, m), 7.17 (1H, m), 7.37 (2H, d, J=8.4 Hz), 7.46 (1H, d, J=7.2 Hz), 7.53 (2H, d, J=8.4 Hz), 8.06 (1H, m), 8.53 (1H, d, J=4.0 Hz)

mp: 142 to 143° C.

Elemental Analysis for C$_{19}$H$_{14}$ClF$_2$NO$_2$S: Calculated: C, 57.94; H, 3.58; N, 3.56; S, 8.12; Cl, 9.00; F, 9.65. Found: C, 58.03; H, 3.66; N, 3.78; S, 8.12; Cl, 9.13; F, 9.59.

Example 15

2-[[(4-Chlorophenyl)sulfonyl]-(2,5-difluorophenyl)methyl]-5-methylpyridine

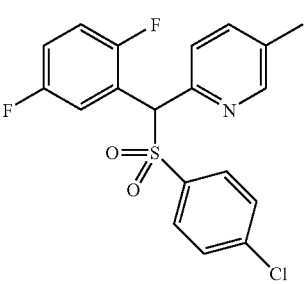

[Chemical formula 57]

1) 2-[[(4-Chlorophenyl)thio]-(2,5-difluorophenyl)methyl]-5-methylpyridine

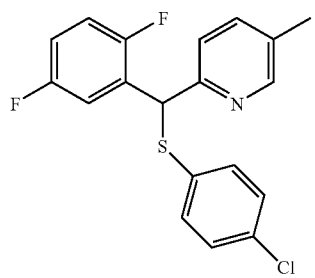

[Chemical formula 58]

The 2-[(2,5-difluorophenyl)-hydroxymethyl]-5-methylpyridine (125 mg, 0.53 mmol) obtained in Referential Example 5 was dissolved in thionyl chloride (1.0 ml). To the resulting solution was added a catalytic amount of dimethylformamide. The resulting mixture was stirred for 14 hours. The reaction mixture was concentrated under reduced pressure. Dioxane was added to the residue, followed by further concentration. The residue was dissolved in dimethylformamide (5 ml). To the resulting solution were added 4-chlorobenzenethiol (115 mg, 0.80 mmol) and potassium carbonate (438 mg, 3.18 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate and concentrated under reduced pressure. The residue was subjected to silica gel chromatography (hexane:ethyl acetate=10:1) to give the title compound (120 mg, 66%) as an oil.

$^1$H-NMR (400 MHz, CDCl$_3$) δ: 2.29 (3H, s), 5.83 (1H, s), 6.80-6.93 (2H, m), 7.16 (2H, m), 7.20 (2H, m), 7.28 (1H, m), 7.43 (1H, m), 8.41 (1H, d, J=0.8 Hz).
MSm/z: 362 (M$^+$+H).

2) 2-[[(4-Chlorophenyl)sulfonyl]-(2,5-difluorophenyl)methyl]-5-methylpyridine In a similar manner to Example 13, the title compound (91 mg, 73%) as colorless needle crystals by the synthesis using the 2-[[(4-chlorophenyl)thio]-(2,5-difluorophenyl)methyl]-5-methylpyridine obtained by the above reaction.

$^1$H-NMR (400 MHz, CDCl$_3$) δ: 2.33 (3H, s), 5.89 (1H, s), 6.88-7.01 (2H, m), 7.37 (2H, d, J=8.8 Hz), 7.48-7.56 (2H, m), 7.53 (2H, d, J=8.8 Hz), 7.99 (1H, m), 8.42 (1H, s).
mp: 159 to 160° C.
Elemental Analysis for C$_{19}$H$_{14}$ClF$_2$NO$_2$S: Calculated: C, 57.94; H, 3.58; N, 3.56; S, 8.12; Cl, 9.00; F, 9.56. Found: C, 57.88; H, 3.61; N, 3.68; S, 8.27; Cl, 9.11; F, 9.70.

Example 16

2-[[(4-Chlorophenyl)sulfonyl]-(2,5-difluorophenyl)methyl]-4-methylpyridine

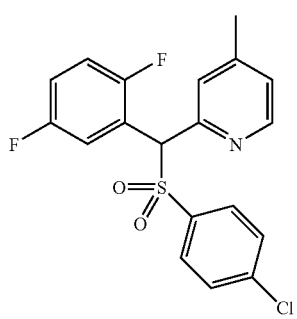

[Chemical formula 59]

In a similar manner to Example 13, the title compound (140 mg, 95%) as colorless needle crystals by the synthesis using the 2-[[(4-chlorophenyl)thio]-(2,5-difluorophenyl)methyl]-4-methylpyridine obtained in Example 8 and purification by silica gel chromatography (hexane:ethyl acetate=3:1).

$^1$H-NMR (400 MHz, CDCl$_3$) δ: 2.36 (3H, s), 5.88 (1H, s), 6.88-7.02 (2H, m), 7.09 (1H, d, J=5.2 Hz), 7.37 (2H, d, J=8.8 Hz), 7.41 (1H, m), 7.52 (2H, d, J=8.8 Hz), 7.97 (1H, m), 8.43 (1H, d, J=5.2 Hz).
mp: 116 to 117° C.
Elemental Analysis for C$_{19}$H$_{14}$ClF$_2$NO$_2$S: Calculated: C, 57.94; H, 3.58; N, 3.56; S, 8.12; Cl, 9.00; F, 9.65. Found: C, 57.80; H, 3.66; N, 3.72; S, 8.29; Cl, 9.05; F, 9.71%.

Example 17

2-[[(4-Chlorophenyl)sulfonyl]-(2,5-difluorophenyl)methyl]-3-methoxypyridine

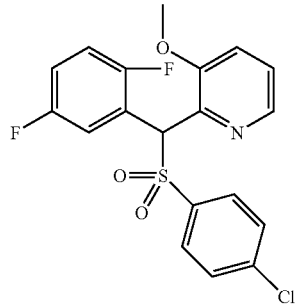

[Chemical formula 60]

In a similar manner to Example 13, the title compound (71 mg, 87%) as colorless columnar crystals by the synthesis using the 2-[[(4-chlorophenyl)thio]-(2,5-difluorophenyl)methyl]-3-methoxypyridine obtained in Example 9 and recrystallization from ethanol.

$^1$H-NMR (400 MHz, CDCl$_3$) δ: 3.72 (3H, s), 6.62 (1H, s), 6.90-7.04 (2H, m), 7.09 (1H, m), 7.24 (1H, m), 7.35 (2H, d, J=8.8 Hz), 7.53 (2H, d, J=8.8 Hz), 8.18 (1H, m), 8.30 (1H, m).
mp: 184 to 185° C.
Elemental Analysis for C$_{19}$H$_{14}$ClF$_2$NO$_3$S: Calculated: C, 55.68; H, 3.44; N, 3.42; S, 7.82; Cl, 8.65; F, 9.27. Found: C, 55.68; H, 3.45; N, 3.60; S, 7.98; Cl, 8.74; F, 9.23.

Example 18

3-Allyloxy-2-[[(4-chlorophenyl)sulfonyl]-(2,5-difluorophenyl)methyl]pyridine

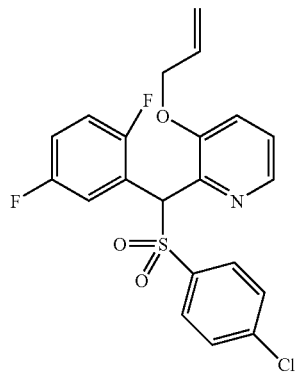

[Chemical formula 61]

In a similar manner to Example 13, the title compound (135 mg, 80%) as colorless needle crystals by the synthesis using the 3-allyloxy-2-[[(4-chlorophenyl)thio]-(2,5-difluorophenyl)methyl]pyridine obtained in Example 10 and crystallization from ethanol.

¹H-NMR (400 MHz, CDCl₃) δ: 4.38 (1H, m), 4.46 (1H, m), 5.29 (1H, dd, J=1.2, 10.4 Hz), 5.35 (1H, dd, J=1.2, 17.2 Hz), 5.93 (1H, m), 6.68 (1H, s), 6.91-7.04 (2H, m), 7.08 (1H, m), 7.22 (1H, dd, J=4.8, 8.4 Hz), 7.34 (2H, d, J=8.8 Hz), 7.53 (2H, d, J=8.8 Hz), 8.17 (1H, m), 8.31 (1H, m).

mp: 119 to 120° C.

Elemental Analysis for C₂₁H₁₆ClF₂NO₃S: Calculated: C, 57.87; H, 3.70; N, 3.21; S, 7.36; Cl, 8.13; F, 8.72. Found: C, 57.90; H, 3.75; N, 3.37; S, 7.51; Cl, 8.20; F, 8.73.

Example 19

3-[[(4-Chlorophenyl)sulfonyl]-(2,5-difluorophenyl)methyl]pyridine

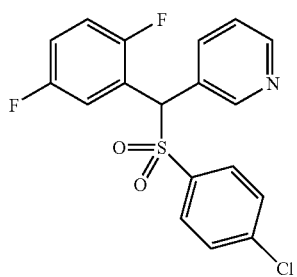

[Chemical formula 62]

In a similar manner to Example 13, the title compound (118 mg, 86%) as colorless needle crystals by the synthesis using the 3-[[(4-chlorophenyl)thio]-(2,5-difluorophenyl)methyl]pyridine obtained in Example 11 and purification by silica gel chromatography (hexane:ethyl acetate=4:1).

¹H-NMR (400 MHz, CDCl₃) δ: 5.68 (1H, s), 6.91-7.07 (2H, m), 7.34 (1H, m), 7.40 (2H, d, J=8.4 Hz), 7.57 (2H, d, J=8.4 Hz), 7.76 (1H, m), 8.04 (1H, m), 8.53 (1H, d, J=2.0 Hz), 8.59 (1H, m).

mp: 130 to 131° C.

Elemental Analysis for C₁₈H₁₂ClF₂NO₂S: Calculated: C, 56.92; H, 3.18; N, 3.69; S, 8.44; Cl, 9.33; F, 10.00. Found: C, 56.87; H, 3.16; N, 3.74; S, 8.51; Cl, 9.34; F, 10.00.

Example 20

4-[[(4-Chlorophenyl)sulfonyl]-(2,5-difluorophenyl)methyl]pyridine

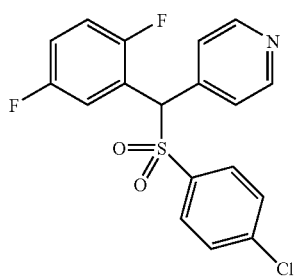

[Chemical formula 63]

The 2,5-difluorophenyl-4-pyridylmethanol (75 mg, 0.34 mmol) obtained in Referential Example 18 was dissolved in thionyl chloride (1.0 ml). A catalytic amount of dimethylformamide was added to the resulting solution and the mixture was stirred for 14 hours. The reaction mixture was concentrated under reduced pressure. To the residue was added dioxane. The resulting mixture was concentrated further. The residue thus obtained was dissolved in dimethylformamide (5 ml), followed by the addition of 4-chlorobenzenethiol (74 mg, 0.51 mmol) and potassium carbonate (281 mg, 2.04 mmol) under a nitrogen atmosphere. The resulting mixture was stirred at 50° C. for 1 hour. After the reaction mixture was cooled to room temperature, diethyl ether (50 ml) was added thereto. The resulting mixture was washed with water and brine. The organic layer was dried over magnesium sulfate, and concentrated under reduced pressure. The residue was subjected to silica gel chromatography (hexane:ethyl acetate=1:1) to give a mixture containing 4-[[(4-chlorophenyl)thio]-(2,5-difluorophenyl)methyl]pyridine.

To a methanol (12 ml) solution of the mixture were added hexaammonium heptamolybdate tetrahydrate (60 mg) and 30% aqueous hydrogen peroxide (6 ml) sequentially. The resulting mixture was stirred for 65 hours. To the reaction mixture was added ethyl acetate (80 ml). The resulting mixture was washed with water and brine, dried over anhydrous magnesium sulfate and concentrated under reduced pressure to remove the solvent. The residue was purified by silica gel chromatography (hexane:ethyl acetate=4:1 to 1:1) to give the title compound (51 mg, 39%). Recrystallization of the compound from ethanol yielded colorless needle crystals.

¹H-NMR (400 MHz, CDCl₃) δ: 5.64 (1H, s), 6.91-7.06 (2H, m), 7.40 (2H, d, J=8.0 Hz), 7.45 (2H, d, J=4.8 Hz), 7.58 (2H, d, J=8.0 Hz), 7.70 (1H, s), 8.61 (2H, d, J=4.8 Hz).

mp: 126 to 127° C.

Elemental Analysis for C₁₈H₁₂ClF₂NO₂S: Calculated: C, 56.92; H, 3.18; N, 3.69; S, 8.44; Cl, 9.33; F, 10.00. Found: C, 56.66; H, 3.16; N, 3.83; S, 8.58; Cl, 9.32; F, 9.99.

Example 21

5-[[(4-Chlorophenyl)sulfonyl]-(2,5-difluorophenyl)methyl]pyrimidine

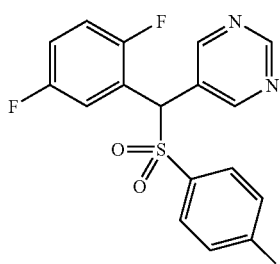

[Chemical formula 64]

In a similar manner to Example 13, the title compound (71 mg, 87%: yield: two steps after the 5-[(2,5-difluorophenyl)-hydroxymethyl]pyrimidine obtained in Referential Example 12) as colorless columnar crystals by the synthesis using the 5-[[(4-chlorophenyl)thio]-(2,5-difluorophenyl)methyl]pyrimidine obtained in Example 12 and purification by silica gel chromatography (hexane:ethyl acetate=5:1).

¹H-NMR (400 MHz, CDCl₃) δ: 5.65 (1H, s), 6.93-7.10 (2H, m), 7.43 (2H, d, J=8.8 Hz), 7.61 (2H, d, J=8.8 Hz), 7.73 (1H, m), 8.90 (2H, s), 9.21 (1H, s). mp: 136 to 137° C.

Elemental Analysis for $C_{17}H_{11}ClF_2N_2O_2S$: Calculated: C, 53.62; H, 2.91; N, 7.36; S, 8.42; Cl, 9.31; F, 9.98. Found: C, 53.64; H, 2.83; N, 7.44; S, 8.61; Cl, 9.34; F, 9.96.

Example 22

3-[[(4-Chlorophenyl)thio]-(2,5-difluorophenyl)methyl]-4-hydroxychromen-2-one

[Chemical formula 65]

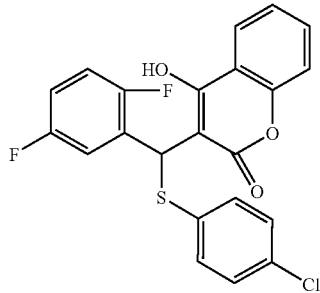

After glacial acetic acid (60 mg, 1 mmol) and pyridine (80.5 μl, 1 mmol) were added to an ethanol (4 ml) solution of 2,5-difluorobenzaldehyde (109 μl, 1 mmol), 4-hydroxycoumarine (162 mg, 1 mmol) and 4-chlorothiophenol (144.6 mg, 1 mmol) at room temperature, the resulting mixture was stirred for 24 hours. The precipitate thus formed was collected by filtration and washed with a small amount of ethanol to give the title compound (345 mg, 80%) as a white solid.

$^1$H-NMR (400 MHz, CDCl$_3$) δ: 6.16 (1H, s), 6.95-7.12 (3H, m), 7.24-7.27 (1H, m), 7.27 (2H, d, J=8.8 Hz), 7.32 (1H, t, J=7.6 Hz), 7.43 (2H, d, J=8.8 Hz), 7.56 (1H, m), 7.94 (1H, dd, J=1.6, 7.6 Hz).

mp: 146 to 147° C.

MS m/z: 431 (M$^+$+H).

Example 23

3-[[(4-Chlorophenyl)sulfonyl]-(2,5-difluorophenyl)methyl]-4-methoxychromen-2-one (Compound A) and 3-[[(4-chlorophenyl)sulfonyl]-(2,5-difluorophenyl)methyl]-2-methoxychromen-4-one (Compound B)

[Chemical formula 66]

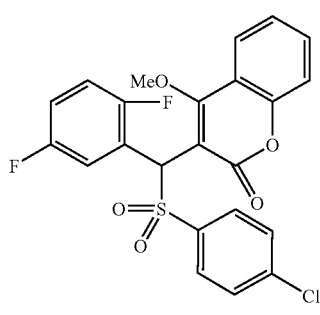

Compound A

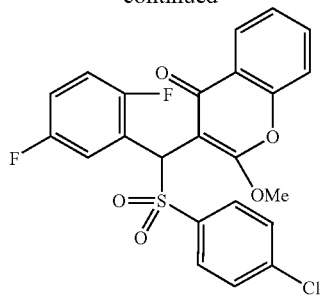

Compound B

A hexane solution of (0.41 ml, 0.822 mmol) of 2N trimethylsilyldiazomethane was added in portions to a benzene-methanol (10:1) solution of 3-[[(4-chlorophenyl)thio]-(2,5-difluorophenyl)methyl]-4-hydroxychromen-2-one (118 mg, 0.274 mmol) at room temperature. The resulting mixture was stirred for 5 minutes. After acetic acid was added until the solution became colorless, the reaction mixture was concentrated under reduced pressure.

The residue was dissolved in methanol (12 ml). To the resulting solution were added 30% aqueous hydrogen peroxide (6 ml) and hexaammonium heptamolybdate tetrahydrate (60 mg). The resulting mixture was stirred for 20 hours. Ethyl acetate (50 ml) was added to the reaction mixture. The resulting mixture was washed with water and brine, dried over anhydrous magnesium sulfate and concentrated under reduced pressure. The residue was purified by silica gel chromatography (hexane:ethyl acetate=5:1 to 3:1) to give a nonpolar compound (22 mg, 17%) as needle crystals, and a polar compound (9.0 mg, 7%) as a white solid after solidification from hexane. As a result of the NOE (nuclear Overhauser effect) test of the nonpolar compound, NOE was observed between the methoxy and hydrogen at the 5-position of the chromenone. In the test of the polar compound, on the other hand, NOE was not observed between the methoxy and the hydrogen on the aromatic ring of chromenone but was observed between the methoxy and the hydrogen at the 6-position on the difluorobenzene ring. Based on this result, the structure of the nonpolar compound was identified as 3-[[(4-chlorophenyl)sulfonyl]-(2,5-difluorophenyl)methyl]-4-methoxychromen-2-one (Compound A) and that of the polar compound was identified as 3-[[(4-chlorophenyl)sulfonyl]-(2,5-difluorophenyl)methyl]-2-methoxychromen-4-one (Compound B).

Compound A $^1$H-NMR (400 MHz, CDCl$_3$) δ: 4.13 (3H, s), 6.39 (1H, s), 6.88 (1H, m), 6.98 (1H, m), 7.3-7.4 (2H, m), 7.43 (2H, d, J=8.8 Hz), 7.58 (1H, m), 7.70 (2H, d, J=8.8 Hz), 7.73 (1H, m), 8.09 (1H, m).

mp: 178 to 179° C.

Elemental Analysis for $C_{23}H_{15}ClF_2O_3S$: Calculated: C, 57.93; H, 3.17; S, 6.72; Cl, 7.43; F, 7.97. Found: C, 57.59; H, 3.14; S, 6.85; Cl, 7.52; F, 8.01.

Compound B $^1$H-NMR (400 MHz, CDCl$_3$) δ: 4.23 (3H, s), 6.54 (1H, s), 6.89 (1H, m); 6.96 (1H, m), 7.41 (2H, d, J=8.4 Hz), 7.4-7.46 (2H, m), 7.63 (1H, m), 7.73 (2H, d, J=8.4 Hz), 8.02 (1H, m), 8.14 (1H, dd, J=1.6, 8.0 Hz).

mp: 162 to 163° C.

FAB-MS: 477.0366 (Calcd for $C_{23}H_{16}ClF_2O_5S$: 477.0375).

Example 24

2-[[(4-Chlorophenyl)thio]-(2,5-difluorophenyl)methyl]-1-methyl-1H-benzimidazole

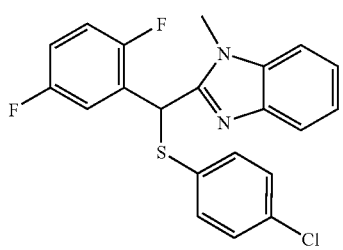

[Chemical formula 67]

Trifluoroacetic acid (2.0 ml) was added to the 2-[(t-butoxycarbonyloxy)-(2,5-difluorophenyl)methyl]-1-methyl-1H-benzimidazole (204 mg, 0.545 mmol) obtained in Referential Example 13. The resulting mixture was stirred at room temperature for 30 minutes. The reaction mixture was concentrated under reduced pressure. Dioxane was added to the residue, followed by further concentration under reduced pressure. The residue was dissolved in thionyl chloride (1.0 ml). One drop of dimethylformamide was added to the resulting solution. The resulting mixture was stirred for 16 hours at room temperature. The reaction mixture was concentrated under reduced pressure. Dioxane was added to the residue and the resulting mixture was concentrated further under reduced pressure. The residue was dissolved in dimethylformamide (5.0 ml). After addition of 4-chlorobenzenethiol (118 mg, 0.82 mmol) and potassium carbonate (451 mg, 3.27 mmol), the resulting mixture was stirred at 50° C. for 2 hours. The reaction mixture was then allowed to stand at room temperature and ethyl acetate (60 ml) was added thereto. The resulting mixture was washed with water and brine, dried over anhydrous magnesium sulfate and concentrated under reduced pressure. The residue thus obtained was purified by silica gel chromatography (hexane:ethyl acetate=10:1 to 5:1) to give the title compound (195 mg, 89%) as a colorless oil.

$^1$H-NMR (400 MHz, CDCl$_3$) δ: 3.67 (3H, s), 5.91 (1H, s), 6.87-6.93 (2H, m), 7.19 (2H, d, J=8.8 Hz), 7.27 (2H, d, J=8.8 Hz), 7.25-7.33 (3H, m), 7.60 (1H, m), 7.85 (1H, m).

MSm/z: 401 (M$^+$+H).

Example 25

2-[[(4-Chlorophenyl)thio]-(2,5-difluorophenyl)methyl]-1-methyl-5-chloro-1H-imidazole

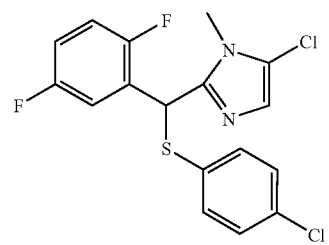

[Chemical formula 68]

Trifluoroacetic acid (10 ml) was added to the 2-[(t-butoxycarbonyloxy)-(2,5-difluorophenyl)methyl]-1-methyl-5-chloro-1H-imidazole (404 mg, 1.13 mmol) obtained in Referential Example 14. The resulting mixture was stirred at room temperature for 3 hours. The reaction mixture was concentrated under reduced pressure. Dioxane was added to the residue, followed by further concentration under reduced pressure. The residue was dissolved in thionyl chloride (2.0 ml) and to the resulting solution was added a drop of dimethylformamide. The mixture was stirred at room temperature for 17 hours. The reaction mixture was concentrated under reduced pressure. Dioxane was added to the residue, followed by further concentration under reduced pressure. The residue was dissolved in dimethylformamide (5.0 ml). To the resulting solution were added 4-chlorobenzenethiol (244 mg, 1.69 mmol) and potassium carbonate (936 mg, 6.78 mmol). The resulting mixture was stirred at 50° C. for 2 hours. The reaction mixture was allowed to stand until it became room temperature. Ethyl ether (60 ml) was added. The resulting mixture was washed with water and brine, dried over anhydrous magnesium sulfate, and concentrated under reduced pressure. The residue was purified by silica gel chromatography (hexane:ethyl acetate=10:1 to 5:1) to give the title compound (195 mg, 89%) as a colorless oil.

$^1$H-NMR (400 MHz, CDCl$_3$) δ: 3.57 (3H, s), 5.67 (1H, s), 6.89-6.95 (2H, m), 6.97 (1H, s), 7.20 (2H, d, J=8.4 Hz), 7.21 (2H, d, J=8.4 Hz), 7.54 (1H, m). MSm/z: 386 (M$^+$+H).

Example 26

2-[[(4-Chlorophenyl)thio]-(2,5-difluorophenyl)methyl]thiazole

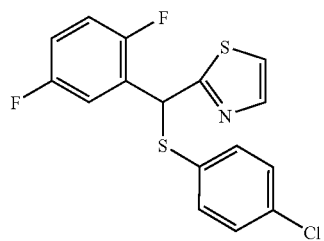

[Chemical formula 69]

The 2-[(2,5-difluorophenyl)-hydroxymethyl]thiazole (348 mg, 1.53 mmol) obtained in Referential Example 15 was dissolved in thionyl chloride (1.5 ml). To the resulting solution was added a drop of dimethylformamide. The resulting mixture was stirred at room temperature for 14 hours. The reaction mixture was concentrated under reduced pressure. Dioxane was added to the residue, followed by further concentration under reduced pressure. The residue was dissolved in dimethylformamide (10.0 ml). To the resulting solution were added 4-chlorobenzenethiol (332 mg, 2.3 mmol) and potassium carbonate (845 mg, 6.12 mmol). The resulting mixture was stirred at 50° C. for 2 hours. After the reaction mixture was allowed to stand until it became room temperature, ethyl acetate (60 ml) was added thereto. The resulting mixture was washed with water and brine, dried over anhydrous magnesium sulfate and concentrated under reduced pressure. The residue was purified by silica gel chromatography (hexane:ethyl acetate=10:1 to 6:1) to give the title compound (130 mg, 24%) as a colorless oil.

$^1$H-NMR (400 MHz, CDCl$_3$) δ: 6.04 (1H, s), 6.90-7.06 (2H, m), 7.22 (2H, d, J=8.4 Hz), 7.30 (2H, d, J=8.4 Hz), 7.15-7.35 (2H, m), 7.76 (1H, d, J=3.2 Hz).

MSm/z: 354 (M$^+$+H).

Example 27

2-[[(4-Chlorophenyl)thio]-(2,5-difluorophenyl)methyl]-1-(4-methoxyphenyl)-1H-imidazole

[Chemical formula 70]

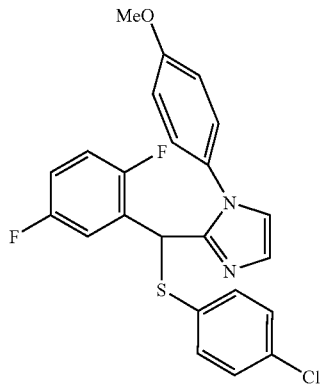

Trifluoroacetic acid (10 ml) was added to the 2-[(t-butoxycarbonyloxy)-(2,5-difluorophenyl)methyl]-1-(4-methoxyphenyl)-1H-imidazole (667 mg, 1.6 mmol) obtained in Referential Example 16. The resulting mixture was stirred at room temperature for 3 hours. The reaction mixture was concentrated under reduced pressure. Dioxane was added to the residue, followed by further concentration under reduced pressure. The residue was dissolved in thionyl chloride (2.0 ml) and to the resulting solution was added a drop of dimethylformamide. The resulting mixture was stirred at room temperature for 17 hours. The reaction mixture was concentrated under reduced pressure. To the residue was added dioxane, followed by further concentration under reduced pressure. The residue was dissolved in dimethylformamide (5.0 ml). To the resulting solution were added 4-chlorobenzenethiol (347 mg, 2.4 mmol) and potassium carbonate (1.32 g, 9.6 mmol). The resulting mixture was stirred at 50° C. for 2 hours. After the reaction mixture was allowed to stand until it became room temperature, ethyl ether (60 ml) was added thereto. The resulting mixture was washed with water and brine, dried over anhydrous magnesium sulfate and concentrated under reduced pressure. The residue was purified by silica gel chromatography (hexane:ethyl acetate=10:1 to 5:1), followed by crystallization from ethanol to give the title compound (535 mg, 75%) as colorless needle crystals.

$^1$H-NMR (400 MHz, CDCl$_3$) δ: 3.86 (3H, s), 5.57 (1H, s), 6.8-6.9 (3H, m), 6.91 (2H, d, J=8.4 Hz), 7.00 (2H, d, J=8.4 Hz), 7.06 (2H, d, J=6.8 Hz), 7.11 (2H, d, J=6.8 Hz), 7.16 (1H, s), 7.81 (1H, m).

MSm/z: 443 (M$^+$+H).

Example 28

2-[[(4-Chlorophenyl)sulfonyl]-(2,5-difluorophenyl)methyl]-1-methyl-1H-benzimidazole (Compound A) and 2-[[(4-chlorophenyl)sulfinyl]-(2,5-difluorophenyl)methyl]-1-methyl-1H-benzimidazole (Compound B)

[Chemical formula 71]

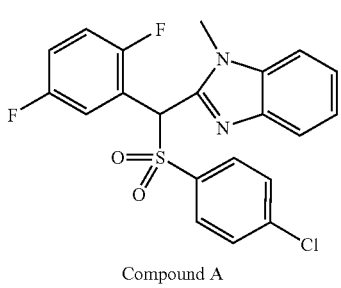

Compound A

-continued

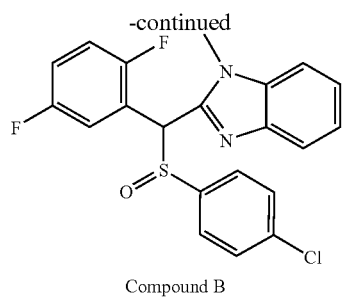

Compound B

Hexaammonium heptamolybdate tetrahydrate (60 mg) was added to a methanol (12 ml) solution of the 2-[[(4-chlorophenyl)thio]-(2,5-difluorophenyl)methyl]-1-methyl-1H-benzimidazole (190 mg, 0.474 mmol) obtained in Example 24. To the resulting mixture was added 30% aqueous hydrogen peroxide (6 ml), followed by stirring for 17 hours. Ethyl acetate (60 ml) was added to the reaction mixture. The resulting mixture was washed with water and brine, dried over anhydrous magnesium sulfate, and concentrated under reduced pressure. The residue was purified by silica gel chromatography (hexane:ethyl acetate=6:1 to 4:1) to give a nonpolar compound (Compound A) (48 mg, 23%) and a polar compound (Compound B) (23 mg, 12%) were obtained as needle crystals and a white solid, respectively.

Compound A $^1$H-NMR (400 MHz, CDCl$_3$) δ: 3.90 (3H, s), 6.14 (1H, s), 6.9-7.1 (2H, m), 7.26-7.42 (3H, m), 7.39 (2H, d, J=8.8 Hz), 7.46 (2H, d, J=8.8 Hz), 7.81 (1H, d, J=8.0 Hz), 8.16 (1H, m).

mp: 213 to 214° C.

Elemental Analysis for C$_{21}$H$_{15}$ClF$_2$N$_2$OS: Calculated: C, 58.27; H, 3.49; N, 6.47; S, 7.41; Cl, 8.19; F, 8.78. Found: C, 58.08; H, 3.62; N, 6.53; S, 7.35; Cl, 8.10; F, 8.74.

Compound B $^1$H-NMR (400 MHz, CDCl$_3$) δ: 3.35 (⅔H, s), 3.78 (⅓H, s), 5.52 (½H, s), 5.57 (½H, s), 6.78-7.1 (2H, m), 7.2-7.4 (7H, m), 7.76-7.95 (2H, m).

mp: 130-131° C.

FAB-MS: 477.0646 (Calcd for C$_{21}$H$_{16}$ClF$_2$N$_2$OS: 477.0640).

Example 29

2-[[(4-Chlorophenyl)sulfonyl]-(2,5-difluorophenyl)methyl]-1-methyl-5-chloro-1H-imidazole

[Chemical formula 72]

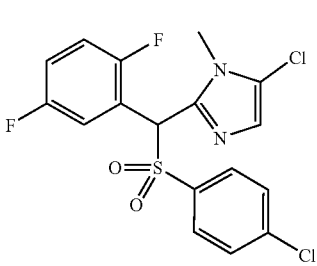

Hexaammonium heptamolybdate tetrahydrate (60 mg) was added to a methanol (12 ml) solution of the 2-[[(4-chlorophenyl)thio]-(2,5-difluorophenyl)methyl]-1-methyl-5-chloro-1H-imidazole (141 mg, 0.37 mmol) obtained in Example 25. To the resulting mixture was added 30% aqueous hydrogen peroxide (6 ml), followed by stirring for 64 hours. Ethyl acetate (60 ml) was added to the reaction mixture. The resulting mixture was washed with water and brine, dried over anhydrous magnesium sulfate and concentrated under reduced pressure. The residue was crystallized from ethanol to give the title compound (103 mg, 67%) as colorless needle crystals.

$^1$H-NMR (400 MHz, CDCl$_3$) δ: 3.71 (3H, s), 5.88 (1H, s), 6.93-7.08 (2H, m), 7.03 (1H, s), 7.43 (4H, s), 7.98 (1H, m).
mp: 179 to 180° C.
Elemental Analysis for C$_{17}$H$_{12}$Cl$_2$F$_2$N$_2$O$_2$S: Calculated: C, 48.90; H, 2.93; N, 6.71; S, 7.68; Cl, 16.99; F, 9.11. Found: C, 48.90; H, 2.93; N, 6.77; S, 7.80; Cl, 17.02; F, 9.19.

Example 30

2-[[(4-Chlorophenyl)sulfonyl]-(2,5-difluorophenyl)methyl]thiazole

[Chemical formula 73]

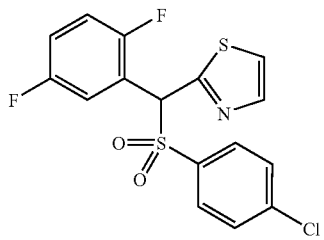

Hexaammonium heptamolybdate tetrahydrate (30 mg) was added to a methanol (6.0 ml) solution of the 2-[[(4-chlorophenyl)thio]-(2,5-difluorophenyl)methyl]thiazole (124 mg, 0.35 mmol) obtained in Example 26. To the resulting mixture was added 30% aqueous hydrogen peroxide (3 ml) and the mixture was stirred for 15 hours. Ethyl acetate (60 ml) was added to the reaction mixture. The resulting mixture was washed with water and brine, dried over anhydrous magnesium sulfate and concentrated under reduced pressure. The residue was crystallized from ethanol to give the title compound (91 mg, 67%) as colorless columnar crystals.
$^1$H-NMR (400 MHz, CDCl$_3$) δ: 6.21 (1H, s), 6.92-7.08 (2H, m), 7.41 (2H, d, J=8.8 Hz), 7.45 (1H, d, J=3.6 Hz), 7.56 (2H, d, J=8.8 Hz), 7.86 (1H, d, J=3.6 Hz), 7.94 (1H, m).
mp: 163 to 164° C.
Elemental Analysis for C$_{16}$H$_{10}$ClF$_2$NO$_2$S$_2$: Calculated: C, 49.81; H, 2.61; N, 3.63; S, 16.62; Cl, 9.19; F, 9.85. Found: C, 49.98; H, 2.61; N, 3.77; S, 16.60; Cl, 9.25; F, 9.87.

Example 31

2-[[(4-Chlorophenyl)sulfonyl]-(2,5-difluorophenyl)methyl]-1-(4-methoxyphenyl)-1H-imidazole

[Chemical formula 74]

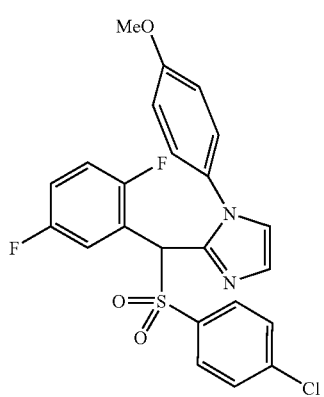

Hexaammonium heptamolybdate tetrahydrate (60 mg) was added to a methanol (12 ml) solution of the 2-[[(4-chlorophenyl)thio]-(2,5-difluorophenyl)methyl]-1-(4-methoxyphenyl)-1H-benzimidazole (118 mg, 0.27 mmol) obtained in Example 27. To the resulting mixture was added 30% aqueous hydrogen peroxide (6 ml), followed by stirring for 64 hours. Ethyl acetate (60 ml) was added to the reaction mixture. The resulting mixture was washed with water and brine, dried over anhydrous magnesium sulfate, and concentrated under reduced pressure. The residue was crystallized from ethanol to give the title compound (76 mg, 60%) as colorless needle crystals.
$^1$H-NMR (400 MHz, CDCl$_3$) δ: 3.89 (3H, s), 5.83 (1H, s), 6.93-7.05 (4H, m), 6.97 (2H, d, J=8.8 Hz), 7.01 (2H, d, J=8.8 Hz), 7.38 (2H, d, J=8.8 Hz), 7.41 (2H, d, J=8.8 Hz), 8.15 (1H, m).
mp: 150 to 151° C.
Elemental Analysis for C$_{23}$H$_{17}$ClF$_2$N$_2$O$_3$S: Calculated: C, 58.13; H, 3.61; N, 5.90; S, 6.75; Cl, 7.47; F, 8.00. Found: C, 58.09; H, 3.51; N, 5.99; S, 6.88; Cl, 7.48; F, 8.06.

Example 32

5-Chloro-2-[(2,5-difluorophenyl-4-pyridylmethyl)thio]pyridine

[Chemical formula 75]

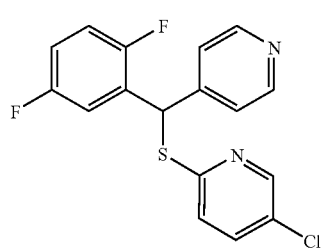

Triethylamine (0.279 ml, 2.00 mmol) and then, methanesulfonyl chloride (0.116 ml, 1.50 mmol) were added to a dichloromethane (10 ml) solution of the 2,5-difluorophenyl-4-pyridylmethanol (221 mg, 1.00 mmol) obtained in Referential Example 18 at 0° C. The resulting mixture was stirred for 3 hours at room temperature. The reaction mixture was washed with a saturated aqueous solution of sodium bicarbonate. The organic layer was dried over anhydrous sodium sulfate and then, filtered. The filtrate was concentrated under reduced pressure. To an N,N-dimethylformamide (10 ml) solution of the residue thus obtained were added the 5-chloro-2-pyridinethiol (145 mg, 1.00 mmol) obtained in Referential Example 17 and potassium carbonate (166 mg, 1.20 mmol) sequentially. The resulting mixture was stirred at room temperature for 2 hours. Ethyl acetate was added to the reaction mixture. The resulting mixture was washed with water. The organic layer was dried over anhydrous sodium sulfate and filtered. The filtrate was concentrated under reduced pressure. The residue was subjected to flash silica gel chromatography, and the fraction obtained from the hexane:ethyl acetate=17:3 eluate was concentrated under reduced pressure to give the title compound (267 mg, 0.77 mmol, 77%) as a yellow solid.
$^1$H-NMR (400 MHz, CDCl$_3$) δ: 6.52 (1H, s), 6.92-6.98 (1H, m), 6.99-7.06 (1H, m), 7.48 (1H, dd, J=8.5, 0.7 Hz), 7.17-7.23 (1H, m), 7.34 (2H, d, J=6.1 Hz), 7.47 (1H, dd, J=8.5, 2.4 Hz), 8.33 (1H, dd, J=2.4, 0.7 Hz), 8.54 (2H, d, J=6.1 Hz).
MSm/z: 349 (M$^+$+H).

Example 33

5-Chloro-2-[(2,5-difluorophenyl-4-pyridylmethyl)sulfonyl]pyridine

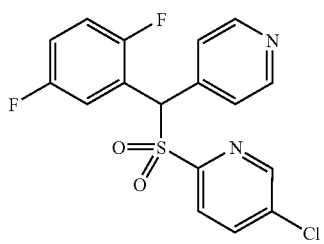

[Chemical formula 76]

To a methanol (6 ml) solution of 5-chloro-2-[(2,5-difluorophenyl-4-pyridylmethyl)thio]pyridine (239 mg, 0.68 mmol) was added a water (12 ml) solution of oxone (potassium peroxomonosulfate compound, 2KHSO$_5$·KHSO$_4$·K$_2$SO$_4$) (631 mg, 1.03 mmol) at 0° C. After the reaction mixture was stirred at room temperature for 3 days, dichloromethane was added thereto. The resulting mixture was washed with a saturated aqueous solution of sodium bicarbonate. The organic layer was dried over anhydrous sodium sulfate and filtered. The filtrate was concentrated under reduced pressure. The residue was purified by preparative high performance liquid chromatography (using a mixed solvent system of water/acetonitrile/formic acid). The solid thus obtained was washed with hexane/diisopropyl ether and then collected by filtration to give the title compound (67 mg, 0.18 mmol, 26%) as a white powder.

$^1$H-NMR (400 MHz, CDCl$_3$) δ: 6.44 (1H, s), 6.96-7.08 (2H, m), 7.48 (2H, d, J=6.3 Hz), 7.70-7.77 (1H, m), 7.79 (1H, dd, J=8.3, 2.2 Hz), 7.84 (1H, dd, J=8.3, 0.7 Hz), 8.61 (2H, d, J=6.3 Hz), 8.67 (1H, dd, J=2.2, 0.7 Hz).

Elemental Analysis for C$_{17}$H$_{11}$ClF$_2$N$_2$O$_2$S: Calculated: C, 53.62; H, 2.91; F, 9.98; N, 7.36; S, 8.42. Found: C, 53.55; H, 2.87; F, 10.10; N, 7.40; S, 8.55.

MSm/z: 381 (M$^+$+H).

Example 34

4-[[(4-Chlorophenyl)sulfonyl](2,5-difluorophenyl)methyl]tetrahydropyrane

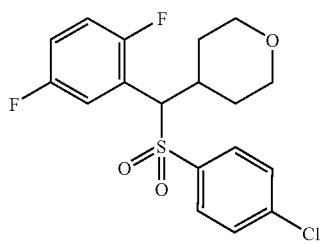

[Chemical formula 77]

The 2-[(4-chlorophenyl)sulfonylmethyl]-1,4-difluorobenzene (200 mg, 0.661 mmol) obtained in Referential Example 1 and tetrahydro-4H-pyran-4-ol (0.13 ml, 1.36 mmol) were dissolved in toluene (10 ml). After addition of cyanomethylenetri-n-butylphosphorane (330 mg, 1.37 mmol), the resulting mixture was heated under reflux for 14 hours in an argon atmosphere. The reaction mixture was then allowed to cool. After the addition of cyanomethylenetri-n-butylphosphorane (200 mg, 0.829 mmol), the resulting mixture was heated under reflux for 14 hours under an argon atmosphere. The reaction mixture was allowed to cool, and then concentrated under reduced pressure. The residue thus obtained was subjected to flash silica gel chromatography, and the fraction obtained from the hexane:ethyl acetate=4:1 eluate was concentrated under reduced pressure to afford a white solid. The resulting white solid was washed with hexane to give the title compound (157 mg, 0.406 mmol, 61%) as a white powder.

$^1$H-NMR (400 MHz, CDCl$_3$) δ: 1.28-1.48 (2H, m), 1.71 (1H, ddd, J=25.3, 11.7, 4.3 Hz), 2.37 (1H, brd, J=12.7 Hz), 2.70-2.88 (1H, m), 3.40 (1H, td, J=11.7, 2.5 Hz), 3.50 (1H, td, J=12.0, 2.2 Hz), 3.91 (1H, dm, J=11.2 Hz), 4.02 (1H, dm, J=11.7 Hz), 4.46 (1H, d, J=8.8 Hz), 6.68-6.80 (1H, m), 6.88-6.98 (1H, m), 7.31 (2H, d, J=8.5 Hz), 7.36-7.45 (1H, m), 7.49 (2H, d, J=8.5 Hz).

mp: 150 to 152° C.

MSm/z: 387 (M$^+$+H).

Elemental Analysis for C$_{18}$H$_{17}$ClF$_2$O$_3$S: Calculated: C, 55.89; H, 4.43; Cl, 9.16; F, 9.82; S, 8.29. Found: C, 55.64; H, 4.27; Cl, 9.41; F, 9.89; S, 8.28.

Example 35

4-[[(4-Chlorophenyl)sulfonyl](2,5-difluorophenyl)methyl]tetrahydrothiopyrane

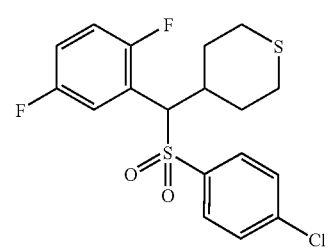

[Chemical formula 78]

The 2-[(4-chlorophenyl)sulfonylmethyl]-1,4-difluorobenzene (500 mg, 1.65 mmol) obtained in Referential Example 1 and the tetrahydrothiopyran-4-ol (400 mg, 3.38 mmol) obtained in Referential Example 19 were dissolved in toluene (20 ml). After addition of cyanomethylenetri-n-butylphosphorane (800 mg, 3.31 mmol), the resulting mixture was heated under reflux for 14 hours under an argon atmosphere. The reaction mixture was allowed to cool, and cyanomethylenetri-n-butylphosphorane (400 mg, 1.66 mmol) was added thereto. Under an argon atmosphere, the resulting mixture was heated under reflux for 14 hours. The reaction mixture was allowed to cool, and then concentrated under reduced pressure. The residue thus obtained was subjected to flash silica gel chromatography. The fraction obtained from the hexane:ethyl acetate=15:1 eluate was concentrated under reduced pressure to afford a white solid. The resulting white solid was washed with a hexane/diisopropyl ether mixture to give the title compound (404 mg, 1.00 mmol, 61%) as a white powder.

$^1$H-NMR (400 MHz, CDCl$_3$) δ: 1.47 (1H, ddd, J=23.4, 10.0, 3.3 Hz), 1.68 (1H, ddd, J=25.0, 11.4, 3.3 Hz), 2.13 (1H, dm, J=11.4 Hz), 2.50-2.78 (5H, m), 2.82 (1H, td, J=12.8, 2.6 Hz), 4.47 (1H, d, J=7.3 Hz), 6.72-6.82 (1H, m), 6.90-7.00 (1H, m), 7.31 (2H, d, J=8.8 Hz), 7.40-7.60 (1H, m), 7.49 (2H, d, J=8.8 Hz).

mp: 150 to 152° C.

MSm/z: 403 (M$^+$+H).

Elemental Analysis for $C_{18}H_{17}ClF_2O_2S_2$: Calculated: C, 53.66; H, 4.25; Cl, 8.80; F, 9.43; S, 15.92. Found: C, 53.52; H, 4.21; Cl, 9.00; F, 9.54; S, 15.88.

Example 36

4-[[(4-Chlorophenyl)sulfonyl](2,5-difluorophenyl)methyl]tetrahydrothiopyrane-1,1-dioxide (Compound A) and 4-[[(4-chlorophenyl)sulfonyl](2,5-difluorophenyl)methyl]tetrahydrothiopyran-1-oxide (Compound B (Isomer A) and Compound B (Isomer B))

[Chemical formula 79]

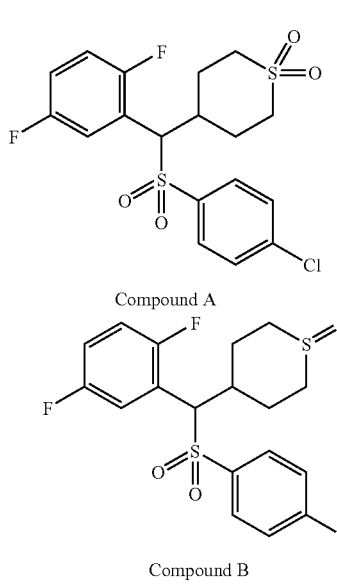

Compound A

Compound B

After 4-[[(4-chlorophenyl)sulfonyl](2,5-difluorophenyl)methyl]tetrahydrothiopyrane (360 mg, 0.893 mmol) was dissolved in dichloromethane (15 ml), 3-chloroperbenzoic acid (320 mg, 1.85 mmol) was added to the resulting solution under ice cooling. After stirring at room temperature for 14 hours, the reaction mixture was concentrated under reduced pressure. The residue thus obtained was subjected to flash silica gel chromatography, and the fraction obtained from the hexane:ethyl acetate=1:1 eluate was concentrated under reduced pressure to afford a white solid. The resulting white solid was dissolved in dichloromethane. The resulting solution was washed sequentially with a 1N aqueous sodium hydroxide solution and brine. The organic layer was dried over anhydrous magnesium sulfate. After filtration, the filtrate was concentrated under reduced pressure to afford a white solid. The resulting white solid was washed with diethyl ether to give the title Compound A (187 mg, 0.430 mmol, 48%) as a white powder. Moreover, the fraction obtained from the dichloromethane:methanol=50:1 eluate was concentrated under reduced pressure to give a mixture of the title Compound B (Isomer A) and the title Compound B (Isomer B) as a white solid. The resulting mixture was separated and purified by flash silica gel chromatography (dichloromethane:methanol=80:1). The white solids thus obtained were washed with diethyl ether to give the title Compound B (Isomer A) (low polarity) (78 mg, 0.19 mmol, 21%) as a white powder and the title Compound B (Isomer B) (high polarity) (69 mg, 0.17 mmol, 19%) as a white powder.

Compound A $^1$H-NMR (400 MHz, CDCl$_3$) δ: 1.85-2.00 (1H, m), 2.18-2.35 (2H, m), 2.68-2.91 (2H, m), 2.98-3.10 (2H, m), 3.10-3.28 (2H, m), 4.54 (1H, brd, J=7.1 Hz), 6.74-6.90 (1H, m), 6.94-7.06 (1H, m), 7.33 (2H, d, J=8.7 Hz), 7.35-7.55 (1H, m), 7.49 (2H, d, J=8.7 Hz).

mp: 245 to 248° C.

Elemental Analysis for $C_{18}H_{17}ClF_2O_4S_2$: Calculated: C, 49.71; H, 3.94; Cl, 8.15; F, 8.74; S, 14.75. Found: C, 49.38; H, 3.87; Cl, 8.50; F, 8.86; S, 14.62.

Compound B (Isomer A)

$^1$H-NMR (400 MHz, CDCl$_3$) δ: 1.76 (1H, brd, J=13.4 Hz), 2.18 (1H, ddm, J=25.4, 12.5 Hz), 2.32-2.70 (4H, m), 2.74-2.90 (1H, m), 2.98 (1H, dm, J=14.0 Hz), 3.09 (1H, dm, J=14.4 Hz), 4.53 (1H, d, J=7.3 Hz), 6.72-6.86 (1H, m), 6.90-7.02 (1H, m), 7.32 (2H, d, J=8.5 Hz), 7.40-7.60 (1H, m), 7.49 (2H, d, J=8.5 Hz).

mp: 255 to 256° C.

Elemental Analysis for $C_{18}H_{17}ClF_2O_3S_2$: Calculated: C, 51.61; H, 4.09; Cl, 8.46; F, 9.07; S, 15.31. Found: C, 51.51; H, 4.04; Cl, 8.69; F, 9.15; S, 15.20.

Compound B (Isomer B)

$^1$H-NMR (400 MHz, CDCl$_3$) δ: 1.42 (1H, ddm, J=22.3, 11.7 Hz), 1.92 (1H, ddm, J=11.7, 11.0 Hz), 2.14-2.27 (1H, m), 2.66 (1H, td, J=12.2, 2.7 Hz), 2.70-2.90 (3H, m), 3.10-3.24 (1H, m), 3.32-3.44 (1H, m), 4.49 (1H, d, J=8.1 Hz), 6.72-6.85 (1H, m), 6.90-7.02 (1H, m), 7.32 (2H, d, J=8.5 Hz), 7.34-7.50 (1H, m), 7.48 (2H, d, J=8.5 Hz)

mp: 184 to 187° C.

Elemental Analysis for $C_{18}H_{17}ClF_2O_3S_2$: Calculated: C, 51.61; H, 4.09; Cl, 8.46; F, 9.07; S, 15.31. Found: C, 51.82; H, 4.23; Cl, 8.42; F, 9.12; S, 15.07.

Example 37 t-Butyl 4-[[(4-chlorophenyl)sulfonyl](2,5-difluorophenyl)methyl]-1-piperidinecarboxylate

[Chemical formula 80]

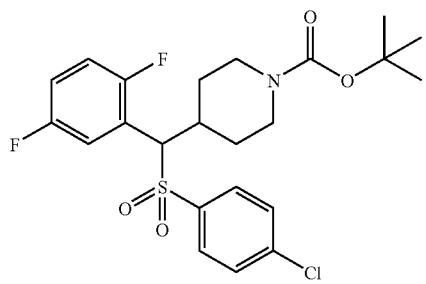

The 2-[(4-chlorophenyl)sulfonylmethyl]-1,4-difluorobenzene (1.25 g, 4.13 mmol) obtained in Referential Example 1 and t-butyl 4-hydroxy-1-piperidinecarboxylate (1.70 g, 8.44 mmol) were dissolved in toluene (50 ml). To the resulting solution was added cyanomethylenetri-n-butylphosphorane (2.00 g, 8.29 mmol). The resulting mixture was heated under reflux for 14 hours under an argon atmosphere. The reaction mixture was allowed to cool and then, concentrated under reduced pressure. The residue thus obtained was subjected to flash silica gel chromatography. The fraction obtained from the hexane:ethyl acetate=1:1 eluate was concentrated under reduced pressure to give a white solid. The resulting white solid was washed with diethyl ether to give the title compound (1.68 g, 3.46 mmol, 84%) as a white powder.

$^1$H-NMR (400 MHz, CDCl$_3$) δ: 1.10-1.25 (1H, m), 1.40-1.70 (2H, m), 1.44 (9H, s), 2.30-2.50 (1H, m), 2.60-2.95 (3H, m), 4.00-4.25 (2H, m), 4.45 (1H, d, J=7.8 Hz), 6.69-6.80 (1H, m), 6.88-6.98 (1H, m), 7.31 (2H, d, J=8.6 Hz), 7.35-7.50 (1H, m), 7.49 (2H, d, J=8.6 Hz).

mp: 193 to 196° C.
Elemental Analysis for $C_{23}H_{26}ClF_2NO_4S$: Calculated: C, 56.84; H, 5.39; Cl, 7.30; F, 7.82; N, 2.88; S, 6.60. Found: C, 56.41; H, 5.43; Cl, 7.77; F, 7.61; N, 2.99; S, 6.58.

Example 38

4-[[(4-Chlorophenyl)sulfonyl](2,5-difluorophenyl)methyl]piperidine hydrochloride

[Chemical formula 81]

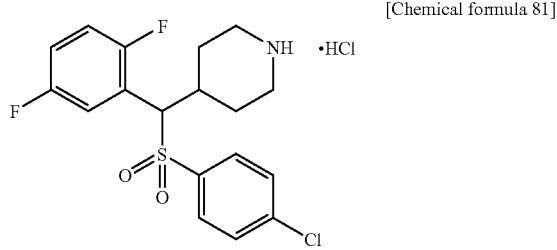

In dichloromethane (50 ml) was dissolved t-butyl 4-[[(4-chlorophenyl)sulfonyl](2,5-difluorophenyl)methyl]-1-piperidinecarboxylate (1.56 g, 3.21 mmol). Trifluoroacetic acid (5.0 ml) was added dropwise to the resulting solution under ice cooling. The reaction mixture was stirred at room temperature for 2 hours and then, concentrated under reduced pressure. To the residue thus obtained were added dichloromethane (10 ml) and a 1N hydrochloric acid-ethanol solution (10 ml). The resulting mixture was concentrated under reduced pressure to give a white solid. The resulting solid was washed with diethyl ether to give the title compound (1.36 g, 3.12 mmol, 97%) as a white powder.

$^1$H-NMR (400 MHz, CD$_3$OD) δ: 1.38-1.52 (1H, m), 1.70-1.92 (2H, m), 2.73 (1H, brd, J=14.2 Hz), 2.86-3.00 (1H, m), 3.05 (1H, td, J=12.9, 3.1 Hz), 3.13 (1H, td, J=13.1, 3.1 Hz), 3.30-3.40 (1H, m), 3.48 (1H, dm, J=13.0 Hz), 4.72 (1H, d, J=8.6 Hz), 6.82-6.98 (1H, m), 7.04-7.12 (1H, m), 7.40-7.55 (1H, m), 7.44 (2H, d, J=8.6 Hz), 7.57 (2H, d, J=8.6 Hz).

mp: 184 to 190° C.

Elemental Analysis for $C_{18}H_{18}ClF_2NO_2S \cdot HCl \cdot 0.75H_2O$: Calculated: C, 49.61; H, 4.74; Cl, 16.27; F, 8.72; N, 3.21; S, 7.36. Found: C, 49.57; H, 4.75; Cl, 15.79; F, 9.16; N, 3.34; S, 7.25.

Example 39

2-[(4-Chlorophenylthio)-(2,5-difluorophenyl)methyl]-5-[(4-chlorophenylthio)methyl]pyridine

[Chemical formula 82]

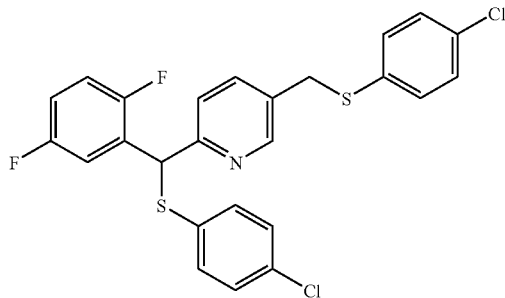

An ethanol (15 ml) suspension of sodium borohydride (33 mg, 0.88 mmol) was cooled to −78° C. While stirring, an ethanol solution (10 ml) of the [6-(2,5-difluorophenylcarbonyl)pyridin-3-yl]methyl acetate (510 mg, 1.75 mmol) obtained in Referential Example 21 was added to the suspension in portions. The reaction mixture was stirred for 30 minutes. An aqueous solution of ammonium chloride was added and the resulting mixture was allowed to stand until it became room temperature. The reaction mixture was extracted with ethyl acetate (100 ml). The extract was washed with water and brine, dried over anhydrous magnesium sulfate and concentrated under reduced pressure. The residue was dissolved in methylene chloride (30 ml), followed by the addition of triethylamine (270 μl) and methanesulfonyl chloride (270 μl) under ice cooling. The reaction mixture was stirred at room temperature for 3 days. After the addition of water, the mixture was extracted with ethyl acetate (60 ml). The extract was washed with water and brine, dried over anhydrous magnesium sulfate and concentrated under reduced pressure. The residue thus obtained was dissolved in N,N-dimethylformamide (25 ml). To the resulting solution were added 4-chlorobenzenethiol (751 mg, 5.3 mmol) and potassium carbonate (718 mg, 5.2 mmol) under a nitrogen atmosphere. The reaction mixture was stirred at 60° C. for 1 hour. After the reaction mixture was cooled to room temperature, diethyl ether (80 ml) was added thereto. The resulting mixture was washed with water and brine. The organic layer was dried over magnesium sulfate, and concentrated under reduced pressure. The residue was subjected to silica gel chromatography (hexane:ethyl acetate=10:1) to give the title compound (237 mg, 27%) as a white solid.

$^1$H-NMR (400 MHz, CDCl$_3$) δ: 3.99 (2H, s), 5.81 (1H, s), 6.90 (2H, m), 7.15 (2H, d, J=8.8 Hz), 7.16 (2H, d, J=8.8 Hz), 7.19 (4H, d, J=8.8 Hz), 7.20 (1H, d, J=7.6 Hz), 7.38 (1H, m), 7.49 (1H, dd, J=2.0, 7.6 Hz), 8.38 (1H, br).

mp: 87 to 88° C.

Example 40

2-[(4-Chlorophenylsulfonyl)-(2,5-difluorophenyl)methyl]-5-[(4-chlorophenylsulfonyl)methyl]pyridine

[Chemical formula 83]

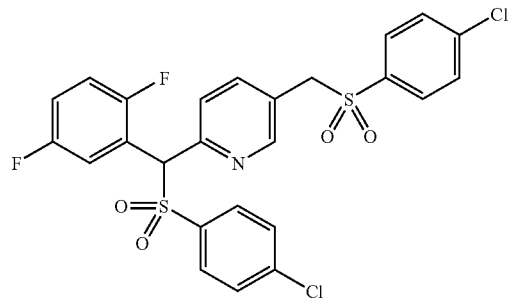

Hexaammonium heptamolybdate tetrahydrate (30 mg) was added to a methanol (6.0 ml) solution of 2-[(4-chlorophenylthio)-(2,5-difluorophenyl)methyl]-5-[(4-chlorophenylthio)methyl]pyridine (75 mg, 0.15 mmol), followed by the addition of 30% aqueous hydrogen peroxide (3 ml). The resulting mixture was stirred for 22 hours. Ethyl acetate was added to the reaction mixture. The resulting mixture was washed with water, an aqueous solution of sodium thiosulfate and brine, dried and concentrated under reduced pressure. The residue thus obtained was purified by silica gel chromatography (2% MeOH/CHCl$_3$) to give the title compound (70 mg, 62%) as colorless needle crystals.

$^1$H-NMR (400 MHz, CDCl$_3$) δ: 4.29 (2H, s), 5.91 (1H, s), 6.90-7.08 (2H, m), 7.39 (2H, dd, J=1.6, 6.8 Hz), 7.45 (2H, dd, J=1.6, 6.8 Hz), 7.51 (2H, d, J=8.8 Hz), 7.55 (2H, d, J=8.8 Hz), 7.60 (1H, d, J=8.0 Hz), 7.65 (1H, dd, J=2.4, 8.0 Hz), 7.91 (1H, m), 8.23 (1H, s).

mp: 186 to 187° C.

Elemental Analysis for $C_{25}H_{17}Cl_2F_2NO_4S_2$: Calculated: C, 52.82; H, 3.01; N, 2.46; S, 11.28; Cl, 12.47; F, 6.68. Found: C, 52.88; H, 3.10; N, 2.63; S, 11.38; Cl, 12.40; F, 6.83.

Example 41

2-[(4-Chlorophenylthio)-(2,5-difluorophenyl)methyl]-5-(1,3-dioxolan-2-yl)pyridine

[Chemical formula 84]

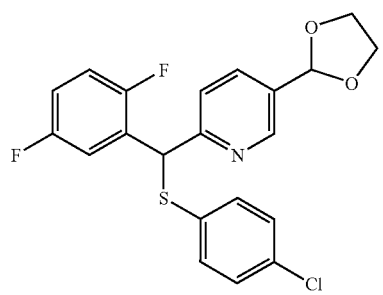

Under a nitrogen atmosphere, triethylamine (1.08 ml, 7.8 mmol) and methanesulfonyl chloride (0.52 ml, 6.8 mmol) were added to a methylene chloride solution (30 ml) of the 2-[(2,5-difluorophenyl)-hydroxymethyl]-5-(1,3-dioxolan-2-yl)pyridine (1.52 g, 5.2 mmol) obtained in Referential Example 22 under ice cooling. The resulting mixture was stirred at room temperature for 3 hours. After addition of a saturated aqueous solution of sodium bicarbonate, the resulting mixture was extracted with ether. The extract was washed with brine, dried over anhydrous magnesium sulfate and concentrated under reduced pressure. The residue thus obtained was dissolved in dimethylformamide (30 ml). To the resulting solution were added chlorobenzenethiol (901 mg, 6.2 mmol) and potassium carbonate (1.08 g, 7.8 mmol), followed by stirring at 60° C. for 3 hours. After cooling to room temperature, the reaction mixture was diluted with ether. The diluted solution was washed with water and brine, dried over anhydrous magnesium sulfate and concentrated under reduced pressure. The residue thus obtained was purified by silica gel chromatography (hexane:ethyl acetate=5:1) to give the title compound (1.56 g, 71%) as colorless needle crystals.

$^1$H-NMR (400 MHz, CDCl$_3$) δ: 4.0-4.15 (4H, m), 5.84 (1H, s), 5.92 (1H, s), 6.85-6.96 (2H, m), 7.19 (2H, d, J=8.8 Hz), 7.25 (2H, d, J=8.8 Hz), 7.43 (1H, d, J=8.0 Hz), 7.43 (1H, m), 7.77 (1H, dd, J=2.0, 8.0 Hz), 8.70 (1H, d, J=2.0 Hz).

mp: 70 to 73° C.

MSm/z: 420 (M$^+$+H).

Example 42

2-[(4-Chlorophenylsulfonyl)-(2,5-difluorophenyl)methyl]-5-(1,3-dioxolan-2-yl)pyridine

[Chemical formula 85]

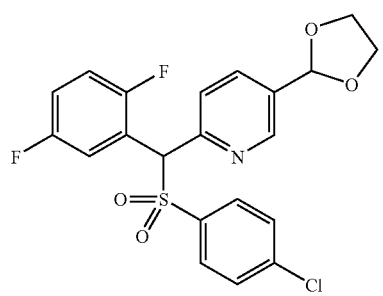

Hexaammonium heptamolybdate tetrahydrate (150 mg) was added to a methanol (30 ml) solution of 2-[(4-chlorophenylthio)-(2,5-difluorophenyl)methyl]-5-(1,3-dioxolan-2-yl)pyridine (1.54 g, 3.67 mmol). To the resulting mixture was added 30% aqueous hydrogen peroxide (15 ml), followed by stirring for 24 hours. After the reaction mixture was diluted with ethyl acetate, the diluted solution was washed with water and brine and concentrated under reduced pressure. The residue thus obtained was crystallized from ethanol to give the title compound (1.22 g, 74%) as colorless needle crystals.

$^1$H-NMR (400 MHz, CDCl$_3$) δ: 4.02-4.10 (4H, m), 5.85 (1H, s), 5.97 (1H, s), 6.91 (1H, m), 6.96 (1H, m), 7.38 (2H, d, J=8.4 Hz), 7.53 (2H, d, J=8.4 Hz), 7.63 (1H, d, J=7.6 Hz), 7.82 (1H, d, J=8.0 Hz), 7.94 (1H, m), 8.67 (1H, br-s).

mp: 167 to 168° C.

FAB-MS: 452.0544 (Calcd for C$_{21}$H$_{17}$ClF$_2$NO$_4$S: 452.0535).

Example 43

2-[(4-Chlorophenylsulfonyl)-(2,5-difluorophenyl)methyl]-5-(hydroxymethyl)pyridine

[Chemical formula 86]

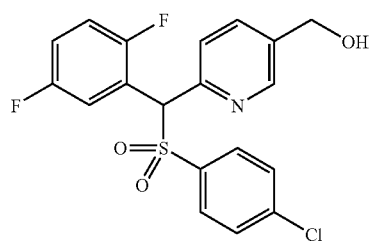

To a 1,4-dioxane solution (30 ml) of 2-[(4-chlorophenylsulfonyl)-(2,5-difluorophenyl)methyl]-5-(1,3-dioxolan-2-yl)pyridine (295 mg, 0.54 mmol) was added 1N hydrochloric acid (30 ml). The resulting mixture was stirred at room temperature for 18 hours. The reaction mixture was extracted with ethyl acetate. The extract was washed with water, a saturated aqueous solution of sodium bicarbonate, and brine, dried over anhydrous magnesium sulfate and concentrated under reduced pressure to give a residue.

The residue thus obtained was dissolved in ethanol (10 ml). Under ice cooling, sodium borohydride (10 mg, 0.27 mmol) was added to the resulting solution. The resulting mixture was stirred for 1 hour. Water was added and the resulting mixture was extracted with ethyl acetate. The extract was washed with water and brine, dried over anhydrous magnesium sulfate, and concentrated under reduced pressure to give a residue. The resulting residue was purified by silica gel chromatography (3% methanol/chloroform) to give the title compound (205 mg, 93%) as needle crystals.

$^1$H-NMR (400 MHz, CDCl$_3$) δ: 4.74 (2H, s), 5.94 (1H, s), 6.91 (1H, m), 6.99 (1H, m), 7.38 (2H, d, J=8.4 Hz), 7.53 (2H, d, J=8.4 Hz), 7.62 (1H, d, J=8.0 Hz), 7.76 (1H, dd, J=2.0, 8.0 Hz), 7.98 (1H, m), 8.58 (1H, d, J=2.0 Hz)

mp: 151 to 152° C.

FAB-MS: 410.0444 (Calcd for C$_{19}$H$_{15}$ClF$_2$NO$_3$S: 410.0429).

Example 44

Methyl 3-[6-[(4-chlorophenylsulfonyl)-(2,5-difluorophenyl)methyl]pyridin-3-yl]acrylate

[Chemical formula 87]

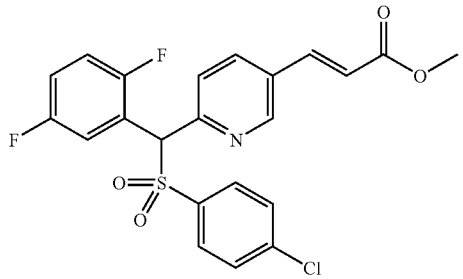

To a 1,4-dioxane solution (10 ml) of the 2-[(4-chlorophenylsulfonyl)-(2,5-difluorophenyl)methyl]-5-(1,3-dioxolan-2-yl)pyridine (212 mg, 0.47 mmol) obtained in Example 42 was added 1N hydrochloric acid (10 ml). The resulting mixture was stirred at room temperature for 19 hours. The reaction mixture was extracted with ethyl acetate. The extract was washed with water, a saturated aqueous solution of sodium bicarbonate and brine, dried over anhydrous magnesium sulfate and concentrated under reduced pressure to afford a residue.

The resulting residue was dissolved in tetrahydrofuran (15 ml). Under a nitrogen atmosphere, methyl (triphenylphosphoranylidene)acetate (188 mg, 0.56 mmol) was added and the resulting mixture was stirred for 17 hours. The reaction mixture was concentrated under reduced pressure to give a residue. The resulting residue thus obtained was purified by silica gel chromatography (hexane:ethyl acetate=5:1) to give the title compound (187 mg, 86%) as needle crystals.

$^1$H-NMR (400 MHz, CDCl$_3$) δ: 3.80 (3H, s), 5.94 (1H, s), 6.50 (1H, d, J=16.0 Hz), 6.91 (1H, m), 6.99 (1H, m), 7.38 (2H, d, J=8.8 Hz), 7.53 (2H, d, J=8.8 Hz), 7.63 (1H, d, J=8.0 Hz), 7.63 (1H, d, J=16.0 Hz), 7.84 (1H, dd, J=2.0, 8.0 Hz), 7.98 (1H, m), 8.70 (1H, d, J=2.0 Hz).

mp: 145 to 146° C.

MSm/z: 464 (M$^+$+H).

Example 45

Methyl 3-[6-[(4-chlorophenylsulfonyl)-(2,5-difluorophenyl)methyl]pyridin-3-yl]propionate

[Chemical formula 88]

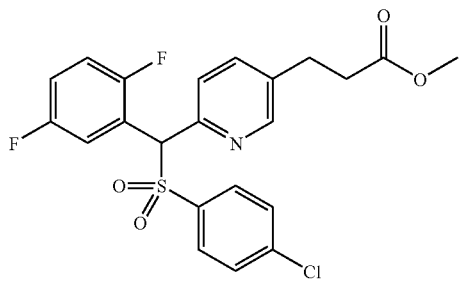

Methyl 3-[6-[(4-chlorophenylsulfonyl)-(2,5-difluorophenyl)methyl]pyridin-3-yl]acrylate (160 mg, 0.34 mmol) was dissolved in ethanol (15 ml). To the resulting solution was added palladium carbon (30 mg). The resulting mixture was vigorously stirred under a hydrogen atmosphere of 1 atmospheric pressure for 24 hours. After the reaction mixture was filtered, the filtrate was concentrated under reduced pressure. The residue thus obtained was purified by silica gel chromatography (hexane:ethyl acetate=5:1) to give the title compound (94 mg, 58%) as needle crystals.

$^1$H-NMR (400 MHz, CDCl$_3$) δ: 2.63 (2H, t, J=7.6 Hz), 2.95 (2H, t, J=7.6 Hz), 3.65 (3H, s), 5.89 (1H, s), 6.90 (1H, m), 6.97 (1H, m), 7.36 (2H, d, J=8.4 Hz), 7.53 (2H, d, J=8.4 Hz), 7.55 (2H, m), 8.00 (1H, m), 8.45 (1H, d, J=1.6 Hz).

mp: 121-123° C.

MSm/z: 466 (M$^+$+H).

Example 46

3-[6-[(4-Chlorophenylsulfonyl)-(2,5-difluorophenyl)methyl]pyridin-3-yl]propionic acid

[Chemical formula 89]

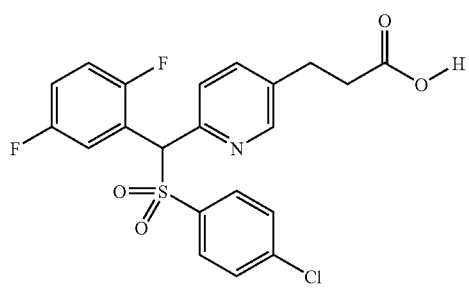

In tetrahydrofuran (5 ml) was dissolved methyl 3-[6-[(4-chlorophenylsulfonyl)-(2,5-difluorophenyl)methyl]pyridin-3-yl]propionate (92 mg, 0.20 mmol). An aqueous solution (3 ml) of lithium hydroxide (23 mg, 0.5 mmol) was added to the resulting solution and the mixture was stirred for 2 hours. After addition of 10% sodium hydrogensulfate, the resulting mixture was extracted with ethyl acetate. The extract was washed with water and brine, dried over anhydrous magnesium sulfate, and concentrated under reduced pressure to give a residue. The resulting residue was crystallized from ethanol to give the title compound (67 mg, 75%) as needle crystals.

$^1$H-NMR (400 MHz, CDCl$_3$) δ: 2.69 (2H, t, J=7.6 Hz), 2.96 (2H, t, J=7.6 Hz), 5.92 (1H, s), 6.90 (1H, m), 6.98 (1H, m), 7.36 (2H, d, J=8.4 Hz), 7.52 (2H, d, J=8.4 Hz), 7.56 (2H, m), 7.99 (1H, m), 8.47 (1H, d, J=2.4 Hz).

mp: 158 to 160° C.

MSm/z: 452 (M$^+$+H).

Elemental Analysis for $C_{21}H_{16}ClF_2NO_4S$: Calculated: C, 55.82; H, 3.57; N, 3.10; S, 7.10; Cl, 7.85; F, 8.41. Found: C, 55.70; H, 3.75; N, 3.19; S, 7.12; Cl, 8.64; F, 8.11.

Example 47

[6-[(4-Chlorophenylsulfonyl)-(2,5-difluorophenyl)methyl]pyridin-3-yl]carbaldehyde

[Chemical formula 90]

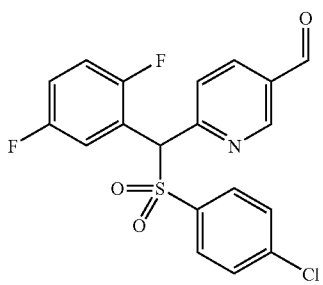

To a 1,4-dioxane solution (30 ml) of the 2-[(4-chlorophenylsulfonyl)-(2,5-difluorophenyl)methyl]-5-(1,3-dioxolan-2-yl)pyridine (602 mg, 1.3 mmol) obtained in Example 42 was added 1N hydrochloric acid (30 ml). The resulting mixture was stirred at room temperature for 18 hours. The reaction mixture was extracted with ethyl acetate. The extract was washed with water, a saturated aqueous solution of sodium bicarbonate and brine, dried over anhydrous magnesium sulfate and concentrated under reduced pressure to give a residue. The resulting residue was purified by silica gel chromatography (hexane:ethyl acetate=5:1) to give the title compound (530 mg, 98%) as needle crystals.

$^1$H-NMR (400 MHz, CDCl$_3$) δ: 6.01 (1H, s), 6.94 (1H, m), 7.01 (1H, m), 7.40 (2H, d, J=8.4 Hz), 7.54 (2H, d, J=8.4 Hz), 7.81 (1H, d, J=8.4 Hz), 7.97 (1H, m), 8.20 (1H, dd, J=2.0, 8.4 Hz), 9.05 (1H, d, J=2.0 Hz), 10.12 (1H, s).

Example 48

2-[(4-Chlorophenylsulfonyl)-(2,5-difluorophenyl)methyl]-5-(piperidin-1-ylmethyl)pyridine

[Chemical formula 91]

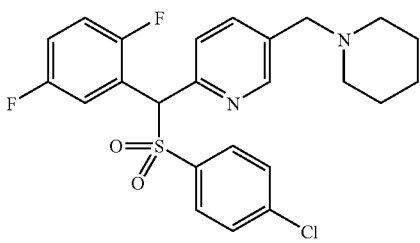

To a methylene chloride solution (5 ml) of [6-[(4-chlorophenylsulfonyl)-(2,5-difluorophenyl)methyl]pyridin-3-yl]carbaldehyde (82 mg, 0.2 mmol) and piperidine (40 μl, 0.4 mmol) were added acetic acid (23 μl, 0.4 mmol) and sodium triacetoxyborohydride (85 mg, 0.4 mmol) at room temperature. The resulting mixture was stirred for 3 hours. After the reaction was terminated by the addition of a saturated aqueous solution of sodium bicarbonate, the reaction mixture was diluted with ethyl acetate (80 ml). The organic layer was collected by separation, washed with water and brine, dried and concentrated under reduced pressure. The residue thus obtained was purified by silica gel chromatography (hexane:ethyl acetate=1:1), followed by crystallization from ethanol to give the title compound (89 mg, 93%).

$^1$H-NMR (400 MHz, CDCl$_3$) δ: 1.5-1.6 (6H, m), 2.3-2.4 (4H, m), 3.45 (2H, s), 5.91 (1H, s), 6.90 (1H, m), 6.98 (1H, m), 7.35 (2H, d, J=8.4 Hz), 7.52 (2H, d, J=8.4 Hz), 7.53 (1H, m), 7.7 (1H, br), 8.02 (1H, m), 8.49 (1H, d, J=2.4 Hz).

mp: 113 to 114° C.

MSm/z: 477 (M$^+$+H).

Elemental Analysis for C$_{24}$H$_{23}$ClF$_2$N$_2$O$_2$S: Calculated: C, 60.44; H, 4.86; N, 5.87; S, 6.72; Cl, 7.43; F, 7.97. Found: C, 59.87; H, 4.81; N, 5.83; S, 6.87; Cl, 7.55; F, 8.02.

Example 49

4-[[6-[(4-Chlorophenylsulfonyl)-(2,5-difluorophenyl)methyl]pyridin-3-yl]methyl]morpholine

[Chemical formula 92]

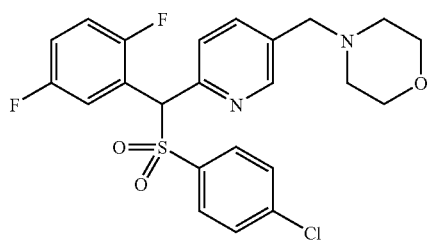

To a methylene chloride solution (5 ml) of the [6-[(4-chlorophenylsulfonyl)-(2,5-difluorophenyl)methyl]pyridin-3-yl]carbaldehyde (82 mg, 0.2 mmol) obtained in Example 47 and morpholine (35 μl, 0.4 mmol) were added acetic acid (23 μl, 0.4 mmol) and sodium triacetoxyborohydride (85 mg, 0.4 mmol) at room temperature. The resulting mixture was stirred for 3 hours. After the reaction was terminated by the addition of a saturated aqueous solution of sodium bicarbonate, the reaction mixture was diluted with ethyl acetate (80 ml). The organic layer was collected by separation, washed with water and brine, dried and then concentrated under reduced pressure to give a residue. The resulting residue was purified by silica gel chromatography (hexane:ethyl acetate=1:1), followed by crystallization from ethanol to give the title compound (90 mg, 94%).

$^1$H-NMR (400 MHz, CDCl$_3$) δ: 2.4 (4H, m), 3.49 (2H, s), 3.6 (4H, m), 5.92 (1H, s), 6.90 (1H, m), 6.98 (1H, m), 7.36 (2H, d, J=8.4 Hz), 7.53 (2H, d, J=8.4 Hz), 7.57 (1H, d, J=8.0 Hz), 7.71 (1H, br-d, J=8.0 Hz), 8.02 (1H, m), 8.53 (1H, d, J=2.0 Hz).

mp: 120 to 121° C.

MSm/z: 479 (M$^+$+H).

Elemental Analysis for C$_{22}$H$_{21}$ClF$_2$N$_2$O$_3$S: Calculated: C, 57.68; H, 4.42; N, 5.85; S, 6.70; Cl, 7.40; F, 7.93. Found: C, 57.41; H, 4.43; N, 5.90; S, 6.82; Cl, 7.52; F, 7.91.

Example 50

[6-[(4-Chlorophenylsulfonyl)-(2,5-difluorophenyl)methyl]pyridin-3-yl]carboxylic acid

[Chemical formula 93]

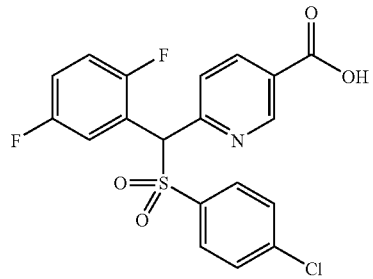

To a t-butanol solution (3.0 ml) of the [6-[(4-chlorophenylsulfonyl)-(2,5-difluorophenyl)methyl]pyridin-3-yl]carbaldehyde (110 mg, 0.27 mmol) obtained in Example 47 was added 2-methyl-2-butene (143 μl, 1.35 mmol). An aqueous solution (0.6 ml) of sodium dihydrogenphosphate (32.4 mg, 0.27 mmol) was added to the resulting suspension. Sodium chlorite (98 mg, 1.08 mmol) was added further and the mixture was stirred for 2 hours. To the reaction mixture were added water (30 ml) and acetic acid (1 ml). The resulting mixture was extracted with ethyl acetate (100 ml). The extract was washed with brine, dried and distilled under reduced pressure. The residue thus obtained was crystallized from ethanol to give the title compound (71 mg, 62%) as colorless needle crystals.

$^1$H-NMR (400 MHz, CDCl$_3$) δ: 6.03 (1H, s), 6.96 (1H, m), 7.03 (1H, m), 7.42 (2H, d, J=8.4 Hz), 7.56 (2H, d, J=8.4 Hz), 7.73 (1H, d, J=8.4 Hz), 7.97 (1H, m), 8.35 (1H, dd, J=2.0, 8.4 Hz), 9.20 (1H, d, J=2.0 Hz).

mp: >230° C.

MSm/z: 424 (M$^+$+H).

Elemental Analysis for C$_{19}$H$_{12}$ClF$_2$NO$_4$S: Calculated: C, 53.84; H, 2.85; N, 3.30; S, 7.57; Cl, 8.37; F, 8.97. Found: C, 53.47; H, 2.81; N, 3.46; S, 7.65; Cl, 8.49; F, 9.00.

Example 51

3-[(4-Chlorophenylsulfonyl)-(2,5-difluorophenyl)methyl]pyridine-N-oxide

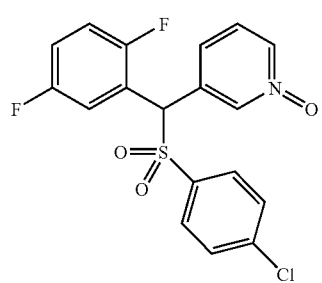

[Chemical formula 94]

To methylene chloride (15 ml) of the 3-[(4-chlorophenylsulfonyl)-(2,5-difluorophenyl)methyl]pyridine (162 mg, 0.427 mmol) obtained in Example 19 was added 3-chloroperbenzoic acid (81 mg, 0.47 mmol). The resulting mixture was stirred for 24 hours. The reaction mixture was diluted with ether (60 ml). The diluted mixture was washed with a saturated aqueous solution of sodium bicarbonate, water and brine, dried and filtered. The filtrate was concentrated under reduced pressure to give a residue. The resulting residue was subjected to silica gel chromatography (ethyl acetate) to give the title compound (68 mg, 40%). The compound was crystallized from ethanol to afford colorless needle crystals.

$^1$H-NMR (400 MHz, CDCl$_3$) δ: 5.58 (1H, s), 6.95 (1H, m), 7.03 (1H, m), 7.29 (1H, dd, J=6.6, 8.0 Hz), 7.42 (2H, d, J=8.6 Hz), 7.57 (1H, d, J=8.0 Hz), 7.62 (2H, d, J=8.4 Hz), 7.66 (1H, m), 8.10 (1H, d, J=6.6 Hz), 8.29 (1H, s).

mp: 183 to 184° C.

Elemental Analysis for C$_{18}$H$_{12}$ClF$_2$NO$_3$S: Calculated: C, 54.62; H, 3.06; N, 3.54; S, 8.10; Cl, 8.96; F, 9.60. Found: C, 54.19; H, 2.99; N, 3.67; S, 8.27; Cl, 8.92; F, 9.53.

Example 52

4-[(4-Chlorophenylsulfonyl)-(2,5-difluorophenyl)methyl]pyridine-N-oxide

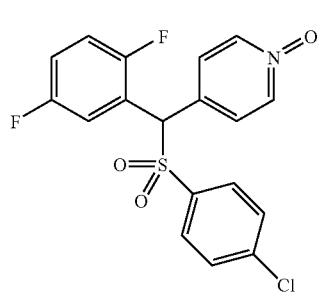

[Chemical formula 95]

To methylene chloride (20 ml) of the 4-[(4-chlorophenylsulfonyl)-(2,5-difluorophenyl)methyl]pyridine (221 mg, 0.58 mmol) obtained in Example 20 was added 3-chloroperbenzoic acid (100 mg, 0.58 mmol). The resulting mixture was stirred for 20 hours. The reaction mixture was diluted with ether (60 ml). The diluted mixture was washed with a saturated aqueous solution of sodium bicarbonate, water and brine, dried and then filtered. The filtrate was concentrated under reduced pressure to afford a residue. The resulting residue was subjected to silica gel chromatography (ethyl acetate) to give the title compound (183 mg, 80%). The compound was crystallized from ethanol to afford colorless needle crystals.

$^1$H-NMR (400 MHz, CDCl$_3$) δ: 5.62 (1H, s), 6.97 (1H, m), 7.06 (1H, m), 7.42 (2H, d, J=7.2 Hz), 7.44 (2H, d, J=8.8 Hz), 7.60 (2H, d, J=8.8 Hz), 7.68 (1H, m), 8.17 (2H, d, J=7.2 Hz).

mp: 211 to 212° C.

Elemental Analysis for C$_{18}$H$_{12}$ClF$_2$NO$_3$S: Calculated: C, 54.62; H, 3.06; N, 3.54; S, 8.10; Cl, 8.96; F, 9.60. Found: C, 54.19; H, 2.92; N, 3.65; S, 8.26; Cl, 8.99; F, 9.61.

Example 53

3-Chloro-4-[(4-chlorophenylthio)-(2,5-difluorophenyl)methyl]pyridine

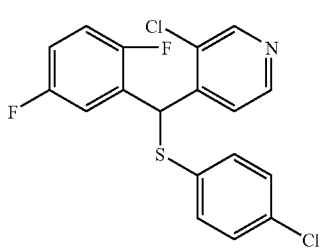

[Chemical formula 96]

The 3-chloro-4-[(2,5-difluorophenyl)-hydroxymethyl]pyridine (511 mg, 2.0 mmol) obtained in Referential Example 23 was dissolved in thionyl chloride (3.0 ml). To the resulting solution was added a catalytic amount of dimethylformamide and the mixture was stirred for 17 hours. The reaction mixture was concentrated under reduced pressure. Toluene was added to the residue, followed by further concentration.

The residue thus obtained was dissolved in dimethylformamide (10 ml). To the resulting solution were added 4-chlorobenzenethiol (375 mg, 2.6 mmol) and potassium carbonate (414 mg, 3 mmol) under a nitrogen atmosphere. The resulting mixture was stirred at 60° C. for 3 hours. After the reaction mixture was cooled to room temperature, diethyl ether (60 ml) was added thereto. The resulting mixture was washed with water and brine. The organic layer was dried over magnesium sulfate and concentrated under reduced pressure. The residue thus obtained was subjected to silica gel chromatography (hexane:ethyl acetate=8:1) to give the title compound (196 mg, 26%) as a solid.

$^1$H-NMR (400 MHz, CDCl$_3$) δ: 6.07 (1H, s), 6.95-7.08 (2H, m), 7.18 (1H, m), 7.23 (2H, d, J=8.8 Hz), 7.26 (2H, d, J=8.8 Hz), 7.58 (1H, d, J=5.2 Hz), 8.51 (1H, d, J=5.2 Hz), 8.58 (1H, s).

mp: 70 to 72° C.

MSm/z: 382 (M$^+$+1).

Example 54

2,5-Dichloro-4-[(4-chlorophenylthio)-(2,5-difluorophenyl)methyl]pyridine

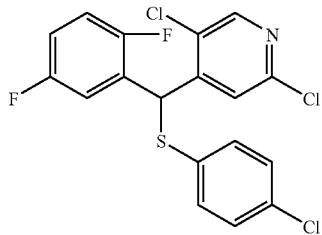

[Chemical formula 97]

The 2,5-dichloro-4-[(2,5-difluorophenyl)-hydroxymethyl]pyridine (580 mg, 2.0 mmol) obtained in Referential Example 24 was dissolved in thionyl chloride (3.0 ml). To the resulting solution was added a catalytic amount of dimethylformamide. The resulting mixture was stirred for 17 hours. The reaction mixture was concentrated under reduced pressure. To the residue was added toluene, followed by further concentration. The residue was dissolved in dimethylformamide (10 ml). To the resulting solution were added 4-chlorobenzenethiol (375 mg, 2.6 mmol) and potassium carbonate (414 mg, 3 mmol) under a nitrogen atmosphere. The resulting mixture was stirred at 50° C. for 17 hours. After the reaction mixture was cooled to room temperature, diethyl ether (60 ml) was added thereto. The resulting mixture was washed with water and brine. The organic layer was dried over magnesium sulfate and concentrated under reduced pressure. The residue thus obtained was subjected to silica gel chromatography (hexane:ether=10:1) to give the title compound (484 mg, 58%) as a solid.

$^1$H-NMR (400 MHz, CDCl$_3$) δ: 5.96 (1H, s), 6.95-7.04 (2H, m), 7.01 (1H, m), 7.23 (2H, d, J=8.8 Hz), 7.26 (2H, d, J=8.8 Hz), 7.54 (1H, s), 8.33 (1H, s).

mp: 128 to 129° C.

MSm/z: 416 (M$^+$+1).

Example 55

3-Chloro-4-[(4-chlorophenylsulfonyl)-(2,5-difluorophenyl)methyl]pyridine

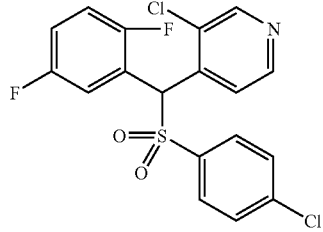

[Chemical formula 98]

To a methanol (12 ml) solution of the 3-chloro-4-[(4-chlorophenylthio)-(2,5-difluorophenyl)methyl]pyridine (122 mg, 0.32 mmol) obtained in Example 53 was added hexaammonium heptamolybdate tetrahydrate (60 mg), followed by the further addition of 30% aqueous hydrogen peroxide (6 ml). The resulting mixture was stirred for 24 hours. The reaction mixture was diluted with ethyl acetate. The diluted solution was washed with water and brine, and concentrated under reduced pressure. The residue thus obtained was crystallized from ethanol to give the title compound (103 mg, 78%) as colorless needle crystals.

$^1$H-NMR (400 MHz, CDCl$_3$) δ: 6.23 (1H, s), 6.94 (1H, m), 7.06 (1H, m), 7.41 (2H, d, J=8.0 Hz), 7.53 (1H, m), 7.59 (2H, d, J=8.0 Hz), 8.11 (1H, d, J=5.2 Hz), 8.55 (1H, s), 8.60 (1H, d, J=5.2 Hz).

mp: 160 to 161° C.

Elemental Analysis for C$_{18}$H$_{11}$Cl$_2$F$_2$NO$_2$S: Calculated: C, 52.19; H, 2.68; N, 3.38; S, 7.74; Cl, 17.12; F, 9.17. Found: C, 52.17; H, 2.69; N, 3.44; S, 7.96; Cl, 17.12; F, 9.00.

Example 56

3-Chloro-4-[(4-chlorophenylsulfinyl)-(2,5-difluorophenyl)methyl]pyridine

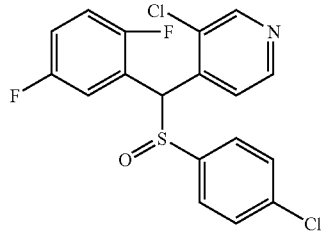

[Chemical formula 99]

To a methylene chloride (10 ml) solution of the 3-chloro-4-[(4-chlorophenylthio)-(2,5-difluorophenyl)methyl]pyridine (75 mg, 0.20 mmol) obtained in Example 53 was added 3-chloroperbenzoic acid (33 mg, 0.20 mmol). Under ice cooling, the resulting mixture was stirred for 3 hours. After dilution with ether (80 ml), the diluted mixture was washed with water and brine and concentrated under reduced pressure. The residue thus obtained was purified by silica gel chromatography (hexane:ethyl acetate=3:1) to give the title compound (48 mg, 60%) as a diastereomer mixture (1:1).

$^1$H-NMR (400 MHz, CDCl$_3$) δ: 5.53 (½H, s), 5.66 (½H, s), 6.83 (½H, s), 6.95-7.08 (⅜H, m), 7.23 (½H, m), 7.25 (1H, d, J=8.4 Hz), 7.26 (1H, d, J=8.4 Hz), 7.34 (1H, d, J=8.4 Hz), 7.36 (1H, d, J=8.4 Hz), 7.37 (½H, m), 7.76 (½H, d, J=5.2 Hz), 7.98 (½H, d, J=5.2 Hz), 8.47 (½H, s), 8.56 (½H, d, J=5.2 Hz), 8.60 (½H, s), 8.61 (½H, d, J=5.2 Hz).

FAB-MS: 397.9992 (Calcd for $C_{18}H_{12}Cl_2F_2NOS$: 397.9985).

Example 57

2,5-Dichloro-4-[(4-chlorophenylsulfonyl)-(2,5-difluorophenyl)methyl]pyridine 0.5 hydrate

[Chemical formula 100]

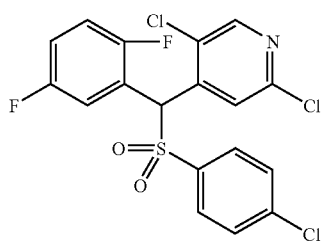

To a methylene chloride (3.0 ml) solution of the 2,5-dichloro-4-[(4-chlorophenylthio)-(2,5-difluorophenyl)methyl]pyridine (60 mg, 0.14 mmol) obtained in Example 54 was added 3-chloroperbenzoic acid (62 mg, 0.36 mmol). The resulting mixture was stirred at room temperature for 3 hours. After dilution with ether (80 ml), the diluted mixture was washed with a saturated aqueous solution of sodium bicarbonate and brine, and concentrated under reduced pressure. The residue thus obtained was purified by silica gel chromatography (hexane:ethyl acetate=5:1) and crystallized from hexane to give the title compound (55 mg, 88%).

$^1$H-NMR (400 MHz, CDCl$_3$) δ: 6.15 (1H, s), 6.93 (1H, m), 7.05 (1H, m), 7.44 (2H, d, J=8.8 Hz), 7.50 (1H, m), 7.59 (2H, d, J=8.8 Hz), 8.13 (1H, s), 8.55 (1H, s), 8.33 (1H, s).

mp: 147 to 148° C.

Elemental Analysis for $C_{18}H_{10}Cl_3F_2NO_2S$, 0.5H$_2$O: Calculated: C, 47.23; H, 2.42; N, 3.06; S, 7.01; Cl, 23.24; F, 8.30. Found: C, 47.25; H, 2.24; N, 3.21; S, 7.19; Cl, 23.25; F, 8.32.

Example 58

4-[5-Chloro-4-[(4-chlorophenylthio)-(2,5-difluorophenyl)methyl]pyridin-2-yl]morpholine

[Chemical formula 101]

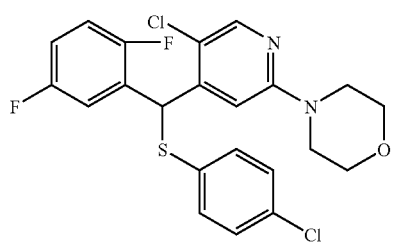

A 1,4-dioxane (1.0 ml) solution of the 2,5-dichloro-4-[(4-chlorophenylthio)-(2,5-difluorophenyl)methyl]pyridine (100 mg, 0.24 mmol) obtained in Example 54 and morpholine (200 μl) was stirred at 100° C. for 2 days under a nitrogen atmosphere. After cooling to room temperature, the reaction mixture was diluted with ethyl acetate (40 ml). The diluted mixture was washed with water and brine, dried and then concentrated under reduced pressure to give a residue. The resulting residue was purified by silica gel chromatography (hexane:ethyl acetate=5:1) to give the title compound (100 mg, 89%) as an oil.

$^1$H-NMR (400 MHz, CDCl$_3$) δ: 3.48 (4H, m), 3.82 (4H, m), 6.00 (1H, s), 6.94 (1H, s), 6.94-7.04 (2H, m), 7.09 (1H, m), 7.23 (2H, d, J=8.4 Hz), 7.24 (2H, d, J=8.4 Hz), 8.12 (1H, s).

MSm/z: 467 (M$^+$+H).

Example 59

4-[5-Chloro-4-[(4-chlorophenylsulfonyl)-(2,5-difluorophenyl)methyl]pyridin-2-yl]morpholine

[Chemical formula 102]

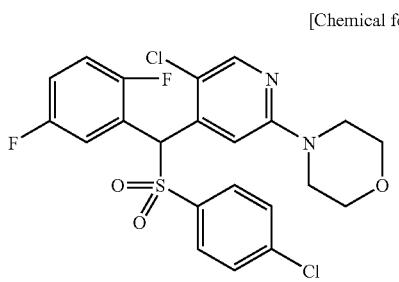

Hexaammonium heptamolybdate tetrahydrate (60 mg) was added to a methanol (12 ml) solution of 4-[5-chloro-4-[(4-chlorophenylthio)-(2,5-difluorophenyl)methyl]pyridin-2-yl]morpholine (90 mg, 0.19 mmol), followed by the further addition of 30% aqueous hydrogen peroxide (6 ml). The resulting mixture was stirred for 6 hours. The reaction mixture was diluted with ethyl acetate. The diluted mixture was washed with water and brine and concentrated under reduced pressure. The residue thus obtained was subjected to silica gel chromatography (hexane:ethyl acetate=3:1) and crystallized from ethanol to give the title compound (80 mg, 83%) as colorless needle crystals.

$^1$H-NMR (400 MHz, CDCl$_3$) δ: 3.54 (4H, m), 3.84 (4H, m), 6.12 (1H, s), 6.90 (1H, m), 7.02 (1H, m), 7.42 (2H, d, J=8.4 Hz), 7.45 (1H, s), 7.46 (1H, m), 7.58 (2H, d, J=8.4 Hz), 8.06 (1H, s).

mp: 180 to 181° C.

Elemental Analysis for $C_{22}H_{18}Cl_2F_2N_2O_3S$: Calculated: C, 52.92; H, 3.63; N, 5.61; S, 6.42; Cl, 14.20; F, 7.61. Found: C, 52.68; H, 3.56; N, 5.69; S, 6.70; Cl, 14.32; F, 7.97.

Example 60

4-[2-[5-Chloro-4-[(4-chlorophenylthio)-(2,5-difluorophenyl)methyl]pyridin-2-yl]aminoethyl]morpholine

[Chemical formula 103]

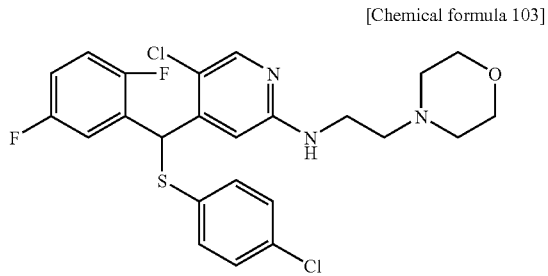

A 1,4-dioxane (1.0 ml) solution of the 2,5-dichloro-4-[(4-chlorophenylthio)-(2,5-difluorophenyl)methyl]pyridine (100 mg, 0.24 mmol) obtained in Example 54 and 4-(2-aminoethyl)morpholine (200 μl) was stirred at 100° C. for 2 days under a nitrogen atmosphere. After cooling to room temperature, the reaction mixture was diluted with ethyl acetate (40 ml). The diluted mixture was washed with water and brine, dried and concentrated under reduced pressure to give a residue. The resulting residue was purified by silica gel chromatography (3% methanol/chloroform) to give the title compound (12 mg, 10%) as an oil.

$^1$H-NMR (400 MHz, CDCl$_3$) δ: 2.42 (4H, m), 2.54 (2H, d, J=6.0 Hz), 3.27 (2H, q, J=6.0 Hz), 3.67 (4H, m), 5.12 (br, 1H), 5.90 (1H, s), 6.61 (1H, s), 6.86-7.0 (2H, m), 7.06 (1H, m), 7.15 (2H, d, J=8.4 Hz), 7.16 (2H, d, J=8.4 Hz), 7.95 (1H, s).

MSm/z: 510 (M$^+$+H).

Example 61

4-[2-[5-Chloro-4-[(4-chlorophenylsulfonyl)-(2,5-difluorophenyl)methyl]pyridin-2-yl]aminoethyl]morpholine-N-oxide

[Chemical formula 104]

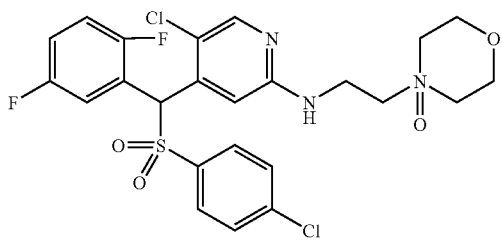

Hexaammonium heptamolybdate tetrahydrate (10 mg) was added to a methanol (12 ml) solution of 4-[2-[5-chloro-4-[(4-chlorophenylthio)-(2,5-difluorophenyl)methyl]pyridin-2-yl]aminoethyl]morpholine (11 mg, 0.032 mmol), followed by the further addition of 30% aqueous hydrogen peroxide (1 ml). The resulting mixture was stirred for 8 hours. The reaction mixture was diluted with ethyl acetate. The diluted mixture was washed with water and brine and concentrated under reduced pressure. The residue thus obtained was purified by silica gel chromatography (3% methanol, 3% t-butylamine/chloroform solution) to give the title compound (5.0 mg, 42%).

$^1$H-NMR (400 MHz, CDCl$_3$) δ: 3.2-3.4 (4H, m), 3.54 (2H, m), 3.81 (2H, m), 3.91 (2H, m), 4.44 (2H, m), 6.09 (1H, s), 6.88 (1H, m), 6.98 (1H, m), 7.22 (1H, s), 7.40 (2H, d, J=8.4 Hz), 7.51 (1H, m), 7.60 (2H, d, J=8.4 Hz), 7.94 (1H, s).

FAB-MS: 558.0837 (Calcd for C$_{24}$H$_{24}$Cl$_2$F$_2$N$_3$O$_4$S: 558.0833).

Example 62

5-Azidomethyl-2-[(4-chlorophenylsulfonyl)(2,5-difluorophenyl)methyl]pyridine

[Chemical formula 105]

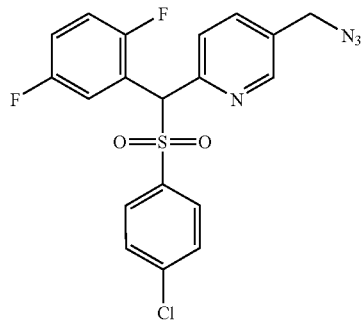

The 2-[(4-chlorophenylsulfonyl)(2,5-difluorophenyl)methyl]-5-(hydroxymethyl)pyridine (471 mg, 1.15 mmol) obtained in Example 43 was dissolved in a mixture of carbon tetrachloride (4 ml) and N,N-dimethylformamide (16 ml). To the resulting solution were added sodium azide (112 mg, 1.72 mmol) and triphenylphosphine (451 mg, 1.72 mmol). The resulting mixture was stirred at 90° C. for 3 hours. Water was added to the reaction mixture, followed by extraction with ethyl acetate. The organic layer was washed sequentially with water and brine. The resulting organic layer was dried over sodium sulfate and then concentrated under reduced pressure. The residue thus obtained was subjected to silica gel column chromatography. The fraction obtained from the hexane:ethyl acetate=3:1 eluate was concentrated under reduced pressure to give the title compound (244 mg, 0.561 mmol, 49%) as a colorless amorphous substance.

$^1$H-NMR (400 MHz, CDCl$_3$) δ: 4.42 (2H, s), 5.96 (1H, s), 6.94 (1H, m), 6.99-7.05 (1H, m), 7.40 (2H, d, J=8.8 Hz), 7.55 (2H, d, J=8.8 Hz), 7.60 (1H, d, J=8.1 Hz), 7.72 (1H, dd, J=8.1, 2.0 Hz), 8.02 (1H, m), 8.57 (1H, d, J=2.0 Hz).

MSm/z: 435 (M$^+$+H).

Example 63

[6-[(4-Chlorophenylsulfonyl)(2,5-difluorophenyl)methyl]pyridin-3-yl]methylamine

[Chemical formula 106]

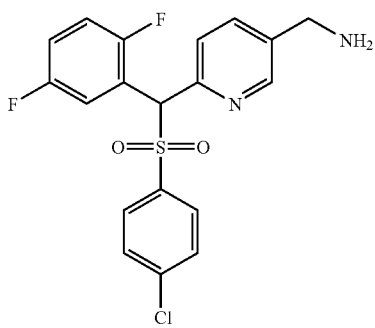

Under an argon atmosphere, 5-azidomethyl-2-[(4-chlorophenylsulfonyl)(2,5-difluorophenyl)methyl]pyridine (77 mg, 0.177 mmol), palladium carbon (14 mg), and ethyl acetate (2 ml) were added to ethanol (10 ml). The resulting mixture was stirred for 50 minutes in a hydrogen atmosphere of 1 atmospheric pressure. The reaction mixture was filtered. The filtrate was concentrated under reduced pressure. The residue thus obtained was subjected to silica gel column chromatography. A fraction obtained from the dichloromethane:methanol=10:1 eluate was concentrated under reduced pressure to give the title compound (28 mg, 0.0685 mmol, 39%) as a white powder.

$^1$H-NMR (400 MHz, CDCl$_3$) δ: 1.84 (2H, brs), 3.92 (2H, s), 5.94 (1H, s), 6.92 (1H, m), 7.03-6.98 (1H, m), 7.39 (2H, d, J=8.3 Hz), 7.56 (2H, d, J=8.3 Hz), 7.60 (1H, d, J=8.1 Hz), 7.74 (1H, d, J=8.1 Hz), 8.01 (1H, m), 8.57 (1H, s).

MSm/z: 409 (M$^+$+H).

Example 64 t-Butyl[[6-[(4-chlorophenylsulfonyl)(2,5-difluorophenyl)methyl]pyridin-3-yl]methyl]carbamate

[Chemical formula 107]

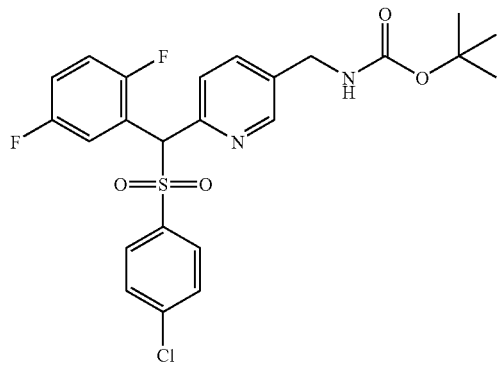

The 5-azidomethyl-2-[(4-chlorophenylsulfonyl)(2,5-difluorophenyl)methyl]pyridine (230 mg, 0.529 mmol) obtained in Example 62 and palladium carbon (46 mg) were added to a mixture of ethyl acetate (15 ml) and ethanol (15 ml). The resulting mixture was stirred for 45 minutes under a hydrogen atmosphere of 1 atmospheric pressure. The reaction mixture was filtered. The filtrate was then concentrated under reduced pressure. The residue thus obtained was dissolved in dichloromethane (5 ml). To the resulting solution were added triethylamine (70 μl, 0.499 mmol) and di-t-butyl carbonate (174 mg, 0.996 mmol). The resulting mixture was stirred at room temperature for 3 days. The reaction mixture was concentrated under reduced pressure. The residue thus obtained was subjected to flash silica gel column chromatography, and the fraction obtained from the hexane:ethyl acetate=4:1 eluate was concentrated under reduced pressure to give the title compound (78 mg, 0.153 mmol, 37%) as a colorless amorphous substance.

$^1$H-NMR (400 MHz, CDCl$_3$) δ: 1.45 (9H, s), 4.34 (2H, d, J=5.6 Hz), 4.91 (1H, brs), 5.93 (1H, s), 6.91 (1H, m), 6.98-7.04 (1H, m), 7.39 (2H, d, J=8.8 Hz), 7.54 (2H, d, J=8.8 Hz), 7.59 (1H, d, J=7.8 Hz), 7.67 (1H, dd, J=7.8, 2.2 Hz), 7.99 (1H, m), 8.53 (1H, d, J=2.2 Hz).

MSm/z: 509 (M$^+$+H).

Example 65 t-Butyl[[6-[(4-chlorophenylsulfonyl)(2,5-difluorophenyl)methyl]pyridin-3-yl]methyl]-N-(t-butoxycarbonyl)carbamate

[Chemical formula 108]

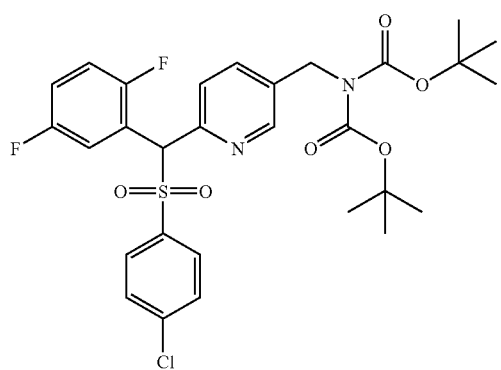

Under a nitrogen atmosphere, diisopropyl azodicarboxylate (128 μl, 0.653 mmol) was added to a tetrahydrofuran (5 ml) solution of the 2-[(4-chlorophenylsulfonyl)(2,5-difluorophenyl)methyl]-5-(hydroxymethyl)pyridine (178 mg, 0.435 mmol) obtained in Example 43, di-t-butyl iminodicarboxylate (142 mg, 0.653 mmol) and triphenylphosphine (171 mg, 0.653 mmol). The resulting mixture was stirred at room temperature for 5 hours. Water was added to the reaction mixture, followed by extraction with ethyl acetate. The organic layer was washed sequentially with water and brine. The resulting organic layer was dried over sodium sulfate and then, concentrated under reduced pressure. The residue thus obtained was subjected to flash silica gel column chromatography, and the fraction obtained from the hexane:ethyl acetate=4:1 eluate was concentrated under reduced pressure to give the title compound (78 mg, 0.128 mmol, 32%) as a colorless oil.

$^1$H-NMR (400 MHz, CDCl$_3$) δ: 1.48 (18H, s), 4.78 (2H, s), 5.94 (1H, s), 6.93 (1H, td, J=9.0, 4.4 Hz), 6.98-7.04 (1H, m), 7.38 (2H, d, J=8.6 Hz), 7.56 (2H, d, J=8.6 Hz), 7.58 (1H, d, J=8.1 Hz), 7.71 (1H, dd, J=8.1, 2.4 Hz), 7.96-8.00 (1H, m), 8.57 (1H, d, J=2.4 Hz).

MSm/z: 609 (M$^+$+H).

Example 66

[6-[(4-Chlorophenylsulfonyl)(2,5-difluorophenyl)methyl]pyridin-3-yl]methylamine hydrochloride

[Chemical formula 109]

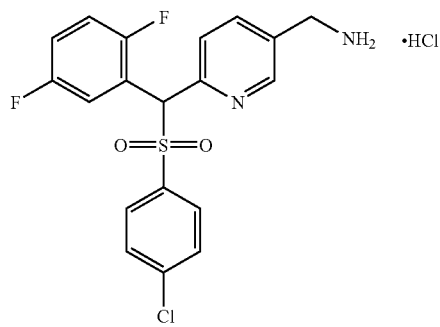

To an ethanol (2 ml) solution of t-butyl[[6-[(4-chlorophenylsulfonyl)(2,5-difluorophenyl)methyl]pyridin-3-yl]methyl]-N-(t-butoxycarbonyl)carbamate (70 mg, 0.115 mmol) was added concentrated hydrochloric acid (2 ml). The resulting mixture was stirred at room temperature for 3 hours. The reaction mixture was concentrated under reduced pressure. To the residue thus obtained was added ethanol. The resulting mixture was concentrated under reduced pressure to give the title compound (51 mg, 0.115 mmol, 100%) as a white powder.

$^1$H-NMR (400 MHz, CD$_3$OD) δ: 4.18 (2H, s), 6.22 (1H, s), 7.03 (1H, td, J=9.3, 4.4 Hz), 7.11-7.17 (1H, m), 7.52 (2H, d, J=8.8 Hz), 7.64 (2H, d, J=8.8 Hz), 7.79 (1H, d, J=8.3 Hz), 7.92 (1H, dd, J=8.3, 2.2 Hz), 8.05-8.09 (1H, m), 8.71 (1H, d, J=2.2 Hz)

Elemental Analysis for C$_{20}$H$_{15}$ClF$_2$N$_2$O$_2$S.HCl: Calculated: C, 51.25; H, 3.62; Cl, 15.92; F, 8.53; N, 6.29. Found: C, 51.11; H, 3.57; Cl, 15.50; F, 8.39; N, 5.83.

Example 67

N-acetyl-N-[[6-[(4-chlorophenylsulfonyl)(2,5-difluorophenyl)methyl]pyridin-3-yl]methyl]acetamide (Compound A) and N-[[6-[(4-chlorophenylsulfonyl)(2,5-difluorophenyl)methyl]pyridin-3-yl]methyl]acetamide (Compound B)

[Chemical formula 110]

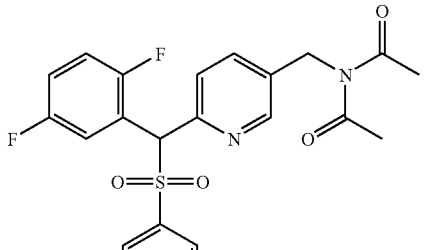

Compound A

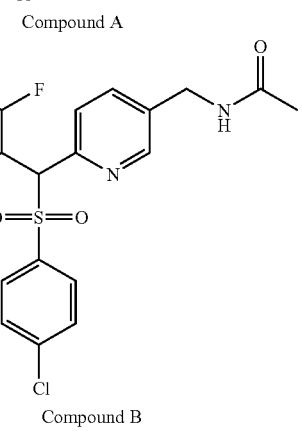

Compound B

To a dichloromethane (3 ml) solution of the [6-[(4-chlorophenylsulfonyl)(2,5-difluorophenyl)methyl]pyridin-3-yl]methylamine (40 mg, 0.0978 mmol) obtained in Example 63 were added N-methylmorpholine (26 μl, 0.234 mmol) and acetyl chloride (16 μl, 0.234 mmol) under ice cooling. The resulting mixture was stirred at room temperature for 16 hours. Water was added to the reaction mixture, followed by extraction with ethyl acetate. The organic layer was washed sequentially with water and brine. The resulting organic layer was dried over sodium sulfate and concentrated under reduced pressure. The residue thus obtained was subjected to flash silica gel column chromatography. The fraction obtained from the hexane:ethyl acetate=2:3 eluate was concentrated under reduced pressure to give the title compound A (low polar compound) (15 mg, 0.0304 mmol, 40%) as a white power and the title Compound B (high polar compound) (12 mg, 0.0266 mmol, 27%) as a white powder.

Compound A $^1$H-NMR (400 MHz, CDCl$_3$) δ: 2.43 (6H, s), 4.96 (2H, s), 5.93 (1H, s), 6.91 (1H, m), 6.98-7.03 (1H, m), 7.39 (2H, d, J=8.5 Hz), 7.54-7.61 (2H, m), 7.55 (2H, d, J=8.5 Hz), 8.02 (1H, m), 8.51 (1H, d, J=1.7 Hz).

mp: 60 to 64° C.

MSm/z: 493 (M$^+$+H).

Compound B $^1$H-NMR (400 MHz, CDCl$_3$) δ: 2.03 and 2.04 (3H, rotamers), 4.42-4.50 (2H, m), 5.89 (1H, brs), 5.93 (1H, s), 6.92 (1H, td, J=9.1, 4.4 Hz), 6.97-7.02 (1H, m), 7.41 (2H, d, J=8.1 Hz), 7.57 (2H, d, J=8.1 Hz), 7.61 (1H, d, J=8.1 Hz), 7.71 (1H, d, J=8.1 Hz), 7.98-8.03 (1H, m), 8.54 (1H, s).

mp: 177 to 178° C.

MSm/z: 451 (M$^+$+H).

Example 68

N-[[6-[(4-Chlorophenylsulfonyl)(2,5-difluorophenyl)methyl]pyridin-3-yl]methyl]-N',N'-dimethylsulfamide

[Chemical formula 111]

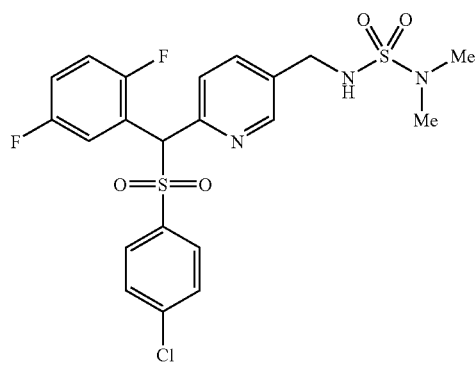

To a dichloromethane (5 ml) solution of the [6-[(4-chlorophenylsulfonyl)(2,5-difluorophenyl)methyl]pyridin-3-yl]methylamine hydrochloride (60 mg, 0.135 mmol) obtained in Example 66 were added N-methylmorpholine (180 μl, 1.62 mmol), 4-dimethylaminopyridine (10 mg, 0.0819 mmol) and N,N-dimethylsulfamoyl chloride (66 μl, 0.609 mmol). The resulting mixture was stirred at room temperature for 24 hours. Water was added to the reaction mixture, followed by extraction with dichloromethane. The organic layer was washed sequentially with a saturated aqueous solution of sodium bicarbonate and brine. The organic layer thus obtained was dried over magnesium sulfate and concentrated under reduced pressure. The residue thus obtained was subjected to flash silica gel column chromatography. The fraction obtained from the hexane:ethyl acetate=3:2 eluate was concentrated under reduced pressure to give the title compound (48 mg, 0.0930 mmol, 70%) as a white powder.

$^1$H-NMR (400 MHz, CDCl$_3$) δ: 2.76 (6H, s), 4.29 (2H, d, J=6.4 Hz), 4.43 (1H, t, J=6.4 Hz), 5.94 (1H, s), 6.92 (1H, m), 6.98-7.04 (1H, m), 7.41 (2H, d, J=8.6 Hz), 7.58 (2H, d, J=8.6 Hz), 7.66 (1H, d, J=8.1 Hz), 7.79 (1H, dd, J=8.1, 2.5 Hz), 8.02 (1H, m), 8.61 (1H, d, J=2.5 Hz)

mp: 177 to 178 (C.

MSm/z: 516 (M$^+$+H).

Example 69

Ethyl 2-[[6-[(4-Chlorophenylsulfonyl)(2,5-difluorophenyl)methyl]pyridin-3-yl]methylamino]-2-oxoacetate

[Chemical formula 112]

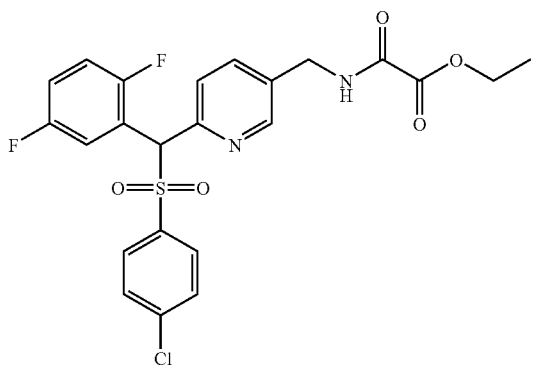

To a dichloromethane (4 ml) solution of the [6-[(4-chlorophenylsulfonyl)(2,5-difluorophenyl)methyl]pyridin-3-yl]methylamine (30 mg, 0.0734 mmol) obtained in Example 63 were added N-methylmorpholine (10 µl, 0.0881 mmol) and ethyl chloroglyoxylate (9 µl, 0.0807 mmol) under ice cooling. The resulting mixture was stirred at room temperature for 1 hour. Water was added to the reaction mixture, followed by extraction with dichloromethane. The organic layer was then sequentially washed with a saturated aqueous solution of sodium bicarbonate and brine. The resulting organic layer was dried over magnesium sulfate and concentrated under reduced pressure. The residue thus obtained was subjected to flash silica gel column chromatography. The fraction obtained from the hexane:ethyl acetate=3:2 eluate was concentrated under reduced pressure to give the title compound (28 mg, 0.0550 mmol, 76%) as a white powder.

$^1$H-NMR (400 MHz, CDCl$_3$) δ: 1.39 (3H, t, J=7.1 Hz), 4.37 (2H, q, J=7.1 Hz), 4.55 (2H, d, J=5.9 Hz), 5.94 (1H, s), 6.89-6.94 (1H, m), 6.98-7.05 (1H, m), 7.40 (2H, d, J=8.3 Hz), 7.56 (2H, d, J=8.3 Hz), 7.53 (1H, brs), 7.62 (1H, d, J=8.1 Hz), 7.72 (1H, d, J=8.1 Hz), 7.97-8.03 (1H, m), 8.58 (1H, s).

mp: 193 to 194° C.
MSm/z: 509 (M$^+$+H).

Example 70

N-[[6-[(4-Chlorophenylsulfonyl)(2,5-difluorophenyl)methyl]pyridin-3-yl]methyl]-2-(4-methylphenylsulfonylamino)acetamide

[Chemical formula 113]

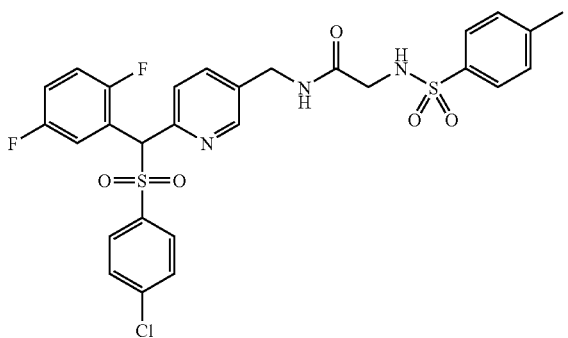

To a dichloromethane (6 ml) solution of the [6-[(4-chlorophenylsulfonyl)(2,5-difluorophenyl)methyl]pyridin-3-yl]methylamine hydrochloride (40 mg, 0.0898 mmol) obtained in Example 66 were added triethylamine (45 µl, 0.324 mmol), 4-dimethylaminopyridine (5 mg, 0.0449 mmol), 1-ethyl-3-(3-dimethylaminopropyl)carbodiimide hydrochloride (21 mg, 0.108 mmol) and N-p-tosylglycine (25 mg, 0.108 mmol). The resulting mixture was stirred at room temperature for 16 hours. The reaction mixture was diluted with dichloromethane. The diluted mixture was then washed sequentially with water, a saturated aqueous solution of sodium bicarbonate and brine. The organic layer thus obtained was dried over magnesium sulfate and then, concentrated under reduced pressure. The residue thus obtained was subjected to flash silica gel column chromatography. The fraction obtained from the hexane:ethyl acetate=2:3 eluate was concentrated under reduced pressure to give the title compound (41 mg, 0.0661 mmol, 73%) as a white powder.

$^1$H-NMR (400 MHz, CDCl$_3$) δ: 2.44 (3H, s), 3.59 (2H, d, J=6.4 Hz), 4.44 (2H, dd, J=6.1, 2.8 Hz), 5.42 (1H, t, J=6.1 Hz), 5.95 (1H, s), 6.91 (1H, m), 6.96-7.03 (2H, m), 7.33 (2H, d, J=8.3 Hz), 7.41 (2H, d, J=8.6 Hz), 7.57 (2H, d, J=8.6 Hz), 7.58 (1H, d, J=8.1 Hz), 7.66 (1H, dd, J=8.1, 2.4 Hz), 7.74 (2H, d, J=8.3 Hz), 8.01 (1H, m), 8.49 (1H, d, J=2.4 Hz).

mp: 217 to 218° C.
MSm/z: 620 (M$^+$+H).

Example 71

N-[[6-[(4-Chlorophenylsulfonyl)(2,5-difluorophenyl)methyl]pyridin-3-yl]methyl]-2-dimethylaminoacetamide

[Chemical formula 114]

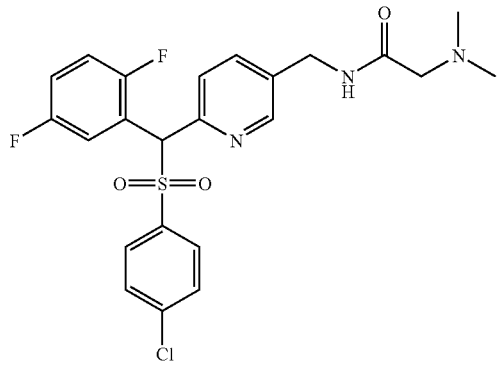

To a dichloromethane (5 ml) solution of the [6-[(4-chlorophenylsulfonyl)(2,5-difluorophenyl)methyl]pyridin-3-yl]methylamine (30 mg, 0.0734 mmol) obtained in Example 63 were added triethylamine (12 µl, 0.0881 mmol), 4-dimethylaminopyridine (5 mg, 0.0367 mmol), 1-ethyl-3-(3-dimethylaminopropyl)carbodiimide hydrochloride (17 mg, 0.0881 mmol) and N,N-dimethylglycine (9 mg, 0.0881 mmol). The resulting mixture was stirred at room temperature for 14 hours. The reaction mixture was diluted with dichloromethane. The diluted mixture was washed sequentially with water, a saturated aqueous solution of sodium bicarbonate and brine. The organic layer thus obtained was dried over magnesium sulfate and then, concentrated under reduced pressure. The residue thus obtained was subjected to flash silica gel column chromatography. The fraction obtained from the hexane:ethyl acetate=1:4 eluate was concentrated under reduced pressure to give the title compound (21 mg, 0.0425 mmol, 58%) as a white powder.

$^1$H-NMR (400 MHz, CDCl$_3$) δ: 2.30 (6H, s), 3.01 (2H, s), 4.50 (2H, d, J=6.1 Hz), 5.93 (1H, s), 6.91 (1H, m), 6.98-7.04 (1H, m), 7.40 (2H, d, J=8.6 Hz), 7.55 (2H, d, J=8.6 Hz), 7.60 (1H, d, J=8.1 Hz), 7.62 (1H, brs), 7.69 (1H, dd, J=8.1, 2.4 Hz), 8.02 (1H, m), 8.56 (1H, d, J=2.4 Hz).

mp: 177 to 179° C.
MSm/z: 494 (M$^+$+H).

Example 72

N-[[6-[(4-Chlorophenylsulfonyl)(2,5-difluorophenyl)methyl]pyridin-3-yl]methyl]-4-(formylmethylamino)benzamide

[Chemical formula 115]

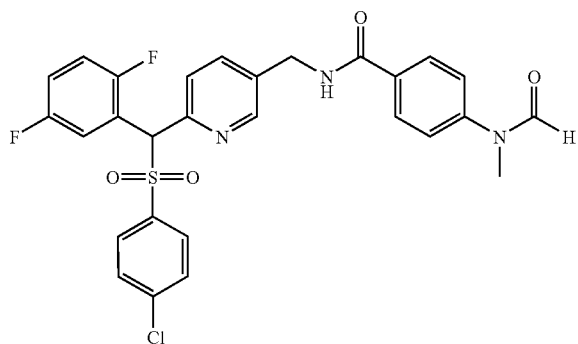

To a dichloromethane (5 ml) solution of the [6-[(4-chlorophenylsulfonyl)(2,5-difluorophenyl)methyl]pyridin-3-yl]methylamine (50 mg, 0.122 mmol) obtained in Example 63 were added triethylamine (21 μl, 0.147 mmol), 4-dimethylaminopyridine (7 mg, 0.0610 mmol), 1-ethyl-3-(3-dimethylaminopropyl)carbodiimide hydrochloride (28 mg, 0.147 mmol) and N-formyl-4-(methylamino)benzoic acid (26 mg, 0.147 mmol). The resulting mixture was stirred at room temperature for 2 hours. The reaction mixture was diluted with dichloromethane. The diluted mixture was washed sequentially with water, a saturated aqueous solution of sodium bicarbonate and brine. The organic layer thus obtained was dried over magnesium sulfate, and then concentrated under reduced pressure. The residue thus obtained was subjected to flash silica gel column chromatography. The fraction obtained from the hexane:ethyl acetate=3:7 eluate was concentrated under reduced pressure to give the title compound (60 mg, 0.105 mmol, 87%) as a colorless amorphous substance.

$^1$H-NMR (400 MHz, CDCl$_3$) δ: 3.35 (3H, s), 4.67-4.71 (2H, m), 5.94 (1H, s), 6.53 (1H, brs), 6.90 (1H, m), 6.97-7.03 (1H, m), 7.25 (2H, d, J=8.6 Hz), 7.40 (2H, d, J=8.6 Hz), 7.56 (2H, d, J=8.6 Hz), 7.63 (1H, d, J=8.1 Hz), 7.78 (1H, dd, J=8.1, 2.2 Hz), 7.86 (2H, d, J=8.6 Hz), 8.03 (1H, m), 8.61 (1H, s), 8.64 (1H, d, J=2.2 Hz).

MSm/z: 570 (M$^+$+H).

Example 73

N-[[6-[(4-Chlorophenylsulfonyl)(2,5-difluorophenyl)methyl]pyridin-3-yl]methyl]-4-(methylthioformylamino)thiobenzamide

[Chemical formula 116]

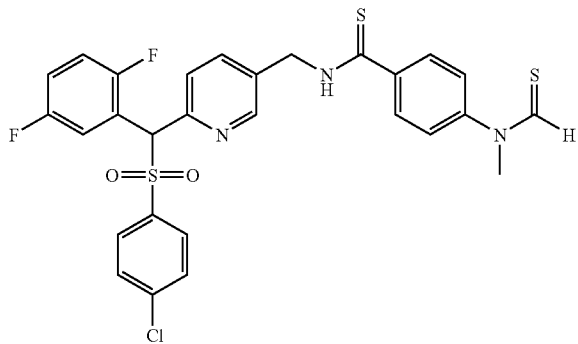

Under an argon atmosphere, a Lawson reagent (69 mg, 0.169 mmol) was added to a toluene (5 ml) solution of N-[[6-[(4-chlorophenylsulfonyl)(2,5-difluorophenyl)methyl]pyridin-3-yl]methyl]-4-(formylmethylamino)benzamide (46 mg, 0.0807 mmol). The resulting mixture was heated under reflux for 12 hours. After cooling to room temperature, the reaction mixture was concentrated under reduced pressure. The residue thus obtained was subjected to flash silica gel column chromatography. The fraction obtained from the hexane:ethyl acetate=4:1 eluate was concentrated under reduced pressure to give the title compound (40 mg, 0.0664 mmol, 83%) as a yellow amorphous substance.

$^1$H-NMR (400 MHz, CDCl$_3$) δ: 3.72 (3H, s), 5.08 (2H, d, J=4.4 Hz), 5.92 (1H, s), 6.89 (1H, td, J=9.0, 4.4 Hz), 6.98-7.05 (1H, m), 7.25 (2H, d, J=8.6 Hz), 7.40 (2H, d, J=8.6 Hz), 7.55 (2H, d, J=8.6 Hz), 7.60 (1H, d, J=8.1 Hz), 7.81 (1H, d, J=8.1 Hz), 7.87 (2H, d, J=8.6 Hz), 8.02-8.06 (1H, m), 8.20 (1H, brs), 8.62 (1H, s), 9.70 (1H, s).

MSm/z: 602 (M$^+$+H)

Example 74

N-[[6-[(4-Chlorophenylsulfonyl)(2,5-difluorophenyl)methyl]pyridin-3-yl]methyl]-2-(pyridin-3-yl)acetamide

[Chemical formula 117]

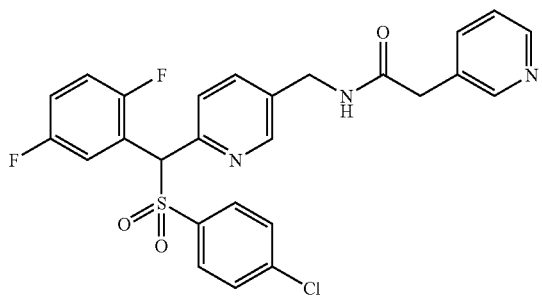

The [6-[(4-chlorophenylsulfonyl)(2,5-difluorophenyl)methyl]pyridin-3-yl]methylamine (30 mg, 0.073 mmol) obtained in Example 63, 3-pyridylacetic acid hydrochloride (16 mg, 0.092 mmol), 4-(dimethylamino)pyridine (5 mg, 0.04 mmol) and triethylamine (0.025 ml, 0.18 mmol) were dissolved in dichloromethane (5 ml). To the resulting solution was added 1-ethyl-3-(3-dimethylaminopropyl)carbodiimide hydrochloride (17 mg, 0.089 mmol) at room temperature. The resulting mixture was stirred at room temperature for 14 hours. To the reaction mixture was added a saturated aqueous solution (0.1 ml) of sodium bicarbonate. The residue obtained by concentrating the reaction mixture under reduced pressure was subjected to flash silica gel chromatography. The fraction obtained from the dichloromethane:methanol=30:1 elute was concentrated under reduced pressure to afford a white solid. The resulting solid was washed with ether to give the title compound (35 mg, 0.066 mmol, 90%) as a white powder.

$^1$H-NMR (400 MHz, CDCl$_3$) δ: 3.59 (2H, s), 4.45 (2H, dd, J=5.9, 1.5 Hz), 5.92 (1H, s), 5.96-6.10 (1H, m), 6.86-6.98 (1H, m), 6.99-7.05 (1H, m), 7.24-7.35 (1H, m), 7.39 (2H, d, J=8.8 Hz), 7.55-7.60 (3H, m), 7.60-7.71 (2H, m), 7.96-8.06 (1H, m), 8.50 (2H, d, J=1.6 Hz), 8.55 (1H, d, J=4.8, 1.6 Hz).

MSm/z: 528 (M$^+$+H).

Example 75

[6-(4-Chlorophenylsulfonyl)(2,5-difluorophenyl)methylpyridin-3-yl]methyl dimethylcarbamate

[Chemical formula 118]

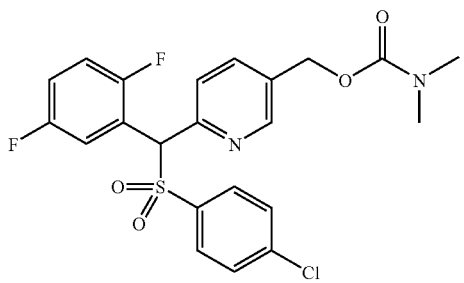

To a dichloromethane (0.3 ml) solution of the 2-[(4-chlorophenylsulfonyl)(2,5-difluorophenyl)methyl]-5-(hydroxylmethyl)pyridine (20 mg, 0.049 mmol) obtained in Example 43 were added N-methylmorpholine (0.011 ml, 0.10 mmol) and p-nitrophenyl chloroformate (15 mg, 0.074 mmol) sequentially at 0° C. The resulting mixture was stirred at room temperature for 30 minute. To the reaction mixture were then added N-methylmorpholine (0.033 ml, 0.30 mmol) and p-nitrophenyl chloroformate (15 mg, 0.074 mmol) sequentially at 0° C. The resulting mixture was stirred at room temperature for 30 minutes. After addition of dimethylamine hydrochloride (20 mg, 0.25 mmol) to the reaction mixture at 0° C. and stirring the mixture for 13 hours, the reaction mixture was washed with a saturated aqueous solution of ammonium chloride. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=7:3 eluate was concentrated under reduced pressure. The solid thus obtained was washed with hexane and collected by filtration to give the title compound (13 mg, 0.027 mmol, 55%) as a white solid.

$^1$H-NMR (400 MHz, CDCl$_3$) δ: 2.94 (6H, s), 5.14 (2H, s), 5.94 (1H, s), 6.87-7.07 (2H, m), 7.39 (2H, d, J=8.5 Hz), 7.55 (2H, d, J=8.5 Hz), 7.62 (1H, d, J=7.8 Hz), 7.75 (1H, dd, J=7.8, 2.0 Hz), 7.99-8.07 (1H, m), 8.63 (1H, d, J=2.0 Hz).

MSm/z: 481 (M$^+$+H).

Example 76

[6-(4-Chlorophenylsulfonyl)(2,5-difluorophenyl)methylpyridin-3-yl]methyl 4-nitrophenyl carbonate

[Chemical formula 119]

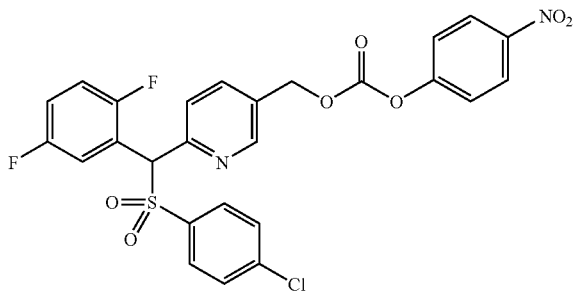

To a dichloromethane (0.5 ml) solution of the 2-[(4-chlorophenylsulfonyl)(2,5-difluorophenyl)methyl]-5-(hydroxylmethyl)pyridine (41 mg, 0.10 mmol) obtained in Example 43 were added N-methylmorpholine (0.033 ml, 0.30 mmol) and 4-nitrophenyl chloroformate (40 mg, 0.20 mmol) sequentially at 0° C. The resulting mixture was stirred at room temperature for 1 hour. The reaction mixture was washed with water. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=4:1 eluate was concentrated under reduced pressure. The solid thus obtained was washed with hexane and collected by filtration to give the title compound (52 mg, 0.090 mmol, 90%) as a white solid.

$^1$H-NMR (400 MHz, CDCl$_3$) δ: 5.33 (2H, s), 5.97 (1H, s), 6.87-6.95 (1H, m), 6.98-7.06 (1H, m), 7.39 (2H, d, J=9.0 Hz), 7.40 (2H, d, J=8.5 Hz), 7.57 (2H, d, J=8.5 Hz), 7.71 (1H, d, J=7.6 Hz), 7.85 (1H, dd, J=7.6, 2.0 Hz), 7.97-8.05 (1H, m), 8.29 (2H, d, J=9.0 Hz), 8.72 (1H, d, J=2.0 Hz).

MSm/z: 575 (M$^+$+H).

Example 77

[6-(4-Chlorophenylsulfonyl)(2,5-difluorophenyl)methylpyridin-3-yl]methyl benzylcarbamate

[Chemical formula 120]

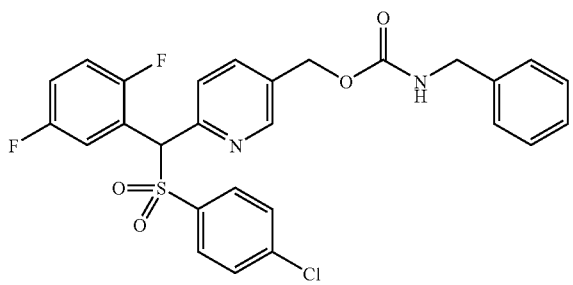

To a dichloromethane (1 ml) solution of [6-(4-chlorophenylsulfonyl)(2,5-difluorophenyl)methylpyridin-3-yl]methyl 4-nitrophenyl carbonate (51 mg, 0.089 mmol) were added N-methylmorpholine (0.020 ml, 0.18 mmol) and benzylamine (0.012 ml, 0.11 mmol) sequentially at 0° C. The resulting mixture was stirred at room temperature for 20 hours. The reaction mixture was washed with a saturated aqueous solution of ammonium chloride. The organic layer was dried over anhydrous sodium sulfate, and filtered. The filtrate was concentrated under reduced pressure. The residue thus obtained was subjected to flash silica gel chromatography. The fraction obtained from the eluate of hexane:ethyl acetate=4:1 was concentrated under reduced pressure. The solid thus obtained was washed with diisopropyl ether and collected by filtration to give the title compound (33 mg, 0.060 mmol, 68%) as a white solid.

$^1$H-NMR (400 MHz, CDCl$_3$) δ: 4.38 (2H, brd, J=5.4 Hz), 5.06 (1H, brs), 5.16 (2H, s), 5.94 (1H, s), 6.87-7.04 (2H, m), 7.22-7.38 (5H, m), 7.39 (2H, d, J=8.3 Hz), 7.54 (2H, d, J=8.3 Hz), 7.62 (1H, d, J=8.3 Hz), 7.74 (1H, d, J=8.3 Hz), 7.96-8.03 (1H, m), 8.61 (1H, s).

MSm/z: 543 (M$^+$+H).

Example 78

N-[[6-(4-Chlorophenylsulfonyl)(2,5-difluorophenyl)methylpyridin-3-yl]methyl]-3-cyanobenzenesulfonamide

[Chemical formula 121]

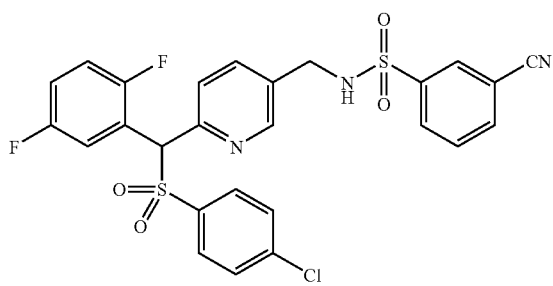

To a dichloromethane (0.5 ml) solution of the [6-[(4-chlorophenylsulfonyl)(2,5-difluorophenyl)methyl]pyridin-3-yl]methylamine (28 mg, 0.068 mmol) obtained in Example 63 were added N-methylmorpholine (0.015 ml, 0.14 mmol) and 3-cyanobenzenesulfonyl chloride (22 mg, 0.10 mmol) sequentially at 0° C. The resulting mixture was stirred at room temperature for 6 hours. The reaction mixture was washed with 1N hydrochloric acid. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=7:3 eluate was concentrated under reduced pressure. The solid thus obtained was washed with hexane and collected by filtration to give the title compound (23 mg, 0.040 mmol, 59%) as a white solid.

$^1$H-NMR (400 MHz, CDCl$_3$) δ: 4.26 (2H, d, J=6.4 Hz), 5.08 (1H, t, J=6.4 Hz), 5.91 (1H, s), 6.86-7.06 (2H, m), 7.40 (2H, d, J=8.1 Hz), 7.55 (2H, d, J=8.1 Hz), 7.57-7.70 (3H, m), 7.81 (1H, d, J=7.4 Hz), 7.94-8.05 (2H, m), 8.11 (1H, s), 8.46 (1H, s).

MSm/z: 574 (M$^+$+H).

Example 79

N-[[6-(4-Chlorophenylsulfonyl)(2,5-difluorophenyl)methylpyridin-3-yl]methyl]-3-cyano-N-methylbenzenesulfonamide

[Chemical formula 122]

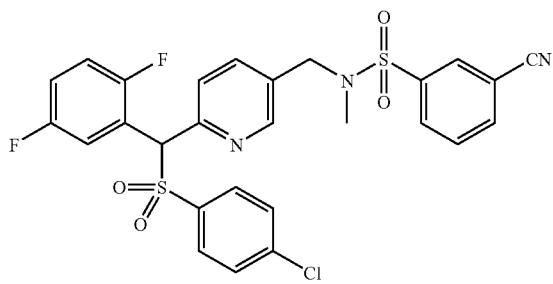

To a tetrahydrofuran (0.5 ml) solution of N-[[6-(4-chlorophenylsulfonyl)(2,5-difluorophenyl)methylpyridin-3-yl]methyl]-3-cyanobenzenesulfonamide (21 mg, 0.037 mmol) were added methanol (0.003 ml, 0.073 mmol), triphenylphosphine (19 mg, 0.073 mmol) and diisopropyl azodicarboxylate (0.014 ml, 0.073 mmol) sequentially at 0° C. The resulting mixture was stirred at room temperature for 2 hours. The reaction mixture was concentrated under reduced pressure. The residue thus obtained was subjected to flash silica gel chromatography. The fraction obtained from the hexane:ethyl acetate=2:1 eluate was concentrated under reduced pressure to give the title compound (13 mg, 0.021 mmol, 58%) as a white solid.

$^1$H-NMR (400 MHz, CDCl$_3$) δ: 2.70 (3H, s), 4.25 (2H, d, J=6.4 Hz), 5.95 (1H, s), 6.87-7.05 (2H, m), 7.40 (2H, d, J=8.5 Hz), 7.56 (2H, d, J=8.5 Hz), 7.66 (1H, d, J=8.1 Hz), 7.73 (1H, t, J=7.8 Hz), 7.81 (1H, dd, J=8.1, 2.2 Hz), 7.91 (1H, d, J=7.8 Hz), 7.99-8.09 (2H, m), 8.12 (1H, s), 8.53 (1H, t, J=2.2 Hz).

MSm/z: 588 (M$^+$+H).

Example 80

3-[[6-(4-Chlorophenylsulfonyl)(2,5-difluorophenyl)methylpyridin-3-yl]methyl]-1,1-dimethylurea

[Chemical formula 123]

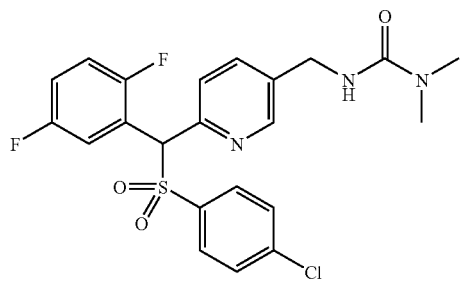

To a dichloromethane (1 ml) solution of the [6-[(4-chlorophenylsulfonyl)(2,5-difluorophenyl)methyl]pyridin-3-yl]methylamine (31 mg, 0.076 mmol) obtained in Example 63 were added triethylamine (0.032 ml, 0.23 mmol) and N,N-dimethylcarbamoyl chloride (0.014 ml, 0.15 mmol) sequentially at 0° C. The resulting mixture was stirred at room temperature for 17 hours. To the reaction mixture were added triethylamine (0.032 ml, 0.23 mmol) and N,N-dimethylcarbamoyl chloride (0.014 ml, 0.15 mmol) sequentially at 0° C. The resulting mixture was stirred at room temperature for 29 hours. The reaction mixture was washed with a saturated aqueous solution of sodium bicarbonate. The organic layer was dried over anhydrous sodium sulfate, and filtered. The filtrate was concentrated under reduced pressure. The residue thus obtained was subjected to flash silica gel chromatography. The fraction obtained from the eluate of ethyl acetate was concentrated under reduced pressure. The solid thus obtained was washed with hexane and collected by filtration to give the title compound (18 mg, 0.036 mmol, 48%) as a white solid.

$^1$H-NMR (400 MHz, CDCl$_3$) δ: 2.93 (6H, s), 4.44 (2H, d, J=4.2 Hz), 4.76 (1H, t, J=4.2 Hz), 5.93 (1H, s), 6.85-7.04 (2H, m), 7.39 (2H, d, J=8.3 Hz), 7.56 (2H, d, J=8.3 Hz), 7.58 (1H, d, J=8.5 Hz), 7.74 (1H, dd, J=8.5, 2.0 Hz), 7.98-8.06 (1H, m), 8.57 (1H, d, J=2.0 Hz)

MSm/z: 480 (M$^+$+H).

Example 81

Methyl[6-(4-chlorophenylsulfonyl)(2,5-difluorophenyl)methylpyridin-3-yl]methylcarbamate

[Chemical formula 124]

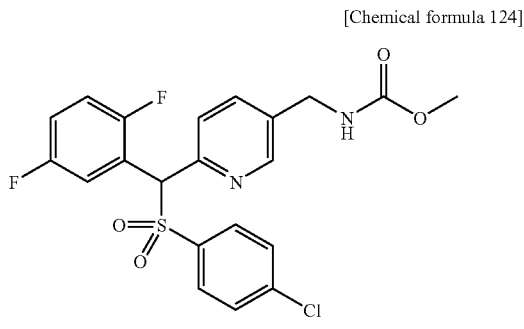

In a similar manner to Example 80, the title compound (16 mg, 0.034 mmol, 42%) as a yellow solid by using the [6-[(4-chlorophenylsulfonyl)(2,5-difluorophenyl)methyl]pyridin-3-yl]methylamine (34 mg, 0.082 mmol) obtained in Example 63 and methyl chlorocarbonate (0.019 ml, 0.25 mmol).

$^1$H-NMR (400 MHz, CDCl$_3$) δ: 3.71 (3H, s), 4.40 (2H, d, J=6.1 Hz), 5.07 (1H, brs), 5.93 (1H, s), 6.87-7.04 (2H, m), 7.39 (2H, d, J=8.5 Hz), 7.55 (2H, d, J=8.5 Hz), 7.60 (1H, d, J=7.8 Hz), 7.70 (1H, d, J=7.8 Hz), 7.97-8.04 (1H, m), 8.55 (1H, s).

MSm/z: 467 (M$^+$+H).

Example 82

N-[[6-(4-Chlorophenylsulfonyl)(2,5-difluorophenyl)methylpyridin-3-yl]methyl]methanesulfonamide

[Chemical formula 125]

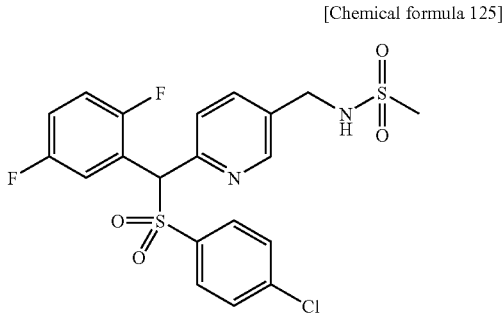

In a similar manner to Example 80, the title compound (20 mg, 0.040 mmol, 49%) as a white solid by using the [6-[(4-chlorophenylsulfonyl)(2,5-difluorophenyl)methyl]pyridin-3-yl]methylamine (34 mg, 0.082 mmol) obtained in Example 63 and methanesulfonyl chloride (0.019 ml, 0.25 mmol).

$^1$H-NMR (400 MHz, CDCl$_3$) δ: 2.97 (3H, s), 4.37 (2H, d, J=6.1 Hz), 4.70 (1H, brs), 5.95 (1H, s), 6.88-7.07 (2H, m), 7.40 (2H, d, J=8.3 Hz), 7.56 (2H, d, J=8.3 Hz), 7.65 (1H, d, J=8.1 Hz), 7.80 (1H, d, J=8.1 Hz), 7.97-8.07 (1H, m), 8.61 (1H, s).

MSm/z: 487 (M$^+$+H).

Example 83

N-[[6-(4-Chlorophenylsulfonyl)(2,5-difluorophenyl)methylpyridin-3-yl]methyl]-1-acetyl-4-piperidinecarboxamide

[Chemical formula 126]

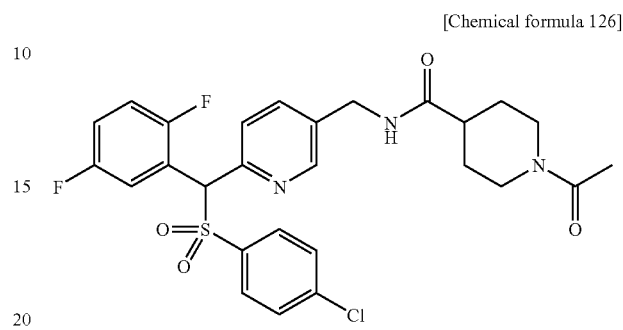

In a similar manner to Example 80, the title compound (24 mg, 0.043 mmol, 52%) as a colorless foamy substance by using the [6-[(4-chlorophenylsulfonyl)(2,5-difluorophenyl)methyl]pyridin-3-yl]methylamine (34 mg, 0.082 mmol) obtained in Example 63 and 1-acetyl-4-piperidinecarbonyl chloride (56 mg, 0.25 mmol).

$^1$H-NMR (400 MHz, CDCl$_3$) δ: 1.58-1.79 (2H, m), 1.82-1.95 (2H, m), 2.09 (3H, s), 2.30-2.41 (1H, m), 2.59-2.70 (1H, m), 3.03-3.13 (1H, m), 3.82-3.92 (1H, m), 4.41-4.53 (2H, m), 4.55-4.63 (1H, m), 5.90-5.98 (2H, m), 6.85-6.94 (1H, m), 6.97-7.04 (1H, m), 7.40 (2H, d, J=8.5 Hz), 7.55 (2H, d, J=8.5 Hz), 7.60 (1H, d, J=8.1 Hz), 7.66 (1H, d, J=8.1 Hz), 7.98-8.05 (1H, m), 8.53 (1H, s).

MSm/z: 562 (M$^+$+H).

Example 84

[6-(4-Chlorophenylsulfonyl)(2,5-difluorophenyl)methylpyridin-3-yl]methyl methylcarbonate

[Chemical formula 127]

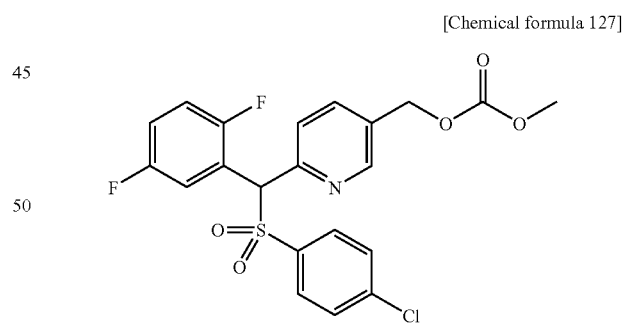

To a dichloromethane (2 ml) solution of the 2-[(4-chlorophenylsulfonyl)(2,5-difluorophenyl)methyl]-5-(hydroxymethyl)pyridine (50 mg, 0.12 mmol) obtained in Example 43 were added pyridine (0.040 ml, 0.49 mmol) and methyl chloroformate (0.019 ml, 0.24 mmol) sequentially at 0° C. The resulting mixture was stirred at room temperature for 1 hour. To the reaction mixture was added methyl chloroformate (0.019 ml, 0.24 mmol) at 0° C. The resulting mixture was stirred at room temperature for 5 hours. The reaction mixture was washed with 1N hydrochloric acid. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=4:1 eluate was concentrated under reduced pressure. The solid thus obtained was washed with hexane and collected by filtration to give the title compound (50 mg, 0.11 mmol, 88%) as a white solid.

$^1$H-NMR (400 MHz, CDCl$_3$) δ: 3.81 (3H, s), 5.18 (2H, s), 5.95 (1H, s), 6.89-7.04 (2H, m), 7.40 (2H, d, J=8.5 Hz), 7.55 (2H, d, J=8.5 Hz), 7.65 (1H, d, J=8.1 Hz), 7.78 (1H, dd, J=8.1, 2.2 Hz), 7.97-8.03 (1H, m), 8.64 (1H, d, J=2.2 Hz).

MSm/z: 468 (M$^+$+H).

Example 85

[6-[(4-Chlorophenylsulfonyl)(2,5-difluorophenyl) methyl]pyridin-3-yl]carbaldehyde oxime (Isomer A and Isomer B)

[Chemical formula 128]

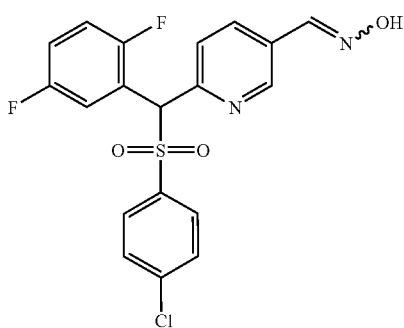

To a dichloromethane (3 ml) solution of the [6-[(4-chlorophenylsulfonyl)(2,5-difluorophenyl)methyl]pyridin-3-yl] carbaldehyde (100 mg, 0.25 mmol) obtained in Example 47 were added N-methylmorpholine (32 μl, 0.29 mmol) and hydroxylamine hydrochloride (26 mg, 0.36 mmol). The resulting mixture was stirred at room temperature for 3 days. The reaction mixture was diluted with dichloromethane, washed sequentially with water, a saturated aqueous solution of sodium bicarbonate and brine. The organic layer thus obtained was dried over magnesium sulfate and concentrated under reduced pressure. The residue thus obtained was subjected to flash silica gel column chromatography. The fraction obtained from the hexane:ethyl acetate=3:2 eluate was concentrated under reduced pressure to give the title Isomer A (low polar compound) (79 mg, 0.19 mmol, 72%) as a white powder and the title Isomer B (high polar compound) (17 mg, 0.040 mmol, 17%) as a white powder.

Isomer A $^1$H-NMR (400 MHz, CDCl$_3$) δ: 5.97 (1H, s), 6.91-6.96 (1H, m), 6.99-7.05 (1H, m), 7.40 (2H, d, J=8.6 Hz), 7.56 (2H, d, J=8.6 Hz), 7.66 (1H, d, J=8.1 Hz), 7.78 (1H, s), 7.96-8.02 (2H, m), 8.14 (1H, s), 8.75 (1H, d, J=1.7 Hz).

mp: 187 to 188° C.

MSm/z: 423 (M$^+$+H).

Isomer B $^1$H-NMR (400 MHz, CDCl$_3$) δ: 5.98 (1H, s), 6.91-6.97 (1H, m), 7.00-7.06 (1H, m), 7.40 (1H, s), 7.41 (2H, d, J=8.6 Hz), 7.57 (2H, d, J=8.6 Hz), 7.71 (1H, d, J=8.3 Hz), 7.90-8.02 (2H, m), 8.41 (1H, dd, J=8.3, 2.1 Hz), 9.00 (1H, s).

mp: 194 to 196° C.

MSm/z: 423 (M$^+$+H).

Example 86

6-[(4-Chlorophenylsulfonyl)(2,5-difluorophenyl) methyl]-N-cyclohexylmethylnicotinamide

[Chemical formula 129]

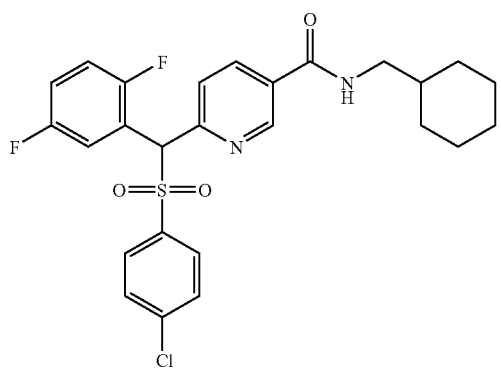

To a dichloromethane (5 ml) solution of the [6-[(4-chlorophenylsulfonyl)(2,5-difluorophenyl)methyl]pyridin-3-yl] carboxylic acid (80 mg, 0.19 mmol) obtained in Example 50 were added triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and aminomethylcyclohexane (30 μl, 0.23 mmol). The resulting mixture was stirred at room temperature for 4.5 hours. The reaction mixture was diluted with dichloromethane and washed sequentially with water, a saturated aqueous solution of sodium bicarbonate and brine. The organic layer thus obtained was dried over magnesium sulfate and concentrated under reduced pressure. The residue thus obtained was subjected to flash silica gel column chromatography. The fraction obtained from the hexane:ethyl acetate=3:1 eluate was concentrated under reduced pressure to give the title compound (58 mg, 0.11 mmol, 59%) as a white powder.

$^1$H-NMR (400 MHz, CDCl$_3$) δ: 0.95-1.80 (11H, m), 3.32 (2H, d, J=6.4 Hz), 5.98 (1H, s), 6.13-6.16 (1H, m), 6.90-6.96 (1H, m), 7.00-706 (1H, m), 7.40 (2H, d, J=8.6 Hz), 7.55 (2H, d, J=8.6 Hz), 7.69 (1H, d, J=8.3 Hz), 7.97-8.02 (1H, m), 8.13 (1H, dd, J=8.3, 2.2 Hz), 8.94 (1H, d, J=2.2 Hz).

MSm/z: 519 (M$^+$+H).

Example 87

6-[(4-Chlorophenylsulfonyl)(2,5-difluorophenyl) methyl]-N-(5-chloropyridin-2-yl)nicotinamide

[Chemical formula 130]

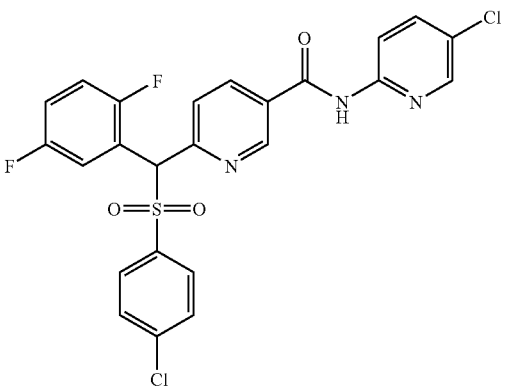

To a dichloromethane (5 ml) solution of the [6-[(4-chlorophenylsulfonyl)(2,5-difluorophenyl)methyl]pyridin-3-yl] carboxylic acid (80 mg, 0.19 mmol) obtained in Example 50 were added triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and 2-amino-5-chloropyridine (29 mg, 0.23 mmol). The resulting mixture was stirred at room temperature for 5 hours. The reaction mixture was diluted with dichloromethane and washed sequentially with water, a saturated aqueous solution of sodium bicarbonate and brine. The organic layer thus obtained was dried over magnesium sulfate and concentrated under reduced pressure. The residue thus obtained was subjected to flash silica gel column chromatography. The fraction obtained from the hexane:ethyl acetate=3:1 eluate was concentrated under reduced pressure to give the title compound (27 mg, 0.051 mmol, 27%) as a white powder.

$^1$H-NMR (400 MHz, CDCl$_3$) δ: 6.04 (1H, s), 6.92-6.97 (1H, m), 7.01-707 (1H, m), 7.42 (2H, d, J=8.6 Hz), 7.57 (2H, d, J=8.6 Hz), 7.75 (1H, dd, J=9.1, 2.4 Hz), 7.80 (1H, d, J=8.1 Hz), 7.97-8.01 (1H, m), 8.26 (1H, dd, J=8.1, 2.2 Hz), 8.28 (1H, d, J=2.4 Hz) 8.33 (1H, d, J=9.1 Hz), 8.51 (1H, s), 9.12 (1H, d, J=2.2 Hz)

MSm/z: 534 (M$^+$+H).

Example 88

6-[(4-Chlorophenylsulfonyl)(2,5-difluorophenyl) methyl]nicotinic acid N',N'-dimethylhydrazide

[Chemical formula 131]

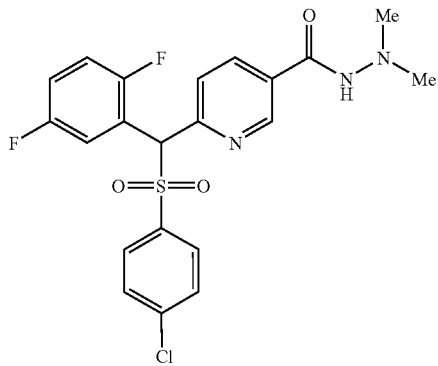

To a dichloromethane (5 ml) solution of the [6-[(4-chlorophenylsulfonyl)(2,5-difluorophenyl)methyl]pyridin-3-yl] carboxylic acid (80 mg, 0.19 mmol) obtained in Example 50 were added triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and 1,1-dimethylhydrazine (21 μl, 0.23 mmol). The resulting mixture was stirred at room temperature for 7 hours. The reaction mixture was diluted with dichloromethane. The diluted mixture was washed sequentially with water, a saturated aqueous solution of sodium bicarbonate and brine. The organic layer thus obtained was dried over magnesium sulfate and concentrated under reduced pressure. The residue thus obtained was subjected to flash silica gel column chromatography. The fraction obtained from the dichloromethane:methanol=50:1 eluate was concentrated under reduced pressure to give the title compound (60 mg, 0.13 mmol, 68%) as a colorless amorphous substance.

$^1$H-NMR (400 MHz, CDCl$_3$) δ: 2.57 (0.9H, s), 2.72 (5.1H, s), 5.98 (1H, s), 6.48 (0.15H, s), 6.90-7.06 (2.85H, m), 7.41 (2H, d, J=8.6 Hz), 7.56 (2H, d, J=8.6 Hz), 7.68 (1H, d, J=8.1 Hz), 7.97-8.04 (1H, m), 8.13-8.17 (1H, m), 8.94 (0.85H, s), 9.07 (0.15H, s)

MSm/z: 466 (M$^+$+H).

Example 89

6-[(4-Chlorophenylsulfonyl)(2,5-difluorophenyl) methyl]nicotinic acid N'-(furan-2-carbonyl)hydrazide

[Chemical formula 132]

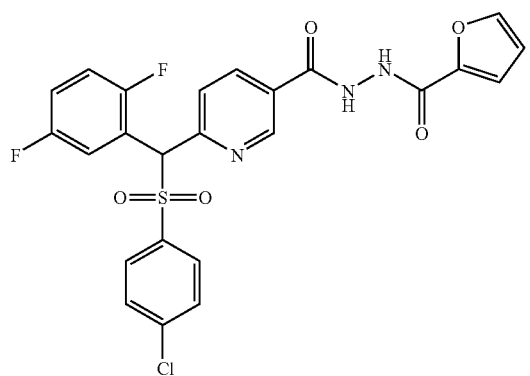

To a dichloromethane (5 ml) solution of the [6-[(4-chlorophenylsulfonyl)(2,5-difluorophenyl)methyl]pyridin-3-yl] carboxylic acid (80 mg, 0.19 mmol) obtained in Example 50 were added triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and 2-furanhydrazide (29 mg, 0.23 mmol). The resulting mixture was stirred at room temperature for 7.5 hours. The reaction mixture was diluted with dichloromethane. The diluted mixture was then washed sequentially with water, a saturated aqueous solution of sodium bicarbonate and brine. The organic layer thus obtained was dried over magnesium sulfate and concentrated under reduced pressure under reduced pressure. The residue thus obtained was subjected to flash silica gel column chromatography. The fraction obtained from the dichloromethane:methanol=50:1 eluate was concentrated under reduced pressure. The solid thus obtained was recrystallized from dichloromethane-hexane to give the title compound (58 mg, 0.11 mmol, 58%) as a white powder.

$^1$H-NMR (400 MHz, CDCl$_3$) δ: 6.01 (0.7H, s), 6.02 (0.3H, s), 6.55 (0.7H, dd, J=3.4, 1.7 Hz), 6.91-6.96 (1H, m), 6.99-7.04 (1H, m), 7.21 (0.7H, d, J=3.4 Hz), 7.41 (2H, d, J=8.6 Hz), 7.53 (0.3H, dd, J=1.7, 0.7 Hz), 7.56-7.60 (3H, m), 7.74 (1H, d, J=8.3 Hz), 7.77 (0.3H, d, J=8.8 Hz), 7.95-7.99 (1H, m), 8.15-8.19 (1H, m), 8.99 (0.3H, s), 9.03 (1H, d, J=2.2 Hz), 9.14 (0.7H, brs), 9.67 (0.7H, brs), 9.98 (0.3H, brs).

MSm/z: 532 (M$^+$+H).

Example 90

N-[[6-[(4-Chlorophenylsulfonyl)(2,5-difluorophenyl)methyl]pyridin-3-yl]methyl]-(E)-3-(pyridin-4-yl)acrylamide

[Chemical formula 133]

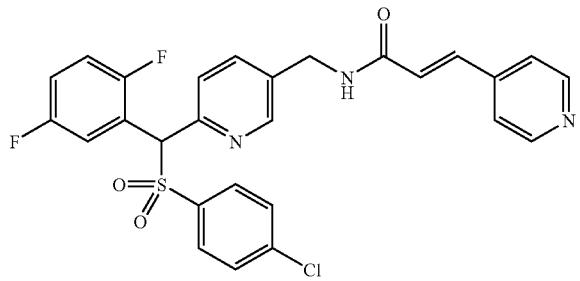

To a dichloromethane (1 ml) solution of the [6-[(4-chlorophenylsulfonyl)(2,5-difluorophenyl)methyl]pyridin-3-yl]methylamine (41 mg, 0.10 mmol) obtained in Example 63, (E)-3-(pyridin-4-yl)acrylic acid (15 mg, 0.10 mmol), benzotriazol-1-ol (14 mg, 0.10 mmol) and N-methylmorpholine (0.011 ml, 0.10 mmol) was added 1-ethyl-3-(3-dimethylaminopropyl)carbodiimide hydrochloride (19 mg, 0.10 mmol) at 0° C. The resulting mixture was stirred at room temperature for 19 hours. The reaction mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel chromatography. The fraction obtained from the ethyl acetate eluate was concentrated under reduced pressure. The solid thus obtained was washed with diethyl ether and collected by filtration to give the title compound (35 mg, 0.065 mmol, 65%) as a white solid.

$^1$H-NMR (400 MHz, CDCl$_3$) δ: 4.53-4.66 (2H, m), 5.93 (1H, s), 6.09-6.17 (1H, m), 6.57 (1H, d, J=15.6 Hz), 6.86-6.93 (1H, m), 6.96-7.04 (1H, m), 7.34 (2H, d, J=5.9 Hz), 7.40 (2H, d, J=8.5 Hz), 7.56 (2H, d, J=8.5 Hz), 7.60 (1H, d, J=15.6 Hz), 7.61 (1H, d, J=8.1 Hz), 7.74 (1H, dd, J=8.1, 2.2 Hz), 7.99-8.06 (1H, m), 8.59 (1H, d, J=2.2 Hz), 8.64 (2H, d, J=5.9 Hz).
MSm/z: 540 (M$^+$+H).

Example 91

[6-[(4-Chlorophenylsulfonyl)(2,5-difluorophenyl)methyl]pyridin-3-yl](thiomorpholin-4-yl)methanone

[Chemical formula 134]

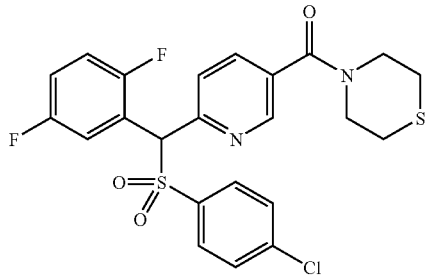

In a similar manner to Example 90, the title compound (240 mg, 0.47 mmol, 94%) as a white solid by using the [6-[(4-chlorophenylsulfonyl)(2,5-difluorophenyl)methyl]pyridin-3-yl]carboxylic acid (212 mg, 0.50 mmol) obtained in Example 50 and thiomorpholine (0.047 ml, 0.50 mmol).

$^1$H-NMR (400 MHz, CDCl$_3$) δ: 2.61 (2H, brs), 2.74 (2H, brs), 3.69 (2H, brs), 4.04 (2H, brs), 5.97 (1H, s), 6.88-6.95 (1H, m), 6.98-7.06 (1H, m), 7.41 (2H, d, J=8.5 Hz), 7.57 (2H, d, J=8.5 Hz), 7.73 (1H, d, J=8.1 Hz), 7.79 (1H, dd, J=8.1, 2.2 Hz), 7.95-8.02 (1H, m), 8.64 (1H, d, J=2.2 Hz).
MSm/z: 509 (M$^+$+H).

Example 92

[6-[(4-Chlorophenylsulfonyl)(2,5-difluorophenyl)methyl]pyridin-3-yl](1,1-dioxo-1λ$^6$-thiomorpholin-4-yl)methanone (Compound A) and [6-[(4-chlorophenylsulfonyl)(2,5-difluorophenyl)methyl]pyridin-3-yl](1-oxo-1λ$^4$-thiomorpholin-4-yl)methanone (Compound B)

[Chemical formula 135]

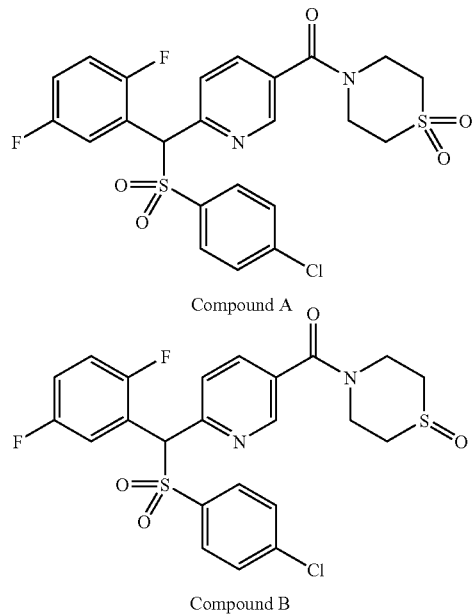

Compound A

Compound B

To a dichloromethane (3 ml) solution of [6-[(4-chlorophenylsulfonyl)(2,5-difluorophenyl)methyl]pyridin-3-yl](thiomorpholin-4-yl)methanone (153 mg, 0.30 mmol) was added 3-chloroperbenzoic acid (96 mg, 0.36 mmol) under ice cooling. The resulting mixture was stirred at room temperature 2 hours. The reaction mixture was diluted with dichloromethane and washed sequentially with a 1N aqueous sodium hydroxide solution and brine. The organic layer thus obtained was dried over magnesium sulfate and concentrated under reduced pressure. The residue thus obtained was subjected to flash silica gel column chromatography. The fraction obtained from the hexane:ethyl acetate=1:2 eluate was concentrated under reduced pressure to give the title compound A (low polar compound) (81 mg, 0.15 mmol, 50%) as a white powder, while the fraction obtained from the dichloromethane:methanol=10:1 eluate was concentrated under reduced pressure to give the title compound B (high polar compound) (73 mg, 0.14 mmol, 46%) as a white powder.

Compound A $^1$H-NMR (400 MHz, CDCl$_3$) δ: 3.10 (4H, brs), 4.13 (4H, brs), 5.99 (1H, s), 6.88-6.93 (1H, m), 7.00-7.06 (1H, m), 7.42 (2H, d, J=8.5 Hz), 7.58 (2H, d, J=8.5 Hz), 7.79 (1H, d, J=8.1 Hz), 7.86 (1H, dd, J=8.1, 1.7 Hz), 7.97-8.02 (1H, m), 8.71 (1H, d, J=1.7 Hz).
MSm/z: 541 (M$^+$+H).

Compound B

¹H-NMR (400 MHz, CDCl₃) δ: 2.70-3.00 (4H, m), 3.74 (1H, brs), 4.10 (2H, brs), 4.63 (1H, brs), 5.98 (1H, s), 6.88-6.94 (1H, m), 7.00-7.06 (1H, m), 7.42 (2H, d, J=8.6 Hz), 7.58 (2H, d, J=8.6 Hz), 7.77 (1H, d, J=8.1 Hz), 7.84 (1H, dd, J=8.1, 2.2 Hz), 7.98-8.02 (1H, m), 8.70 (1H, d, J=2.2 Hz).

MSm/z: 525 (M⁺+H).

Example 93

N-(3-Methylthiopropyl)-6-[(4-chlorophenylsulfonyl)(2,5-difluorophenyl)methyl]nicotinamide

[Chemical formula 136]

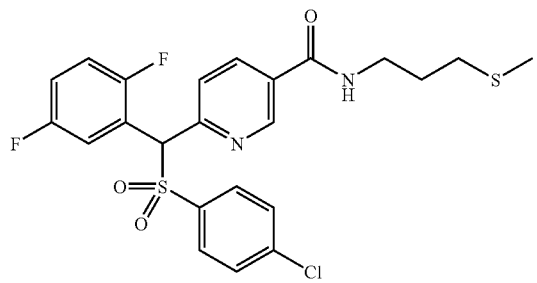

In a similar manner to Example 90, the title compound (238 mg, 0.47 mmol, 93%) as a white solid by using the [6-[(4-chlorophenylsulfonyl)(2,5-difluorophenyl)methyl]pyridin-3-yl]carboxylic acid (212 mg, 0.50 mmol) obtained in Example 50 and 3-methylthiopropylamine (0.055 ml, 0.50 mmol).

¹H-NMR (400 MHz, CDCl₃) δ: 1.92-2.01 (2H, m), 2.14 (3H, s), 2.63 (2H, t, J=6.8 Hz), 3.58-3.64 (2H, m), 5.99 (1H, s), 6.57-6.64 (1H, m), 6.90-6.97 (1H, m), 6.99-7.06 (1H, m), 7.41 (2H, d, J=8.5 Hz), 7.56 (2H, d, J=8.5 Hz), 7.71 (1H, d, J=8.1 Hz), 7.96-8.03 (1H, m), 8.16 (1H, dd, J=8.1, 2.2 Hz), 8.96 (1H, d, J=2.2 Hz).

MSm/z: 511 (M⁺+H).

Example 94

N-(3-Methylsulfonylpropyl)-6-[(4-chlorophenylsulfonyl)(2,5-difluorophenyl)methyl]nicotinamide (Compound A) and N-(3-methylsulfinylpropyl)-6-[(4-chlorophenylsulfonyl)(2,5-difluorophenyl)methyl]nicotinamide (Compound B)

[Chemical formula 137]

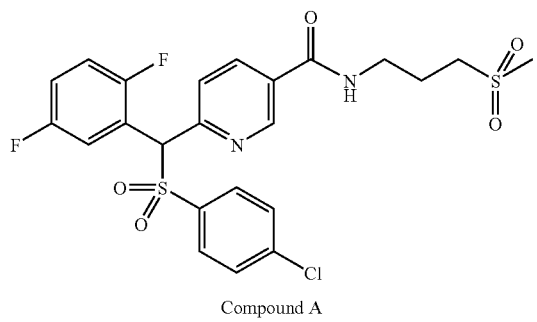

Compound A

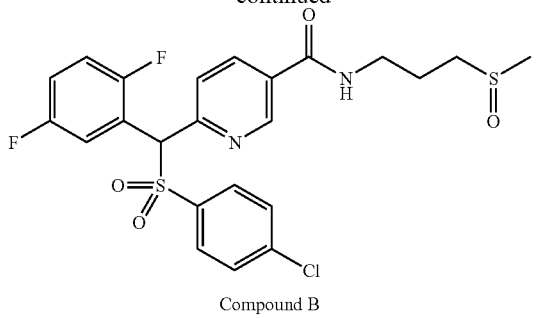

Compound B

To a dichloromethane (3 ml) solution of N-(3-methylthiopropyl)-6-[(4-chlorophenylsulfonyl)(2,5-difluorophenyl)methyl]nicotinamide (153 mg, 0.30 mmol) was added 3-chloroperbenzoic acid (purity: 65% or greater) (96 mg, 0.36 mmol) at 0° C. The resulting mixture was stirred at room temperature for 3 hours. The reaction mixture was washed with a 1N aqueous sodium hydroxide solution. The organic layer was dried over anhydrous sodium sulfate and filtered. The filtrate was concentrated under reduced pressure. The residue thus obtained was subjected to flash silica gel chromatography. The fraction obtained from the ethyl acetate eluate was concentrated under reduced pressure. The solid thus obtained was washed with diethyl ether and collected by filtration to afford the title Compound A (53 mg, 0.098 mmol, 32%) as a white solid. The fraction obtained from the dichloromethane:methanol=15:1 eluate was then concentrated under reduced pressure. The solid thus obtained was washed with diethyl ether and collected by filtration to give the title compound B (68 mg, 0.13 mmol, 43%) as a white solid.

Compound A

¹H-NMR (400 MHz, CDCl₃) δ: 2.20-2.30 (2H, m), 2.98 (3H, s), 3.17 (2H, t, J=6.8 Hz), 3.65-3.72 (2H, m), 5.99 (1H, s), 6.82-6.88 (1H, m), 6.90-6.97 (1H, m), 6.99-7.06 (1H, m), 7.41 (2H, d, J=8.5 Hz), 7.56 (2H, d, J=8.5 Hz), 7.72 (1H, d, J=8.1 Hz), 7.96-8.02 (1H, m), 8.16 (1H, dd, J=8.1, 2.2 Hz), 9.00 (1H, d, J=2.2 Hz).

MSm/z: 543 (M⁺+H).

Compound B

¹H-NMR (400 MHz, CDCl₃) δ: 2.11-2.23 (1H, m), 2.26-2.37 (1H, m), 2.63 (3H, s), 2.78-2.86 (1H, m), 2.92-3.00 (1H, m), 3.51-3.61 (1H, m), 3.66-3.75 (1H, m), 5.99 (1H, s), 6.90-6.98 (1H, m), 6.99-7.06 (1H, m), 7.40 (2H, d, J=8.5 Hz), 7.55 (2H, d, J=8.5 Hz), 7.69 (1H, d, J=8.1 Hz), 7.88-8.01 (2H, m), 8.22 (1H, dd, J=8.1, 2.2 Hz), 9.08 (1H, d, J=2.2 Hz).

MSm/z: 527 (M⁺+H).

Example 95

2-Chloro-5-[(3-chloropyridin-4-yl)(2,5-difluorophenyl)methylthio]pyridine

[Chemical formula 138]

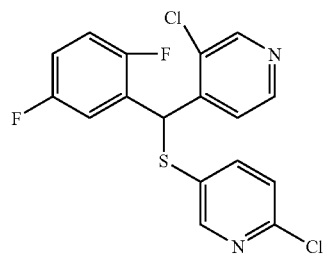

To an ethanol (7 ml) solution of the O-ethyl S-(6-chloro-3-pyridyl) dithiocarbonate (164 mg, 0.70 mmol) obtained in Referential Example 26 was added a 1N aqueous sodium hydroxide solution (7 ml). The resulting mixture was stirred at 80° C. for 3 hours. After the reaction mixture was cooled to room temperature, 1N hydrochloric acid was added thereto. The resulting mixture was extracted with dichloromethane. The organic layer was dried over anhydrous sodium sulfate and filtered. The filtrate was concentrated under reduced pressure to afford 6-chloro-3-pyridinethiol as a yellow solid.

To a dichloromethane (3 ml) solution of the 3-chloro-4-[(2,5-difluorophenyl)-hydroxymethyl]pyridine (153 mg, 0.60 mmol) obtained in Referential Example 23 were added triethylamine (0.167 ml, 1.20 mmol) and methanesulfonyl chloride (0.070 ml, 0.90 mmol) sequentially at 0° C. The resulting mixture was stirred at room temperature for 2 hours. The reaction mixture was washed with a saturated aqueous solution of sodium bicarbonate. The organic layer was then dried over anhydrous sodium sulfate and filtered. The filtrate was concentrated under reduced pressure. To an N,N-dimethylformamide (3 ml) solution of the residue thus obtained was added an N,N-dimethylformamide (2 ml) solution of 6-chloro-3-pyridinethiol and potassium carbonate (100 mg, 0.72 mmol) sequentially. The resulting mixture was stirred at room temperature for 18 hours. Ethyl acetate was added to the reaction mixture. The resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=17:3 eluate was concentrated under reduced pressure to give the title compound (111 mg, 0.29 mmol, 48%) as a white solid.

$^1$H-NMR (400 MHz, CDCl$_3$) δ: 6.04 (1H, s), 6.95-7.05 (2H, m), 7.10-7.20 (1H, m), 7.25 (1H, d, J=8.1 Hz), 7.57 (1H, d, J=5.1 Hz), 7.60 (1H, dd, J=8.1, 2.5 Hz), 8.31 (1H, d, J=2.5 Hz), 8.54 (1H, d, J=5.1 Hz), 8.59 (1H, s).

MSm/z: 383 (M$^+$+H).

Example 96

2-Chloro-5-[(3-chloropyridin-4-yl)(2,5-difluorophenyl)methylsulfonyl]pyridine

[Chemical formula 139]

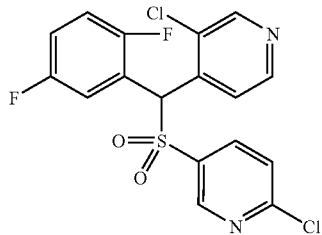

To a methanol (4 ml) solution of 2-chloro-5-[(3-chloropyridin-4-yl)(2,5-difluorophenyl)methylthio]pyridine (109 mg, 0.28 mmol) were added 31% aqueous hydrogen peroxide (2 ml) and hexaammonium heptamolybdate tetrahydrate (30 mg). The resulting mixture was stirred at room temperature for 17 hours. Ethyl acetate was added to the reaction mixture. The resulting mixture was washed with a saturated aqueous solution of sodium bicarbonate. The organic layer was dried over anhydrous sodium sulfate and filtered. The filtrate was concentrated under reduced pressure. The residue was subjected to flash silica gel column chromatography. The fraction obtained from the hexane:ethyl acetate=17:3 eluate was concentrated under reduced pressure to give the title compound (108 mg, 0.26 mmol, 92%) as a white solid.

$^1$H-NMR (400 MHz, CDCl$_3$) δ: 6.26 (1H, s), 6.94-7.03 (1H, m), 7.06-7.15 (1H, m), 7.44 (1H, d, J=8.3 Hz), 7.50-7.56 (1H, m), 7.89 (1H, dd, J=8.3, 2.7 Hz), 8.12 (1H, d, J=5.1 Hz), 8.59 (1H, d, J=2.7 Hz), 8.61 (1H, s), 8.66 (1H, d, J=5.1 Hz).

MSm/z: 415 (M$^+$+H).

Example 97

5-[(3-Chloropyridin-4-yl)(2,5-difluorophenyl)methylsulfonyl]-2-fluoropyridine

[Chemical formula 140]

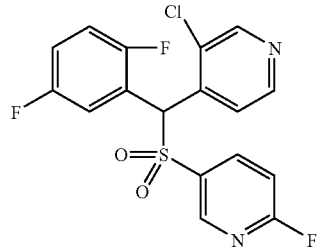

To an acetonitrile (2 ml) solution of 2-chloro-5-[(3-chloropyridin-4-yl)(2,5-difluorophenyl)methylsulfonyl]pyridine (66 mg, 0.16 mmol) were added potassium fluoride (94 mg, 1.60 mmol) and tetraphenylphosphonium bromide (134 mg, 0.32 mmol). The resulting mixture was heated under reflux for 16 hours. After the reaction mixture was cooled to room temperature, dichloromethane was added thereto. The resulting mixture was washed with water. The organic layer was dried over anhydrous sodium sulfate and filtered. The filtrate was concentrated under reduced pressure. The residue was subjected to flash silica gel column chromatography. The fraction obtained from the hexane:ethyl acetate=17:3 eluate is concentrated under reduced pressure to give the title compound (4.5 mg, 0.011 mmol, 7%) as a white solid.

$^1$H-NMR (400 MHz, CDCl$_3$) δ: 6.26 (1H, s), 6.93-7.13 (3H, m), 7.50-7.56 (1H, m), 8.01-8.08 (1H, m), 8.13 (1H, d, J=5.1 Hz), 8.48 (1H, d, J=2.2 Hz), 8.60 (1H, s), 8.66 (1H, d, J=5.1 Hz).

MSm/z: 440 (M$^+$+H+ MeCN).

Example 98

N'-[6-[(4-Chlorophenylsulfonyl)(2,5-difluorophenyl)methyl]pyridin-3-ylmethylidene]-2-thiophenecarbohydrazide

[Chemical formula 141]

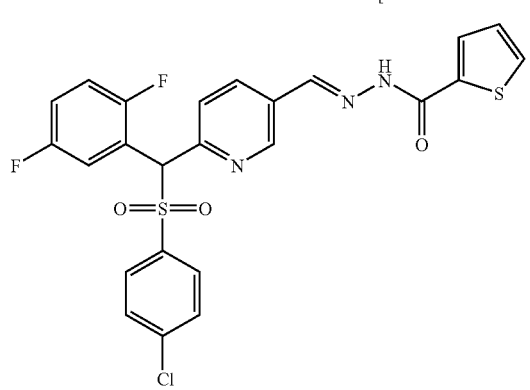

The [6-[(4-chlorophenylsulfonyl)-(2,5-difluorophenyl)methyl]pyridin-3-yl]carbaldehyde (100 mg, 0.245 mmol) obtained in Example 47 and 2-thiophenecarbohydrazide (41.7 mg, 0.294 mmol) were dissolved in ethanol (3 ml). The resulting mixture was stirred at room temperature for 3 days. The solid thus precipitated was collected by filtration and washed with ethanol. The solid thus obtained was recrystallized from ethanol to give the title compound (91.0 mg, 0.171 mmol, 70%) as a white solid.

$^1$H-NMR (400 MHz, CDCl$_3$/DMSO-d$_6$) δ: 5.98 (1H, s), 6.93-7.01 (1H, m), 7.02-7.09 (1H, m), 7.14-7.20 (1H, brm), 7.42 (2H, d, J=8.5 Hz), 7.57 (2H, d, J=8.5 Hz), 7.62-7.73 (2H, brm), 8.02-8.20 (3H, m), 8.95 (1H, s), 11.5 (1H, s).
MSm/z: 532 (M$^+$+H).

Example 99

6-[(4-Chlorophenylsulfonyl)(2,5-difluorophenyl)methyl]nicotinamide

[Chemical formula 142]

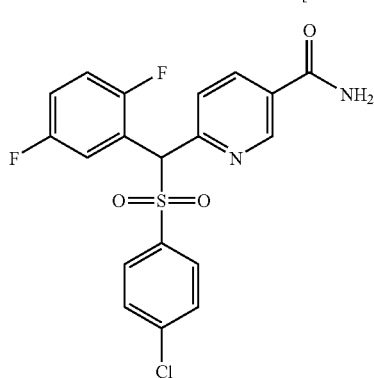

To a dichloromethane (4 ml) suspension of the [6-[(4-chlorophenylsulfonyl)(2,5-difluorophenyl)methyl]pyridin-3-yl]carboxylic acid (100 mg, 0.236 mmol) obtained in Example 50 were added thionyl chloride (1.00 ml) and N,N-dimethylformamide (one drop). The resulting mixture was stirred at room temperature for 18 hours. The reaction mixture was concentrated to dryness. The residue thus obtained was dissolved in dichloromethane (6 ml). A 28% aqueous ammonia (2 ml) was added to the resulting solution. After the mixture was stirred at room temperature for 3 hours, the reaction mixture was acidified with 1N hydrochloric acid. The resulting mixture was concentrated and the solid thus formed was collected by filtration. The solid thus obtained was washed with water and ethanol and then, recrystallized from ethanol to give the title compound (47.9 mg, 0.113 mmol, 46%) as a white solid.
$^1$H-NMR (400 MHz, CDCl$_3$/DMSO-d$_6$) δ: 6.00 (1H, s), 6.38 (1H, brs), 6.94-6.99 (1H, m), 7.02-7.08 (1H, m), 7.43 (2H, d, J=8.5 Hz), 7.56 (2H, d, J=8.5 Hz), 7.67 (1H, d, J=7.6 Hz), 7.65-7.75 (1H, brm), 7.99-8.04 (1H, m), 8.26 (1H, dd, J=8.1, 2.4 Hz), 9.12 (1H, d, J=1.7 Hz).
MSm/z: 423 (M$^+$+H).

Example 100

6-[(4-Chlorophenylsulfonyl)(2,5-difluorophenyl)methyl]-N-(4-methylcyclohexyl)nicotinamide

[Chemical formula 143]

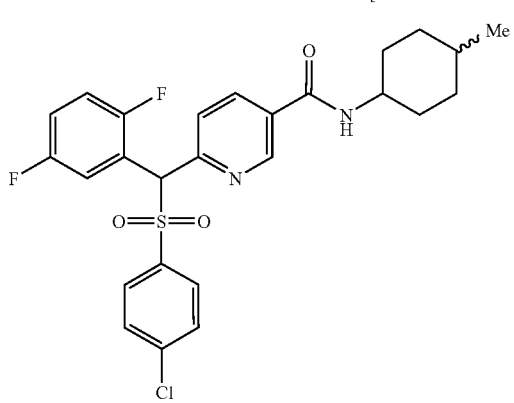

To a dichloromethane (4 ml) suspension of the [6-[(4-chlorophenylsulfonyl)(2,5-difluorophenyl)methyl]pyridin-3-yl]carboxylic acid (100 mg, 0.236 mmol) obtained in Example 50 were added thionyl chloride (1.00 ml) and N,N-dimethylformamide (one drop). The resulting mixture was stirred at room temperature for 6 hours. The reaction mixture was concentrated to dryness and the residue thus obtained was dissolved in dichloromethane (6 ml). To the resulting solution were added N-methylmorpholine (51.8 μl, 0.472 mmol) and 4-methylcyclohexylamine (37.4 μl, 0.283 mmol). The resulting mixture was stirred at room temperature for 18 hours, followed by dilution with dichloromethane. The diluted mixture was washed sequentially with 1N hydrochloric acid, water and brine, dried over magnesium sulfate and concentrated. The residue thus obtained was subjected to flash silica gel column chromatography. The fraction obtained from the hexane:ethyl acetate=3:1 eluate was concentrated to give a white solid. The solid thus obtained was recrystallized from ethyl acetate-hexane to give the title compound (70.3 mg, 0.135 mmol, 57%) as a white powder.
$^1$H-NMR (400 MHz, CDCl$_3$) δ: 0.92 (1.8H, d, J=6.6 Hz), 0.96 (1.2H, d, J=6.4 Hz), 1.05-1.30 (3H, m), 1.32-1.43 (0.6H, m), 1.55-1.83 (4.4H, m), 2.03-2.12 (1H, m), 3.86-3.97 (0.6H, m), 4.20-4.28 (0.4H, m), 5.88 (0.6H, d, J=7.1 Hz), 5.98 (1H, s), 6.18 (0.4H, d, J=7.3 Hz), 6.90-6.96 (1H, m), 6.98-7.06 (1H, m), 7.41 (1.2H, d, J=8.1 Hz), 7.41 (0.8H, d, J=8.1 Hz), 7.56 (1.2H, d, J=8.1 Hz), 7.57 (0.8H, d, J=8.1 Hz), 7.67-7.72 (1H, m), 7.97-8.05 (1H, m), 8.10-8.18 (1H, m), 8.93 (0.6H, d, J=2.2 Hz), 8.96 (0.4H, d, J=2.2 Hz).
MSm/z: 519 (M$^+$+H).

Example 101

6-[(4-Chlorophenylsulfonyl)(2,5-difluorophenyl)methyl]-N-methoxynicotinamide

[Chemical formula 144]

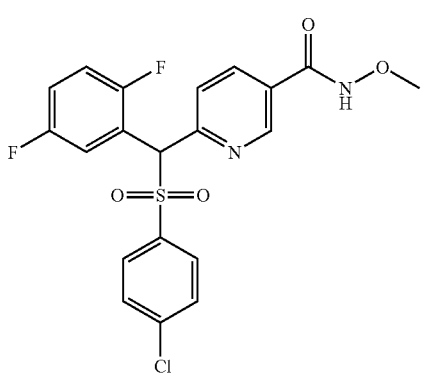

To a dichloromethane (6 ml) suspension of the [6-[(4-chlorophenylsulfonyl)(2,5-difluorophenyl)methyl]pyridin-3-yl]carboxylic acid (100 mg, 0.236 mmol) obtained in Example 50 were added N-methylmorpholine (77.7 μl, 0.708 mmol), O-methylhydroxylamine hydrochloride (23.6 mg, 0.283 mmol), and 1-ethyl-3-(3-dimethylaminopropyl)carbodiimide hydrochloride (54.3 mg, 0.283 mmol). The resulting mixture was stirred at room temperature for 1 hour. To the reaction mixture was added tetrahydrofuran (1 ml). After stirring at room temperature for 18 hours, the reaction mixture was diluted with dichloromethane. The diluted mixture was washed with water and brine. The organic layer thus obtained was dried over magnesium sulfate and concentrated under reduced pressure. The residue thus obtained was subjected to flash silica gel column chromatography. The fraction obtained from the hexane:ethyl acetate=1:1 eluate was concentrated to give a white solid. The resulting solid was washed with ethyl acetate to give the title compound (55.1 mg, 0.122 mmol, 52%) as a white powder.

$^1$H-NMR (400 MHz, CDCl$_3$) δ: 3.90 (2.4H, s), 3.97 (0.6H, s), 5.97 (0.2H, s), 5.98 (0.8H, s), 6.90-7.07 (2H, m), 7.39-7.46 (2H, m), 7.54-7.59 (2H, m), 7.63 (0.2H, d, J=8.3 Hz), 7.73 (0.8H, d, J=8.1 Hz), 7.94-8.00 (1H, m), 8.10-8.15 (1H, m), 8.76 (1H, brs), 8.92 (0.8H, d, J=1.7 Hz), 9.01 (0.2H, d, J=1.5 Hz).

MSm/z: 453 (M$^+$+H).

Example 102

N,N-Dimethyl-[6-[(4-chlorophenylsulfonyl)(2,5-difluorophenyl)methyl]pyridin-3-yl]methylamine

[Chemical formula 145]

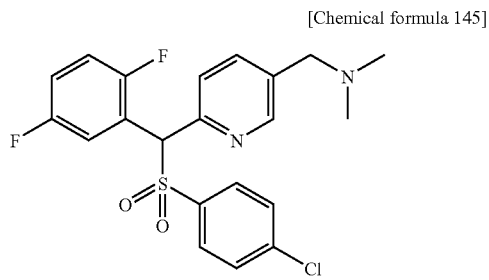

The [6-[(4-chlorophenylsulfonyl)(2,5-difluorophenyl)methyl]pyridin-3-yl]carbaldehyde (100 mg, 0.245 mmol) obtained in Example 47, a tetrahydrofuran solution (2.0M, 0.25 ml, 0.50 mmol) of dimethylamine and acetic acid (0.029 ml, 0.51 mmol) were dissolved in 1,2-dichloroethane (5 ml), followed by the addition of sodium triacetoxyborohydride (115 mg, 0.515 mmol) at room temperature. The resulting mixture was stirred at room temperature for 3 days. To the reaction mixture were added a saturated aqueous solution of sodium bicarbonate and ethyl acetate. The resulting mixture was separated into layers. The organic layer thus obtained was washed sequentially with a saturated aqueous solution of sodium bicarbonate and brine, and dried over anhydrous magnesium sulfate. After filtration, the filtrate was concentrated under reduced pressure. The residue thus obtained was subjected to flash silica gel chromatography. The fraction obtained from the dichloromethane:methanol=40:1 eluate was concentrated under reduced pressure to yield a white solid. The resulting solid was washed with hexane to give the title compound (88 mg, 0.20 mmol, 82%) as a white powder.

$^1$H-NMR (400 MHz, CDCl$_3$) δ: 2.23 (6H, s), 3.43 (2H, s), 5.94 (1H, s), 6.88-6.98 (1H, m), 6.98-7.06 (1H, m), 7.38 (2H, d, J=8.6 Hz), 7.52-7.62 (3H, m), 7.71 (1H, dd, J=8.1, 2.1 Hz), 7.98-8.08 (1H, m), 8.51 (1H, d, J=2.1 Hz).

MSm/z: 437 (M$^+$+H).

Example 103

N-[[6-[(4-chlorophenylsulfonyl)(2,5-difluorophenyl)methyl]pyridin-3-yl]methyl]bis(2-methoxyethyl)amine

[Chemical formula 146]

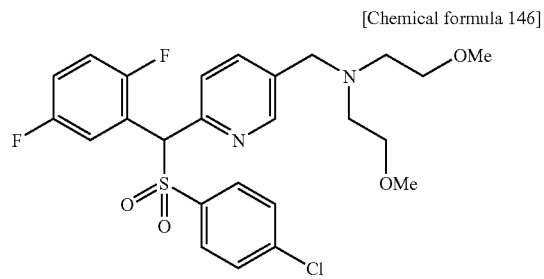

The [6-[(4-chlorophenylsulfonyl)(2,5-difluorophenyl)methyl]pyridin-3-yl]carbaldehyde (100 mg, 0.245 mmol) obtained in Example 47, bis(2-methoxyethyl)amine (70 mg, 0.53 mmol) and acetic acid (0.029 ml, 0.51 mmol) were dissolved in 1,2-dichloroethane (5 ml). To the resulting solution was added sodium triacetoxyborohydride (115 mg, 0.515 mmol) at room temperature. The resulting mixture was stirred at room temperature for 3 days. To the reaction mixture were added a saturated aqueous solution of sodium bicarbonate and ethyl acetate. The resulting mixture was separated into layers. The organic layer thus obtained was washed sequentially with a saturated aqueous solution of sodium bicarbonate and brine, and dried over anhydrous magnesium sulfate. After filtration, the filtrate was concentrated under reduced pressure. The residue thus obtained was subjected to flash silica gel chromatography. The fraction obtained from the hexane:ethyl acetate=3:2 eluate was concentrated under reduced pressure to afford a white solid. The resulting solid was washed with hexane to give the title compound (101 mg, 0.192 mmol, 78%) as a white powder.

$^1$H-NMR (400 MHz, CDCl$_3$) δ: 2.73 (4H, t, J=5.8 Hz), 3.31 (6H, s), 3.47 (4H, d, J=5.8 Hz), 3.75 (2H, s), 5.93 (1H, s), 6.88-6.97 (1H, m), 6.97-7.07 (1H, m), 7.38 (2H, d, J=8.8 Hz), 7.50-7.60 (3H, m), 7.76 (1H, dd, J=8.1, 2.0 Hz), 7.98-8.08 (1H, m), 8.54 (1H, d, J=2.0 Hz).

MSm/z: 525 (M$^+$+H).

Example 104

6-[(4-Chlorophenylsulfonyl)(2,5-difluorophenyl)methyl]-N,N-dimethylnicotinamide

[Chemical formula 147]

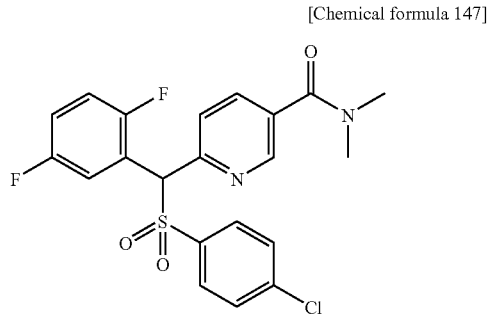

The [6-[(4-chlorophenylsulfonyl)(2,5-difluorophenyl)methyl]pyridin-3-yl]carboxylic acid (90 mg, 0.21 mmol) obtained in Example 50, a tetrahydrofuran solution (2.0M, 0.21 ml, 0.42 mmol) of dimethylamine, 4-(dimethylamino)

pyridine (15 mg, 0.12 mmol) and triethylamine (0.045 ml, 0.32 mmol) were dissolved in dichloromethane (5 ml). To the resulting solution was added 1-ethyl-3-(3-dimethylaminopropyl)carbodiimide hydrochloride (61 mg, 0.32 mmol) at room temperature, followed by stirring at room temperature for 14 hours. The residue obtained by concentrating the reaction mixture under reduced pressure was subjected to flash silica gel chromatography. The fraction obtained from the hexane:ethyl acetate=2:1 eluate was concentrated under reduced pressure to give the title compound (35 mg, 0.066 mmol, 90%) as a white powder.

$^1$H-NMR (400 MHz, CDCl$_3$) δ: 3.01 (3H, s), 3.14 (3H, s), 5.97 (1H, s), 6.88-6.99 (1H, m), 6.99-7.08 (1H, m), 7.40 (2H, d, J=8.7 Hz), 7.57 (2H, d, J=8.7 Hz), 7.70 (1H, dd, J=8.0, 0.7 Hz), 7.82 (1H, dd, J=8.0, 2.2 Hz), 7.93-8.04 (1H, m), 8.68 (1H, dd, J=2.2, 0.7 Hz).

MSm/z: 451 (M$^+$+H).

Example 105

[6-[(4-Chlorophenylsulfonyl)(2,5-difluorophenyl)methyl]pyridin-3-yl](4-methylpiperazin-1-yl)methanone

[Chemical formula 148]

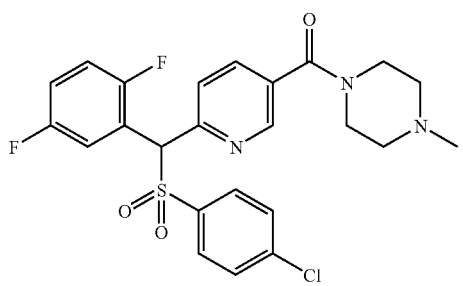

The [6-[(4-chlorophenylsulfonyl)(2,5-difluorophenyl)methyl]pyridin-3-yl]carboxylic acid (90 mg, 0.21 mmol) obtained in Example 50, N-methylpiperazine (0.036 ml, 0.33 mmol), 4-(dimethylamino)pyridine (15 mg, 0.12 mmol) and triethylamine (0.045 ml, 0.32 mmol) were dissolved in dichloromethane (5 ml). To the resulting solution was added 1-ethyl-3-(3-dimethylaminopropyl)carbodiimide hydrochloride (61 mg, 0.32 mmol) at room temperature. The resulting mixture was stirred at room temperature for 14 hours. To the reaction mixture were added N-methylpiperazine (0.036 ml, 0.33 mmol), triethylamine (0.045 ml, 0.32 mmol) and 1-ethyl-3-(3-dimethylaminopropyl)carbodiimide hydrochloride (61 mg, 0.32 mmol). The resulting mixture was stirred at room temperature for 14 hours. The reaction mixture was then concentrated under reduced pressure. The residue thus obtained was subjected to flash silica gel chromatography. The fraction obtained from the dichloromethane:methanol=25:1 eluate was concentrated under reduced pressure to afford the title compound (86 mg, 0.17 mmol, 80%) as a white powder.

$^1$H-NMR (400 MHz, CDCl$_3$) δ: 2.33 (3H, s), 2.38 (2H, brs), 2.50 (2H, brs), 3.44 (2H, brs), 3.81 (2H, brs), 5.97 (1H, s), 6.87-6.98 (1H, m), 6.98-7.08 (1H, m), 7.40 (2H, d, J=8.8 Hz), 7.57 (2H, d, J=8.8 Hz), 7.71 (1H, dd, J=8.1, 0.7 Hz), 7.81 (1H, dd, J=8.1, 2.2 Hz), 7.94-8.04 (1H, m), 8.66 (1H, dd, J=2.2, 0.7 Hz).

MSm/z: 506 (M$^+$+H).

Example 106

4-[2-[5-Chloro-4-[(4-chlorophenylsulfonyl)-(2,5-difluorophenyl)methyl]pyridin-2-yl]aminoethyl]morpholine

[Chemical formula 149]

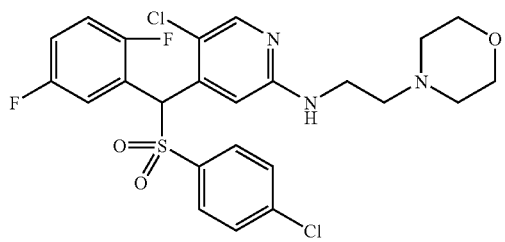

The 4-[2-[5-chloro-4-[(4-chlorophenylsulfonyl)-(2,5-difluorophenyl)methyl]pyridin-2-yl]aminoethyl]morpholine-N-oxide (78 mg, 0.14 mmol) obtained in Example 61 was dissolved in a mixed solvent of acetic acid (2.0 ml) and water (2.0 ml). The resulting solution was heated to 60° C. and iron powder (40 mg, 0.72 mmol) was added thereto. The resulting mixture was stirred for 30 minutes. After cooling, the reaction mixture was poured into a saturated aqueous solution of potassium carbonate, followed by extraction with ethyl acetate (60 ml). The extract was washed with brine, dried and concentrated under reduced pressure. The residue thus obtained was purified by silica gel chromatography (3% methanol/chloroform solution) to give the title compound (30 mg, 40%).

$^1$H-NMR (400 MHz, CDCl$_3$) δ: 2.5-2.8 (6H, m), 3.59 (2H, br), 3.81 (4H, br), 5.45 (1H, br), 6.10 (1H, s), 6.88 (1H, m), 7.01 (1H, m), 7.25 (1H, s), 7.42 (2H, d, J=8.8 Hz), 7.49 (1H, m), 7.60 (2H, d, J=8.4 Hz), 7.97 (1H, s).

MSm/z: 542 (M$^+$+H).

Example 107 t-Butyl 2-[N-[5-chloro-4-[(4-chlorophenylthio)-(2,5-difluorophenyl)methyl]pyridin-2-yl]-N-methylamino]ethyl-methylcarbamate

[Chemical formula 150]

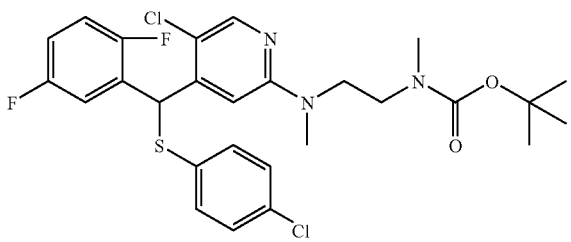

A 1,4-dioxane (2.0 ml) solution of the 2,5-dichloro-4-[(4-chlorophenylthio)-(2,5-difluorophenyl)methyl]pyridine (78 mg, 0.19 mmol) obtained in Example 54 and N,N'-dimethylethylenediamine (400 μl) were stirred at 100° C. for 2 days under a nitrogen atmosphere. After cooling to room temperature, the reaction mixture was diluted with ethyl acetate (40 ml). The diluted mixture was washed with water and brine, dried and then concentrated under reduced pressure to give a residue. The residue thus obtained was dissolved in tetrahydrofuran (10 ml). To the resulting solution were added triethylamine (31 μl, 0.22 mmol) and di-t-butyl dicarbonate (49 mg, 0.22 mmol) at room temperature. The resulting mixture was stirred for 15-hours. The reaction mixture was concentrated under reduced pressure. The residue thus obtained was purified by silica gel chromatography (hexane:ethyl acetate=4:1) to give the title compound (68 mg, 64%) as an oil.

$^1$H-NMR (400 MHz, CDCl$_3$) δ: 1.26 and 1.32 (9H, br-s, rotamer), 2.75 and 2.78 (3H, br-s, rotamer), 2.95 (3H, br-s), 3.30 (2H, m), 3.65 (2H, m), 5.92 (1H, s), 6.6-6.8 (1H, m), 6.84-6.97 (2H, m), 7.05 (1H, m), 7.14 (2H, d, J=8.8 Hz), 7.17 (2H, d, J=8.4 Hz), 7.98 (1H, s).

MSm/z: 568 (M$^+$+H).

Example 108 t-Butyl 2-[N-[5-chloro-4-[(4-chlorophenylsulfonyl)-(2,5-difluorophenyl)methyl]pyridin-2-yl]-N-methylamino]ethyl-methylcarbamate

[Chemical formula 151]

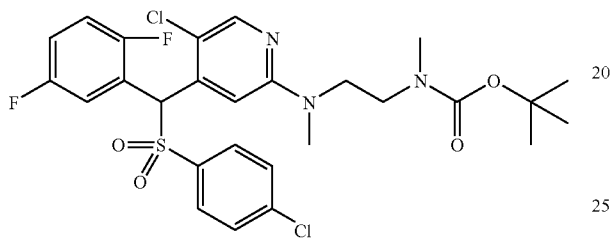

To a methanol (6 ml) solution of t-butyl 2-[N-[5-chloro-4-[(4-chlorophenylthio)-(2,5-difluorophenyl)methyl]pyridin-2-yl]-N-methylamino]ethylmethylcarbamate (67 mg, 0.12 mmol) were added hexaammonium heptamolybdate tetrahydrate (30 mg), followed by the further addition of 30% aqueous hydrogen peroxide (3 ml). The resulting mixture was stirred for 17 hours. After the reaction mixture was diluted with ethyl acetate, the diluted mixture was washed with water and brine, and then concentrated under reduced pressure. The residue thus obtained was purified by silica gel chromatography (hexane:ethyl acetate=3:1) to give the title compound (64 mg, 91%).

$^1$H-NMR (400 MHz, CDCl$_3$) δ: 1.33 and 1.38 (9H, br-s, rotamer), 2.87 and 2.89 (3H, br-s, rotamer), 3.11 (3H, br-s), 3.3-3.4 (2H, m), 3.6-3.9 (2H, m), 6.12 (1H, s), 6.89 (1H, m), 7.00 (1H, m), 7.26 (1H, m), 7.41 (2H, d, J=8.4 Hz), 7.53 (1H, m), 7.59 (2H, d, J=8.4 Hz), 8.00 (1H, s).

EI-MS: 599.1204 (Calcd for C$_{27}$H$_{29}$Cl$_2$F$_2$N$_3$O$_4$S: 599.1224).

Example 109

5-Chloro-4-[(4-chlorophenylsulfonyl)-(2,5-difluorophenyl)methyl]-2-[N-methyl-N-[2-(methylamino)ethyl]amino]pyridine

[Chemical formula 152]

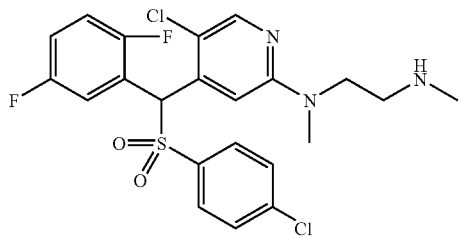

In methylene chloride (2.0 ml) was dissolved t-butyl 2-[N-[5-chloro-4-[(4-chlorophenylsulfonyl)-(2,5-difluorophenyl)methyl]pyridin-2-yl]-N-methylamino]ethylmethylcarbamate (61 mg, 0.10 mmol). To the resulting solution were added anisole (40 μl) and trifluoroacetic acid (200 μl) at room temperature and the resulting mixture was stirred for 1 hour. The residue obtained by concentrating the reaction mixture under reduced pressure was purified by silica gel chromatography (3% methanol/chloroform 3%→methanol, 3% t-butylamine/chloroform) to give the title compound (21 mg, 41%) as an oil.

$^1$H-NMR (400 MHz, CDCl$_3$) δ: 2.51 (3H, s), 2.90 (2H, d, J=6.0 Hz), 3.14 (3H, s), 3.72 (2H, m), 6.13 (1H, s), 6.89 (1H, m), 7.00 (1H, m), 7.36 (1H, m), 7.41 (2H, d, J=8.4 Hz), 7.52 (1H, m), 7.60 (2H, d, J=8.4 Hz), 8.00 (1H, s).

FAB-MS: 500.0770 (Calcd for C$_{22}$H$_{22}$Cl$_2$F$_2$N$_3$O$_2$S: 500.0778).

Example 110

(2'S)-5-Chloro-4-[(4-chlorophenylthio)-(2,5-difluorophenyl)methyl]-2-[2'-(hydroxymethyl)pyrrolidin-1'-yl]pyridine

[Chemical formula 153]

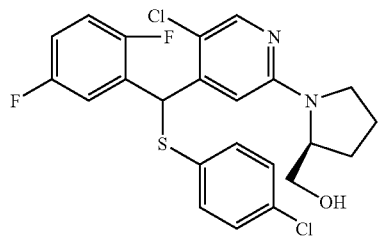

A 1,4-dioxane (1.0 ml) solution of the 2,5-dichloro-4-[(4-chlorophenylthio)-(2,5-difluorophenyl)methyl]pyridine (60 mg, 0.14 mmol) obtained in Example 54 and (S)-2-pyrrolidinemethanol (200 μl) was stirred at 100° C. for 3 days under a nitrogen atmosphere. After cooling to room temperature, the reaction mixture was diluted with ethyl acetate (50 ml). The diluted mixture was washed with water and brine, dried and then concentrated under reduced pressure. The residue thus obtained was purified by silica gel chromatography (hexane:ethyl acetate=5:1) to give the title compound (40 mg, 58%) as an oil.

$^1$H-NMR (400 MHz, CDCl$_3$) δ: 1.78 (1H, m), 2.06 (3H, m), 3.29 (1H, m), 3.50 (1H, m), 3.66 (1H, m), 3.72 (1H, m), 4.33 (1H, m), 5.97 and 5.98 (1H, s, rotamer), 6.73 and 6.77 (1H, s, rotamer), 6.92-7.15 (3H, m), 7.25 (4H, m), 7.98 (1H, s).

MSm/z: 481 (M$^+$+H).

Example 111

(2'S)-5-Chloro-4-[(4-chlorophenylsulfonyl)-(2,5-difluorophenyl)methyl-2-[2'-(hydroxymethyl)pyrrolidin-1'-yl]pyridine

[Chemical formula 154]

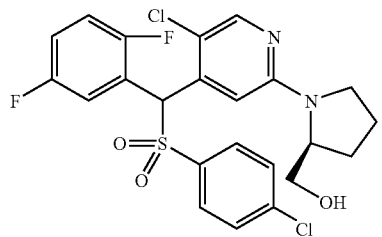

Hexaammonium heptamolybdate tetrahydrate (30 mg) was added to a methanol (6 ml) solution of (2'S)-5-chloro-4-[(4-chlorophenylthio)-(2,5-difluorophenyl)methyl]-2-[2'-(hydroxymethyl)pyrrolidin-1'-yl]pyridine (39 mg, 0.08 mmol), followed by the further addition of 30% aqueous hydrogen peroxide (3 ml). The resulting mixture was stirred for 17 hours. The reaction mixture was diluted with ethyl acetate (60 ml). The diluted mixture was washed with water and brine and concentrated under reduced pressure. The residue thus obtained was purified by silica gel chromatography (hexane:ethyl acetate=1:1) to give the title compound (33 mg, 79%) as an oil.

$^1$H-NMR (400 MHz, CDCl$_3$) δ: 1.75 (1H, m), 2.02 (3H, m), 3.3-3.5 (1H, m), 3.52-3.75 (3H, m), 4.2-4.35 (1H, m), 6.05 (1H, br-s), 6.84 (1H, m), 6.96 (1H, m), 7.36 (1H, s), 7.36 and 7.37 (2H, d, J=8.8 Hz, rotamer), 7.43 (1H, m), 7.53 and 7.54 (2H, d, J=8.8 Hz, rotamer), 7.89 and 7.90 (1H, s, rotamer). FAB-MS: 513.0627 (Calcd for C$_{23}$H$_{21}$Cl$_2$F$_2$N$_2$O$_3$S: 513.0618).

Example 112 t-Butyl[4-[5-chloro-4-[(4-chlorophenylthio)-(2,5-difluorophenyl)methyl]pyridin-2-yl]morpholin-2-yl]methylcarbamate

[Chemical formula 155]

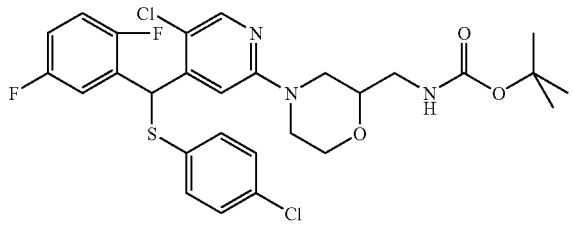

A 1,4-dioxane (1.0 ml) solution of the t-butyl 2,5-dichloro-4-[(4-chlorophenylthio)-(2,5-difluorophenyl)methyl]pyridine (60 mg, 0.14 mmol) obtained in Example 54 and t-butyl (morpholin-2-yl)methylcarbamate (200 mg) was stirred at 100° C. for 2 days under a nitrogen atmosphere. After cooling to room temperature, the reaction mixture was diluted with ethyl acetate (50 ml). The diluted mixture was washed with water and brine, dried and concentrated under reduced pressure. The residue thus obtained was purified by silica gel chromatography (hexane:ether=5:1) to give the title compound (45 mg, 52%) as an oil.

$^1$H-NMR (400 MHz, CDCl$_3$) δ: 1.46 (9H, s), 2.72 (1H, m), 3.00 (1H, m), 3.22 (1H, m), 3.44 (1H, m), 3.6-3.75 (2H, m), 3.9-4.1 (3H, m), 4.95 (1H, br), 5.99 and 6.00 (1H, s, rotamer), 6.96 and 6.97 (1H, s, rotamer), 6.9-7.1 (3H, m), 7.24 (4H, s), 8.11 (1H, s). MSm/z: 596 (M$^+$+H).

Example 113 t-Butyl[4-[5-chloro-4-[(4-chlorophenylsulfonyl)-(2,5-difluorophenyl)methyl]pyridin-2-yl]morpholin-2-yl]methylcarbamate

[Chemical formula 156]

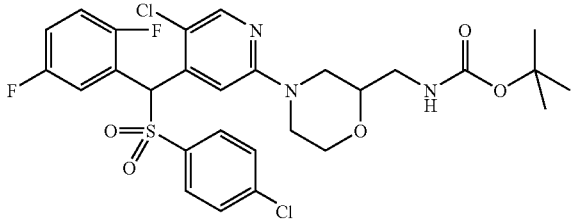

Hexaammonium heptamolybdate tetrahydrate (30 mg) was added to a methanol (6 ml) solution of t-butyl[4-[5-chloro-4-[(4-chlorophenylthio)-(2,5-difluorophenyl)methyl]pyridin-2-yl]morpholin-2-yl]methylcarbamate (44 mg, 0.074 mmol), followed by the further addition of 30% aqueous hydrogen peroxide (3 ml). The resulting mixture was stirred for 17 hours. After the reaction mixture was diluted with ethyl acetate (60 ml), the diluted mixture was washed with water and brine, and concentrated under reduced pressure. The residue thus obtained was purified by silica gel chromatography (hexane:ethyl acetate=3:1) to give the title compound (31 mg, 67%) as an oil.

$^1$H-NMR (400 MHz, CDCl$_3$) δ: 1.40 (9H, s), 2.69 (1H, m), 3.02 (1H, m), 3.18 (1H, m), 3.41 (1H, br), 3.6-3.75 (2H, m), 3.92 (1H, m), 4.02 (1H, m), 4.13 (1H, m), 4.91 (1H, br), 6.07 (1H, s), 6.85 (1H, m), 6.99 (1H, m), 7.37 (2H, d, J=8.4 Hz), 7.35-7.45 (2H, m), 7.53 (2H, d, J=8.4 Hz), 8.17 (1H, s).

FAB-MS: 628.1255 (Calcd for C$_{28}$H$_{30}$Cl$_2$F$_2$N$_3$O$_5$S: 628.1251).

Example 114

2-Aminomethyl-4-[5-chloro-4-[(4-chlorophenylsulfonyl)-(2,5-difluorophenyl)methyl]pyridin-2-yl]morpholine

[Chemical formula 157]

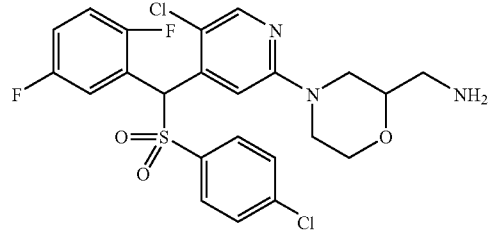

In methylene chloride (1.5 ml) was dissolved t-butyl [4-[5-chloro-4-[(4-chlorophenylsulfonyl)-(2,5-difluorophenyl)methyl]pyridin-2-yl]morpholin-2-yl]methylcarbamate (30 mg, 0.05 mmol). To the resulting solution were added anisole (30 μl) and trifluoroacetic acid (150 μl) at room temperature. The resulting mixture was stirred for 1 hour. The residue obtained by concentrating the reaction mixture under reduced pressure was purified by silica gel chromatography (3% methanol/chloroform→3% methanol, 3% t-butylamine/chloroform) to give the title compound (17 mg, 67%) as an oil.

$^1$H-NMR (400 MHz, CDCl$_3$) δ: 2.77 (1H, m), 2.9-3.3 (2H, m), 3.5-3.85 (3H, m), 3.97 (1H, m), 4.04-4.25 (2H, m), 6.12 (1H, s), 6.90 (1H, m), 7.02 (1H, m), 7.42 (2H, d, J=8.4 Hz), 7.4-7.55 (2H, m), 7.58 (2H, d, J=8.4 Hz), 8.05 (1H, s).

FAB-MS: 528.0695 (Calcd for C$_{23}$H$_{22}$Cl$_2$F$_2$N$_3$O$_3$S: 528.0727).

Example 115

5-Chloro-4-[(4-chlorophenylthio)-(2,5-difluorophenyl)methyl]-2-(4'-hydroxypiperidin-1'-yl)pyridine

[Chemical formula 158]

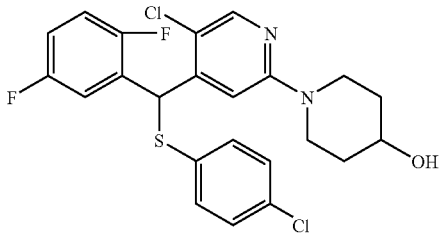

A 1,4-dioxane (1.0 ml) solution of the 2,5-dichloro-4-[(4-chlorophenylthio)-(2,5-difluorophenyl)methyl]pyridine (60 mg, 0.14 mmol) obtained in Example 54 and 4-hydroxypiperidine (200 mg) was stirred at 100° C. for 1 day under a nitrogen atmosphere. After cooling to room temperature, the reaction mixture was diluted with diethyl ether (50 ml). The diluted mixture was washed with water and brine, dried and then concentrated under reduced pressure. The residue thus obtained was purified by silica gel chromatography (hexane:ethyl acetate=3:1) to give the title compound (30 mg, 43%) as an oil.

$^1$H-NMR (400 MHz, CDCl$_3$) δ: 1.62 (0.2H, m), 2.05 (2H, m), 3.30 (2H, m), 3.98 (3H, m), 5.97 (1H, s), 6.96-7.12 (3H, m), 7.23 (4H, m), 7.26 (1H, s), 8.10 (1H, s).

MS m/z: 481 (M$^+$+H).

Example 116

5-Chloro-4-[(4-chlorophenylsulfonyl)-(2,5-difluorophenyl)methyl]-2-(4'-hydroxypiperidin-1'-yl)pyridine

[Chemical formula 159]

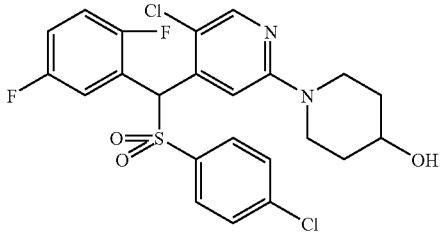

Hexaammonium heptamolybdate tetrahydrate (30 mg) was added to a methanol (6 ml) solution of 5-chloro-4-[(4-chlorophenylthio)-(2,5-difluorophenyl)methyl]-2-(4'-hydroxypiperidin-1'-yl)pyridine (29 mg, 0.06 mmol), followed by the further addition of 30% aqueous hydrogen peroxide (3 ml). The resulting mixture was stirred for 17 hours. The reaction mixture was diluted with ethyl acetate (60 ml). The diluted mixture was washed with water and brine, and concentrated under reduced pressure. The residue thus obtained was purified by silica gel chromatography (hexane:ethyl acetate=2:1), followed by crystallization from ether to give the title compound (17 mg, 55%) as a solid.

$^1$H-NMR (400 MHz, CDCl$_3$) δ: 1.64 (2H, m), 2.02 (2H, m), 3.33 (2H, m), 3.98 (1H, m), 4.08 (2H, m), 6.11 (1H, s), 6.92 (1H, m), 7.02 (1H, m), 7.42 (2H, d, J=8.8 Hz), 7.45 (1H, m), 7.53 (1H, s), 7.58 (2H, d, J=8.8 Hz), 8.05 (1H, s).

mp: 146 to 148° C.

FAB-MS: 513.0588 (Calcd for C$_{23}$H$_{21}$Cl$_2$F$_2$N$_2$O$_3$S: 513.0618).

Example 117

3,6-Dichloro-2-[(4-chlorophenylsulfonyl)(pyridin-4-yl)methyl]pyridine

[Chemical formula 160]

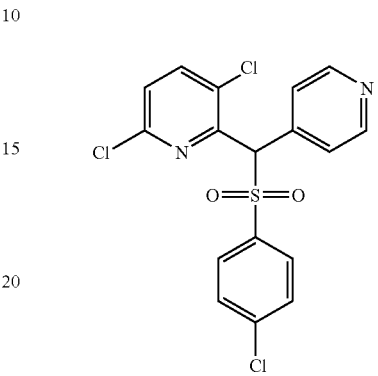

To a methylene chloride (10 ml) solution of the (3,6-dichloropyridin-2-yl)(pyridin-4-yl)methanol (161 mg, 0.631 mmol) obtained in Referential Example 25 were added triethylamine (208 μl, 1.89 mmol) and thionyl chloride (138 μl, 1.89 mmol). The resulting mixture was stirred at room temperature for 4 hours, followed by concentration under reduced pressure. To the residue thus obtained was added ethyl acetate. The resulting mixture was washed sequentially with a saturated aqueous solution of sodium bicarbonate and brine, dried over anhydrous sodium sulfate and filtered. The filtrate was concentrated under reduced pressure. The residue thus obtained was dissolved in acetonitrile (10 ml). To the resulting solution were added 4-chlorobenzenethiol (137 mg, 0.947 mmol) and potassium carbonate (131 mg, 0.947 mmol). Under a nitrogen atmosphere, the resulting mixture was stirred at room temperature for 2 days and then, stirred at 60° C. for 4 hours. After cooling to room temperature, the reaction mixture was concentrated under reduced pressure. To the residue was added ethyl acetate. The resulting mixture was washed sequentially with water and brine, dried over anhydrous sodium sulfate and filtered. The filtrate was concentrated under reduced pressure. The residue thus obtained was subjected to flash chromatography. The fraction obtained from the 40% ethyl acetate/hexane eluate was concentrated under reduced pressure. The residue thus obtained was dissolved in methanol (10 ml). To the resulting solution were added 30% aqueous hydrogen peroxide (3 ml) and hexaammonium heptamolybdate tetrahydrate (73 mg). After the resulting mixture was stirred at room temperature for 5 hours, methanol was distilled off under reduced pressure. To the solution thus obtained was added a saturated aqueous solution of sodium bicarbonate, followed by extraction with methylene chloride. The organic layer was dried over anhydrous sodium sulfate and filtered. The filtrate was concentrated under reduced pressure. The residue thus obtained was subjected to flash chromatography. The fraction obtained from the methanol:methylene chloride=1:80 eluate was concentrated under reduced pressure to give the title compound (49 mg, 0.118 mmol, 19%) as a white solid.

$^1$H-NMR (400 MHz, CDCl$_3$) δ: 6.08 (1H, s), 7.31 (1H, d, J=8.3 Hz), 7.41 (2H, d, J=8.8 Hz), 7.45 (2H, d, J=6.0 Hz), 7.51 (2H, d, J=8.8 Hz), 7.69 (1H, d, J=8.3 Hz), 8.58 (2H, d, J=6.0 Hz).

MS (m/z): 413, 415 (M$^+$+H).

Example 118

2-[1-(4-Chlorophenylsulfonyl)-1-(2,5-difluorophenyl)ethyl]-5-methylpyridine

[Chemical formula 161]

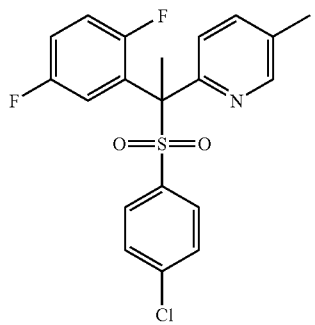

An N,N-dimethylformamide (5 ml) solution of the 2-[[(4-chlorophenyl)sulfonyl](2,5-difluorophenyl)methyl]-5-methylpyridine (52 mg, 0.132 mmol) obtained in Example 15 was added dropwise to an N,N-dimethylformamide (5 ml) suspension of sodium hydride (60% in oil) (30 mg, 0.75 mmol) under ice cooling. After the reaction mixture was stirred for 15 minutes under ice cooling, methyl iodide (12 μl, 0.198 mmol) was added thereto. After stirring at room temperature for 1 hour, water was added to the reaction mixture under ice cooling. The resulting mixture was concentrated under reduced pressure. To the residue was added water and the resulting mixture was extracted with ethyl acetate. The organic layer was washed with brine, dried over anhydrous sodium sulfate and filtered. The filtrate was concentrated under reduced pressure. The residue thus obtained was subjected to silica gel column chromatography. The fraction obtained from the hexane:ethyl acetate=8:1 eluate was concentrated under reduced pressure. The residue thus obtained was solidified with hexane and collected by filtration to give the title compound (50 mg, 0.122 mmol, 93%) as a white powder.

$^1$H-NMR (400 MHz, CDCl$_3$) δ: 2.14 (3H, s), 2.33 (3H, s), 6.80-7.10 (2H, m), 7.23-7.34 (4H, m), 7.39-7.51 (2H, m), 7.88-8.00 (1H, m), 8.15 (1H, s).

MS (m/z): 408 (M$^+$+H).

Example 119

3,6-Dichloro-2-[(6-chloropyridin-3-ylthio)(pyridin-4-yl)methyl]pyridine

[Chemical formula 162]

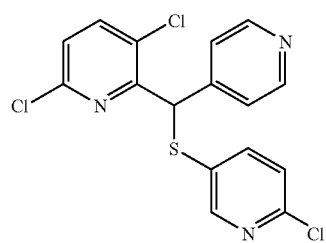

To an ethanol (7 ml) solution of the O-ethyl S-(6-chloro-3-pyridyl) dithiocarbonate (164 mg, 0.70 mmol) obtained in Referential Example 26 was added a 1N aqueous sodium hydroxide solution (7 ml). The resulting mixture was stirred at 80° C. for 3 hours. After the reaction mixture was cooled to room temperature, 1N hydrochloric acid was added thereto. The resulting mixture was extracted with dichloromethane. The organic layer was dried over anhydrous sodium sulfate and filtered. The filtrate was concentrated under reduced pressure to give 6-chloro-3-pyridinethiol as a yellow solid.

To a dichloromethane (3 ml) solution of the (3,6-dichloropyridin-2-yl)(pyridin-4-yl)methanol (153 mg, 0.60 mmol) obtained in Referential Example 25 were added triethylamine (0.167 ml, 1.20 mmol) and methanesulfonyl chloride (0.070 ml, 0.90 mmol) sequentially at 0° C. The resulting mixture was stirred at room temperature for 2 hours. After the reaction mixture was washed with a saturated aqueous solution of sodium bicarbonate, the organic layer was dried over anhydrous sodium sulfate, and filtered. The filtrate was concentrated under reduced pressure. To an N,N-dimethylformamide (3 ml) solution of the residue thus obtained were added an N,N-dimethylformamide (2 ml) solution of 6-chloro-3-pyridinethiol and then, potassium carbonate (100 mg, 0.72 mmol). The resulting mixture was stirred at room temperature for 18 hours. To the reaction mixture was added ethyl acetate. The resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=7:3 eluate was concentrated under reduced pressure to give the title compound (83 mg, 0.22 mmol, 36%) as a yellow oil.

$^1$H-NMR (400 MHz, CDCl$_3$) δ: 5.69 (1H, s), 7.20 (1H, d, J=8.3 Hz), 7.24 (1H, d, J=8.3 Hz), 7.35 (2H, d, J=6.1 Hz), 7.52 (1H, dd, J=8.3, 2.4 Hz), 7.62 (1H, d, J=8.3 Hz), 8.32 (1H, d, J=2.4 Hz), 8.55 (2H, d, J=6.1 Hz).

MSm/z: 382 (M$^+$+H).

Example 120

3,6-Dichloro-2-[(6-chloropyridin-3-ylsulfonyl)(pyridin-4-yl)methyl]pyridine (Compound A) and 3,6-dichloro-2-[(6-chloropyridin-3-ylsulfinyl)(pyridin-4-yl)methyl]pyridine (Compound B (Isomer A) and Compound B (Isomer B))

[Chemical formula 163]

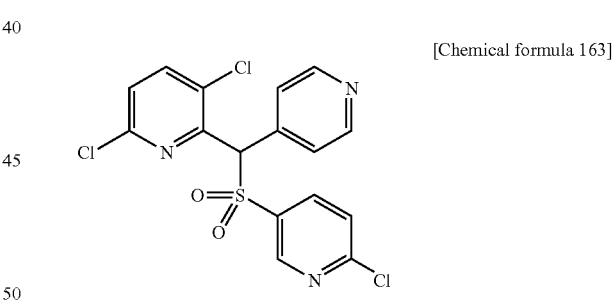

Compound A

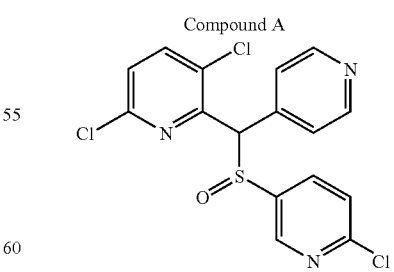

Compound B

To a methanol (4 ml) solution of 3,6-dichloro-2-[(6-chloropyridin-3-ylthio)(pyridin-4-yl)methyl]pyridine (82 mg, 0.24 mmol) were added 31% aqueous hydrogen peroxide (2 ml) and hexaammonium heptamolybdate tetrahydrate (30 mg). The resulting mixture was stirred at room temperature for 2 hours. To the reaction mixture was added ethyl acetate. The resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel column chromatography. The fraction obtained from the hexane:ethyl acetate=3:2 eluate was concentrated under reduced pressure to give the title Compound A (41 mg, 0.098 mmol, 46%), while the fraction obtained from the hexane:ethyl acetate=1:1 eluate was concentrated under reduced pressure to give the title Compound B (Isomer A) (low polarity) (8 mg, 9%) and the title Compound B (Isomer B) (high polarity) (8 mg, 9%), each as a white solid.

Compound A $^1$H-NMR (400 MHz, CDCl$_3$) δ: 6.11 (1H, s), 7.35 (1H, d, J=8.3 Hz), 7.36 (2H, d, J=6.1 Hz), 7.40 (1H, d, J=8.3 Hz), 7.73 (1H, d, J=8.3 Hz), 7.78 (1H, dd, J=8.3, 2.4 Hz), 8.48 (1H, d, J=2.4 Hz), 8.61 (2H, d, J=6.1 Hz).

MSm/z: 414 (M$^+$+H).

Compound B (Isomer A)

$^1$H-NMR (400 MHz, CDCl$_3$) δ: 5.54 (1H, s), 6.99 (2H, d, J=6.1 Hz), 7.27 (1H, d, J=8.3 Hz), 7.37 (1H, d, J=8.3 Hz), 7.55 (1H, dd, J=8.3, 2.2 Hz), 7.73 (1H, d, J=8.3 Hz), 8.47 (1H, d, J=2.2 Hz), 8.51 (2H, d, J=6.1 Hz).

MSm/z: 398 (M$^+$+H).

Compound B (Isomer B)

$^1$H-NMR (400 MHz, CDCl$_3$) δ: 5.40 (1H, s), 7.26 (1H, d, J=8.5 Hz), 7.42 (1H, d, J=8.3 Hz), 7.53 (2H, d, J=6.1 Hz), 7.57 (1H, d, J=8.5 Hz), 7.96 (1H, dd, J=8.3, 2.4 Hz), 8.34 (1H, d, J=2.4 Hz), 8.68 (2H, d, J=6.1 Hz).

MSm/z: 398 (M$^+$+H).

Example 121

2-[[(3-Chloropyridin-4-yl)(2,5-difluorophenyl)methyl]sulfonyl]pyrimidine

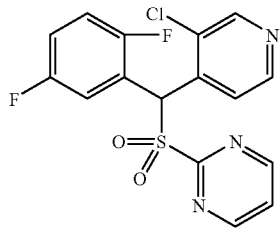

[Chemical formula 1]

To a dichloromethane (4 ml) solution of the 3-chloro-4-[(2,5-difluorophenyl)-hydroxymethyl]pyridine (102 mg, 0.40 mmol) obtained in Referential Example 23 were added triethylamine (0.112 ml, 0.80 mmol) and methanesulfonyl chloride (0.046 ml, 0.60 mmol) sequentially at 0° C. The resulting mixture was stirred at room temperature for 17 hours. The reaction mixture was washed with a saturated aqueous solution of sodium bicarbonate. The organic layer was dried over anhydrous sodium sulfate and filtered. The filtrate was then concentrated under reduced pressure.

To an N,N-dimethylformamide (4 ml) solution of the resulting residue were added 2-pyrimidinethiol (45 mg, 0.40 mmol) and then, potassium carbonate (83 mg, 0.60 mmol). The resulting mixture was stirred at room temperature for 23 hours. To the reaction mixture was added ethyl acetate. The resulting mixture was washed with water. The organic layer was dried over anhydrous sodium sulfate and filtered. The filtrate was concentrated under reduced pressure. To a dichloromethane (4 ml) solution of the resulting residue was added 3-chloroperbenzoic acid (purity: 65% or greater) (212 mg, 0.80 mmol) at 0° C. The resulting mixture was stirred at room temperature for 3 hours. After the reaction mixture was washed with a 1N aqueous solution of sodium hydroxide, the organic layer was dried over anhydrous sodium sulfate and filtered. The filtrate was concentrated under reduced pressure. The residue thus obtained was subjected to flash silica gel chromatography. The fraction obtained from the hexane:ethyl acetate=2:3 eluate was concentrated under reduced pressure to give the title compound (19 mg, 0.049 mmol, 12%) as a colorless foamy substance.

$^1$H-NMR (400 MHz, CDCl$_3$) δ: 6.26 (1H, s), 6.93-7.13 (3H, m), 7.50-7.56 (1H, m), 8.01-8.08 (1H, m), 8.13 (1H, d, J=5.1 Hz), 8.48 (1H, d, J=2.2 Hz), 8.60 (1H, s), 8.66 (1H, d, J=5.1 Hz).

MSm/z: 382 (M$^+$+H).

Example 122

6-(4-Chlorophenylthio)(2,5-difluorophenyl)methyl-5-fluoronicotinamide

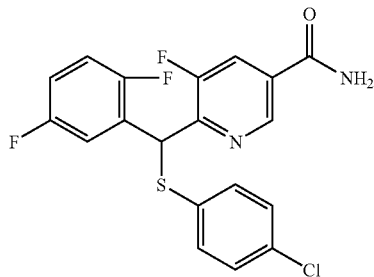

[Chemical formula 2]

To a dichloromethane (4 ml) solution of the 6-(2,5-difluorophenyl)hydroxymethyl-5-fluoronicotinamide (114 mg, 0.40 mmol) obtained in Referential Example 31 were added triethylamine (0.113 ml, 0.81 mmol) and methanesulfonyl chloride (0.047 ml, 0.61 mmol) sequentially at 0° C. The resulting mixture was stirred at room temperature for 2 hours. The reaction mixture was washed with a saturated aqueous solution of sodium bicarbonate. The organic layer was dried over anhydrous sodium sulfate and filtered. The filtrate was concentrated under reduced pressure.

To an N,N-dimethylformamide (6 ml) solution of the residue thus obtained were added 4-chlorobenzenethiol (70 mg, 0.49 mmol) and then, potassium carbonate (67 mg, 0.49 mmol). The resulting mixture was stirred at room temperature for 15 hours. To the reaction mixture was added ethyl acetate. The resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=1:1 eluate was concentrated under reduced pressure to give the title compound (120 mg, 0.29 mmol, 73%) as a yellow solid.

$^1$H-NMR (400 MHz, CDCl$_3$): 6.14 (1H, s), 6.88-6.96 (2H, m), 7.21 (2H, d, J=8.5 Hz), 7.28 (2H, d, J=8.5 Hz), 7.58-7.74 (1H, m), 7.85 (1H, dd, J=9.4, 1.6 Hz), 8.80 (1H, s).

MSm/z: 409 (M$^+$+H).

Example 123

6-(4-Chlorophenylsulfonyl)(2,5-difluorophenyl)methyl-5-fluoronicotinamide (Compound A) and 6-(4-chlorophenylsulfinyl)(2,5-difluorophenyl)methyl-5-fluoronicotinamide (Compound B)

[Chemical formula 3]

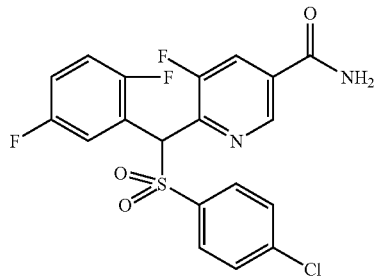

Compound A

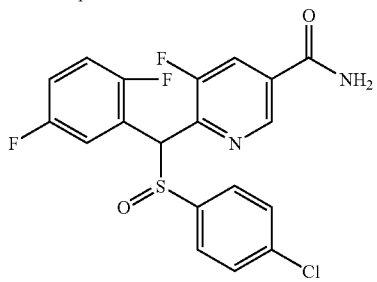

Compound B

To a methanol (3 ml) solution of 6-(4-chlorophenylthio)(2,5-difluorophenyl)methyl-5-fluoronicotinamide (120 mg, 0.29 mmol) were added 30% aqueous hydrogen peroxide (2 ml) and hexaammonium heptamolybdate tetrahydrate (73 mg). The resulting mixture was stirred at room temperature for 3 hours. To the reaction mixture was added dichloromethane. The resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel column chromatography. The fraction obtained from the hexane:ethyl acetate=1:1 eluate was concentrated under reduced pressure to give the title Compound A (33 mg, 0.075 mmol, 25%) as a white solid. The fraction obtained from the hexane:ethyl acetate=1:3 eluate was concentrated under reduced pressure to give the title Compound B (39 mg, 0.092 mmol, 31%) as a white solid.

Compound A $^1$H-NMR (400 MHz, CDCl$_3$) δ: 6.37 (1H, s), 6.90-6.97 (1H, m), 7.01-7.08 (1H, m), 7.43 (2H, d, J=8.5 Hz), 7.58 (2H, d, J=8.5 Hz), 7.94 (1H, dd, J=9.2, 1.8 Hz), 8.17-8.22 (1H, m), 8.91 (1H, s).

mp: 222 to 224° C.

MSm/z: 441 (M$^+$+H).

Compound B $^1$H-NMR (400 MHz, CD$_3$OD) δ: 5.86 (1H, s), 6.94-7.02 (1H, m), 7.06-7.14 (1H, m), 7.44 (2H, d, J=8.8 Hz), 7.48 (2H, d, J=8.8 Hz), 7.66-7.71 (1H, m), 8.07 (1H, dd, J=9.8, 1.7 Hz), 9.09 (1H, s).

mp: 171 to 173° C.

Elemental Analysis for C$_{19}$H$_{12}$ClF$_3$N$_2$O$_2$S: Calculated: C, 53.72; H, 2.85; Cl, 8.35; F, 13.42; N, 6.59; S, 7.55. Found: C, 53.44; H, 2.96; Cl, 8.37; F, 13.34; N, 6.66; S, 7.54.

Example 124

[6-(4-Chlorophenylthio)(2,5-difluorophenyl)methyl-5-fluoropyridin-3-yl]methanol

[Chemical formula 4]

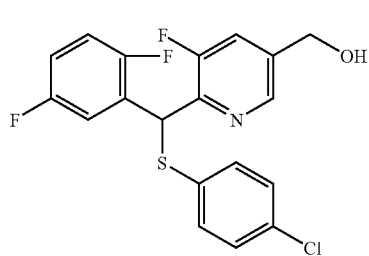

To a dichloromethane (180 ml) solution of the [5-(t-butyldiphenylsilyloxymethyl)-3-fluoropyridin-2-yl](2,5-difluorophenyl)methanol (17.0 g, 33.5 mmol) obtained in Referential Example 29 were added triethylamine (7.00 ml, 50.2 mmol) and methanesulfonyl chloride (3.11 ml, 40.2 mmol) at room temperature. The resulting mixture was stirred for 2 hours. The reaction mixture was washed with a saturated aqueous solution of sodium bicarbonate. The organic layer was then dried over anhydrous sodium sulfate and filtered. The filtrate was concentrated under reduced pressure.

To an N,N-dimethylformamide (300 ml) solution of the residue thus obtained were added 4-chlorobenzenethiol (5.33 g, 36.8 mmol) and potassium carbonate (5.55 g, 40.2 mmol) sequentially. The resulting mixture was stirred at room temperature for 18 hours. To the reaction mixture was added ethyl acetate. The resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=30:1 eluate was concentrated under reduced pressure.

To a tetrahydrofuran (200 ml) solution of the residue thus obtained was added a tetrahydrofuran solution (42.3 ml, 42.3 mmol) of tetrabutylammonium fluoride. The resulting mixture was stirred at room temperature for 4 hours. The reaction mixture was concentrated under reduced pressure and the residue thus obtained was dissolved in ethyl acetate. The resulting solution was washed with a saturated aqueous solution of sodium bicarbonate. The organic layer was dried over anhydrous sodium sulfate, and filtered. The filtrate was then concentrated under reduced pressure. The residue thus obtained was subjected to flash silica gel chromatography. The fraction obtained from the hexane:ethyl acetate=3:1 eluate was concentrated under reduced pressure to give the title compound (9.80 g, 24.8 mmol, 74%) as a colorless oil.

$^1$H-NMR (400 MHz, CDCl$_3$) δ: 4.76 (2H, s), 6.13 (1H, s), 6.84-6.96 (2H, m), 7.20 (2H, d, J=8.7 Hz), 7.27 (2H, d, J=8.7 Hz), 7.43 (1H, d, J=9.8 Hz), 7.57-7.64 (1H, m), 8.43 (1H, s).

Example 125

[6-(4-Chlorophenylsulfonyl)(2,5-difluorophenyl)methyl-5-fluoropyridin-3-yl]methanol

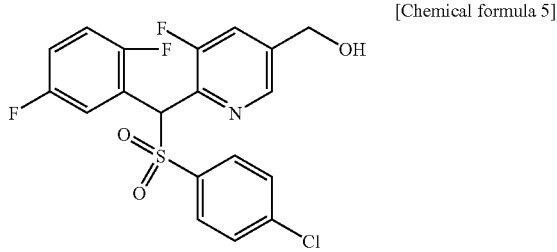

[Chemical formula 5]

To a methanol (200 ml) solution of [6-(4-chlorophenylthio)(2,5-difluorophenyl)methyl-5-fluoropyridin-3-yl]methanol (9.80 g, 24.8 mmol) were added 30% aqueous hydrogen peroxide (14.0 ml) and hexaammonium heptamolybdate tetrahydrate (612 mg). The resulting mixture was stirred at room temperature for 18 hours. To the reaction mixture was added 30% aqueous hydrogen peroxide (14.0 ml). The resulting mixture was stirred at room temperature for 3 days. To the reaction mixture was added 30% aqueous hydrogen peroxide (14.0 ml) further. The resulting mixture was stirred at 50° C. for 5 hours. To the reaction mixture was added water and the solid thus precipitated was collected by filtration. The resulting solid was washed with water and dried under reduced pressure. The solid was dissolved in ethyl acetate. The resulting solution was washed with a saturated aqueous solution of sodium bicarbonate. The organic layer was dried over anhydrous sodium sulfate and filtered. The filtrate was concentrated under reduced pressure. The residue was recrystallized from ethanol to give the title compound (6.41 g, 15.0 mmol, 61%) as a white solid. After the base liquid was concentrated under reduced pressure, the residue was recrystallized from ethanol to give the title compound (2.14 g, 5.00 mmol, 20%) as a white solid. After the base liquid was concentrated under reduced pressure further, the residue was washed with diethyl ether and collected by filtration to give the title compound (780 mg, 1.82 mmol, 7%) as a white solid.

$^1$H-NMR (400 MHz, CDCl$_3$) δ: 1.90 (1H, t, J=5.6 Hz), 4.80 (2H, d, J=5.6 Hz), 6.32 (1H, s), 6.89-6.97 (1H, m), 6.99-7.06 (1H, m), 7.41 (2H, d, J=8.8 Hz), 7.49 (1H, d, J=9.8 Hz), 7.57 (2H, d, J=8.8 Hz), 8.18-8.24 (1H, m), 8.52 (1H, s).

mp: 181 to 183° C.

MSm/z: 428 (M$^+$+H).

Example 126

[6-[(4-Chlorophenylsulfonyl)(2,5-difluorophenyl)methyl]-5-fluoropyridin-3-yl]carbaldehyde

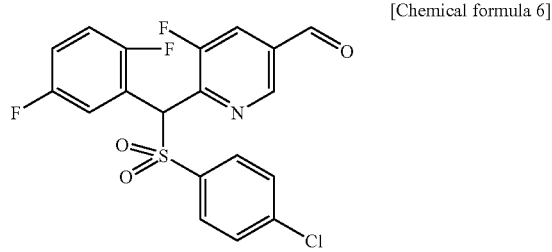

[Chemical formula 6]

To a dichloromethane (100 ml) solution of [6-(4-chlorophenylsulfonyl)(2,5-difluorophenyl)methyl-5-fluoropyridin-3-yl]methanol (8.46 g, 19.8 mmol), triethylamine (13.8 ml, 98.9 mmol) and dimethylsulfoxide (7.02 ml, 98.9 ml) was added sulfur trioxide pyridine complex (9.44 g, 59.3 mmol) at room temperature. The resulting mixture was stirred for 16 hours. After the reaction mixture was washed with brine, the organic layer was dried over anhydrous sodium sulfate and filtered. The filtrate was concentrated under reduced pressure. The residue was subjected to flash silica gel chromatography. The fraction obtained from the dichloromethane eluate was concentrated under reduced pressure. The residue thus obtained was washed with diethyl ether and collected by filtration to give the title compound (6.33 g, 14.9 mmol, 75%) as a yellow solid.

$^1$H-NMR (400 MHz, CDCl$_3$) δ: 6.40 (1H, s), 6.91-6.98 (1H, m), 7.02-7.09 (1H, m), 7.43 (2H, d, J=8.6 Hz), 7.59 (2H, d, J=8.6 Hz), 7.89 (1H, dd, J=8.6, 1.7 Hz), 8.17-8.23 (1H, m), 9.02 (1H, s), 10.15 (1H, d, J=2.2 Hz).

Example 127

6-(4-Chlorophenylsulfonyl)(2,5-difluorophenyl)methyl-5-fluoronicotinic acid

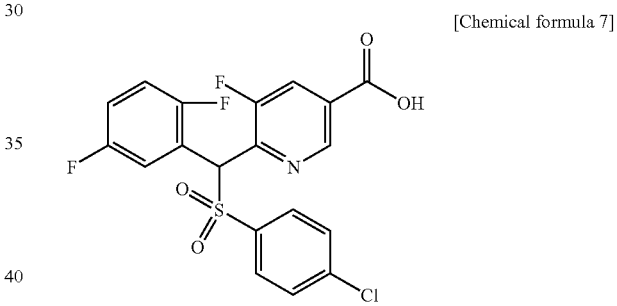

[Chemical formula 7]

To a formic acid (30 ml) solution of [6-[(4-chlorophenylsulfonyl)(2,5-difluorophenyl)methyl]-5-fluoropyridin-3-yl]carbaldehyde (1.28 g, 3.00 mmol) was added 30% aqueous hydrogen peroxide (1.02 ml, 9.00 ml) at room temperature. The resulting mixture was stirred at room temperature for 1 hour. The reaction mixture was stirred further at 50° C. for 1 hour. After cooling to room temperature, water was added thereto. The solid thus precipitated was collected by filtration, washed with water, and dried under reduced pressure. The solid thus obtained was dissolved in ethyl acetate. The resulting solution was washed with a saturated aqueous solution of ammonium chloride. The organic layer was dried over anhydrous sodium sulfate and filtered. The filtrate was concentrated under reduced pressure. The residue was washed with ethanol and collected by filtration to give the title compound (1.19 g, 2.69 mmol, 89%) as a white solid.

$^1$H-NMR (400 MHz, DMSO-d$_6$) δ: 6.37 (1H, s), 7.27-7.42 (2H, m), 7.64 (2H, d, J=8.8 Hz), 7.67 (2H, d, J=8.8 Hz), 8.01-8.07 (1H, m), 8.17 (1H, dd, J=9.6, 1.7 Hz), 9.04 (1H, s).

mp: 249 to 251° C.

Elemental Analysis for C$_{19}$H$_{11}$ClF$_3$NO$_4$S: Calculated: C, 51.65; H, 2.51; Cl, 8.02; F, 12.90; N, 3.17; S, 7.26. Found: C, 51.70; H, 2.73; Cl, 7.96; F, 12.81; N, 3.36; S, 7.39.

Example 128

6-(4-Chlorophenylsulfonyl)(2,5-difluorophenyl)methyl-5-fluoro-N-thiazol-2-ylnicotinamide

[Chemical formula 8]

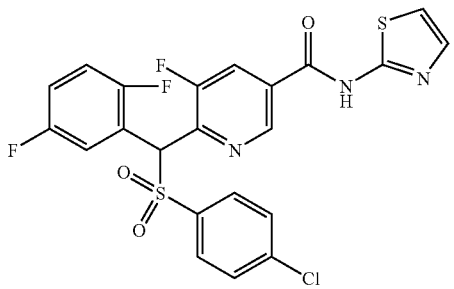

To a dichloromethane (2 ml) solution were added 6-(4-chlorophenylsulfonyl)(2,5-difluorophenyl)methyl-5-fluoronicotinic acid (100 mg, 0.23 mmol) were added thiazol-2-ylamine (25 mg, 0.25 mmol), benzotriazol-1-ol (34 mg, 0.25 mmol), 4-methylmorpholine (0.027 ml, 0.25 mmol) and 1-ethyl-3-(3-dimethylaminopropyl)carbodiimide hydrochloride (48 mg, 0.25 mmol) at room temperature. The resulting mixture was stirred at room temperature for 14 hours. To the reaction mixture was added ethyl acetate. The resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=3:1 eluate was concentrated under reduced pressure. The residue was washed with ethanol and collected by filtration to give the title compound (72 mg, 0.14 mmol, 60%) as a white solid.

$^1$H-NMR (400 MHz, DMSO-$d_6$) δ: 6.38 (1H, s), 7.24-7.42 (2H, m), 7.60 (1H, d, J=3.7 Hz), 7.65 (2H, d, J=9.1 Hz), 7.68 (2H, d, J=9.1 Hz), 8.03-8.10 (1H, m), 8.38 (1H, d, J=9.6 Hz), 9.17 (1H, s), 13.00 (1H, s).

mp: 243 to 245° C.

Elemental Analysis for Calcd for $C_{22}H_{13}ClF_3N_3O_3S_2$: Calculated: C, 50.43; H, 2.50; Cl, 6.77; F, 10.88; N, 8.02; S, 12.24. Found: C, 50.34; H, 2.48; Cl, 6.93; F, 10.82; N, 8.11; S, 12.29.

Example 129

6-(4-Chlorophenylsulfonyl)(2,5-difluorophenyl)methyl-5-fluoro-N-isoxazol-3-ylnicotinamide

[Chemical formula 9]

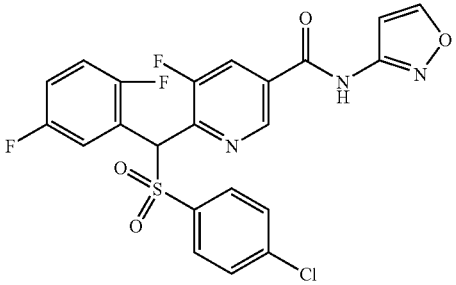

In a similar manner to Example 128, the title compound (43 mg, 0.085 mmol, 37%) as a white solid by using the 6-(4-chlorophenylsulfonyl)(2,5-difluorophenyl)methyl-5-fluoronicotinic acid (100 mg, 0.23 mmol) obtained in Example 127 and isoxazol-3-ylamine (0.018 ml, 0.25 mmol).

$^1$H-NMR (400 MHz, CDCl$_3$) δ: 6.41 (1H, s), 6.92-7.00 (1H, m), 7.03-7.11 (1H, m), 7.25 (1H, d, J=1.7 Hz), 7.44 (2H, d, J=8.6 Hz), 7.60 (2H, d, J=8.6 Hz), 8.05 (1H, dd, J=9.1, 2.0 Hz), 8.20-8.26 (1H, m), 8.40 (1H, d, J=1.7 Hz), 9.14 (1H, d, J=1.5 Hz), 10.25 (1H, s).

mp: 200 to 202° C.

Elemental Analysis for Calcd for $C_{22}H_{13}ClF_3N_3O_4S$: Calculated: C, 52.03; H, 2.58; Cl, 6.98; F, 11.22; N, 8.27; S, 6.31. Found: C, 51.84; H, 2.55; Cl, 7.36; F, 11.19; N, 8.36; S, 6.46.

Example 130

6-(4-Chlorophenylsulfonyl)(2,5-difluorophenyl)methyl-5-fluoro-N-pyridin-2-ylmethylnicotinamide

[Chemical formula 10]

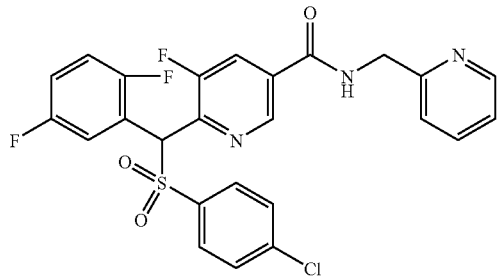

In a similar manner to Example 128, the title compound (86 mg, 0.16 mmol, 72%) as a colorless amorphous substance by using the 6-(4-chlorophenylsulfonyl)(2,5-difluorophenyl)methyl-5-fluoronicotinic acid (100 mg, 0.23 mmol) obtained in Example 127 and pyridin-2-ylmethylamine (0.026 ml, 0.25 mmol).

$^1$H-NMR (400 MHz, CDCl$_3$) δ: 4.77 (2H, d, J=4.4 Hz), 6.37 (1H, s), 6.91-7.09 (2H, m), 7.25-7.34 (2H, m), 7.43 (2H, d, J=8.8 Hz), 7.58 (2H, d, J=8.8 Hz), 7.72 (1H, td, J=7.6, 1.7 Hz), 7.94 (1H, s), 7.96 (1H, dd, J=9.3, 2.0 Hz), 8.19-8.25 (1H, m), 8.59 (1H, d, J=4.4 Hz), 9.03 (1H, s).

Elemental Analysis for Calcd for $C_{25}H_{17}ClF_3N_3O_3S$: Calculated: C, 56.45; H, 3.22; Cl, 6.66; F, 10.71; N, 7.90; S, 6.03. Found: C, 56.32; H, 3.30; Cl, 6.63; F, 10.61; N, 7.88; S, 6.14.

Example 131

Methyl(E)-3-[6-(4-chlorophenylsulfonyl)(2,5-difluorophenyl)methyl-5-fluoropyridin-3-yl]acrylate

[Chemical formula 11]

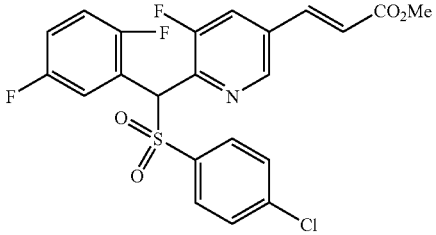

To a tetrahydrofuran (15 ml) solution of the [6-[(4-chlorophenylsulfonyl)(2,5-difluorophenyl)methyl]-5-fluoropyridin-3-yl]carbaldehyde (1.70 g, 4.00 mmol) obtained in Example 126 was added methyl(triphenylphosphoranylidene)acetate (1.47 g, 4.40 mmol) at room temperature. The resulting mixture was stirred at room temperature for 18 hours. The reaction mixture was concentrated under reduced pressure. The residue thus obtained was subjected to flash silica gel chromatography. The fraction obtained from the dichloromethane eluate was concentrated under reduced pressure. The residue thus obtained was washed with a mixed solvent of ethanol and hexane and then, collected by filtration to give the title compound (1.60 g, 3.31 mmol, 83%) as a white solid.

$^1$H-NMR (400 MHz, CDCl$_3$) δ: 3.84 (3H, s), 6.33 (1H, s), 6.53 (1H, d, J=16.7 Hz), 6.89-6.97 (1H, m), 6.99-7.08 (1H, m), 7.42 (2H, d, J=8.3 Hz), 7.55 (1H, d, J=9.6, 1.5 Hz), 7.58 (2H, d, J=8.3 Hz), 7.65 (1H, d, J=16.7 Hz), 8.18-8.24 (1H, m), 8.67 (1H, s).

MSm/z: 482 (M$^+$+H).

Example 132

Methyl 3-[6-(4-chlorophenylsulfonyl)(2,5-difluorophenyl)methyl-5-fluoropyridin-3-yl]propionate

[Chemical formula 12]

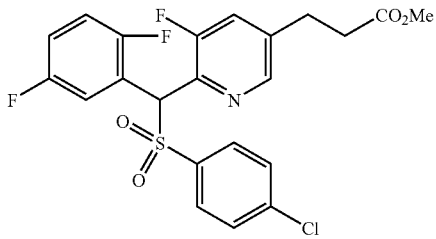

A Raney nickel suspension ("R-100", product of Nikko Rica Corporation) (1 ml) was washed sequentially with water and ethanol to give an ethanol (10 ml) suspension. The resulting suspension was added to an ethanol (40 ml) solution of methyl 3-[6-(4-chlorophenylsulfonyl)(2,5-difluorophenyl)methyl-5-fluoropyridin-3-yl]acrylate (1.38 g, 2.86 mmol). Under a hydrogen atmosphere, the resulting mixture was stirred at room temperature for 1 hour. The reaction mixture was filtered through Celite and the filtrate was concentrated under reduced pressure. The residue thus obtained was dissolved in dichloromethane. The resulting solution was dried over anhydrous sodium sulfate and filtered. The filtrate was concentrated under reduced pressure to give the title compound 1.37 g, 2.83 mmol, 99%) as a white solid.

$^1$H-NMR (400 MHz, CDCl$_3$) δ: 2.66 (2H, t, J=7.4 Hz), 3.00 (2H, t, J=7.4 Hz), 3.69 (3H, s), 6.29 (1H, s), 6.88-6.96 (1H, m), 6.98-7.06 (1H, m), 7.29 (1H, dd, J=10.1, 1.5 Hz), 7.40 (2H, d, J=8.3 Hz), 7.56 (2H, d, J=8.3 Hz), 8.20-8.26 (1H, m), 8.42 (1H, s).

MSm/z: 484 (M$^+$+H).

Example 133

3-[6-(4-Chlorophenylsulfonyl)(2,5-difluorophenyl)methyl-5-fluoropyridin-3-yl]propionic acid

[Chemical formula 13]

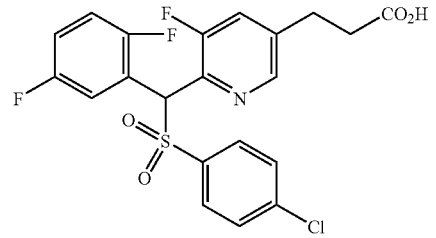

To an ethanol (8 ml) solution of methyl 3-[6-(4-chlorophenylsulfonyl)(2,5-difluorophenyl)methyl-5-fluoropyridin-3-yl]propionate (387 mg, 0.80 mmol) was added a 1N aqueous sodium hydroxide solution (4 ml). The resulting mixture was stirred at room temperature for 3 hours. The reaction mixture was acidified with 1N hydrochloric acid, followed by extraction with dichloromethane. The organic layer was dried over anhydrous sodium sulfate and filtered. The filtrate was concentrated under reduced pressure. The residue thus obtained was washed with a mixed solvent of diethyl ether and hexane and then collected by filtration to give the title compound (349 mg, 0.74 mmol, 93%) as a white solid.

$^1$H-NMR (400 MHz, CDCl$_3$) δ: 2.73 (2H, t, J=7.4 Hz), 3.01 (2H, t, J=7.4 Hz), 6.29 (1H, s), 6.89-6.96 (1H, m), 6.99-7.06 (1H, m), 7.30 (1H, dd, J=9.8, 1.7 Hz), 7.40 (2H, d, J=8.6 Hz), 7.56 (2H, d, J=8.6 Hz), 8.19-8.26 (1H, m), 8.44 (1H, s).

mp: 174 to 176° C.

MSm/z: 470 (M$^+$+H).

Elemental Analysis for C$_{21}$H$_{15}$ClF$_3$NO$_4$S: Calculated: C, 53.68; H, 3.22; Cl, 7.55; F, 12.13; N, 2.98; S, 6.82. Found: C, 53.68; H, 3.35; Cl, 7.42; F, 12.09; N, 3.16; S, 6.92.

Example 134

3-[6-(4-Chlorophenylsulfonyl)(2,5-difluorophenyl)methyl-5-fluoropyridin-3-yl]-1-(4-methylpiperazin-1-yl)propan-1-one hydrochloride

[Chemical formula 14]

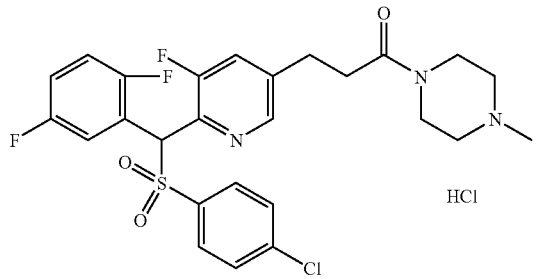

To a dichloromethane (3 ml) solution of 3-[6-(4-chlorophenylsulfonyl)(2,5-difluorophenyl)methyl-5-fluoropyridin-3-yl]propionic acid (100 mg, 0.21 mmol) were added 1-methylpiperazine (0.026 ml, 0.23 mmol), benzotriazol-1-ol (32 mg, 0.23 mmol), 4-methylmorpholine (0.026 ml, 0.23 mmol) and 1-ethyl-3-(3-dimethylaminopropyl)carbodiimide hydrochloride (45 mg, 0.23 mmol) at room temperature. The resulting mixture was stirred at room temperature for 16 hours. After the reaction mixture was washed with a saturated aqueous solution of sodium bicarbonate, the organic layer was dried over anhydrous sodium sulfate and filtered. The filtrate was concentrated under reduced pressure. The residue thus obtained was subjected to flash silica gel chromatography. The fraction obtained from the dichloromethane:methanol=19:1 eluate was concentrated under reduced pressure. The residue was dissolved in ethanol (3 ml), followed by the addition of 1N hydrochloric acid (0.224 ml). After stirring at room temperature for 30 minutes, the reaction mixture was concentrated under reduced pressure. The residue thus obtained was washed with ethanol and collected by filtration to give the title compound (111 mg, 0.19 mmol, 89%) as a white solid.

$^1$H-NMR (400 MHz, DMSO-d$_6$) δ: 2.40-3.08 (6H, m), 2.75 (3H, s), 2.90 (2H, t, J=7.1 Hz), 3.19-3.50 (2H, m), 3.92-4.17 (1H, m), 4.29-4.52 (1H, m), 6.23 (1H, s), 7.24-7.39 (2H, m), 7.61 (2H, d, J=8.8 Hz), 7.66 (2H, d, J=8.8 Hz), 7.75 (1H, dd, J=10.8, 1.5 Hz), 8.10-8.16 (1H, m), 8.53 (1H, s), 10.70 (1H, s).

mp: 243 to 245° C.

Elemental Analysis for C$_{26}$H$_{25}$ClF$_3$N$_3$O$_3$S—HCl: Calculated: C, 53.07; H, 4.45; Cl, 12.05; F, 9.69; N, 7.14; S, 5.45. Found: C, 52.81; H, 4.51; Cl, 11.74; F, 9.48; N, 7.09; S, 5.50.

Example 135

(E)-3-[6-[(4-Chlorophenylsulfonyl)(2,5-difluorophenyl)methyl]pyridin-3-yl]acrylic acid

[Chemical formula 15]

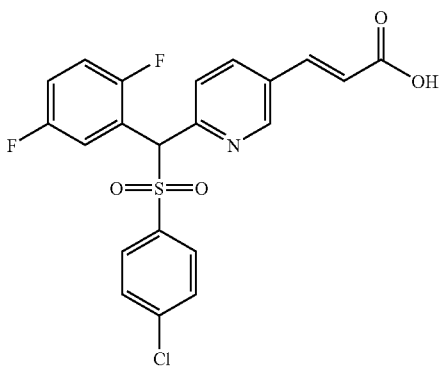

A tetrahydrofuran solution (5 ml) of the methyl(E)-3-[6-[(4-chlorophenylsulfonyl)(2,5-difluorophenyl)methyl]pyridin-3-yl]acrylate (460 mg, 0.991 mmol) obtained in Example 44 was added a 1N sodium hydroxide solution (3.0 ml). The resulting mixture was stirred at room temperature for 4 hours. The reaction mixture was acidified with 1N hydrochloric acid, followed by extraction with ethyl acetate. The extract was washed with water and brine, dried over magnesium sulfate and concentrated. The crude title compound was obtained at a stoichiometric ratio. A portion of the resulting solid was recrystallized from ethyl acetate-hexane to give the title compound (29.4 mg, 0.0653 mmol) as a colorless solid.

$^1$H-NMR (400 MHz, CDCl$_3$) δ: 5.96 (1H, s), 6.52 (1H, d, J=16.1 Hz), 6.94 (1H, td, J=9.0, 4.6 Hz), 6.99-7.06 (1H, m), 7.41 (2H, d, J=8.6 Hz), 7.56 (2H, d, J=8.6 Hz), 7.64 (1H, d, J=16.1 Hz), 7.64 (1H, d, J=8.1 Hz), 7.88 (1H, dd, J=8.1, 2.2 Hz), 8.01 (1H, ddd, J=9.0, 5.6, 3.4 Hz), 8.72 (1H, d, J=2.2 Hz).

mp: 236 to 238° C.

Elemental Analysis for C$_{21}$H$_{14}$ClF$_2$NO$_4$S: Calculated: C, 56.07; H, 3.14; Cl, 7.88; F, 8.45; N, 3.11; S, 7.13. Found: C, 55.98; H, 3.21; Cl, 7.90; F, 8.45; N, 3.21; S, 7.12.

Example 136

(E)-3-[6-[(4-Chlorophenylsulfonyl)(2,5-difluorophenyl)methyl]pyridin-3-yl]acrylamide

[Chemical formula 16]

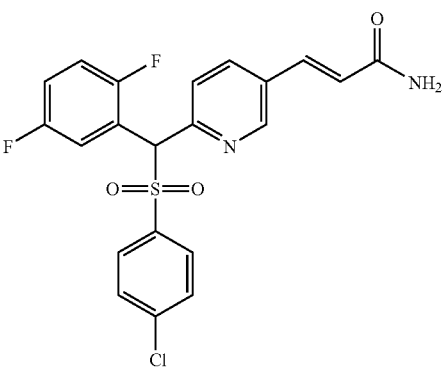

In dichloromethane (6 ml) was dissolved (E)-3-[6-[(4-chlorophenylsulfonyl)(2,5-difluorophenyl)methyl]pyridin-3-yl]acrylic acid (370 mg, 0.822 mmol). To the resulting solution were added thionyl chloride (2.00 ml) and N,N-dimethylformamide (one drop). The resulting mixture was stirred at room temperature for 4 hours. The reaction mixture was concentrated to dryness. The residue thus obtained was dissolved in dichloromethane (6 ml), followed by the addition of aqueous concentrated ammonia (2.00 ml). After stirring at room temperature for 2 hours, the reaction mixture was diluted with dichloromethane. The diluted mixture was washed with water, 0.1N hydrochloric acid and brine, dried over magnesium sulfate, and concentrated. The solid thus obtained was recrystallized from ethanol to give the title compound (250 mg, 0.558 mmol, 68%) as a white solid.

$^1$H-NMR (400 MHz, CDCl$_3$/DMSO-d$_6$) δ: 5.79 (1H, brs), 5.95 (1H, s), 6.42 (1H, brs), 6.63 (1H, d, J=15.9 Hz), 6.94 (1H, td, J=9.0, 4.4 Hz), 7.00-7.07 (1H, m), 7.41 (2H, d, J=8.5 Hz), 7.56 (2H, d, J=8.5 Hz), 7.62 (1H, d, J=15.9 Hz), 7.64 (1H, d, J=8.1 Hz), 7.85 (1H, dd, J=8.1, 2.2 Hz), 8.02 (1H, ddd, J=9.0, 5.4, 3.2 Hz), 8.74 (1H, d, J=2.2 Hz).

mp: 219 to 220° C.

Elemental Analysis for C$_{21}$H$_{15}$ClF$_2$N$_2$O$_3$S: Calculated: C, 56.19; H, 3.37; Cl, 7.90; F, 8.46; N, 6.24; S, 7.14. Found: C, 55.98; H, 3.34; Cl, 8.03; F, 8.45; N, 6.39; S, 7.23.

Example 137

Ethyl N-[6-[(4-chlorophenylsulfonyl)(2,5-difluorophenyl)methyl]nicotinoyl]glycine

[Chemical formula 17]

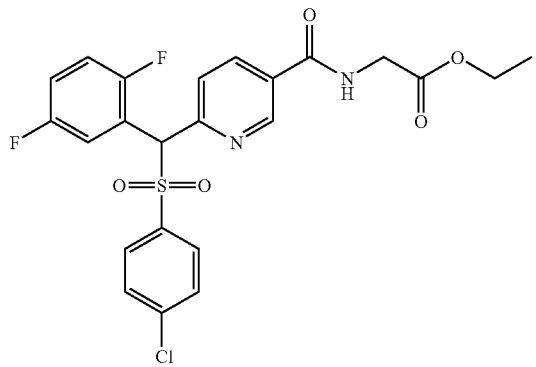

To a dichloromethane (5 ml) solution of the [6-[(4-chlorophenylsulfonyl)(2,5-difluorophenyl)methyl]pyridin-3-yl]carboxylic acid (100 mg, 0.236 mmol) obtained in Example 50 were added triethylamine (80 μl, 0.566 mmol), 4-dimethylaminopyridine (14 mg, 0.118 mmol), 1-ethyl-3-(3-dimethylaminopropyl)carbodiimide hydrochloride (54 mg, 0.283 mmol) and ethyl glycine hydrochloride (40 mg, 0.283 mmol). The resulting mixture was stirred at room temperature for 7 hours. The reaction mixture was diluted with dichloromethane. The diluted mixture was washed sequentially with water, a saturated aqueous solution of sodium bicarbonate and brine. The organic layer thus obtained was dried over magnesium sulfate, and concentrated under reduced pressure. The residue thus obtained was subjected to flash silica gel column chromatography. The fraction obtained from the hexane:ethyl acetate=2:1 eluate was concentrated under reduced pressure to give the title compound (95 mg, 0.187 mmol, 79%) as a colorless amorphous substance.

$^1$H-NMR (400 MHz, CDCl$_3$) δ: 1.33 (3H, t, J=7.1 Hz), 4.25 (2H, d, J=5.1 Hz), 4.28 (2H, q, J=7.1 Hz), 6.00 (1H, s), 6.99 (1H, brs), 6.91-6.97 (1H, m), 7.00-7.06 (1H, m), 7.42 (2H, d, J=8.5 Hz), 7.56 (2H, d, J=8.5 Hz), 7.73 (1H, d, J=8.3 Hz), 7.96-8.00 (1H, m), 8.18 (1H, dd, J=8.3, 2.2 Hz), 9.01 (1H, d, J=2.2 Hz).

MSm/z: 509 (M$^+$+H).

Example 138 t-Butyl[2-[[6-[(4-chlorophenylsulfonyl)(2,5-difluorophenyl)methyl]pyridine-3-carbonyl]amino]ethyl]carbamate

[Chemical formula 18]

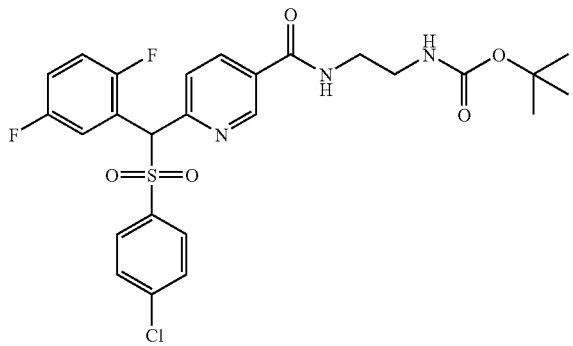

To a dichloromethane (5 ml) solution of the [6-[(4-chlorophenylsulfonyl)(2,5-difluorophenyl)methyl]pyridin-3-yl]carboxylic acid (100 mg, 0.236 mmol) obtained in Example 50 were added triethylamine (40 μl, 0.283 mmol), 4-dimethylaminopyridine (14 mg, 0.118 mmol), 1-ethyl-3-(3-dimethylaminopropyl)carbodiimide hydrochloride (54 mg, 0.283 mmol) and t-butyl N-(2-aminoethyl)carbamate (45 μl, 0.283 mmol). The resulting mixture was stirred at room temperature for 6 hours. The reaction mixture was diluted with dichloromethane. The diluted mixture was washed sequentially with water, a saturated aqueous solution of sodium bicarbonate and brine. The resulting organic layer was dried over magnesium sulfate, and concentrated under reduced pressure. The residue thus obtained was subjected to flash silica gel column chromatography. The fraction obtained from the hexane:ethyl acetate=1:1 eluate was concentrated under reduced pressure to give the title compound (57 mg, 0.101 mmol, 43%) as a white powder.

$^{1}$H-NMR (400 MHz, CDCl$_{3}$) δ: 1.44 (9H, s), 3.37-3.43 (2H, m), 3.55-3.59 (2H, m), 4.97 (1H, brs), 6.00 (1H, s), 6.92-7.05 (2H, m), 7.40 (2H, d, J=8.6 Hz), 7.55 (2H, d, J=8.6 Hz), 7.60 (1H, brs), 7.70 (1H, d, J=8.3 Hz), 7.92-7.97 (1H, m), 8.17 (1H, dd, J=8.3, 2.4 Hz), 9.03 (1H, d, J=2.4 Hz).

MSm/z: 566 (M$^{+}$+H).

Example 139

N-(2-Aminoethyl)-6-[(4-chlorophenylsulfonyl)(2,5-difluorophenyl)methyl]nicotinamide

[Chemical formula 19]

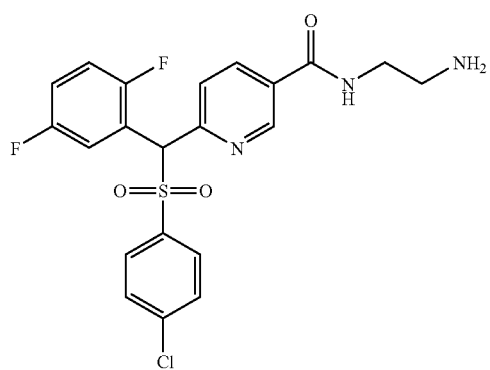

To an ethanol (2 ml) solution of t-butyl[2-[[6-[(4-chlorophenylsulfonyl)(2,5-difluorophenyl)methyl]pyridine-3-carbonyl]amino]ethyl]carbamate (50 mg, 0.0880 mmol) was added concentrated hydrochloric acid (2 ml). The resulting mixture was stirred at room temperature for 20 minutes. The reaction mixture was concentrated under reduced pressure. The solid thus obtained was washed with diethyl ether to give the title compound (44 mg, 0.0880 mmol, quant.) as 1.5 hydrochloride (white powder).

$^{1}$H-NMR (400 MHz, CD$_{3}$OD) δ: 3.19 (2H, t, J=5.9 Hz), 3.69 (2H, d, J=5.9 Hz), 6.27 (1H, s), 7.03-7.09 (1H, m), 7.12-7.18 (1H, m), 7.54 (2H, d, J=8.6 Hz), 7.66 (2H, d, J=8.6 Hz), 7.83 (1H, d, J=8.3 Hz), 8.06-8.10 (1H, m), 8.27 (1H, dd, J=8.3, 2.4 Hz), 9.08 (1H, d, J=2.4 Hz).

mp: >250° C. (decomp.).

Elemental Analysis for C$_{21}$H$_{18}$ClF$_{2}$N$_{3}$O$_{3}$S.1.5H$_{2}$O.1.5HCl: Calculated: C, 46.06; H, 4.14; Cl, 16.18; F, 6.94; N, 7.67; S, 5.86. Found: C, 46.39; H, 3.93; Cl, 16.58; F, 6.84; N, 7.74; S, 5.94.

Example 140

6-[(4-Chlorophenylsulfonyl)(2,5-difluorophenyl)methyl]-N-(2-hydroxyethyl)nicotinamide

[Chemical formula 20]

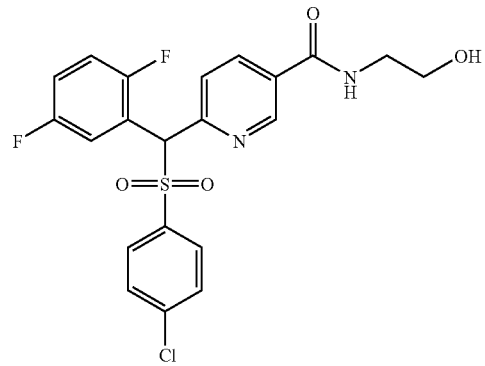

A dichloromethane (5 ml) solution of the [6-[(4-chlorophenylsulfonyl)(2,5-difluorophenyl)methyl]pyridin-3-yl]carboxylic acid (100 mg, 0.236 mmol) obtained in Example 50 were added triethylamine (80 μl, 0.566 mmol), 4-dimethylaminopyridine (15 mg, 0.118 mmol), 1-ethyl-3-(3-dimethylaminopropyl)carbodiimide hydrochloride (54 mg, 0.283 mmol) and ethanolamine hydrochloride (28 mg, 0.283 mmol). The resulting mixture was stirred at room temperature for 17.5 hours. The reaction mixture was diluted with dichloromethane. The diluted mixture was washed sequentially with water, a saturated aqueous solution of sodium bicarbonate and brine. The organic layer thus obtained was dried over magnesium sulfate and concentrated under reduced pressure. The residue thus obtained was subjected to flash silica gel column chromatography. The fraction obtained from the dichloromethane:methanol=30:1 eluate was concentrated under reduced pressure to give the title compound (69 mg, 0.148 mmol, 63%) as a white powder.

$^{1}$H-NMR (400 MHz, CDCl$_{3}$) δ: 2.38 (1H, t, J=4.9 Hz), 3.65 (2H, td, J=5.4, 4.9 Hz), 3.85 (2H, q, J=4.6 Hz), 5.99 (1H, s), 6.77 (1H, brs), 6.90-6.96 (1H, m), 7.00-7.06 (1H, m), 7.42 (2H, d, J=8.6 Hz), 7.56 (2H, d, J=8.6 Hz), 7.70 (1H, d, J=8.1 Hz), 7.97-8.01 (1H, m), 8.15 (1H, dd, J=8.1, 2.2 Hz), 8.99 (1H, d, J=2.2 Hz) H, m), mp: 179 to 181° C.

Elemental Analysis for C$_{21}$H$_{17}$ClF$_{2}$N$_{2}$O$_{4}$S: Calculated: C, 54.02; H, 3.67; Cl, 7.59; F, 8.14; N, 6.00; S, 6.87. Found: C, 53.83; H, 3.63; Cl, 7.72; F, 8.14; N, 6.06; S, 7.02.

Example 141 t-Butyl[2-[[6-[(4-chlorophenylsulfonyl)(2,5-difluorophenyl)methyl]pyridine-3-carbothioyl]amino]ethyl]carbamate

[Chemical formula 21]

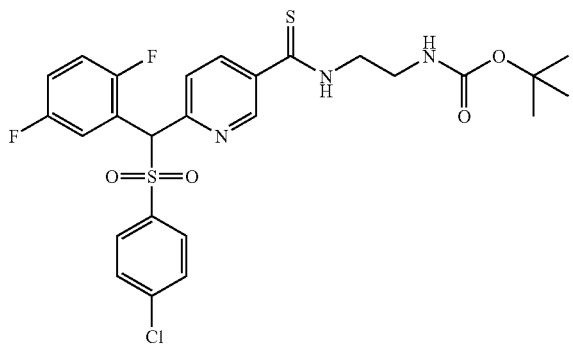

Under an argon atmosphere, a Lawson reagent (94 mg, 0.233 mmol) was added to a toluene (8 ml) solution of the t-butyl[2-[[6-[(4-chlorophenylsulfonyl)(2,5-difluorophenyl)methyl]pyridine-3-carbonyl]amino]ethyl]carbamate (120 mg, 0.212 mmol) obtained in Example 138. Under heating under reflux, the resulting mixture was stirred for 1.5 hours. After cooling, the solvent was concentrated under reduced pressure. The residue thus obtained was subjected to flash silica gel column chromatography. The fraction obtained from the hexane:ethyl acetate=1:1 eluate was concentrated to give the title compound (84 mg, 0.144 mmol, 68%) as a yellow amorphous substance.

$^1$H-NMR (400 MHz, CDCl$_3$) δ: 1.46 (9H, s), 3.52-3.57 (2H, m), 3.82-3.86 (2H, m), 5.09 (1H, brs), 5.99 (1H, s), 6.92-6.98 (1H, m), 6.99-7.05 (1H, m), 7.41 (2H, d, J=8.6 Hz), 7.55 (2H, d, J=8.6 Hz), 7.63 (1H, d, J=8.3 Hz), 7.89-7.94 (1H, m), 8.21 (1H, dd, J=8.3, 2.2 Hz), 9.06 (1H, d, J=2.2 Hz), 9.61 (1H, brs).

MSm/z: 582 (M$^+$+H).

Example 142

N-(2-Aminoethyl)-6-[(4-chlorophenylsulfonyl)(2,5-difluorophenyl)methyl]thionicotinamide

[Chemical formula 22]

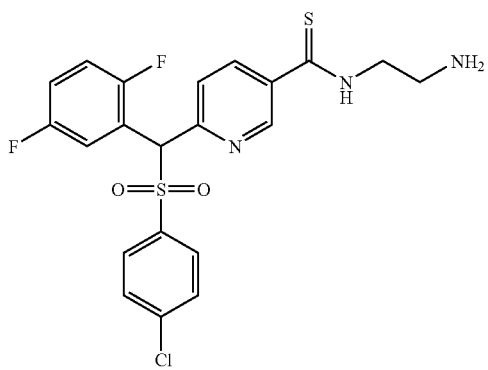

To an ethanol (3 ml) solution of t-butyl[2-[[6-[(4-chlorophenylsulfonyl)(2,5-difluorophenyl)methyl]pyridine-3-carbothioyl]amino]ethyl]carbamate (80 mg, 0.137 mmol) was added concentrated hydrochloric acid (2 ml). The resulting mixture was stirred at room temperature for 20 minutes. The reaction mixture was concentrated under reduced pressure. To the residue thus obtained was added ethanol, followed by concentration. This operation was conducted three times to give the title compound (76 mg, 0.137 mmol, quant.) as a 1.75 hydrochloride (yellow powder).

$^1$H-NMR (400 MHz, DMSO-d$_6$) δ: 3.07-3.12 (2H, m), 3.93-3.97 (2H, m), 6.46 (1H, s), 7.20-7.26 (1H, m), 7.28-7.34 (1H, m), 7.66 (2H, d, J=9.0 Hz), 7.69 (2H, d, J=9.0 Hz), 7.88 (1H, d, J=8.3 Hz), 8.05-8.12 (1H, m), 8.14 (2H, brs), 8.24 (1H, dd 8.3, 2.4), 9.05 (1H, d, J=2.4 Hz), 10.74 (1H, brs).

mp: 164 to 166° C.

Elemental Analysis for C$_{21}$H$_{18}$ClF$_2$N$_3$O$_2$S$_2$·0.5H$_2$O·1.75HCl: Calculated: C, 45.46; H, 3.77; Cl, 17.57; F, 6.85; N, 7.57; S, 11.56. Found: C, 45.02; H, 3.83; Cl, 17.37; F, 6.36; N, 7.54; S, 11.36.

Example 143

2-[(4-Chlorophenylthio)(2,5-difluorophenyl)methyl]-6-(1,3-dioxolan-2-yl)pyridine

[Chemical formula 23]

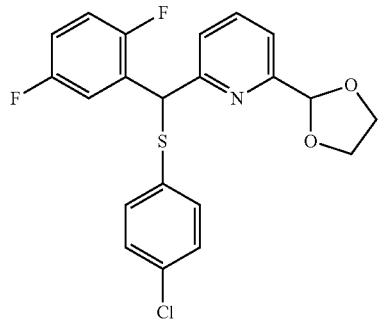

Under an argon atmosphere, triethylamine (1.77 ml, 12.7 mmol) and methanesulfonyl chloride (851 µl, 11.0 mmol) were added to a dichloromethane solution (30 ml) of the 2-[(2,5-difluorophenyl)hydroxymethyl]-6-(1,3-dioxolan-2-yl)pyridine (2.48 g, 8.46 mmol) obtained in Referential Example 32 under ice cooling. The resulting mixture was stirred at room temperature for 3.5 hours. To the reaction mixture was added a saturated aqueous solution of sodium bicarbonate, followed by extraction with diethyl ether. The extract was washed with brine, dried over anhydrous sodium sulfate and concentrated under reduced pressure.

To a dimethylformamide (20 ml) solution of the residue (2.14 g, 5.76 mmol) were added 4-chlorobenzenethiol (1.0 g, 6.91 mmol) and potassium carbonate (1.19 g, 8.64 mmol). The resulting mixture was stirred at 50° C. for 2 hours. After cooling to room temperature, the reaction mixture was diluted with diethyl ether. The diluted solution was washed sequentially with water and brine. The organic layer thus obtained was dried over sodium sulfate, and concentrated under reduced pressure. The residue thus obtained was subjected to flash silica gel column chromatography. The fraction obtained from the hexane:ethyl acetate=5:1 eluate was concentrated under reduced pressure to give the title compound (2.12 g, 5.05 mmol, 88%) as a pale yellow oil.

$^1$H-NMR (400 MHz, CDCl$_3$) δ: 4.06-4.20 (4H, m), 5.84 (1H, s), 5.89 (1H, s), 6.86-6.96 (2H, m), 7.17 (2H, d, J=8.8 Hz), 7.23 (2H, d, J=8.8 Hz), 7.38 (1H, d, J=7.8 Hz), 7.43 (1H, d, J=7.8 Hz), 7.44-7.48 (1H, m), 7.69 (1H, t, J=7.8 Hz).

MSm/z: 420 (M$^+$+H).

Example 144

2-[(4-Chlorophenylsulfonyl)(2,5-difluorophenyl)methyl]-6-(1,3-dioxolan-2-yl)pyridine

[Chemical formula 24]

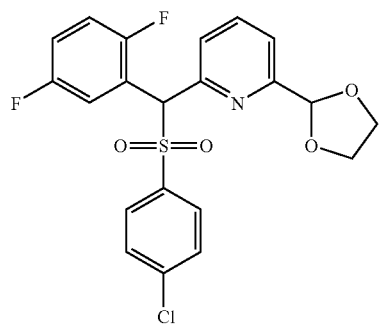

To a methanol (40 ml) solution of 2-[(4-chlorophenylthio)(2,5-difluorophenyl)methyl]-6-(1,3-dioxolan-2-yl)pyridine (2.40 g, 5.72 mmol) were added hexaammonium heptamolybdate tetrahydrate (200 mg) and 30% aqueous hydrogen peroxide (20 ml). The resulting mixture was stirred for 5 days. Water was added to the reaction mixture and the solid thus precipitated was collected by filtration. The residue was washed with water. The residue was dissolved in ethyl acetate. The resulting solution was washed sequentially with water and brine. The organic layer was concentrated under reduced pressure. The residue was washed with ethyl acetate to give the title compound (2.09 g, 4.63 mmol, 81%) as a white powder.

$^1$H-NMR (400 MHz, CDCl$_3$) δ: 4.05-4.17 (4H, m), 5.73 (1H, s), 5.98 (1H, s), 6.93-7.05 (2H, m), 7.41 (2H, d, J=8.8 Hz), 7.52 (2H, d, J=8.8 Hz), 7.50-7.53 (1H, m), 7.64 (1H, dd, J=7.6, 1.0 Hz), 7.80 (1H, t, J=7.6 Hz), 7.91-7.95 (1H, m).

MSm/z: 452 (M$^+$+H).

Example 145

[6-[(4-Chlorophenylsulfonyl)(2,5-difluorophenyl)methyl]pyridin-2-yl]carbaldehyde

[Chemical formula 25]

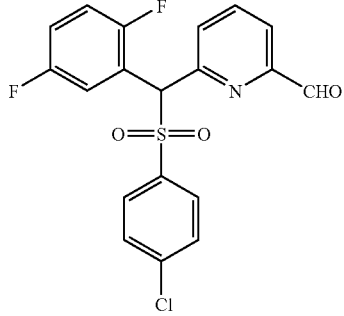

To a 1,4-dioxane (40 ml) solution of 2-[(4-chlorophenylsulfonyl)(2,5-difluorophenyl)methyl]-6-(1,3-dioxolan-2-yl)pyridine (2.05 g, 4.54 mmol) was added concentrated hydrochloric acid (10 ml). The resulting mixture was stirred at room temperature for 20 hours. The solvent was concentrated under reduced pressure. To the residue was added ethyl acetate. The resulting mixture was washed sequentially with water, a saturated aqueous solution of sodium bicarbonate and brine. The organic layer thus obtained was dried over magnesium sulfate, and concentrated under reduced pressure to give the title compound (1.85 g, 4.54 mmol, quant.) as a white powder.

$^1$H-NMR (400 MHz, CDCl$_3$) δ: 6.05 (1H, s), 6.92-6.98 (1H, m), 7.02-7.08 (1H, m), 7.43 (2H, d, J=8.8 Hz), 7.58 (2H, d, J=8.8 Hz), 7.90 (1H, dd, J=7.1, 2.0 Hz), 7.93-7.99 (2H, m), 8.04-8.09 (1H, m), 10.00 (1H, s).

MSm/z: 408 (M$^+$+H).

Example 146

6-[(4-Chlorophenylsulfonyl)(2,5-difluorophenyl)methyl]picolinic acid

[Chemical formula 26]

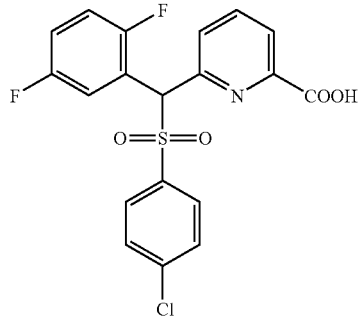

To a formic acid (5 ml) solution of [6-[(4-chlorophenylsulfonyl)(2,5-difluorophenyl)methyl]pyridin-2-yl]carbaldehyde (390 mg, 0.956 mmol) was added 30% aqueous hydrogen peroxide (325 μl, 2.87 mmol). The resulting mixture was stirred at room temperature for 4 hours. Water was added to the reaction mixture, followed by filtration. The residue was washed with water. The resulting residue was dissolved in ethyl acetate. The resulting solution was washed sequentially with a saturated aqueous solution of ammonium chloride, water and brine. The organic layer thus obtained was dried over magnesium sulfate and concentrated under reduced pressure. The residue thus obtained was recrystallized from ethanol to give the title compound (310 mg, 0.731 mmol, 77%) as a white powder.

$^1$H-NMR (400 MHz, CDCl$_3$) δ: 6.01 (1H, s), 6.93-6.99 (1H, m), 7.04-7.10 (1H, m), 7.44 (2H, d, J=8.6 Hz), 7.61 (2H, d, J=8.6 Hz), 7.78-7.82 (1H, m), 7.99 (1H, d, J=7.8 Hz), 8.06 (1H, t, J=7.8 Hz), 8.26 (1H, d, J=7.8 Hz).

mp: 200 to 201° C.

Elemental Analysis for C$_{19}$H$_{12}$ClF$_2$NO$_4$S: Calculated: C, 53.84; H, 2.85; Cl, 8.37; F, 8.97; N, 3.30; S, 7.57. Found: C, 53.55; H, 2.80; Cl, 8.23; F, 9.00; N, 3.55; S, 7.68.

Example 147

[6-[(4-Chlorophenylsulfonyl)(2,5-difluorophenyl)methyl]pyridin-2-yl](4-methylpiperazin-1-yl)methanone

[Chemical formula 27]

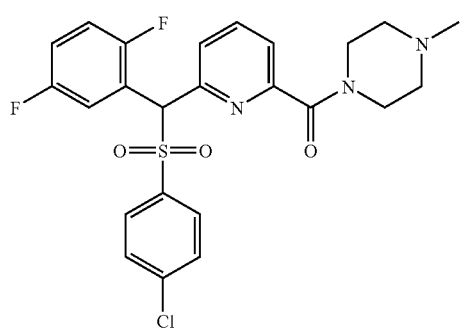

To a dichloromethane (5 ml) solution of 6-[(4-chlorophenylsulfonyl)(2,5-difluorophenyl)methyl]picolinic acid (130 mg, 0.307 mmol) were added N-methylmorpholine (41 μl, 0.368 mmol), 1-hydroxybenzotriazole (13 mg, 0.368 mmol), 1-ethyl-3-(3-dimethylaminopropyl)carbodiimide hydrochloride (71 mg, 0.368 mmol) and 1-methylpiperazine (40 μl, 0.368 mmol). The resulting mixture was stirred at room temperature for 15 hours. The reaction mixture was diluted with dichloromethane. The diluted mixture was washed sequentially with water, a saturated aqueous solution of sodium bicarbonate and brine. The organic layer thus obtained was dried over magnesium sulfate, and concentrated under reduced pressure. The residue thus obtained was subjected to flash silica gel column chromatography. The fraction obtained from the dichloromethane:methanol=30:1 eluate was concentrated under reduced pressure to give the title compound (40 mg, 0.0791 mmol, 26%) as a white amorphous substance.

$^1$H-NMR (400 MHz, CDCl$_3$) δ: 2.36 (3H, s), 2.44-2.65 (4H, m), 3.48-4.00 (4H, m), 5.91 (1H, s), 6.87-6.94 (1H, m), 6.98-7.05 (1H, m), 7.41 (2H, d, J=7.8 Hz), 7.55-7.60 (3H, m), 7.74 (1H, d, J=7.3 Hz), 7.85 (1H, t, J=7.6 Hz), 8.06-8.13 (1H, m).

FAB-MS: 506.1085 (Calcd for C$_{24}$H$_{23}$ClF$_2$N$_3$O$_3$S: 506.1117).

Example 148 t-Butyl[6-[(4-chlorophenylsulfonyl)(2,5-difluorophenyl)methyl]pyridin-2-yl]carbamate

[Chemical formula 28]

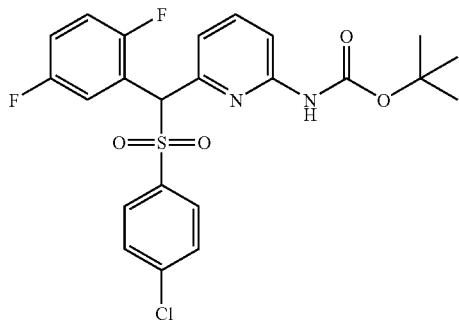

Under an argon atmosphere, diphenylphosphoryl azide (428 μl, 2.00 mmol) and triethylamine (394 μl, 2.83 mmol) were added to a solution of the 6-[(4-chlorophenylsulfonyl)(2,5-difluorophenyl)methyl]picolinic acid (600 mg, 1.42 mmol) obtained in Example 146 in a mixture of butanol (2 ml) and toluene (10 ml). The resulting mixture was stirred for 23 hours under heating and refluxing. The reaction mixture was washed with brine. The organic layer thus obtained was dried over magnesium sulfate, and then concentrated under reduced pressure. The residue thus obtained was subjected to flash silica gel column chromatography. The fraction obtained from the hexane:ethyl acetate=4:1 eluate was concentrated under reduced pressure to give the title compound (380 mg, 0.768 mmol, 54%) as a pale yellow amorphous substance.

$^1$H-NMR (400 MHz, CDCl$_3$) δ: 1.54 (9H, s), 5.76 (1H, s), 6.90-6.95 (1H, m), 6.99-7.05 (1H, m), 7.14 (1H, d, J=7.3 Hz), 7.19 (1H, brs), 7.40 (2H, d, J=8.8 Hz), 7.55 (2H, d, J=8.8 Hz), 7.65 (1H, dd, J=8.3, 7.3 Hz), 7.95 (1H, d, J=8.3 Hz), 8.01-8.05 (1H, m).

MS m/z: 495 (M$^+$+H).

Example 149

6-[(4-Chlorophenylsulfonyl)(2,5-difluorophenyl)methyl]pyridin-2-ylamine

[Chemical formula 29]

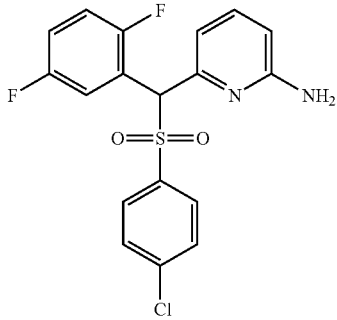

To an ethanol (5 ml) solution of t-butyl[6-[(4-chlorophenylsulfonyl)(2,5-difluorophenyl)methyl]pyridin-2-yl]carbamate (370 mg, 0.748 mmol) was added concentrated hydrochloric acid (5 ml). The resulting mixture was stirred at room temperature for 6 hours. The reaction mixture was concentrated under reduced pressure. To the residue thus obtained was added ethyl acetate. The resulting mixture was washed sequentially with saturated sodium bicarbonate and brine. The organic layer thus obtained was dried over magnesium sulfate and concentrated under reduced pressure to give the title compound (210 mg, 0.537 mmol, 71%) as a white powder.

$^1$H-NMR (400 MHz, CDCl$_3$) δ: 4.46 (2H, brs), 5.72 (1H, s), 6.45 (1H, d, J=8.1 Hz), 6.88 (1H, d, J=7.3 Hz), 6.91-7.03 (2H, m), 7.39 (2H, d, J=8.6 Hz), 7.39-7.43 (1H, m), 7.56 (2H, d, J=8.6 Hz), 7.98-8.03 (1H, m).

mp: 183 to 184° C.

Elemental Analysis for C$_{18}$H$_{13}$ClF$_2$N$_2$O$_2$S: Calculated: C, 54.76; H, 3.32; Cl, 8.98; F, 9.62; N, 7.10; S, 8.12. Found: C, 54.46; H, 3.22; Cl, 8.82; F, 9.55; N, 7.07; S, 8.11.

Example 150

N-[6-[(4-Chlorophenylsulfonyl)(2,5-difluorophenyl)methyl]pyridin-2-yl]-2-(pyridin-2-yl)acetamide

[Chemical formula 30]

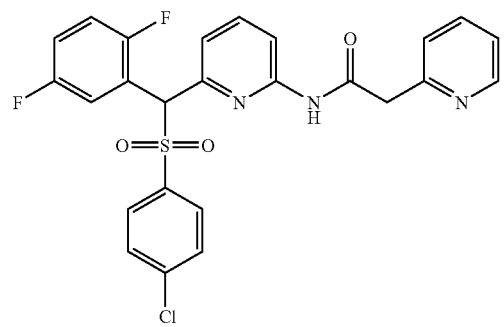

To a dichloromethane (5 ml) solution of 6-[(4-chlorophenylsulfonyl)(2,5-difluorophenyl)methyl]pyridin-2-ylamine (74 mg, 0.187 mmol) were added N-methylmorpholine (90 μl, 0.818 mmol), 1-hydroxybenzotriazole (11 mg, 0.313 mmol), 1-ethyl-3-(3-dimethylaminopropyl)carbodiimide hydrochloride (60 mg, 0.312 mmol) and 2-pyridylacetic acid hydrochloride (54 mg, 0.312 mmol). The resulting mixture was stirred at room temperature for 24 hours. The reaction mixture was diluted with dichloromethane. The diluted solution was washed sequentially with water, a saturated aqueous solution of sodium bicarbonate and brine. The organic layer thus obtained was dried over magnesium sulfate, and concentrated under reduced pressure. The residue thus obtained was subjected to flash silica gel column chromatography. The fraction obtained from the hexane:ethyl acetate=4:1 eluate was concentrated under reduced pressure to give the title compound (48 mg, 0.0934 mmol, 50%) as a white amorphous substance.

$^1$H-NMR (400 MHz, CDCl$_3$) δ: 3.86 (1H, d, J=15.9 Hz), 3.95 (1H, d, J=15.9 Hz), 5.82 (1H, s), 6.92-6.96 (1H, m), 6.98-7.08 (1H, m), 7.21 (1H, d, J=7.6 Hz), 7.25-7.33 (3H, m), 7.39 (2H, d, J=8.5 Hz), 7.54 (2H, d, J=8.5 Hz), 7.66-7.73 (2H, m), 8.07-8.11 (1H, m), 8.20 (1H, d, J=8.6 Hz), 8.69 (1H, d, J=4.4 Hz).

FAB-MS: 514.0800 (Calcd for C$_{25}$H$_{19}$ClF$_2$N$_3$O$_3$S: 514.0804).

Example 151

(E)-2-[(4-Chlorophenylsulfonyl)(2,5-difluorophenyl)methyl]-6-(2-pyridin-2-ylvinyl)pyridine

[Chemical formula 31]

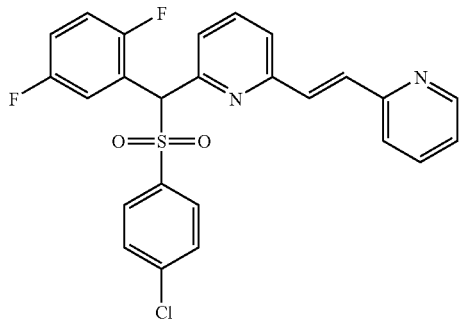

To a 1,4-dioxane (5 ml) solution of the 6-[(4-chlorophenylsulfonyl)(2,5-difluorophenyl)methyl]pyridin-2-yl]carbaldehyde (100 mg, 0.245 mmol) obtained in Example 145 were added triphenyl(2-pyridylmethyl)phosphonium chloride hydrochloride (336 mg, 0.773 mmol) and triethylamine (215 µl, 1.55 mmol). The resulting mixture was stirred at room temperature for 5 hours. After the reaction mixture was concentrated, ethyl acetate was added to the concentrate. The resulting mixture was washed sequentially with water and brine. The organic layer was dried over magnesium sulfate and concentrated under reduced pressure. The residue thus obtained was subjected to flash silica gel column chromatography. The fraction obtained from the hexane:ethyl acetate=4:1 eluate was concentrated under reduced pressure to give the title compound (202 mg, 0.418 mmol, 81%) as a colorless amorphous substance.

$^1$H-NMR (400 MHz, CDCl$_3$) δ: 5.99 (1H, s), 6.98-7.08 (2H, m), 7.21-7.25 (1H, m), 7.37-7.48 (6H, m), 7.54 (2H, d, J=8.1 Hz), 7.64 (1H, d, J=15.4 Hz), 7.69-7.75 (2H, m), 8.04-8.09 (1H, m), 8.65 (1H, d, J=4.4 Hz).

FAB-MS: 483.0739 (Calcd for C$_{25}$H$_{18}$ClF$_2$N$_2$O$_2$S: 483.0746).

Example 152

2-[(4-Chlorophenylsulfonyl)(2,5-difluorophenyl)methyl]-6-(2-pyridin-2-ylethyl)pyridine

[Chemical formula 32]

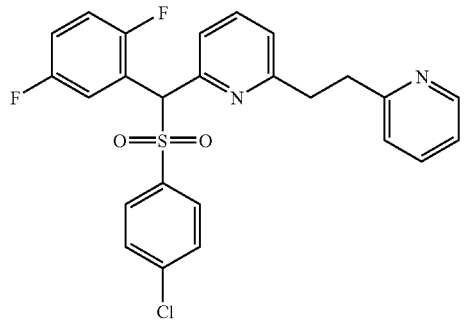

To a mixed solution of (E)-2-[(4-chlorophenylsulfonyl)(2,5-difluorophenyl)methyl]-6-(2-pyridin-2-ylvinyl)pyridine (180 mg, 0.373 mmol) in ethanol (5 ml) and 1,4-dioxane (2 ml) was added an ethanol suspension (1 ml) of Raney nickel. Under a hydrogen atmosphere of 1 atmospheric pressure, the resulting mixture was vigorously stirred for 1.5 hours. After filtration of the reaction mixture, the filtrate was concentrated under reduced pressure. The residue thus obtained was subjected to flash silica gel column chromatography. The fraction obtained from the hexane:ethyl acetate=3:2 eluate was concentrated under reduced pressure, followed by recrystallization from hexane:ethyl acetate to give the title compound (110 mg, 0.227 mmol, 61%) as a white powder.

$^1$H-NMR (400 MHz, CDCl$_3$) δ: 3.13-3.23 (4H, m), 5.92 (1H, s), 6.93-7.06 (2H, m), 7.07-7.12 (3H, m), 7.37-7.40 (3H, m), 7.52-7.60 (4H, m), 8.05-8.09 (1H, m), 8.52 (1H, d, J=3.7 Hz).

mp: 88 to 89° C.

Elemental Analysis for C$_{25}$H$_{19}$ClF$_2$N$_2$O$_2$S: Calculated: C, 61.92; H, 3.95; Cl, 7.31; F, 7.84; N, 5.78; S, 6.61. Found: C, 61.84; H, 4.08; Cl, 7.26; F, 7.69; N, 5.90; S, 6.75.

Example 153

3-[(4-Chlorophenylsulfonyl)(2,5-difluorophenyl)methyl]-1-(3-hydroxypropyl)piperidin-2-one

[Chemical formula 33]

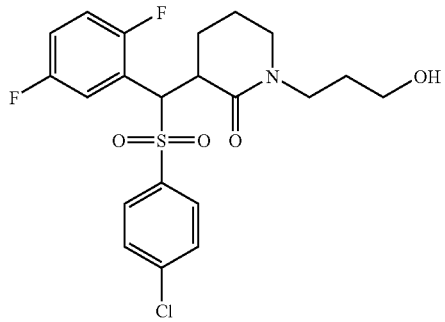

Under an argon atmosphere, n-butyl lithium (a 1.56M hexane solution, 0.140 ml, 0.218 mmol) was added at −78° C. to a 1,2-dimethoxyethane solution (2 ml) of the 2-[(4-chlorophenyl)sulfonylmethyl]-1,4-difluorobenzene (63.0 mg, 0.208 mmol) obtained in Referential Example 1. The resulting mixture was stirred at −78° C. for 5 minutes. After addition of the 3-bromo-1-[3-(t-butyldimethylsilyloxy)propyl]piperidin-2-one (72.8 mg, 0.208 mmol) obtained in Referential Example 34, the resulting mixture was stirred at room temperature for 15 hours. The reaction mixture was cooled to 0° C. After addition of water, the resulting mixture was extracted with ethyl acetate. The extract was washed with water and brine, dried over magnesium sulfate and concentrated. The residue thus obtained was purified by flash silica gel column chromatography (hexane:ethyl acetate=4:1) to give a low polar silyl-protected compound (30.0 mg) and a high polar silyl-protected compound (30.0 mg), each as a colorless oil. The resulting high polar silyl-protected compound (30.0 mg) was dissolved in tetrahydrofuran (3 ml), followed by the addition of hydrogen fluoride-pyridine (0.5 ml). The resulting mixture was stirred at room temperature for 3 hours. After dilution with ethyl acetate, the diluted mixture was washed with water brine, dried over magnesium sulfate and concentrated. The residue thus obtained was subjected to silica gel column chromatography. The fraction obtained from the hexane:ethyl acetate=2:3 eluate was concentrated to yield a white solid. The resulting solid was recrystallized from ethyl acetate-hexane to give the title compound (11.8 mg, 0.0258 mmol, 12%) as colorless needle crystals.

$^1$H-NMR (400 MHz, CDCl$_3$) δ: 1.50-1.60 (2H, m), 1.88-2.08 (3H, m), 2.70-2.77 (1H, m), 2.86-2.93 (1H, m), 3.20-3.36 (5H, m), 3.62 (1H, ddd, J=13.7, 9.0, 4.6 Hz), 3.70-3.78 (1H, m), 5.71-5.73 (1H, m), 6.86 (1H, td, J=9.0, 4.6 Hz), 6.96-7.02 (1H, m), 7.37 (2H, d, J=8.8 Hz), 7.55-7.62 (3H, m). mp: 120 to 121° C.

FAB-MS: 458.0966 (Calcd for C$_{21}$H$_{23}$ClF$_2$NO$_4$S: 458.1004).

Example 154 t-Butyl 3-[[5-chloro-4-[(4-chlorophenylthio)-(2,5-difluorophenyl)methyl]pyridin-2-yl]amino]propionate

[Chemical formula 34]

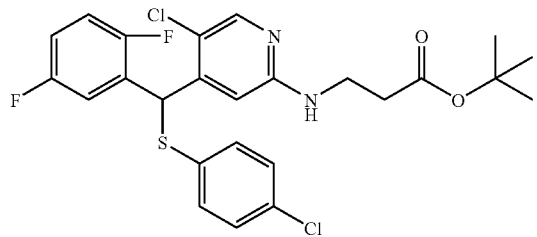

In a small amount of a saturated aqueous solution of potassium carbonate was dissolved β-alanine t-butyl ester hydrochloride (1.5 g), followed by extraction with methylene chloride. The extract was dried and concentrated into 720 mg of β-alanine t-butyl ester in the free form. The resulting ester and a 1,4-dioxane (2.0 ml) solution of the 2,5-dichloro-4-[(4-chlorophenylthio)-(2,5-difluorophenyl)methyl]pyridine (300 mg, 0.72 mmol) obtained in Example 54 was stirred at 120° C. for 4 days under an argon atmosphere. After cooling to room temperature, the reaction mixture was diluted with ethyl acetate. The diluted mixture was washed with water and brine, dried and then concentrated under reduced pressure. The residue thus obtained was purified by silica gel chromatography (hexane:ethyl acetate=5:1) to give the title compound (79 mg, 16%) as an oil.

$^1$H-NMR (400 MHz, CDCl$_3$) δ: 1.46 (9H, s), 2.52 (2H, t, J=6.0 Hz), 3.58 (2H, q, J=6.0 Hz), 4.95 (1H, br), 5.96 (1H, s), 6.68 (1H, s), 6.9-7.05 (2H, m), 7.11 (1H, m), 7.22 (2H, d, J=8.4 Hz), 7.23 (2H, d, J=8.4 Hz), 8.02 (1H, s).

MS: 525 (M$^+$+H).

Example 155

3-[[5-Chloro-4-[(4-chlorophenylsulfonyl)-(2,5-difluorophenyl)methyl]pyridin-2-yl]amino]propionic acid

[Chemical formula 35]

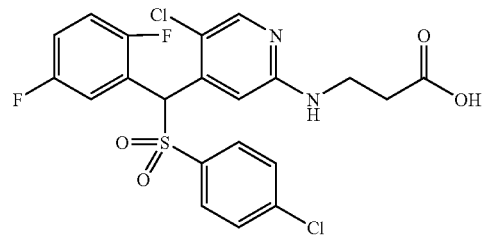

To a methanol (6 ml) solution of t-butyl 3-[[5-chloro-4-[(4-chlorophenylthio)-(2,5-difluorophenyl)methyl]pyridin-2-yl]amino]propionate (79 mg) was added hexaammonium heptamolybdate tetrahydrate (30 mg). To the resulting mixture was added 30% aqueous hydrogen peroxide (3 ml) and the mixture was stirred for 16 hours. The reaction mixture was diluted with ethyl acetate (60 ml). The diluted mixture was washed with water and brine and concentrated under reduced pressure. To the residue thus obtained was added trifluoroacetic acid (1.0 ml). The resulting mixture was stirred for 1 hour. From the reaction mixture, trifluoroacetic acid was distilled off under reduced pressure. The residue was dissolved in water-ethanol (1:1). The resulting solution was basified by the addition of a saturated aqueous solution (0.2 ml) of sodium bicarbonate thereto. An aqueous solution of sodium bisulfate was added and the resulting mixture was extracted with ethyl acetate (80 ml). The extract was washed with brine, dried and concentrated under reduced pressure. The residue was crystallized in ether to give the title compound (61 mg, 81%) as a 0.5 hydrate.

$^1$H-NMR (400 MHz, CDCl$_3$) δ: 2.76 (2H, m), 3.72 (2H, m), 6.11 (1H, s), 6.92 (1H, m), 7.04 (1H, m), 7.44 (2H, d, J=8.8 Hz), 7.46 (1H, s), 7.48 (1H, m), 7.61 (2H, d, J=8.8 Hz), 7.94 (1H, s).

mp: 200 to 205° C.

Elemental Analysis for C$_{21}$H$_{16}$Cl$_2$F$_2$N$_2$O$_4$S.0.5H$_2$O: Calculated: C, 49.42; H, 3.36; N, 5.49; S, 6.28; Cl, 13.89; F, 7.44. Found: C, 49.51; H, 3.28; N, 5.52; S, 6.35; Cl, 13.75; F, 7.77.

Example 156

2-[[5-Chloro-4-[(4-chlorophenylthio)-(2,5-difluorophenyl)methyl]pyridin-2-yl](methyl)amino]ethanol

[Chemical formula 36]

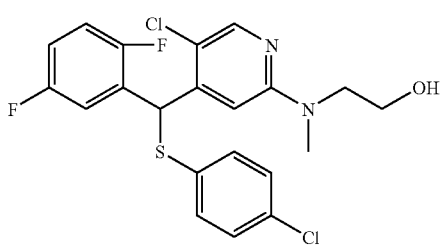

A 1,4-dioxane (2.0 ml) solution of the 2,5-dichloro-4-[(4-chlorophenylthio)-(2,5-difluorophenyl)methyl]pyridine (200 mg, 0.48 mmol) obtained in Example 54 and methylaminoethanol (200 µl) was stirred at 110° C. for 3 days under an argon atmosphere. After cooling to room temperature, the reaction mixture was concentrated under reduced pressure. The residue thus obtained was purified by silica gel chromatography (hexane:ethyl acetate=3:1) to give the title compound (164 mg, 75%) as an oil.

$^1$H-NMR (400 MHz, CDCl$_3$) δ: 3.07 (3H, s), 3.73 (2H, d, J=4.8 Hz), 3.85 (2H, d, J=4.8 Hz), 5.99 (1H, s), 6.86 (1H, s), 6.91-7.12 (3H, m), 7.23 (2H, d, J=8.8 Hz), 7.25 (2H, d, J=8.8 Hz), 8.00 (1H, s).

MSm/z: 455 (M$^+$+H).

Example 157

5-Chloro-4-[(4-chlorophenylthio)-(2,5-difluorophenyl)methyl]-2-[2-(pyridin-2-yl)ethylamino]pyridine

[Chemical formula 37]

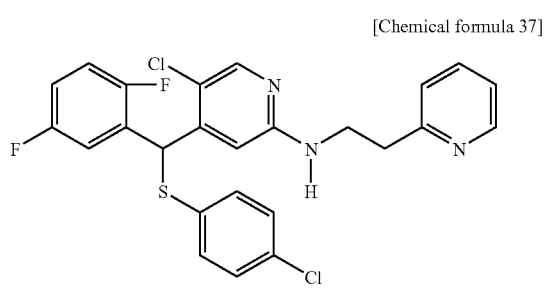

A 1,4-dioxane (1.5 ml) solution of the 2,5-dichloro-4-[(4-chlorophenylthio)-(2,5-difluorophenyl)methyl]pyridine (150 mg, 0.36 mmol) obtained in Example 54 and 2-pyridin-2-ylethylamine (400 µl) was stirred at 120° C. for 5 days under an argon atmosphere. After cooling to room temperature, the reaction mixture was concentrated under reduced pressure. The residue thus obtained was purified by silica gel chromatography (hexane:ethyl acetate=1:1) to give the title compound (126 mg, 70%) as an oil.

$^1$H-NMR (400 MHz, CDCl$_3$) δ: 3.07 (2H, d, J=6.4 Hz), 3.71 (2H, q, J=6.4 Hz), 5.24 (1H, br), 5.96 (1H, s), 6.69 (1H, s), 6.93-7.30 (9H, m), 7.61 (1H, dt, J=2.0, 7.6 Hz), 8.01 (1H, s), 8.56 (1H, m).

MSm/z: 502 (M$^+$+H).

Example 158

5-Chloro-4-[(4-chlorophenylthio)-(2,5-difluorophenyl)methyl]-2-[3-(imidazol-1-yl)propylamino]pyridine

[Chemical formula 38]

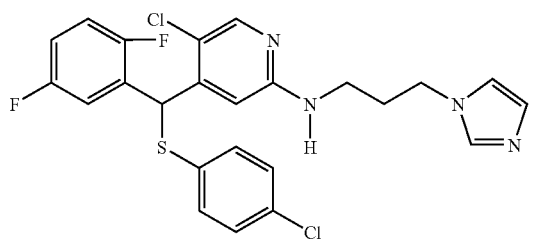

A 1,4-dioxane (1.5 ml) solution of the 2,5-dichloro-4-[(4-chlorophenylthio)-(2,5-difluorophenyl)methyl]pyridine (200 mg, 0.48 mmol) obtained in Example 54 and 3-(imidazol-1-yl)propylamine (400 µl) was stirred at 120° C. for 5 days under an argon atmosphere. After cooling to room temperature, the reaction mixture was concentrated under reduced pressure. The residue thus obtained was purified by silica gel chromatography (hexane:ethyl acetate=1:1) to give the title compound (94 mg, 39%) as an oil.

$^1$H-NMR (400 MHz, CDCl$_3$) δ: 2.11 (2H, m), 3.35 (2H, m), 4.11 (2H, d, J=6.8 Hz), 4.86 (1H, m), 5.94 (1H, s), 6.69 (1H, s), 6.96 (1H, s), 6.95-7.26 (3H, m), 7.12 (1H, s), 7.21 (2H, d, J=8.8 Hz), 7.23 (2H, d, J=8.8 Hz), 7.92 (1H, m), 8.02 (1H, s).

MSm/z: 505 (M$^+$+H).

Example 159

2-[[5-Chloro-4-[(4-chlorophenylthio)-(2,5-difluorophenyl)methyl]pyridin-2-yl]amino]ethanol

[Chemical formula 39]

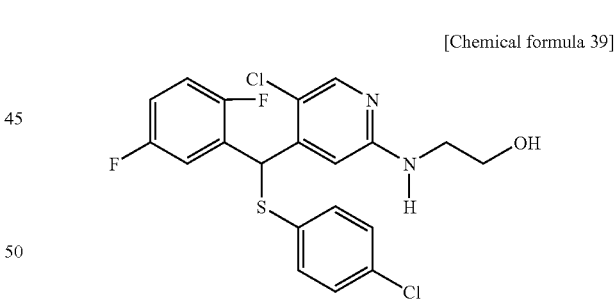

A 1,4-dioxane (1.5 ml) solution of the 2,5-dichloro-4-[(4-chlorophenylthio)-(2,5-difluorophenyl)methyl]pyridine (180 mg, 0.43 mmol) obtained in Example 54 and 2-aminoethanol (300 µl) was stirred at 120° C. for 64 hours under an argon atmosphere. After cooling to room temperature, the reaction mixture was concentrated under reduced pressure. The residue thus obtained was purified by silica gel chromatography (hexane:ethyl acetate=1:1) to give the title compound (106 mg, 56%) as an oil.

$^1$H-NMR (400 MHz, CDCl$_3$) δ: 3.00 (1H, br), 3.51 (2H, br), 3.81 (2H, d, J=4.8 Hz), 5.05 (1H, br), 5.95 (1H, s), 6.74 (1H, s), 6.92-7.06 (2H, m), 7.13 (1H, m), 7.23 (4H, s), 7.99 (1H, s).

MSm/z: 441 (M$^+$+H).

Example 160

1-[3-[[5-Chloro-4-[(4-chlorophenylthio)-(2,5-difluorophenyl)methyl]pyridin-2-yl]amino]propyl]pyrrolidin-2-one

[Chemical formula 40]

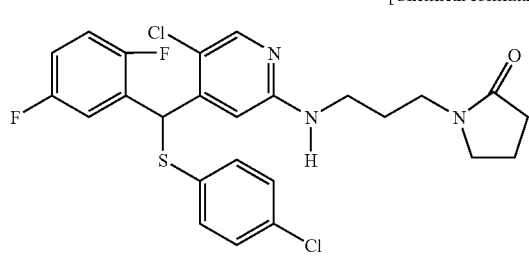

A 1,4-dioxane (1.5 ml) solution of the 2,5-dichloro-4-[(4-chlorophenylthio)-(2,5-difluorophenyl)methyl]pyridine (200 mg, 0.48 mmol) obtained in Example 54 and 1-(3-aminopropyl)pyrrolidin-2-one (400 μl) was stirred at 120° C. for 17 hours under an argon atmosphere. After cooling to room temperature, the reaction mixture was concentrated under reduced pressure. The residue thus obtained was purified by silica gel chromatography (hexane:ethyl acetate=1:1) to give the title compound (68 mg, 27%) as an oil.

$^1$H-NMR (400 MHz, CDCl$_3$) δ: 1.77 (2H, m), 2.04 (2H, m), 2.41 (2H, m), 3.30-3.40 (6H, m), 5.53 (1H, br), 5.94 (1H, s), 6.72 (1H, s), 6.90-7.03 (2H, m), 7.13 (1H, m), 7.22 (2H, d, J=8.0 Hz), 7.25 (2H, d, J=8.0 Hz), 7.99 (1H, s).

MSm/z: 522 (M$^+$+H).

Example 161 t-Butyl 4-[[5-chloro-4-[(4-chlorophenylthio)-(2,5-difluorophenyl)methyl]pyridin-2-yl]amino]piperidine-1-carboxylate

[Chemical formula 41]

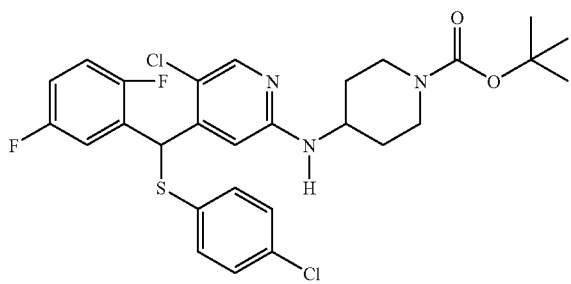

A 1,4-dioxane (2.2 ml) solution of the 2,5-dichloro-4-[(4-chlorophenylthio)-(2,5-difluorophenyl)methyl]pyridine (300 mg, 0.48 mmol) obtained in Example 54 and t-butyl 4-aminopiperidine-1-carboxylate (600 mg) was stirred at 120° C. for 5 days under an argon atmosphere. After cooling to room temperature, the reaction mixture was concentrated under reduced pressure. The residue thus obtained was purified by silica gel chromatography (hexane:ethyl acetate=3:1) to give the title compound (36 mg, 9%) as an oil.

$^1$H-NMR (400 MHz, CDCl$_3$) δ: 1.34 (2H, m), 1.47 (9H, s), 1.98 (2H, m), 2.94 (2H, m), 3.79 (1H, m), 4.11 (2H, m), 4.58 (1H, br), 5.95 (1H, s), 6.63 (1H, s), 6.93-7.04 (2H, m), 7.12 (1H, m), 7.22 (4H, m), 8.01 (1H, s).

MSm/z: 580 (M$^+$+H).

Example 162 t-Butyl 3-[[5-chloro-4-[(4-chlorophenylthio)-(2,5-difluorophenyl)methyl]pyridin-2-yl]amino]propyl-carbamate

[Chemical formula 42]

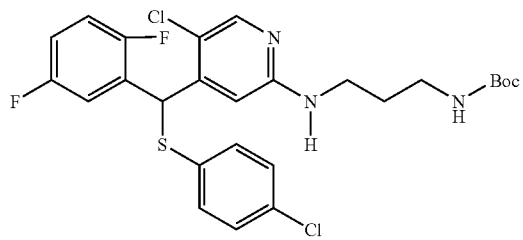

A 1,4-dioxane (1.5 ml) solution of the 2,5-dichloro-4-[(4-chlorophenylthio)-(2,5-difluorophenyl)methyl]pyridine (300 mg, 0.48 mmol) obtained in Example 54 and t-butyl(3-aminopropyl)carbamate (400 μl) was stirred at 120° C. for 2 days under an argon atmosphere. After cooling to room temperature, the reaction mixture was concentrated under reduced pressure. The residue thus obtained was purified by silica gel chromatography (hexane:ethyl acetate=1:1) to give the title compound (71 mg, 27%) as an oil.

$^1$H-NMR (400 MHz, CDCl$_3$) δ: 1.45 (9H, s), 1.73 (2H, m), 3.21 (2H, m), 3.38 (2H, m), 4.85 (1H, br), 5.10 (1H, br), 5.95 (1H, s), 6.96-7.04 (2H, m), 7.12 (1H, m), 7.22 (2H, d, J=8.8 Hz), 7.24 (2H, d, J=8.8 Hz), 8.00 (1H, s).

MSm/z: 554 (M$^+$+H).

Example 163

5-Chloro-4-[(4-chlorophenylthio)-(2,5-difluorophenyl)methyl]-2-[(2-methylthioethyl)amino]pyridine

[Chemical formula 43]

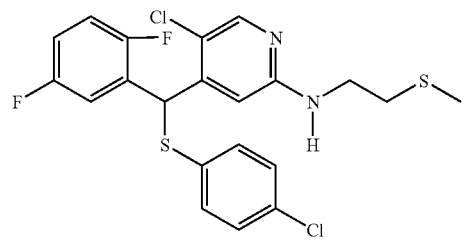

A 1,4-dioxane (1.5 ml) solution of the 2,5-dichloro-4-[(4-chlorophenylthio)-(2,5-difluorophenyl)methyl]pyridine (200 mg, 0.48 mmol) obtained in Example 54 and 2-methylthioethylamine (200 μl) was stirred at 120° C. for 2 days under an argon atmosphere. After cooling to room temperature, the reaction mixture was concentrated under reduced pressure. The residue thus obtained was purified by silica gel chromatography (hexane:ethyl acetate=3:1) to give the title compound (29 mg, 13%) as an oil.

$^1$H-NMR (400 MHz, CDCl$_3$) δ: 2.12 (3H, s), 2.74 (2H, d, J=6.4 Hz), 3.52 (2H, m), 4.98 (1H, br), 5.96 (1H, s), 6.69 (1H, s), 6.92-7.05 (2H, m), 7.13 (1H, m), 7.23 (4H, m), 8.02 (1H, s).

MSm/z: 471 (M$^+$+H).

Example 164

2-[[5-Chloro-4-[(4-chlorophenylsulfonyl)-(2,5-difluorophenyl)methyl]pyridin-2-yl](methyl)amino]ethanol

[Chemical formula 44]

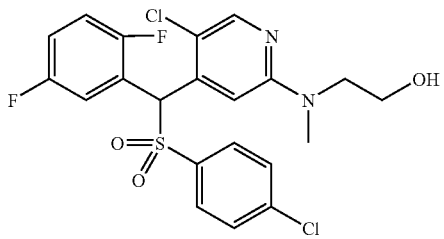

To a methanol (6 ml) solution of the 2-[[5-chloro-4-[(4-chlorophenylthio)-(2,5-difluorophenyl)methyl]pyridin-2-yl](methyl)amino]ethanol (160 mg, 0.35 mmol) obtained in Example 156 was added hexaammonium heptamolybdate tetrahydrate (30 mg), followed by further addition of 30% aqueous hydrogen peroxide (3 ml). The resulting mixture was stirred for 17 hours. The reaction mixture was diluted with ethyl acetate (60 ml). The diluted mixture was washed with water and brine, and concentrated under reduced pressure. The residue thus obtained was purified by silica gel chromatography (hexane:ethyl acetate=2:1), followed by crystallization from hexane-ethanol to give the title compound (162 mg, 95%) as needle crystals.

$^1$H-NMR (400 MHz, CDCl$_3$) δ: 3.20 (3H, s), 3.7-3.85 (2H, m), 3.89 (2H, m), 6.14 (1H, s), 6.94 (1H, m), 7.04 (1H, m), 7.42 (1H, br), 7.44 (2H, d, J=8.8 Hz), 7.52 (1H, m), 7.62 (2H, d, J=8.8 Hz), 7.99 (1H, s).

mp: 88 to 89° C.

Elemental Analysis for C$_{21}$H$_{18}$Cl$_2$F$_2$N$_2$O$_3$S·0.5H$_2$O: Calculated: C, 50.82; H, 3.86; N, 5.64; S, 6.46; Cl, 14.29; F, 7.66. Found: C, 51.16; H, 3.66; N, 5.78; S, 6.62; Cl, 14.32; F, 7.73.

Example 165

2-[[5-Chloro-4-[(4-chlorophenylsulfonyl)-(2,5-difluorophenyl)methyl]pyridin-2-yl](methyl)amino]ethyl ethylcarbamate

[Chemical formula 45]

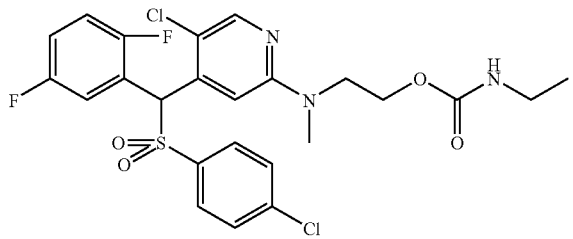

To a methylene chloride (1.0 ml) solution of 2-[[5-chloro-4-[(4-chlorophenylsulfonyl)-(2,5-difluorophenyl)methyl]pyridin-2-yl](methyl)amino]ethanol (73 mg, 0.15 mmol) was added pyridine (0.5 ml), followed by further addition of ethyl isocyanate (100 μl). The resulting mixture was stirred for 19 hours. After the reaction mixture was concentrated under reduced pressure, the residue thus obtained was purified by silica gel chromatography (hexane:ethyl acetate=3:1) to yield the title compound (65 mg, 74%) as an oil.

$^1$H-NMR (400 MHz, CDCl$_3$) δ: 1.06 (3H, t, J=7.2 Hz), 3.19 (3H, s), 3.20 (2H, m), 3.68 (1H, m), 3.91 (1H, m), 4.25 (1H, m), 4.40 (1H, m), 5.15 (1H, br), 6.16 (1H, s), 6.92 (1H, m), 7.03 (1H, m), 7.45 (2H, d, J=8.4 Hz), 7.49 (1H, s), 7.55 (1H, m), 7.60 (2H, d, J=8.4 Hz), 8.03 (1H, s).

EI-MS: 557.0714 (Calcd for C$_{24}$H$_{23}$Cl$_2$F$_2$N$_3$O$_4$S: 557.0754).

Example 166

5-Chloro-4-[(4-chlorophenylsulfonyl)-(2,5-difluorophenyl)methyl]-2-[2-(pyridin-2-yl)ethylamino]pyridine

[Chemical formula 46]

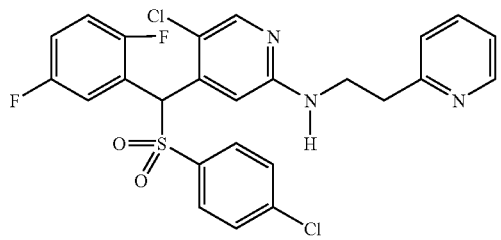

To a methanol (6 ml) solution of the 5-chloro-4-[(4-chlorophenylthio)-(2,5-difluorophenyl)methyl]-2-[2-(pyridin-2-yl)ethylamino]pyridine (120 mg, 0.35 mmol) obtained in Example 157 was added hexaammonium heptamolybdate tetrahydrate (30 mg), followed by further addition of 30% aqueous hydrogen peroxide (3 ml). The resulting mixture was stirred for 2 days. The reaction mixture was diluted with ethyl acetate (80 ml). The diluted mixture was washed with water and brine and concentrated under reduced pressure. The residue thus obtained was purified by silica gel chromatography (hexane:ethyl acetate=3:1) to give the title compound (43 mg, 33%) as an amorphous substance.

$^1$H-NMR (400 MHz, CDCl$_3$) δ: 3.19 (2H, t, J=5.2 Hz), 3.81 (2H, m), 5.51 (1H, br), 6.13 (1H, s), 6.91 (1H, m), 7.03 (1H, m), 7.20-7.30 (3H, m), 7.43 (2H, d, J=8.8 Hz), 7.50 (1H, m), 7.62 (2H, d, J=8.8 Hz), 7.68 (1H, s), 7.98 (1H, s), 8.60 (1H, m).

FAB-MS: 534.0651 (Calcd for C$_{25}$H$_{20}$Cl$_2$F$_2$N$_3$O$_2$S: 534.0621).

Example 167

5-Chloro-4-[(4-chlorophenylsulfonyl)-(2,5-difluorophenyl)methyl]-2-[3-(imidazol-1-yl)propylamino]pyridine

[Chemical formula 47]

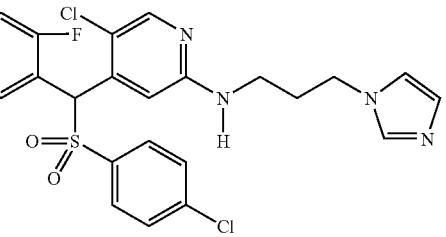

To a methanol (6 ml) solution of the 5-chloro-4-[(4-chlorophenylthio)-(2,5-difluorophenyl)methyl]-2-[3-(imidazol-1-yl)propylamino]pyridine (94 mg, 0.19 mmol) obtained in Example 158 was added hexaammonium heptamolybdate tetrahydrate (30 mg), followed by the addition of 30% aqueous hydrogen peroxide (3 ml). The resulting mixture was stirred for 17 hours. After the reaction mixture was diluted with ethyl acetate (80 ml), the diluted mixture was washed with water and brine, and concentrated under reduced pressure. The residue thus obtained was purified by silica gel chromatography (7% methanol-chloroform) to give the title compound (5 mg, 5%) as an oil.

¹H-NMR (400 MHz, CDCl₃) δ: 2.20 (2H, m), 3.44 (2H, m), 4.32 (2H, m), 5.77 (1H, br), 6.13 (1H, s), 6.91 (1H, m), 7.02 (1H, m), 7.10 (1H, s), 7.30 (1H, s), 7.40 (1H, s), 7.44 (2H, d, J=8.4 Hz), 7.54 (1H, m), 7.65 (2H, d, J=8.4 Hz), 7.97 (s, 1H), 8.05 (1H, s), 8.89 (1H, s).

FAB-MS: 537.0737 (Calcd for C$_{24}$H$_{21}$Cl$_2$F$_2$N$_4$O$_2$S: 537.0730).

Example 168

2-[[5-Chloro-4-[(4-chlorophenylsulfonyl)-(2,5-difluorophenyl)methyl]pyridin-2-yl]amino]ethanol

[Chemical formula 48]

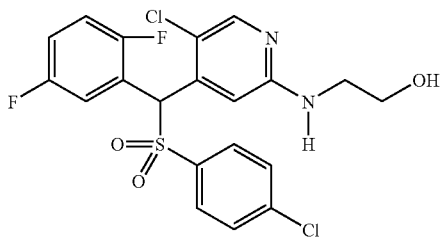

To a methanol (6 ml) solution of the 2-[[5-chloro-4-[(4-chlorophenylthio)-(2,5-difluorophenyl)methyl]pyridin-2-yl]amino]ethanol (143 mg, 0.33 mmol) obtained in Example 159 was added hexaammonium heptamolybdate tetrahydrate (30 mg), followed by further addition of 30% aqueous hydrogen peroxide (3 ml). The resulting mixture was stirred for 17 hours. After the reaction mixture was diluted with ethyl acetate (60 ml), the diluted solution was washed with water and brine, and concentrated under reduced pressure. The residue thus obtained was purified by silica gel chromatography (hexane:ethyl acetate=1:1) and crystallized from ethanol to give the title compound (98 mg, 63%) as needle crystals.

¹H-NMR (400 MHz, CDCl₃) δ: 3.60 (2H, m), 3.87 (2H, m), 5.53 (1H, br), 6.11 (1H, s), 6.92 (1H, m), 7.03 (1H, m), 7.40 (1H, s), 7.45 (2H, d, J=8.8 Hz), 7.48 (1H, m), 7.61 (2H, d, J=8.8 Hz), 7.96 (1H, s). mp: 168 to 169° C.

Elemental Analysis for C$_{20}$H$_{16}$Cl$_2$F$_2$N$_2$O$_3$S: Calculated: C, 50.75; H, 3.41; N, 5.92; S, 6.77; Cl, 14.98; F, 8.03. Found: C, 50.33; H, 3.40; N, 5.95; S, 6.90; Cl, 14.93; F, 8.04.

Example 169

1-[3-[[5-Chloro-4-[(4-chlorophenylsulfonyl)-(2,5-difluorophenyl)methyl]pyridin-2-yl]amino]propyl]pyrrolidin-2-one

[Chemical formula 49]

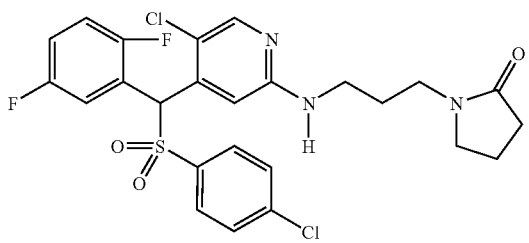

To a methanol (6 ml) solution of the 1-[3-[[5-chloro-4-[(4-chlorophenylthio)-(2,5-difluorophenyl)methyl]pyridin-2-yl]amino]propyl]pyrrolidin-2-one (143 mg, 0.33 mmol) obtained in Example 160 was added hexaammonium heptamolybdate tetrahydrate (30 mg), followed by the addition of 30% aqueous hydrogen peroxide (3 ml). The resulting mixture was stirred for 17 hours. After the reaction mixture was diluted with ethyl acetate (60 ml), the diluted mixture was washed with water and brine, and concentrated under reduced pressure. The residue thus obtained was purified by silica gel chromatography (2% methanol-ethyl acetate) and crystallized from ether to give the title compound (42 mg, 60%) as needle crystals.

¹H-NMR (400 MHz, CDCl₃) δ: 1.82 (2H, m), 2.05 (2H, m), 2.43 (2H, m), 3.35-3.50 (6H, m), 5.53 (1H, br), 6.12 (1H, s), 6.92 (1H, m), 7.02 (1H, m), 7.23 (1H, s), 7.42 (2H, d, J=8.4 Hz), 7.53 (1H, m), 7.62 (2H, d, J=8.4 Hz), 7.96 (1H, s).

mp: 78 to 80° C.

Elemental Analysis for C$_{25}$H$_{23}$Cl$_2$F$_2$N$_3$O$_3$S: Calculated: C, 54.16; H, 4.18; N, 7.58; S, 5.78; Cl, 12.79; F, 6.85. Found: C, 54.15; H, 4.37; N, 7.39; S, 5.60; Cl, 12.20; F, 6.64.

Example 170 t-Butyl 4-[[5-chloro-4-[(4-chlorophenylsulfonyl)-(2,5-difluorophenyl)methyl]pyridin-2-yl]amino]piperidine-1-carboxylate

[Chemical formula 50]

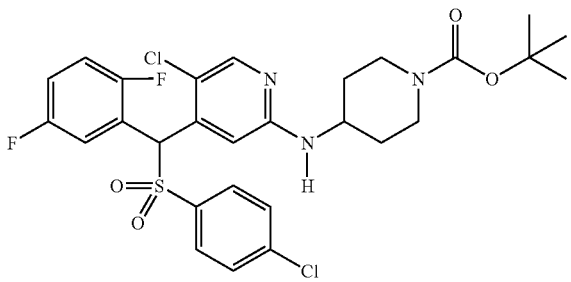

To a methanol (6 ml) solution of the t-butyl 4-[[5-chloro-4-[(4-chlorophenylthio)-(2,5-difluorophenyl)methyl]pyridin-2-yl]amino]piperidine-1-carboxylate (41 mg, 0.070 mmol) obtained in Example 161 was added hexaammonium heptamolybdate tetrahydrate (30 mg), followed by further addition of 30% aqueous hydrogen peroxide (3 ml). The resulting mixture was stirred for 20 hours. After dilution with ethyl acetate (80 ml), the diluted mixture was washed with water and brine, and concentrated under reduced pressure. The residue was purified by silica gel chromatography (hexane:ethyl acetate=4:1) to give the title compound (41 mg, 95%) as an oil.

¹H-NMR (400 MHz, CDCl₃) δ: 1.43 (2H, m), 1.47 (9H, s), 2.04 (2H, m), 2.97 (2H, m), 3.88 (1H, m), 4.08 (2H, m), 6.08 (1H, s), 6.89 (1H, m), 7.02 (1H, m), 7.25 (1H, s), 7.43 (2H, d, J=8.0 Hz), 7.46 (1H, m), 7.58 (2H, d, J=8.0 Hz), 7.96 (1H, s).

MSm/z: 612 (M⁺+H).

Example 171

4-[[5-Chloro-4-[(4-chlorophenylsulfonyl)-(2,5-difluorophenyl)methyl]pyridin-2-yl]amino]piperidine dihydrochloride

[Chemical formula 51]

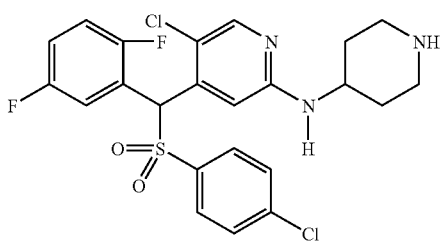

To t-butyl 4-[[5-chloro-4-[(4-chlorophenylsulfonyl)-(2,5-difluorophenyl)methyl]pyridin-2-yl]amino]piperidine-1-carboxylate (41 mg, 0.067 mmol) was added a 20% hydrochloric acid-methanol solution. The resulting mixture was stirred for 2 hours. The reaction mixture was concentrated under reduced pressure. The residue thus obtained was dissolved in chloroform, followed by further concentration. The amorphous substance thus obtained was dried under reduced pressure to afford the title compound (34 mg, 84%).

$^1$H-NMR (400 MHz, CD$_3$OD) δ: 1.90 (2H, m), 2.33 (2H, m), 3.22 (2H, m), 3.52 (2H, m), 4.10 (1H, m), 6.28 (1H, s), 7.09 (1H, m), 7.23 (1H, m), 7.53 (1H, m), 7.61 (2H, d, J=6.4 Hz), 7.75 (2H, d, J=6.4 Hz), 7.89 (1H, s), 8.05 (1H, s).

Elemental Analysis for C$_{23}$H$_{21}$Cl$_2$F$_2$N$_3$O$_2$S.2HCl.H$_2$O: Calculated: C, 45.79; H, 4.18; N, 6.96; S, 5.31; Cl, 23.50; F, 6.30. Found: C, 45.48; H, 4.17; N, 7.2; S, 5.24; Cl, 22.82; F, 6.02.

Example 172 t-Butyl 3-[[5-chloro-4-[(4-chlorophenylsulfonyl)-(2,5-difluorophenyl)methyl]pyridin-2-yl]amino]propylcarbamate

[Chemical formula 52]

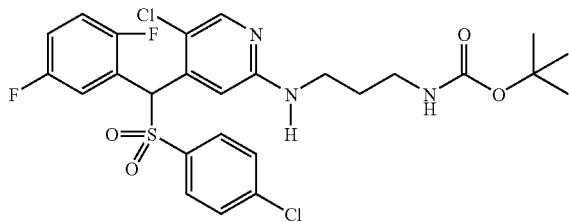

To a methanol (6 ml) solution of the t-butyl 3-[[5-chloro-4-[(4-chlorophenylthio)-(2,5-difluorophenyl)methyl]pyridin-2-yl]amino]propylcarbamate (70 mg, 0.13 mmol) obtained in Example 162 was added hexaammonium heptamolybdate tetrahydrate (30 mg), followed by further addition of 30% aqueous hydrogen peroxide (3 ml). The resulting mixture was stirred for 20 hours. After dilution with ethyl acetate (80 ml), the diluted mixture was washed with water and brine, and concentrated under reduced pressure. The residue thus obtained was purified by silica gel chromatography (hexane:ethyl acetate=2:1) to give the title compound (61 mg, 82%) as an oil.

$^1$H-NMR (400 MHz, CDCl$_3$) δ: 1.45 (9H, s), 1.77 (2H, m), 3.23 (2H, m), 3.42 (2H, m), 4.89 (1H, br), 5.36 (1H, br), 6.10 (1H, s), 6.90 (1H, m), 7.02 (1H, m), 7.24 (1H, s), 7.42 (2H, d, J=8.8 Hz), 7.49 (1H, m), 7.59 (2H, d, J=8.8 Hz), 7.95 (1H, s). MSm/z: 586 (M$^+$+H).

Example 173

N-[5-Chloro-4-[(4-chlorophenylsulfonyl)-(2,5-difluorophenyl)methyl]pyridin-2-yl]propane-1,3-diamine dihydrochloride

[Chemical formula 53]

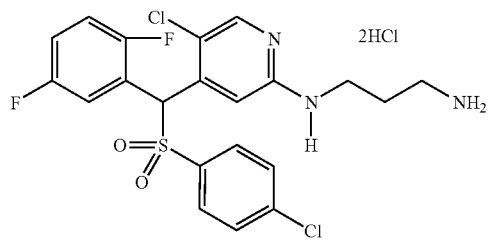

To t-butyl 3-[[5-chloro-4-[(4-chlorophenylsulfonyl)-(2,5-difluorophenyl)methyl]pyridin-2-yl]amino]propylcarbamate (70 mg, 0.13 mmol) was added a 20% hydrochloric acid-methanol solution (2 ml). The resulting mixture was stirred for 2 hours. The residue obtained by concentrating the reaction mixture under reduced pressure was crystallized from ethanol to give the title compound as a white solid (42 mg, 83%).

$^1$H-NMR (400 MHz, DMSO-d$_6$) δ: 1.83 (2H, m), 2.87 (2H, m), 3.33 (2H, m), 6.16 (1H, s), 7.28 (1H, m), 7.36 (1H, s), 7.38 (1H, m), 7.52 (1H, m), 7.69 (2H, d, J=8.4 Hz), 7.74 (2H, d, J=8.4 Hz), 8.05 (1H, s).

mp: 193 to 195° C.

Elemental Analysis for C$_{21}$H$_{19}$Cl$_2$F$_2$N$_3$O$_2$S$_2$HCl: Calculated: C, 45.10; H, 3.78; N, 7.51; S, 5.73; Cl, 25.36; F, 6.79. Found: C, 44.55; H, 3.74; N, 7.52; S, 5.73; Cl, 25.09; F, 6.73.

Example 174

N-[3-[[5-Chloro-4-[(4-chlorophenylsulfonyl)-(2,5-difluorophenyl)methyl]pyridin-2-yl]amino]propyl]acetamide

[Chemical formula 54]

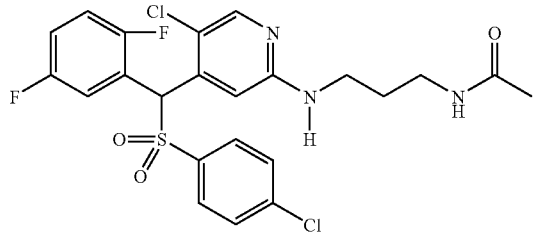

To a methylene chloride solution (5.0 ml) of N-[5-chloro-4-[(4-chlorophenylsulfonyl)-(2,5-difluorophenyl)methyl]pyridin-2-yl]propane-1,3-diamine dihydrochloride (47 mg, 0.084 mmol) were added pyridine (17 µl, 0.34 mmol) and acetic anhydride (9.5 µl, 0.10 mmol). The resulting mixture was stirred for 1 hour. The residue obtained by concentrating the reaction mixture was purified by silica gel chromatography (ethyl acetate:methanol=10:1) to give the title compound (35 mg, 79%). The compound was crystallized in ether to afford a white solid (27 mg).

$^1$H-NMR (400 MHz, CDCl$_3$) δ: 1.80 (2H, m), 2.02 (3H, s), 3.36 (2H, m), 3.45 (2H, m), 5.25 (1H, br), 6.12 (1H, s), 6.15 (1H, m), 6.93 (1H, m), 7.04 (1H, m), 7.44 (2H, d, J=8.8 Hz), 7.50 (1H, m), 7.62 (2H, d, J=8.8 Hz), 7.97 (1H, s).

mp: 103 to 105° C.

FAB-MS: 528.0740 (Calcd for C$_{23}$H$_{22}$Cl$_2$F$_2$N$_3$O$_3$S: 528.0727).

Example 175

N-[5-Chloro-4-[(4-chlorophenylsulfonyl)-(2,5-difluorophenyl)methyl]pyridin-2-yl]-N'-(pyrimidin-2-yl)propane-1,3-diamine

[Chemical formula 55]

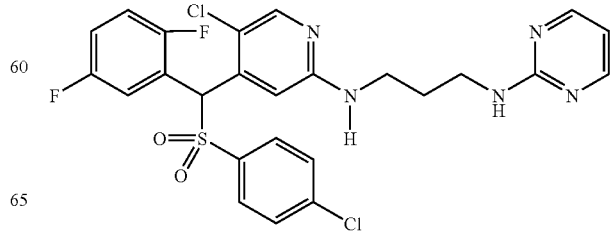

To a 1,4-dioxane solution (1.0 ml) of the N-[5-chloro-4-[(4-chlorophenylsulfonyl)-(2,5-difluorophenyl)methyl]pyridin-2-yl]propane-1,3-diamine dihydrochloride (76 mg, 0.136 mmol) obtained in Example 173 were added triethylamine (76 μl, 0.54 mmol) and 2-chloropyrimidine (23 mg, 0.20 mmol). The resulting mixture was stirred at 80° C. for 19 hours. The reaction mixture was allowed to cool to room temperature, followed by dilution with ethyl acetate. The diluted mixture was washed with water and brine, dried and concentrated. The residue thus obtained was purified by silica gel chromatography (hexane:ethyl acetate=1:2) to give the title compound (50 mg, 65%). The compound was crystallized in ethanol to afford a white solid (36 mg).

$^1$H-NMR (400 MHz, CDCl$_3$) δ: 1.94 (2H, m), 3.48 (2H, m), 3.59 (2H, m), 5.33 (1H, br), 5.60 (1H, br), 6.12 (1H, s), 6.56 (1H, t, J=4.8 Hz), 6.92 (1H, m), 7.03 (1H, m), 7.24 (1H, s), 7.44 (2H, d, J=8.0 Hz), 7.51 (1H, m), 7.61 (2H, d, J=8.0 Hz), 8.00 (1H, s), 8.32 (1H, d, J=4.8 Hz).

mp: 176 to 178° C.

FAB-MS: 564.0811 (Calcd for C$_{25}$H$_{22}$Cl$_2$F$_2$N$_5$O$_2$S: 564.0839).

Example 176

5-Chloro-4-[(4-chlorophenylsulfonyl)-(2,5-difluorophenyl)methyl]-2-[(2-methylsulfonylethyl)amino]pyridine

[Chemical formula 56]

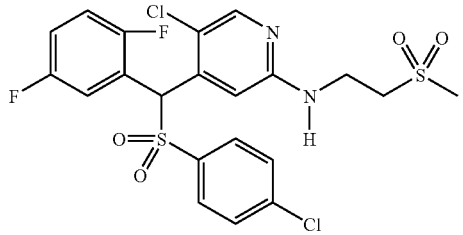

To a methanol (3 ml) solution of the 5-chloro-4-[(4-chlorophenylthio)-(2,5-difluorophenyl)methyl]-2-[(2-methylthioethyl)amino]pyridine (29 mg, 0.061 mmol) obtained in Example 163 was added hexaammonium heptamolybdate tetrahydrate (15 mg), followed by further addition of 30% aqueous hydrogen peroxide (1.5 ml). The resulting mixture was stirred for 20 hours. After dilution with ethyl acetate (80 ml), the diluted mixture was washed with water and brine, and concentrated under reduced pressure. The residue thus obtained was purified by silica gel chromatography (hexane:ethyl acetate=1:1), followed by crystallization from ether to give the title compound (24 mg, 73%) as a white solid.

$^1$H-NMR (400 MHz, CDCl$_3$) δ: 2.98 (3H, s), 3.37 (2H, t, J=6.0 Hz), 3.94 (2H, m), 5.38 (1H, m), 6.10 (1H, s), 6.90 (1H, m), 7.01 (1H, m), 7.32 (1H, s), 7.42 (2H, d, J=8.8 Hz), 7.45 (1H, m), 7.59 (2H, d, J=8.8 Hz), 8.00 (1H, s).

mp: 134 to 136° C.

Elemental Analysis for C$_{21}$H$_{18}$Cl$_2$F$_2$N$_2$O$_4$S: Calculated: C, 47.11; H, 3.39; N, 5.23; S, 11.98. Found: C, 46.80; H, 3.35; N, 5.30; S, 11.84.

Example 177

2,5-Dichloro-4-[(2,5-difluorophenyl)-(4-fluorophenylthio)methyl]pyridine

[Chemical formula 57]

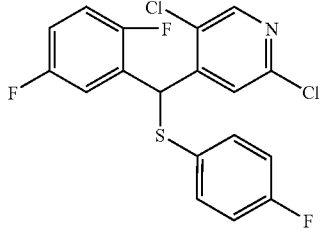

The 2,5-dichloro-4-[(2,5-difluorophenyl)-hydroxymethyl]pyridine (1.22 g, 4.8 mmol) obtained in Referential Example 24 was dissolved in thionyl chloride (5.0 ml). To the resulting solution was added a catalytic amount of dimethylformamide. The resulting mixture was stirred for 4 hours.

The reaction mixture was concentrated under reduced pressure. To the residue thus obtained was added 1,4-dioxane, followed by further concentration. The residue was dissolved in dimethylformamide (10 ml). To the resulting solution were added 4-fluorobenzenethiol (730 mg, 5.7 mmol) and potassium carbonate (2.07 g, 15 mmol). Under a nitrogen atmosphere, the resulting solution was stirred at room temperature for 24 hours. To the reaction mixture was added diethyl ether (120 ml). The resulting mixture was washed with water and brine. The organic layer was dried over magnesium sulfate, and concentrated under reduced pressure. The residue was crystallized in ethanol to give the title compound (950 mg, 49%) as colorless needle crystals.

$^1$H-NMR (400 MHz, CDCl$_3$) δ: 5.92 (1H, s), 6.94-7.04 (4H, m), 7.19 (1H, m), 7.33-7.4 (2H, m), 7.57 (1H, s), 8.33 (1H, s).

mp: 95 to 97° C.

MSm/z: 400 (M$^+$+1)

Example 178

2-[[5-Chloro-4-[(2,5-difluorophenyl)-(4-fluorophenylthio)methyl]pyridin-2-yl]amino]ethanol

[Chemical formula 58]

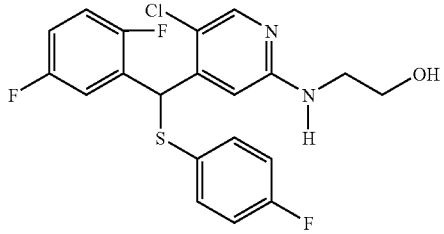

A 1,4-dioxane (1.5 ml) solution of 2,5-dichloro-4-[(2,5-difluorophenyl)-(4-fluorophenylthio)methyl]pyridine (200 mg, 0.50 mmol) and 2-aminoethanol (300 μl) was stirred at 120° C. for 2 days under an argon atmosphere. After cooling to room temperature, the reaction mixture was concentrated under reduced pressure. The residue was purified by silica gel chromatography (hexane:ethyl acetate=1:1) to give the title compound (120 mg, 56%) as an oil.

$^1$H-NMR (400 MHz, CDCl$_3$) δ: 3.53 (2H, m), 3.82 (2H, m), 4.95 (1H, br), 5.89 (1H, s), 6.74 (1H, s), 6.90-7.00 (4H, m), 7.16 (1H, m), 7.31-7.36 (2H, m), 7.99 (1H, s).

MSm/z: 425 (M$^+$+H).

Example 179

2-[[5-Chloro-4-[(2,5-difluorophenyl)-(4-fluorophenylsulfonyl)methyl]pyridin-2-yl]amino]ethanol

[Chemical formula 59]

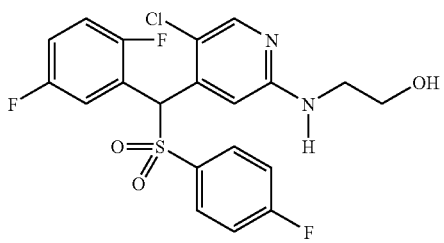

To a methanol (6 ml) solution of the 2-[[5-chloro-4-[(2,5-difluorophenyl)-(4-fluorophenylthio)methyl]pyridin-2-yl]amino]ethanol (119 mg, 0.27 mmol) was added hexaammonium heptamolybdate tetrahydrate (30 mg), followed by further addition of 30% aqueous hydrogen peroxide (3 ml). The resulting mixture was stirred for 19 hours. After dilution with ethyl acetate (80 ml), the diluted mixture was washed with water and brine, and concentrated under reduced pressure. The residue thus obtained was purified by silica gel chromatography (hexane:ethyl acetate=1:1) and crystallized from ethanol to give the title compound (65 mg, 56%) as needle crystals.

$^1$H-NMR (400 MHz, CDCl$_3$) δ: 3.61 (2H, m), 3.88 (2H, d, J=4.8 Hz), 6.09 (1H, s), 6.90 (1H, m), 7.04 (1H, m), 7.10-7.18 (2H, m), 7.42 (1H, s), 7.49 (1H, m), 7.66-7.71 (2H, m), 7.95 (1H, s).

mp: 157 to 158° C.

Elemental Analysis for C$_{20}$H$_{16}$ClF$_3$N$_2$O$_3$S: Calculated: C, 52.58; H, 3.53; N, 6.13; S, 7.02; Cl, 7.76; F, 12.48. Found: C, 52.18; H, 3.51; N, 6.19; S, 7.10; Cl, 7.82; F, 12.38.

Example 180

5-Chloro-4-[(4-chlorophenylthio)(2,5-difluorophenyl)methyl]-2-[2-(pyridin-4-yl)ethylamino]pyridine

[Chemical formula 60]

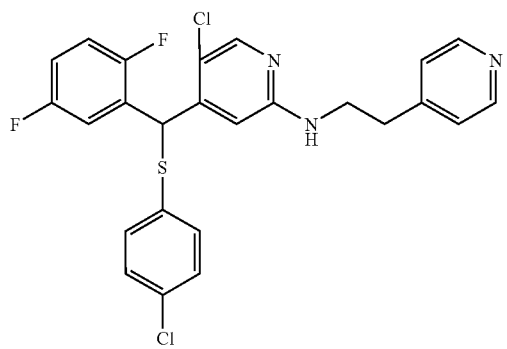

A dioxane (1.5 ml) solution of the 2,5-dichloro-4-[(4-chlorophenylthio)(2,5-difluorophenyl)methyl]pyridine (220 mg, 0.528 mmol) obtained in Example 54 and 4-(2-aminoethyl)pyridine (400 μl) was heated at 120° C. for 3 days in a sealed tube. The reaction mixture was cooled to room temperature and then, concentrated under reduced pressure. Water was added to the residue thus obtained, followed by extraction with ethyl acetate. The organic layer was washed with brine, dried over anhydrous sodium sulfate, and filtered. The filtrate was concentrated under reduced pressure. The residue thus obtained was subjected to silica gel column chromatography. The fraction obtained from the methanol:methylene chloride=1:30 eluate was concentrated under reduced pressure to give the title compound (114 mg, 0.227 mmol, 43%) as a colorless oil.

$^1$H-NMR (400 MHz, CDCl$_3$) δ: 2.90 (2H, t, J=7.1 Hz), 3.54-3.65 (2H, m), 4.70-4.81 (1H, m), 5.96 (1H, s), 6.64 (1H, s), 6.90-7.03 (2H, m), 7.05-7.16 (3H, m), 7.22 (4H, s), 8.03 (1H, s), 8.53 (2H, d, J=6.1 Hz).

MS m/z: 501 (M+).

Example 181

5-Chloro-4-[(4-chlorophenylsulfonyl)(2,5-difluorophenyl)methyl]-2-[2-(pyridin-4-yl)ethylamino]pyridine

[Chemical formula 61]

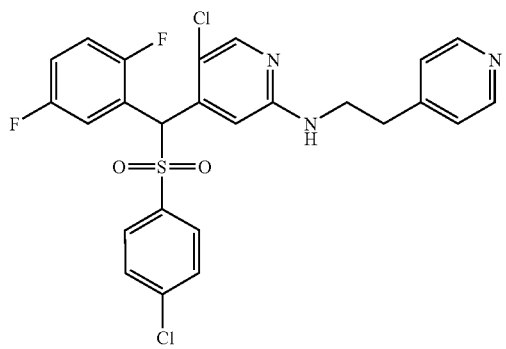

To a methanol (6 ml) solution of 5-chloro-4-[(4-chlorophenylthio)(2,5-difluorophenyl)methyl]-2-[2-(pyridin-4-yl)ethylamino]pyridine (110 mg, 0.219 mmol) were added 30% aqueous hydrogen peroxide (3 ml) and hexaammonium heptamolybdate tetrahydrate (34 mg) under ice cooling. After the reaction mixture was stirred at room temperature for 22 hours, methanol was distilled off under reduced pressure. To the residue thus obtained was added ethyl acetate. The resulting mixture was washed sequentially with saturated sodium bicarbonate, an aqueous solution of sodium thiosulfate and brine, dried over anhydrous sodium sulfate and filtered. The filtrate was concentrated under reduced pressure. The residue thus obtained was subjected to silica gel column chromatography. The fraction obtained from the hexane:ethyl acetate=2:3 eluate was concentrated under reduced pressure to give the title compound (102 mg, 0.191 mmol, 87%) as a pale yellowish white solid. The resulting solid was washed with diisopropyl ether-hexane and collected by filtration to afford the title compound (87 mg) as a white powder.

$^1$H-NMR (400 MHz, CDCl$_3$) δ: 2.96 (2H, t, J=7.1 Hz), 3.68 (2H, q, J=6.8 Hz), 4.72 (1H, t, J=6.1 Hz), 6.12 (1H, s), 6.89-6.96 (1H, m), 6.98-7.08 (1H, m), 7.20 (2H, d, J=5.9 Hz), 7.24 (1H, s), 7.40-7.50 (3H, m), 7.60 (2H, d, J=8.6 Hz), 8.03 (1H, s), 8.56 (2H, d, J=5.9 Hz).

mp: 148 to 150° C.

Elemental Analysis for C$_{25}$H$_{19}$N$_3$O$_2$Cl$_2$F$_2$S: Calculated: C, 56.19; H, 3.58; N, 7.86; Cl, 13.27; F, 7.11; S, 6.00. Found: C, 56.01; H, 3.57; N, 7.93; Cl, 13.27; F, 7.04; S, 6.16.

Example 182

2-[2-[5-Chloro-4-[(4-chlorophenylthio)(2,5-difluorophenyl)methyl]pyridin-2-ylamino]ethoxy]ethanol

[Chemical formula 62]

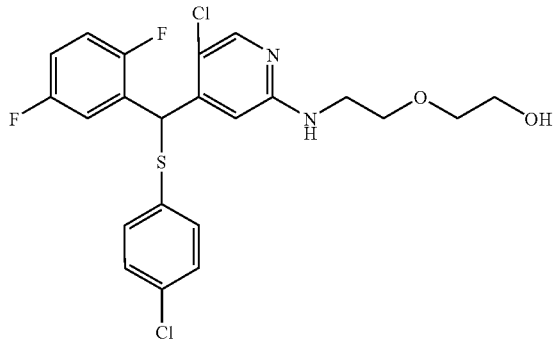

A dioxane (1.5 ml) solution of the 2,5-dichloro-4-[(4-chlorophenylthio)(2,5-difluorophenyl)methyl]pyridine (210 mg, 0.504 mmol) obtained in Example 54 and 2-(2-aminoethoxy)ethanol (400 µl) was heated at 120° C. for 3 days in a sealed tube. The reaction mixture was cooled to room temperature and then, concentrated under reduced pressure. Water was added to the residue thus obtained, followed by extraction with ethyl acetate. The organic layer was washed with brine, dried over anhydrous sodium sulfate, and filtered. The filtrate was concentrated under reduced pressure. The residue thus obtained was subjected to silica gel column chromatography. The fraction obtained from the 30% methanol/methylene chloride eluate was concentrated under reduced pressure to give the title compound (85 mg, 0.175 mmol, 35%) as a colorless oil.

$^1$H-NMR (400 MHz, CDCl$_3$) δ: 2.11 (1H, brs), 3.53 (2H, q, J=5.3 Hz), 3.61 (2H, t, J=4.4 Hz), 3.70 (2H, t, J=5.1 Hz), 3.72-3.80 (2H, m), 4.95 (1H, t, J=5.6 Hz), 5.97 (1H, s), 6.71 (1H, s), 6.80-7.03 (2H, s), 7.08-7.17 (1H, m), 7.18-7.30 (4H, m), 8.03 (1H, s).

MS (m/z): 484 (M$^+$).

Example 183

2-[2-[5-Chloro-4-[(4-chlorophenylsulfonyl)(2,5-difluorophenyl)methyl]pyridin-2-ylamino]ethoxy]ethanol

[Chemical formula 63]

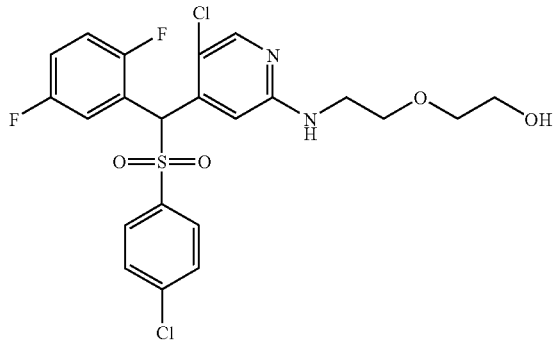

To a methanol (6 ml) solution of 2-[2-[5-chloro-4-[(4-chlorophenylthio)(2,5-difluorophenyl)methyl]pyridin-2-ylamino]ethoxy]ethanol (80 mg, 0.155 mmol) were added 30% aqueous hydrogen peroxide (3 ml) and hexaammonium heptamolybdate tetrahydrate (32 mg) under ice cooling. After the resulting mixture was stirred at room temperature for 24 hours, methanol was distilled off under reduced pressure. To the residue was added ethyl acetate. The resulting mixture was washed sequentially with saturated sodium bicarbonate, an aqueous solution of sodium thiosulfate and brine, dried over anhydrous sodium sulfate and filtered. The filtrate was concentrated under reduced pressure. The residue thus obtained was subjected to silica gel column chromatography. The fraction obtained from the hexane:ethyl acetate=2:3 eluate was concentrated under reduced pressure to give the title compound (70 mg, 0.135 mmol, 87%) as an amorphous substance. The resulting amorphous substance was solidified with ether-hexane, followed by filtration to afford the title compound (55 mg) as a white powder.

$^1$H-NMR (400 MHz, CDCl$_3$) δ: 2.11 (1H, brs), 3.55-3.63 (2H, m), 3.66 (2H, t, J=4.5 Hz), 3.74 (2H, t, J=5.1 Hz), 3.78-3.85 (2H, m), 5.03-5.13 (1H, m), 6.13 (1H, s), 6.89-6.97 (1H, m), 6.98-7.08 (1H, m), 7.30 (1H, s), 7.45 (2H, d, J=8.5 Hz), 7.48-7.56 (1H, m), 7.62 (2H, d, J=8.5 Hz), 8.00 (1H, s). mp: 113 to 115° C.

Elemental Analysis for C$_{22}$H$_{20}$N$_2$O$_4$Cl$_2$F$_2$S: Calculated: C, 51.07; H, 3.90; N, 5.41; Cl, 13.70; F, 7.34; S, 6.20. Found: C, 50.81; H, 3.83; N, 5.49; Cl, 13.64; F, 7.46; S, 6.34.

Example 184

5-Chloro-4-[(4-chlorophenylthio)(2,5-difluorophenyl)methyl]-2-[(3-methoxypropyl)amino]pyridine

[Chemical formula 64]

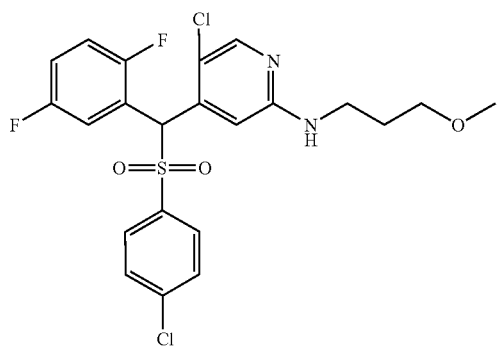

A dioxane (1.5 ml) solution of the 2,5-dichloro-4-[(4-chlorophenylthio)(2,5-difluorophenyl)methyl]pyridine (216 mg, 0.518 mmol) obtained in Example 54 and 3-methoxypropylamine (200 µl) was heated at 120° C. for 3 days in a sealed tube. The reaction mixture was cooled to room temperature, and then concentrated under reduced pressure. The residue thus obtained was subjected to silica gel column chromatography. The fraction obtained from the hexane:ethyl acetate (=3:1) eluate was concentrated under reduced pressure to give a pale yellow oil (101 mg).

To a methanol (6 ml) solution of the resulting pale yellow oil (101 mg) were added 30% aqueous hydrogen peroxide (3 ml) and hexaammonium heptamolybdate tetrahydrate (41 mg) under ice cooling. After the reaction mixture was stirred at room temperature for 16 hours, methanol was distilled off under reduced pressure. To the residue thus obtained was added ethyl acetate. The resulting mixture was washed sequentially with saturated sodium bicarbonate, an aqueous solution of sodium thiosulfate and brine, dried over anhydrous sodium sulfate and filtered. The filtrate was concentrated under reduced pressure. The residue thus obtained was subjected to silica gel column chromatography. The fraction obtained from the hexane:ethyl acetate=3:1 eluate was concentrated under reduced pressure to give the title compound (90 mg, 0.180 mmol, 35%) as a white solid. The solid thus obtained was washed with ether-hexane and collected by filtration to afford the title compound (64 mg) as a white powder.

¹H-NMR (400 MHz, CDCl₃) δ: 1.87-1.98 (2H, m), 3.39 (3H, s), 3.46 (2H, q, J=6.1 Hz), 3.55 (2H, t, J=5.8 Hz), 5.09 (1H, brt, J=5.3 Hz), 6.13 (1H, s), 6.88-6.96 (1H, m), 6.98-7.08 (1H, m), 7.20 (1H, s), 7.43 (2H, d, J=8.7 Hz), 7.50-7.57 (1H, m), 7.62 (2H, d, J=8.7 Hz), 7.98 (1H, s).

mp: 146 to 148° C.

Elemental Analysis for $C_{22}H_{20}N_2O_3Cl_2F_2S$: Calculated: C, 52.70; H, 4.02; N, 5.59; Cl, 14.14; F, 7.58; S, 6.40. Found: C, 52.72; H, 3.95; N, 5.78; Cl, 14.14; F, 7.75; S, 6.54.

Example 185

5-Chloro-4-[(4-chlorophenylthio)(2,5-difluorophenyl)methyl]-2-(3,4-dimethoxybenzylamino)pyridine

[Chemical formula 65]

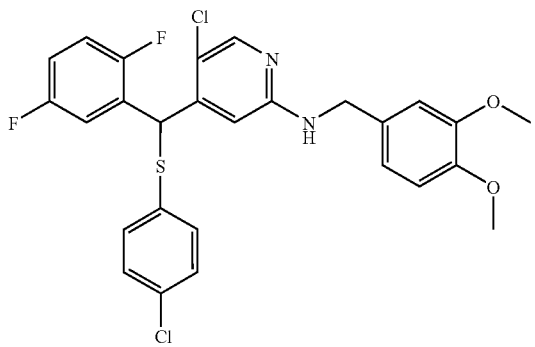

A dioxane (1.5 ml) solution of the 2,5-dichloro-4-[(4-chlorophenylthio)(2,5-difluorophenyl)methyl]pyridine (218 mg, 0.523 mmol) obtained in Example 54 and 3,4-dimethoxybenzylamine (400 μl) was heated at 120° C. for 3 days in a sealed tube. The reaction mixture was cooled to room temperature and then, concentrated under reduced pressure. The residue thus obtained was subjected to silica gel column chromatography. The fraction obtained from the hexane:ethyl acetate=4:1 eluate was concentrated under reduced pressure to give the title compound (140 mg, 0.256 mmol, 49%) as an amorphous substance.

¹H-NMR (400 MHz, CDCl₃) δ: 3.86 (3H, s), 3.88 (3H, s), 4.42 (2H, d, J=5.6 Hz), 4.99 (1H, t, J=5.6 Hz), 5.95 (1H, s), 6.68 (1H, s), 6.80-7.02 (6H, m), 7.12-7.21 (4H, m), 8.05 (1H, s).

MSm/z: 547 (M⁺+H).

Example 186

5-Chloro-4-[(4-chlorophenylsulfonyl)(2,5-difluorophenyl)methyl]-2-(3,4-dimethoxybenzylamino)pyridine

[Chemical formula 66]

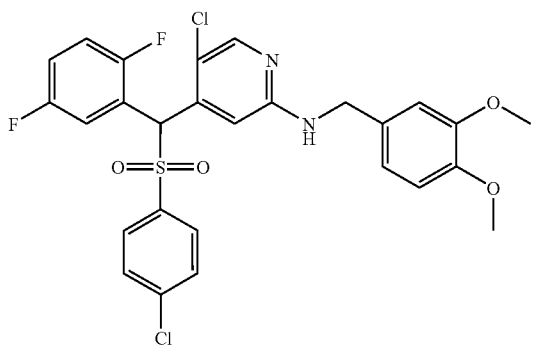

To a methanol (6 ml) solution of 5-chloro-4-[(4-chlorophenylthio)(2,5-difluorophenyl)methyl]-2-(3,4-dimethoxybenzylamino)pyridine (131 mg, 0.239 mmol) were added 30% aqueous hydrogen peroxide (3 ml) and hexaammonium heptamolybdate tetrahydrate (31 mg) under ice cooling. After the reaction mixture was stirred at room temperature for 16 hours, methanol was distilled off under reduced pressure. Ethyl acetate was added to the residue thus obtained. The resulting mixture was washed sequentially with saturated sodium bicarbonate, an aqueous solution of sodium thiosulfate and brine, dried over anhydrous sodium sulfate and filtered. The filtrate was concentrated under reduced pressure. The residue thus obtained was subjected to flash silica gel column chromatography. The fraction obtained from the 35% ethyl acetate/hexane eluate was concentrated under reduced pressure to give the title compound (75 mg, 0.129 mmol, 54%) as a white solid. The resulting white solid was washed with ether-hexane, and filtered to give the title compound as a white powder.

¹H-NMR (400 MHz, CDCl₃) δ: 3.89 (6H, s), 4.48-4.51 (2H, m), 5.08-5.15 (1H, m), 6.12 (1H, s), 6.85-7.05 (5H, m), 7.24 (1H, s), 7.28-7.35 (1H, m), 7.40 (2H, d, J=8.5 Hz), 7.55 (2H, d, J=8.5 Hz), 8.01 (1H, s).

mp: 204 to 206° C.

Elemental Analysis for $C_{27}H_{22}N_2O_4Cl_2F_2S$: Calculated: C, 55.97; H, 3.83; N, 4.83; Cl, 12.24; F, 6.56; S, 5.53. Found: C, 56.05; H, 3.82; N, 4.87; Cl, 12.30; F, 6.60; S, 5.73.

Example 187

5-Chloro-4-[(4-chlorophenylthio)(2,5-difluorophenyl)methyl]-2-[(pyridin-4-ylmethyl)amino]pyridine

[Chemical formula 67]

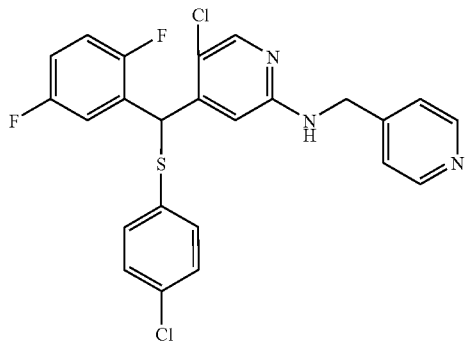

A dioxane (1.5 ml) solution of the 2,5-dichloro-4-[(4-chlorophenylthio)(2,5-difluorophenyl)methyl]pyridine (229 mg, 0.550 mmol) obtained in Example 54 and 4-aminomethylpyridine (200 μl) was heated at 120° C. for 3 days in a sealed tube. The reaction mixture was cooled to room temperature and then concentrated under reduced pressure. The residue thus obtained was subjected to silica gel column chromatography. The fraction obtained from the hexane:ethyl acetate=1:3 eluate was concentrated under reduced pressure to give the title compound (37 mg, 0.076 mmol, 14%) as an amorphous substance.

¹H-NMR (400 MHz, CDCl₃) δ: 4.55 (2H, d, J=6.1 Hz), 5.06 (1H, t, J=6.0 Hz), 5.94 (1H, s), 6.61 (1H, s), 6.90-7.09 (3H, m), 7.13-7.30 (6H, m), 8.05 (1H, s), 8.55 (2H, d, J=6.1 Hz).

MSm/z: 488 (M⁺+H).

Example 188

5-Chloro-4-[(4-chlorophenylsulfonyl)(2,5-difluorophenyl)methyl]-2-[(pyridin-4-ylmethyl)amino]pyridine

[Chemical formula 68]

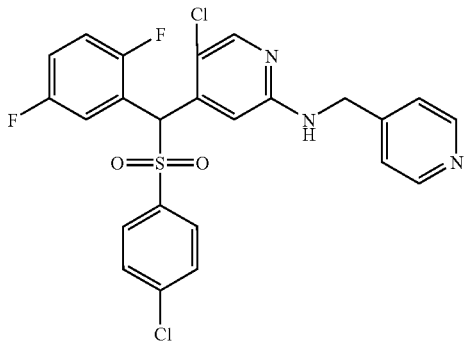

To a methanol (2 ml) solution of 5-chloro-4-[(4-chlorophenylthio)(2,5-difluorophenyl)methyl]-2-[(pyridin-4-ylmethyl)amino]pyridine (35 mg, 0.072 mmol) were added 30% aqueous hydrogen peroxide (3 ml) and hexaammonium heptamolybdate tetrahydrate (23 mg) under ice cooling After the reaction mixture was stirred at room temperature for 22 hours, methanol was distilled off under reduced pressure. Ethyl acetate was added the residue. The resulting mixture was washed sequentially with saturated sodium bicarbonate, an aqueous solution of sodium thiosulfate and brine, dried over anhydrous sodium sulfate and filtered. The filtrate was concentrated under reduced pressure. The residue thus obtained was subjected to silica gel column chromatography. The fraction obtained from the methanol:methylene chloride=1:30 eluate was concentrated under reduced pressure to give a pale yellow solid. The resulting pale yellow solid was washed with ether-hexane and filtered to give the title compound (16 mg, 0.031 mmol, 43%) as a white powder.

$^1$H-NMR (400 MHz, CDCl$_3$) δ: 4.63 (2H, dd, J=6.1, 2.9 Hz), 5.20 (1H, t, J=6.4 Hz), 6.11 (1H, s), 6.87-6.95 (1H, m), 6.99-7.08 (1H, m), 7.25 (1H, s), 7.30 (2H, d, J=6.0 Hz), 7.35-7.40 (1H, m), 7.42 (2H, d, J=8.9 Hz), 7.56 (2H, d, J=8.9 Hz), 8.02 (1H, s), 8.59 (2H, d, J=6.0 Hz).

mp: 141 to 142° C.

FAB-MS: 520.0465 (Calcd for C$_{24}$H$_{18}$O$_2$N$_3$Cl$_2$F$_2$S: 520.0461).

Example 189

N-[3-[[5-Chloro-4-[(4-chlorophenylsulfonyl)-(2,5-difluorophenyl)methyl]pyridin-2-yl]amino]propyl]methanesulfonamide

[Chemical formula 69]

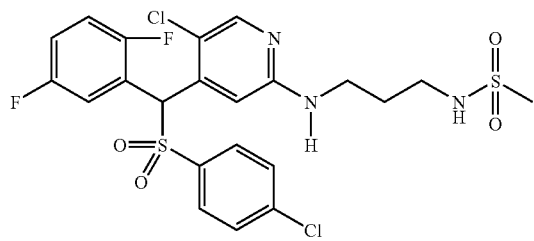

To a methylene chloride solution (5.0 ml) of the N-[5-chloro-4-[(4-chlorophenylsulfonyl)-(2,5-difluorophenyl)methyl]pyridin-2-yl]propane-1,3-diamine dihydrochloride (60 mg, 0.107 mmol) obtained in Example 173 were added triethylamine (70 μl, 0.05 mmol) and methanesulfonyl chloride (10 μl, 0.13 mmol). The resulting mixture was stirred for 20 minutes. To the reaction mixture was added ether (50 ml). The resulting mixture was washed with water and brine, dried and concentrated under reduced pressure. The residue thus obtained was purified by silica gel chromatography (hexane:ethyl acetate=2:1) to give the title compound (60 mg, 99%). The resulting compound was crystallized in ethanol to afford a white solid (46 mg).

$^1$H-NMR (40 MHz, CDCl$_3$) δ: 1.86 (2H, quint, J=6.0 Hz), 2.95 (3H, s), 3.21 (2H, q, J=6.0 Hz), 3.55 (2H, q, J=6.0 Hz), 4.99 (1H, br), 5.65 (1H, br), 6.11 (1H, s), 6.91 (1H, m), 7.03 (1H, m), 7.29 (1H, s), 7.44 (2H, d, J=8.8 Hz), 7.49 (1H, m), 7.60 (2H, d, J=8.8 Hz), 8.00 (1H, s).

mp: 138 to 139° C.

Elemental Analysis for C$_{22}$H$_{21}$Cl$_2$F$_2$N$_3$O$_4$S$_2$: Calculated: C, 46.81; H, 3.75; N, 7.44; S, 11.36; F, 6.73; Cl, 12.56. Found: C, 46.81; H, 3.72; N, 7.43; S, 11.39; F, 6.80; Cl, 12.41.

Example 190

1-[5-Chloro-4-[(4-chlorophenylsulfonyl)-(2,5-difluorophenyl)methyl]pyridin-2-yl]tetrahydropyrimidin-2-one

[Chemical formula 70]

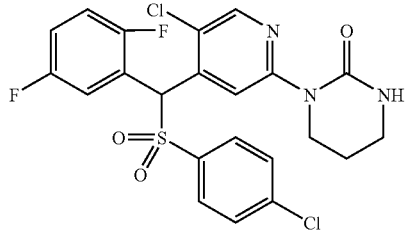

To a methylene chloride solution (5.0 ml) of the N-[5-chloro-4-[(4-chlorophenylsulfonyl)-(2,5-difluorophenyl)methyl]pyridin-2-yl]propane-1,3-diamine dihydrochloride (51 mg, 0.091 mmol) obtained in Example 173 were added triethylamine (51 μl, 0.36 mmol) and 1,1'-carbonyldiimidazole (16.2 mg, 0.10 mmol). The resulting mixture was stirred for 17 hours. To the reaction mixture was added ethyl acetate (80 ml). The resulting mixture was washed with water and brine, dried and concentrated under reduced pressure. The residue thus obtained was dissolved in dimethylformamide (1.0 ml). To the resulting solution was added potassium carbonate (27.2 mg, 0.2 mol), followed by stirring under heat at 50° C. for 24 hours. After cooling to room temperature, water was added to the reaction mixture. The resulting mixture was diluted with ethyl acetate (60 ml). The organic layer obtained by separation was washed with brine, dried and concentrated under reduced pressure. The residue thus obtained was purified by silica gel chromatography (hexane:ethyl acetate=1:2) to give the title compound (15 mg, 99%) as a white solid.

$^1$H-NMR (400 MHz, CDCl$_3$) δ: 2.12 (2H, m), 3.46 (2H, m), 3.99 (2H, m), 5.22 (1H, br), 6.26 (1H, s), 6.96 (1H, m), 7.03 (1H, m), 7.43 (2H, d, J=8.8 Hz), 7.68 (1H, m), 7.76 (2H, d, J=8.8 Hz), 8.23 (1H, s), 8.93 (1H, s).

MS m/z: 512 (M$^+$+H).

mp: >230° C.

Example 191 t-Butyl 2-[[5-chloro-4-[(4-chlorophenylthio)-(2,5-difluorophenyl)methyl]pyridin-2-yl]amino]ethylcarbamate

[Chemical formula 71]

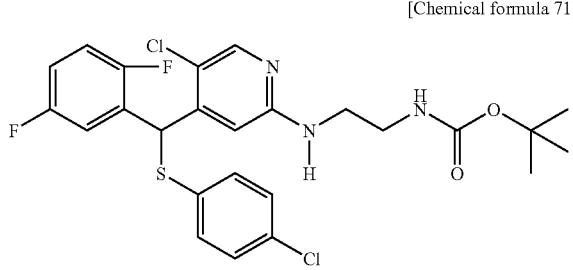

A 1,4-dioxane (6.0 ml) solution of the 2,5-dichloro-4-[(4-chlorophenylthio)-(2,5-difluorophenyl)methyl]pyridine (610 mg, 1.46 mmol) obtained in Example 54 and t-butyl(2-aminoethyl)carbamate (700 mg, 4.38 mmol) was stirred at 120° C. for 4 days under an argon atmosphere. After cooling to room temperature, the reaction mixture was concentrated under reduced pressure. The residue was purified by silica gel chromatography (hexane:ethyl acetate=4:1) to give the title compound (176 mg, 22%) as an oil.

$^1$H-NMR (400 MHz, CDCl$_3$) δ: 1.43 (9H, s), 3.36 (2H, m), 3.42 (2H, m), 5.01 (1H, br), 5.12 (1H, br), 5.95 (1H, s), 6.90-7.04 (2H, m), 7.13 (1H, m), 7.21 (2H, d, J=8.4 Hz), 7.23 (2H, d, J=8.4 Hz), 8.00 (1H, s).

MSm/z: 540 (M$^+$+H).

Example 192 t-Butyl 2-[[5-chloro-4-[(4-chlorophenylsulfonyl)-(2,5-difluorophenyl)methyl]pyridin-2-yl]amino]ethylcarbamate

[Chemical formula 72]

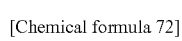

To a methanol (6 ml) solution of t-butyl 2-[[5-chloro-4-[(4-chlorophenylthio)-(2,5-difluorophenyl)methyl]pyridin-2-yl]amino]ethylcarbamate (176 mg, 0.32 mmol) was added hexaammonium heptamolybdate tetrahydrate (30 mg), followed by further addition of 30% aqueous hydrogen peroxide (3 ml). The resulting mixture was stirred for 20 hours. After the reaction mixture was diluted with ethyl acetate (80 ml), the diluted mixture was washed with water and brine, and concentrated under reduced pressure. The residue thus obtained was purified by silica gel chromatography (hexane:ethyl acetate=3:1) to give the title compound (148 mg, 81%) as an oil.

$^1$H-NMR (400 MHz, CDCl$_3$) δ: 1.45 (9H, s), 3.39 (2H, m), 3.49 (2H, m), 5.03 (1H, br), 5.29 (1H, br), 6.12 (1H, s), 6.91 (1H, m), 7.03 (1H, m), 7.24 (1H, s), 7.43 (2H, d, J=8.8 Hz), 7.52 (1H, m), 7.61 (2H, d, J=8.8 Hz), 7.98 (1H, s).

MSm/z: 572 (M$^+$+H).

Example 193

N-[5-Chloro-4-[(4-chlorophenylsulfonyl)-(2,5-difluorophenyl)methyl]pyridin-2-yl]ethane-1,2-diamine dihydrochloride

[Chemical formula 73]

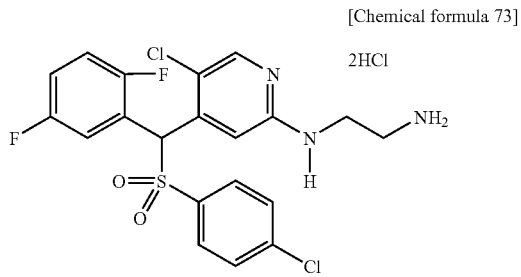

To t-butyl 2-[[5-chloro-4-[(4-chlorophenylsulfonyl)-(2,5-difluorophenyl)methyl]pyridin-2-yl]amino]ethylcarbamate (146 mg, 0.25 mmol) was added a 20% hydrochloric acid-methanol solution (1 ml). The resulting mixture was stirred for 1 hour. The residue obtained by concentrating the reaction mixture under reduced pressure was crystallized from ethanol to give the title compound (106 mg, 76%).

$^1$H-NMR (400 MHz, DMSO-d$_6$) δ: 2.99 (2H, m), 3.51 (2H, m), 6.17 (1H, s), 7.28 (1H, m), 7.38 (1H, m), 7.39 (1H, s), 7.52 (1H, m), 7.69 (2H, d, J=8.8 Hz), 7.75 (2H, d, J=8.8 Hz), 8.04 (1H, s).

mp: 163 to 166° C.

Elemental Analysis for C$_{20}$H$_{17}$Cl$_2$F$_2$N$_3$O$_2$S.2HCl.0.5H$_2$O: Calculated: C, 43.34; H, 3.64; N, 7.58; S, 5.78; Cl, 25.59; F, 6.86. Found: C, 43.32; H, 3.55; N, 7.67; S, 5.83; Cl, 25.84; F, 6.87.

Example 194

3-[5-Chloro-4-[(4-chlorophenylthio)(2,5-difluorophenyl)methyl]pyridin-2-ylamino]-2,2-dimethylpropan-1-ol

[Chemical formula 74]

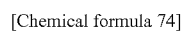

A dioxane (1.5 ml) solution of the 2,5-dichloro-4-[(4-chlorophenylthio)(2,5-difluorophenyl)methyl]pyridine (191 mg, 0.458 mmol) obtained in Example 54 and 3-amino-2,2-dimethylpropan-1-ol (515 mg, 5.00 mmol) was heated at 120° C. for 3 days in a sealed tube. The reaction mixture was cooled to room temperature and then, concentrated under reduced pressure. Ethyl acetate was added to the residue. The resulting mixture was washed sequentially with water and brine, dried over anhydrous sodium sulfate, and filtered. The filtrate was concentrated under reduced pressure. The residue thus obtained was subjected to silica gel column chromatography.

Example 195

3-[5-Chloro-4-[(4-chlorophenylsulfonyl)(2,5-difluorophenyl)methyl]pyridin-2-ylamino]-2,2-dimethylpropan-1-ol

[Chemical formula 75]

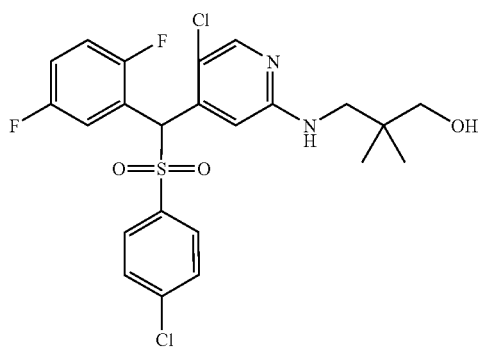

To a methanol (6 ml) solution of 3-[5-chloro-4-[(4-chlorophenylthio)(2,5-difluorophenyl)methyl]pyridin-2-ylamino]-2,2-dimethylpropan-1-ol (188 mg, 0.389 mmol) were added 30% aqueous hydrogen peroxide (3 ml) and hexaammonium heptamolybdate tetrahydrate (35 mg) under ice cooling. After the resulting mixture was stirred at room temperature for 13 hours, methanol was distilled off under reduced pressure. To the residue thus obtained was added ethyl acetate. The resulting mixture was washed sequentially with saturated sodium bicarbonate, an aqueous solution of sodium thiosulfate and brine, dried over anhydrous sodium sulfate, and filtered. The filtrate was concentrated under reduced pressure. The residue thus obtained was subjected to silica gel column chromatography. The fraction obtained from the hexane:ethyl acetate=3:1 eluate was concentrated under reduced pressure to give a white solid. The resulting white solid was solidified with ether-hexane, washed and collected by filtration to afford the title compound (156 mg, 0.303 mmol, 78%) as a white powder.

$^1$H-NMR (400 MHz, CDCl$_3$) δ: 0.94 (3H, s), 0.95 (3H, s), 3.20 (2H, d, J=6.6 Hz), 3.27 (2H, d, J=7.1 Hz), 4.68 (1H, brs), 4.94 (1H, t, J=6.9 Hz), 6.09 (1H, s), 6.86-6.95 (1H, m), 7.00-7.09 (1H, m), 7.29 (1H, s), 7.40-7.52 (3H, m), 7.60 (2H, d, J=8.6 Hz), 7.94 (1H, s).

mp: 176 to 178° C.

Elemental Analysis for C$_{23}$H$_{22}$N$_2$O$_3$Cl$_2$F$_2$S: Calculated: C, 53.60; H, 4.30; N, 5.44; Cl, 13.76; F, 7.37; S, 6.22. Found: C, 53.50; H, 4.26; N, 5.44; Cl, 13.78; F, 7.31; S, 6.30.

The fraction obtained from the hexane:ethyl acetate=3:1 eluate was concentrated under reduced pressure to give the title compound (199 mg, 0.412 mmol, 90%) as an amorphous substance.

$^1$H-NMR (400 MHz, CDCl$_3$) δ: 0.91 (6H, s), 3.12-3.28 (4H, m), 4.73 (1H, t, J=6.4 Hz), 4.87 (1H, brs), 5.92 (1H, s), 6.62 (1H, s), 6.92-7.07 (2H, m), 7.16-7.32 (5H, m), 7.96 (1H, m).

MSm/z: 483 (M$^+$+H).

Example 196

[5-Chloro-4-[(4-chlorophenylsulfonyl)(2,5-difluorophenyl)methyl]pyridin-2-yl]amine

[Chemical formula 76]

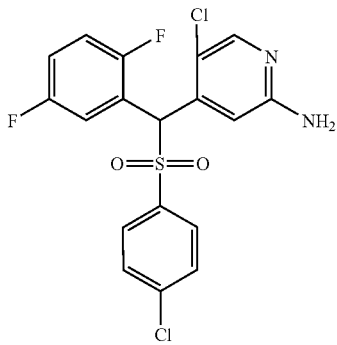

To an acetonitrile (4 ml)/water (1 ml) mixed solution of the 5-chloro-4-[(4-chlorophenylsulfonyl)(2,5-difluorophenyl)methyl]-2-(3,4-dimethoxybenzylamino)pyridine (43 mg, 0.074 mmol) obtained in Example 186 was added cerium (IV) diammonium nitrate (100 mg) under ice cooling. The resulting mixture was stirred for 1.5 hours. To the reaction mixture was added saturated sodium bicarbonate, followed by extraction with methylene chloride. The organic layer was dried over anhydrous sodium sulfate, and filtered. The filtrate was concentrated under reduced pressure. The residue thus obtained was purified by silica gel thin-layer chromatography (hexane:ethyl acetate=3:1) to give the title compound (12 mg, 0.028 mmol, 38%) as a pale yellowish white powder.

$^1$H-NMR (400 MHz, CDCl$_3$) δ: 4.65 (2H, brs), 6.13 (1H, s), 6.89-6.98 (1H, m), 7.00-7.09 (1H, m), 7.33 (1H, s), 7.44 (2H, d, J=8.8 Hz), 7.49-7.57 (1H, m), 7.62 (2H, d, J=8.8 Hz), 7.99 (1H, s).

mp: 147 to 150° C.

MSm/z: 429 (M$^+$+H).

Elemental Analysis for C$_{18}$H$_{12}$N$_2$O$_2$Cl$_2$F$_2$S: Calculated: C, 50.36; H, 2.82; N, 6.53; Cl, 16.52; F, 8.85; S, 7.47. Found: C, 50.46; H, 2.68; N, 6.63; Cl, 16.42; F, 9.00; S, 7.66.

Example 197

N-[5-Chloro-4-[(4-chlorophenylsulfonyl)(2,5-difluorophenyl)methyl]pyridin-2-yl]methanesulfonamide

[Chemical formula 77]

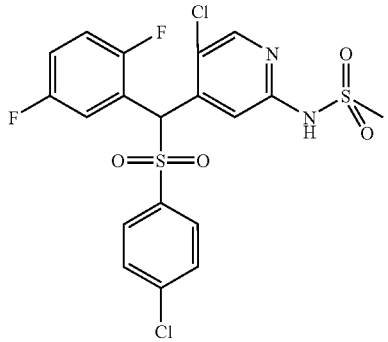

To a pyridine (2 ml) solution of the [5-chloro-4-[(4-chlorophenylsulfonyl)(2,5-difluorophenyl)methyl]pyridin-2-yl]amine (106 mg, 0.247 mmol) obtained in Example 196 was added methanesulfonyl chloride (29 μl, 0.370 mmol) under ice cooling. The resulting mixture was stirred at room temperature for 3 days and concentrated under reduced pressure. To the residue thus obtained was added ethyl acetate. The resulting mixture was washed sequentially with a saturated aqueous solution of sodium bicarbonate, water and brine, dried over anhydrous sodium sulfate, and filtered. The filtrate was concentrated under reduced pressure. The residue thus obtained was subjected to flash silica gel column chromatography. The fraction obtained from the hexane:ethyl acetate=3:1 eluate was concentrated under reduced pressure to give the title compound (58 mg, 0.114 mmol, 46%) as a white solid. The resulting white solid was washed with hexane-ether and collected by filtration to give the title compound (28 mg) as a white powder.

$^1$H-NMR (400 MHz, CDCl$_3$) δ: 3.35 (3H, s), 6.19 (1H, s), 6.90-6.99 (1H, m), 7.01-7.10 (1H, m), 7.42-7.53 (3H, m), 7.60-7.70 (3H, m), 7.97 (1H, s), 8.32 (1H, s).

mp: 220 to 222° C.

MSm/z: 507 (M$^+$+H).

FAB-MS: 506.9824 (cald for $C_{19}H_{15}O_4N_2Cl_2F_2S_2$: 506.9818).

Elemental Analysis for $C_{19}H_{14}N_2O_4Cl_2F_2S_2$: Calculated: C, 44.98; H, 2.78; N, 5.52; Cl, 13.98; F, 7.49; S, 12.64. Found: C, 45.35; H, 2.85; N, 5.63; Cl, 13.49; F, 7.34; S, 12.69.

Referential Example 35

5-Fluoropyridine-2-carbonitrile

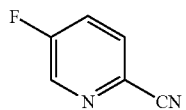

[Chemical formula 78]

To hydrogen fluoride-pyridine (100 ml) was added 5-amino-2-cyanopyridine (24.5 g, 0.206 mol) under ice cooling. The resulting mixture was stirred for 10 minutes. To the reaction mixture was added sodium nitrite (15.6 g, 0.226 mol). The resulting mixture was stirred at room temperature for 10 minutes, and then stirred at 50° C. for 2 hours. To the reaction mixture was added a 20% aqueous solution of sodium hydroxide. The resulting mixture was extracted with diethyl ether. The organic layer thus obtained was dried over sodium sulfate, and concentrated under reduced pressure. The residue thus obtained was subjected to silica gel column chromatography. The fraction obtained from the hexane:ethyl acetate=3:1 eluate was concentrated under reduced pressure to give the title compound (16.0 g, 0.131 mmol, 64%) as colorless needle crystals.

$^1$H-NMR (400 MHz, CDCl$_3$) δ: 7.57 (1H, ddd, J=8.6, 8.6, 3.1 Hz), 7.77 (1H, dd, J=8.6, 4.4 Hz), 8.60 (1H, d, J=3.1 Hz).

IR(ATR)cm$^{-1}$: 3095, 2237, 1577, 1467, 1409, 1375, 1272, 1240, 1197, 1120, 1010.

MSm/z: 122 (M$^+$).

EI-MS: 122.0293 (Calcd for $C_6H_3FN_2$: 122.0280).

Referential Example 36

2-(1,3-dioxolan-2-yl)-5-fluoropyridine

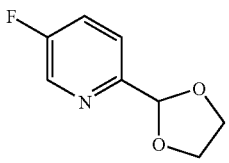

[Chemical formula 79]

Diisobutylaluminum hydride (a 1.01M hexane solution, 58 ml, 58.9 mmol) was added dropwise to a dichloromethane (150 ml) solution of 5-fluoropyridine-2-carbonitrile (6.54 g, 53.8 mmol) at −75° C. under an argon atmosphere. The reaction mixture was stirred for 3 hours. At the same temperature, hydrochloric acid (80 ml) (concentrated hydrochloric acid: water=1:3) was added, followed by heating to room temperature. From the reaction mixture, a dichloromethane layer was separated. To the water layer was then added sodium bicarbonate. The resulting mixture was extracted with diethyl ether. The organic layer thus obtained was dried over magnesium sulfate, and concentrated under reduced pressure. The dichloromethane layer obtained previously was washed with water, dried over magnesium sulfate, and concentrated under reduced pressure.

To a benzene (150 ml) solution of the combined residues were added p-toluenesulfonic acid monohydrate (1.02 g, 5.36 mmol) and ethylene glycol (30 ml, 0.536 mol). Under heating under reflux, the resulting mixture was stirred for 2 hours. After cooling, a saturated aqueous solution of sodium bicarbonate was added and the resulting mixture was extracted with diethyl ether. The extract was washed with brine. The organic layer thus obtained was dried over magnesium sulfate, and concentrated under reduced pressure. The residue thus obtained was subjected to flash silica gel column chromatography. The fraction obtained from the hexane:ethyl acetate=4:1 eluate was concentrated under reduced pressure to give the title compound (3.33 g, 19.7 mmol, 37%) as a reddish brown oil.

$^1$H-NMR (400 MHz, CDCl$_3$) δ: 4.02-4.21 (4H, m), 5.85 (1H, s), 7.45 (1H, ddd, J=8.3, 8.3, 2.9 Hz), 7.57 (1H, dd, J=8.3, 4.5 Hz), 8.48 (1H, d, J=2.9 Hz).

MSm/z: 170 (M$^+$+H)

Referential Example 37

4-[(2,5-Difluorophenyl)hydroxymethyl]-2-(1,3-dioxolan-2-yl)-5-fluoropyridine

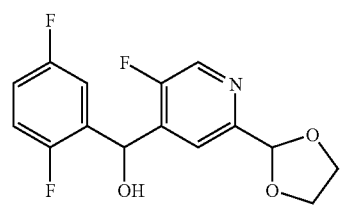

[Chemical formula 80]

Lithium diisopropylamide (a 1.8M heptane solution, 12 ml, 21.5 mmol) was added to a tetrahydrofuran (100 ml) solution of 2-(1,3-dioxolan-2-yl)-5-fluoropyridine (690 mg, 4.08 mmol) at −75° C. under an argon atmosphere. The resulting mixture was stirred for 2 hours. To the reaction mixture was added dropwise 2,5-difluorobenzaldehyde (2.1 ml, 19.5 mmol), followed by stirring for 2.5 hours. To the reaction mixture were added water and a saturated aqueous solution of sodium bicarbonate. The resulting mixture was extracted with diethyl ether. The extract was washed with brine. The organic layer thus obtained was dried over magnesium sulfate and concentrated under reduced pressure. The residue thus obtained was subjected to flash silica gel column chromatography. The fraction obtained from the hexane:ethyl acetate (=3:1) eluate was concentrated under reduced pressure to give the title compound (2.53 g, 8.03 mmol, 73%) as a white powder.

$^1$H-NMR (400 MHz, CDCl$_3$) δ: 2.65 (1H, d, J=4.6 Hz), 4.05-4.21 (4H, m), 5.84 (1H, s), 6.35 (1H, d, J=4.6 Hz), 6.96-7.05 (2H, m), 7.09-7.26 (1H, m), 7.76 (1H, d, J=5.9 Hz), 8.40 (1H, d, J=1.5 Hz).

MSm/z: 312 (M$^+$+H).

Example 198

4-[(4-Chlorophenylthio)(2,5-difluorophenyl)methyl]-2-(1,3-dioxolan-2-yl)-5-fluoropyridine

[Chemical formula 81]

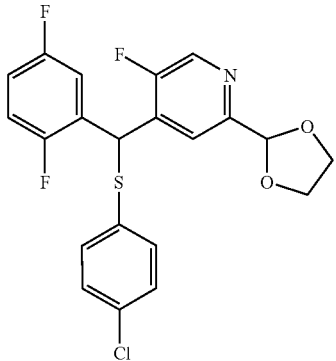

Under an argon atmosphere, triethylamine (1.7 ml, 12.0 mmol) and methanesulfonyl chloride (850 μl, 10.4 mmol) were added to a dichloromethane solution (30 ml) of 4-[(2,5-difluorophenyl)hydroxymethyl]-2-(1,3-dioxolan-2-yl)-5-fluoropyridine (2.5 g, 8.03 mmol) under ice cooling. The resulting mixture was stirred at room temperature for 2 hours. A saturated aqueous solution of sodium bicarbonate was added to the reaction mixture, followed by extraction with diethyl ether. The extract was washed with brine, dried over anhydrous sodium sulfate, and concentrated under reduced pressure.

To a dimethylformamide (20 ml) solution of the residue were added 4-chlorobenzenethiol (1.39 g, 9.64 mmol) and potassium carbonate (1.66 g, 12.0 mmol). The resulting mixture was stirred at 50° C. for 3 hours. After cooling to room temperature, the reaction mixture was diluted with diethyl ether. The diluted solution was washed sequentially with water and brine. The organic layer thus obtained was dried over sodium sulfate, and concentrated under reduced pressure. The residue thus obtained was subjected to flash silica gel column chromatography. The fraction obtained from the hexane:ethyl acetate (=4:1) eluate was concentrated under reduced pressure to give the title compound (2.86 g, 5.85 mmol, 81%) as a yellow oil.

$^1$H-NMR (40.0 MHz, CDCl$_3$) δ: 4.06-4.18 (4H, m), 5.82 (1H, s), 5.94 (1H, s), 6.96-7.03 (2H, m), 7.20-7.28 (5H, m), 7.71 (1H, d, J=5.9 Hz), 8.38 (1H, d, J=1.2 Hz).

MSm/z: 438 (M$^+$+H).

Example 199

4-[(4-Chlorophenylsulfonyl)(2,5-difluorophenyl)methyl]-2-(1,3-dioxolan-2-yl)-5-fluoropyridine

[Chemical formula 82]

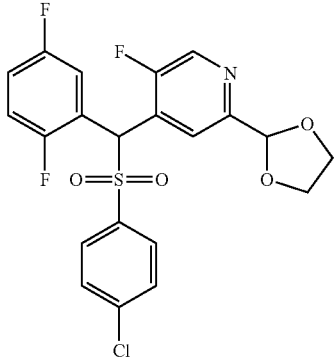

To a methanol (50 ml) solution of 4-[(4-chlorophenylthio)(2,5-difluorophenyl)methyl]-2-(1,3-dioxolan-2-yl)-5-fluoropyridine (2.80 g, 6.39 mmol) were added hexaammonium heptamolybdate tetrahydrate (200 mg) and 30% aqueous hydrogen peroxide (30 ml). The resulting mixture was stirred for 3 hours. Water was added do the reaction mixture. The solid thus precipitated was collected by filtration and then, washed with water. The resulting solid was dissolved in ethyl acetate. The resulting solution was washed with water and brine. The organic layer was concentrated under reduced pressure. The residue thus obtained was subjected to flash silica gel column chromatography. The fraction obtained from the hexane:ethyl acetate (=3:1) eluate was concentrated under reduced pressure to give the title compound (1.39 g, 2.96 mmol, 46%) as a white powder.

$^1$H-NMR (400 MHz, CDCl$_3$) δ: 4.08-4.28 (4H, m), 4.08-4.28 (4H, m), 5.88 (1H, s), 6.10 (1H, s), 6.94-7.00 (1H, m), 7.03-7.10 (1H, m), 7.43 (2H, d, J=8.3 Hz), 7.62 (2H, d, J=8.3 Hz), 7.66-7.70 (1H, m), 8.17 (1H, d, J=5.9 Hz), 8.41 (1H, s).

MSm/z: 470 (M$^+$+H)

Example 200

[4-[(4-Chlorophenylsulfonyl)(2,5-difluorophenyl)methyl]-5-fluoropyridin-2-yl]carbaldehyde

[Chemical formula 83]

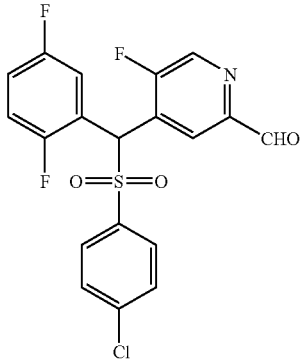

To a 1,4-dioxane (40 ml) solution of 4-[(4-chlorophenylsulfonyl)(2,5-difluorophenyl)methyl]-2-(1,3-dioxolan-2-yl)-5-fluoropyridine (2.60 g, 5.53 mmol) was added concentrated hydrochloric acid (20 ml). The resulting mixture was stirred at room temperature for 5 hours. The solvent was concentrated under reduced pressure. To the residue was added ethyl acetate. The resulting mixture was washed sequentially with water, a saturated aqueous solution of sodium bicarbonate and brine. The organic layer thus obtained was dried over magnesium sulfate, and concentrated under reduced pressure. The residue thus obtained was subjected to flash silica gel column chromatography. The fraction obtained from the hexane:ethyl acetate (=3:1) eluate was concentrated under reduced pressure to give the title compound (1.86 g, 4.37 mmol, 79%) as a white powder.

$^1$H-NMR (400 MHz, CDCl$_3$) δ: 6.13 (1H, s), 6.93-6.99 (1H, m), 7.05-7.10 (1H, m), 7.45 (2H, d, J=7.8 Hz), 7.65 (2H, d, J=7.8 Hz), 7.70-7.75 (1H, m), 8.59 (1H, s), 8.60 (1H, s), 10.06 (1H, s).

MSm/z: 426 (M$^+$+H).

Example 201

4-[(4-Chlorophenylsulfonyl)(2,5-difluorophenyl)methyl]-5-fluoropicolinic acid

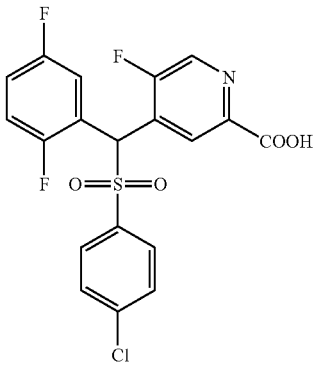

[Chemical formula 84]

To a formic acid (10 ml) solution of [4-[(4-chlorophenylsulfonyl)(2,5-difluorophenyl)methyl]-5-fluoropyridin-2-yl]carbaldehyde (700 mg, 1.64 mmol) were added 30% aqueous hydrogen peroxide (562 μl, 4.93 mmol). The resulting mixture was stirred at room temperature for 2.5 hours. Water was added to the reaction mixture. The solid thus precipitated was collected by filtration and washed with water. The resulting solid was dissolved in ethyl acetate. The resulting solution was washed sequentially with a saturated aqueous solution of ammonium chloride, water and brine. The organic layer thus obtained was dried over magnesium sulfate, and concentrated under reduced pressure. The residue thus obtained was recrystallized from ethanol to give the title compound (656 mg, 1.48 mmol, 91%) as a white powder.

$^1$H-NMR (400 MHz, CDCl$_3$) δ: 6.14 (1H, s), 6.93-7.00 (1H, m), 7.05-7.11 (1H, m), 7.46 (2H, d, J=8.6 Hz), 7.67 (2H, d, J=8.6 Hz), 7.75-7.79 (1H, m), 8.47 (1H, s), 8.85 (1H, d, J=5.6 Hz).

IR(ATR)cm$^{-1}$: 3288, 2942, 1751, 1722, 1693, 1608, 1575, 1492, 1398, 1326, 1290, 1241, 1182, 1147, 1089, 1043, 1014)

mp: 208 to 209° C.

MSm/z: 442 (M$^+$+H).

Elemental Analysis for C$_{19}$H$_{11}$ClF$_3$NO$_4$S.0.75H$_2$O: Calculated: C, 50.12; H, 2.77; Cl, 7.79; F, 12.52; N, 3.08; S, 7.04. Found: C, 50.49; H, 2.97; Cl, 7.53; F, 12.02; N, 3.11, S, 6.89.

Example 202 t-Butyl[4-[(4-chlorophenylsulfonyl)(2,5-difluorophenyl)methyl]-5-fluoropyridin-2-yl]carbamate

[Chemical formula 85]

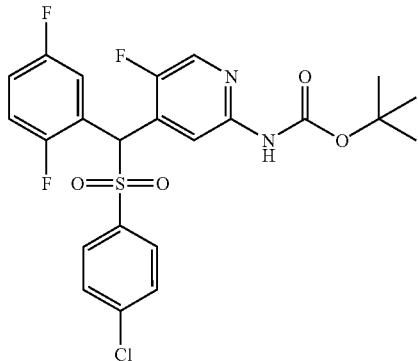

Under an argon atmosphere, diphenylphosphoryl azide (162 μl, 0.762 mmol) and triethylamine (151 μl, 1.09 mmol) were added to a solution of 4-[-chlorophenylsulfonyl)(2,5-difluorophenyl)methyl]-5-fluoropicolinic acid (240 mg, 0.543 mmol) in a mixture of t-butanol (2 ml) and toluene (5 ml). The reaction mixture was heated under reflux for 15 hours. After cooling, ethyl acetate was added to the reaction mixture. The resulting mixture was washed sequentially with a saturated aqueous solution of sodium bicarbonate and brine. The organic layer thus obtained was dried over magnesium sulfate, and concentrated under reduced pressure. The residue thus obtained was subjected to flash silica gel column chromatography. The fraction obtained from the hexane:ethyl acetate (=4:1) eluate was concentrated under reduced pressure to give the title compound (181 mg, 0.353 mmol, 65%) as a white powder.

$^1$H-NMR (400 MHz, CDCl$_3$) δ: 1.57 (9H, s), 6.07 (1H, s), 6.93-6.99 (1H, m), 7.02-7.08 (1H, m), 7.43 (2H, d, J=8.6 Hz), 7.49 (1H, brs), 7.70 (2H, d, J=8.6 Hz), 7.71-7.75 (1H, m), 8.04 (1H, s), 8.65 (1H, d, J=4.9 Hz).

MSm/z: 442 (M$^+$-tBu+2H).

Example 203

[4-[(4-Chlorophenylsulfonyl)(2,5-difluorophenyl)methyl]-5-fluoropyridin-2-yl]amine

[Chemical formula 86]

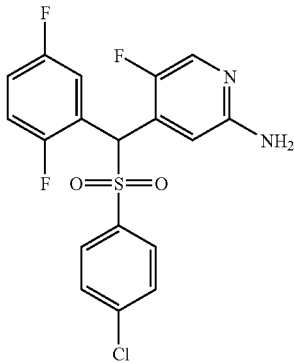

To an ethanol (5 ml) solution of t-butyl[4-[(4-chlorophenylsulfonyl)(2,5-difluorophenyl)methyl]-5-fluoropyridin-2-yl]carbamate (170 mg, 0.331 mmol) was added concentrated hydrochloric acid (5 ml). The resulting mixture was stirred at room temperature for 2 hours. The reaction mixture was concentrated under reduced pressure. To the residue thus obtained was added a saturated aqueous solution of sodium bicarbonate, followed by extraction with ethyl acetate. The organic layer was washed with brine, dried over magnesium sulfate, and concentrated under reduced pressure. The residue thus obtained was recrystallized from hexane:ethyl acetate to give the title compound (110 mg, 0.266 mmol, 81%) as a pale violet powder.

$^1$H-NMR (400 MHz, CDCl$_3$) δ: 4.51 (2H, s), 5.99 (1H, s), 6.92-6.97 (1H, m), 7.02-7.08 (1H, m), 7.16 (1H, d, J=4.6 Hz), 7.44 (2H, d, J=8.6 Hz), 7.61-7.65 (1H, m), 7.63 (2H, d, J=8.6 Hz), 7.86 (1H, s).

IR(ATR)cm$^{-1}$: 3645, 3174, 1631, 583, 1565, 1496, 1427, 1396, 1330, 1278, 1236, 1178, 1151, 1085, 1014.

mp: 181 to 183° C.

MSm/z: 413 (M$^+$+H).

Elemental Analysis for $C_{18}H_{12}ClF_3N_2O_2S$: Calculated: C, 52.37; H, 2.93; Cl, 8.59; F, 13.81; N, 6.79; S, 7.77. Found: C, 52.09; H, 2.88; Cl, 8.57; F, 13.54; N, 6.90; S, 7.81.

Example 204

N-[4-[(4-Chlorophenylsulfonyl)(2,5-difluorophenyl)methyl]-5-fluoropyridin-2-yl]methanesulfonamide

[Chemical formula 87]

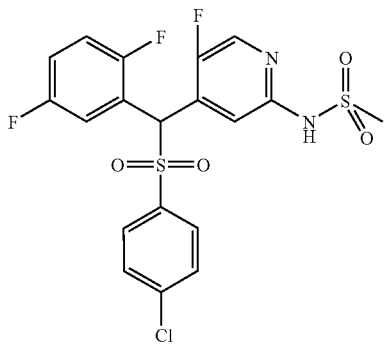

Under ice cooling, methanesulfonyl chloride (12 μl, 0.157 mmol) was added to a methylene chloride (5 ml) solution of [4-[(4-chlorophenylsulfonyl)(2,5-difluorophenyl)methyl]-5-fluoropyridin-2-yl]amine (54 mg, 0.131 mmol) and pyridine (16 μl, 0.197 mmol). The resulting mixture was stirred at room temperature for 7 hours, followed by the addition of pyridine (16 μl, 0.197 mmol) and methanesulfonyl chloride (12 μl, 0.157 mmol). After the reaction mixture was stirred at room temperature for 17 hours, pyridine (16 μl, 0.197 mmol) and methanesulfonyl chloride (12 μl, 0.157 mmol) were added thereto. The resulting mixture was stirred at room temperature for 2 hours and then, pyridine (16 μl, 0.197 mmol) and methanesulfonyl chloride (12 μl, 0.157 mmol) were added thereto. After the resulting mixture was stirred at room temperature for 21 hours, pyridine (16 μl, 0.197 mmol) and methanesulfonyl chloride (12 μl, 0.157 mmol) were added thereto. The resulting mixture was stirred at room temperature for 2 hour and then, concentrated under reduced pressure. To the residue thus obtained was added ethyl acetate. The resulting mixture was washed with a saturated aqueous solution of sodium bicarbonate, dried over anhydrous sodium sulfate, and filtered. The filtrate was concentrated under reduced pressure. The residue thus obtained was subjected to flash silica gel column chromatography. The fraction obtained from the hexane:ethyl acetate (=2:1) eluate was concentrated under reduced pressure to give the title compound (54 mg, 0.110 mmol, 84%) as a white solid. The resulting white solid was washed with hexane-ether, and collected by filtration to afford the title compound as a white powder.

$^1$H-NMR (400 MHz, CDCl$_3$) δ: 3.30 (3H, s), 6.06 (1H, s), 6.90-6.99 (1H, m), 7.02-7.10 (1H, m), 7.46 (2H, d, 8.8 Hz), 7.58-7.69 (3H, m), 7.83-7.91 (2H, m), 8.21 (1H, s).

mp: 217 to 219° C.

MSm/z: 490 (M$^+$).

EI-MS: 490.0008 (calculated as $C_{19}H_{14}O_4N_2ClF_3S_2$: 490.0036).

Elemental Analysis for $C_{19}H_{14}N_2O_4ClF_3S_2$: Calculated: C, 46.49; H, 2.87; N, 5.71; Cl, 7.22; F, 11.61; S, 13.06. Found: C, 46.90; H, 2.95; N, 5.78; Cl, 7.33; F, 11.56; S, 13.04.

Referential Example 38

(4-Bromo-5-methylpyridin-2-yl)methanol

[Chemical formula 88]

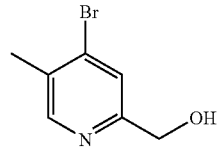

Under an argon atmosphere, trifluoroacetic anhydride (20.6 ml, 0.146 mol) was added to a dichloromethane solution (100 ml) of 4-bromo-2,5-dimethylpyridine 1-oxide (9.8 g, 48.5 mmol) under ice cooling. The resulting mixture was stirred for 20 minutes and then, stirred at room temperature for 7.5 hours. The reaction mixture was concentrated under reduced pressure. To a dichloromethane solution (50 ml) of the residue was added a saturated aqueous solution (100 ml) of sodium bicarbonate. The resulting mixture was stirred for 14 hours. The reaction mixture was extracted with dichloromethane. The extract was dried over anhydrous sodium sulfate, and concentrated under reduced pressure. The residue thus obtained was subjected to silica gel column chromatography. The fraction obtained from the hexane:ethyl acetate (=1:1) eluate was concentrated under reduced pressure to give the title compound (8.17 g, 40.4 mmol, 83%) as a yellow powder.

$^1$H-NMR (400 MHz, CDCl$_3$) δ: 2.38 (3H, s), 3.42 (1H, s), 4.71 (2H, s), 7.48 (1H, s), 8.35 (1H, s).

MSm/z: 202 (M$^+$+H).

Referential Example 39

4-Bromo-2-[(t-butyldimethylsilyloxy)methyl]-5-methylpyridine

[Chemical formula 89]

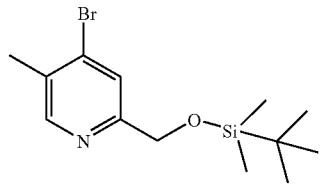

Under a nitrogen atmosphere, imidazole (2.95 g, 43.3 mmol), 4-dimethylaminopyridine (481 mg, 3.94 mmol) and t-butylchlorodimethylsilane (6.53 g, 43.3 mmol) were added to a dichloromethane solution (100 ml) of (4-bromo-5-methylpyridin-2-yl)methanol (7.96 g, 39.4 mmol) under ice cooling. The resulting mixture was stirred at room temperature for 1 hour. Water was added to the reaction mixture, followed by extraction with dichloromethane. The extract was dried over anhydrous sodium sulfate, and concentrated under reduced pressure. The residue thus obtained was subjected to silica gel column chromatography. The fraction obtained from the hexane:ethyl acetate=4:1 eluate was concentrated under reduced pressure to give the title compound (12.4 g, 39.4 mmol, quant.) as a pale yellow oil.

$^1$H-NMR (400 MHz, CDCl$_3$) δ: 0.12 (6H, s), 0.96 (9H, s), 2.36 (3H, s), 4.78 (2H, s), 7.67 (1H, s), 8.29 (1H, s).

MSm/z: 316 (M$^+$+H).

Referential Example 40

2-[(t-Butyldimethylsilyloxy)methyl]-4-[(2,5-difluorophenyl)hydroxymethyl]-5-methylpyridine

[Chemical formula 90]

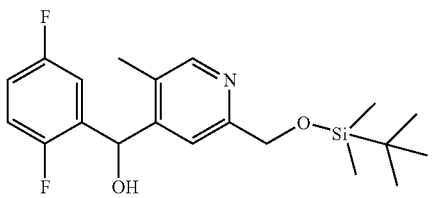

Under an argon atmosphere, n-butyl lithium (a 1.58M hexane solution, 400 μl, 0.632 mmol) was added to a diethyl ether (3 ml) solution of 4-bromo-2-[(t-butyldimethylsilyloxy)methyl]-5-methylpyridine (200 mg, 0.632 mmol) at −78° C. The resulting mixture was stirred for 1 hour. After 2,5-difluorobenzaldehyde (69 μl, 0.632 mmol) was added dropwise, the reaction mixture was stirred for 1 hour. To the reaction mixture were added water and a saturated aqueous solution of sodium bicarbonate, followed by extraction with diethyl ether. The extract was washed with brine. The organic layer thus obtained was dried over magnesium sulfate, and concentrated under reduced pressure. The residue thus obtained was subjected to flash silica gel column chromatography. The fraction obtained from the hexane:ethyl acetate=2:1 eluate was concentrated under reduced pressure to give the title compound (178 mg, 0.469 mmol, 74%) as a white powder.

$^1$H-NMR (400 MHz, CDCl$_3$) δ: 0.06 (3H, s), 0.09 (3H, s), 0.91 (9H, s), 2.26 (3H, s), 2.52 (1H, brs), 4.79 (2H, s), 6.24 (1H, s), 6.95-7.10 (3H, m), 7.58 (1H, s), 8.27 (1H, s).

MSm/z: 380 (M$^+$+H).

Example 205

2-[(t-Butyldimethylsilyloxy)methyl]-4-[(4-chlorophenylthio)(2,5-difluorophenyl)methyl]-5-methylpyridine

[Chemical formula 91]

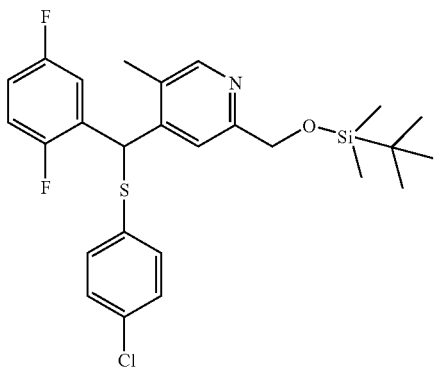

Under an argon atmosphere, triethylamine (4.41 ml, 31.7 mmol) and methanesulfonyl chloride (2.2 ml, 27.4 mmol) were added to a dichloromethane solution (100 ml) of 2-[(t-butyldimethylsilyloxy)methyl]-4-[(2,5-difluorophenyl)hydroxymethyl]-5-methylpyridine (8.0 g, 21.1 mmol) under ice cooling. The resulting mixture was stirred at room temperature for 50 minutes. A saturated aqueous solution of sodium bicarbonate was added to the reaction mixture, followed by extraction with diethyl ether. The extract was washed with brine, dried over anhydrous magnesium sulfate, and concentrated under reduced pressure.

To a dimethylformamide (100 ml) solution of the residue thus obtained were added 4-chlorobenzenethiol (3.66 g, 25.3 mmol) and potassium carbonate (4.38 g, 31.7 mmol). The resulting mixture was stirred at 50° C. for 1.5 hours. After cooling to room temperature, the reaction mixture was diluted with diethyl ether. The diluted solution was washed sequentially with water and brine. The organic layer thus obtained was dried over magnesium sulfate, and concentrated under reduced pressure. The residue thus obtained was subjected to silica gel column chromatography. The fraction obtained from the hexane:ethyl acetate=5:1 eluate was concentrated under reduced pressure to give the title compound (9.3 g, 18.4 mmol, 87%) as a pale yellow oil.

$^1$H-NMR (400 MHz, CDCl$_3$) δ: 0.04 (3H, s), 0.08 (3H, s), 0.91 (9H, s), 2.33 (3H, s), 4.77 (2H, d, J=4.2 Hz), 5.83 (1H, s), 6.92-7.00 (2H, m), 7.20 (4H, s), 7.33-7.38 (1H, m), 7.56 (1H, s), 8.29 (1H, s).

MSm/z: 506 (M$^+$+H).

Example 206

[4-[(4-Chlorophenylthio)(2,5-difluorophenyl)methyl]-5-methylpyridin-2-yl]methanol

[Chemical formula 92]

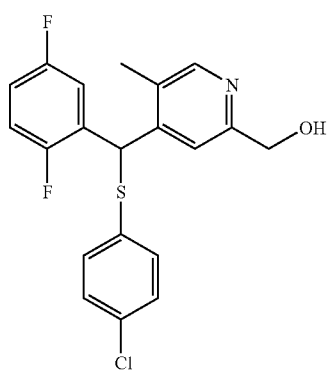

To a tetrahydrofuran solution (3 ml) of 2-[(t-butyldimethylsilyloxy)methyl]-4-[(4-chlorophenylthio)(2,5-difluorophenyl)methyl]-5-methylpyridine (200 mg, 0.395 mmol) was added tetrabutylammonium fluoride (a 1.0M tetrahydrofuran solution, 593 μl, 0.593 mmol). The resulting mixture was stirred for 20 minutes. Water was added to the reaction mixture, followed by extraction with ethyl acetate. The organic layer was washed with brine, dried over anhydrous magnesium sulfate, and concentrated under reduced pressure. The residue thus obtained was subjected to flash silica gel column chromatography. The fraction obtained from the hexane:ethyl acetate=3:1 eluate was concentrated under reduced pressure to give the title compound (150 mg, 0.384 mmol, 97%) as a colorless oil.

$^1$H-NMR (400 MHz, CDCl$_3$) δ: 2.31 (3H, s), 3.54 (1H, brs), 4.72 (2H, s), 5.81 (1H, s), 6.94-7.03 (2H, m), 7.20 (4H, s), 7.22-7.28 (1H, m), 7.33 (1H, s), 8.35 (1H, s).

MSm/z: 392 (M$^+$+H).

Example 207

[4-[(4-Chlorophenylsulfonyl)(2,5-difluorophenyl)methyl]-5-methylpyridin-2-yl]methanol

[Chemical formula 93]

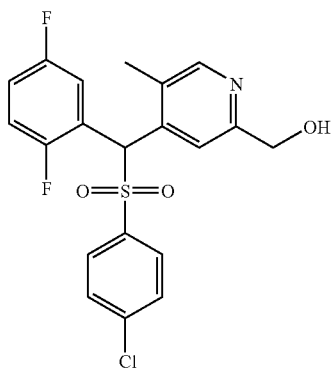

To a methanol (150 ml) solution of [4-[(4-chlorophenylthio)(2,5-difluorophenyl)methyl]-5-methylpyridin-2-yl]methanol (6.5 g, 16.6 mmol) were added hexaammonium heptamolybdate tetrahydrate (500 mg) and 30% aqueous hydrogen peroxide (150 ml). The resulting mixture was stirred for 23 hours. Water was added to the reaction mixture. The solid thus precipitated was collected by filtration, and then washed with water. The resulting solid was dissolved in ethyl acetate. The resulting solution was washed with water and brine. The organic layer was concentrated under reduced pressure. The residue thus obtained was subjected to silica gel column chromatography. The fraction obtained from the hexane:ethyl acetate=1:1 eluate was concentrated under reduced pressure to give the title compound (4.0 g, 9.44 mmol, 57%) as a white powder.

$^1$H-NMR (400 MHz, CDCl$_3$) δ: 2.13 (3H, s), 3.53 (1H, brs), 4.80 (1H, d, J=14.4 Hz), 4.85 (1H, d, J=14.4 Hz), 5.88 (1H, s), 6.90-6.96 (1H, m), 7.01-7.07 (1H, m), 7.43 (2H, d, J=8.8 Hz), 7.60 (2H, d, J=8.8 Hz), 7.60 (2H, d, J=8.8 Hz), 7.63-7.67 (1H, m), 7.93 (1H, s), 8.36 (1H, s).

IR(ATR)cm$^{-1}$: 3179, 1604, 1573, 1492, 1427, 1394, 1349, 1322, 1280, 1234, 1151, 1085, 039, 1010.

mp: 196 to 198° C.

MSm/z: 424 (M$^+$+H).

Elemental Analysis for C$_{20}$H$_{16}$ClF$_2$NO$_3$S: Calculated: C, 56.67; H, 3.80; Cl, 8.36; F, 8.96; N, 3.30; S, 7.56. Found: C, 56.41; H, 3.83; Cl, 8.28; F, 8.89; N, 3.31; S, 7.67.

Example 208

[4-[(4-Chlorophenylsulfonyl)(2,5-difluorophenyl)methyl]-5-methylpyridin-2-yl]carbaldehyde

[Chemical formula 94]

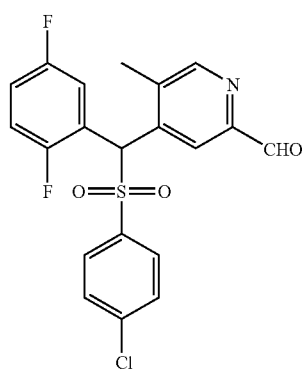

Under a nitrogen atmosphere, dimethyl sulfoxide (164 μl, 2.36 mmol), triethylamine (329 μl, 2.36 mmol) and sulfur trioxide pyridine complex (255 mg, 1.42 mmol) were added to a dichloromethane (5 ml) solution of [4-[(4-chlorophenylsulfonyl)(2,5-difluorophenyl)methyl]-5-methylpyridin-2-yl]methanol (200 mg, 0.472 mmol). The resulting mixture was stirred at room temperature for 16 hours. The reaction mixture was concentrated under reduced pressure. The residue thus obtained was subjected to flash silica gel column chromatography. The fraction obtained from the hexane:ethyl acetate=3:1 eluate was concentrated under reduced pressure to give the title compound (160 mg, 0.379 mmol, 80%) as a white powder.

$^1$H-NMR (400 MHz, CDCl$_3$) δ: 2.29 (3H, s), 5.94 (1H, s), 6.92-6.97 (1H, m), 7.02-7.08 (1H, m), 7.43 (2H, d, J=8.8 Hz), 7.62 (2H, d, J=8.8 Hz), 7.70-7.75 (1H, m), 8.57 (1H, s), 8.59 (1H, s), 10.08 (1H, s).

MSm/z: 422 (M$^+$+H).

Example 209

4-[(4-Chlorophenylsulfonyl)(2,5-difluorophenyl)methyl]-5-methylpicolinic acid

[Chemical formula 95]

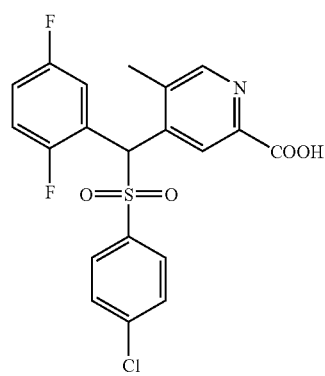

To a formic acid (3 ml) solution of [4-[(4-chlorophenylsulfonyl)(2,5-difluorophenyl)methyl]-5-methylpyridin-2-yl]carbaldehyde (150 mg, 0.356 mmol) was added 30% aqueous hydrogen peroxide (121 μl, 1.07 mmol). The resulting mixture was stirred at room temperature for 2 hours. Water was added to the reaction mixture. The solid thus precipitated was collected by filtration and washed with water. The resulting solid was dissolved in ethyl acetate. The resulting solution was washed sequentially with water and brine. The organic layer thus obtained was dried over magnesium sulfate, and concentrated under reduced pressure. The residue thus obtained was recrystallized from ethanol to give the title compound (140 mg, 0.320 mmol, 90%) as a white powder.

$^1$H-NMR (400 MHz, CDCl$_3$) δ: 2.33 (3H, s), 5.96 (1H, s), 6.92-6.98 (1H, m), 7.02-7.08 (1H, s), 7.44 (2H, d, J=8.6 Hz), 7.64 (2H, d, J=8.6), 7.74-7.78 (1H, m), 8.45 (1H, s), 8.81 (1H, s).

IR(ATR)cm$^{-1}$: 1922, 1683, 1598, 1488, 1450, 1428, 1396, 1375, 1326, 1290, 1236, 1174, 47, 1085, 1047, 1014.

mp: 105 to 107° C.

MSm/z: 438 (M$^+$+H).

Elemental Analysis for C$_{20}$H$_{14}$ClF$_2$NO$_4$S.0.75H$_2$O: Calculated: C, 53.22; H, 3.46; Cl, 7.85; F, 8.42; N, 3.10; S, 7.10. Found: C, 53.44; H, 3.90; Cl, 7.47; F, 8.06; N, 3.07; S, 6.95.

Example 210 t-Butyl[4-[(4-chlorophenylsulfonyl)(2,5-difluorophenyl)methyl]-5-methylpyridin-2-yl]carbamate

[Chemical formula 96]

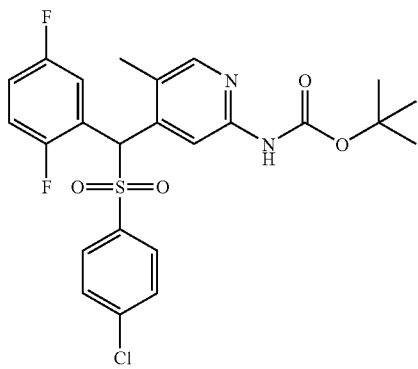

Under an argon atmosphere, diphenylphosphoryl azide (2.9 ml, 13.6 mmol) and triethylamine (2.7 ml, 19.4 mmol) were added to a solution of 4-[(4-chlorophenylsulfonyl)(2,5-difluorophenyl)methyl]-5-methylpicolinic acid (2.8 mg, 6.40 mmol) in a mixture of t-butanol (20 ml) and toluene (40 ml). The resulting mixture was stirred for 16 hours under heating and refluxing. After cooling, ethyl acetate was added to the reaction mixture. The resulting mixture was washed sequentially with a saturated aqueous solution of sodium bicarbonate and brine. The organic layer thus obtained was dried over magnesium sulfate, and concentrated under reduced pressure. The residue thus obtained was washed sequentially with hexane and ethyl acetate to give the title compound (2.60 g, 5.11 mmol, 80%) as a white powder.

$^1$H-NMR (400 MHz, CDCl$_3$) δ: 1.58 (9H, s), 2.07 (3H, s), 5.88 (1H, s), 6.92-6.98 (1H, m), 7.00-7.06 (1H, m), 7.42 (2H, d, J=8.8 Hz), 7.42 (2H, d, J=8.8 Hz), 7.57 (1H, brs), 7.67-7.72 (1H, m), 7.71 (2H, d, J=8.8 Hz), 8.02 (1H, s), 8.67 (1H, s).

MSm/z: 509 (M$^+$+H).

Example 211

[4-[(4-Chlorophenylsulfonyl)(2,5-difluorophenyl)methyl]-5-methylpyridin-2-yl]amine

[Chemical formula 97]

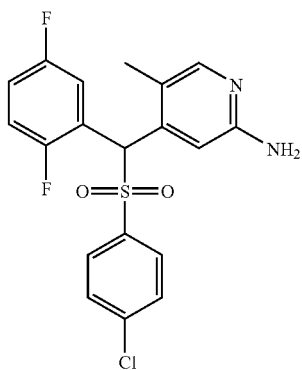

To an ethanol (5 ml) solution of t-butyl[4-[(4-chlorophenylsulfonyl)(2,5-difluorophenyl)methyl]-5-methylpyridin-2-yl]carbamate (200 mg, 0.393 mmol) was added concentrated hydrochloric acid (6 ml). The resulting mixture was stirred at room temperature for 2.5 hours. The reaction mixture was concentrated under reduced pressure. To the residue thus obtained was added a saturated aqueous solution of sodium bicarbonate, followed by extraction with ethyl acetate. The organic layer was washed sequentially with water and brine, dried over magnesium sulfate, and concentrated under reduced pressure. The residue thus obtained was recrystallized from hexane:ethyl acetate to give the title compound (125 mg, 0.306 mmol, 78%) as a white powder.

$^1$H-NMR (400 MHz, CDCl$_3$) δ: 1.89 (3H, s), 5.95-5.96 (3H, m), 7.12 (1H, s), 7.22-7.34 (2H, m), 7.51-7.55 (1H, m), 7.65 (2H, d, J=8.8 Hz), 7.69 (1H, s), 7.78 (2H, d, J=8.8 Hz).

IR(ATR)cm$^{-1}$: 3424, 1637, 1554, 1492, 1457, 1411, 1309, 1276, 1230, 1151, 1089, 1039, 1008.

mp: 188 to 189° C.

Elemental Analysis for C$_{19}$H$_{15}$ClF$_2$N$_2$O$_2$S: Calculated: C, 55.82; H, 3.70; Cl, 8.67; F, 9.29; N, 6.85; S, 7.84. Found: C, 55.58; H, 3.95; Cl, 8.61; F, 9.13; N, 6.91; S, 7.89.

Example 212

N-[4-[(4-Chlorophenylsulfonyl)(2,5-difluorophenyl)methyl]-5-methylpyridin-2-yl]methanesulfonamide

[Chemical formula 98]

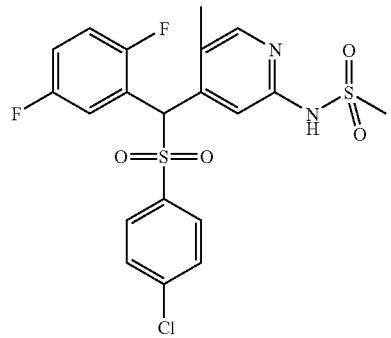

To a methylene chloride (5 ml) solution of [4-[(4-chlorophenylsulfonyl)(2,5-difluorophenyl)methyl]-5-methylpyridin-2-yl]amine (133 mg, 0.325 mmol) and pyridine (39 µl, 0.488 mmol) was added methanesulfonyl chloride (28 µl, 0.358 mmol) under ice cooling. The reaction mixture was stirred at room temperature for 2.5 hours. To the reaction mixture were added pyridine (26 µl, 0.325 mmol) and methanesulfonyl chloride (25 µl, 0.325 mmol). After the resulting mixture was stirred at room temperature for 16 hours, pyridine (26 µl, 0.325 mmol) and methanesulfonyl chloride (25 µl, 0.325 mmol) were added thereto. The resulting mixture was stirred at room temperature for 1.5 hours. The reaction mixture was concentrated under reduced pressure. To the residue thus obtained was added ethyl acetate. The resulting mixture was washed sequentially with water and brine, dried over anhydrous sodium sulfate and filtered. The filtrate was concentrated under reduced pressure. The residue thus obtained was subjected to flash silica gel column chromatography. The fraction obtained from the hexane:ethyl acetate=3:2 eluate was concentrated under reduced pressure to give the title compound (108 mg, 0.222 mmol, 68%) as a white solid. The resulting white solid was washed with hexane-ether, and collected by filtration to give the title compound (67 mg) as a white powder.

$^1$H-NMR (400 MHz, CDCl$_3$): 2.13 (3H, s), 3.29 (3H, s), 5.85 (1H, s), 6.89-6.99 (1H, m), 7.01-7.10 (1H, m), 7.45 (2H, d, J=8.3 Hz), 7.59-7.69 (3H, m), 7.90 (1H, s), 8.12 (1H, s).

mp: 214 to 217° C.

MSm/z: 486 (M$^+$).

Elemental Analysis for $C_{20}H_{17}N_2O_4ClF_2S_2$: Calculated: C, 49.33; H, 3.52; N, 5.75; Cl, 7.28; F, 7.80; S, 13.17. Found: C, 49.18; H, 3.45; N, 5.82; Cl, 7.18; F, 7.98; S, 13.14.

Example 213

2,5-Dichloro-4-[(2,5-difluorophenyl)-(4-fluorophenylthio)methyl]pyridine

[Chemical formula 99]

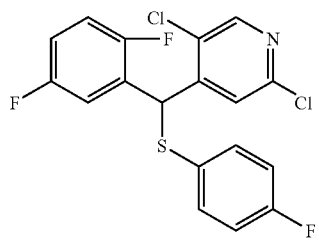

The 2,5-dichloro-4-[(2,5-difluorophenyl)-hydroxymethyl]pyridine (1.22 g, 4.8 mmol) obtained in Referential Example 24 was dissolved in thionyl chloride (5.0 ml). To the resulting solution was added a catalytic amount of dimethylformamide and the resulting mixture was stirred for 4 hours. The reaction mixture was concentrated under reduced pressure. To the residue was added 1,4-dioxane, followed by further concentration.

The residue thus obtained was dissolved in dimethylformamide (10 ml). To the resulting solution were added 4-fluorobenzenethiol (730 mg, 5.7 mmol) and potassium carbonate (2.07 g, 15 mmol) under a nitrogen atmosphere. The resulting mixture was stirred at room temperature for 24 hours. To the reaction mixture was added diethyl ether (120 ml). The resulting mixture was washed with water and brine. The organic layer was dried over magnesium sulfate, and concentrated under reduced pressure. The residue thus obtained was crystallized in ethanol to give the title compound (950 mg, 49%) as colorless needle crystals.

$^1$H-NMR (400 MHz, CDCl$_3$) δ: 5.92 (1H, s), 6.94-7.04 (4H, m), 7.19 (1H, m), 7.33-7.4 (2H, m), 7.57 (1H, s), 8.33 (1H, s).

IR(ATR)cm$^{-1}$: 1571, 1489, 1329, 1222, 1157, 1109, 835.

mp: 95 to 97° C.

MSm/z: 400 (M$^+$+H).

Example 214

[5-Chloro-4-[(2,5-difluorophenyl)-(4-fluorophenylsulfonyl)methyl]pyridin-2-yl](3,4-dimethoxybenzyl)amine

[Chemical formula 100]

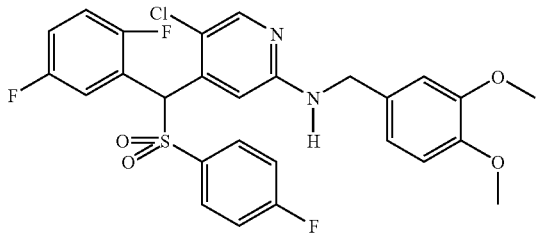

A 1,4-dioxane (3.0 ml) solution of 2,5-dichloro-4-[(2,5-difluorophenyl)-(4-fluorophenylthio)methyl]pyridine (740 mg, 1.85 mmol) and 3,4-dimethoxybenzylamine (836 μl, 5.55 mmol) was stirred at 120° C. for 3 days under an argon atmosphere in a sealed tube. After cooling to room temperature, ethyl acetate (80 ml) was added to the reaction mixture. The resulting mixture was washed with brine, dried and concentrated under reduced pressure. The residue thus obtained was purified by silica gel chromatography (hexane:ethyl acetate=3:1) to give an amine compound (235 mg) as an oil.

The resulting compound was dissolved in methanol (9.0 ml). To the resulting solution were added hexaammonium heptamolybdate tetrahydrate (30 mg) and 30% aqueous hydrogen peroxide (3.0 ml). The resulting mixture was stirred at room temperature for 20 hours. After dilution with ethyl acetate (80 ml), the diluted solution was washed with water and brine, dried and concentrated under reduced pressure. To the residue thus obtained was added ethanol, followed by crystallization to give the title compound (159 mg, 15%) as a white solid.

$^1$H-NMR (400 MHz, CDCl$_3$) δ: 3.89 (6H, s), 4.50 (2H, m), 6.10 (1H, s), 6.85-7.05 (5H, m), 7.11 (2H, t, J=8.4 Hz), 7.25-7.35 (1H, m), 7.29 (1H, s), 7.61 (2H, dd, J=5.2, 8.4), 7.99 (1H, s).

IR(ATR)cm$^{-1}$: 3249, 1589, 1490, 1236, 1147, 817.

mp: 158 to 159° C.

MSm/z: 563 (M$^+$+H).

Example 215

[5-Chloro-4-[(2,5-difluorophenyl)-(4-fluorophenylsulfonyl)methyl]pyridin-2-yl]amine

[Chemical formula 101]

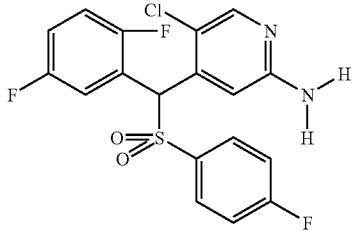

[5-Chloro-4-[(2,5-difluorophenyl)-(4-fluorophenylsulfonyl)methyl]pyridin-2-yl](3,4-dimethoxybenzyl)amine (157 mg, 0.28 mmol) was dissolved in trifluoroacetic acid (5.0 ml). The resulting solution was stirred at 65° C. for 17 hours. After cooling, the reaction mixture was concentrated under reduced pressure. To the residue thus obtained was added a saturated aqueous solution of sodium bicarbonate. The resulting mixture was extracted with ethyl acetate. The extract was washed with brine, dried and concentrated under reduced pressure. The residue thus obtained was purified by silica gel chromatography (hexane:ethyl acetate=3:1) to give the title compound (114 mg, 99%) as a white solid.

$^1$H-NMR (400 MHz, CDCl$_3$) δ: 4.76 (2H, br), 6.12 (1H, s), 6.91 (1H, m), 7.06 (1H, m), 7.14 (2H, t, J=8.4), 7.37 (1H, s), 7.53 (1H, m), 7.69 (2H, dd, J=4.8, 8.4 Hz), 7.98 (1H, s).

IR(ATR)cm$^{-1}$: 3456, 3167, 1639, 1591, 1491, 1417, 1327, 1238, 1140, 1084.

mp: 157 to 159° C.

MSm/z: 413 (M$^+$+H).

Elemental Analysis for $C_{18}H_{12}ClF_3N_2O_2S$: Calculated: C, 52.37; H, 2.93; Cl, 8.59; F, 13.81; N, 6.79; S, 7.77. Found: C, 52.45; H, 2.96; Cl, 8.62; F, 13.69; N, 6.82; S, 7.83.

Example 216

N-[5-Chloro-4-[(2,5-difluorophenyl)-(4-fluorophenylsulfonyl)methyl]pyridin-2-yl]methanesulfonamide

[Chemical formula 102]

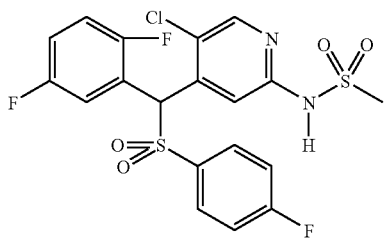

To a methylene chloride solution (10.0 ml) of [5-chloro-4-[(2,5-difluorophenyl)-(4-fluorophenylsulfonyl)methyl]pyridin-2-yl]amine (114 mg, 0.276 mmol) was added pyridine (440 μl, 5.5 mmol). To the resulting mixture was added methanesulfonyl chloride (addition of 77 μl once a day for 3 days, 230 μl in total, 3.0 mmol). The resulting mixture was stirred for 4 days in total. The reaction mixture was concentrated under reduced pressure. The residue thus obtained was purified by silica gel chromatography (hexane:ethyl acetate=2:1), followed by crystallization in ether to give the title compound (51 mg, 38%) as a white solid.

$^1$H-NMR (400 MHz, CDCl$_3$) δ: 3.35 (3H, s), 6.19 (1H, s), 6.92 (1H, m), 7.08 (1H, m), 7.15 (2H, t, J=8.8 Hz), 7.50 (1H, m), 7.73 (2H, m), 8.00 (1H, s), 8.32 (1H, s),

MS m/z: 491 (M$^+$+H).

IR(ATR)cm$^{-1}$: 1590, 1490, 1330, 1149, 968, 852. mp: 178 to 179° C.

Elemental Analysis for C$_{19}$H$_{14}$ClF$_3$N$_2$O$_4$S$_2$: Calculated: C, 46.49; H, 2.87; N, 5.71; S, 13.06; Cl, 7.22; F, 11.61. Found: C, 46.55; H, 2.96; N, 5.73; S, 13.02; Cl, 7.13; F, 11.39.

Example 217

Optical resolution of N-[5-chloro-4-[(2,5-difluorophenyl)(4-fluorophenylsulfonyl)methyl]pyridin-2-yl]methanesulfonamide (Optical Isomer A; Optical Isomer B)

[Chemical formula 103]

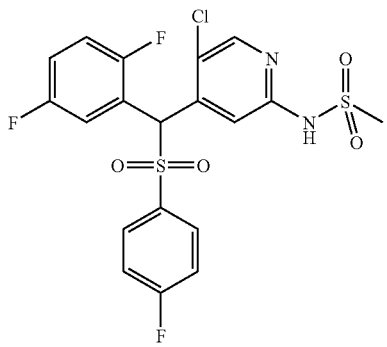

The N-[5-chloro-4-[(2,5-difluorophenyl)(4-fluorophenylsulfonyl)methyl]pyridin-2-yl]methanesulfonamide obtained in Example 216 was optically resolved under the below-described conditions by using supercritical chromatography (product of Gilson) using a chiral column. Column: CHIRALPAK AD, 2.0 cmϕ×25 cm, product of Daicel Chemical Industries, Ltd.

Mobile phase: 2-propanol:carbon dioxide=1:99→50:50 (three minutes and after, 50:50)

Flow rate: 6.0 ml/min

Pressure: 14 MPa

Temperature: 35° C.

Detection: UV (254 nm)

The retention time and apparatus data of each optical isomer will next be described.

Optical Isomer A: 16.3 Minutes $^1$H-NMR (400 MHz, CDCl$_3$) δ: 3.35 (3H, s), 6.18 (1H, s), 6.89-6.97 (1H, m), 7.02-7.10 (1H, m), 7.12-7.20 (2H, m), 7.47-7.54 (1H, m), 7.69-7.76 (2H, m), 7.83 (1H, brs), 7.98 (1H, s), 8.32 (1H, s).

Optical Isomer B: 18.4 Minutes $^1$H-NMR (400 MHz, CDCl$_3$) δ: 3.36 (3H, s), 6.18 (1H, s), 6.89-6.96 (1H, m), 7.02-7.10 (1H, m), 7.12-7.20 (2H, m), 7.46-7.54 (1H, m), 7.69-7.76 (2H, m), 7.99 (1H, s), 8.32 (1H, s).

$[α]_D^{25}$: +102.6° (c=0.5, CHCl$_3$).

Example 218

Sodium salt of N-[5-chloro-4-[(4-chlorophenylsulfinyl)(2,5-difluorophenyl)methyl]pyridin-2-yl]methanesulfonamide

[Chemical formula 104]

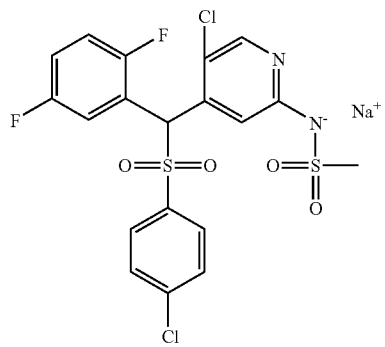

To an ethanol (100 ml) solution of the N-[5-chloro-4-[(4-chlorophenylsulfonyl)(2,5-difluorophenyl)methyl]pyridin-2-yl]methanesulfonamide (15.1 g, 29.8 mmol) obtained in Example 197 was added a 1N aqueous sodium hydroxide solution (32.8 ml). The resulting mixture was concentrated under reduced pressure. To the residue thus obtained was added 2-propanol to dissolve the former in the latter while warming. The resulting solution was allowed to stand at room temperature. The solid thus precipitated was collected by filtration to give the title compound (9.10 g, 16.6 mmol, 56%).

$^1$H-NMR (400 MHz, DMSO-d$_6$) δ: 2.79 (3H, s), 6.10 (1H, s), 7.14 (1H, s), 7.23-7.40 (2H, m), 7.48-7.57 (1H, m), 7.68 (2H, d, J=8.8 Hz), 7.75 (2H, d, J=8.8 Hz), 7.89 (1H, s).

IR(ATR)cm$^{-1}$: 1583, 1494, 1463, 1384, 1326, 1230, 1151, 1108, 1089, 1012, 813, 755.

Elemental Analysis for C$_{19}$H$_{13}$N$_2$O$_4$Cl$_2$F$_2$S$_2$Na.1.0H$_2$O: Calculated: C, 41.69; H, 2.76; N, 5.12; Cl, 12.95; F, 6.94; S, 11.72. Found: C, 41.77; H, 2.66; N, 5.18; Cl, 13.02; F, 7.03; S, 11.78.

Example 219

[5-Chloro-4-[(4-chlorophenylthio)(2,5-difluorophenyl)methyl]pyridin-2-yl]amine

[Chemical formula 105]

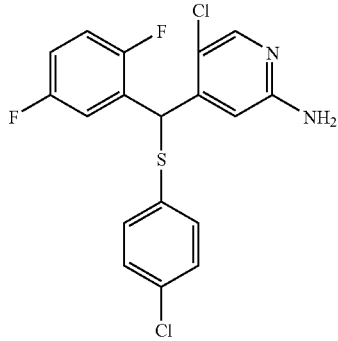

A trifluoroacetic acid (5 ml) solution of the 5-chloro-4-[(4-chlorophenylthio)(2,5-difluorophenyl)methyl]-2-(3,4-dimethoxybenzylamino)pyridine (1.89 g, 3.45 mmol) obtained in Example 185 was stirred at 65° C. for 2 hours. The reaction mixture was concentrated under reduced pressure. To the residue thus obtained was added a saturated aqueous solution of sodium bicarbonate, followed by extraction with methylene chloride. The organic layer was dried over anhydrous sodium sulfate, and filtered. The filtrate was concentrated under reduced pressure. The residue thus obtained was subjected to silica gel column chromatography. The fraction obtained from the hexane:ethyl acetate (=2:1) eluate was concentrated under reduced pressure to yield a white solid. The resulting white solid was washed with hexane-ether, and collected by filtration to give the title compound (1.06 g, 2.67 mmol, 77%) as a white powder.

$^1$H-NMR (400 MHz, CDCl$_3$) δ: 4.50 (2H, s), 5.96 (1H, s), 6.76 (1H, s), 6.90-7.10 (2H, m), 7.12-7.35 (5H, m), 8.02 (1H, s).

IR(ATR)cm$^{-1}$: 3129, 1635, 1602, 1540, 1490, 1469, 1415, 1093, 1012, 819, 728.

MS m/z: 397 (M$^+$+H).

Example 220

N-[5-Chloro-4-[(4-chlorophenylthio)(2,5-difluorophenyl)methyl]pyridin-2-yl]-N-(methylsulfonyl)methanesulfonamide (Compound A), and N-[5-chloro-4-[(4-chlorophenylthio)(2,5-difluorophenyl)methyl]pyridin-2-yl]methanesulfonamide (Compound B)

[Chemical formula 106]

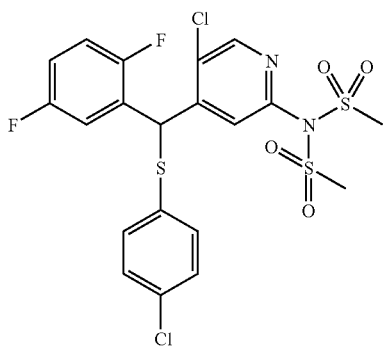

Compound A

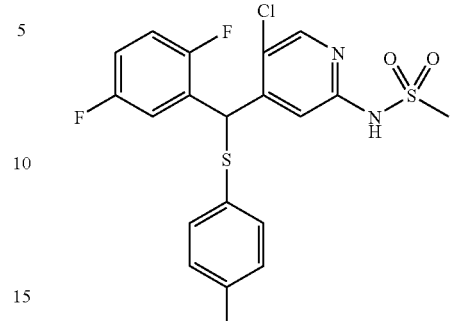

Compound B

To a pyridine (5 ml) solution of [5-chloro-4-[(4-chlorophenylthio)(2,5-difluorophenyl)methyl]pyridin-2-yl]amine (575 mg, 1.45 mmol) was added methanesulfonyl chloride (0.123 ml, 1.59 mmol) at 0° C. The resulting mixture was stirred at room temperature for 16 hours. To the reaction mixture was added methanesulfonyl chloride (0.123 ml, 1.59 mmol) at 0° C. The resulting mixture was stirred at room temperature for 22 hours. To the reaction mixture was added pyridine (3 ml), followed by further addition of methanesulfonyl chloride (0.123 ml, 1.59 mmol) at 0° C. After stirring at room temperature for 25 hours, the reaction mixture was concentrated under reduced pressure. The residue thus obtained was diluted with ethyl acetate. The diluted solution was washed sequentially with water and brine, dried over anhydrous sodium sulfate and filtered. The filtrate was concentrated under reduced pressure. The residue thus obtained was subjected to flash silica gel column chromatography. The fraction obtained from the hexane:ethyl acetate (=4:1) eluate was concentrated under reduced pressure to give the title Compound A (low polar compound) (334 mg, 0.603 mmol, 42%) as an amorphous substance and the title Compound B (high polar compound) (269 mg, 0.566 mmol, 39%) as a white solid.

Compound A $^1$H-NMR (400 MHz, CDCl$_3$) δ: 3.56 (6H, s), 5.97 (1H, s), 6.95-7.09 (3H, m), 7.20-7.31 (4H, m), 7.76 (1H, s), 8.45 (1H, s).

IR(ATR)cm$^{-1}$: 1583, 1492, 1367, 1321, 1159, 1093, 1006, 962, 931, 821, 759.

MS m/z: 552 (M$^+$).

Compound B $^1$H-NMR (400 MHz, CDCl$_3$) δ: 3.15 (3H, s), 6.02 (1H, s), 6.94-7.13 (3H, m), 7.20-7.35 (4H, m), 7.59 (1H, s), 8.07 (1H, brs), 8.30 (1H, s).

mp: 149 to 151° C.

IR(ATR)cm$^{-1}$: 1590, 1556, 1488, 1475, 1380, 1348, 1149, 993, 962, 831, 784.

MS m/z: 475 (M$^+$+H).

FAB-MS: 474.9925 (Calcd for C$_{19}$H$_{15}$O$_2$N$_2$Cl$_2$F$_2$S$_2$: 474.9920).

Elemental Analysis for $C_{19}H_{14}N_2O_2Cl_2F_2S_2$: Calculated: C, 48.01; H, 2.97; N, 5.89; Cl, 14.92; F, 7.99; S, 13.49. Found: C, 48.27; H, 2.95; N, 5.91; Cl, 14.79; F, 7.96; S, 13.61.

Example 221

N-[5-Chloro-4-[(4-chlorophenylsulfinyl)(2,5-difluorophenyl)methyl]pyridin-2-yl]methanesulfonamide

[Chemical formula 107]

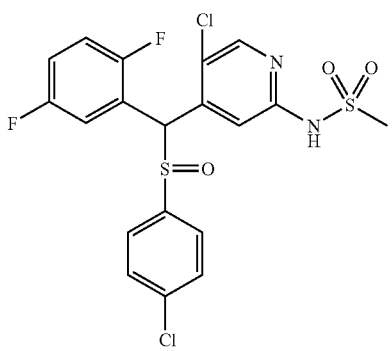

To a methylene chloride (10 ml) solution of N-[5-chloro-4-[(4-chlorophenylthio)(2,5-difluorophenyl)methyl]pyridin-2-yl]methanesulfonamide (331 mg, 0.696 mmol) was added 3-chloroperbenzoic acid (120 mg, 0.696 mmol) at 0° C. The resulting mixture was stirred at 0° C. for 50 minutes. At the same temperature, 3-chloroperbenzoic acid (60 mg, 0.348 mmol) was added to the reaction mixture. After stirring at 0° C. for 10 minutes, a saturated aqueous solution of sodium thiosulfate was added to the reaction mixture. The resulting mixture was extracted with methylene chloride. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate (=2:1) eluate was concentrated under reduced pressure. To the residue thus obtained was added ether and the solid thus precipitated was collected by filtration to give the title compound (281 mg, 0.572 mmol, 82%) as a white powder.

$^1$H-NMR (400 MHz, CDCl$_3$) δ: 3.36 (3H, s), 5.48 (0.5H, s), 5.66 (0.5H, s), 6.79-6.88 (0.5H, m), 6.95-7.09 (1.5H, m), 7.18-7.44 (5H, m), 7.64 (0.5H, s), 7.83 (0.5H, s), 8.23 (0.5H, s), 8.36 (0.5H, s), 8.70 (1H, brs).

IR(ATR)cm$^{-1}$: 3124, 3081, 1594, 1492, 1463, 1334, 1143, 964, 871, 821, 742.

MS m/z: 491 (M$^+$+H).

FAB-MS: 490.9853 (Calcd for $C_{19}H_{15}O_3N_2Cl_2F_2S_2$: 490.9869).

Elemental Analysis for $C_{19}H_{14}N_2O_3Cl_2F_2S_2$: Calculated: C, 46.44; H, 2.87; N, 5.70; Cl, 14.43; F, 7.73; S, 13.05. Found: C, 46.64; H, 3.02; N, 5.64; Cl, 14.31; F, 7.74; S, 13.02.

Example 222

[5-Chloro-4-[(4-chlorophenylsulfonyl)(2,5-difluorophenyl)methyl]pyridin-2-yl]hydrazine

[Chemical formula 108]

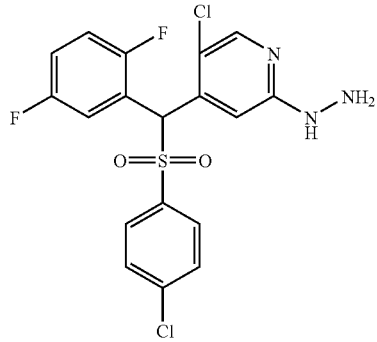

To an ethanol (10 ml) solution of the 2,5-dichloro-4-[(4-chlorophenylsulfonyl)(2,5-difluorophenyl)methyl]pyridine (524 mg, 1.17 mmol) obtained in Example 57 was added hydrazine monohydrate (2 ml). The resulting mixture was heated under reflux for 3 hours. After cooling to room temperature, the reaction mixture was concentrated under reduced pressure. The residue thus obtained was subjected to silica gel column chromatography. The fraction obtained from the hexane:ethyl acetate (=1:1) eluate was concentrated under reduced pressure to afford a pale yellow oil. To the resulting oil was added hexane-ether and the solid thus precipitated was collected by filtration to give the title compound (95 mg, 0.214 mmol, 18%) as a white powder.

$^1$H-NMR (400 MHz, CDCl$_3$) δ: 3.89 (2H, s), 6.03 (1H, s), 6.16 (1H, s), 6.89-6.97 (1H, m), 7.00-7.09 (1H, m), 7.44 (2H, d, J=8.8 Hz), 7.50-7.58 (1H, m), 7.60-7.68 (3H, m), 8.03 (1H, s).

IR(ATR)cm$^{-1}$: 3249, 1590, 1550, 1492, 1413, 1315, 1174, 1149, 1083, 811, 754.

MS m/z: 443 (M$^+$).

Elemental Analysis for $C_{18}H_{13}N_3O_2Cl_2F_2S$: Calculated: C, 48.66; H, 2.95; N, 9.46; Cl, 15.96; F, 8.55; S, 7.22. Found: C, 48.48; H, 2.81; N, 9.40; Cl, 15.80; F, 8.59; S, 7.23.

Example 223 t-Butyl N'-[5-chloro-4-[(4-chlorophenylsulfonyl)(2,5-difluorophenyl)methyl]pyridin-2-yl]hydrazine carboxylate

[Chemical formula 109]

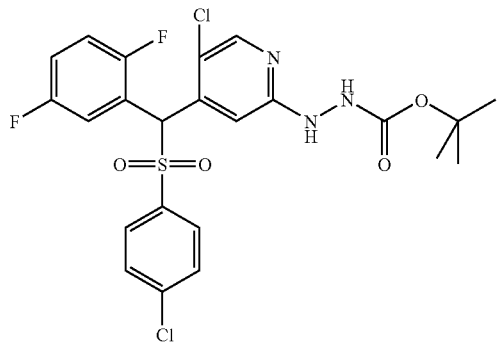

To a methylene chloride (5 ml) solution of [5-chloro-4-[(4-chlorophenylsulfonyl)(2,5-difluorophenyl)methyl]pyridin-2-yl]hydrazine (166 mg, 0.374 mmol) was added di-t-butyl dicarbonate (122 mg, 0.560 mmol). The resulting mixture was stirred at room temperature for 16 hours. The reaction mixture was concentrated under reduced pressure. The residue thus obtained was subjected to flash silica gel column chromatography. The fraction obtained from the hexane:ethyl acetate (=3:1) eluate was concentrated under reduced pressure to give the title compound (166 mg, 0.305 mmol, 82%) as a white solid.

$^1$H-NMR (400 MHz, CDCl$_3$) δ: 1.51 (9H, s), 6.19 (1H, s), 6.42 (1H, s), 6.59 (1H, brs), 6.91-7.09 (2H, m), 7.43 (2H, d, J=8.8 Hz), 7.50-7.56 (1H, m), 7.57 (1H, s), 7.63 (2H, d, J=8.8 Hz), 8.06 (1H, s).

IR(ATR)cm$^{-1}$: 3336, 3295, 1681, 1596, 1558, 1496, 1477, 1321, 1151, 1091, 809.

MS m/z: 544 (M$^+$+H).

Example 224 t-Butyl N'-[5-chloro-4-[(4-chlorophenylsulfonyl)(2,5-difluorophenyl)methyl]pyridin-2-yl]-N'-methylsulfonylhydrazine carboxylate

[Chemical formula 110]

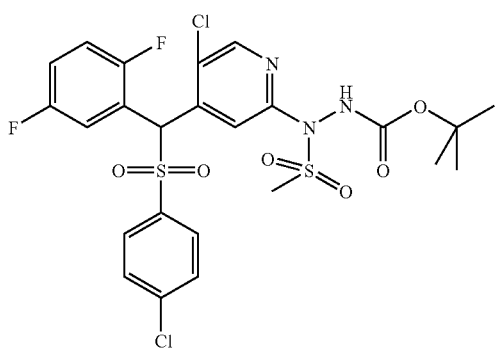

To a methylene chloride (5 ml) solution of t-butyl N'-[5-chloro-4-[(4-chlorophenylsulfonyl)(2,5-difluorophenyl)methyl]pyridin-2-yl]hydrazine carboxylate (178 mg, 0.327 mmol) and triethylamine (43 μl, 0.392 mmol) was added methanesulfonyl chloride (30 μl, 0.392 mmol) at 0° C. The resulting mixture was stirred at room temperature for 16 hours. To the reaction mixture were added triethylamine (43 μl, 0.392 mmol) and methanesulfonyl chloride (30 μl, 0.392 mmol). After stirring at room temperature for 3 hours, the reaction mixture was concentrated under reduced pressure. The residue thus obtained was diluted with ethyl acetate. The diluted solution was washed sequentially with a saturated aqueous solution of sodium bicarbonate and brine, dried over anhydrous sodium sulfate and filtered. The filtrate was concentrated under reduced pressure. The residue thus obtained was subjected to flash silica gel column chromatography. The fraction obtained from the hexane:ethyl acetate (=4:1) eluate was concentrated under reduced pressure to give the title compound (174 mg, 0.280 mmol, 85%) as a white solid.

$^1$H-NMR (400 MHz, CDCl$_3$) δ: 1.52 (9H, s), 3.56 (3H, s), 6.21 (1H, s), 6.92-7.10 (2H, m), 7.31 (1H, brs), 7.44 (2H, d, J=8.7 Hz), 7.47-7.54 (1H, m), 7.63 (2H, d, J=8.7 Hz), 8.05 (1H, s), 8.28 (1H, s).

IR(ATR)cm$^{-1}$: 3320, 1731, 1583, 1494, 1353, 1326, 1236, 1149, 1091, 958, 754, 728.

MS m/z: 622 (M$^+$+H).

Example 225

1-[5-Chloro-4-[(4-chlorophenylsulfonyl)(2,5-difluorophenyl)methyl]pyridin-2-yl]-1-methylsulfonylhydrazine

[Chemical formula 111]

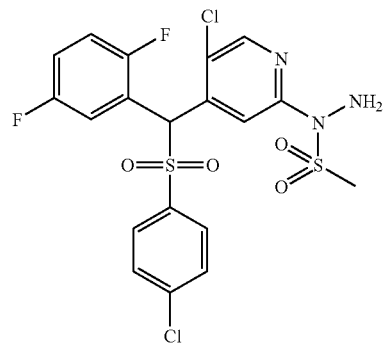

To a methylene chloride (5 ml) solution of t-butyl N'-[5-chloro-4-[(4-chlorophenylsulfonyl)(2,5-difluorophenyl)methyl]pyridin-2-yl]-N'-methylsulfonylhydrazine carboxylate (167 mg, 0.268 mmol) was added trifluoroacetic acid (2.5 ml). The resulting mixture was stirred at room temperature for 21 hours, followed by concentration under reduced pressure. To the residue thus obtained was added a saturated aqueous solution of sodium bicarbonate. The resulting mixture was extracted with methylene chloride. The organic layer obtained by separation was dried over anhydrous sodium sulfate, and filtered. The filtrate was concentrated under reduced pressure. The residue thus obtained was subjected to flash silica gel column chromatography. The fraction obtained from the hexane:ethyl acetate (=2:1) eluate was concentrated under reduced pressure to afford the title compound (91 mg, 0.174 mmol, 65%) as a white solid. The resulting solid was washed with ether and collected by filtration to give the title compound (60 mg) as a white powder.

$^1$H-NMR (400 MHz, CDCl$_3$) δ: 3.25 (3H, s), 4.80 (2H, brs), 6.25 (1H, s), 6.90-7.10 (2H, m), 7.44 (2H, d, J=8.6 Hz), 7.53-7.61 (1H, m), 7.68 (2H, d, J=8.6 Hz), 8.32 (1H, s), 8.44 (1H, s).

mp: 152 to 154° C.

IR(ATR)cm$^{-1}$: 1583, 1490, 1361, 1319, 1149, 1079, 958, 833, 754.

MS m/z: 522 (M$^+$+H).

Elemental Analysis for $C_{19}H_{15}N_3O_4Cl_2F_2S_2$: Calculated: C, 43.69; H, 2.89; N, 8.04; Cl, 13.57; F, 7.27; S, 12.28. Found: C, 43.86; H, 2.93; N, 7.91; Cl, 13.19; F, 7.31; S, 12.28.

Referential Example 41

2,5-Dibromo-4-[(2,5-difluorophenyl)hydroxymethyl]pyridine

[Chemical formula 112]

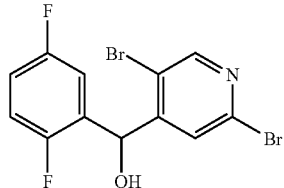

Under an argon atmosphere, n-butyl lithium (a 1.59M hexane solution, 76 ml, 121 mmol) was added to a tetrahydrofuran (400 ml) solution of diisopropylamine (17 ml, 121 mmol) at −70° C. The reaction mixture was stirred for 1 hour. To the reaction mixture was added dropwise a tetrahydrofuran (100 ml) solution of 2,5-dibromopyridine and the resulting mixture was stirred for 2 hours. To the reaction mixture was added dropwise 2,5-difluorobenzaldehyde (15 ml, 139 mmol) and the mixture was stirred for 1 hour. After addition of water, the resulting mixture was concentrated under reduced pressure. The residue thus obtained was extracted with dichloromethane. The organic layer thus obtained was dried over magnesium sulfate, and concentrated under reduced pressure. The residue thus obtained was washed with dichloromethane:hexane to yield a pale yellow powder. The filtrate was subjected to silica gel column chromatography. The fraction obtained from the hexane:ethyl acetate=6:1 eluate was concentrated under reduced pressure. The residue thus obtained and the above-described pale yellow powder were combined to give the title compound (18.4 g, 48.6 mmol, 52%) as a pale yellow powder.

$^1$H-NMR (400 MHz, CDCl$_3$) δ: 2.62 (1H, s), 6.24 (1H, s), 6.85-6.89 (1H, m), 7.00-7.10 (2H, m), 7.79 (1H, s), 8.43 (1H, s).

MS m/z: 378 (M$^+$+H).

Example 226

2,5-Dibromo-4-[(4-chlorophenylthio)(2,5-difluorophenyl)methyl]pyridine

[Chemical formula 113]

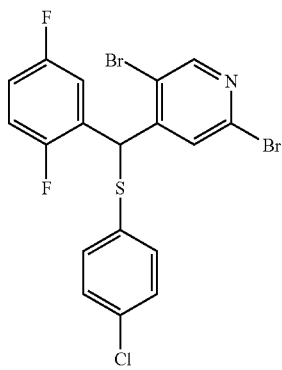

Under an argon atmosphere, triethylamine (5.1 ml, 36.8 mmol) and methanesulfonyl chloride (2.6 ml, 31.9 mmol) were added to a dichloromethane solution (200 ml) of 2,5-dibromo-4-[(2,5-difluorophenyl)hydroxymethyl]pyridine (9.3 g, 24.5 mmol) under ice cooling. The reaction mixture was stirred at room temperature for 30 minutes. After addition of water, the resulting mixture was concentrated under reduced pressure. The residue thus obtained was extracted with diethyl ether. The organic layer was washed with brine, dried over anhydrous magnesium sulfate, and concentrated under reduced pressure.

To a dimethylformamide (200 ml) solution of the residue thus obtained were added 4-chlorobenzenethiol (4.3 g, 29.4 mmol) and potassium carbonate (5.1 g, 36.8 mmol). The resulting mixture was stirred at room temperature for 17 hours. After addition of water, the resulting mixture was extracted with diethyl ether. The organic layer was washed with brine, dried over anhydrous magnesium sulfate, and concentrated under reduced pressure. The residue thus obtained was washed with hexane to afford a white powder. The filtrate was subjected to flash silica gel column chromatography. The fraction obtained from the dichloromethane eluate was concentrated under reduced pressure. The residue thus obtained and the above-described white powder were combined to give the title compound (9.1 g, 18.0 mmol, 73%) as a white powder.

$^1$H-NMR (400 MHz, CDCl$_3$) δ: 5.94 (1H, s), 7.00-7.05 (2H, m), 7.15-7.20 (1H, m), 7.25 (2H, d, J=8.6 Hz), 7.29 (2H, d, J=8.6 Hz), 7.68 (1H, s), 8.45 (1H, s).

MS m/z: 504 (M$^+$+H).

Example 227

[5-Bromo-4-[(4-chlorophenylthio)(2,5-difluorophenyl)methyl]pyridin-2-yl]methanol

[Chemical formula 114]

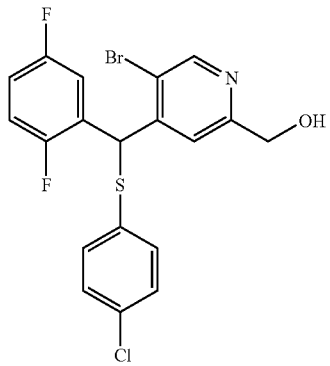

Under an argon atmosphere, n-butyl lithium (a 1.59M hexane solution, 0.27 ml, 0.435 mmol) was added to a toluene (10 ml) solution of 2,5-dibromo-4-[(4-chlorophenylthio)(2,5-difluorophenyl)methyl]pyridine (200 mg, 0.396 mmol) at −78° C. The reaction mixture was stirred for 2 hours. To the reaction mixture was added dropwise dimethylformamide (40 μl, 0.514 mmol), followed by stirring for 1 hour. To the reaction mixture were added methanol (10 ml) and sodium borohydride (30 mg, 0.791 mmol). The temperature of the resulting mixture was raised to room temperature. The reaction mixture was stirred for 1 hour. After addition of water, the resulting mixture was extracted with ethyl acetate. The extract was washed with brine. The organic layer thus obtained was dried over magnesium sulfate, and concentrated under reduced pressure. The residue thus obtained was subjected to flash silica gel column chromatography. The fraction obtained from the hexane:ethyl acetate=3:1 eluate was concentrated under reduced pressure to give the title compound (160 mg, 0.350 mmol, 89%) as a colorless amorphous substance.

$^1$H-NMR (400 MHz, CDCl$_3$) δ: 3.18 (1H, t, J=5.2 Hz), 4.72 (2H, d, J=5.2 Hz), 6.04 (1H, s), 6.95-7.05 (2H, m), 7.16-7.21 (1H, m), 7.22 (2H, d, J=7.8 Hz), 7.25 (2H, d, J=7.8 Hz), 7.51 (1H, s), 8.64 (1H, s)

MS m/z: 456 (M$^+$+H).

Example 228

[5-Bromo-4-[(4-chlorophenylsulfonyl)(2,5-difluorophenyl)methyl]pyridin-2-yl]methanol

[Chemical formula 115]

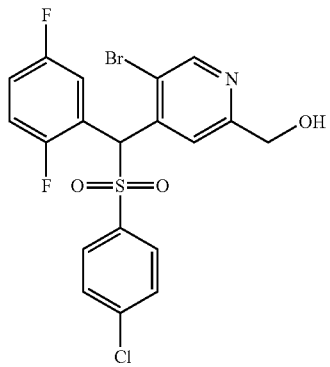

To a solution of [5-bromo-4-[(4-chlorophenylthio)(2,5-difluorophenyl)methyl]pyridin-2-yl]methanol (550 mg, 1.20 mmol) in a mixture of methanol (10 ml) and ethyl acetate (10 ml) were added hexaammonium heptamolybdate tetrahydrate (100 mg) and 30% aqueous hydrogen peroxide (10 ml). The resulting mixture was stirred for 19 hours. After addition of water, the resulting mixture was extracted with ethyl acetate. The extract was washed sequentially with water, a saturated aqueous solution of sodium bicarbonate, a saturated aqueous solution of sodium thiosulfate and brine. The organic layer thus obtained was dried over magnesium sulfate, and concentrated under reduced pressure. The residue thus obtained was subjected to flash silica gel column chromatography. The fraction obtained from the hexane:ethyl acetate=2:1 eluate was concentrated under reduced pressure, followed by recrystallization from hexane:ethyl acetate to give the title compound (506 mg, 1.04 mmol, 86%) as a white powder.

$^1$H-NMR (400 MHz, CDCl$_3$) δ: 3.18 (1H, t, J=5.0 Hz), 4.79-4.88 (2H, m), 6.24 (1H, s), 6.92-6.97 (1H, m), 7.03-7.09 (1H, m), 7.45 (2H, d, J=8.6 Hz), 7.51-7.55 (1H, m), 7.61 (2H, d, J=8.6 Hz), 8.11 (1H, s), 8.65 (1H, s).

IR(ATR)cm$^{-1}$: 3262, 1583, 1492, 1427, 1392, 1330, 1280, 1236, 1157, 1083, 1033.

mp: 172 to 173° C.

MS m/z: 488 (M$^+$+H).

Elemental Analysis for C$_{19}$H$_{13}$BrClF$_2$NO$_3$S: Calculated: C, 46.69; H, 2.68; Br, 16.35; Cl, 7.25; F, 7.77; N, 2.87; S, 6.56. Found: C, 46.59; H, 2.55; Br, 16.31; Cl, 7.05; F, 7.78; N, 2.89; S, 6.70.

Example 229

[5-Bromo-4-[(4-chlorophenylsulfonyl)(2,5-difluorophenyl)methyl]pyridin-2-yl]carbaldehyde

[Chemical formula 116]

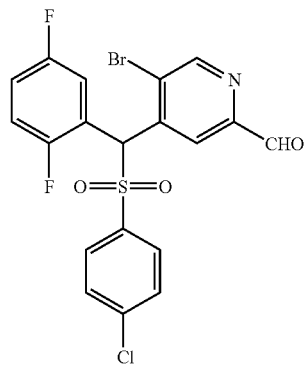

Under a nitrogen atmosphere, dimethyl sulfoxide (218 μl, 3.07 mmol), triethylamine (428 μl, 3.07 mmol) and sulfur trioxide pyridine complex (293 mg, 1.84 mmol) were added to a dichloromethane (10 ml) solution of [5-bromo-4-[(4-chlorophenylsulfonyl)(2,5-difluorophenyl)methyl]pyridin-2-yl]methanol (300 mg, 0.614 mmol). The reaction mixture was stirred at room temperature for 4 hours. The reaction mixture was concentrated under reduced pressure. The residue thus obtained was subjected to flash silica gel column chromatography. The fraction obtained from the hexane:ethyl acetate=3:1 eluate was concentrated under reduced pressure to give the title compound (227 mg, 0.466 mmol, 76%) as a colorless amorphous substance.

$^1$H-NMR (400 MHz, CDCl$_3$) δ: 6.29 (1H, s), 6.93-7.00 (1H, m), 7.04-7.10 (1H, m), 7.44 (2H, d, J=8.8 Hz), 7.57-7.62 (1H, m), 7.62 (2H, d, J=8.8 Hz), 8.68 (1H, s), 8.88 (1H, s), 10.09 (1H, s).

MS m/z: 486 (M$^+$+H).

Example 230

5-Bromo-4-[(4-chlorophenylsulfonyl)(2,5-difluorophenyl)methyl]picolinic acid

[Chemical formula 117]

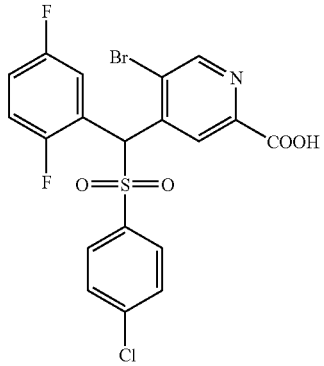

To a formic acid (5 ml) solution of [5-bromo-4-[(4-chlorophenylsulfonyl)(2,5-difluorophenyl)methyl]pyridin-2-yl]carbaldehyde (225 mg, 0.462 mmol) was added 30% aqueous hydrogen peroxide (157 μl, 1.39 mmol). The resulting mixture was stirred at room temperature for 3 hours. To the reaction mixture was added water and the solid thus precipitated was filtered. The solid thus obtained was washed with water. The resulting solid was dissolved in ethyl acetate. The resulting solution was washed sequentially with water and brine. The organic layer thus obtained was dried over magnesium sulfate and concentrated under reduced pressure to give the title compound (226 mg, 0.461 mmol, 97%) as a white powder.

$^1$H-NMR (400 MHz, CDCl$_3$) δ: 6.30 (1H, s), 6.94-6.99 (1H, m), 7.05-7.11 (1H, m), 7.46 (2H, d, J=8.8 Hz), 7.61-7.66 (1H, m), 7.65 (2H, d, J=8.8 Hz), 8.75 (1H, s), 8.94 (1H, s).

MS m/z: 502 (M$^+$+H).

Example 231 t-Butyl[5-bromo-4-[(4-chlorophenylsulfonyl)(2,5-difluorophenyl)methyl]pyridin-2-yl]carbamate

[Chemical formula 118]

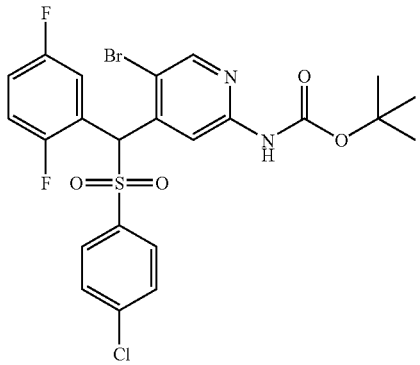

Under an argon atmosphere, diphenylphosphoryl azide (131 μl, 0.613 mmol) and triethylamine (122 μl, 0.875 mmol) were added to a solution of 5-bromo-4-[(4-chlorophenylsulfonyl)(2,5-difluorophenyl)methyl]picolinic acid (220 mg, 0.438 mmol) in a mixture of t-butanol (5 ml) and toluene (5 ml). The reaction mixture was stirred for 14 hours under heating and refluxing. After cooling, ethyl acetate was added to the residue. The resulting mixture was washed sequentially with a saturated aqueous solution of sodium bicarbonate and brine. The organic layer thus obtained was dried over magnesium sulfate, and concentrated under reduced pressure. The residue thus obtained was subjected to flash silica gel column chromatography. The fraction obtained from the hexane:ethyl acetate=4:1 eluate was concentrated under reduced pressure to give the title compound (128 mg, 0.223 mmol, 51%) as a white powder.

$^1$H-NMR (400 MHz, CDCl$_3$) δ: 1.59 (9H, s), 6.23 (1H, s), 6.92-7.00 (1H, m), 7.02-7.08 (1H, m), 7.33 (1H, brs), 7.43 (2H, d, J=8.4 Hz), 7.57-7.62 (1H, m), 7.71 (2H, d, J=8.4 Hz), 8.28 (1H, s), 8.86 (1H, s).

MS m/z: 573 (M$^+$+H).

Example 232

[5-Bromo-4-[(4-chlorophenylsulfonyl)(2,5-difluorophenyl)methyl]pyridin-2-yl]amine

[Chemical formula 119]

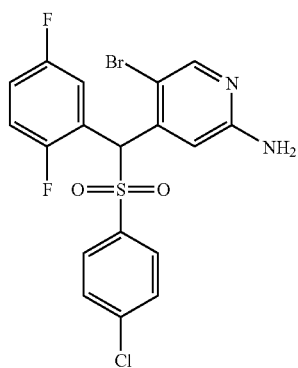

To an ethanol (2 ml) solution of t-butyl[5-bromo-4-[(4-chlorophenylsulfonyl)(2,5-difluorophenyl)methyl]pyridin-2-yl]carbamate (130 mg, 0.227 mmol) was added concentrated hydrochloric acid (2 ml). The resulting mixture was stirred at room temperature for 63 hours. The reaction mixture was concentrated under reduced pressure. To the residue thus obtained was added saturated sodium bicarbonate, followed by extraction with ethyl acetate. The organic layer was washed with brine, dried over magnesium sulfate, and concentrated under reduced pressure. The residue thus obtained was recrystallized from hexane:ethyl acetate to give the title compound (72 mg, 0.152 mmol, 67%) as a pale yellow powder.

$^1$H-NMR (400 MHz, CDCl$_3$) δ: 4.67 (2H, s), 6.12 (1H, s), 6.91-6.97 (1H, m), 7.02-7.08 (1H, m), 7.36 (1H, s), 7.45 (2H, d, J=8.6 Hz), 7.48-7.54 (1H, m), 7.62 (2H, d, J=8.6 Hz), 8.11 (1H, s).

IR(ATR)cm$^{-1}$: 3467, 3372, 1617, 1585, 1540, 1492, 1475, 1413, 1330, 1311, 1280, 1238, 1178, 1151, 1081, 1033, 1012.

mp: 204 to 206° C.

MS m/z: 473 (M$^+$+H).

Elemental Analysis for C$_{18}$H$_{12}$BrClF$_2$N$_2$O$_2$S: Calculated: C, 45.64; H, 2.55; Br, 16.87; Cl, 7.48; F, 8.02; N, 5.91; S, 6.77. Found: C, 45.87; H, 2.58; Br, 16.61; Cl, 7.56; F, 8.05; N, 5.90; S, 6.90.

Referential Example 42

5-Cyano-2-fluorobenzaldehyde

[Chemical formula 120]

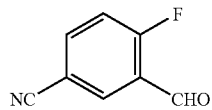

Diisopropylamine (2.80 ml, 19.8 mmol) was dissolved in tetrahydrofuran (20 ml). At −78° C., a hexane solution (1.60M, 11.4 ml, 18.2 mmol) of n-butyl lithium was added dropwise to the resulting solution. The reaction mixture was stirred at the same temperature for 30 minutes, followed by the dropwise addition of a tetrahydrofuran solution (20 ml) of 4-fluorobenzonitrile (2.00 g, 16.5 mmol). After stirring further at the same temperature for 30 minutes, N,N-dimethylformamide (1.7 ml, 21.5 mmol) was added dropwise to the reaction mixture. At the same temperature, the reaction mixture was stirred for 10 minutes. To the reaction mixture were added acetic acid and a saturated aqueous solution of ammonium chloride, followed by extraction with ethyl acetate. The organic layers were combined and dried over anhydrous sodium sulfate, and filtered. The filtrate was concentrated under reduced pressure. The residue thus obtained was subjected to silica gel chromatography. The fraction obtained from the n-hexane:ethyl acetate=10:2 eluate was concentrated under reduced pressure to give the title compound (1.83 g, 12.3 mmol, 74%) as a pale yellowish brown oil.

$^1$H-NMR (400 MHz, CD$_3$OD) δ: 7.37 (1H, t, J=9.0 Hz), 7.92 (1H, ddd, J=9.0, 6.4, 2.2 Hz), 8.21 (1H, dd, J=6.4, 2.2 Hz), 10.4 (1H, s).

IR(ATR)cm$^{-1}$: 1953, 1695, 1600, 1482, 1236, 1105, 846, 624, 580.

MS m/z: 150 (M$^+$+H).

Referential Example 43

3-[(2,5-Dichloropyridin-4-yl)hydroxymethyl]-4-fluorobenzonitrile

[Chemical formula 121]

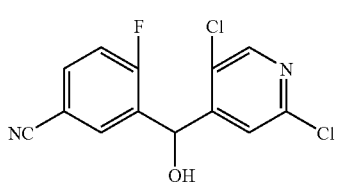

Diisopropylamine (0.52 ml, 3.70 mmol) was dissolved in tetrahydrofuran (5 ml). At −78° C., a hexane solution (1.54M, 2.20 ml, 3.39 mmol) of n-butyl lithium was added dropwise to the resulting solution. The reaction mixture was stirred at the same temperature for 30 minutes. A tetrahydrofuran solution (20 ml) of 2,5-dichloropyridine (0.46 g, 3.08 mmol) was added dropwise to the reaction mixture. After stirring further at the same temperature for 1 hour, a tetrahydrofuran solution (5 ml) of 5-cyano-2-fluorobenzaldehyde (0.46 g, 3.08 mmol) was added dropwise to the reaction mixture. The resulting mixture was stirred at the same temperature for 30 minutes. To the reaction mixture was added a saturated aqueous solution of ammonium chloride, followed by extraction with ethyl acetate. The organic layers were combined, dried over anhydrous magnesium sulfate, and filtered. The filtrate was concentrated under reduced pressure. The residue thus obtained was subjected to silica gel chromatography. The fraction obtained from the n-hexane:ethyl acetate=10:2 eluate was concentrated under reduced pressure to give the title compound (0.68 g, 2.28 mmol, 74%) as a pale yellowish brown oil.

¹H-NMR (400 MHz, CDCl₃) δ: 6.33 (1H, s), 7.22 (1H, t, J=8.3 Hz), 7.60 (1H, dd, J=6.6, 2.2 Hz), 7.66 (1H, s), 7.66-7.69 (1H, m), 8.34 (1H, s).
IR(ATR)cm⁻¹: 3413, 1577, 1492, 1334, 1247, 1110, 829, 534.
MS m/z: 297 (M⁺+H).

Example 233

3-[(4-Chlorophenylsulfonyl)(2,5-dichloropyridin-4-yl)methyl]-4-fluorobenzonitrile

[Chemical formula 122]

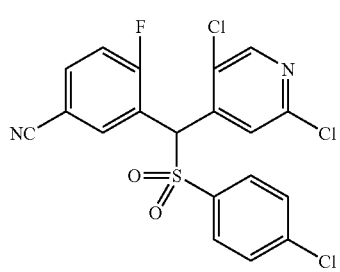

Under ice cooling, thionyl chloride (3 ml) and a catalytic amount of N,N-dimethylformamide were added to a dichloromethane solution (5 ml) of 3-[(2,5-dichloropyridin-4-yl)hydroxymethyl]-4-fluorobenzonitrile (677 mg, 2.28 mmol). The resulting mixture was stirred at room temperature for 4 hours. Water was added to the reaction mixture, followed by extraction with dichloromethane. The organic layers were combined, dried over anhydrous sodium sulfate, and filtered. The filtrate was concentrated under reduced pressure.

The residue thus obtained was dissolved in N,N-dimethylformamide (5 ml). To the resulting solution was added sodium 4-chlorobenzenesulfinate (905 mg, 4.56 mmol). The resulting mixture was stirred at room temperature for 20 hours. Water was added to the reaction mixture, followed by extraction with ethyl acetate. The organic layers were combined, dried over anhydrous sodium sulfate, and filtered. The filtrate was concentrated under reduced pressure. The residue thus obtained was subjected to silica gel chromatography. The fraction obtained from the n-hexane:ethyl acetate=10:2 eluate was concentrated under reduced pressure to give the title compound (170 mg, 0.37 mmol, 16%) as a pale yellowish brown solid.

¹H-NMR (400 MHz, CDCl₃) δ: 6.19 (1H, s), 7.15 (1H, t, J=8.5 Hz), 7.48 (2H, d, J=8.5 Hz), 7.62 (2H, d, J=8.5 Hz), 7.72 (1H, ddd, J=8.5, 5.4, 2.4 Hz), 8.12 (1H, dd, J=5.4, 2.4 Hz), 8.13 (1H, s), 8.36 (1H, s).
IR(ATR)cm⁻¹: 1569, 1494, 1315, 1257, 1120, 1081, 752, 617, 570, 536.
MS m/z: 456 (M⁺).

Example 234

3-[(2-Amino-5-chloropyridin-4-yl)(4-chlorophenylsulfonyl)methyl]-4-fluorobenzonitrile

[Chemical formula 123]

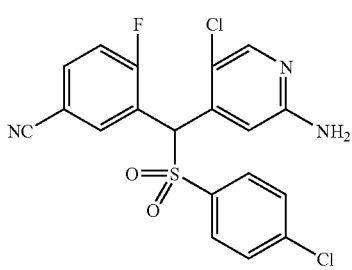

In N-methylpyrrolidone (12 ml) was dissolved 3-[(4-chlorobenzenesulfonyl)(2,5-dichloropyridin-4-yl)methyl]-4-fluorobenzonitrile (559 mg, 1.23 mmol), followed by the addition of 3,4-dimethoxybenzylamine (0.91 ml, 6.13 mmol). The resulting mixture was stirred under heating at 140° C. for 4 hours. Water was added to the reaction mixture, followed by extraction with ethyl acetate. The extract was washed with brine. The organic layer was dried over anhydrous sodium sulfate, and filtered. The filtrate was concentrated under reduced pressure. The residue thus obtained was subjected to silica gel chromatography. The fraction obtained from the n-hexane:ethyl acetate=2:1 eluate was concentrated under reduced pressure.

The residue thus obtained was dissolved in trifluoroacetic acid (5 ml) and the resulting solution was stirred under heating at 70° C. for 2 hours. The reaction mixture was concentrated under reduced pressure. The residue thus obtained was subjected to silica gel chromatography. The fraction obtained from the n-hexane:ethyl acetate=2:1 eluate was concentrated under reduced pressure to give the title compound (50 mg 0.11 mmol, 9%) as a white powder.

¹H-NMR (400 MHz, CDCl₃) δ: 4.74 (2H, s), 6.16 (1H, s), 7.12 (1H, t, J=8.8 Hz), 7.32 (1H, s), 7.48 (2H, d, J=8.5 Hz), 7.62 (2H, d, J=8.5 Hz), 7.98 (1H, s), 8.15 (1H, dd, J=8.8, 2.0 Hz), 8.55 (1H, d, J=2.0 Hz).
IR(ATR)cm⁻¹: 1614, 1475, 1411, 1311, 1259, 1145, 1091, 755, 642, 620, 561, 543, 460.
mp: >220° C.
MS m/z: 436 (M⁺+H).
Elemental Analysis for C₁₉H₁₂Cl₂FN₃O₂S: Calculated: C, 52.31; H, 2.77; Cl, 16.25; F, 4.35; N, 9.63; S, 7.35. Found: C, 52.17; H, 2.85; Cl, 16.50; F, 4.32; N, 9.40; S, 7.30.

Example 235

N-[5-Chloro-4-[(4-chlorophenylsulfonyl)(5-cyano-2-fluorophenyl)methyl]pyridin-2-yl]-N-(methylsulfonyl)methanesulfonamide

[Chemical formula 124]

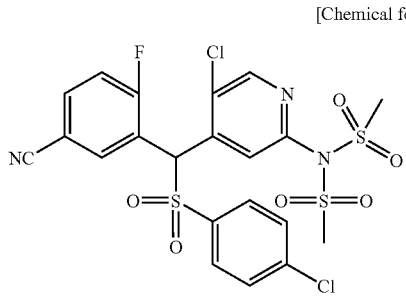

After 3-[(2-amino-5-chloropyridin-4-yl)(4-chlorophenylsulfonyl)methyl]-4-fluorobenzonitrile (50 mg, 0.11 mmol) was dissolved in dichloromethane (5 ml), ethanesulfonyl chloride (27 μl, 0.39 mmol), triethylamine (48 μl, 0.39 mmol) and a catalytic amount of 4-dimethylaminopyridine were added to the resulting solution at 0° C. The resulting mixture was stirred at the same temperature for 30 minutes. Water was added and the resulting mixture was extracted with dichloromethane. The extract was washed with brine. The organic layer was dried over anhydrous sodium sulfate and filtered. The filtrate was concentrated under reduced pressure. The residue thus obtained was subjected to silica gel chromatography. The fraction obtained from the n-hexane:ethyl acetate=10:3 eluate was concentrated under reduced pressure to give the title compound (80 mg, 0.11 mmol, 99%) as a white powder.

¹H-NMR (400 MHz, CDCl₄) δ: 3.65 (6H, s), 6.25 (1H, s), 7.24 (1H, t, J=8.8 Hz), 7.45 (2H, d, J=8.5 Hz), 7.66 (2H, d, J=8.5 Hz), 7.75 (1H, ddd, J=8.8, 6.6, 2.0 Hz), 8.16 (1H, s), 8.19 (1H, dd, J=6.6, 2.0 Hz), 8.43 (1H, s).

IR(ATR)cm$^{-1}$: 1725, 1583, 1492, 1369, 1326, 1164, 931, 835, 757, 628, 551, 505, 460.
MS m/z: 592 (M$^+$+H).

Example 236

N-[5-Chloro-4-[(4-chlorophenylsulfonyl)(5-cyano-2-fluorophenyl)methyl]pyridin-2-yl]methanesulfonamide

[Chemical formula 125]

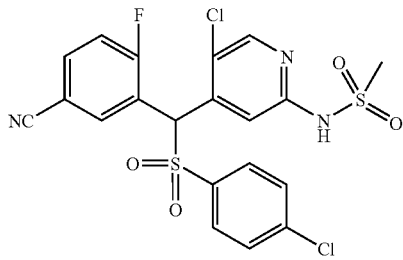

After N-[5-chloro-4-[(4-chlorophenylsulfonyl)(5-cyano-2-fluorophenyl)methyl]pyridin-2-yl]-N-(methylsulfonyl)methanesulfonamide (80 mg, 0.11 mmol) was dissolved in tetrahydrofuran (3 ml), a tetrahydrofuran solution (1.0M, 0.15 ml, 0.15 mmol) of tetrabutylammonium fluoride was added to the resulting solution at 0° C. The resulting mixture was stirred at room temperature for 1 hour. The residue obtained by concentrating the reaction mixture under reduced pressure was subjected to silica gel chromatography. The fraction obtained from the n-hexane:ethyl acetate=2:1 eluate was concentrated under reduced pressure to afford a white solid. The resulting white solid was washed with ether to give the title compound (32 mg, 0.06 mmol, 46%) as a white powder.

$^1$H-NMR (400 MHz, CDCl$_3$) δ: 3.37 (3H, s), 6.20 (1H, s), 7.14 (1H, d, J=8.8 Hz), 7.48 (2H, d, J=8.5 Hz), 7.62 (2H, d, J=8.5 Hz), 7.68-7.72 (1H, m), 7.92 (1H, s), 8.11 (1H, dd, J=6.6, 2.0 Hz), 8.34 (1H, s).
IR(ATR)cm$^{-1}$: 1596, 1494, 1473, 1328, 1151, 1089, 755, 636, 541, 516.
mp: 118 to 120° C.
MS m/z: 514 (M$^+$+H).
Elemental Analysis for C$_{20}$H$_{14}$Cl$_2$FN$_3$O$_4$S$_2$: Calculated: C, 46.70; H, 2.74; Cl, 13.78; F, 3.69; N, 8.17; S, 12.47. Found: C, 47.00; H, 2.94; Cl, 13.64; F, 3.58; N, 8.15; S, 12.44.

Referential Example 44

5-Chloro-2-(2,2,5,5-tetramethyl-1,2,5-azadisilolidin-1-yl)pyridine

[Chemical formula 126]

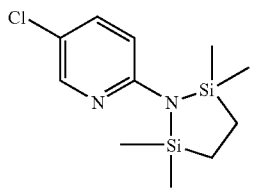

To a tetrahydrofuran (350 ml) solution of 5-chloropyridin-2-ylamine (10.28 g, 80.0 mmol) was added a hexane solution (1.58M, 50.6 ml, 80.0 mmol) of n-butyl lithium at −78° C. The resulting mixture was stirred for 1 hour. At the same temperature, a tetrahydrofuran (50 ml) solution of 1,2-bis(chlorodimethylsilyl)ethane (17.22 g, 80.0 mmol) was added to the reaction mixture, followed by stirring for 1 hour. A hexane solution (1.58M, 50.6 ml, 80.0 mmol) of n-butyl lithium was added at the same temperature and the resulting mixture was stirred for 30 minutes. At room temperature, a saturated aqueous solution of sodium chloride was added to the reaction mixture. Diethyl ether was added to the resulting mixture to separate it into layers. The organic layer was dried over anhydrous sodium sulfate, and filtered. The filtrate was concentrated under reduced pressure. The residue thus obtained was distilled under reduced pressure (120° C./3.0 mmHg) to give the title compound (12.97 g, 47.9 mmol, 60%) as a colorless acicular substance.

$^1$H-NMR (400 MHz, CDCl$_3$) δ: 0.29 (12H, s), 0.82 (4H, s), 6.50 (1H, d, J=8.8 Hz), 7.34 (1H, dd, J=8.8, 2.7 Hz), 8.05 (1H, d, J=2.7 Hz).

Referential Example 45

(2-Amino-5-chloropyridin-4-yl)(2,5-difluorophenyl)methanol

[Chemical formula 127]

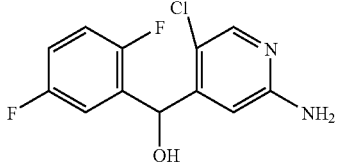

To a mixture of a hexane solution (1.58M, 8.41 ml, 13.3 mmol) of n-butyl lithium and tetrahydrofuran (40 ml) was added diisopropylamine (1.86 ml, 13.3 mmol) at −78° C. After the resulting mixture was stirred at 0° C. for 1 hour, the reaction mixture was cooled to −78° C. To the reaction mixture was added a tetrahydrofuran (10 ml) solution of 5-chloro-2-(2,2,5,5-tetramethyl-1,2,5-azadisilolidin-1-yl)pyridine (3.27 g, 12.1 mmol). At the same temperature, the resulting mixture was stirred for 1 hour. Then, a tetrahydrofuran (10 ml) solution of 2,5-difluorobenzaldehyde (1.89 g, 13.3 mmol) was added to the reaction mixture. After stirring at the same temperature for 30 minutes, 1N hydrochloric acid (50 ml) was added at 0° C. To the reaction mixture was added a 1N aqueous solution (100 ml) of sodium hydroxide. The product thus obtained was extracted with diethyl ether. The organic layer was dried over anhydrous sodium sulfate and filtered. The filtrate was concentrated under reduced pressure. The residue thus obtained was washed with a mixed solvent of dichloromethane/hexane, and collected by filtration to give the title compound (1.76 g, 6.50 mmol, 54%) as a white solid.

$^1$H-NMR (400 MHz, DMSO-d$_6$) δ: 5.96 (1H, d, J=4.9 Hz), 6.17 (2H, s), 6.31 (1H, d, J=4.9 Hz), 6.68 (1H, s), 6.97-7.04 (1H, m), 7.15-7.29 (2H, m), 7.82 (1H, s).
MS m/z: 271 (M$^+$+H).

Referential Example 46

(2-Amino-5-chloropyridin-4-yl)(2,5-difluorophenyl)methyl t-butyl carbonate

[Chemical formula 128]

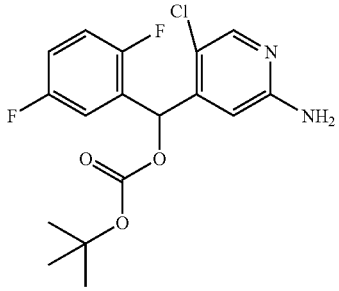

Under a nitrogen atmosphere, di-t-butyl dicarbonate (3.63 g, 16.6 mmol) and 4-dimethylaminopyridine (203 mg, 1.66 mmol) were added to a dichloromethane (150 ml) solution of (2-amino-5-chloropyridin-4-yl)(2,5-difluorophenyl)methanol (4.50 g, 16.6 mmol) at room temperature. The resulting mixture was stirred at room temperature for 2 hours. The reaction mixture was concentrated under reduced pressure. The residue thus obtained was subjected to flash silica gel chromatography. The fraction obtained from the dichloromethane:methanol=50:1 eluate was concentrated under reduced pressure to give the title compound (5.70 g, 15.4 mmol, 92%) as a white solid.

$^1$H-NMR (400 MHz, CDCl$_3$) δ: 1.49 (9H, s), 4.53 (2H, s), 6.66 (1H, s), 6.89-6.95 (1H, m), 6.99-7.09 (2H, m), 7.00 (1H, s), 8.01 (1H, s).

MS m/z: 371 (M$^+$+H).

Referential Example 47 t-Butyl[5-chloro-4-[(2,5-difluorophenyl)(hydroxy)methyl]pyridin-2-yl]carbamate

[Chemical formula 129]

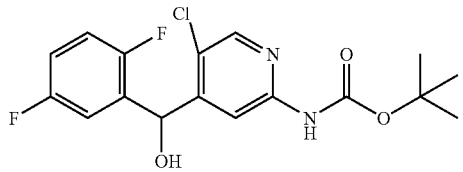

Under a nitrogen atmosphere, a tetrahydrofuran solution (1M, 33.8 ml, 33.8 mmol) of sodium bis(trimethylsilyl)amide was added to a tetrahydrofuran (80 ml) solution of (2-amino-5-chloropyridin-4-yl)(2,5-difluorophenyl)methyl t-butyl carbonate (5.70 g, 15.4 mmol) at 0° C., followed by further addition of a tetrahydrofuran (20 ml) solution of di-t-butyl dicarbonate (3.69 g, 16.9 mmol). After stirring at room temperature for 30 minutes, a saturated aqueous solution of ammonium chloride was added to the reaction mixture. The product thus obtained was extracted with dichloromethane. The organic layer was dried over anhydrous sodium sulfate, and filtered. The filtrate was concentrated under reduced pressure.

The residue thus obtained was dissolved in a mixed solvent of tetrahydrofuran (50 ml) and methanol (50 ml). To the resulting solution was added 1N sodium hydroxide (50 ml) at room temperature. The resulting mixture was stirred at 50° C. for 2 hours and concentrated under reduced pressure. The product thus obtained was extracted with dichloromethane. The residue was washed with an ethanol/hexane mixed solvent and collected by filtration to afford the title compound (3.49 g, 9.41 mmol, 61%) as a white solid. The filtrate was concentrated under reduced pressure. The residue thus obtained was washed with an ethanol/diethyl ether/hexane mixed solvent and collected by filtration to give the title compound (828 mg, 2.23 mmol, 15%) as a white solid.

$^1$H-NMR (400 MHz, CDCl$_3$) δ: 1.54 (9H, s), 2.69 (1H, d, J=4.9 Hz), 6.32 (1H, d, J=4.9 Hz), 6.88-7.08 (3H, m), 7.81 (1H, s), 8.17 (1H, s), 8.33 (1H, s).

MS m/z: 371 (M$^+$+H).

Referential Example 48

O-Ethyl S-(4-chloro-3-methoxyphenyl)dithiocarbonate

[Chemical formula 130]

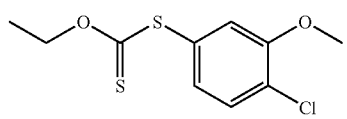

In 1N hydrochloric acid (80 ml) was dissolved 4-chloro-3-methoxyaniline (2.77 g, 17.6 mmol). After dropwise addition of a water (10 ml) solution of sodium nitrite (1.33 g, 19.3 mmol) to the resulting solution at 0° C., the reaction mixture was stirred at the same temperature for 30 minutes. The temperature of the reaction mixture was raised to 60° C. At the same temperature, a water (30 ml) solution of potassium O-ethyl dithiocarbonate (3.10 g, 19.3 mmol) was added dropwise to the reaction mixture. The temperature of the reaction mixture was raised to 90° C. After stirring for 1 hour, the reaction mixture was cooled to room temperature. A saturated aqueous solution of sodium bicarbonate was added to the reaction mixture. The product thus obtained was extracted with ethyl acetate. The organic layer was dried over anhydrous sodium sulfate, and filtered. The filtrate was concentrated under reduced pressure and the residue thus obtained was subjected to flash silica gel column chromatography. The fraction obtained from the hexane:dichloromethane=9:1 eluate was concentrated under reduced pressure to give the title compound (1.05 g, 4.00 mmol, 23%) as a yellow oil.

$^1$H-NMR (400 MHz, CDCl$_3$) δ: 1.35 (3H, t, J=7.1 Hz), 3.91 (3H, s), 4.62 (2H, q, J=7.1 Hz), 7.03-7.08 (2H, m), 7.41 (1H, d, J=8.1 Hz).

MS m/z: 263 (M$^+$+H).

Example 237 t-Butyl[5-chloro-4-[(4-chloro-3-methoxyphenylthio)(2,5-difluorophenyl)methyl]pyridin-2-yl]carbamate

[Chemical formula 131]

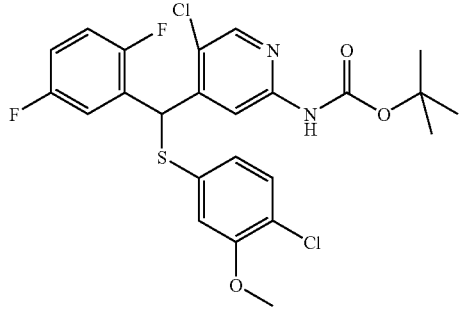

To an ethanol (5 ml) solution of O-ethyl S-(4-chloro-3-methoxyphenyl) dithiocarbonate (394 mg, 1.50 mmol) was added a 1N aqueous solution of sodium hydroxide (5 ml). The resulting mixture was heated under reflux for 1 hour. After the reaction mixture was cooled to room temperature, ethanol was distilled off under reduced pressure. The residue was washed with dichloromethane. The water layer was acidified with acetic acid. The product thus obtained was extracted with dichloromethane. The organic layer was dried over anhydrous sodium sulfate and filtered. The filtrate was concentrated under reduced pressure to give 4-chloro-3-methoxybenzenethiol as a colorless oil.

To a dichloromethane solution of the t-butyl[5-chloro-4-[(2,5-difluorophenyl)(hydroxy)methyl]pyridin-2-yl]carbamate (371 mg, 1.00 mmol) obtained in Referential Example 47 were added methanesulfonyl chloride (0.155 ml, 2.00 mmol) and then, triethylamine (0.418 ml, 3.00 mmol) at 0° C. The resulting mixture was stirred at room temperature for 2 hours. The reaction mixture was washed with a saturated aqueous solution of sodium bicarbonate. The organic layer was dried over anhydrous sodium sulfate, and filtered. The filtrate was concentrated under reduced pressure.

To an N,N-dimethylformamide (10 ml) solution of the residue were sequentially added an N,N-dimethylformamide (5 ml) solution of the 4-chloro-3-methoxybenzenethiol obtained above and potassium carbonate (207 mg, 1.50 mmol) under a nitrogen atmosphere. The resulting mixture was stirred at room temperature for 20 hours. Ethyl acetate was added to the reaction mixture. The resulting mixture was washed with a saturated aqueous solution of sodium bicarbonate. The organic layer was dried over anhydrous sodium sulfate, and filtered. The filtrate was concentrated under reduced pressure. The residue thus obtained was subjected to flash silica gel chromatography. The fraction obtained from the hexane:ethyl acetate=19:1 eluate was concentrated under reduced pressure to give the title compound (354 mg, 0.67 mmol, 67%) as a white solid.

$^1$H-NMR (400 MHz, CDCl$_3$) δ: 1.55 (9H, s), 3.81 (3H, s), 6.07 (1H, s), 6.91-7.08 (3H, m), 6.97 (1H, dd, J=7.8, 2.0 Hz), 7.00 (1H, d, J=2.0 Hz), 7.23 (1H, d, J=7.8 Hz), 7.86 (1H, s), 8.18 (1H, s), 8.55 (1H, s).

MS m/z: 527 (M$^+$+H).

Example 238 t-Butyl[5-chloro-4-[(4-chloro-3-methoxyphenylsulfonyl)(2,5-difluorophenyl)methyl]pyridin-2-yl]carbamate

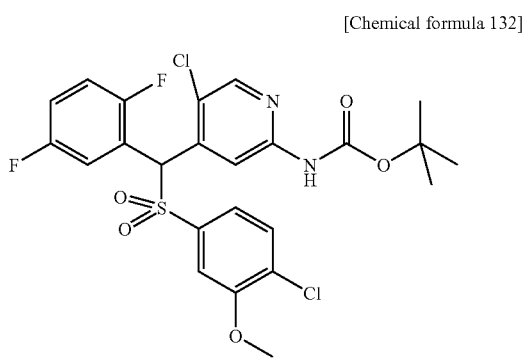

[Chemical formula 132]

To an ethyl acetate (8 ml) solution of t-butyl[5-chloro-4-[(4-chloro-3-methoxyphenylthio)(2,5-difluorophenyl)methyl]pyridin-2-yl]carbamate (354 mg, 0.67 mmol) were added methanol (8 ml), 31% aqueous hydrogen peroxide (8 ml) and hexaammonium heptamolybdate tetrahydrate (166 mg, 0.13 mmol). The resulting mixture was stirred at room temperature for 20 hours. Water was added to the reaction mixture and ethyl acetate and methanol were distilled off under reduced pressure. To the residue was added a saturated aqueous solution of sodium bicarbonate. The product thus obtained was extracted with dichloromethane. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=9:1 eluate was concentrated under reduced pressure. The residue thus obtained was washed with a diethyl ether/hexane mixed solvent and collected by filtration to give the title compound (308 mg, 0.55 mmol, 82%) as a white solid.

$^1$H-NMR (400 MHz, CDCl$_3$) δ: 1.58 (9H, s), 3.82 (3H, s), 6.27 (1H, s), 6.94-7.09 (2H, m), 7.24 (1H, d, J=2.0 Hz), 7.36 (1H, dd, J=8.3, 2.0 Hz), 7.46 (1H, d, J=8.3 Hz), 7.56-7.62 (2H, s), 8.18 (1H, s), 8.89 (1H, s).

MS m/z: 559 (M$^+$+H).

Example 239

[5-Chloro-4-[(4-chloro-3-methoxyphenylsulfonyl)(2,5-difluorophenyl)methyl]pyridin-2-yl]amine

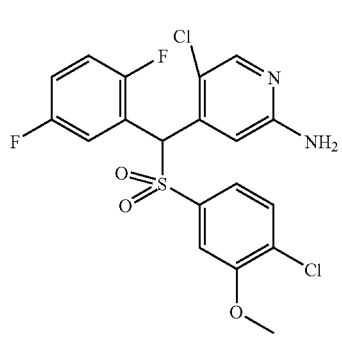

[Chemical formula 133]

To a dichloromethane (5 ml) solution of t-butyl[5-chloro-4-[(4-chloro-3-methoxyphenylsulfonyl)(2,5-difluorophenyl)methyl]pyridin-2-yl]carbamate (300 mg, 0.54 mmol) was added trifluoroacetic acid (5 ml) at 0° C. The resulting mixture was stirred at room temperature for 2 hours. The reaction mixture was concentrated under reduced pressure. The residue thus obtained was dissolved in dichloromethane. The resulting solution was washed with a 1N aqueous sodium hydroxide solution. The organic layer was dried over anhydrous sodium sulfate, and filtered. The filtrate was concentrated under reduced pressure. The residue thus obtained was washed with diethyl ether and then collected by filtration to give the title compound (208 mg, 0.45 mmol, 84%) as a white solid.

$^1$H-NMR (400 MHz, CDCl$_3$) δ: 3.82 (3H, s), 4.66 (2H, s), 6.14 (1H, s), 6.91-6.98 (1H, m), 7.02-7.09 (1H, m), 7.09 (1H, d, J=2.0 Hz), 7.25 (1H, dd, J=8.3, 2.0 Hz), 7.34 (1H, s), 7.46 (1H, d, J=8.3 Hz), 7.51-7.57 (1H, s), 7.99 (1H, s).

IR(ATR)cm$^{-1}$: 3151, 1645, 1595, 1481, 1414, 1390, 1325, 1254, 1140, 1055, 1026.

mp: 198 to 200° C.

Elemental Analysis for C$_{19}$H$_{14}$Cl$_2$F$_2$N$_2$O$_3$S: Calculated: C, 49.69; H, 3.07; Cl, 15.44; F, 8.27; N, 6.10; S, 6.98. Found: C, 49.56; H, 3.03; Cl, 15.29; F, 8.58; N, 6.08; S, 7.07.

MS m/z: 459 (M$^+$+H).

Example 240

[5-Chloro-4-[(2,5-difluorophenyl)(4-methoxyphenylsulfonyl)methyl]pyridin-2-yl]amine

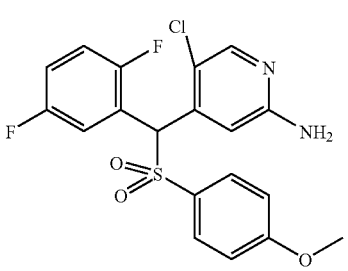

[Chemical formula 134]

To a dichloromethane solution of the t-butyl[5-chloro-4-[(2,5-difluorophenyl)(hydroxy)methyl]pyridin-2-yl]carbamate (148 mg, 0.40 mmol) obtained in Referential Example 47 were added methanesulfonyl chloride (0.046 ml, 0.60 mmol) and then, triethylamine (0.167 ml, 1.20 mmol) at 0° C. The resulting mixture was stirred at room temperature for 16 hours. The reaction mixture was washed with a saturated aqueous solution of sodium bicarbonate. The organic layer was dried over anhydrous sodium sulfate, and filtered. The filtrate was concentrated under reduced pressure.

To an N,N-dimethylformamide (4 ml) solution of the residue thus obtained were added 4-methoxybenzenethiol (56 mg, 0.40 mmol) and then potassium carbonate (66 mg, 0.48 mmol) under a nitrogen atmosphere. The resulting mixture was stirred at room temperature for 19 hours. Ethyl acetate was added to the reaction mixture. The resulting mixture was washed with a saturated aqueous solution of sodium bicarbonate. The organic layer was dried over anhydrous sodium sulfate and filtered. The filtrate was concentrated under reduced pressure.

To an ethyl acetate (8 ml) solution of the residue thus obtained were added methanol (8 ml), 31% aqueous hydrogen peroxide (4 ml) and hexaammonium heptamolybdate tetrahydrate (99 mg, 0.08 mmol). The resulting mixture was stirred at room temperature for 20 hours. Water was added to the reaction mixture. Ethyl acetate and methanol were distilled off under reduced pressure. To the residue was added a saturated aqueous solution of sodium bicarbonate. The product thus obtained was extracted with dichloromethane. The organic layer was dried over anhydrous sodium sulfate, and filtered. The filtrate was concentrated under reduced pressure.

To a dichloromethane (3 ml) solution of the residue thus obtained was added trifluoroacetic acid (3 ml) at 0° C. The resulting mixture was stirred at room temperature for 2 hours. The reaction mixture was concentrated under reduced pressure. The residue was dissolved in dichloromethane. The resulting solution was washed with a saturated aqueous solution of sodium bicarbonate. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=3:2 eluate was concentrated under reduced pressure. The residue was washed with a diethyl ether/hexane mixed solvent and then collected by filtration to give the title compound (67 mg, 0.16 mmol, 40%) as a white solid.

$^1$H-NMR (400 MHz, CDCl$_3$) δ: 3.87 (3H, s), 4.63 (2H, s), 6.10 (1H, s), 6.87-6.94 (1H, m), 6.90 (2H, d, J=8.8 Hz), 6.98-7.06 (1H, m), 7.31 (1H, s), 7.51-7.57 (1H, m), 7.59 (2H, d, J=8.8 Hz), 7.97 (1H, s).

IR(ATR)cm$^{-1}$: 3469, 3294, 3172, 1630, 1593, 1491, 1419, 1327, 1261, 1244, 1230, 1142, 1092.

mp: 153-155° C.

Elemental Analysis for C$_{19}$H$_{15}$ClF$_2$N$_2$O$_3$S: Calculated: C, 53.71; H, 3.56; Cl, 8.34; F, 8.94; N, 6.59; S, 7.55. Found: C, 53.53; H, 3.55; Cl, 8.34; F, 9.06; N, 6.31; S, 7.79.

MS m/z: 425 (M$^+$+H).

Example 241

[5-Chloro-4-[(5-chloropyridin-2-ylsulfonyl)(2,5-difluorophenyl)methyl]pyridin-2-yl]amine

[Chemical formula 135]

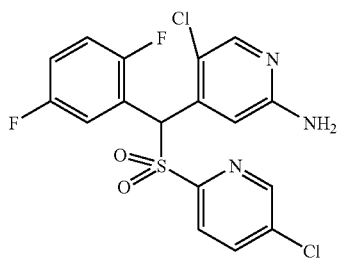

In a similar manner to Example 240, the title compound (74 mg, 0.17 mmol, 43%) was obtained as a white solid by using the t-butyl[5-chloro-4-[(2,5-difluorophenyl)(hydroxy)methyl]pyridin-2-yl]carbamate (148 mg, 0.40 mmol) obtained in Referential Example 47 and the 5-chloro-2-pyridinethiol (58 mg, 0.40 mmol) obtained in Referential Example 17.

$^1$H-NMR (400 MHz, CDCl$_3$) δ: 4.62 (2H, s), 6.77 (1H, s), 6.95-7.08 (2H, m), 7.28 (1H, s), 7.40-7.47 (1H, m), 7.82-7.84 (2H, m), 8.00 (1H, s), 8.68-8.70 (1H, m).

IR(ATR)cm$^{-1}$: 3427, 3317, 3199, 1635, 1491, 1477, 1327, 1238, 1163, 1113, 1018.

mp: 187 to 189° C.

Elemental Analysis for C$_{17}$H$_{11}$Cl$_2$F$_2$N$_3$O$_2$S: Calculated: C, 47.46; H, 2.58; Cl, 16.48; F, 8.83; N, 9.77; S, 7.45. Found: C, 47.43; H, 2.64; Cl, 16.52; F, 8.98; N, 9.69; S, 7.71.

MS m/z: 430 (M$^+$+H).

Example 242

N-[5-Chloro-4-[(5-chloropyridin-2-ylsulfonyl)(2,5-difluorophenyl)methyl]pyridin-2-yl]methanesulfonamide

[Chemical formula 136]

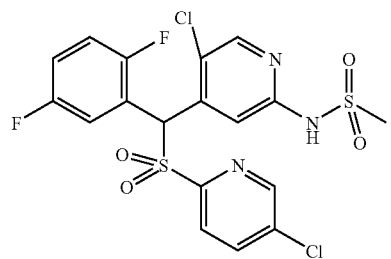

Under an argon atmosphere, a tetrahydrofuran solution (1M, 0.705 ml, 0.71 mmol) of sodium bis(trimethylsilyl)amide was added to a tetrahydrofuran (4 ml) solution of [5-chloro-4-[(5-chloropyridin-2-ylsulfonyl)(2,5-difluorophenyl)methyl]pyridin-2-yl]amine (92 mg, 0.21 mmol) at 0° C. The resulting mixture was stirred for 30 minutes. To the reaction mixture was added methanesulfonyl chloride (0.055 ml, 0.71 mmol). At the same temperature, the resulting mixture was stirred for 2 hours. The temperature of the reaction mixture was then raised to room temperature. To the reaction mixture was added a saturated aqueous solution of ammonium chloride. The product thus obtained was extracted with diethyl ether. The organic layer was dried over anhydrous sodium sulfate, and filtered. The filtrate was concentrated under reduced pressure. The residue thus obtained was subjected to flash silica gel column chromatography. The fraction obtained from the dichloromethane:ethyl acetate=19:1 eluate was concentrated under reduced pressure. The residue thus obtained was washed with an ethanol/hexane mixed solvent and then, collected by filtration to give the title compound (27 mg, 0.053 mmol, 25%) as a white solid.

$^1$H-NMR (400 MHz, CDCl$_3$) δ: 3.32 (3H, s), 6.86 (1H, s), 6.98-7.09 (2H, m), 7.36-7.43 (1H, m), 7.75 (1H, s), 7.85 (1H, dd, J=8.3, 2.2 Hz), 7.90 (1H, d, J=8.3 Hz), 7.93 (1H, s), 8.32 (1H, s), 8.67 (1H, d, J=2.2 Hz).

IR(ATR)cm$^{-1}$: 1603, 1568, 1493, 1389, 1329, 1240, 1144, 1109.

mp: 214 to 216° C.

Elemental Analysis for C$_{18}$H$_{13}$Cl$_2$F$_2$N$_3$O$_4$S$_2$: Calculated: C, 42.53; H, 2.58; Cl, 13.95; F, 7.47; N, 8.27; S, 12.62. Found: C, 42.56; H, 2.56; Cl, 14.03; F, 7.54; N, 8.23; S, 12.58.

MS m/z: 508 (M$^+$+H).

Referential Example 49

5-Chlorothiophene-2-thiol

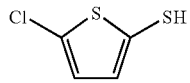

[Chemical formula 137]

To an acetic acid (15 ml) solution of 5-chlorothiophene-2-sulfonyl chloride (0.557 ml, 4.00 mmol) was added a 1N hydrochloric acid (3 ml) solution of tin (II) chloride (3.03 g, 16.0 mmol) at 75° C. The reaction mixture was cooled to room temperature, followed by the addition of water thereto. The product was extracted with dichloromethane. The organic layer was dried over anhydrous sodium sulfate, and filtered. The filtrate was concentrated under reduced pressure. To the residue thus obtained was added toluene, followed by concentration under reduced pressure again. The residue thus obtained was washed with diethyl ether, and collected by filtration to give the title compound (98 mg, 0.65 mmol, 16%) as a yellow solid. The filtrate was concentrated under reduced pressure. The residue thus obtained was washed with a mixed solvent of diethyl ether/hexane and collected by filtration to give the title compound (118 mg, 0.78 mmol, 20%) as a yellow solid.

$^1$H-NMR (400 MHz, CDCl$_3$) δ: 6.81 (1H, d, J=3.9 Hz), 6.85 (1H, d, J=3.9 Hz).

Example 243

[5-Chloro-4-[(5-chlorothiophen-2-ylsulfonyl)(2,5-difluorophenyl)methyl]pyridin-2-yl]amine

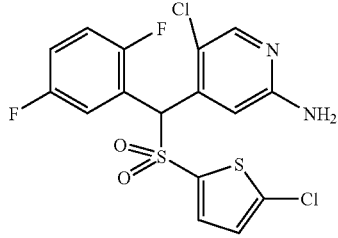

[Chemical formula 138]

In a similar manner to Example 240, the title compound (96 mg, 0.22 mmol, 55%) was obtained as a white solid by using the t-butyl[5-chloro-4-[(2,5-difluorophenyl)(hydroxy)methyl]pyridin-2-yl]carbamate (148 mg, 0.40 mmol) obtained in Referential Example 47 and 5-chlorothiophene-2-thiol (90 mg, 0.60 mmol).

$^1$H-NMR (400 MHz, CDCl$_3$) δ: 4.66 (2H, s), 6.25 (1H, s), 6.93 (1H, d, J=4.2 Hz), 6.97-7.11 (2H, m), 7.28 (1H, s), 7.29 (1H, d, J=4.2 Hz), 7.47-7.53 (1H, m), 8.02 (1H, s).

IR(ATR)cm$^{-1}$: 3438, 3180, 1643, 1595, 1543, 1485, 1404, 1315, 1242, 1138, 993.

mp: 170 to 171° C.

Elemental Analysis for C$_{16}$H$_{10}$Cl$_2$F$_2$N$_2$O$_2$S$_2$: Calculated: C, 44.15; H, 2.32; Cl, 16.29; F, 8.73; N, 6.44; S, 14.73. Found: C, 44.22; H, 2.41; Cl, 16.00; F, 8.77; N, 6.46; S, 14.81.

MS m/z: 435 (M$^+$+H).

Example 244 t-Butyl[5-chloro-4-[(6-chloropyridin-3-ylthio)(2,5-difluorophenyl)methyl]pyridin-2-yl]carbamate

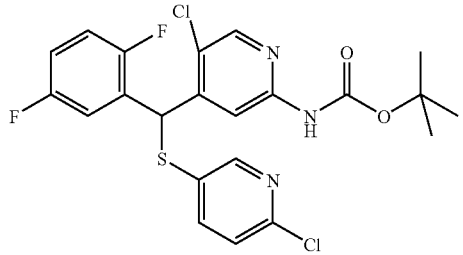

[Chemical formula 139]

In a similar manner to Example 237, the title compound (190 mg, 0.38 mmol, 94%) was obtained as a white solid by using the O-ethyl S-(6-chloropyridin-3-yl) dithiocarbonate (187 mg, 0.80 mmol) obtained in Referential Example 26 and the t-butyl[5-chloro-4-[(2,5-difluorophenyl)(hydroxy)methyl]pyridin-2-yl]carbamate (151 mg, 0.41 mmol) obtained in Referential Example 47.

$^1$H-NMR (400 MHz, CDCl$_3$) δ: 1.56 (9H, s), 6.01 (1H, s), 6.93-7.08 (3H, m), 7.22 (1H, d, J=8.3 Hz), 7.42 (1H, s), 7.71 (1H, dd, J=8.3, 2.5 Hz), 8.16 (1H, s), 8.37 (1H, d, J=2.5 Hz), 8.50 (1H, s).

MS m/z: 498 (M$^+$+H).

Example 245

[5-Chloro-4-[(6-chloropyridin-3-ylsulfonyl)(2,5-difluorophenyl)methyl]pyridin-2-yl]amine

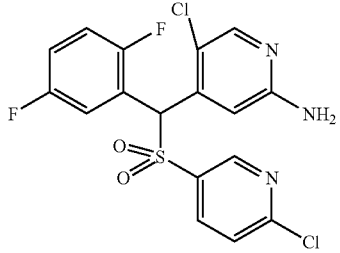

[Chemical formula 140]

To a dichloromethane (5 ml) solution of t-butyl[5-chloro-4-[(6-chloropyridin-3-ylthio)(2,5-difluorophenyl)methyl]pyridin-2-yl]carbamate (187 mg, 0.38 mmol) was added 3-chloroperbenzoic acid (199 mg, 0.75 mmol) at room temperature. The resulting mixture was stirred for 2 hours. The reaction mixture was washed with a 1N aqueous sodium hydroxide solution. The organic layer was dried over anhydrous sodium sulfate, and filtered. The filtrate was concentrated under reduced pressure.

The residue thus obtained was dissolved in dichloromethane (3 ml). At 0° C., trifluoroacetic acid (3 ml) was added and the resulting mixture was stirred at room temperature for 1 hour. The reaction mixture was concentrated under reduced pressure. The residue was dissolved in dichloromethane. The resulting solution was washed with a 1N aqueous solution of sodium hydroxide. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=3:1 eluate was concentrated under reduced pressure. The residue thus obtained was washed with an ethanol/hexane mixed solvent, and collected by filtration to give the title compound (90 mg, 0.21 mmol, 55%) as a white solid.

$^1$H-NMR (400 MHz, CDCl$_3$) δ: 4.68 (2H, s), 6.15 (1H, s), 6.93-7.00 (1H, m), 7.05-7.12 (1H, m), 7.29 (1H, s), 7.44 (1H, d, J=8.3 Hz), 7.48-7.54 (1H, m), 7.91 (1H, dd, J=8.3, 2.4 Hz), 8.01 (1H, s), 8.58 (1H, d, J=2.4 Hz).

IR(ATR)cm$^{-1}$: 3342, 3167, 1495, 1479, 1331, 1240, 1161, 1115.

mp: 157 to 158° C.

Elemental Analysis for C$_{17}$H$_{11}$Cl$_2$F$_2$N$_3$O$_2$S: Calculated: C, 47.46; H, 2.58; Cl, 16.48; F, 8.83; N, 9.77; S, 7.45. Found: C, 47.24; H, 2.59; Cl, 16.50; F, 8.80; N, 9.82; S, 7.61.

MS m/z: 430 (M$^+$+H).

Example 246

4-[(2-Amino-5-chloropyridin-4-yl)(2,5-difluorophenyl)methylsulfonyl]benzonitrile

[Chemical formula 141]

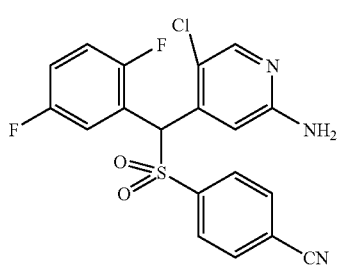

In a similar manner to Example 240, the title compound (99 mg, 0.24 mmol, 59%) was obtained as a white solid by using the t-butyl[5-chloro-4-[(2,5-difluorophenyl)(hydroxy)methyl]pyridin-2-yl]carbamate (148 mg, 0.40 mmol) obtained in Referential Example 47 and 4-mercaptobenzonitrile (56 mg, 0.41 mmol).

$^1$H-NMR (400 MHz, CDCl$_3$): 4.68 (2H, s), 6.15 (1H, s), 6.89-6.96 (1H, m), 7.03-7.10 (1H, m), 7.31 (1H, s), 7.49-7.55 (1H, m), 7.76 (2H, d, J=8.5 Hz), 7.81 (2H, d, J=8.5 Hz), 7.99 (1H, s).

IR(ATR)cm$^1$: 3388, 1618, 1495, 1415, 1331, 1149.

mp: 233 to 235° C.

Elemental Analysis for C$_{19}$H$_{12}$ClF$_2$N$_3$O$_2$S: Calculated: C, 54.36; H, 2.88; Cl, 8.44; F, 9.05; N, 10.01; S, 7.64. Found: C, 54.41; H, 2.93; Cl, 8.41; F, 8.92; N, 9.92; S, 7.69.

MS m/z: 420 (M$^+$+H).

Example 247

[5-Chloro-4-[(2,5-difluorophenyl)(3,4-difluorophenylsulfonyl)methyl]pyridin-2-yl]amine

[Chemical formula 142]

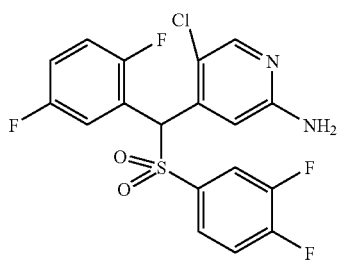

In a similar manner to Example 240, the title compound (59 mg, 0.14 mmol, 27%) was obtained as a white solid by using the t-butyl[5-chloro-4-[(2,5-difluorophenyl)(hydroxy)methyl]pyridin-2-yl]carbamate (185 mg, 0.50 mmol) obtained in Referential Example 47 and 3,4-difluorobenzenethiol (84 mg, 0.55 mmol).

$^1$H-NMR (400 MHz, CDCl$_3$) δ: 4.67 (2H, s), 6.13 (1H, s), 6.91-6.98 (1H, m), 7.03-7.10 (1H, m), 7.23-7.31 (1H, m), 7.31 (1H, s), 7.45-7.55 (3H, m), 8.00 (1H, s).

IR(ATR)cm$^{-1}$: 3452, 3168, 1635, 1599, 1493, 1415, 1325, 1281, 1244, 1144, 1120.

mp: 140 to 141° C.

Elemental Analysis for C$_{18}$H$_{11}$ClF$_4$N$_2$O$_2$S: Calculated: C, 50.18; H, 2.57; Cl, 8.23; F, 17.64; N, 6.50; S, 7.44. Found: C, 50.12; H, 2.60; Cl, 8.25; F, 17.35; N, 6.51; S, 7.58.

MS m/z: 431 (M$^+$+H).

Example 248

N-[5-Chloro-4-[(2,5-difluorophenyl)(3,4-difluorophenylsulfonyl)methyl]pyridin-2-yl]-N-(methylsulfonyl)methanesulfonamide

[Chemical formula 143]

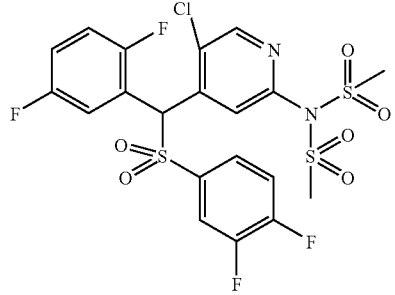

Under a nitrogen atmosphere, methanesulfonyl chloride (0.034 ml, 0.44 mmol), triethylamine (0.062 ml, 0.44 mmol) and 4-dimethylaminopyridine (4 mg, 0.03 mmol) were added to a dichloromethane (3 ml) solution of [5-chloro-4-[(2,5-difluorophenyl)(3,4-difluorophenylsulfonyl)methyl]pyridin-2-yl]amine (63 mg, 0.15 mmol) at 0° C. The resulting mixture was stirred at room temperature for 17 hours. The reaction mixture was washed with 1N hydrochloric acid. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=3:1 eluate was concentrated under reduced pressure to give the title compound (73 mg, 0.12 mmol, 85%) as a white solid.

$^1$H-NMR (400 MHz, CDCl$_3$) δ: 3.63 (6H, s), 6.22 (1H, s), 7.02-7.16 (2H, m), 7.22-7.31 (1H, m), 7.45-7.51 (2H, m), 7.56-7.62 (1H, m), 8.17 (1H, s), 8.45 (1H, s).

MS m/z: 587 (M$^+$+H).

Example 249

N-[5-Chloro-4-[(2,5-difluorophenyl)(3,4-difluorophenylsulfonyl)methyl]pyridin-2-yl]methanesulfonamide

[Chemical formula 144]

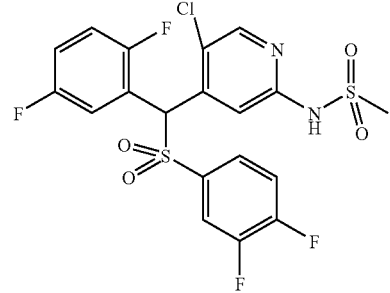

Under a nitrogen atmosphere, a tetrahydrofuran solution (1M, 0.147 ml, 0.15 mmol) of tetrabutylammonium fluoride was added to a tetrahydrofuran (2 ml) solution of N-[5-chloro-4-[(2,5-difluorophenyl)(3,4-difluorophenylsulfonyl)methyl]pyridin-2-yl]-N-(methylsulfonyl)methanesulfonamide (72 mg, 0.12 mmol). The resulting mixture was stirred at room temperature for 2 hours. After the reaction mixture was concentrated under reduced pressure, the residue thus obtained was dissolved in ethyl acetate. The resulting solution was washed sequentially with 1N hydrochloric acid and a saturated aqueous solution of ammonium chloride. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=3:1 eluate was concentrated under reduced pressure. The residue thus obtained was washed with a mixed solvent of diethyl ether/hexane and collected by filtration to give the title compound (53 mg, 0.10 mmol, 84%) as a white solid.

$^1$H-NMR (400 MH, CDCl$_3$) δ: 3.35 (3H, s), 6.19 (1H, s), 6.92-6.99 (1H, m), 7.04-7.12 (1H, m), 7.25-7.32 (1H, m), 7.44-7.60 (3H, m), 7.98 (1H, s), 7.99 (1H, s), 8.34 (1H, s).

IR(ATR)cm$^{-1}$: 1599, 1495, 1468, 1333, 1281, 1146, 1003, 970.

mp: 118 to 120° C.

MS m/z: 509 (M$^+$+H).

FAB-MS: 509.0044 (Calcd for Cl$_9$H$_{14}$ClF$_4$N$_2$O$_4$S$_2$: 509.0020).

Referential Example 50

O-Ethyl S-(6-trifluoromethylpyridin-3-yl) dithiocarbonate

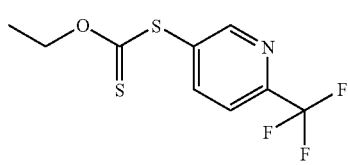

[Chemical formula 145]

After 6-trifluoromethylpyridin-3-ylamine (1.00 g, 6.02 mmol) was dissolved in 1N hydrochloric acid (15 ml) and methanol (3 ml), a water (3 ml) solution of sodium nitrite (506 mg, 7.22 mmol) was added dropwise to the resulting solution at −10° C. The reaction mixture was added dropwise to a water (15 ml) solution of potassium o-ethyl dithiocarbonate (1.93 g, 12.0 mmol) heated to 65° C. At the same temperature, the reaction mixture was stirred for 30 minutes. After the reaction mixture was cooled to room temperature, the product thus obtained was extracted with ethyl acetate. The extract was washed with brine. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=100:1 eluate was concentrated under reduced pressure to give the title compound (895 mg, 3.35 mmol, 56%) as a yellow oil.

$^1$H-NMR (400 MHz, CDCl$_3$) δ: 1.38 (3H, t, J=7.1 Hz), 4.65 (2H, q, J=7.1 Hz), 7.76 (1H, d, J=8.1 Hz), 8.01 (1H, dd, J=8.1, 2.0 Hz), 8.79 (1H, d, J=2.0 Hz).

MS m/z: 268 (M$^+$+H).

Example 250

[5-Chloro-4-[(2,5-difluorophenyl)(6-trifluoromethylpyridin-3-ylsulfonyl)methyl]pyridin-2-yl]amine

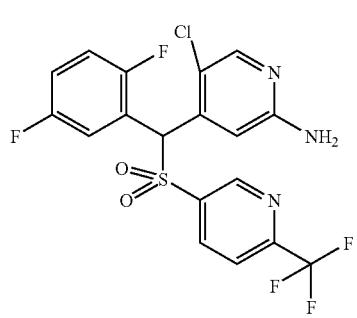

[Chemical formula 146]

To an ethanol (2 ml) solution of O-ethyl S-(6-trifluoromethylpyridin-3-yl) dithiocarbonate (160 mg, 0.60 mmol) was added a 1N aqueous sodium hydroxide solution (2 ml). The resulting mixture was stirred at 65° C. for 2 hours. After the reaction mixture was cooled to room temperature and then, water was added thereto. The resulting mixture was washed with dichloromethane. The water layer was acidified with 1N hydrochloric acid, and the product was extracted with dichloromethane. The organic layer was dried over anhydrous sodium sulfate and then filtered. The filtrate was concentrated under reduced pressure to afford 6-trifluoromethylpyridine-3-thiol as a colorless oil.

To a dichloromethane solution of the t-butyl[5-chloro-4-[(2,5-difluorophenyl)(hydroxy)methyl]pyridin-2-yl]carbamate (185 mg, 0.50 mmol) obtained in Referential Example 47 were sequentially added methanesulfonyl chloride (0.077 ml, 1.00 mmol) and triethylamine (0.279 ml, 2.00 mmol) at room temperature. The resulting mixture was stirred at room temperature for 1 hour. The reaction mixture was washed with a saturated aqueous solution of sodium bicarbonate. The organic layer was dried over anhydrous sodium sulfate, and filtered. The filtrate was concentrated under reduced pressure.

To an N,N-dimethylformamide (5 ml) solution of the residue thus obtained were added an N,N-dimethylformamide (5 ml) solution of the 6-trifluoromethylpyridine-3-thiol obtained above and potassium carbonate (104 mg, 0.75 mmol) sequentially under a nitrogen atmosphere. The resulting mixture was stirred at room temperature for 15 hours. Ethyl acetate was added to the reaction mixture. The resulting mixture was washed sequentially with a saturated aqueous solution of sodium bicarbonate and brine. The organic layer was dried over anhydrous sodium sulfate, and filtered. The filtrate was concentrated under reduced pressure.

To an ethyl acetate (10 ml) solution of the residue thus obtained were added methanol (10 ml), 31% aqueous hydrogen peroxide (5 ml) and hexaammonium heptamolybdate tetrahydrate (99 mg, 0.08 mmol). The resulting mixture was stirred at 50° C. for 4 hours. To the reaction mixture was added water and ethyl acetate and methanol were distilled off under reduced pressure. A saturated aqueous solution of sodium bicarbonate was added to the residue. The product thus obtained was extracted with dichloromethane. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=9:1 eluate was concentrated under reduced pressure.

To a dichloromethane (5 ml) solution of the residue thus obtained was added trifluoroacetic acid (5 ml) at 0° C. The resulting mixture was stirred at room temperature for 2 hours. After the reaction mixture was concentrated under reduced pressure, the residue was dissolved in dichloromethane. The resulting solution was washed with a saturated aqueous solution of sodium bicarbonate. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=4:1 eluate was concentrated under reduced pressure. The residue thus obtained was washed with an ethanol/hexane mixed solvent and collected by filtration to give the title compound (75 mg, 0.16 mmol, 32%) as a white solid.

$^1$H-NMR (400 MHz, CDCl$_3$) δ: 4.71 (2H, s), 6.18 (1H, s), 6.91-6.99 (1H, m), 7.06-7.14 (1H, m), 7.30 (1H, s), 7.50-7.56 (1H, m), 7.81 (1H, d, J=8.1 Hz), 8.01 (1H, s), 8.20 (1H, dd, J=8.1, 2.0 Hz), 8.90 (1H, d, J=2.0 Hz).

IR(ATR)cm$^{-1}$: 3446, 3157, 1649, 1601, 1485, 1419, 1325, 1147, 1101, 1076.

mp: 201 to 202° C.

Elemental Analysis for C$_{18}$H$_{11}$ClF$_5$N$_3$O$_2$S.0.25H$_2$O: Calculated: C, 46.16; H, 2.48; Cl, 7.57; F, 20.28; N, 8.97; S, 6.85. Found: C, 46.30; H, 2.36; Cl, 7.61; F, 19.96; N, 8.93; S, 7.12.

MS m/z: 464 (M$^+$+H).

Referential Example 51

O-Ethyl S-(4-chloro-3-fluorophenyl) dithiocarbonate

[Chemical formula 147]

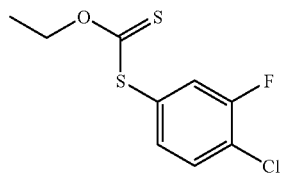

In a similar manner to Referential Example 50, the title compound (379 mg, 1.51 mmol, 38%) was obtained as a yellow oil by using 4-chloro-3-fluoroaniline (582 mg, 4.00 mmol).

$^1$H-NMR (400 MHz, CDCl$_3$) δ: 1.36 (3H, t, J=7.1 Hz), 4.63 (2H, q, J=7.1 Hz), 7.22-7.25 (1H, m), 7.30-7.35 (1H, m), 7.43-7.49 (1H, m).

Example 251

[5-Chloro-4-[(4-chloro-3-fluorophenylsulfonyl)(2,5-difluorophenyl)methyl]pyridin-2-yl]amine

[Chemical formula 148]

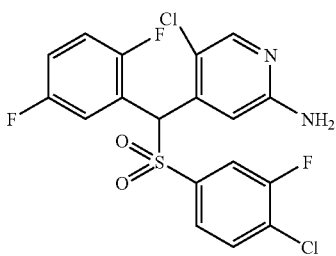

In a similar manner to Example 250, the title compound (78 mg, 0.17 mmol, 35%) was obtained as a white solid by using O-ethyl S-(4-chloro-3-fluorophenyl) dithiocarbonate (150 mg, 0.60 mmol) and the t-butyl[5-chloro-4-[(2,5-difluorophenyl)(hydroxy)methyl]pyridin-2-yl]carbamate (185 mg, 0.50 mmol) obtained in Referential Example 47.

$^1$H-NMR (400 MHz, CDCl$_3$) δ: 4.68 (2H, s), 6.14 (1H, s), 6.92-6.99 (1H, m), 7.03-7.10 (1H, m), 7.31 (1H, s), 7.40-7.55 (4H, m), 8.00 (1H, s).

IR(ATR)cm$^{-1}$: 3159, 1628, 1543, 1495, 1473, 1408, 1335, 1238, 1149, 1055.

mp: 159 to 160° C.

Elemental Analysis for C$_{18}$H$_{11}$Cl$_2$F$_3$N$_2$O$_2$S: Calculated: C, 48.34; H, 2.48; Cl, 15.85; F, 12.74; N, 6.26; S, 7.17. Found: C, 48.22; H, 2.47; Cl, 15.89; F, 12.75; N, 6.24; S, 7.34.

MS m/z: 447 (M$^+$+H).

Example 252

Methyl(E)-3-[4-[(4-chlorophenylsulfonyl)(2,5-difluorophenyl)methyl]-5-fluoropyridin-2-yl]acrylate

[Chemical formula 149]

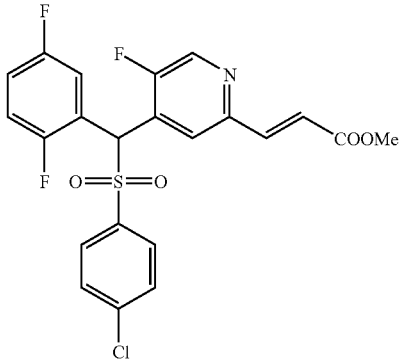

Under an argon atmosphere, methyl (triphenylphosphoranylidene)acetate (259 mg, 0.775 mmol) was added to a tetrahydrofuran (5 ml) solution of the [4-[(4-chlorophenylsulfonyl)(2,5-difluorophenyl)methyl]-5-fluoropyridin-2-yl]carbaldehyde (300 mg, 0.705 mmol) obtained in Example 200. The resulting mixture was stirred at room temperature for 6 hours. The reaction mixture was concentrated under reduced pressure. The residue thus obtained was subjected to flash silica gel column chromatography. The fraction obtained from the hexane:ethyl acetate=4:1 eluate was concentrated under reduced pressure to give the title compound (303 mg, 0.629 mmol, 89%) as a colorless amorphous substance.

$^1$H-NMR (400 MHz, CDCl$_3$) δ: 3.84 (3H, s), 6.07 (1H, s), 6.92 (1H, d, J=15.6 Hz), 6.94-6.99 (1H, m), 7.05-7.11 (1H, m), 7.45 (2H, d, J=8.3 Hz), 7.63 (2H, d, J=8.3 Hz), 7.65-7.69 (1H, m), 7.73 (1H, d, J=15.6 Hz), 8.05 (1H, d, J=5.6 Hz), 8.44 (1H, s).

MS m/z: 482 (M$^+$+H).

Example 253

Methyl 3-[4-[(4-chlorophenylsulfonyl)(2,5-difluorophenyl)methyl]-5-fluoropyridin-2-yl]propionate

[Chemical formula 150]

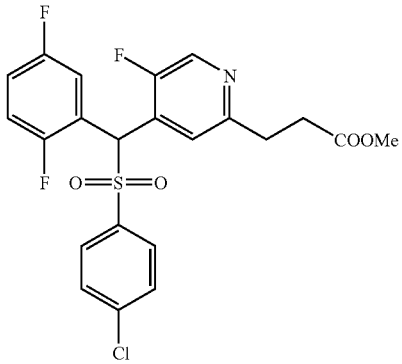

A Raney nickel suspension ("R-100", product of Nikko Rika Corporation) was washed sequentially with water and ethanol to give a corresponding ethanol suspension. The resulting ethanol suspension (1 ml) was added to a solution of methyl(E)-3-[4-[(4-chlorophenylsulfonyl)(2,5-difluorophenyl)methyl]-5-fluoropyridin-2-yl]acrylate (290 mg, 0.602 mmol) in a mixture of ethanol (6 ml) and 1,4-dioxane (4 ml). The resulting mixture was stirred vigorously for 30 minutes under a hydrogen atmosphere of 1 atmospheric pressure. The reaction mixture was filtered, followed by concentration under reduced pressure. The residue thus obtained was dissolved in dichloromethane. The resulting solution was dried over magnesium sulfate and concentrated under reduced pressure. The residue thus obtained was washed with hexane to give the title compound (252 mg, 0.521 mmol, 87%) as a white powder.

$^1$H-NMR (400 MHz, CDCl$_3$) δ: 2.83 (2H, t, J=7.1 Hz), 3.19 (2H, t, J=7.1 Hz), 3.71 (3H, s), 6.06 (1H, s), 6.93-6.99 (1H, m), 7.03-7.09 (1H, m), 7.44 (2H, d, J=8.6 Hz), 7.63 (2H, d, J=8.6 Hz), 7.64-7.69 (1H, m), 7.88 (1H, d, J=5.4 Hz), 8.31 (1H, s).

MS m/z: 484 (M$^+$+H).

Example 254

3-[4-[(4-Chlorophenylsulfonyl)(2,5-difluorophenyl)methyl]-5-fluoropyridin-2-yl]propionic acid

[Chemical formula 151]

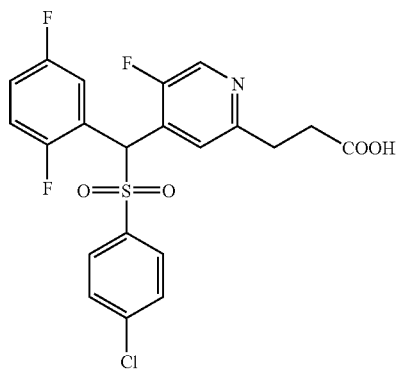

To a solution of methyl 3-[4-[(4-chlorophenylsulfonyl)(2,5-difluorophenyl)methyl]-5-fluoropyridin-2-yl]propionate (150 mg, 0.310 mmol) in a mixture of methanol (2 ml) and tetrahydrofuran (2 ml) was added a 1N aqueous sodium hydroxide solution. The resulting mixture was stirred at room temperature for 10 minutes. The reaction mixture was made weakly acidic by the addition of 1N hydrochloric acid, followed by extraction with dichloromethane. The organic layer was dried over magnesium sulfate and concentrated under reduced pressure to give the title compound (145 mg, 0.310 mmol, quant.) as a white powder.

$^1$H-NMR (400 MHz, CDCl$_3$) δ: 2.88 (2H, t, J=6.6 Hz), 3.21-3.25 (2H, m), 6.07 (1H, s), 6.93-6.99 (1H, m), 7.04-7.10 (1H, m), 7.45 (2H, d, J=8.6 Hz), 7.62 (2H, d, J=8.6 Hz), 7.63-7.67 (1H, m), 7.92 (1H, d, J=5.4 Hz), 8.33 (1H, s).

IR(ATR)cm$^{-1}$: 3453, 1716, 1664, 1614, 1571, 1496, 1430, 1394, 1330, 1284, 1238, 1187, 1151, 1089, 1010.

mp: 89 to 91° C.

MS m/z: 470 (M$^+$+H).

Elemental Analysis for C$_{21}$H$_{15}$ClF$_3$NO$_4$S.0.75H$_2$O: Calculated: C, 52.18; H, 3.44; Cl, 7.33; F, 11.79; N, 2.90; S, 6.63. Found: C, 52.20; H, 3.65; Cl, 7.11; F, 11.43; N, 2.99; S, 6.58.

Referential Example 52

2-Bromo-5-chloro-4-[(2,5-difluorophenyl)hydroxymethyl]pyridine

[Chemical formula 152]

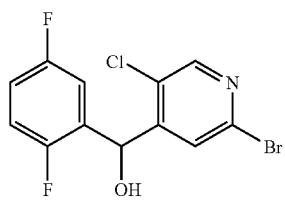

Under an argon atmosphere, n-butyl lithium (a 1.58M hexane solution, 88 ml, 138 mmol) was added to a tetrahydrofuran (200 ml) solution of diisopropylamine (21 ml, 150 mmol) at −78° C. The resulting mixture was stirred for 1 hour. To the reaction mixture was added dropwise a tetrahydrofuran (100 ml) solution of 2-bromo-5-chloropyridine (19 g, 98.7 mmol). The resulting mixture was stirred for 1.5 hours. To the reaction mixture was added dropwise 2,5-difluorobenzaldehyde (16 ml, 148 mmol), followed by stirring for 2 hours. After addition of water, the resulting mixture was concentrated under reduced pressure. The residue was extracted with dichloromethane. The organic layer thus obtained was dried over magnesium sulfate, and concentrated under reduced pressure. The residue thus obtained was subjected to silica gel column chromatography. The fraction obtained from the hexane:ethyl acetate=6:1 eluate was concentrated under reduced pressure to give the title compound (24.8 g, 74.1 mmol, 75%) as a pale yellow powder.

$^1$H-NMR (400 MHz, CDCl$_3$) δ: 2.65 (1H, d, J=4.2 Hz), 6.20 (1H, d, J=4.2 Hz), 6.88-6.92 (1H, m), 7.01-7.27 (2H, m), 7.81 (1H, s), 8.30 (1H, s).

MS m/z: 334 (M$^+$+H).

Example 255

2-Bromo-5-chloro-4-[(4-chlorophenylthio)(2,5-difluorophenyl)methyl]pyridine

[Chemical formula 153]

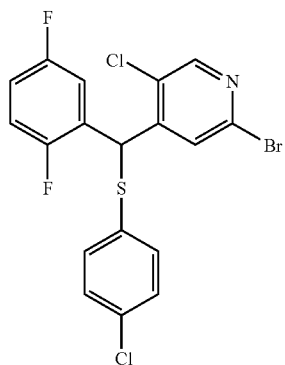

Under an argon atmosphere, triethylamine (2.6 ml, 18.5 mmol) and methanesulfonyl chloride (1.3 ml, 16.0 mmol) were added to a dichloromethane solution (80 ml) of 2-bromo-5-chloro-4-[(2,5-difluorophenyl)hydroxymethyl]pyridine (4.12 g, 12.3 mmol) under ice cooling. The resulting mixture was stirred at room temperature for 1.5 hours. To the reaction mixture was added a saturated aqueous solution of sodium bicarbonate, followed by extraction with diethyl ether. The extract was washed with brine, dried over anhydrous magnesium sulfate, and concentrated under reduced pressure.

To a dimethylformamide (40 ml) solution of the residue thus obtained were added 4-chlorobenzenethiol (2.1 g, 14.8 mmol) and potassium carbonate (2.6 g, 18.5 mmol). The resulting mixture was stirred at 50° C. for 4 hours. After cooling to room temperature, the reaction mixture was diluted with diethyl ether. The diluted mixture was washed sequentially with water and brine. The organic layer thus obtained was dried over magnesium sulfate, and concentrated under reduced pressure. The residue thus obtained was subjected to flash silica gel column chromatography. The fraction obtained from the hexane:ethyl acetate=10:1 eluate was concentrated under reduced pressure to give the title compound (3.3 g, 7.16 mmol, 58%) as a white powder.

$^1$H-NMR (400 MHz, CDCl$_3$) δ: 5.96 (1H, s), 6.99-7.06 (2H, m), 7.15-7.20 (1H, m), 7.25 (2H, d, J=8.8 Hz), 7.28 (2H, d, J=8.8 Hz), 7.69 (1H, s), 8.32 (1H, s).

MS m/z: 460 (M$^+$+H).

Example 256

[5-Chloro-4-[(4-chlorophenylthio)(2,5-difluorophenyl)methyl]pyridin-2-yl]methanol

[Chemical formula 154]

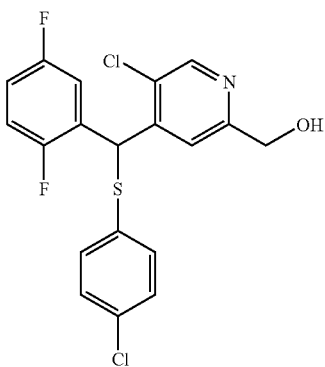

Under an argon atmosphere, n-butyl lithium (a 1.58M hexane solution, 0.33 ml, 0.520 mmol) was added to a toluene (5 ml) solution of 2-bromo-5-chloro-4-[(4-chlorophenylthio)(2,5-difluorophenyl)methyl]pyridine (200 mg, 0.434 mmol) at −78° C. The resulting mixture was stirred for 2 hours. To the reaction mixture was added dropwise dimethylformamide (44 µl, 0.564 mmol). The reaction mixture was stirred for 1 hour. To the reaction mixture were added methanol (5 ml) and sodium borohydride (33 mg, 0.868 mmol). The temperature of the resulting mixture was raised to room temperature, followed by stirring for 2 hours. Water was added to the reaction mixture and then, the resulting mixture was extracted with ethyl acetate. The extract was washed with brine. The organic layer thus obtained was dried over magnesium sulfate, and concentrated under reduced pressure. The residue thus obtained was subjected to flash silica gel column chromatography. The fraction obtained from the hexane:ethyl acetate=2:1 eluate was concentrated under reduced pressure to give the title compound (142 mg, 0.344 mmol, 80%) as a colorless amorphous substance.

$^1$H-NMR (400 MHz, CDCl$_3$) δ: 3.19 (1H, t, J=5.4 Hz), 4.75 (2H, d, J=5.4 Hz), 6.06 (1H, s), 6.96-7.04 (2H, m), 7.16-7.21 (1H, m), 7.22 (2H, d, J=8.8 Hz), 7.25 (2H, d, J=8.8 Hz), 7.52 (1H, s), 8.51 (1H, s).

MS m/z: 412 (M$^+$+H).

Example 257

[5-Chloro-4-[(4-chlorophenylsulfonyl)(2,5-difluorophenyl)methyl]pyridin-2-yl]methanol

[Chemical formula 155]

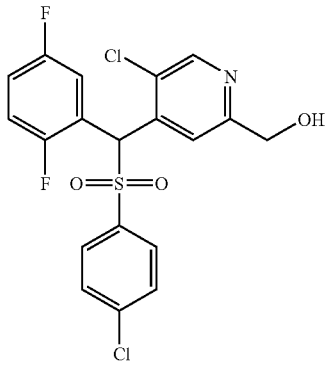

To a methanol (5 ml) solution of [5-chloro-4-[(4-chlorophenylthio)(2,5-difluorophenyl)methyl]pyridin-2-yl]methanol (130 mg, 0.315 mmol) were added hexaammonium heptamolybdate tetrahydrate (20 mg) and 30% aqueous hydrogen peroxide (3 ml). The resulting mixture was stirred for 6 hours. After water was added to the reaction mixture, the resulting mixture was extracted with ethyl acetate. The extract was washed sequentially with water, a saturated aqueous solution of sodium bicarbonate, a saturated aqueous solution of sodium thiosulfate and brine. The organic layer thus obtained was dried over magnesium sulfate, and concentrated under reduced pressure. The residue thus obtained was subjected to flash silica gel column chromatography. The fraction obtained from the hexane:ethyl acetate=2:1 eluate was concentrated under reduced pressure. The residue was recrystallized from hexane:ethyl acetate to give the title compound (101 mg, 0.227 mmol, 72%) as a white powder.

$^1$H-NMR (400 MHz, CDCl$_3$) δ: 3.22 (1H, t, J=5.4 Hz), 4.86 (2H, dd, J=5.4, 2.0 Hz), 6.24 (1H, s), 6.91-6.97 (1H, m), 7.02-7.09 (1H, m), 7.45 (2H, d, J=8.8 Hz), 7.52-7.57 (1H, m), 7.61 (2H, d, J=8.8 Hz), 8.10 (1H, s), 8.52 (1H, s).

IR(ATR)cm$^{-1}$: 3255, 1583, 1492, 1428, 1394, 1330, 1280, 1236, 1159, 1085, 1035.

mp: 164 to 165° C.

MS m/z: 444 (M$^+$+H).

Elemental Analysis for C$_{19}$H$_{13}$Cl$_2$F$_2$NO$_3$S: Calculated: C, 51.36; H, 2.95; Cl, 15.96; F, 8.55; N, 3.15; S, 7.22. Found: C, 51.26; H, 2.91; Cl, 15.97; F, 8.72; N, 3.11; S, 7.45.

Example 258

[5-Chloro-4-[(4-chlorophenylsulfonyl)(2,5-difluorophenyl)methyl]pyridin-2-yl]carbaldehyde

[Chemical formula 156]

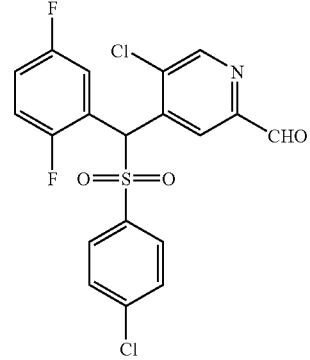

Under a nitrogen atmosphere, dimethyl sulfoxide (880 μl, 11.3 mmol), triethylamine (1.14 ml, 11.3 mmol) and sulfur trioxide pyridine complex (1.07 g, 6.75 mmol) were added to a dichloromethane (25 ml) solution of [5-chloro-4-[(4-chlorophenylsulfonyl)(2,5-difluorophenyl)methyl]pyridin-2-yl] methanol (1.0 g, 2.25 mmol). The resulting mixture was stirred at room temperature for 18 hours. The reaction mixture was concentrated under reduced pressure. The residue thus obtained was subjected to flash silica gel column chromatography. The fraction obtained from the hexane:ethyl acetate=2:1 eluate was concentrated under reduced pressure to give the title compound (770 mg, 1.74 mmol, 77%) as a colorless amorphous substance.

$^1$H-NMR (400 MHz, CDCl$_3$) δ: 6.23 (1H, s), 6.93-6.99 (1H, m), 7.04-7.10 (1H, m), 7.44 (2H, d, J=8.8 Hz), 7.59-7.64 (1H, m), 7.62 (2H, d, J=8.8 Hz), 8.69 (1H, s), 8.73 (1H, s), 10.09 (1H, s).

MS m/z: 442 (M$^+$+H).

Example 259

Methyl(E)-3-[5-Chloro-4-[(4-chlorophenylsulfonyl) (2,5-difluorophenyl)methyl]pyridin-2-yl]acrylate

[Chemical formula 157]

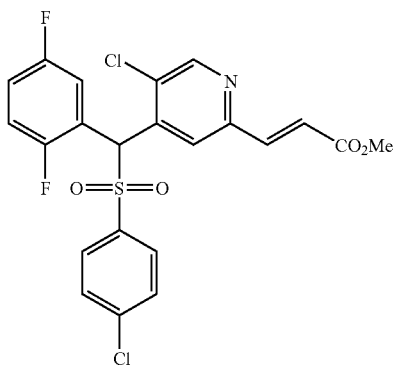

Under an argon atmosphere, methyl (triphenylphosphoranylidene)acetate (632 mg, 1.89 mmol) was added to a tetrahydrofuran (15 ml) solution of [5-chloro-4-[(4-chlorophenylsulfonyl)(2,5-difluorophenyl)methyl]pyridin-2-yl] carbaldehyde (760 mg, 1.72 mmol). The resulting mixture was stirred at room temperature for 3 hours. The reaction mixture was concentrated under reduced pressure. The residue thus obtained was subjected to flash silica gel column chromatography. The fraction obtained from the hexane:ethyl acetate=4:1 eluate was concentrated under reduced pressure to give the title compound (776 mg, 1.56 mmol, 91%) as a colorless amorphous substance.

$^1$H-NMR (400 MHz, CDCl$_3$) δ: 3.85 (3H, s), 6.22 (1H, s), 6.93-6.98 (1H, m), 6.99 (1H, d, J=15.6 Hz), 7.03-7.10 (1H, m), 7.44 (2H, d, J=8.6 Hz), 7.54-7.58 (1H, m), 7.60 (2H, d, J=8.6 Hz), 7.73 (1H, d, J=15.6 Hz), 8.17 (1H, s), 8.56 (1H, s).

MS m/z: 498 (M$^+$+H).

Example 260

Methyl 3-[5-chloro-4-[(4-chlorophenylsulfonyl)(2,5-difluorophenyl)methyl]pyridin-2-yl]propionate

[Chemical formula 158]

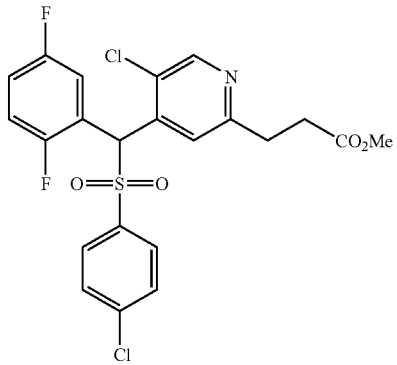

A Raney nickel suspension ("R-100", product of Nikko Rika Corporation) was washed sequentially with water and ethanol to give a corresponding ethanol suspension. The resulting ethanol suspension (2 ml) was added to a solution of methyl(E)-3-[5-chloro-4-[(4-chlorophenylsulfonyl)(2,5-difluorophenyl)methyl]pyridin-2-yl]acrylate (770 mg, 1.55 mmol) in a mixture of ethanol (10 ml) and 1,4-dioxane (5 ml). Under a hydrogen atmosphere of 1 atmospheric pressure, the resulting mixture was stirred vigorously for 30 minutes. After the reaction mixture was filtered, the filtrate was concentrated under reduced pressure. The residue thus obtained was dissolved in dichloromethane (15 ml). The resulting solution was dried over magnesium sulfate, and concentrated under reduced pressure to give the title compound (720 mg, 1.44 mmol, 93%) as a white powder.

$^1$H-NMR (400 MHZ, CDCl$_3$) δ: 2.84 (2H, t, J=7.1 Hz), 3.20 (2H, t, J=7.1 Hz), 3.70 (3H, s), 6.22 (1H, s), 6.92-6.97 (1H, m), 7.02-7.08 (1H, m), 7.43 (2H, d, J=8.6 Hz), 7.53-7.58 (1H, m), 7.61 (2H, d, J=8.6 Hz), 8.03 (1H, s), 8.44 (1H, s).

MS m/z: 500 (M$^+$+H).

Example 261

3-[5-Chloro-4-[(4-chlorophenylsulfonyl)(2,5-difluorophenyl)methyl]pyridin-2-yl]propionic acid

[Chemical formula 159]

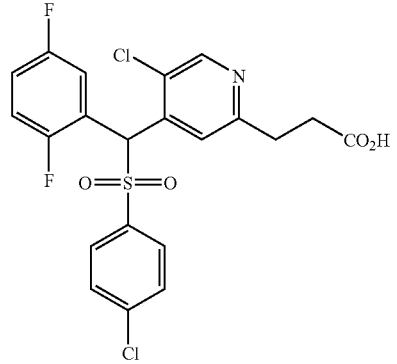

To a solution of methyl 3-[5-chloro-4-[(4-chlorophenylsulfonyl)(2,5-difluorophenyl)methyl]pyridin-2-yl]propionate (200 mg, 0.400 mmol) in a mixture of methanol (2 ml) and tetrahydrofuran (2 ml) was added a 1N aqueous sodium hydroxide solution (2 ml). The resulting mixture was stirred at room temperature for 1 hour. The reaction mixture was made weakly acidic by the addition of 1N hydrochloric acid, followed by extraction with dichloromethane. The organic layer was dried over magnesium sulfate, and concentrated under reduced pressure. The residue thus obtained was recrystallized from hexane:ethyl acetate to give the title compound (161 mg, 0.331 mmol, 83%) as a white powder.

$^1$H-NMR (400 MHz, CDCl$_3$): 2.90 (2H, t, J=6.7 Hz), 3.24 (2H, t, J=6.7 Hz), 6.21 (1H, s), 6.92-6.97 (1H, m), 7.03-7.08 (1H, m), 7.44 (2H, d, J=8.6 Hz), 7.51-7.56 (1H, m), 7.61 (2H, d, J=8.6 Hz), 8.06 (1H, s), 8.47 (1H, s).

IR(ATR)cm$^{-1}$: 1718, 1587, 1496, 1423, 1396, 1365, 1321, 1280, 1240, 1205, 1174, 1083, 1054, 1014.

mp: 194 to 196° C.

MS m/z: 486 (M$^+$+H).

Elemental Analysis for C$_{21}$H$_{15}$Cl$_2$F$_2$NO$_4$S: Calculated: C, 51.86; H, 3.11; Cl, 14.58; F, 7.81; N, 2.88; S, 6.59. Found: C, 51.87; H, 3.07; Cl, 14.37; F, 7.77; N, 2.95; S, 6.75.

Example 262

5-Chloro-4-[(4-chlorophenylsulfonyl)(2,5-difluorophenyl)methyl]picolinic acid

[Chemical formula 160]

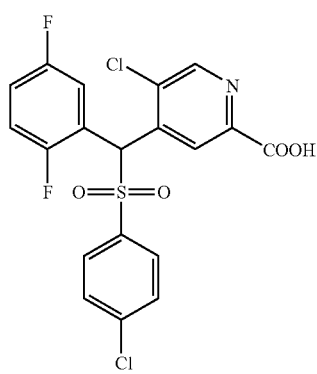

To a formic acid (3 ml) solution of the [5-chloro-4-[(4-chlorophenylsulfonyl)(2,5-difluorophenyl)methyl]pyridin-2-yl]carbaldehyde (150 mg, 0.339 mmol) obtained in Example 258 was added 30% aqueous hydrogen peroxide (115 μl, 1.02 mmol). The resulting mixture was stirred at room temperature for 3 hours. Water was added to the reaction mixture and the solid thus precipitated was filtered. The solid was washed with water. The resulting solid was dissolved in ethyl acetate. The resulting solution was washed sequentially with water and brine. The organic layer thus obtained was dried over magnesium sulfate, and concentrated under reduced pressure. The residue thus obtained was recrystallized from hexane:ethyl acetate to give the title compound (88 mg, 0.192 mmol, 57%) as a white powder.

$^1$H-NMR (400 MHz, CDCl$_3$) δ: 6.30 (1H, s), 6.93-7.00 (1H, m), 7.05-7.11 (1H, m), 7.45 (2H, d, J=8.8 Hz), 7.62-7.66 (1H, m), 7.64 (2H, d, J=8.8 Hz), 8.95 (1H, s), 9.24 (1H, s).

IR(ATR)cm$^{-1}$: 1758, 1712, 1583, 1542, 1494, 1425, 1396, 1328, 1280, 1228, 1153, 1085, 1054, 1014.

mp: 94 to 96° C.

MS m/z: 458 (M$^+$+H).

Elemental Analysis for C$_{19}$H$_{11}$Cl$_2$F$_2$NO$_4$S: Calculated: C, 49.80; H, 2.42; Cl, 15.47; F, 8.29; N, 3.06; S, 7.00. Found: C, 50.05; H, 2.58; Cl, 15.17; F, 8.28; N, 3.06; S, 7.05.

Example 263

2-Bromo-5-chloro-4-[(2,5-difluorophenyl)(4-trifluoromethylphenylthio)methyl]pyridine

[Chemical formula 161]

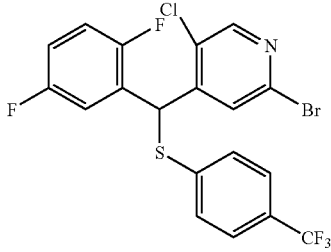

To a dichloromethane solution of the 2-bromo-5-chloro-4-[(2,5-difluorophenyl)hydroxymethyl]pyridine (1.34 g, 4.00 mmol) obtained in Referential Example 52 were sequentially added methanesulfonyl chloride (0.619 ml, 8.00 mmol) and triethylamine (2.23 ml, 16.0 mmol) under a nitrogen atmosphere. The resulting mixture was stirred at room temperature for 1 hour. The reaction mixture was washed sequentially with water and brine. The organic layer was dried over anhydrous sodium sulfate, and filtered. The filtrate was concentrated under reduced pressure.

To an N,N-dimethylformamide (60 ml) solution of the resulting residue were sequentially added 4-trifluorobenzenethiol (784 mg, 4.40 mmol) and potassium carbonate (663 mg, 4.80 mmol) under a nitrogen atmosphere. The resulting mixture was stirred at room temperature for 17 hours. Ethyl acetate was added to the reaction mixture and the resulting mixture was washed with a saturated aqueous solution of sodium bicarbonate. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=50:1 eluate was concentrated under reduced pressure to give the title compound (1.33 g, 2.69 mmol, 67%) as a white solid.

$^1$H-NMR (400 MHz, CDCl$_3$) δ: 6.10 (1H, s), 6.99-7.11 (2H, m), 7.14-7.20 (1H, m), 7.36 (2H, d, J=8.1 Hz), 7.52 (2H, d, J=8.1 Hz), 7.69 (1H, s), 8.36 (1H, s).

MS m/z: 494, 496 (M$^+$+H)

Example 264

Methyl(E)-3-[5-chloro-4-[(2,5-difluorophenyl)(4-trifluoromethylphenylthio)methyl]pyridin-2-yl]acrylate

[Chemical formula 162]

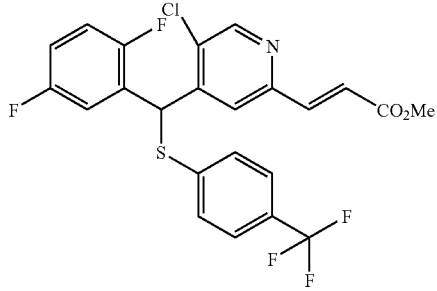

To a toluene (12 ml) solution of 2-bromo-5-chloro-4-[(2,5-difluorophenyl)(4-trifluoromethylphenylthio)methyl]pyridine (396 mg, 0.80 mmol) was added a hexane solution (1.59M, 0.604 ml, 0.96 mmol) of n-butyl lithium at −78° C. under an argon atmosphere. The resulting mixture was stirred for 30 minutes. At the same temperature, N,N-dimethylformamide (0.081 ml, 1.04 mmol) was added and the resulting mixture was stirred for 30 minutes. To the reaction mixture were added a saturated aqueous solution of ammonium chloride and then water. After the temperature of the resulting mixture was raised to room temperature, the product thus obtained was extracted with diethyl ether. The organic layer was dried over anhydrous sodium sulfate and filtered. The filtrate was concentrated under reduced pressure. The residue thus obtained was subjected to flash silica gel chromatography. The fraction obtained from the hexane:ethyl acetate=9:1 eluate was concentrated under reduced pressure to give an aldehyde compound (186 mg).

The aldehyde compound (133 mg) was dissolved in tetrahydrofuran (2 ml). To the resulting solution was added methyl(triphenylphosphoranylidene)acetate (120 mg, 0.36 mmol) at room temperature. The resulting mixture was stirred at the same temperature for 18 hours. After the reaction mixture was concentrated under reduced pressure, the residue thus obtained was subjected to flash silica gel chromatography. The fraction obtained from the hexane:ethyl acetate=19:1 eluate was concentrated under reduced pressure to give the title compound (132 mg, 0.26 mmol, 46%) as a white solid.

$^1$H-NMR (400 MHz, $CDCl_3$) δ: 3.82 (3H, s), 6.17 (1H, s), 6.92 (1H, d, J=15.7 Hz), 6.99-7.09 (2H, m), 7.13-7.18 (1H, m), 7.35 (2H, d, J=8.1 Hz), 7.50 (2H, d, J=8.1 Hz), 7.61 (1H, s), 7.61 (1H, d, J=15.7 Hz), 8.59 (1H, s).

MS m/z: 500 ($M^+$+H).

Example 265

Methyl(E)-3-[5-chloro-4-[(2,5-difluorophenyl)(4-trifluoromethylphenylsulfonyl)methyl]pyridin-2-yl]acrylate

[Chemical formula 163]

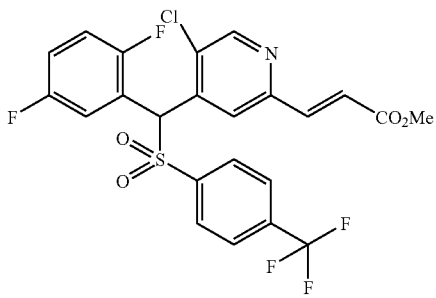

To an ethyl acetate (6 ml) solution of methyl(E)-3-[5-chloro-4-[(2,5-difluorophenyl)(4-trifluoromethylphenylthio)methyl]pyridin-2-yl]acrylate (118 mg, 0.24 mmol) were added methanol (6 ml), 31% aqueous hydrogen peroxide (6 ml) and hexaammonium heptamolybdate tetrahydrate (58 mg, 0.05 mmol). The resulting mixture was stirred at room temperature for 11 hours. To the reaction mixture was added water. After ethyl acetate and methanol were distilled off under reduced pressure, brine was added to the residue. The product thus obtained was extracted with ethyl acetate. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=9:1 eluate was concentrated under reduced pressure to give the title compound (111 mg, 0.21 mmol, 88%) as a white solid.

$^1$H-NMR (400 MHz, $CDCl_3$) δ: 3.86 (3H, s), 6.25 (1H, s), 6.91-6.98 (1H, m), 7.01 (1H, d, J=15.7 Hz), 7.04-7.11 (1H, m), 7.53-7.59 (1H, m), 7.74 (1H, d, J=15.7 Hz), 7.74 (2H, d, J=8.3 Hz), 7.83 (2H, d, J=8.3 Hz), 8.18 (1H, s), 8.56 (1H, s).

MS m/z: 532 ($M^+$+H).

Example 266

Methyl 3-[5-chloro-4-[(2,5-difluorophenyl)(4-trifluoromethylphenylsulfonyl)methyl]pyridin-2-yl]propionate

[Chemical formula 164]

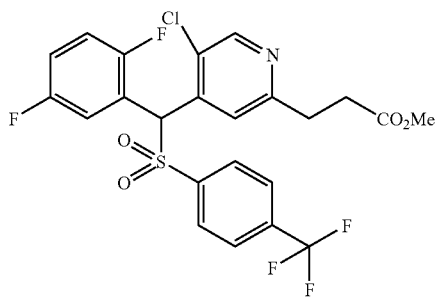

In a mixed solvent of ethyl acetate (3 ml) and methanol (3 ml) was dissolved methyl(E)-3-[5-chloro-4-[(2,5-difluorophenyl)(4-trifluoromethylphenylsulfonyl)methyl]pyridin-2-yl]acrylate (110 mg, 0.21 mmol). To the resulting solution was added 10% palladium-carbon catalyst (60 mg). Under a hydrogen atmosphere, the resulting mixture was stirred at room temperature for 2 hours. After the catalyst was removed by Celite filtration, the filtrate was concentrated under reduced pressure. The residue thus obtained was subjected to flash silica gel column chromatography. The fraction obtained from the hexane:ethyl acetate=4:1 eluate was concentrated under reduced pressure to give the title compound (94 mg, 0.18 mmol, 85%) as a white solid.

$^1$H-NMR (400 MHz, $CDCl_3$) δ: 2.82-2.89 (2H, m), 3.21 (2H, t, J=7.1 Hz), 3.70 (3H, s), 6.25 (1H, s), 6.90-6.97 (1H, m), 7.03-7.10 (1H, m), 7.54-7.60 (1H, m), 7.73 (2H, d, J=8.3 Hz), 7.84 (2H, d, J=8.3 Hz), 8.04 (1H, s), 8.44 (1H, s).

MS m/z: 534 ($M^+$+H)

Example 267

3-[5-Chloro-4-[(2,5-difluorophenyl)(4-trifluoromethylphenylsulfonyl)methyl]pyridin-2-yl]propionic acid

[Chemical formula 165]

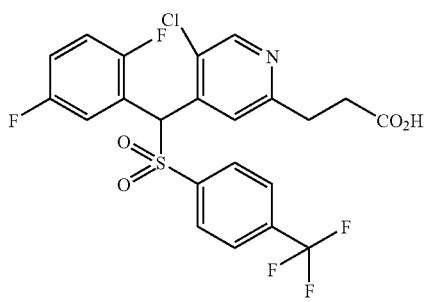

To a tetrahydrofuran (2 ml) solution of methyl 3-[5-chloro-4-[(2,5-difluorophenyl)(4-trifluoromethylphenylsulfonyl)methyl]pyridin-2-yl]propionate (92 mg, 0.17 mmol) were added methanol (2 ml) and a 1N aqueous solution of sodium hydroxide (2 ml) at 0° C. The resulting mixture was stirred at room temperature for 2 hours. To the reaction mixture was added 1N hydrochloric acid and the product thus obtained was extracted with dichloromethane. The organic layer was dried over anhydrous sodium sulfate, and filtered. The filtrate was concentrated under reduced pressure. The residue thus obtained was washed with ethanol and collected by filtration to give the title compound (61 mg, 0.12 mmol, 68%) as a white solid.

$^1$H-NMR (400 MHz, CDCl$_3$) δ: 2.90 (2H, t, J=6.7 Hz), 3.18-3.31 (2H, m), 6.25 (1H, s), 6.90-6.97 (1H, m), 7.03-7.10 (1H, m), 7.51-7.57 (1H, m), 7.74 (2H, d, J=8.3 Hz), 7.82 (2H, d, J=8.3 Hz), 8.07 (1H, s), 8.47 (1H, s).

IR(ATR)cm$^{-1}$: 1707, 1495, 1408, 1321, 1244, 1174, 1159, 1124, 1063.

mp: 166 to 167° C.

Elemental Analysis for C$_{22}$H$_{15}$ClF$_5$NO$_4$S: Calculated: C, 50.83; H, 2.91; Cl, 6.82; F, 18.27; N, 2.69; S, 6.17. Found: C, 50.66; H, 2.93; Cl, 6.87; F, 17.83; N, 2.75; S, 6.28.

MS m/z: 520 (M$^+$+H).

Example 268

N-[5-Chloro-4-[(4-chlorophenylsulfonyl)(2,5-difluorophenyl)methyl]pyridin-2-yl]-1-methyl-1H-imidazole-4-sulfonamide

[Chemical formula 166]

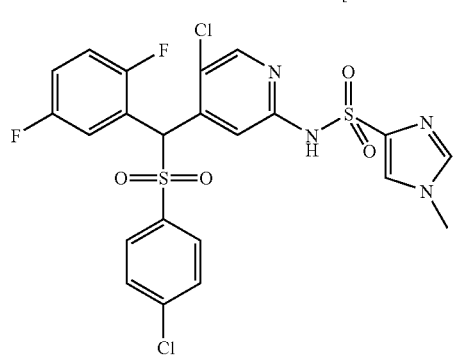

To a methylene chloride (5 ml) solution of the [5-chloro-4-[(4-chlorophenylsulfonyl)(2,5-difluorophenyl)methyl]pyridin-2-yl]amine (93 mg, 0.217 mmol) obtained in Example 196 and pyridine (21 μl, 0.260 mmol) was added 1-methyl-1H-imidazole-4-sulfonyl chloride (47 mg, 0.260 mmol). The resulting mixture was stirred at room temperature for 18 hours. After pyridine (1 ml) was added to the reaction mixture and the resulting mixture was stirred at room temperature for 7 hours, the reaction mixture was concentrated under reduced pressure. To the residue thus obtained was added ethyl acetate. The resulting mixture was washed sequentially with a saturated aqueous solution of sodium bicarbonate and brine, dried over anhydrous sodium sulfate and filtered. The filtrate was concentrated under reduced pressure. The residue thus obtained was subjected to silica gel column chromatography. The fraction obtained from the methanol:methylene chloride (=1:50) eluate was concentrated under reduced pressure to yield a white solid. The resulting white solid was washed with ethanol, and collected by filtration to give the title compound (68 mg, 0.119 mmol, 55%) as a white powder.

$^1$H-NMR (400 MHz, DMSO-d$_6$) δ: 3.69 (3H, s), 6.25 (1H, s), 7.29-7.45 (2H, m), 7.47-7.54 (1H, m), 7.68 (2H, d, J=8.8 Hz), 7.75 (2H, d, J=8.8 Hz), 7.77 (1H, s), 7.94 (1H, s), 8.10 (1H, s), 8.26 (1H, s), 11.40 (1H, brs).

mp: 294 to 296° C.

IR(ATR)cm$^{-1}$: 1594, 1562, 1494, 1382, 1332, 1159, 1118, 993, 817, 755, 723.

MS m/z: 572 (M$^+$).

EI-MS: 571.9962 (Calcd for C$_{22}$H$_{16}$O$_4$N$_4$Cl$_2$F$_2$S$_2$: 571.9958).

Elemental Analysis for C$_{22}$H$_{16}$N$_4$O$_4$Cl$_2$F$_2$S$_2$: Calculated: C, 46.08; H, 2.81; N, 9.77; Cl, 12.37; F, 6.63; S, 11.18. Found: C, 46.04; H, 2.77; N, 9.74; Cl, 12.46; F, 6.90; S, 11.21.

Example 269

N-[5-Chloro-4-[(4-chlorophenylsulfonyl)(2,5-difluorophenyl)methyl]pyridin-2-yl]-1-pyridin-4-yl-methanesulfonamide

[Chemical formula 167]

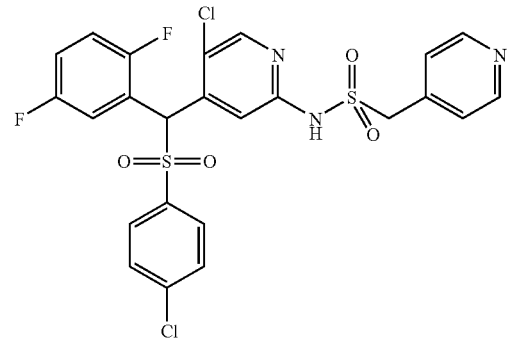

To a methylene chloride (2 ml) solution of the [5-chloro-4-[(4-chlorophenylsulfonyl)(2,5-difluorophenyl)methyl]pyridin-2-yl]amine (104 mg, 0.242 mmol) obtained in Example 196 and pyridine (74 μl, 0.533 mmol) was added (4-pyridylmethyl)sulfonyl chloride triflate (91 mg, 0.266 mmol). The resulting mixture was stirred at room temperature for 17 hours. To the reaction mixture were added pyridine (74 μl, 0.533 mmol) and (4-pyridylmethyl)sulfonyl chloride triflate (91 mg, 0.266 mmol). The resulting mixture was stirred at room temperature for 19 hours. The reaction mixture was diluted with ethyl acetate. The diluted solution was washed with water and brine, dried over anhydrous sodium sulfate, and filtered. The filtrate was concentrated under reduced pressure. The residue thus obtained was subjected to silica gel column chromatography. The fraction obtained from the methanol:methylene chloride (=1:40) eluate was concentrated under reduced pressure to give the title compound (66 mg, 0.113 mmol, 47%) as a white solid.

$^1$H-NMR (400 MHz, DMSO-d$_6$) δ: 4.88 (2H, s), 6.30 (1H, s), 7.27 (2H, d, J=6.0 Hz), 7.29-7.49 (3H, m), 7.70 (2H, d, J=8.8 Hz), 7.74 (1H, s), 7.79 (2H, d, J=8.8 Hz), 8.45 (1H, s), 8.53 (2H, d, J=6.0 Hz), 11.00 (1H, brs).

mp: 257° C. (decomp.)

IR(ATR)cm$^{-1}$: 1592, 1490, 1467, 1340, 1326, 1280, 1238, 1186, 1155, 1128, 1085, 1004, 966, 902, 869, 823.

MS m/z: 584 (M$^+$+H).

Elemental Analysis for $C_{24}H_{17}N_3O_4Cl_2F_2S_2$: Calculated: C, 49.32; H, 2.93; N, 7.19; Cl, 12.13; F, 6.50; S, 10.97. Found: C, 49.35; H, 3.12; N, 7.17; Cl, 12.05; F, 6.43; S, 10.93.

Example 270

N-[5-Chloro-4-[(4-chlorophenylsulfonyl)(2,5-difluorophenyl)methyl]pyridin-2-yl]piperidine-1-sulfonamide

[Chemical formula 168]

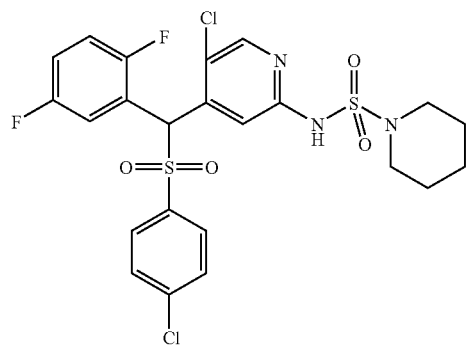

A pyridine (2 ml) solution of the [5-chloro-4-[(4-chlorophenylsulfonyl)(2,5-difluorophenyl)methyl]pyridin-2-yl]amine (101 mg, 0.235 mmol) obtained in Example 196 and piperidine-1-sulfonyl chloride (48 mg, 0.259 mmol) was stirred at 70° C. for 19 hours. To the reaction mixture was added piperidine-1-sulfonyl chloride (48 mg, 0.259 mmol) and the resulting mixture was stirred at 70° C. for 4 days. The reaction mixture was returned to room temperature and then, concentrated under reduced pressure. The residue thus obtained was diluted with ethyl acetate. The diluted solution was washed with water and brine, dried over anhydrous sodium sulfate, and filtered. The filtrate was concentrated under reduced pressure. The residue thus obtained was subjected to flash silica gel column chromatography. The fraction obtained from the hexane:ethyl acetate (=4:1) eluate was concentrated under reduced pressure to yield a white solid. The resulting solid was washed with hexane-ether, and collected by filtration to give the title compound (63 mg, 0.109 mmol, 47%) as a white powder.

$^1$H-NMR (400 MHz, CDCl$_3$) δ: 1.51-1.61 (2H, m), 1.65-1.75 (4H, m), 3.38 (4H, t, J=4.6 Hz), 6.21 (1H, s), 6.94-7.10 (2H, m), 7.41-7.52 (3H, m), 7.70 (2H, d, J=8.6 Hz), 8.24 (1H, s), 8.29 (1H, s), 8.71 (1H, brs)

mp: 192 to 194° C.

IR(ATR)cm$^{-1}$: 1598, 1563, 1492, 1396, 1346, 1322, 1234, 1145, 1083, 998, 923, 900, 833.

MS m/z: 576 (M$^+$+H).

Elemental Analysis for $C_{23}H_{21}N_3O_4Cl_2F_2S_2$: Calculated: C, 47.92; H, 3.67; N, 7.29; Cl, 12.30; F, 6.59; S, 11.12. Found: C, 47.87; H, 3.66; N, 7.33; Cl, 12.12; F, 6.66; S, 11.25.

Example 271

N-[5-Chloro-4-[(4-chlorophenylsulfonyl)(2,5-difluorophenyl)methyl]pyridin-2-yl]-4-methylpiperidine-1-sulfonamide

[Chemical formula 169]

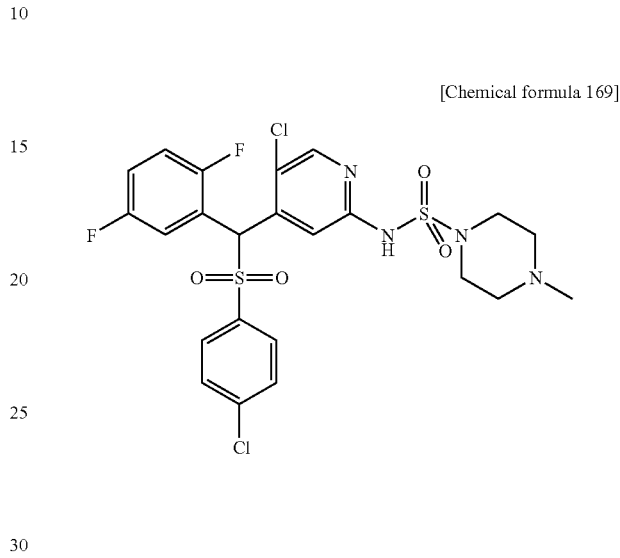

An acetonitrile (5 ml) solution of the [5-chloro-4-[(4-chlorophenylsulfonyl)(2,5-difluorophenyl)methyl]pyridin-2-yl]amine (101 mg, 0.235 mmol) obtained in Example 196, 4-methylpiperazine-1-sulfonyl chloride hydrochloride (126 mg, 0.534 mmol) and triethylamine (150 μl, 1.07 mmol) was heated under reflux for 23 hours. To the reaction mixture were added 4-methylpiperazine-1-sulfonyl chloride hydrochloride (126 mg, 0.534 mmol) and triethylamine (150 μl, 1.07 mmol). The resulting mixture was heated under reflux for 22 hours. The reaction mixture was returned to room temperature and then, concentrated under reduced pressure. To the residue thus obtained was added water and the resulting mixture was extracted with ethyl acetate. The organic layer was washed with brine, dried over anhydrous sodium sulfate, and filtered. The filtrate was concentrated under reduced pressure. The residue thus obtained was subjected to flash silica gel column chromatography. The fraction obtained from the methanol:methylene chloride (=1:20) eluate was concentrated under reduced pressure to give the title compound (34 mg, 0.057 mmol, 16%) as a pale yellow solid.

$^1$H-NMR (400 MHz, CDCl$_3$) δ: 2.31 (3H, s), 2.45-2.60 (4H, m), 3.38-3.52 (4H, m), 6.20 (1H, s), 6.95-7.10 (2H, m), 7.41-7.50 (3H, m), 7.69 (2H, d, J=8.8 Hz), 8.24 (1H, s), 8.26 (1H, s).

mp: 215 to 218° C.

IR(ATR)cm$^{-1}$: 1600, 1565, 1496, 1392, 1348, 1330, 1157, 1093, 935, 835, 819.

MS m/z: 591 (M$^+$+H).

Elemental Analysis for $C_{23}H_{22}N_4O_4Cl_2F_2S_2$: Calculated: C, 46.70; H, 3.75; N, 9.47; Cl, 11.99; F, 6.42; S, 10.84. Found: C, 46.89; H, 3.76; N, 9.40; Cl, 11.78; F, 6.42; S, 10.72.

Example 272

3-Chloro-N-[5-chloro-4-[(4-chlorophenylsulfonyl)(2,5-difluorophenyl)methyl]pyridin-2-yl]-N-(3-chloropropylsulfonyl)propane-1-sulfonamide

[Chemical formula 170]

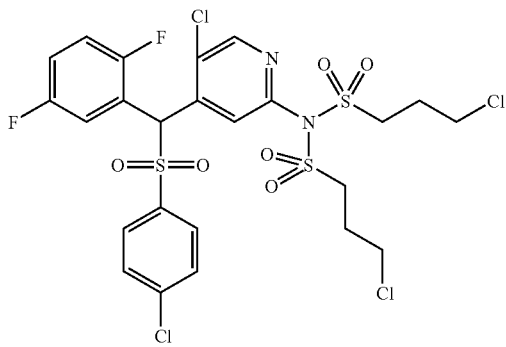

To a methylene chloride (5 ml) solution of the [5-chloro-4-[(4-chlorophenylsulfonyl)(2,5-difluorophenyl)methyl]pyridin-2-yl]amine (130 mg, 0.303 mmol) obtained in Example 196 and triethylamine (42 μl, 0.303 mmol) was added 3-chloropropanesulfonyl chloride (37 μl, 0.303 mmol) at 0° C. The reaction mixture was stirred at room temperature for 2.5 hours. At 0° C., triethylamine (42 μl, 0.303 mmol) and 3-chloropropanesulfonyl chloride (37 μl, 0.303 mmol) were added sequentially. The resulting mixture was stirred at room temperature for 7 hours. To the reaction mixture was added ethyl acetate. The resulting mixture was washed with a saturated aqueous solution of sodium bicarbonate, dried over anhydrous sodium sulfate and filtered. The filtrate was concentrated under reduced pressure. The residue thus obtained was subjected to silica gel column chromatography. The fraction obtained from the hexane:ethyl acetate (=5:1) eluate was concentrated under reduced pressure. To the residue thus obtained was added ether and the solid thus precipitated was collected by filtration to give the title compound as a white powder.

$^1$H-NMR (400 MHz, CDCl$_3$) δ: 2.47-2.57 (4H, m), 3.74 (4H, t, J=6.1 Hz), 3.96-4.05 (4H, m), 6.20 (1H, s), 6.98-7.15 (2H, m), 7.40-7.53 (3H, m), 7.62 (2H, d, J=8.3 Hz), 8.22 (1H, s), 8.64 (1H, s).

MS m/z: 709, 711 (M$^+$+H).

Example 273

3-Chloro-N-[5-chloro-4-[(4-chlorophenylsulfonyl)(2,5-difluorophenyl)methyl]pyridin-2-yl]propane-1-sulfonamide

[Chemical formula 171]

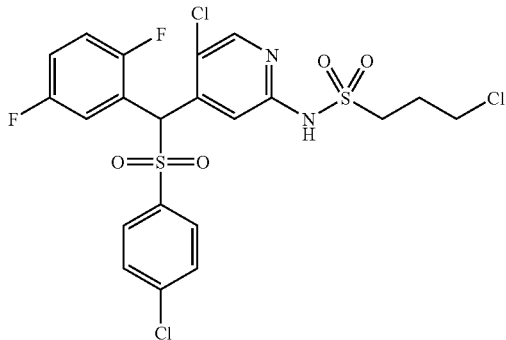

To a tetrahydrofuran (5 ml) solution of 3-chloro-N-[5-chloro-4-[(4-chlorophenylsulfonyl)(2,5-difluorophenyl)methyl]pyridin-2-yl]-N-(3-chloropropylsulfonyl)propane-1-sulfonamide (193 mg, 0.272 mmol) was added to a tetrahydrofuran solution (11.0M, 0.28 ml, 0.28 mmol) of tetrabutylammonium fluoride. The resulting mixture was stirred at room temperature for 1 hour. To the reaction mixture was added a saturated aqueous solution of ammonium chloride, followed by extraction with ethyl acetate. The organic layer was washed with brine, dried over anhydrous sodium sulfate, and filtered. The filtrate was concentrated under reduced pressure. The residue thus obtained was subjected to silica gel column chromatography. The fraction obtained from the hexane:ethyl acetate (=4:1) eluate was concentrated under reduced pressure to give the title compound (108 mg, 0.190 mmol, 70%) as a white solid.

$^1$H-NMR (400 MHz, CDCl$_3$) δ: 2.35-2.44 (2H, m), 3.61-3.67 (2H, m), 3.70 (2H, t, J=6.1 Hz), 6.19 (1H, s), 6.90-6.99 (1H, m), 7.02-7.10 (1H, m), 7.42-7.53 (3H, m), 7.64 (2H, d, J=8.3 Hz), 7.84 (1H, brs), 8.01 (1H, s), 8.31 (1H, s).

IR(ATR)cm$^{-1}$: 1596, 1560, 1488, 1384, 1336, 1234, 1145, 1083, 997, 925, 844.

MS m/z: 568, 570 (M$^+$).

Example 274

5-Chloro-4-[(4-chlorophenylsulfonyl)(2,5-difluorophenyl)methyl]-2-(1,1-dioxo-1λ$^6$-isothiazolidin-2-yl)pyridine

[Chemical formula 172]

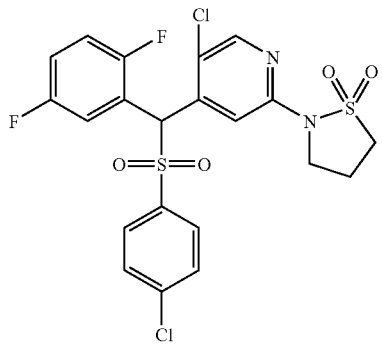

An acetonitrile (5 ml) solution of 3-chloro-N-[5-chloro-4-[(4-chlorophenylsulfonyl)(2,5-difluorophenyl)methyl]pyridin-2-yl]propane-1-sulfonamide (83 mg, 0.146 mmol) and 1,8-diazabicyclo[5.4.0]-7-undecene (26 μl, 0.175 mmol) was stirred at 70° C. for 4.5 hours. The reaction mixture was returned to room temperature and then, concentrated under reduced pressure. The residue thus obtained was diluted with ethyl acetate. The diluted solution was washed sequentially with 1N hydrochloric acid, a saturated aqueous solution of sodium bicarbonate and brine, dried over anhydrous sodium sulfate, and filtered. The filtrate was concentrated under reduced pressure. The residue thus obtained was subjected to flash silica gel column chromatography. The fraction obtained from the hexane:ethyl acetate (=1:1) eluate was concentrated under reduced pressure to give the title compound (75 mg, 0.141 mmol, 96%) as a white solid.

$^1$H-NMR (400 MHz, CDCl$_3$) δ: 2.52-2.62 (2H, m), 3.47 (2H, t, J=7.6 Hz), 4.02 (2H, t, J=6.6 Hz), 6.24 (1H, s), 6.95-7.10 (2H, m), 7.44 (2H, d, J=8.6 Hz), 7.49-7.56 (1H, m), 7.74 (2H, d, J=8.6 Hz), 8.13 (1H, s), 8.24 (1H, s).

mp: 219 to 221° C.

IR(ATR)cm$^{-1}$: 1587, 1496, 1467, 1386, 1346, 1315, 1278, 1238, 1137, 1089, 998, 831.

MS m/z: 532 (M$^+$).

Elemental Analysis for C$_{21}$H$_{16}$N$_2$O$_4$Cl$_2$F$_2$S$_2$: Calculated: C, 47.29; H, 3.02; N, 5.25; Cl, 13.29; F, 7.12; S, 12.02. Found: C, 47.39; H, 3.02; N, 5.37; Cl, 13.32; F, 7.24; S, 11.95.

Example 275

N-[5-Chloro-4-[(4-chlorophenylsulfonyl)(2,5-difluorophenyl)methyl]pyridin-2-yl]-N-(trifluoromethylsulfonyl)trifluoromethanesulfonamide

[Chemical formula 173]

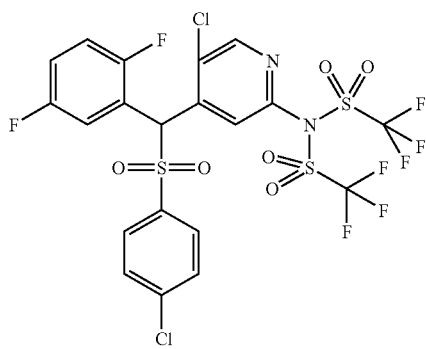

To a methylene chloride (5 ml) solution of the [5-chloro-4-[(4-chlorophenylsulfonyl)(2,5-difluorophenyl)methyl]pyridin-2-yl]amine (103 mg, 0.240 mmol) obtained in Example 196 and pyridine (19 μl, 0.240 mmol) was added trifluoromethanesulfonic anhydride (39 μl, 0.240 mmol) at 0° C. After the resulting mixture was stirred at room temperature for 3 hours, pyridine (19 μl, 0.240 mmol) and trifluoromethanesulfonic anhydride (39 μl, 0.240 mmol) were added at 0° C. The resulting mixture was stirred at room temperature for 15 hours, followed by concentration under reduced pressure. The residue thus obtained was subjected to flash silica gel column chromatography. The fraction obtained from the hexane:ethyl acetate (=5:1) eluate was concentrated under reduced pressure to give the title compound (84 mg, 0.120 mmol, 50%) as a white solid.

$^1$H-NMR (400 MHz, CDCl$_3$) δ: 6.23 (1H, s), 6.99-7.15 (2H, m), 7.38-7.48 (3H, m), 7.62 (2H, d, J=8.8 Hz), 8.36 (1H, s), 8.53 (1H, s).

IR(ATR)cm$^{-1}$: 1581, 1498, 1442, 1332, 1214, 1159, 1122, 1085, 997, 944, 923, 865, 755.

MS m/z: 693 (M$^+$+H).

Example 276

N-[5-Chloro-4-[(4-chlorophenylsulfonyl)(2,5-difluorophenyl)methyl]pyridin-2-yl]trifluoromethanesulfonamide

[Chemical formula 174]

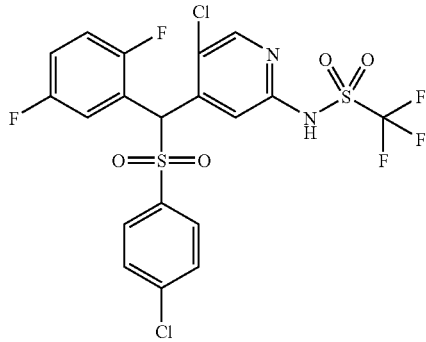

To a solution of N-[5-chloro-4-[(4-chlorophenylsulfonyl)(2,5-difluorophenyl)methyl]pyridin-2-yl]-N-(trifluoromethylsulfonyl)trifluoromethanesulfonamide (77 mg, 0.111 mmol) in a mixture of tetrahydrofuran (5 ml) and water (1 ml) was added lithium hydroxide monohydrate (5.0 mg, 0.111 mmol). The resulting mixture was stirred at room temperature for 5 hours. To the reaction mixture was added a saturated aqueous solution of ammonium chloride, followed by extraction with ethyl acetate. The organic layer was washed with brine, dried over anhydrous sodium sulfate, and filtered. The filtrate was concentrated under reduced pressure. The residue thus obtained was subjected to silica gel column chromatography. The fraction obtained from the hexane:ethyl acetate (=2:1) eluate containing 0.5% trifluoroacetic acid was concentrated under reduced pressure. To the residue thus obtained was added ether, and the solid thus precipitated was collected by filtration to give the title compound (39 mg, 0.069 mmol, 63%) as a white powder.

$^1$H-NMR (400 MHz, CDCl$_3$) δ: 6.21 (1H, s), 6.95-7.03 (1H, m), 7.06-7.15 (1H, m), 7.42-7.52 (3H, m), 7.71 (2H, d, J=8.8 Hz), 8.23 (1H, s), 8.71 (1H, s).

mp: 221 to 223° C.

IR(ATR)cm$^{-1}$: 1637, 1496, 1382, 1336, 1195, 1157, 1130, 1085, 1010, 923, 779, 754.

MS m/z: 560 (M$^+$).

Elemental Analysis for $C_{19}H_{11}N_2O_4Cl_2F_5S_2$: Calculated: C, 40.65; H, 1.98; N, 4.99; Cl, 12.63; F, 16.92; S, 11.42. Found: C, 40.68; H, 1.94; N, 5.06; Cl, 12.46; F, 16.91; S, 11.47.

Example 277

N-[5-Chloro-4-[(4-chlorophenylsulfonyl)(2,5-difluorophenyl)methyl]pyridin-2-yl]ethylenesulfonamide

[Chemical formula 175]

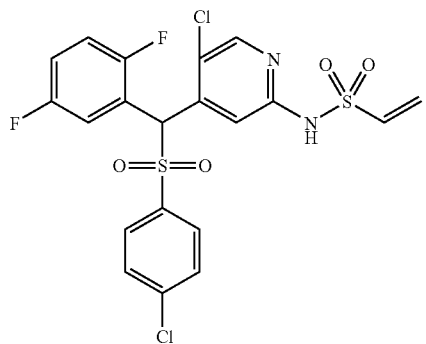

To a methylene chloride (10 ml) solution of the [5-chloro-4-[(4-chlorophenylsulfonyl)(2,5-difluorophenyl)methyl]pyridin-2-yl]amine (982 mg, 2.29 mmol) obtained in Example 196 and 2-chloroethanesulfonyl chloride (0.29 ml, 2.74 mmol) was added pyridine (0.44 ml, 5.49 mmol). The resulting mixture was stirred at room temperature for 3.5 hours. To the reaction mixture were added 2-chloroethanesulfonyl chloride (143 μl, 1.37 mmol) and pyridine (222 μl, 2.75 mmol). The resulting mixture was stirred at room temperature for 1 hour. Ethyl acetate was added to the reaction mixture. The resulting mixture was washed with a saturated aqueous solution of sodium bicarbonate, dried over anhydrous sodium sulfate and filtered. The filtrate was concentrated under reduced pressure. The residue thus obtained was subjected to flash silica gel column chromatography. The fraction obtained from the hexane:ethyl acetate (=3:1) eluate was concentrated under reduced pressure to give the title compound (573 mg, 1.10 mmol, 48%) as a white solid.

$^1$H-NMR (400 MHz, CDCl$_3$) δ: 6.17-6.25 (2H, m), 6.65-6.70 (2H, m), 6.91-7.10 (2H, m), 7.41-7.49 (3H, m), 7.66 (2H, d, J=8.6 Hz), 8.16 (1H, s), 8.33 (1H, s)

IR(ATR)cm$^{-1}$: 1600, 1565, 1492, 1388, 1349, 1322, 1147, 1081, 998, 916, 821, 757.

MS m/z: 519 (M$^+$+H).

Example 278

N-[5-Chloro-4-[(4-chlorophenylsulfonyl)(2,5-difluorophenyl)methyl]pyridin-2-yl]-2-piperidin-1-ylethanesulfonamide

[Chemical formula 176]

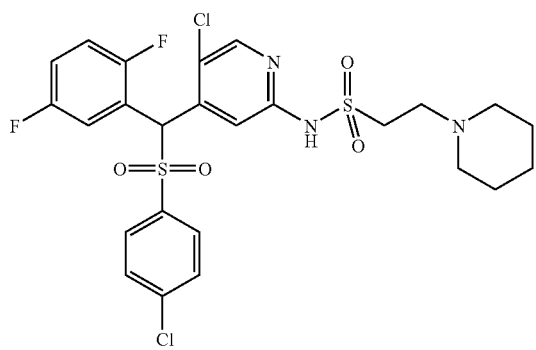

To an ethanol (5 ml) solution of N-[5-chloro-4-[(4-chlorophenylsulfonyl)(2,5-difluorophenyl)methyl]pyridin-2-yl]ethylenesulfonamide (34 mg, 0.065 mmol) was added piperidine (10 μl, 0.098 mmol). The resulting mixture was stirred at room temperature for 3 days. The reaction mixture was concentrated under reduced pressure. The residue thus obtained was subjected to flash silica gel column chromatography. The fraction obtained from the methanol:methylene chloride (=1:30) eluate was concentrated under reduced pressure to give the title compound (35 mg, 0.058 mmol, 89%) as an amorphous substance. The resulting amorphous substance was solidified by adding ethanol thereto and collected by filtration to give the title compound as a white powder.

$^1$H-NMR (400 MHz, CDCl$_3$) δ: 1.45-1.76 (6H, m), 2.50-2.65 (4H, m), 2.97 (2H, t, J=5.9 Hz), 3.30-3.38 (2H, m), 6.21 (1H, s), 6.92-7.10 (2H, m), 7.44 (2H, d, J=8.6 Hz), 7.52-7.59 (1H, m), 7.69 (2H, d, J=8.6 Hz), 8.06 (1H, s), 8.22 (1H, s).
mp: 200 to 203° C.
IR(ATR)cm$^{-1}$: 1600, 1571, 1492, 1390, 1332, 1141, 1083, 1002, 962, 919, 811, 754.
MS m/z: 604 (M$^+$+H).
Elemental Analysis for C$_{25}$H$_{25}$N$_3$O$_4$Cl$_2$F$_2$S$_2$: Calculated: C, 49.67; H, 4.17; N, 6.95; Cl, 11.73; F, 6.29; S, 10.61. Found: C, 49.90; H, 4.13; N, 6.88; Cl, 11.64; F, 6.17; S, 10.52.

Example 279

N-[5-Chloro-4-[(4-chlorophenylsulfonyl)(2,5-difluorophenyl)methyl]pyridin-2-yl]-2-(dimethylamino)ethanesulfonamide

[Chemical formula 177]

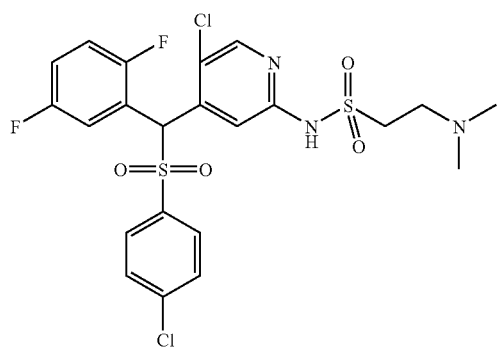

To a tetrahydrofuran (3 ml) solution of the N-[5-chloro-4-[(4-chlorophenylsulfonyl)(2,5-difluorophenyl)methyl]pyridin-2-yl]ethylenesulfonamide (64 mg, 0.123 mmol) obtained in Example 277 was added a dimethylamine tetrahydrofuran solution (2M, 0.18 ml, 0.36 mmol). The resulting mixture was stirred at room temperature for 3 days, followed by concentration under reduced pressure. The residue thus obtained was subjected to flash silica gel column chromatography. The fraction obtained from the methanol:methylene chloride (=1:20) eluate was concentrated under reduced pressure to give the title compound (67 mg, 0.117 mmol, 97%) as a white solid. The resulting solid was washed with ethanol and collected by filtration to give the title compound (43 mg) as a white powder.

$^1$H-NMR (400 MHz, CD$_3$OD) δ: 2.73 (6H, s), 3.37 (2H, t, J=7.0 Hz), 3.82 (2H, t, J=7.0 Hz), 6.31 (1H, s), 7.16-7.26 (2H, m), 7.53-7.65 (3H, m), 7.75 (2H, d, J=8.8 Hz), 7.84 (1H, s), 8.24 (1H, s).
IR(ATR)cm$^{-1}$: 1587, 1494, 1455, 1321, 1151, 1087, 998, 757.
MS m/z: 564 (M$^+$+H).
FAB-MS: 564.0399 (Calcd for C$_{22}$H$_{22}$O$_4$N$_3$Cl$_2$F$_2$S$_2$: 564.0397).

Example 280

N-[5-Chloro-4-[(4-chlorophenylsulfonyl)(2,5-difluorophenyl)methyl]pyridin-2-yl]-2-morpholin-4-ylethanesulfonamide

[Chemical formula 178]

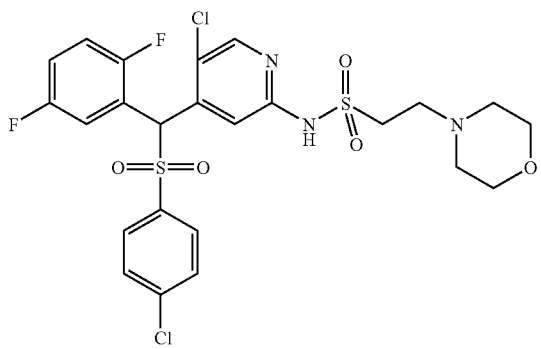

To an ethanol (3 ml) solution of the N-[5-chloro-4-[(4-chlorophenylsulfonyl)(2,5-difluorophenyl)methyl]pyridin-2-yl]ethylenesulfonamide (53 mg, 0.102 mmol) obtained in Example 277 was added morpholine (18 μl, 0.204 mmol). The resulting mixture was stirred at room temperature for 3 days, followed by concentration under reduced pressure. The residue thus obtained was subjected to flash silica gel column chromatography. The fraction obtained from the methanol:methylene chloride (=1:40) eluate was concentrated under reduced pressure. Ether was added to the residue thus obtained. The solid thus precipitated was collected by filtration to give the title compound (45 mg, 0.074 mmol, 73%) as a white powder.

$^1$H-NMR (400 MHz, CDCl$_3$) δ: 2.51-2.60 (4H, m), 2.96 (2H, t, J=6.1 Hz), 3.36-3.45 (2H, m), 3.70-3.80 (4H, m), 6.22 (1H, s), 6.90-7.10 (2H, m), 7.45 (2H, d, J=8.8 Hz), 7.50-7.59 (1H, m), 7.68 (2H, d, J=8.8 Hz), 8.19 (1H, s), 8.24 (1H, s).
mp: 219 to 221° C.
IR(ATR)cm$^{-1}$: 1602, 1565, 1492, 1388, 1321, 1286, 1238, 1147, 1116, 1083, 998.
MS m/z: 606 (M$^+$+H)
FAB-MS: 606.0499 (Calcd for C$_{24}$H$_{24}$O$_5$N$_3$Cl$_2$F$_2$S$_2$: 606.0503).

Elemental Analysis for $C_{24}H_{23}N_3O_5Cl_2F_2S_2$: Calculated: C, 47.53; H, 3.82; N, 6.93; Cl, 11.69; F, 6.27; S, 10.57. Found: C, 47.73; H, 3.84; N, 6.97; Cl, 11.72; F, 6.25; S, 10.72.

Example 281 t-Butyl 4-[2-[[[5-chloro-4-[(4-chlorophenylsulfonyl)(2,5-difluorophenyl)methyl]pyridin-2-yl]amino]sulfonyl]ethyl]piperazine-1-carboxylate

[Chemical formula 179]

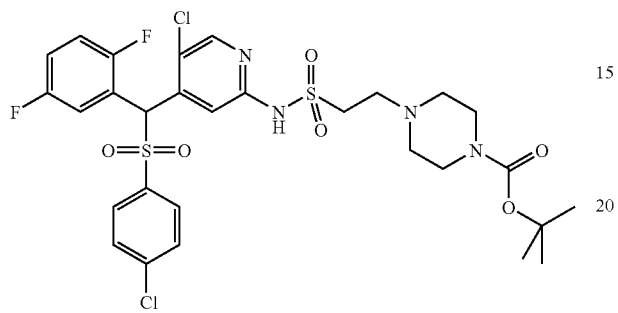

To an ethanol (3 ml) solution of the N-[5-chloro-4-[(4-chlorophenylsulfonyl)(2,5-difluorophenyl)methyl]pyridin-2-yl]ethylenesulfonamide (59 mg, 0.114 mmol) obtained in Example 277 was added 1-(t-butoxycarbonyl)piperazine (32 mg, 0.170 mmol). The resulting mixture was stirred at room temperature for 3 days, followed by concentration under reduced pressure. The residue thus obtained was subjected to flash silica gel column chromatography. The fraction obtained from the methanol:methylene chloride (=1:40) eluate was concentrated under reduced pressure to give the title compound (75 mg, 0.106 mmol, 93%) as an amorphous substance.

$^1$H-NMR (400 MHz, CDCl$_3$) δ: 1.46 (9H, s), 2.50 (4H, t, J=5.0 Hz), 2.97 (2H, t, J=6.0 Hz), 3.35-3.42 (2H, m), 3.44-3.54 (4H, m), 6.22 (1H, s), 6.90-7.10 (2H, m), 7.45 (2H, d, J=8.8 Hz), 7.50-7.58 (1H, m), 7.68 (2H, d, J=8.8 Hz), 8.19 (1H, s), 8.24 (1H, s).

IR(ATR)cm$^{-1}$: 1691, 1592, 1494, 1330, 1240, 1147, 1083, 998, 755.

MS m/z: 705 (M$^+$+H).

Example 282

N-[5-Chloro-4-[(4-chlorophenylsulfonyl)(2,5-difluorophenyl)methyl]pyridin-2-yl]-2-piperazin-1-ylethanesulfonamide

[Chemical formula 180]

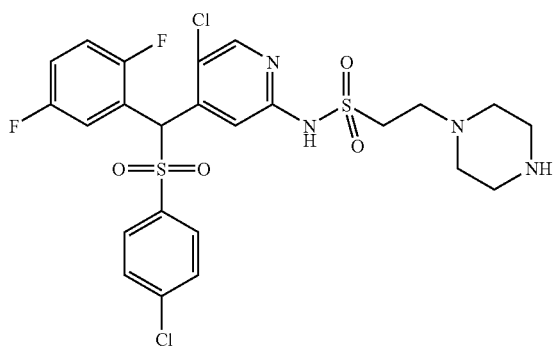

To an ethanol (5 ml) solution of t-butyl 4-[2-[[[5-chloro-4-[(4-chlorophenylsulfonyl)(2,5-difluorophenyl)methyl]pyridin-2-yl]amino]sulfonyl]ethyl]piperazine-1-carboxylate (72 mg, 0.102 mmol) was added concentrated hydrochloric acid (1 ml). The resulting mixture was stirred at room temperature for 2 days, followed by concentration under reduced pressure. To the residue thus obtained was added a saturated aqueous solution of sodium bicarbonate. The resulting mixture was extracted with methylene chloride. The organic layer was dried over anhydrous sodium sulfate, and filtered. The filtrate was concentrated under reduced pressure. The residue thus obtained was washed with ether to give the title compound (23 mg, 0.038 mmol, 37%) as a white powder.

$^1$H-NMR (400 MHz, DMSO-d$_6$) δ: 2.40-2.47 (4H, m), 2.62-2.70 (2H, m), 2.83-2.90 (4H, m), 6.15 (1H, s), 7.25-7.42 (3H, m), 7.47-7.55 (1H, m), 7.68 (2H, d, J=8.7 Hz), 7.77 (2H, d, J=8.7 Hz), 8.03 (1H, s).

MS m/z: 605 (M$^+$+H).

Example 283

Ethyl[[[5-Chloro-4-[(4-chlorophenylsulfonyl)(2,5-difluorophenyl)methyl]pyridin-2-yl]amino]sulfonyl]acetate

[Chemical formula 181]

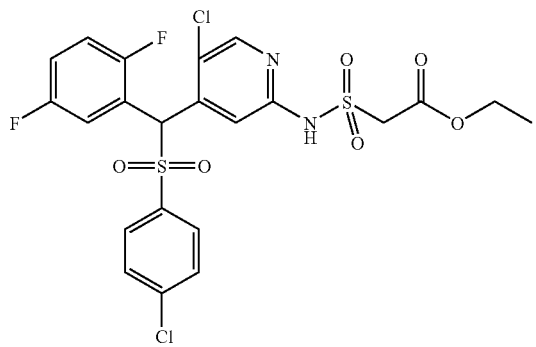

To a methylene chloride (10 ml) solution of the [5-chloro-4-[(4-chlorophenylsulfonyl)(2,5-difluorophenyl)methyl]pyridin-2-yl]amine (331 mg, 0.771 mmol) obtained in Example 196 and pyridine (94 μl, 1.16 mmol) was added a methylene chloride (2 ml) solution of ethyl chlorosulfonylacetate (216 mg, 1.16 mmol) at 0° C. After the resulting mixture was stirred at room temperature for 12 hours, pyridine (94 up, 1.16 mmol) and a methylene chloride (2 ml) solution of ethyl chlorosulfonylacetate (216 mg, 1.16 mmol) were added sequentially at 0° C. The resulting mixture was stirred at room temperature for 9 hours and then, the reaction mixture was concentrated under reduced pressure. To the residue thus obtained was added ethyl acetate. The resulting mixture was washed sequentially with a saturated aqueous solution of sodium bicarbonate and brine, dried over anhydrous sodium sulfate, and filtered. The filtrate was concentrated under reduced pressure. The residue thus obtained was subjected to flash silica gel column chromatography. The fraction obtained from the hexane:ethyl acetate (=3:1) eluate was concentrated under reduced pressure to give the title compound (239 mg, 0.412 mmol, 53%) as a white solid.

$^1$H-NMR (400 MHz, CDCl$_3$) δ: 1.29 (3H, t, J=7.2 Hz), 4.25 (2H, q, J=7.2 Hz), 4.37 (2H, s), 6.21 (1H, s), 6.91-7.10 (2H, m), 7.45 (2H, d, J=8.6 Hz), 7.50-7.58 (1H, m), 7.66 (2H, d, J=8.6 Hz), 8.09 (1H, s), 8.30 (1H, s).

IR(ATR)cm$^{-1}$: 1745, 1600, 1567, 1496, 1386, 1355, 1317, 1280, 1232, 1147, 1081.

MS m/z: 579 (M$^+$+H).

Example 284

N-[5-Chloro-4-[(4-chlorophenylsulfonyl)(2,5-difluorophenyl)methyl]pyridin-2-yl]-2-hydroxyethanesulfonamide

[Chemical formula 182]

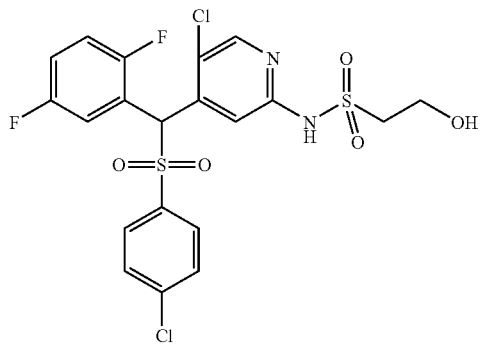

To a tetrahydrofuran (5 ml) solution of ethyl[[[5-chloro-4-[(4-chlorophenylsulfonyl)(2,5-difluorophenyl)methyl]pyridin-2-yl]amino]sulfonyl]acetate (67 mg, 0.116 mmol) was added an ether solution (0.18 ml) of 1M lithium aluminum hydride at 0° C. The resulting mixture was stirred at 0° C. After the termination of the reaction was confirmed by TLC, a saturated aqueous solution of ammonium chloride was added to the reaction mixture. The resulting mixture was filtered through Celite. The filtrate was dried over anhydrous sodium sulfate, and filtered. The filtrate was concentrated under reduced pressure. The residue thus obtained was subjected to flash silica gel column chromatography. The fraction obtained from the hexane:ethyl acetate (=2:1) eluate was concentrated under reduced pressure to give the title compound (39 mg, 0.073 mmol, 63%) as a white solid.

$^1$H-NMR (400 MHz, DMSO-d$_6$) δ: 3.63 (2H, t, J=6.3 Hz), 3.75-3.85 (2H, m), 4.94 (1H, brs), 6.28 (1H, s), 7.28-7.55 (3H, m), 7.70 (2H, d, J=8.7 Hz), 7.80 (2H, d, J=8.7 Hz), 7.81 (1H, s), 8.37 (1H, s), 10.91 (1H, brs).

mp: 155 to 158° C.

IR(ATR)cm$^{-1}$: 3093, 2867, 1600, 1565, 1492, 1392, 1322, 1139, 1083, 813, 754.

MS m/z: 536 (M$^+$).

EI-MS: 535.9835 (Calcd for C$_{20}$H$_{16}$O$_5$N$_2$Cl$_2$F$_2$S$_2$: 535.9846).

Elemental Analysis for C$_{20}$H$_{16}$N$_2$O$_5$Cl$_2$F$_2$S$_2$.0.5H$_2$O: Calculated: C, 43.96; H, 3.14; N, 5.13; Cl, 12.98; F, 6.95; S, 11.74. Found: C, 44.22; H, 3.07; N, 5.13; Cl, 12.89; F, 7.10; S, 11.65.

Example 285

2-[[[5-Chloro-4-[(4-chlorophenylsulfonyl)(2,5-difluorophenyl)methyl]pyridin-2-yl]amino]sulfonyl]acetamide

[Chemical formula 183]

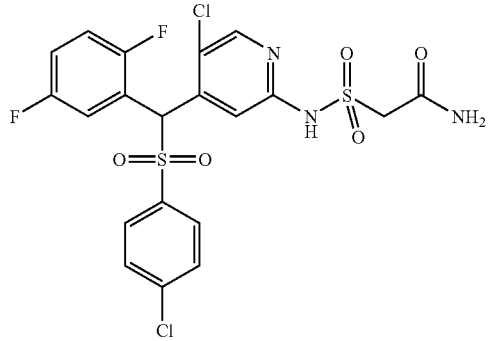

To a methanol solution (5 ml) of 7N ammonia was added the ethyl[[[5-chloro-[(4-chlorophenylsulfonyl)(2,5-difluorophenyl)methyl]pyridin-2-yl]amino]sulfonyl]acetate (78 mg, 0.135 mmol) obtained in Example 283. The resulting mixture was stirred at room temperature for 3 days, followed by concentration under reduced pressure. The residue thus obtained was subjected to flash silica gel column chromatography. The fraction obtained from the methanol:methylene chloride (=1:25) eluate was concentrated under reduced pressure to give the title compound (66 mg, 0.120 mmol, 89%) as a white solid.

$^1$H-NMR (400 MHz, DMSO-d$_6$) δ: 4.33 (2H, s), 6.29 (1H, s), 7.29-7.56 (4H, m), 7.64-7.72 (3H, m), 7.76-7.84 (3H, m), 8.35 (1H, s), 11.16 (1H, brs).

IR(ATR)cm$^{-1}$: 1691, 1596, 1565, 1492, 1382, 1322, 1238, 1149, 1083, 995, 966, 811.

MS m/z: 550 (M$^+$+H).

Elemental Analysis for C$_{20}$H$_{15}$N$_3$O$_5$Cl$_2$F$_2$S$_2$.0.5H$_2$O: Calculated: C, 42.94; H, 2.88; N, 7.51; Cl, 12.68; F, 6.79; S, 11.46. Found: C, 42.64; H, 2.73; N, 7.46; Cl, 12.57; F, 6.97; S, 11.48.

Example 286

[[[5-Chloro-4-[(4-chlorophenylsulfonyl)(2,5-difluorophenyl)methyl]pyridin-2-yl]amino]sulfonyl]acetic acid

[Chemical formula 184]

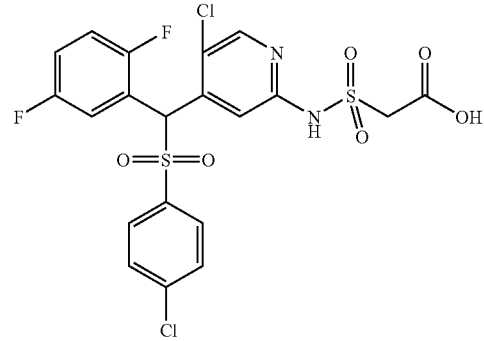

To a solution of the ethyl[[[5-chloro-4-[(4-chlorophenylsulfonyl)(2,5-difluorophenyl)methyl]pyridin-2-yl]amino]sulfonyl]acetate (60 mg, 0.104 mmol) obtained in Example 283 in a mixture of tetrahydrofuran (5 ml) and water (1 ml) was added lithium hydroxide monohydrate (9.1 mg, 0.218 mmol). The resulting mixture was stirred at room temperature for 2 hours. To the reaction mixture was added 1N hydrochloric acid. The resulting mixture was extracted with methylene chloride. The extract was dried over anhydrous sodium sulfate, and filtered. The filtrate was concentrated under reduced pressure. The residue thus obtained was subjected to silica gel column chromatography. The fraction obtained from the methanol:methylene chloride (=1:30) eluate containing 0.5% trifluoroacetic acid was concentrated under reduced pressure to give the title compound (54 mg, 0.098 mmol, 94%) as a white solid.

$^1$H-NMR (400 MHz, DMSO-$d_6$) δ: 4.45-4.60 (2H, m), 6.29 (1H, s), 7.29-7.55 (3H, m), 7.69 (2H, d, J=8.9 Hz), 7.80 (2H, d, J=8.9 Hz), 7.81 (1H, s), 8.38 (1H, s).

MS m/z: 551 (M$^+$+H).

Example 287

(Z)-5-Chloro-4-[(4-chlorophenylsulfonyl)(2,5-difluorophenyl)methyl]-2-(3-[1,3]dioxolan-2-ylpropenyl)pyridine (Isomer 287-A) and (E)-5-chloro-4-[(4-chlorophenylsulfonyl)(2,5-difluorophenyl)methyl]-2-(3-[1,3]dioxolan-2-ylpropenyl)pyridine (Isomer 287-B)

[Chemical formula 185]

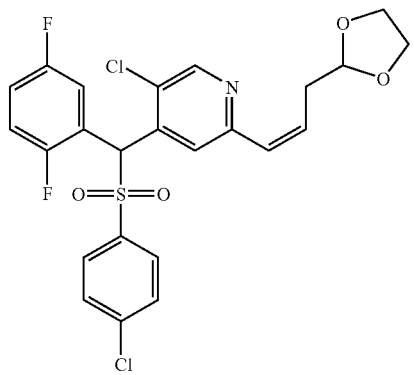

Isomer 287-A

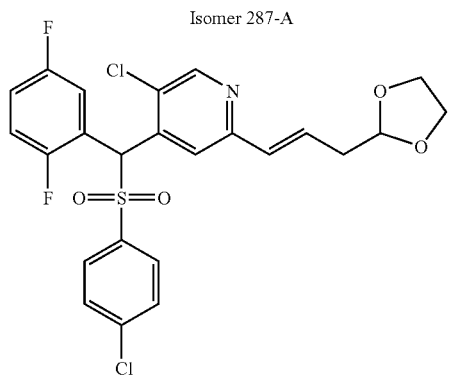

Isomer 287-B

Under an argon atmosphere, n-butyl lithium (a 1.59M hexane solution, 1.3 ml, 1.99 mmol) was added to a tetrahydrofuran (30 ml) solution of 2-(1,3-dioxolan-2-yl)ethyltriphenylphosphonium bromide (738 mg, 1.99 mmol) at −78° C. The resulting mixture was stirred for 1 hour. To the reaction mixture was added the [5-chloro-4-[(4-chlorophenylsulfonyl)(2,5-difluorophenyl)methyl]pyridin-2-yl]carbaldehyde (400 mg, 0.904 mmol) obtained in Example 258. The temperature of the resulting mixture was raised to room temperature, followed by stirring for 4 hours. To the reaction mixture was added a saturated aqueous solution of ammonium chloride. The resulting mixture was then extracted with dichloromethane. The organic layer was dried over magnesium sulfate, and concentrated under reduced pressure. The residue thus obtained was subjected to flash silica gel column chromatography. The fraction obtained from the hexane:ethyl acetate=4:1 eluate was concentrated under reduced pressure to give Isomer 287-A (low polar) (140 mg, 0.266 mmol, 29%) as a colorless amorphous substance and Isomer 287-B (high polar) (170 mg, 0.323 mmol, 36%) as a colorless amorphous substance.

Isomer 287-A $^1$H-NMR (400 MHz, CDCl$_3$) δ: 3.03-3.17 (2H, m), 3.88-4.10 (4H, m), 5.11 (1H, t, J=4.3 Hz), 6.10 (1H, dt, J=12.0, 7.6 Hz), 6.25 (1H, s), 6.65 (1H, d, J=12.0 Hz), 6.93-6.99 (1H, m), 7.03-7.09 (1H, m), 7.44 (2H, d, J=8.6 Hz), 7.61 (2H, d, J=8.6 Hz), 7.67-7.71 (1H, m), 8.10 (1H, s), 8.49 (1H, s).

MS m/z: 526 (M$^+$+H).

Isomer 287-B $^1$H-NMR (400 MHz, CDCl$_3$) δ: 2.67-2.71 (2H, m), 3.88-4.08 (4H, m), 5.07 (1H, t, J=4.6 Hz), 6.20 (1H, s), 6.68 (1H, d, J=15.9 Hz), 6.85-7.00 (2H, m), 7.02-7.08 (1H, m), 7.44 (2H, d, J=8.1 Hz), 7.55-7.62 (1H, m), 7.61 (2H, d, J=8.1 Hz), 7.96 (1H, s), 8.43 (1H, s).

MS m/z: 526 (M$^+$+H).

Example 288

4-[5-Chloro-4-[(4-chlorophenylsulfonyl)(2,5-difluorophenyl)methyl]pyridin-2-yl]butylaldehyde

[Chemical formula 186]

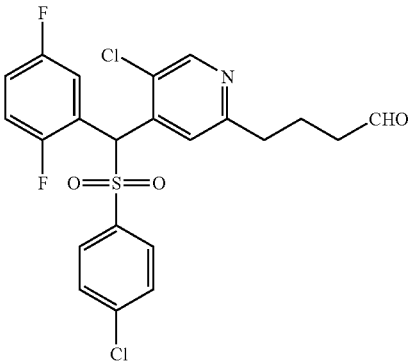

After a water suspension of Raney nickel ("R-100", product of Nikko Rica Corporation) was washed sequentially with water and ethanol, ethanol was added thereto to give a corresponding ethanol suspension. The resulting ethanol suspension (1 ml) was added to a solution of (Z) and (E)-5-chloro-4-[(4-chlorophenylsulfonyl)(2,5-difluorophenyl)methyl]-2-(3-[1,3]dioxolan-2-ylpropenyl)pyridine (80 mg, 0.152 mmol) in a mixture of ethanol (5 ml) and 1,4-dioxane (3 ml). Under a hydrogen atmosphere of 1 atmospheric pressure, the resulting mixture was stirred vigorously for 30 minutes. After the reaction mixture was filtered, the filtrate was concentrated under reduced pressure.

To a 1,4 dioxane (4 ml) solution of the residue thus obtained was added concentrated hydrochloric acid (1 ml) and the resulting mixture was stirred at room temperature for 1 hour. The solvent was then concentrated under reduced pressure. To the residue thus obtained was added a saturated aqueous solution of sodium bicarbonate, followed by extraction with ethyl acetate. The organic layer was washed with brine. The organic layer thus obtained was dried over magnesium sulfate, and concentrated under reduced pressure. The residue thus obtained was subjected to flash silica gel column chromatography. The fraction obtained from the hexane:ethyl acetate=4:1 eluate was concentrated under reduced pressure to give the title compound (44 mg, 0.0908 mmol, 59%) as a colorless amorphous substance.

$^1$H-NMR (400 MHz, CDCl$_3$) δ: 2.09-2.17 (2H, m), 2.56 (2H, td, J=7.3, 1.5 Hz), 2.92 (2H, t, J=7.7 Hz), 6.21 (1H, s), 6.92-6.97 (1H, m), 7.03-7.08 (1H, m), 7.45 (2H, d, J=8.6 Hz), 7.51-7.55 (1H, m), 7.61 (2H, d, J=8.6 Hz), 7.95 (1H, s), 8.47 (1H, s), 9.81 (1H, t, J=1.5 Hz)

MS m/z: 484 (M$^+$+H).

Example 289

4-[5-Chloro-4-[(4-chlorophenylsulfonyl)(2,5-difluorophenyl)methyl]pyridin-2-yl]butyric acid

[Chemical formula 187]

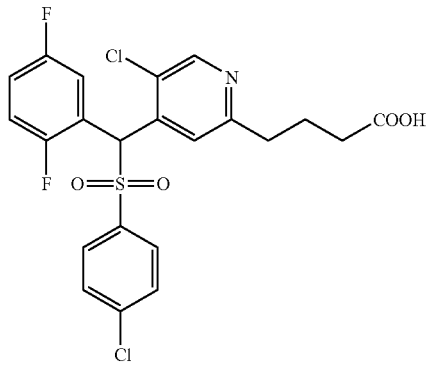

To a formic acid (1 ml) solution of 4-[5-chloro-4-[(4-chlorophenylsulfonyl)(2,5-difluorophenyl)methyl]pyridin-2-yl]butylaldehyde (40 mg, 0.0828 mmol) was added 30% aqueous hydrogen peroxide (84 μl, 0.745 mmol). The resulting mixture was stirred at room temperature for 9 hours. Water was added to the reaction mixture, followed by extraction with ethyl acetate. The organic layer was washed sequentially with water and brine. The organic layer was dried over magnesium sulfate, and concentrated under reduced pressure. The residue thus obtained was recrystallized from hexane:ethyl acetate to give the title compound (13 mg, 0.0260 mmol, 32%) as a white powder.

$^1$H-NMR (400 MHz, CDCl$_3$) δ: 2.16-2.18 (2H, m), 2.46 (2H, t, J=7.2 Hz), 2.99 (2H, t, J=7.5 Hz), 6.22 (1H, s), 6.92-6.98 (1H, m), 7.03-7.08 (1H, m), 7.45 (2H, d, J=8.6 Hz), 7.51-7.56 (1H, m), 7.61 (2H, d, J=8.6 Hz), 8.00 (1H, s), 8.49 (1H, s).

mp: 147 to 148° C.

MS m/z: 500 (M$^+$+H).

Example 290

2-Bromomethyl-5-chloro-4-[(4-chlorophenylthio)(2,5-difluorophenyl)methyl]pyridine

[Chemical formula 188]

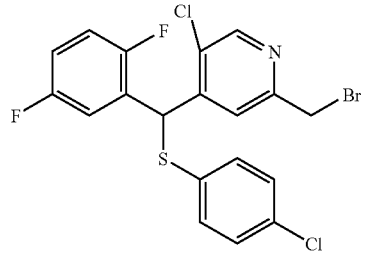

To a dichloromethane (15 ml) solution of the [5-chloro-4-[(4-chlorophenylthio)(2,5-difluorophenyl)methyl]pyridin-2-yl]methanol (582 mg, 1.41 mmol) obtained in Example 256 were sequentially added carbon tetrabromide (936 mg, 2.82 mmol) and triphenylphosphine (407 mg, 1.55 mmol) at 0° C. The resulting mixture was stirred at room temperature for 15 hours. The reaction mixture was concentrated under reduced pressure. The residue thus obtained was subjected to flash silica gel column chromatography. The fraction obtained from the hexane:ethyl acetate=20:1 eluate was concentrated under reduced pressure to give the title compound (518 mg, 1.09 mmol, 77%) as a colorless oil.

$^1$H-NMR (400 MHz, CDCl$_3$) δ: 4.51 (1H, d, J=10.5 Hz), 4.54 (1H, d, J=10.5 Hz), 6.03 (1H, s), 6.94-7.06 (2H, m), 7.10-7.16 (1H, m), 7.23 (2H, d, J=8.5 Hz), 7.28 (2H, d, J=8.5 Hz), 7.73 (1H, s), 8.49 (1H, s).

MS m/z: 474, 476 (M$^+$+H).

Example 291

[5-Chloro-4-[(4-chlorophenylthio)(2,5-difluorophenyl)methyl]pyridin-2-yl]acetonitrile

[Chemical formula 189]

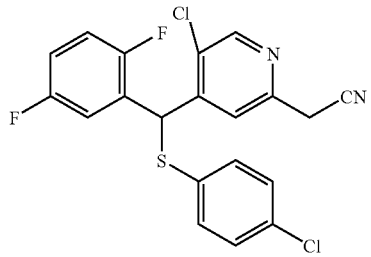

Under an argon atmosphere, trimethylsilylnitrile (0.226 ml, 1.63 mmol) and a tetrahydrofuran solution (1M, 1.63 ml, 1.63 mmol) of tetrabutylammonium fluoride were added sequentially to an acetonitrile (10 ml) solution of 2-bromomethyl-5-chloro-4-[(4-chlorophenylthio)(2,5-difluorophenyl)methyl]pyridine (516 mg, 1.09 mmol) at room temperature. The resulting mixture was stirred for 30 minutes. The reaction mixture was concentrated under reduced pressure. The residue thus obtained was subjected to flash silica gel column chromatography. The fraction obtained from the hexane:ethyl acetate=9:1 eluate was concentrated under reduced pressure to give the title compound (390 mg, 0.93 mmol, 85%) as a brown oil.

$^1$H-NMR (400 MHz, CDCl$_3$) δ: 3.90 (1H, d, J=19.0 Hz), 3.95 (1H, d, J=19.0 Hz), 6.04 (1H, s), 6.96-7.07 (2H, m), 7.12-7.18 (1H, m), 7.24 (2H, d, J=8.8 Hz), 7.29 (2H, d, J=8.8 Hz), 7.67 (1H, s), 8.52 (1H, s).

MS m/z: 421 (M$^+$+H).

Example 292

[5-Chloro-4-[(4-chlorophenylsulfonyl)(2,5-difluorophenyl)methyl]pyridin-2-yl]acetonitrile

[Chemical formula 190]

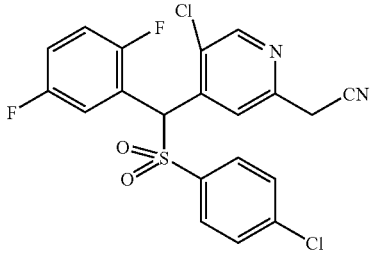

To an ethyl acetate (5 ml) solution of [5-chloro-4-[(4-chlorophenylthio)(2,5-difluorophenyl)methyl]pyridin-2-yl]acetonitrile (387 mg, 0.92 mmol) were added methanol (5 ml), 31% aqueous hydrogen peroxide (3 ml) and hexaammonium heptamolybdate tetrahydrate (227 mg, 0.18 mmol). The resulting mixture was stirred at room temperature for 2 hours.

Water was added to the reaction mixture. Ethyl acetate and methanol were distilled off under reduced pressure. To the residue was added a saturated aqueous solution of sodium bicarbonate. The product thus obtained was extracted with dichloromethane. The organic layer was dried over anhydrous sodium sulfate, and filtered. The filtrate was concentrated under reduced pressure. The residue thus obtained was subjected to flash silica gel column chromatography. The fraction obtained from the hexane:ethyl acetate=17:3 eluate was concentrated under reduced pressure to give the title compound (364 mg, 0.80 mmol, 87%) as a white solid.

$^1$H-NMR (400 MHz, CDCl$_3$) δ: 4.02 (2H, s), 6.22 (1H, s), 6.92-6.99 (1H, m), 7.04-7.11 (1H, m), 7.46 (2H, d, J=8.6 Hz), 7.48-7.54 (1H, m), 7.62 (2H, d, J=8.6 Hz), 8.15 (1H, s), 8.56 (1H, s).

MS m/z: 453 (M$^+$+H).

Example 293

[5-Chloro-4-[(4-chlorophenylsulfonyl)(2,5-difluorophenyl)methyl]pyridin-2-yl]acetic acid

[Chemical formula 191]

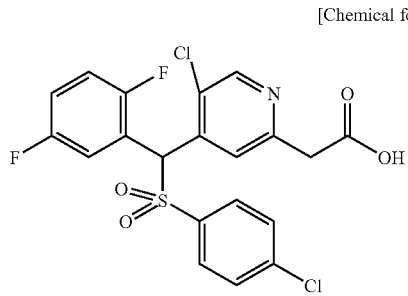

To an acetic acid (2 ml) solution of [5-chloro-4-[(4-chlorophenylsulfonyl)(2,5-difluorophenyl)methyl]pyridin-2-yl]acetonitrile (113 mg, 0.25 mmol) was added a mixture of water (2 ml) and concentrated sulfuric acid (2 ml) at room temperature. The resulting mixture was stirred at 100° C. for 2 hours. After the reaction mixture was cooled to room temperature, water was added thereto. The resulting mixture was extracted with dichloromethane. The organic layer was dried over anhydrous sodium sulfate, and filtered. The filtrate was concentrated under reduced pressure. The residue thus obtained was washed with a mixed solvent of diethyl ether/hexane and then, collected by filtration to give the title compound (101 mg, 0.21 mmol, 86%) as a white solid.

$^1$H-NMR (400 MHz, CDCl$_3$) δ: 1.74 (1H, brs), 4.00 (1H, d, J=17.9 Hz), 4.05 (1H, d, J=17.9 Hz), 6.23 (1H, s), 6.92-6.99 (1H, m), 7.04-7.11 (1H, m), 7.45 (2H, d, J=8.6 Hz), 7.48-7.54 (1H, m), 7.62 (2H, d, J=8.6 Hz), 8.12 (1H, s), 8.52 (1H, s).

MS m/z: 472 (M$^+$+H).

Referential Example 53

(2,5-Dichloro-4-pyridyl)(2,6-difluorophenyl)methanol

[Chemical formula 192]

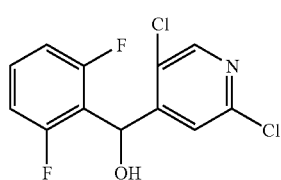

Under an argon atmosphere, n-butyl lithium (a 1.60M hexane solution, 2.33 ml, 3.72 mmol) was added to a tetrahydrofuran solution (12 ml) of diisopropylamine (0.520 ml, 3.72 mmol) at −78° C. The resulting mixture was then stirred at −78° C. for 30 minutes. To the reaction mixture was added a tetrahydrofuran solution (2 ml) of 2,5-dichloropyridine (500 mg, 3.38 mmol). The resulting mixture was stirred at −78° C. for 1 hour. A tetrahydrofuran solution (2 ml) of 2,6-difluorobenzaldehyde (395 mg, 3.72 mmol) was then added to the reaction mixture, followed by stirring at −78° C. for 2 hours. To the reaction mixture was added 1N hydrochloric acid (7 ml) and then, the temperature of the reaction mixture was raised to room temperature. The reaction mixture was diluted with ethyl acetate. The diluted mixture was washed with water and brine, dried over magnesium sulfate, and concentrated. The solid thus obtained was washed with dichloromethane to give the title compound (746 mg, 2.57 mmol, 76%) as a white solid.

$^1$H-NMR (400 MHz, CDCl$_3$) δ: 2.62 (1H, brd, J=3.7 Hz), 6.30 (1H, brs), 6.87-6.93 (2H, m), 7.28-7.37 (1H, m), 7.91 (1H, s), 8.25 (1H, s).

MSm/z: 290 (M$^+$+H).

Example 294

2,5-Dichloro-4-[(4-chlorophenylsulfonyl)(2,6-difluorophenyl)methyl]pyridine

[Chemical formula 193]

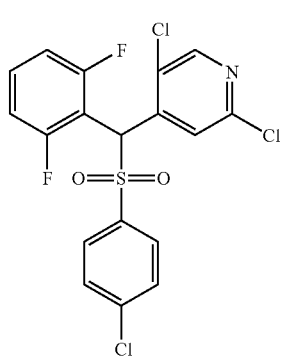

The (2,5-dichloro-4-pyridyl)(2,6-difluorophenyl)methanol (744 mg, 2.57 mmol) obtained in Referential Example 53 was suspended in dichloromethane (6 ml), followed by the addition of thionyl chloride (0.5 ml) and dimethylformamide (one drop). The resulting mixture was stirred at room temperature for 5 hours. To the reaction mixture was added thionyl chloride (1.0 ml) further. The resulting mixture was stirred at room temperature for 24 hours. The reaction mixture was concentrated. The residue thus obtained was neutralized with a saturated solution of sodium bicarbonate and then, extracted with dichloromethane. The extract was washed with water and brine, dried over magnesium sulfate and concentrated. The residue thus obtained was dissolved in dimethylformamide (10 ml). After the addition of sodium 4-chlorobenzenesulfinate (613 mg, 3.08 mmol), the resulting mixture was heated at 50° C. for 5 hours and then, 80° C. for 3 hours. The reaction mixture was diluted with ethyl acetate. The diluted solution was washed with water and brine, dried over magnesium sulfate, and concentrated. The residue thus obtained was subjected to flash silica gel column chromatography. The fraction obtained from the hexane:ethyl acetate=4:1 eluate was concentrated. The resulting solid was recrystallized from diethyl ether-hexane to give the title compound (761 mg, 1.69 mmol, 66%) as a white solid.

$^1$H-NMR (400 MHz, CDCl$_3$) δ: 6.02 (1H, s), 6.84-6.90 (2H, m), 7.32-7.40 (1H, m), 7.46 (2H, d, J=8.5 Hz), 7.65 (2H, d, J=8.5 Hz), 8.35 (1H, s), 8.43-8.46 (1H, m).

MSm/z: 448 (M$^+$+H).

Example 295

5-Chloro-4-[(4-chlorophenylsulfonyl)(2,6-difluorophenyl)methyl]-2-(3,4-dimethoxybenzylamino)pyridine

[Chemical formula 194]

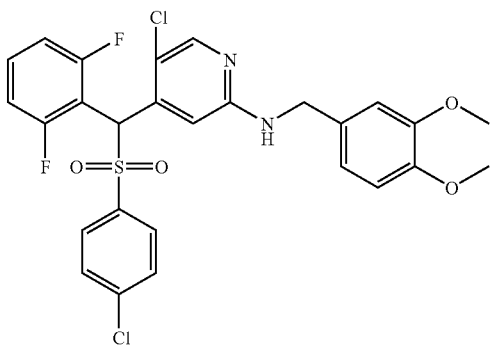

To an N-methyl-2-pyrrolidone solution (20 ml) of the 2,5-dichloro-4-[(4-chlorophenylsulfonyl)(2,6-difluorophenyl)methyl]pyridine (755 mg, 1.68 mmol) obtained in Example 294 was added 3,4-dimethoxybenzylamine (0.745 ml, 5.04 mmol) under an argon atmosphere. The resulting mixture was heated at 150° C. for 5 hours. The reaction mixture was returned to room temperature and then, diluted with ethyl acetate. The diluted solution was washed with a saturated aqueous solution of ammonium chloride, a saturated aqueous solution of sodium bicarbonate, water and brine, dried over magnesium sulfate, and concentrated. The residue thus obtained was subjected to flash silica gel column chromatography. The fraction obtained from the hexane:ethyl acetate=2:1 eluate was concentrated to give the title compound (295 mg, 0.509 mmol, 30%) as a white amorphous substance.

$^1$H-NMR (400 MHz CDCl$_3$) δ: 3.89 (3H, s), 3.90 (3H, s), 4.48 (2H, d, J=5.6 Hz), 5.06 (1H, t, J=5.6 Hz), 6.02 (1H, s), 6.81-6.88 (3H, m), 6.93-7.00 (2H, m), 7.28-7.36 (1H, m), 7.40 (2H, d, J=8.3 Hz), 7.51 (1H, s), 7.56 (2, d, J=8.3 Hz), 8.00 (1H, s).
MSm/z: 579 (M$^+$+H).

Example 296

5-Chloro-4-[(4-chlorophenylsulfonyl)(2,6-difluorophenyl)methyl]pyridin-2-ylamine

[Chemical formula 195]

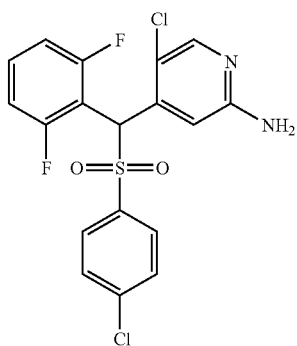

The 5-chloro-4-[(4-chlorophenylsulfonyl)(2,6-difluorophenyl)methyl]-2-(3,4-dimethoxybenzylamino)pyridine (293 mg, 0.506 mmol) obtained in Example 295 was dissolved in trifluoroacetic acid (4 ml). The resulting solution was heated at 65° C. for 2 hours. The reaction mixture was concentrated. The residue thus obtained was basified with a saturated aqueous solution of sodium bicarbonate, followed by extraction with ethyl acetate. The extract was washed with water and brine, dried over magnesium sulfate, and concentrated. The residue thus obtained was subjected to flash silica gel column chromatography. The fraction obtained from the hexane:ethyl acetate=2:1 eluate was concentrated. The solid thus obtained was recrystallized from ethyl acetate-hexane to give the title compound (147 mg, 0.343 mmol, 68%) as a white solid.

$^1$H-NMR (400 MHz, CDCl$_3$) δ: 4.62 (2H, s), 6.01 (1H, s), 6.82-6.89 (2H, m), 7.29-7.38 (1H, m), 7.44 (2H, d, J=8.5 Hz), 7.59 (1H, brs), 7.65 (2H, d, J=8.5 Hz), 7.99 (1H, s).

IR(ATR)cm$^{-1}$: 3502, 3400, 1620, 1603, 1545, 1471, 1412, 1333, 1279, 1230, 1151, 1084, 993, 928, 891, 829, 795, 756, 623, 559, 513, 459.

mp: 179 to 181° C.
MSm/z: 429 (M$^+$+H).

Elemental Analysis for $C_{18}H_{12}Cl_2F_2N_2O_2S$: Calculated: C, 50.36; H, 2.82; Cl, 16.52; F, 8.85; N, 6.53; S, 7.47. Found: C, 50.36; H, 2.83; Cl, 16.39; F, 8.88; N, 6.48; S, 7.56.

Test Example

Measuring Method of an Inhibitor of the Production or Secretion of β-Amyloid Protein The inhibitory activity against formation of β amyloid protein of the compounds obtained in Examples was tested in the method described bellow.

E35 cells were established by transfecting APP751 gene which is a wild type human β-amyloid protein precursor into human glioma cells (H4 cells).

E35 cells were seeded in 96-well plates and cultured in an incubator of 37° C. by using a Dulbecco's Modified Eagle's Medium containing 10% inactivated fetal bovine serum (10% FBS-DMEM). Twenty-four hours after seeding, a test compound dissolved in DMSO so as to give its concentration to be 2000 times as much as that of the final concentration was added to the medium in an amount of 1/2000 capacity of the culture medium. The cells were cultured for additional twenty-four hours, and then the supernatant was collected. The amount of β amyloid protein (Aβ) secreted in the supernatant was measured by the sandwich enzyme-linked immunosorbent assay (ELISA). Described specifically, a monoclonal antibody 25-1, which recognized Aβ25-35, was immobilized onto a 96-well ELISA plate, followed by the incubation at 4° C. for 16 to 20 hours. After washing with a phosphate buffer (pH 7.4) (PBS), a biotinylated monoclonal antibody MA32-40, which recognized Aβ1-8, was added, and the plate was kept at 4° C. for 2 hours. After the supernatant was removed and the well was washed sufficiently with PBS, alkaline phosphatase-conjugated streptavidin was added to the plate. Absorbance was measured while adding BlouPhos (manufactured by KPL) as a substrate. An amount of Aβ contained in the supernatant was calculated using a calibration curve separately created using Aβ of a known concentration. IC$_{50}$ of the test compound was presented as the concentration at which 50% inhibition of Aβ production was observed compared to the amount of Aβ of the control cells to which only DMSO was added.

On the other hand, cytotoxicity of the test compound was assayed in the following manner. The test compound dissolved in DMSO was added to H4 cells cultured on 10% FBS-DMEM. After incubation for 72 hours, a viable cell count was measured using Alamar Blue (manufactured by BIOSOURCE). Concentration of the test compounds at which the viable cell count was 80% or less of the control cells to which only DMSO was added was defined as the concentration at which cytotoxicity appears.

When there is at least 10-times difference between the $IC_{50}$ and the concentration at which cytotoxicity appears, then the compound is judged as a compound having an inhibitory activity against production or secretion of β amyloid protein.

The results of evaluation of the compound of the present invention using the above-described assay are shown in Table 1. Compounds exhibiting $IC_{50}$ not higher than 5 nM are evaluated as +++, those exhibiting $IC_{50}$ ranging from 5 nM to 50 nM are evaluated as ++ and those exhibiting $IC_{50}$ ranging from 50 to 500 nM are evaluated as +.

TABLE 1

| Compound | Activity |
| --- | --- |
| 1 | + |
| 19 | + |
| 20 | + |
| 23 (Compound A) | ++ |
| 42 | + |
| 43 | + |
| 46 | + |
| 55 | ++ |
| 56 | ++ |
| 57 | ++ |
| 59 | ++ |
| 61 | +++ |
| 82 | + |
| 84 | + |
| 106 | +++ |
| 109 | ++ |
| 111 | ++ |
| 114 | ++ |
| 115 | +++ |
| 116 | ++ |
| 164 | +++ |
| 168 | +++ |
| 176 | +++ |
| 196 | +++ |
| 197 | +++ |
| 203 | ++ |
| 211 | +++ |
| 215 | +++ |
| 216 | +++ |
| 220 (B) | + |
| 221 | +++ |
| 222 | ++ |
| 225 | ++ |
| 234 | +++ |
| 236 | +++ |
| 239 | + |
| 240 | ++ |
| 241 | ++ |
| 242 | + |
| 243 | ++ |
| 245 | ++ |
| 246 | ++ |
| 247 | +++ |
| 249 | +++ |
| 250 | ++ |
| 251 | +++ |
| 254 | + |
| 261 | ++ |
| 267 | ++ |
| 268 | +++ |
| 269 | +++ |
| 270 | ++ |
| 271 | +++ |
| 274 | ++ |
| 276 | ++ |
| 278 | +++ |
| 279 | +++ |
| 280 | +++ |

The invention claimed is:
1. A compound represented by formula (I):

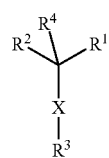

wherein,
$R^1$ represents phenyl which may have 1 to 3 substituents selected from halogen atoms, $C_{1-6}$ alkyl groups, trihalogenomethyl groups, $C_{1-6}$ alkoxy groups, formyl group, $C_{2-6}$ alkanoyl groups, carboxyl group, carboxyamino $C_{1-6}$ alkyl groups, $C_{1-6}$ alkoxycarbonylamino $C_{1-6}$ alkyl groups, oxo group, nitro group, cyano group, amidino group, $C_{2-6}$ alkenyloxy groups, hydroxy group, thioxo group, amino group, $C_{1-6}$ alkylamino groups, di($C_{1-6}$ alkyl)amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, mercapto group, $C_{1-6}$ alkylthio groups, $C_{1-6}$ alkylsulfinyl groups and $C_{1-6}$ alkylsulfonyl groups,
$R^2$ represents a pyridyl group which may be substituted with 1 to 3 substituents selected from halogen atoms, cyano group, $C_{1-6}$ alkyl groups, hydroxy group, $C_{1-6}$ alkoxy groups, $C_{2-6}$ alkenyloxy groups, carboxy $C_{1-6}$ alkyl groups, $C_{1-6}$ alkoxycarbonyl $C_{1-6}$ alkyl groups, hydroxy $C_{1-6}$ alkyl groups, $C_{6-10}$ aromatic hydrocarbon-sulfonyl $C_{1-6}$ alkyl groups, N,N-di($C_{1-6}$ alkyl)aminosulfonyl $C_{1-6}$ alkyl groups, $C_{6-10}$ aromatic hydrocarbon-$C_{1-6}$ alkyl groups, $C_{6-10}$ aromatic hydrocarbon-thio $C_{1-6}$ alkyl groups, azido-$C_{1-6}$ alkyl groups, amino $C_{1-6}$ alkyl groups, $C_{1-6}$ alkylamino $C_{1-6}$ alkyl groups, di($C_{1-6}$ alkyl) amino $C_{1-6}$ alkyl groups, hydroxy $C_{1-6}$ alkylamino $C_{1-6}$ alkyl groups, $C_{1-6}$ alkoxy $C_{1-6}$ alkylamino $C_{1-6}$ alkyl groups, bis($C_{1-6}$ alkoxy $C_{1-6}$ alkyl)amino $C_{1-6}$ alkyl groups, (hydroxy $C_{1-6}$ alkyl)($C_{1-6}$ alkoxy $C_{1-6}$ alkyl) amino $C_{1-6}$ alkyl groups, $C_{2-6}$ alkanoylamino $C_{1-6}$ alkyl groups, di($C_{2-6}$ alkanoyl)amino $C_{1-6}$ alkyl groups, carboxyamino $C_{1-6}$ alkyl groups, di($C_{1-6}$ alkylcarbonylamino $C_{1-6}$ alkyl)amino $C_{1-6}$ alkyl groups, $C_{1-6}$ alkoxycarbonylamino $C_{1-6}$ alkyl groups, di($C_{1-6}$ alkoxycarbonyl)amino $C_{1-6}$ alkyl groups, carbamoylamino $C_{1-6}$ alkyl groups, N—$C_{1-6}$ alkylcarbamoylamino $C_{1-6}$ alkyl groups, N,N-di($C_{1-6}$ alkyl)carbamoylamino $C_{1-6}$ alkyl groups, aminosulfonylamino $C_{1-6}$ alkyl groups, N—$C_{1-6}$ alkylsulfonylamino $C_{1-6}$ alkyl groups, di($C_{1-6}$ alkyl)aminosulfonylamino $C_{1-6}$ alkyl groups, $C_{6-10}$ aromatic hydrocarbon-sulfonylamino-$C_{2-6}$ alkanoylamino $C_{1-6}$ alkyl groups, amino $C_{1-6}$ alkylcarbonylamino $C_{1-6}$ alkyl groups, N—$C_{1-6}$ alkylamino $C_{1-6}$ alkylcarbonylamino $C_{1-6}$ alkyl groups, N,N-di($C_{1-6}$ alkyl)amino $C_{1-6}$ alkylcarbonylamino $C_{1-6}$ alkyl groups, $C_{6-10}$ aromatic hydrocarbon-$C_{2-6}$ alkenylcarbonylamino $C_{1-6}$ alkyl groups, $C_{6-10}$ aromatic hydrocarbon-carbonylamino $C_{1-6}$ alkyl groups, $C_{6-10}$ aromatic hydrocarbon-thiocarbonylamino $C_{1-6}$ alkyl groups, $C_{1-6}$ alkoxyoxalylamino $C_{1-6}$ alkyl groups, ($C_{6-10}$ aromatic hydrocarbonsulfonyl)($C_{1-6}$ alkyl)amino $C_{1-6}$ alkyl groups, $C_{1-6}$ alkylsulfonylamino $C_{1-6}$ alkyl groups, $C_{1-6}$ alkylsulfonylamino $C_{1-6}$ alkyl groups, carbamoyloxy $C_{1-6}$ alkyl groups, N—$C_{1-6}$ alkylcarbamoyloxy $C_{1-6}$ alkyl groups, N,N-di($C_{1-6}$ alkyl)carbamoyloxy $C_{1-6}$ alkyl groups, $C_{6-10}$ aromatic hydrocarbon-$C_{1-6}$ alkylcarbamoyloxy $C_{1-6}$ alkyl groups, $C_{1-6}$ alkoxycarbonyloxy-$C_{1-6}$ alkyl groups, $C_{6-10}$ aromatic hydrocarbonoxycarbonyloxy $C_{1-6}$ alkyl groups, $C_{6-10}$ aromatic hydrocarbon carbonylhydrazonomethyl groups, $C_{2-6}$ alkenyl groups, carboxy-$C_{2-5}$ alkenyl groups, $C_{1-6}$ alkoxycarbonyl-$C_{2-6}$ alkenyl groups, carbamoyl $C_{2-6}$ alkenyl groups, formyl group, carboxyl group, $C_{6-10}$ aromatic hydrocarbon-carbonyl groups, $C_{1-6}$ alkoxycarbonyl groups, carbamoyl group, N—$C_{1-6}$ alkylcarbamoyl groups, N,N-di($C_{1-6}$ alkyl)carbamoyl groups, $C_{3-8}$ cycloalkyl-$C_{1-6}$ alkylcarbamoyl groups, $C_{1-6}$ alkylthio $C_{1-6}$ alkylcarbamoyl groups, $C_{1-6}$ alkylsulfinyl $C_{1-6}$ alkylcarbamoyl groups, $C_{1-6}$ alkylsulfonyl $C_{1-6}$ alkylcarbamoyl groups, hydroxyaminocarbonyl group, $C_{1-6}$ alkoxycarbamoyl groups, hydroxy $C_{1-6}$ alkylcarbamoyl groups, $C_{1-6}$ alkoxy $C_{1-6}$ alkylcarbamoyl groups, amino $C_{1-6}$ alkylcarbamoyl groups, amino $C_{1-6}$ alkylthiocarbamoyl groups, hydroxy $C_{1-6}$ alkylcarbamoyl groups, $C_{1-6}$ alkoxycarbonyl $C_{1-6}$ alkylcarbamoyl groups, $C_{1-6}$ alkoxycarbonylamino $C_{1-6}$ alkylcarbamoyl groups, $C_{1-6}$ alkoxycarbonylamino $C_{1-6}$ alkylthiocarbamoyl groups, $C_{6-10}$ aromatic hydrocarbon-carbamoyl groups, hydrazinocarbonyl groups, N—$C_{1-6}$ alkylhydrazinocarbonyl groups, N'—$C_{1-6}$ alkylhydrazinocarbonyl groups, N',N'-di($C_{1-6}$ alkyl)hydrazinocarbonyl groups, N,N'-di($C_{1-6}$ alkyl)hydrazinocarbonyl groups, N,N',N'-tri($C_{1-6}$ alkyl)hydrazinocarbonyl groups, amino group, $C_{1-6}$ alkoxy $C_{1-6}$ alkylamino groups, amino $C_{1-6}$ alkylamino groups, ($C_{1-6}$ alkylamino $C_{1-6}$ alkylamino groups, ($C_{1-6}$ alkylamino $C_{1-6}$ alkyl)($C_{1-6}$ alkyl)amino groups, $C_{1-6}$ alkoxycarbonylamino $C_{1-6}$ alkylamino groups, di($C_{1-6}$ alkyl)amino $C_{1-6}$ alkylamino groups, carboxyl $C_{1-6}$ alkylamino groups, (carboxyl $C_{1-6}$ alkyl)($C_{1-6}$ alkyl) amino groups, hydroxy $C_{1-6}$ alkylamino groups, (hydroxy $C_{1-6}$ alkyl)($C_{1-6}$ alkyl)amino groups, $C_{1-6}$ alkylthio $C_{1-6}$ alkylamino groups, $C_{1-6}$ alkylaminocarbonyloxy $C_{1-6}$ alkylamino groups, ($C_{1-6}$ alkylaminocarbonyloxy $C_{1-6}$ alkyl)($C_{1-6}$ alkyl)amino groups, $C_{1-6}$ alkylsulfinyl $C_{1-6}$ alkylamino groups, $C_{1-6}$ alkylsulfonyl $C_{1-6}$ alkylamino groups, groups represented by the formula: —N($R^{12}$)$SO_2R^{11}$ (wherein, $R^{11}$ represents a $C_{1-6}$ alkyl group, hydroxy $C_{1-6}$ alkyl group, amino $C_{1-6}$ alkyl group, $C_{1-6}$ alkylamino $C_{1-6}$ alkyl group, di($C_{1-6}$ alkyl)amino $C_{1-6}$ alkyl group, carboxy $C_{1-6}$ alkyl group, carbamoyl $C_{1-6}$ alkyl group, trifluoromethyl group, difluoromethyl group, fluoromethyl group, amino group, $C_{1-6}$ alkylamino group or di($C_{1-6}$ alkyl)amino group, $R^{12}$ represents a hydrogen atom, $C_{1-6}$ alkyl group, hydroxy group or amino group), hydroxy $C_{1-6}$ alkoxy $C_{1-6}$ alkylamino groups, $C_{6-10}$ aromatic hydrocarbon-$C_{1-6}$ alkylamino groups, $C_{1-6}$ alkoxycarbonylamino groups, $C_{6-10}$ aromatic hydrocarbon-carbonylamino groups, hydroxyimino group, $C_{1-6}$ alkoxyimino groups, oxo group, hydroxyimino $C_{1-6}$ alkyl groups, $C_{1-6}$ alkoxycarbonyl $C_{1-6}$ alkylamino groups, ($C_{2-6}$ alkanoylamino $C_{1-6}$ alkyl)amino groups, and $C_{6-10}$ aromatic hydrocarbon groups (in which, the $C_{6-10}$ aromatic hydrocarbon group may be substituted with 1 to 3 substituents selected from halogen atoms, $C_{1-6}$ alkyl groups, $C_{1-6}$ alkoxy groups, $C_{2-6}$ alkenyl groups, formyl group, $C_{2-6}$ alkanoyl groups, carboxyl group, carboxyamino $C_{1-6}$ alkyl groups, $C_{1-6}$ alkoxycarbonylamino $C_{1-6}$ alkyl groups, oxo group, nitro group, cyano group, amidino group, $C_{2-6}$ alkenyloxy groups, hydroxy group, thioxo group, amino group, $C_{1-6}$ alkylamino groups, di($C_{1-6}$ alkyl)amino groups, amino $C_{1-6}$ alkyl groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, $C_{2-6}$ alkanoylamino groups, $C_{2-6}$ alkanoyl($C_{1-6}$ alkyl) amino groups, thio $C_{2-6}$ alkanoylamino groups, thio $C_{2-6}$ alkanoyl($C_{1-6}$ alkyl)amino groups, formylamino group, formyl($C_{1-6}$ alkyl)amino groups, thioformylamino group, thioformyl($C_{1-6}$ alkyl)amino groups, $C_{2-6}$ alkanoyloxy groups, formyloxy group, mercapto group, $C_{1-6}$ alkylthio groups, $C_{1-6}$ alkylsulfinyl groups, $C_{1-6}$ alkylsulfonyl groups, aminosulfonyl group, $C_{1-6}$ alkylaminosulfonyl groups, di($C_{1-6}$ alkyl)aminosulfonyl groups, $C_{1-6}$ alkylsulfonylamino groups, and $C_{1-6}$ alkylsulfonyl($C_{1-6}$ alkyl)amino groups;

$R^3$ represents pyridyl which may have 1 to 3 substituents selected from halogen atoms, $C_{1-6}$ alkyl groups, trihalogenomethyl groups, $C_{1-6}$ alkoxy groups, formyl group, $C_{2-6}$ alkanoyl groups, carboxyl group, carboxyamino $C_{1-6}$ alkyl groups, $C_{1-6}$ alkoxycarbonylamino $C_{1-6}$ alkyl groups, oxo group, nitro group, cyano group, amidino group, $C_{2-6}$ alkenyloxy groups, hydroxy group, thioxo group, amino group, $C_{1-6}$ alkylamino groups, di($C_{1-6}$ alkyl)amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, mercapto group, $C_{1-6}$ alkylthio groups, $C_{1-6}$ alkylsulfinyl groups and $C_{1-6}$ alkylsulfonyl groups, $R^4$ represents a hydrogen atom or a $C_{1-6}$ alkyl group, X represents —S—, —SO— or —$SO_2$—;

an N-oxide thereof; or a salt thereof.

2. A compound according to claim 1, wherein $R^2$ represents a group represented by the following formula:

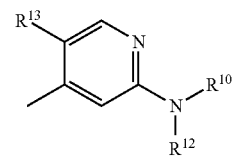

wherein, $R^{10}$ represents a hydrogen atom, $C_{1-6}$ alkyl group, hydroxy $C_{1-6}$ alkyl group, $C_{1-6}$ alkylsulfinyl $C_{1-6}$ alkyl group, $C_{1-6}$ alkylsulfonyl $C_{1-6}$ alkyl group, carboxy $C_{1-6}$ alkyl group, a group represented by the formula: —$SO_2$—$R^{11}$ (in which, $R^{11}$ represents a $C_{1-6}$ alkyl, hydroxy $C_{1-6}$ alkyl, amino $C_{1-6}$ alkyl, $C_{1-6}$ alkylamino $C_{1-6}$ alkyl, di($C_{1-6}$ alkyl)amino $C_{1-6}$ alkyl, carboxy $C_{1-6}$ alkyl, carbamoyl $C_{1-6}$ alkyl, trifluoromethyl, difluoromethyl, fluoromethyl, amino, $C_{1-6}$ alkylamino or di($C_{1-6}$ alkyl)amino), $R^{12}$ represents a hydrogen atom, $C_{1-6}$ alkyl group, hydroxy group, or amino group, and $R^{13}$ represents a $C_{1-6}$ alkyl group, halogen atom or cyano group; an N-oxide thereof or a salt thereof.

3. A compound according to claim 1, wherein $R^2$ represents a group represented by the following formula:

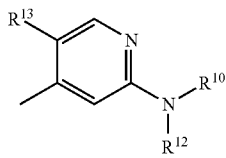

wherein,
R[10] represents a group represented by the formula: —SO$_2$—R[11] (in which, R[11] represents a C$_{1-6}$ alkyl, hydroxy C$_{1-6}$ alkyl, amino C$_{1-6}$ alkyl, C$_{1-6}$ alkylamino C$_{1-6}$ alkyl, di(C$_{1-6}$ alkyl)amino C$_{1-6}$ alkyl, carboxy C$_{1-6}$ alkyl, carbamoyl C$_{1-6}$ alkyl, trifluoromethyl, difluoromethyl, fluoromethyl, amino, C$_{1-6}$ alkylamino or di(C$_{1-6}$ alkyl)amino), R[12] represents a hydrogen atom, C$_{1-6}$ alkyl group, hydroxy group or amino group, and R[13] represents a C$_{1-6}$ alkyl group, halogen atom or cyano group; an N-oxide thereof; or a salt thereof.

4. A compound according to claim 1, wherein R$^2$ represents a compound represented by the formula:

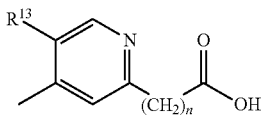

wherein,
R[13] represents a C$_{1-6}$ alkyl group, halogen atom or cyano group, and n stands for an integer of from 0 to 6; an N-oxide thereof; or a salt thereof.

5. A compound according to claim 1, wherein R$^1$ represents a 2,5-difluorophenyl or 2-fluoro-5-cyanophenyl group, R$^3$ represents a 5-chloro-2-pyridyl, 6-chloro-3-pyridyl, or 6-trifluoromethyl-3-pyridyl group; R$^2$ represents a group represented by the following formula:

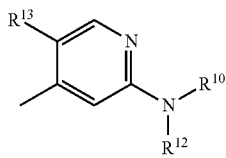

wherein,
R[10] represents a hydrogen atom, C$_{1-6}$ alkyl group, hydroxy C$_{1-6}$ alkyl group, C$_{1-6}$ alkylsulfinyl C$_{1-6}$ alkyl group, C$_{1-6}$ alkylsulfonyl C$_{1-6}$ alkyl group, carboxy C$_{1-6}$ alkyl group, or a group represented by the formula: —SO$_2$—R[11] (in which, R[11] represents a C$_{1-6}$ alkyl, hydroxy C$_{1-6}$ alkyl, amino C$_{1-6}$ alkyl, C$_{1-6}$ alkylamino C$_{1-6}$ alkyl, di(C$_{1-6}$ alkyl)amino C$_{1-6}$ alkyl, carboxy C$_{1-6}$ alkyl, carbamoyl C$_{1-6}$ alkyl, trifluoromethyl, difluoromethyl, fluoromethyl, amino, C$_{1-6}$ alkylamino, or di(C$_{1-6}$ alkyl)amino), R[12] represents a hydrogen atom, C$_{1-6}$ alkyl group, hydroxy group, or amino group, and R[13] represents a C$_{1-6}$ alkyl group, halogen atom or cyano group; an N-oxide thereof; or a salt thereof.

6. A compound according to claim 1, wherein R$^1$ represents a 2,5-difluorophenyl or 2-fluoro-5-cyanophenyl group, R$^3$ represents a 5-chloro-2-pyridyl, 6-chloro-3-pyridyl or 6-trifluoromethyl-3-pyridyl group;

R$^2$ represents a group represented by the following formula:

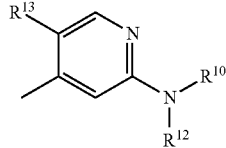

wherein,
R[10] represents a group represented by the formula: —SO$_2$—R[11] (in which, R[11] represents a C$_{1-6}$ alkyl, hydroxy C$_{1-6}$ alkyl, amino C$_{1-6}$ alkyl, C$_{1-6}$ alkylamino C$_{1-6}$ alkyl, di(C$_{1-6}$ alkyl)amino C$_{1-6}$ alkyl, trifluoromethyl, difluoromethyl, fluoromethyl, amino, C$_{1-6}$ alkylamino or di(C$_{1-6}$ alkyl)amino), R[12] represents a hydrogen atom, C$_{1-6}$ alkyl group, hydroxy group or amino group, and R[13] represents a C$_{1-6}$ alkyl group, halogen atom or cyano group; an N-oxide thereof; or a salt thereof.

7. A compound according to claim 1, wherein R$^1$ represents a 2,5-difluorophenyl or 2-fluoro-5-cyanophenyl group, R$^3$ represents a 5-chloro-2-pyridyl, 6-chloro-3-pyridyl, or 6-trifluoromethyl-3-pyridyl group;

R$^2$ represents a group represented by the following formula:

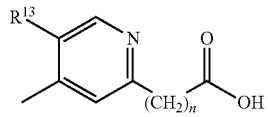

wherein,
R[13] represents a C$_{1-6}$ alkyl group, halogen atom or cyano group and n stands for an integer of from 0 to 6; an N-oxide thereof; or a salt thereof.

8. A pharmaceutical composition comprising a compound as claimed in claim 1, an N-oxide thereof, or a salt thereof and a pharmaceutically acceptable carrier.

9. A method of treating a disease resulting from abnormal production or secretion of β-amyloid protein, which comprises administering an effective amount of a compound as claimed in claim 1, an N-oxide thereof, or a salt thereof.

10. A method according to claim 9, wherein the disease resulting from abnormal production or secretion of β amyloid protein is Alzheimer disease or Down syndrome.

11. A compound according to claim 1, comprising at least one selected from the group consisting of:
[5-Chloro-4-[(5-chloropyridin-2-ylsulfonyl)(2,5-difluorophenyl)methyl]pyridin-2-yl]amine,
N-[5-Chloro-4-[(5-chloropyridin-2-ylsulfonyl)(2,5-difluorophenyl)methyl]pyridin-2-yl]methanesulfonamide,
t-Butyl[5-chloro-4-[(6-chloropyridin-3-ylthio)(2,5-difluorophenyl)methyl]pyridin-2-yl]carbamate,
[5-Chloro-4-[(6-chloropyridin-3-ylsulfonyl)(2,5-difluorophenyl)methyl]pyridin-2-yl]amine, and
[5-Chloro-4-[(2,5-difluorophenyl)(6-trifluoromethylpyridin-3-ylsulfonyl)methyl]pyridin-2-yl]amine.

* * * * *